US012378215B2

(12) United States Patent
Ma et al.

(10) Patent No.: US 12,378,215 B2
(45) Date of Patent: Aug. 5, 2025

(54) ORGANIC COMPOUND, COMPOSITION, ORGANIC ELECTROLUMINESCENT DEVICE, AND ELECTRONIC APPARATUS

(71) Applicant: Shaanxi Lighte Optoelectronics Material Co., Ltd., Xi'an (CN)

(72) Inventors: Tiantian Ma, Xi'an (CN); Lei Yang, Xi'an (CN); Zhen Feng, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 18/860,313

(22) PCT Filed: Oct. 10, 2023

(86) PCT No.: PCT/CN2023/123855

§ 371 (c)(1),
(2) Date: Oct. 25, 2024

(87) PCT Pub. No.: WO2024/148883

PCT Pub. Date: Jul. 18, 2024

(65) Prior Publication Data

US 2025/0122168 A1 Apr. 17, 2025

(30) Foreign Application Priority Data

Jan. 11, 2023 (CN) ......................... 202310071951.7
Mar. 1, 2023 (CN) ......................... 202310184175.1

(51) Int. Cl.
*C07D 401/04* (2006.01)
*C07B 59/00* (2006.01)
(Continued)

(52) U.S. Cl.
CPC .......... *C07D 401/04* (2013.01); *C07B 59/004* (2013.01); *C07D 401/10* (2013.01);
(Continued)

(58) Field of Classification Search
None
See application file for complete search history.

(56) References Cited

FOREIGN PATENT DOCUMENTS

CN 104812750 A 7/2015
CN 112673005 A 4/2021
(Continued)

OTHER PUBLICATIONS

International Search Report from corresponding International Application No. PCT/CN2023/123855, Dec. 4, 2023, 4 pages with translation.

(Continued)

*Primary Examiner* — Anthony Ho
(74) *Attorney, Agent, or Firm* — Tucker Ellis LLP

(57) ABSTRACT

The present disclosure belongs to the technical field of organic electroluminescence, and relates to an organic compound, and a composition, an organic electroluminescent
(Continued)

device, and an electronic apparatus using the same. The organic compound has a structure as shown in a formula 1, and when the organic compound is used in an organic electroluminescent device, the performance of the organic electroluminescent device can be significantly improved.

Formula 1

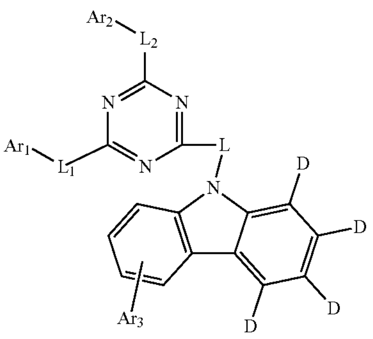

14 Claims, 1 Drawing Sheet

(51) Int. Cl.
*C07D 401/10* (2006.01)
*C07D 405/14* (2006.01)
*C07D 409/14* (2006.01)
*H10K 85/60* (2023.01)

(52) U.S. Cl.
CPC ......... *C07D 405/14* (2013.01); *C07D 409/14* (2013.01); *H10K 85/615* (2023.02); *H10K 85/654* (2023.02); *H10K 85/6572* (2023.02); *H10K 85/6574* (2023.02); *H10K 85/6576* (2023.02); *C07B 2200/05* (2013.01)

(56) References Cited

FOREIGN PATENT DOCUMENTS

| | | | |
|---|---|---|---|
| CN | 113527268 | A | 10/2021 |
| CN | 115611871 | A | 1/2023 |
| EP | 4074706 | A1 | 10/2022 |
| JP | 2013505982 | A | 2/2013 |
| JP | 2017125087 | A | 7/2017 |
| KR | 20220031339 | A | 3/2022 |
| KR | 20220051731 | A | 4/2022 |
| WO | 2022211594 | A1 | 10/2022 |
| WO | 2023128513 | A1 | 7/2023 |

OTHER PUBLICATIONS

Japanese Notice of Allowance from corresponding Application No. 2024-563308 mailed on Apr. 1, 2025, 4 pages.

ORGANIC COMPOUND, COMPOSITION, ORGANIC ELECTROLUMINESCENT DEVICE, AND ELECTRONIC APPARATUS

CROSS REFERENCE TO RELATED APPLICATIONS

The present disclosure claims the priority of Chinese patent application No. CN202310071951.7 filed on Jan. 11, 2023, and Chinese patent application No. CN202310184175.1 filed on Mar. 1, 2023, the contents of which are incorporated here by reference in their entirety as part of the present disclosure.

TECHNICAL FIELD

The present disclosure relates to the technical field of organic compounds, in particular to an organic compound, and a composition, an organic electroluminescent device and an electronic apparatus including the same.

BACKGROUND

With the development of electronic technology and the advancement of material science, the application range of electronic components for realizing electroluminescence is becoming more and more extensive. The electronic component generally includes a cathode and an anode which are oppositely disposed, and a functional layer disposed between the cathode and the anode. The functional layer is composed of a plurality of organic or inorganic film layers and generally includes an organic light-emitting layer, a hole transport layer located between the organic light-emitting layer and the anode, and an electron transport layer located between the organic light-emitting layer and the cathode. Taking an organic electroluminescent device as an example, the organic electroluminescent device generally includes an anode, a hole transport layer, an organic light-emitting layer, an electron transport layer and a cathode which are sequentially stacked. When a voltage is applied to the cathode and the anode, an electric field is generated between the two electrodes, electrons on the cathode side move towards the organic light-emitting layer and holes on the anode side also move towards the organic light-emitting layer under the action of the electric field. The electrons and the holes are combined in the organic light-emitting layer to form excitons, the excitons are in an excited state and release energy outwards, and then the organic light-emitting layer emits light outwards.

The prior art discloses a host material for the organic light-emitting layer that can be prepared in the organic electroluminescent device. However, it is still necessary to continue to develop new materials to further improve the performance of the electronic components.

SUMMARY

In order to solve the above problems, an object of the present disclosure is to provide an organic compound, and a composition, an organic electroluminescent device, and an electronic apparatus including the same. The organic compound can improve the performance of the organic electroluminescent device and the electronic apparatus, such as reducing the driving voltage of the device, and improving the efficiency and service life of the device.

According to a first aspect of the present disclosure, provided is an organic compound, having a structure as shown in a formula 1:

Formula 1

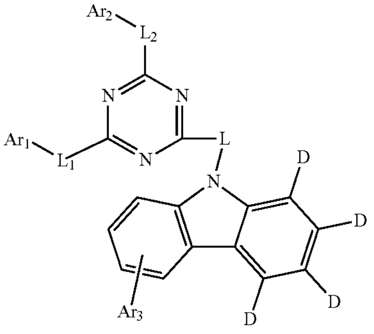

wherein $Ar_1$ and $Ar_2$ are the same or different, and are respectively and independently selected from a substituted or unsubstituted aryl with 6 to 30 carbon atoms, a substituted or unsubstituted dibenzofuranyl, or a substituted or unsubstituted dibenzothienyl;

L, $L_1$ and $L_2$ are the same or different, and are respectively and independently selected from a single bond or a substituted or unsubstituted arylene with 6 to 30 carbon atoms;

$Ar_3$ is

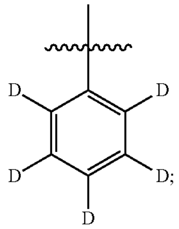

and substituent(s) in L, $L_1$, $L_2$, $Ar_1$ and $Ar_2$ are the same or different, and are each independently selected from deuterium, a cyano, a halogen group, an alkyl with 1 to 10 carbon atoms, a haloalkyl with 1 to 10 carbon atoms, a deuteroalkyl with 1 to 10 carbon atoms, an aryl with 6 to 20 carbon atoms, a deuteroaryl with 6 to 20 carbon atoms, a haloaryl with 6 to 20 carbon atoms, or a cycloalkyl with 3 to 10 carbon atoms.

According to a second aspect of the present disclosure, provided is a composition, including a first compound disclosed in the first aspect of the present disclosure and a second compound having a structure as shown in a formula 2:

Formula 2

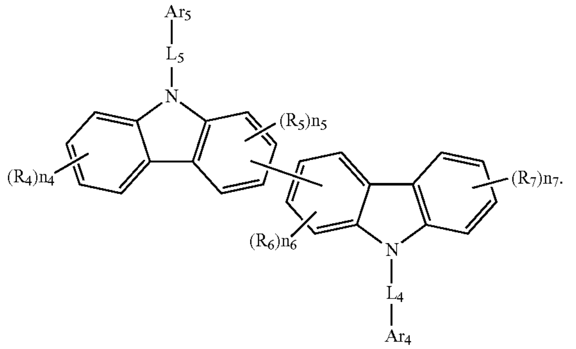

According to a third aspect of the present disclosure, provided is an organic electroluminescent device, including an anode and a cathode which are oppositely disposed, and a functional layer disposed between the anode and the cathode, where the functional layer includes the organic compound disclosed in the first aspect of the present disclosure or the composition disclosed in the second aspect of the present disclosure.

According to a fourth aspect of the present disclosure, provided is an electronic apparatus, including the organic electroluminescent device disclosed in the third aspect of the present disclosure.

A core structure of the organic compound of the present disclosure is phenylcarbazole connected to a triazine group through a nitrogen atom, and one of benzene rings on the carbazole ring is fully deuterated and the other benzene ring is connected to pentadeuterophenyl. Pentadeuterophenyl is introduced as a substituent on one side of the carbazole group, and thus, molecular symmetry is reduced while expanding the aromatic conjugation range of the molecular structure, so that a material has better energy transfer characteristics, and the crystallinity can be reduced; the specific asymmetric deuteration of the carbazole group can effectively improve the stability of the molecular structure and can further reduce the molecular symmetry, thus significantly improving the photoelectric stability and film-forming properties of the material. The organic compound of the present disclosure has good carrier transport characteristics, energy transfer characteristics and photoelectric stability, and is suitable for use as a host material of an organic light-emitting layer in an organic electroluminescent device, and the organic electroluminescent device using the organic compound as the host material has significantly improved service life characteristics while maintaining a low driving voltage and high luminous efficiency.

Other features and advantages of the present disclosure will be described in detail in the subsequent detailed description.

BRIEF DESCRIPTION OF THE DRAWINGS

The accompanying drawings are used to provide a further understanding of the present disclosure and constitute a part of the specification, and together with the detailed description below, serve to explain the present disclosure, but do not constitute limitations on the present disclosure.

REFERENCE SIGNS

Figure 1:
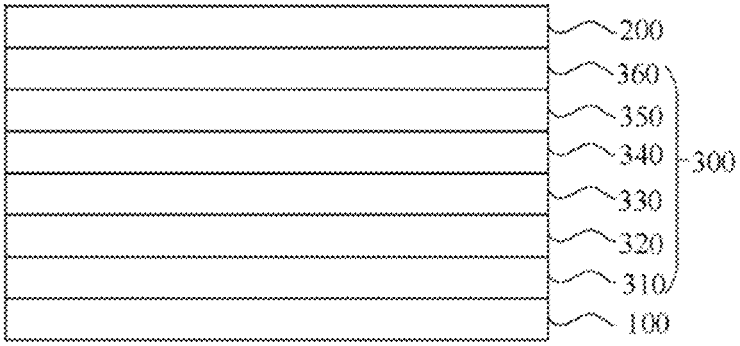
FIG. 1 is a structural schematic diagram of an organic electroluminescent device according to the present disclosure.

- 100, anode; 200, cathode; 300, functional layer; 310, hole injection layer;
- 320, hole transport layer; 330, hole auxiliary layer; 340, organic light-emitting layer;
- 350, electron transport layer; 360, electron injection layer; 400, first electronic apparatus.

DETAILED DESCRIPTION

In view of the above problems existing in the prior art, an object of the present disclosure is to provide an organic compound, an organic electroluminescent device including the same, and an electronic device. The organic compound can improve the performance of the organic electroluminescent device and the electronic device, such as reducing the driving voltage of the device, and improving the efficiency and service life of the device.

According to a first aspect of the present disclosure, provided is an organic compound, having a structure as shown in a formula 1:

Formula 1

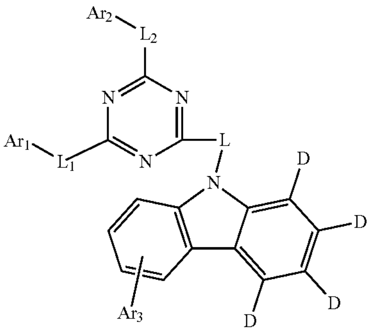

Wherein, $Ar_1$ and $Ar_2$ are the same or different, and are respectively and independently selected from a substituted or unsubstituted aryl with 6 to 30 carbon atoms, a substituted or unsubstituted dibenzofuranyl, or a substituted or unsubstituted dibenzothienyl;

L, $L_1$ and $L_2$ are the same or different, and are respectively and independently selected from a single bond or a substituted or unsubstituted arylene with 6 to 30 carbon atoms;

$Ar_3$ is

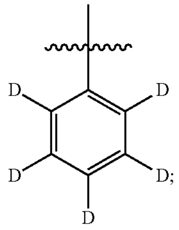

and substituent(s) in L, $L_1$, $L_2$, $Ar_1$ and $Ar_2$ are the same or different, and are each independently selected from deuterium, a cyano, a halogen group, an alkyl with 1 to 10 carbon atoms, a haloalkyl with 1 to 10 carbon atoms, a deuteroalkyl with 1 to 10 carbon atoms, an aryl with 6 to 20 carbon atoms, a deuteroaryl with 6 to 20 carbon atoms, a haloaryl with 6 to 20 carbon atoms, or a cycloalkyl with 3 to 10 carbon atoms.

In the present disclosure, the adopted description modes “each . . . is independently”, “ . . . is respectively and independently” and “ . . . is each independently” can be interchanged, and should be understood in a broad sense, which means that in different groups, specific options expressed between the same symbols do not influence each other, or in a same group, specific options expressed between the same symbols do not influence each other. For example, the meaning of “

Q-1

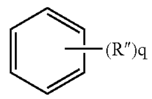

Q-2

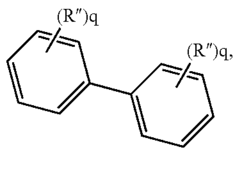

where each q is independently 0, 1, 2 or 3, and each R" is independently selected from hydrogen, deuterium, fluorine and chlorine” is as follows: a formula Q-1 represents that q substituents R" exist on a benzene ring, each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present disclosure, the term such as “substituted or unsubstituted” means that a functional group described behind the term may have or may not have a substituent (in the below, the substituent is collectively referred to as Rc in order to facilitate description). For example, the “substituted or unsubstituted aryl” refers to aryl having the substituent Rc or unsubstituted aryl. Where the above substituent, i.e., Rc, for example, can be deuterium, cyano, a halogen group, alkyl, haloalkyl, deuteroalkyl, aryl, deuteroaryl, haloaryl, heteroaryl, cycloalkyl, or the like. The number of the substituents may be one or more.

In the present disclosure, “a plurality of” means two or more, e.g., two, three, four, five, six, etc.

In the present disclosure, the number of carbon atoms of a substituted or unsubstituted functional group refers to the number of all carbon atoms. For example, if $L_1$ is a substituted arylene with 12 carbon atoms, then the number of all carbon atoms of the arylene and substituents on the arylene is 12.

In the present disclosure, aryl refers to an optional functional group or substituent derived from an aromatic carbocyclic ring. The aryl can be monocyclic aryl (e.g., phenyl) or polycyclic aryl, in other words, the aryl can be monocyclic aryl, fused aryl, two or more monocyclic aryl linked by carbon-carbon bonds, monocyclic aryl and fused aryl which are linked by a carbon-carbon bond, or two or more fused aryl linked by carbon-carbon bonds. That is, unless otherwise indicated, two or more aromatic groups conjugatedly linked by carbon-carbon bonds may also be considered as the aryl in the present disclosure. The fused aryl may include, for example, bicyclic fused aryl (e.g., naphthyl), tricyclic fused aryl (e.g., phenanthryl, fluorenyl, and anthryl), and the like. The aryl does not contain heteroatoms such as B, N, O, S, P, Se, and Si. Examples of the aryl can include, but are not limited to, phenyl, naphthyl, fluorenyl, anthryl, phenanthryl, biphenyl, terphenyl, triphenylene, perylenyl, benzo[9,10] phenanthryl, pyrenyl, benzofluoranthenyl, chrysenyl, spirobifluorenyl, and the like. In the present disclosure, the arylene involved refers to a divalent group formed by further loss of one hydrogen atom from the aryl.

In the present disclosure, terphenyl includes

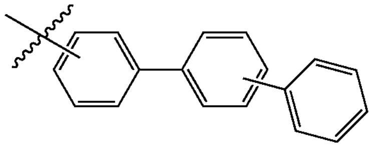

and

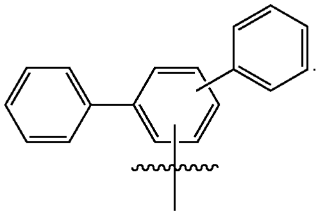

In the present disclosure, the number of carbon atoms of substituted aryl refers to the total number of carbon atoms of the aryl and substituents on the aryl, e.g., a substituted aryl with 18 carbon atoms means that the total number of carbon atoms of the aryl and substituents is 18.

In the present disclosure, the number of carbon atoms of the substituted or unsubstituted aryl may be 6, 10, 12, 13, 14, 15, 16, 17, 18, 20, 24, 25, or 30. In some embodiments, the substituted or unsubstituted aryl is a substituted or unsubstituted aryl with 6 to 30 carbon atoms, in other embodiments, the substituted or unsubstituted aryl is a substituted or unsubstituted aryl with 6 to 25 carbon atoms, in other embodiments, the substituted or unsubstituted aryl is a substituted or unsubstituted aryl with 6 to 20 carbon atoms, and in other embodiments, the substituted or unsubstituted aryl is a substituted or unsubstituted aryl with 6 to 12 carbon atoms.

In the present disclosure, fluorenyl may be substituted by one or more substituents, where any two adjacent substituents may be bonded to each other to form a ring structure. In the case where the above fluorenyl is substituted, the substituted fluorenyl may be

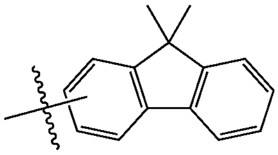

,

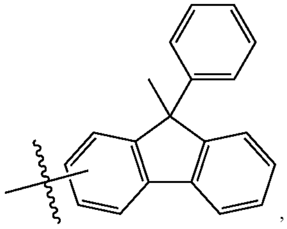

,

-continued

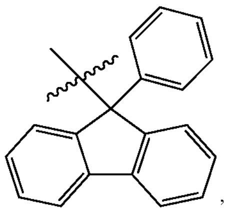,
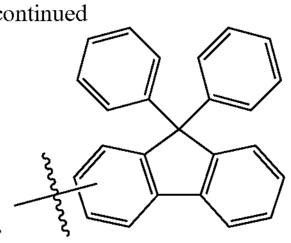

or the like, but is not limited to this.

In the present disclosure, aryl as a substituent of L, $L_1$, $L_2$, $Ar_1$ and $Ar_2$ is, for example, but is not limited to, phenyl, naphthyl or the like.

In the present disclosure, heteroaryl refers to a monovalent aromatic ring containing 1, 2, 3, 4, 5 or 6 heteroatoms in the ring or its derivative, and the heteroatom may be one or more of B, O, N, P, Si, Se and S. The heteroaryl may be monocyclic heteroaryl or polycyclic heteroaryl, in other words, the heteroaryl may be a single aromatic ring system or a plurality of aromatic ring systems linked by carbon-carbon bonds, and any one aromatic ring system is a monocyclic aromatic ring or a fused aromatic ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, and N-phenylcarbazolyl, N-pyridylcarbazolyl, N-methylcarbazolyl, and the like, but is not limited to this.

In the present disclosure, the number of carbon atoms of the substituted or unsubstituted heteroaryl may be selected from 3, 4, 5, 6, 7, 8, 9, 10, 11, 12, 13, 14, 15, 16, 17, 18, 20, 21, 22, 23, 24, 25, 26, 27, 28, 29 or 30. In some embodiments, the substituted or unsubstituted heteroaryl is a substituted or unsubstituted heteroaryl with 5 to 20 carbon atoms, and in other embodiments, the substituted or unsubstituted heteroaryl is a substituted or unsubstituted heteroaryl with 12 to 18 carbon atoms.

In the present disclosure, the substituted heteroaryl may be that one or two or more hydrogen atoms in the heteroaryl are substituted by groups such as deuterium atom, halogen group, —CN, aryl, heteroaryl, trialkylsilyl, alkyl, cycloalkyl, haloalkyl, and the like. It should be understood that the number of carbon atoms of the substituted heteroaryl refers to the total number of carbon atoms of the heteroaryl and substituents on the heteroaryl.

In the present disclosure, the alkyl with 1 to 10 carbon atoms may include linear alkyl with 1 to 10 carbon atoms and branched alkyl with 3 to 10 carbon atoms. The number of carbon atoms of the alkyl can be, for example, 1, 2, 3, 4, 5, 6, 7, 8, 9, or 10, and specific examples of the alkyl include, but are not limited to, methyl, ethyl, n-propyl, isopropyl, n-butyl, isobutyl, tert-butyl, n-pentyl, isopentyl, neopentyl, n-hexyl, and the like.

In the present disclosure, the halogen group may be, for example, fluorine, chlorine, bromine, or iodine.

In the present disclosure, specific examples of trialkylsilyl include, but are not limited to, trimethylsilyl and the like.

In the present disclosure, specific examples of haloalkyl includes, but are not limited to, trifluoromethyl.

In the present disclosure, specific examples of deuteroalkyl include, but are not limited to, trideuteromethyl.

In the present disclosure, the number of carbon atoms of cycloalkyl with 3 to 10 carbon atoms may be, for example, 3, 4, 5, 6, 7, 8, or 10. Specific examples of cycloalkyl include, but are not limited to, cyclopentyl, cyclohexyl, and adamantyl.

In the present disclosure, an unpositioned connecting bond refers to a single bond "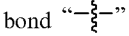" extending from a ring system, which means that one end of the connecting bond can be connected with any position in the ring system through which the bond penetrates, and the other end of the connecting bond is connected with the remaining part of a compound molecule. For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10).

(f)

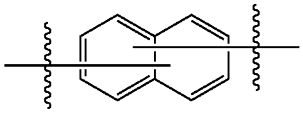

(f-1)

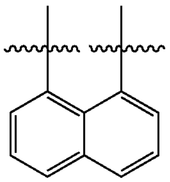

(f-2)

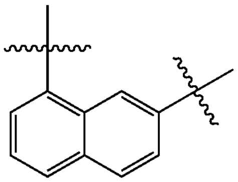

(f-3)

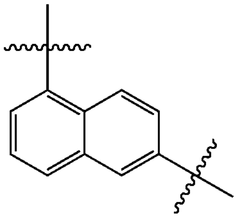

(f-4)

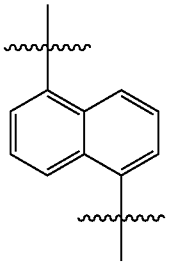

-continued (f-5)

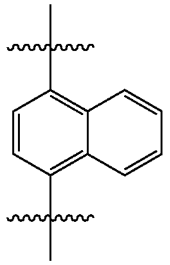

(f-6)

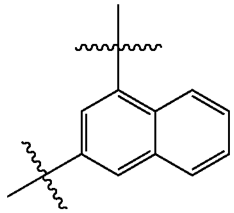

(f-7)

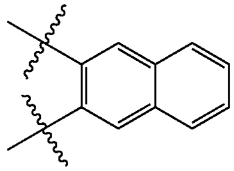

(f-8)

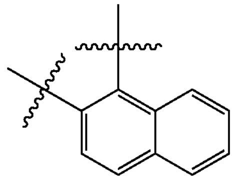

(f-9)

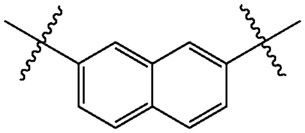

(f-10)

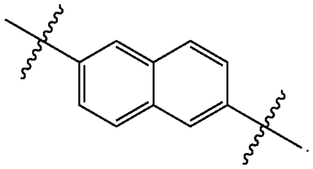

For another example, as shown in the following formula (X'), dibenzofuranyl represented by the formula (X') is connected with other positions of a molecule through one unpositioned connecting bond extending from the middle of a benzene ring on one side, and its meaning includes any one possible connecting mode represented by formulae (X'-1) to (X'-4).

(X')

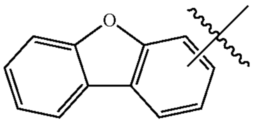

-continued (X'-1)

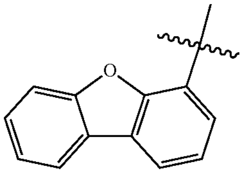

(X'-2)

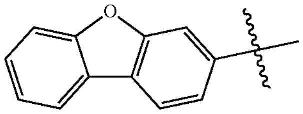

(X'-3)

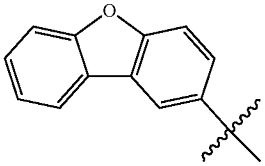

(X'-4)

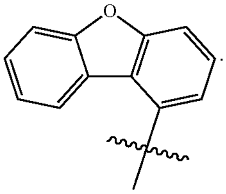

In some specific embodiments of the present disclosure, the organic compound is selected from compounds shown in a Formula AA, a Formula BB, a Formula CC or a Formula DD:

Formula AA

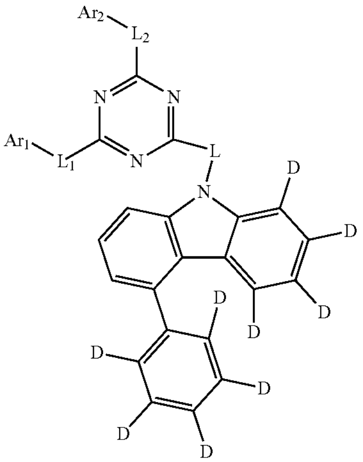

-continued

Formula BB

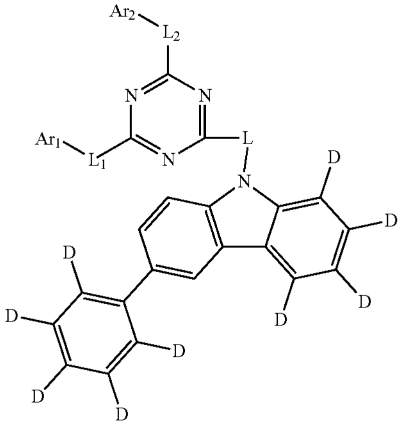

Formula CC

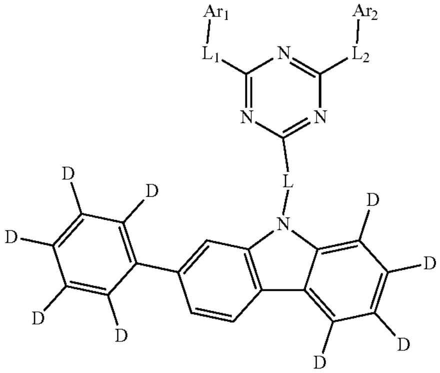

Formula DD

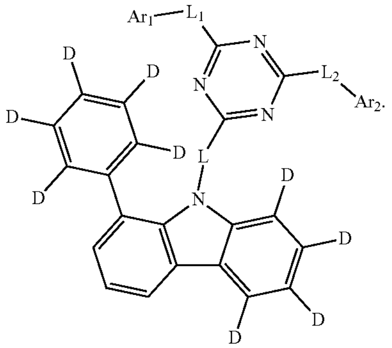

In some embodiments of the present disclosure, L, $L_1$ and $L_2$ are the same or different, and are respectively and independently selected from a single bond or a substituted or unsubstituted arylene with 6 to 12 carbon atoms.

Optionally, substituent(s) in L, $L_1$ and $L_2$ are the same or different, and are respectively and independently selected from deuterium, a halogen group, a cyano, an alkyl with 1 to 5 carbon atoms, or a phenyl.

In other embodiments of the present disclosure, L, $L_1$ and $L_2$ are the same or different, and are respectively and independently selected from a single bond, a substituted or unsubstituted phenylene, a substituted or unsubstituted naphthylene, or a substituted or unsubstituted biphenylene.

Optionally, L, $L_1$ and $L_2$ are the same or different, and are respectively and independently selected from deuterium, a fluorine, a cyano, a methyl, an ethyl, a n-propyl, an isopropyl, a tert-butyl, or a phenyl.

Further optionally, L, $L_1$ and $L_2$ are the same or different, and are respectively and independently selected from a single bond or the group consisting of:

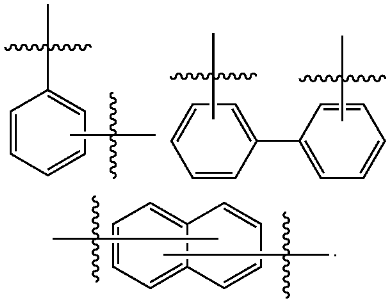

In particular, L, $L_1$ and $L_2$ are the same or different, and are respectively and independently selected from a single bond or the group consisting of:

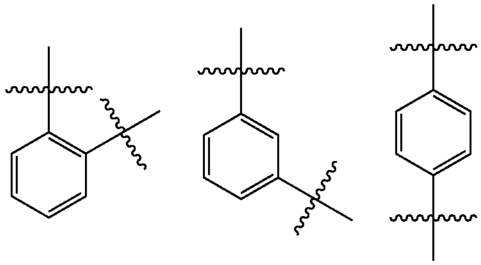

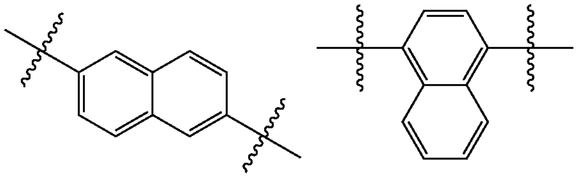

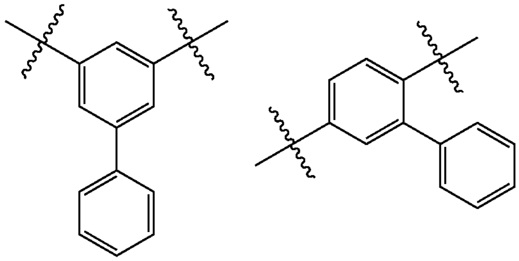

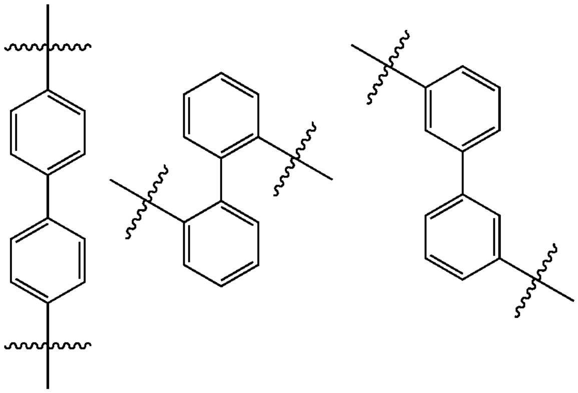

-continued

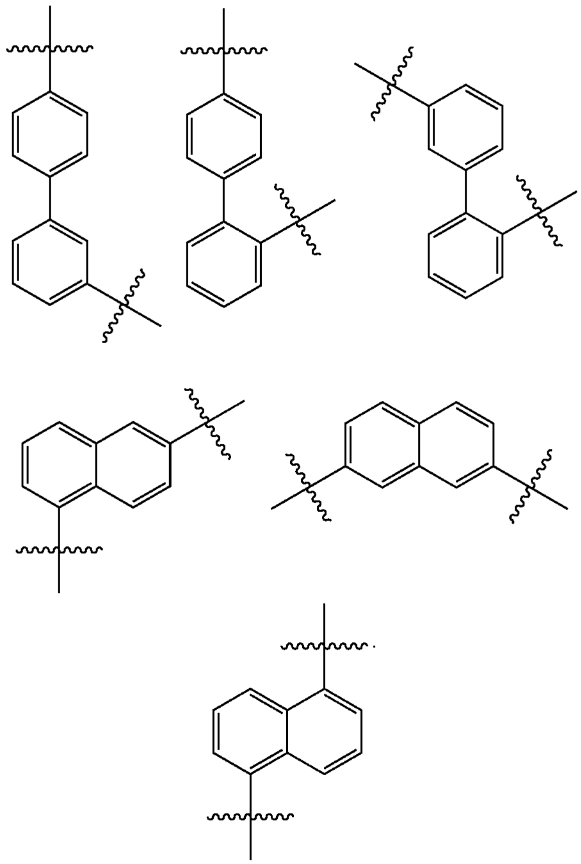

In some embodiments of the present disclosure, $Ar_1$ and $Ar_2$ are the same or different, and are respectively and independently selected from a substituted or unsubstituted aryl with 6 to 20 carbon atoms, a substituted or unsubstituted dibenzofuranyl, or a substituted or unsubstituted dibenzothienyl.

Optionally, substituent(s) in $Ar_1$ and $Ar_2$ are the same or different, and are respectively and independently selected from deuterium, a halogen group, a cyano, an alkyl with 1 to 5 carbon atoms, a phenyl, or a pentadeuterophenyl.

In other embodiments of the present disclosure, $Ar_1$ and $Ar_2$ are the same or different, and are respectively and independently selected from a substituted or unsubstituted phenyl, substituted or unsubstituted naphthyl, a substituted or unsubstituted biphenyl, a substituted or unsubstituted phenanthryl, a substituted or unsubstituted fluorenyl, a substituted or unsubstituted terphenyl, a substituted or unsubstituted dibenzofuranyl, or a substituted or unsubstituted dibenzothienyl.

Optionally, substituent(s) in $Ar_1$ and $Ar_2$ are the same or different, and are respectively and independently selected from deuterium, fluorine, a cyano, a methyl, an ethyl, a n-propyl, an isopropyl, a tert-butyl, a phenyl, or a pentadeuterophenyl.

In other embodiments of the present disclosure, $Ar_1$ and $Ar_2$ are the same or different, and are respectively and independently selected from a substituted or unsubstituted group W, where the unsubstituted group W is selected from the group consisting of:

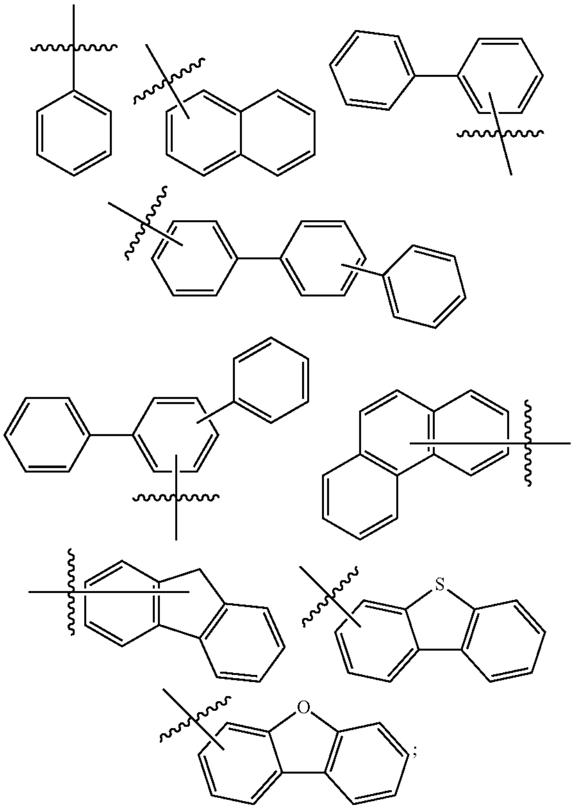

;

where  represents a chemical bond; the substituted group W has one or two or more substituents each independently selected from deuterium, fluorine, cyano, methyl, ethyl, n-propyl, isopropyl, tert-butyl, phenyl or pentadeuterophenyl, and when the number of the substituents on the group W is greater than 1, the substituents are the same or different.

Optionally, $Ar_1$ and $Ar_2$ are the same or different, and are respectively and independently selected from the group consisting of:

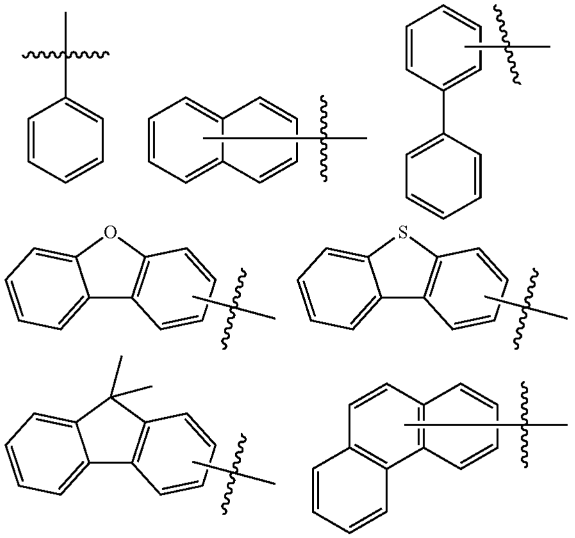

-continued
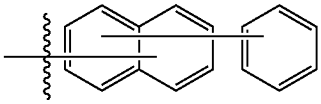
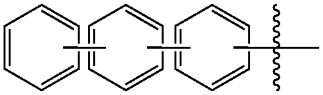
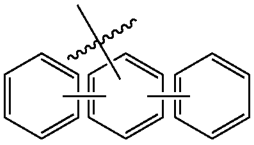
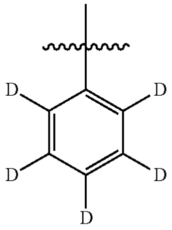
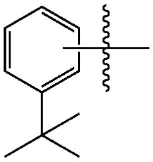
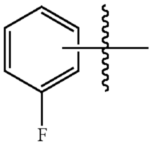
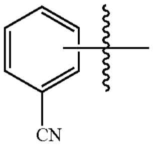
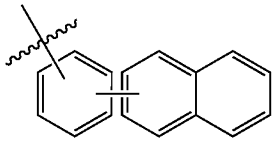
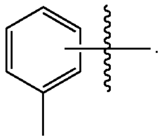
In particular, $Ar_1$ and $Ar_2$ are the same or different, and are respectively and independently selected from the group consisting of:
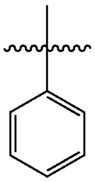
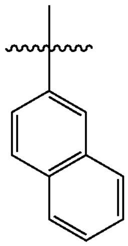
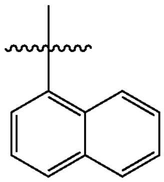
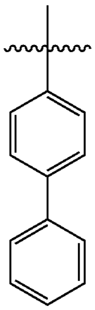
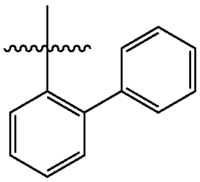
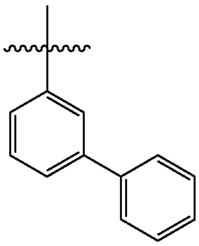
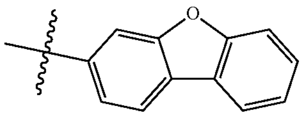
-continued
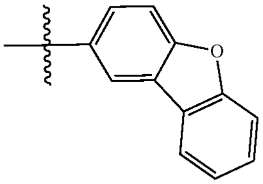
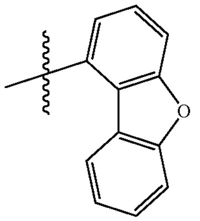
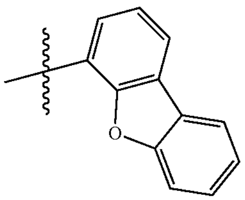
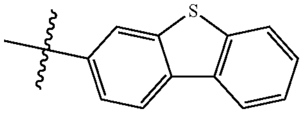
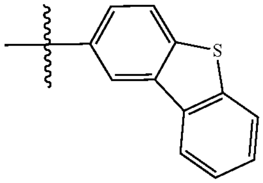
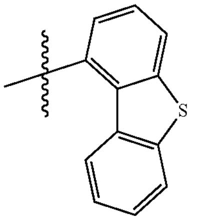
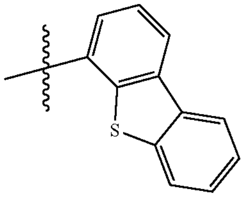
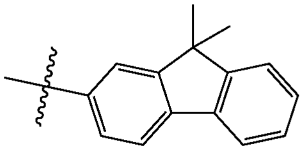
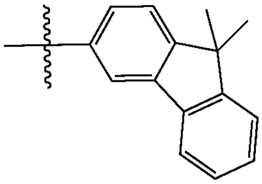
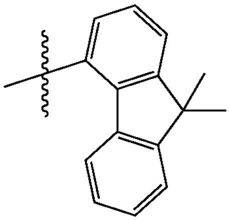
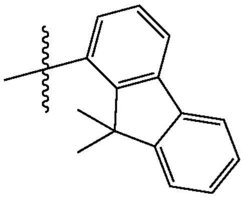
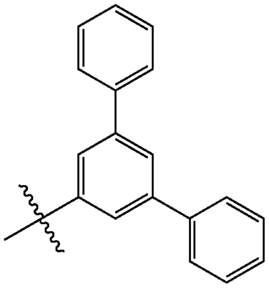
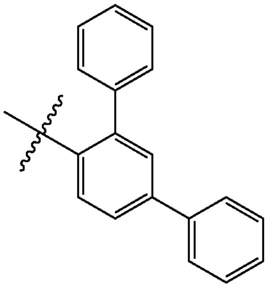

-continued
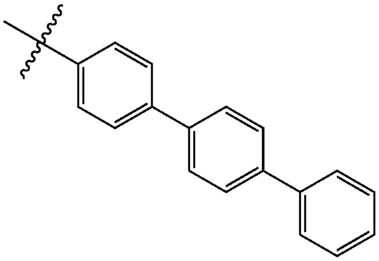
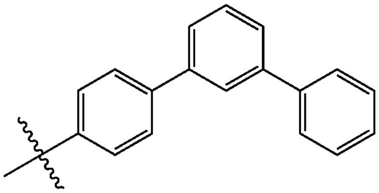
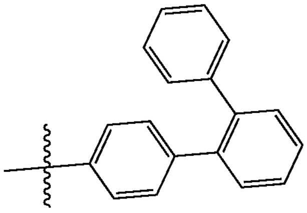
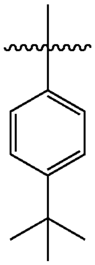
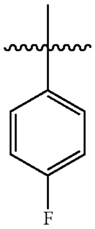
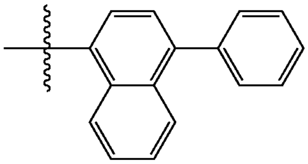
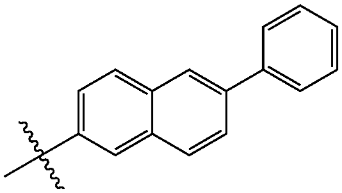
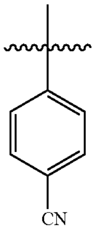
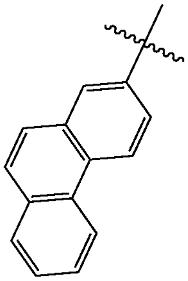
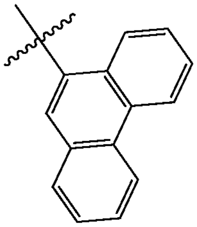
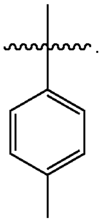.
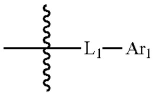 and 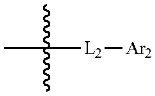
In some embodiments of the present disclosure, are respectively and independently selected from the group consisting of:
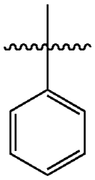
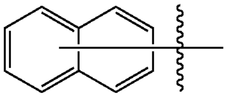
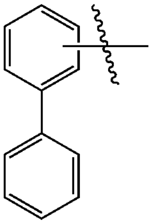
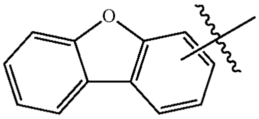
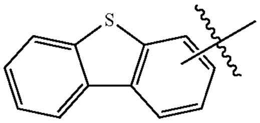
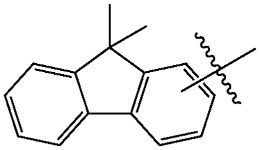
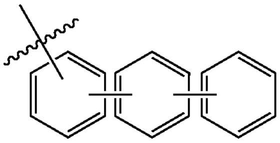
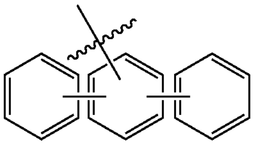
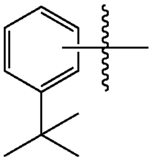
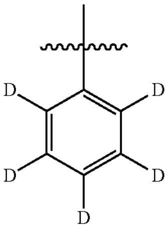
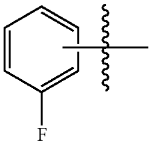
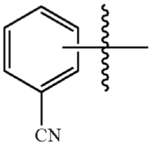
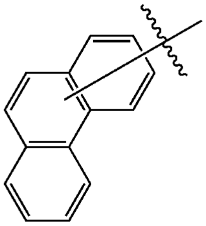
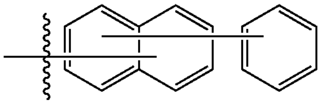
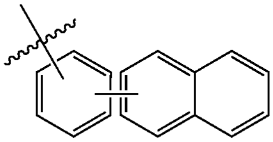
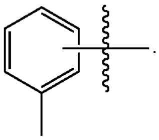.
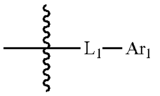 and 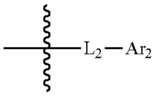

In particular, are respectively and independently selected from the group consisting of:
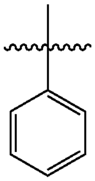
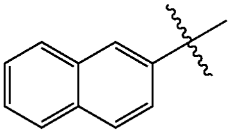
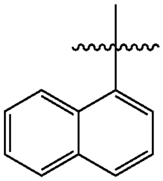
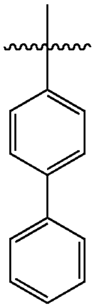
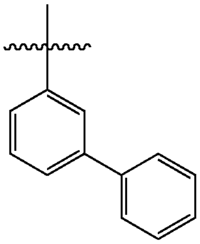
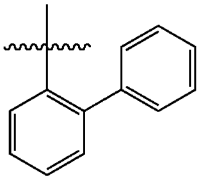
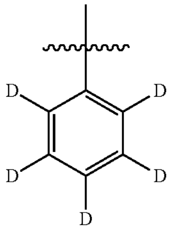
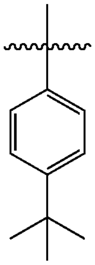
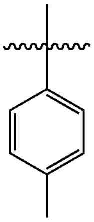
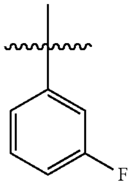
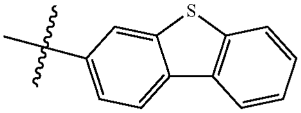
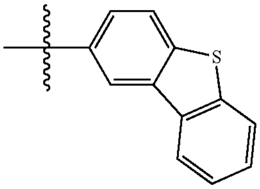
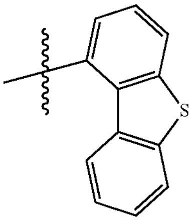
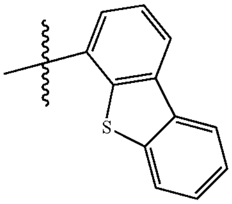
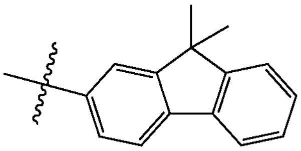
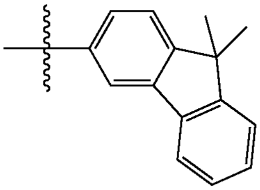
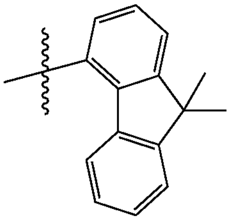
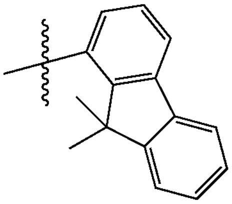
-continued
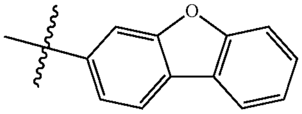
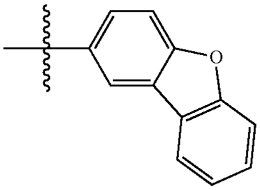
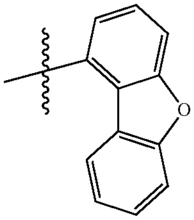
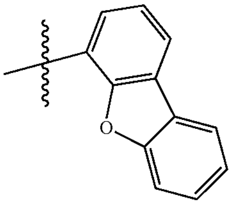
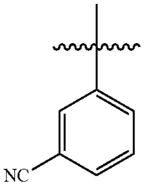
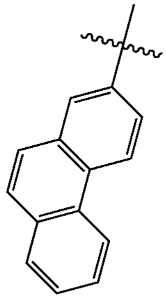
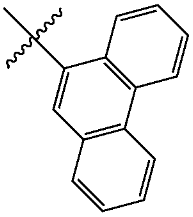
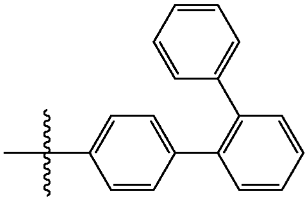
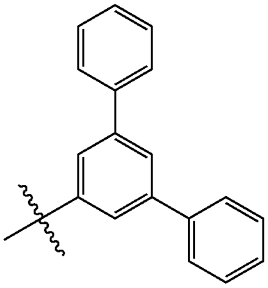
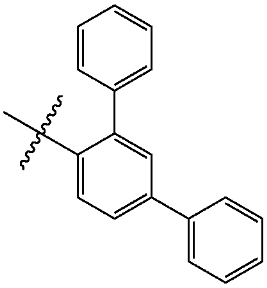
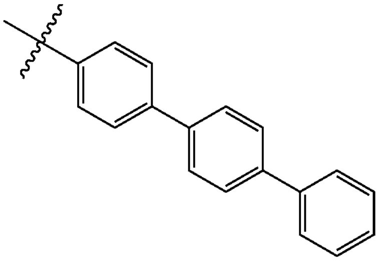

-continued
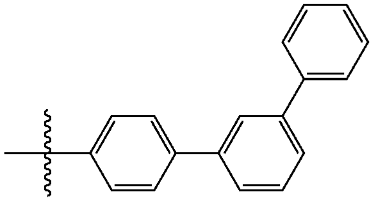
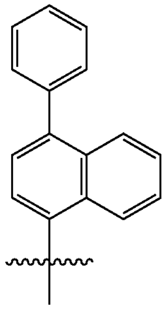
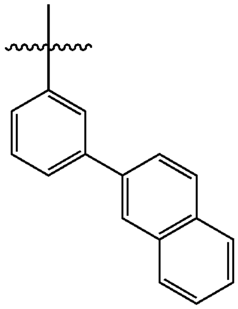
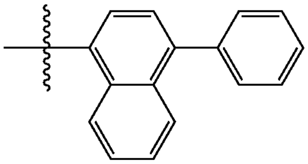
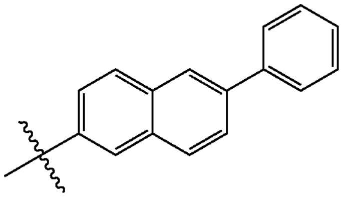
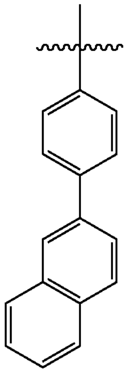
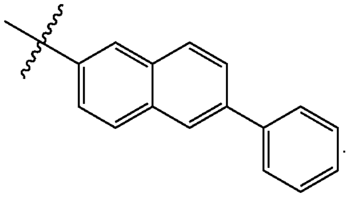.
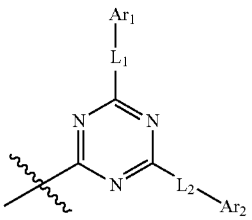
In some embodiments of the present disclosure, selected from the group consisting of:
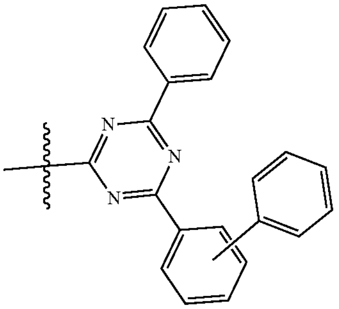
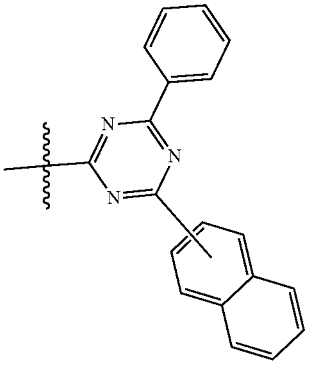
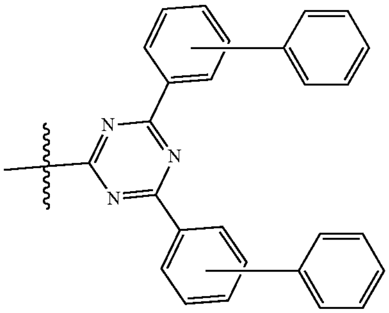
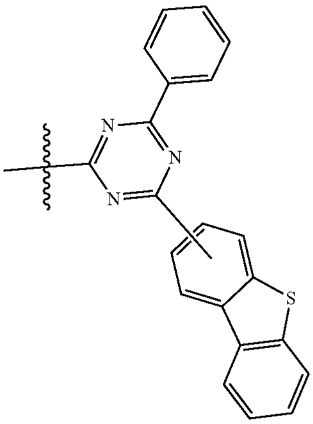

-continued
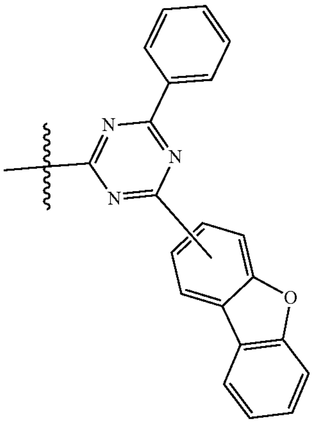
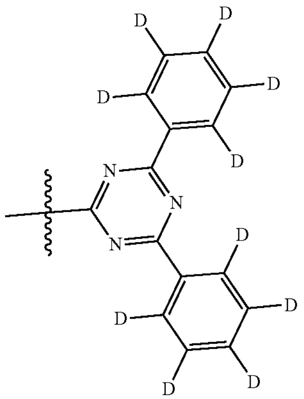
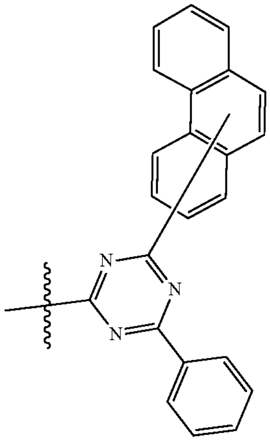
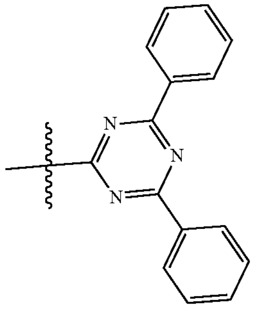
-continued
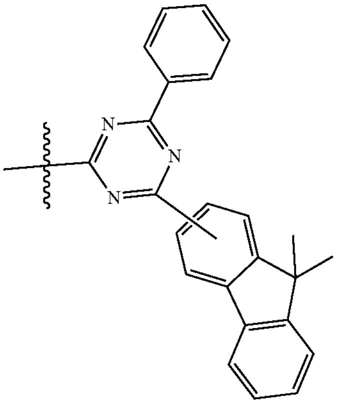
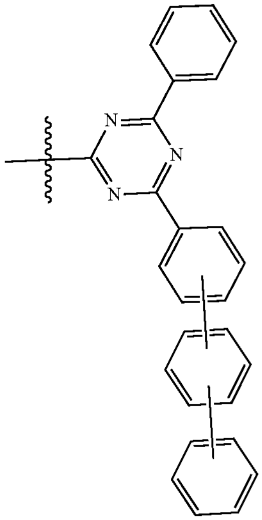
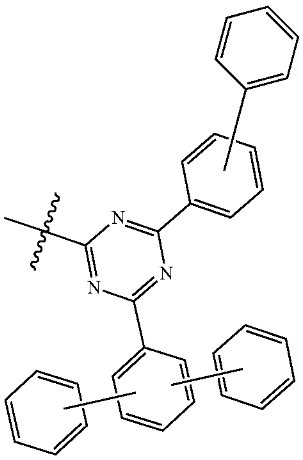

-continued
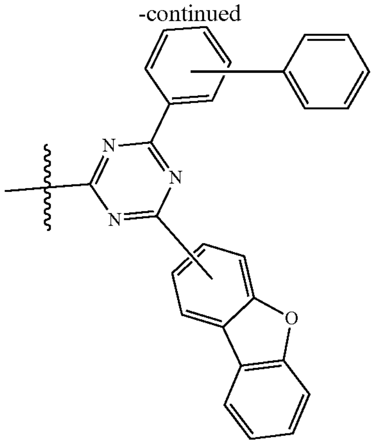
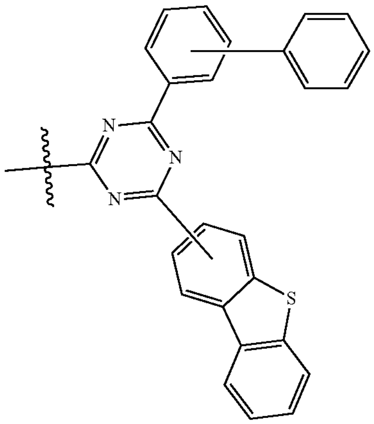
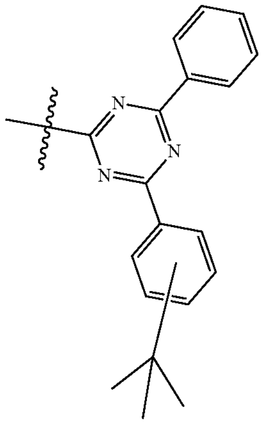
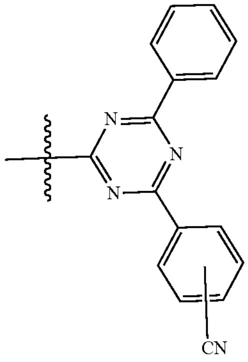
-continued
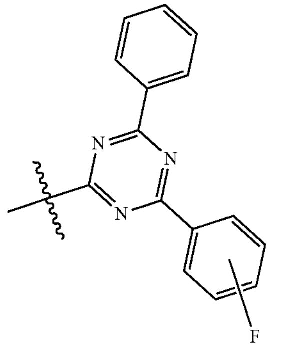
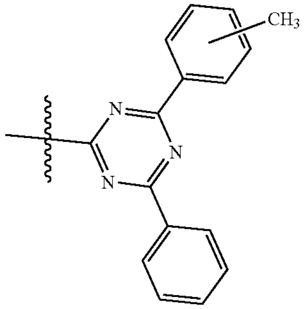
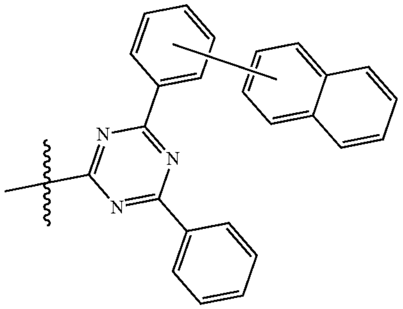
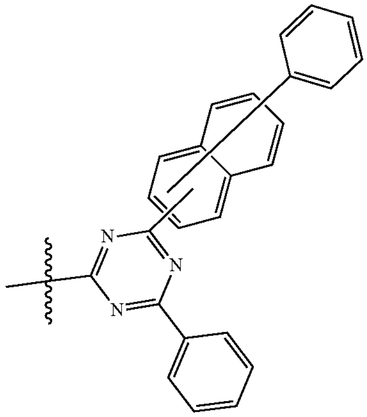

-continued
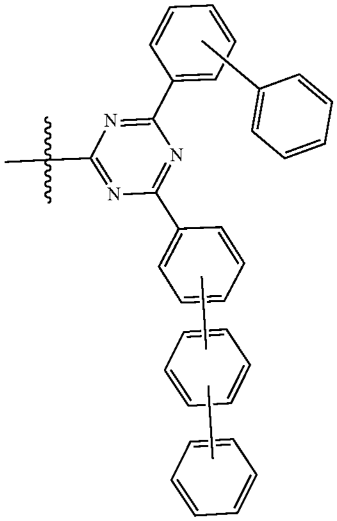
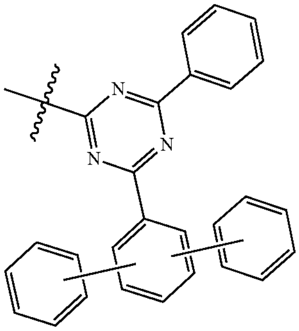
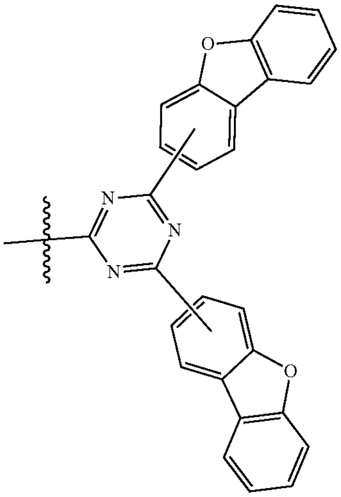
-continued
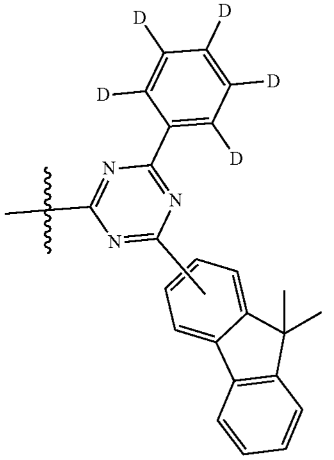
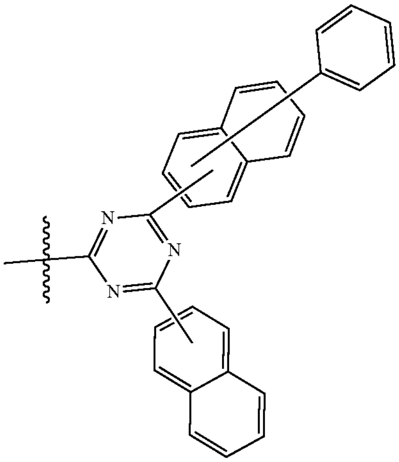
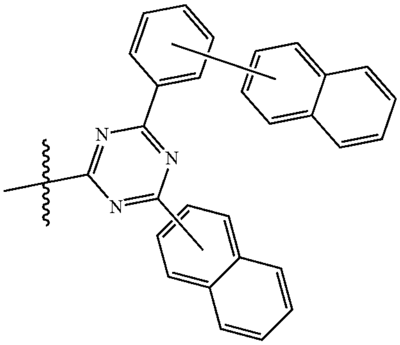
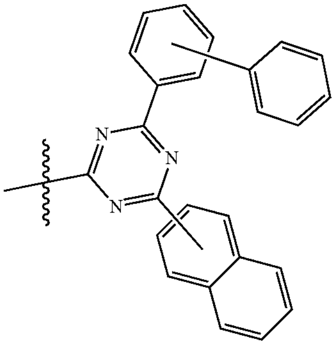

-continued
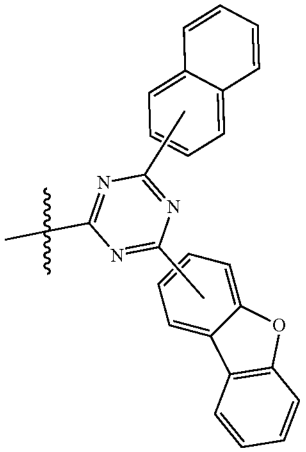
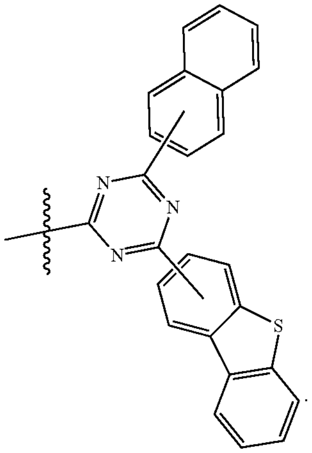
in the formula 1 is
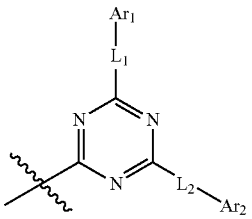
In particular,
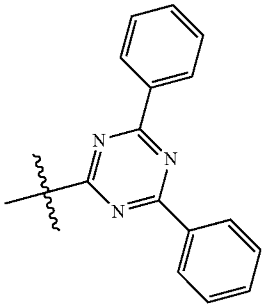
-continued
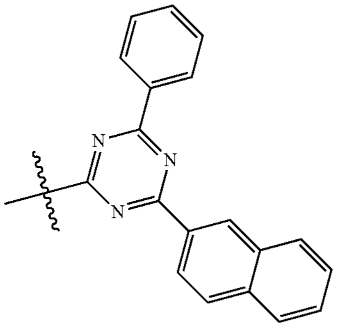
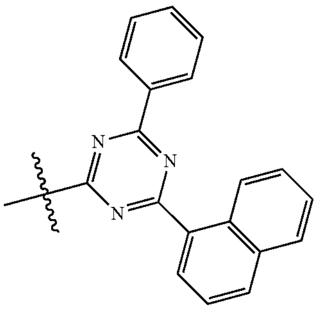
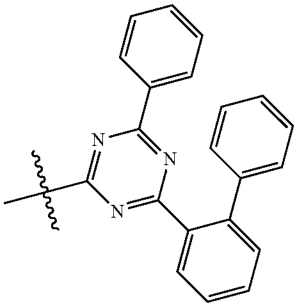
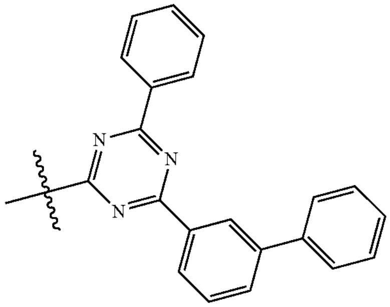
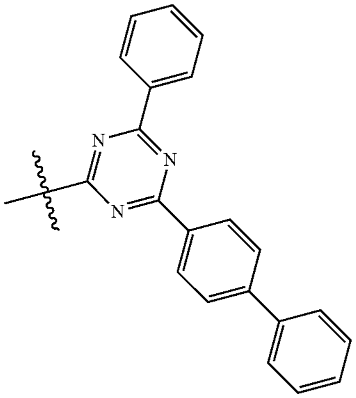

-continued
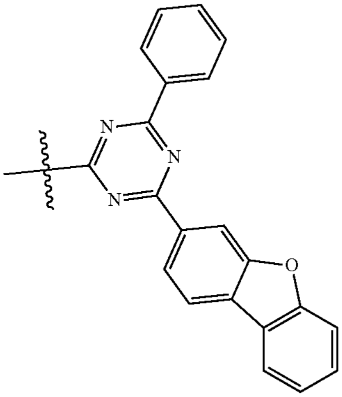
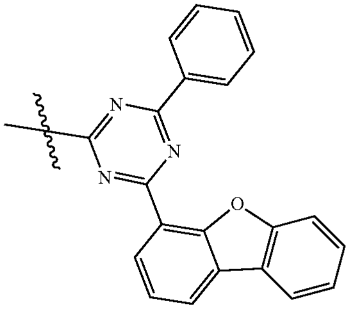
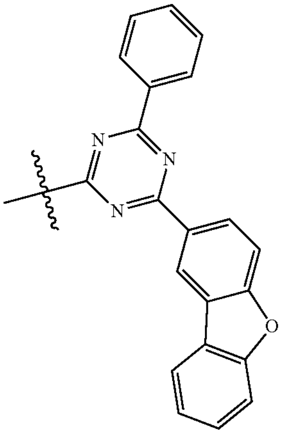
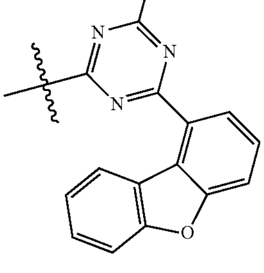
-continued
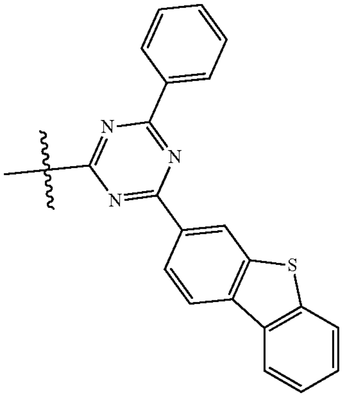
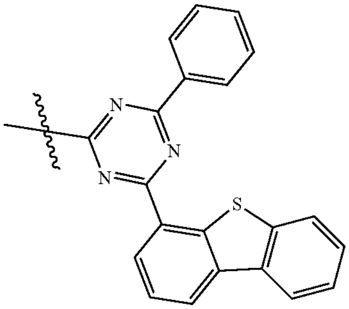
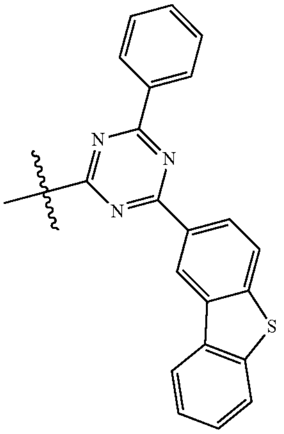
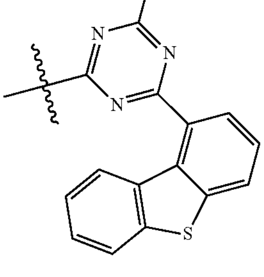

-continued
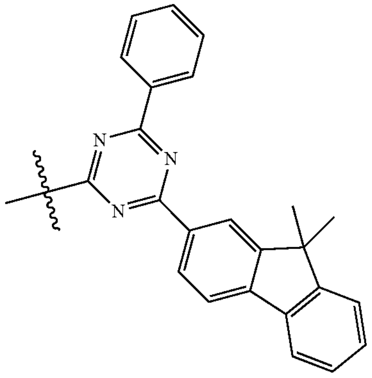
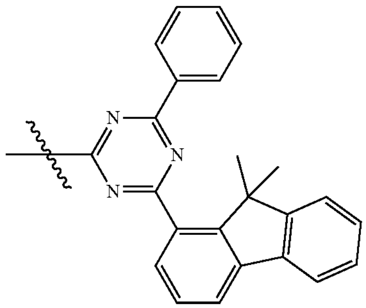
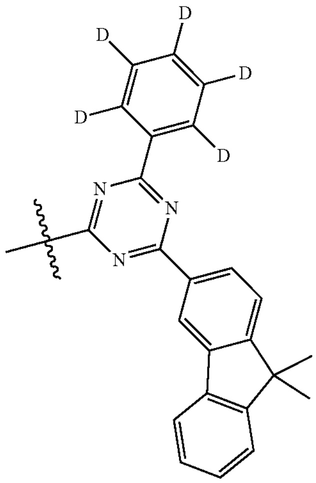
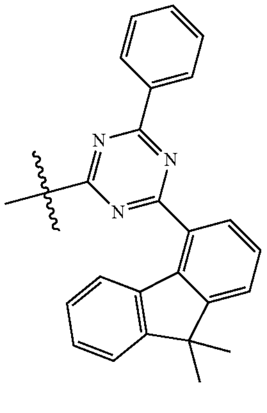
-continued
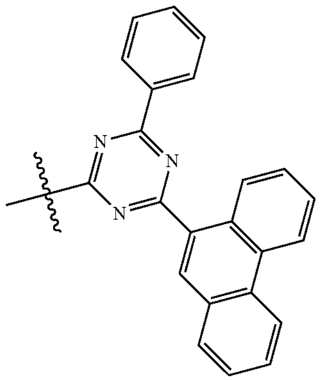
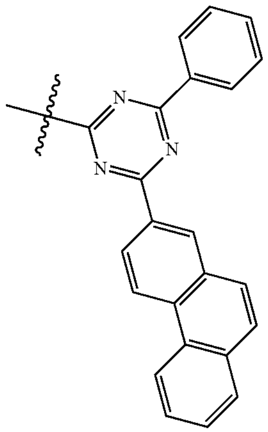
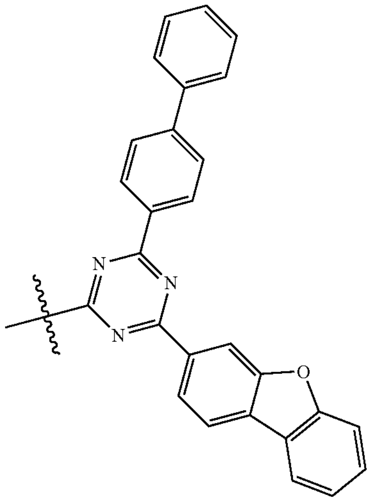
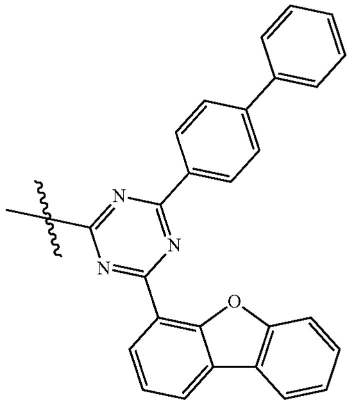

-continued
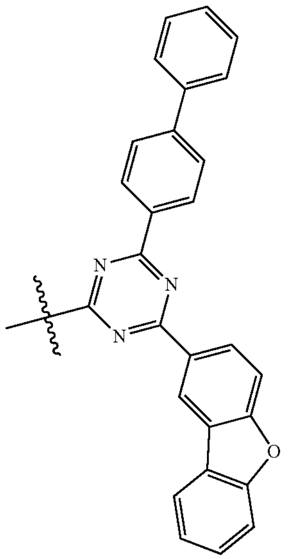
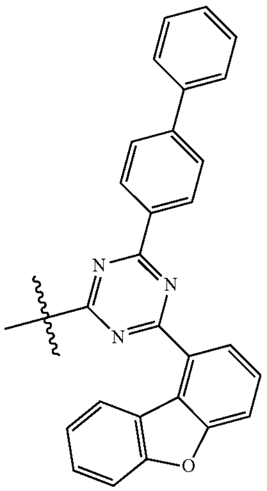
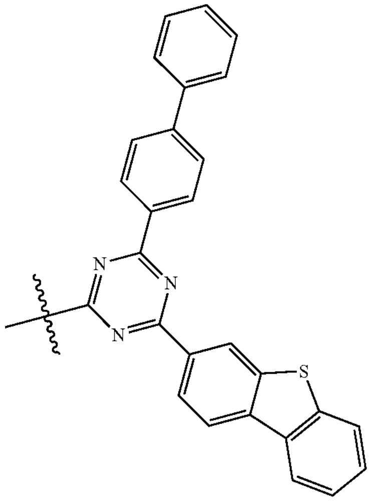
-continued
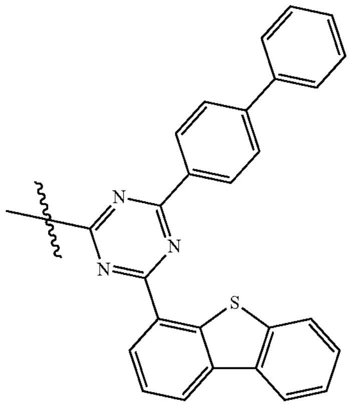
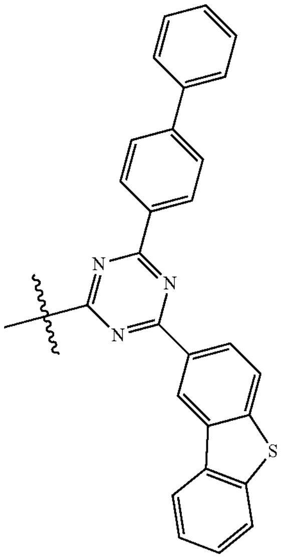
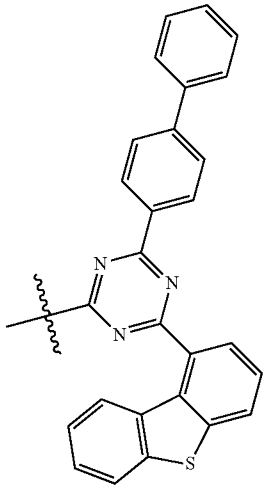

-continued
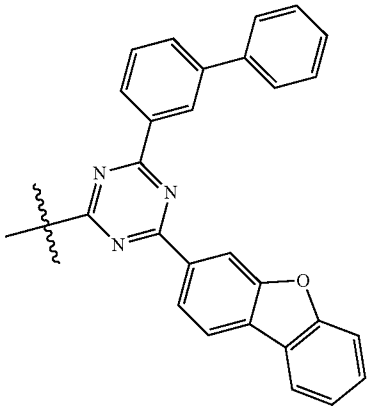
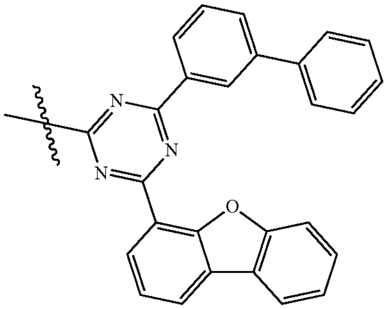
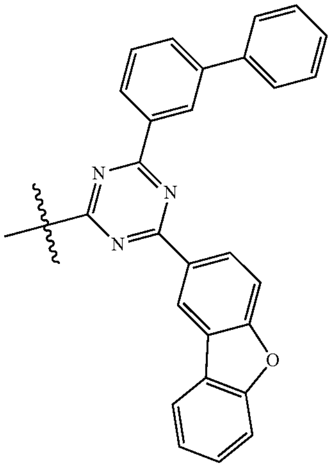
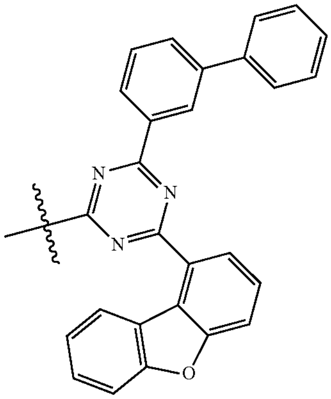
-continued
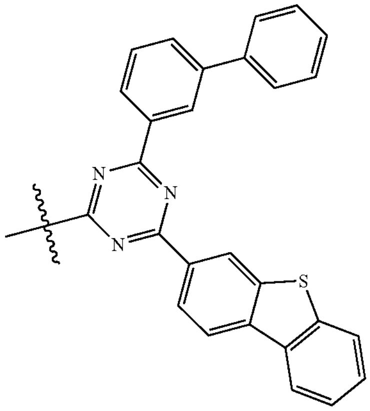
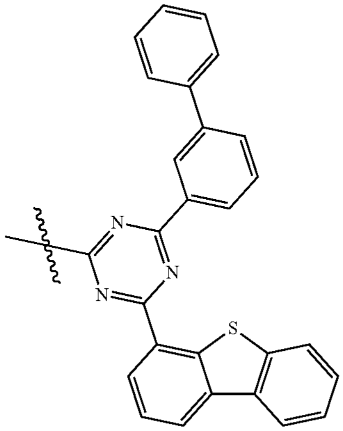
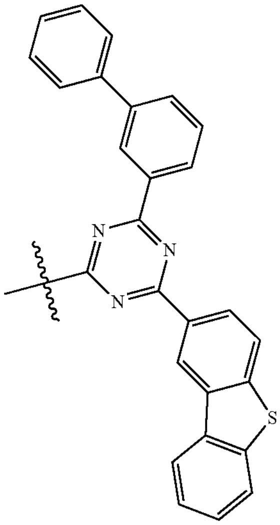

-continued
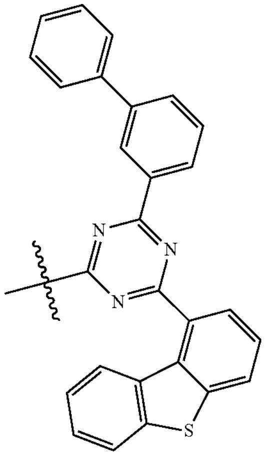 [SMILES: *c1nc(-c2cccc(-c3ccccc3)c2)nc(-c2cccc3sc4ccccc4c23)n1]
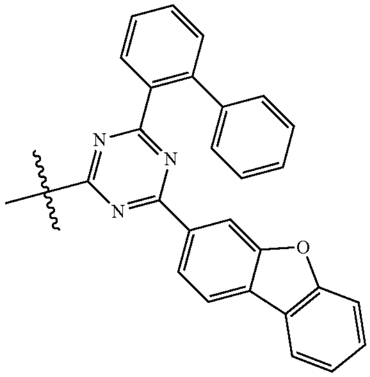
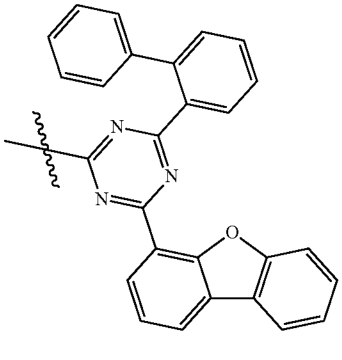
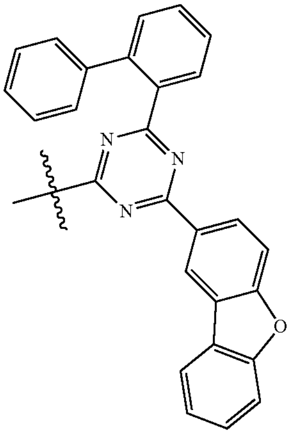
-continued
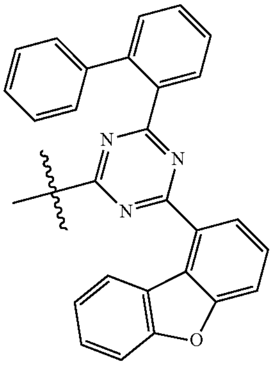
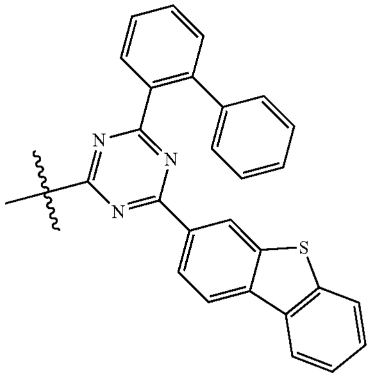
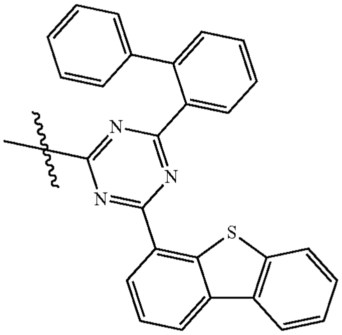
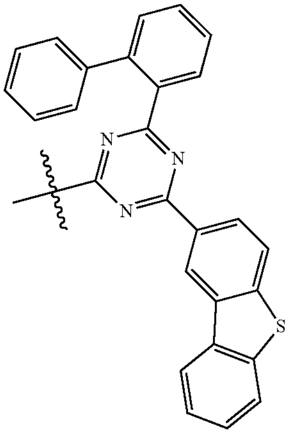

-continued
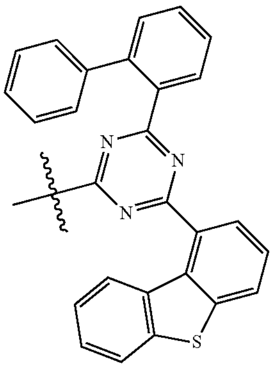
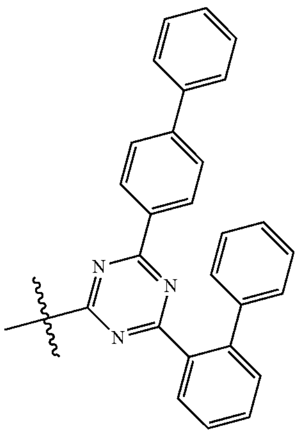
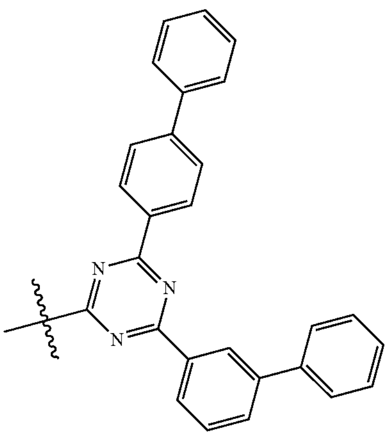
-continued
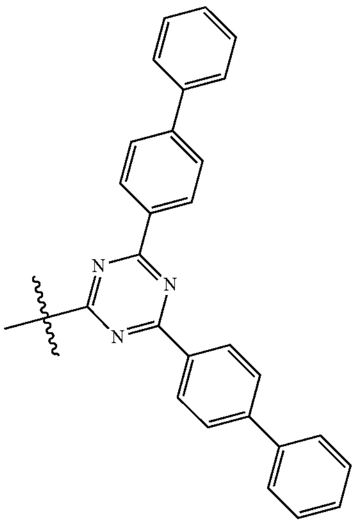
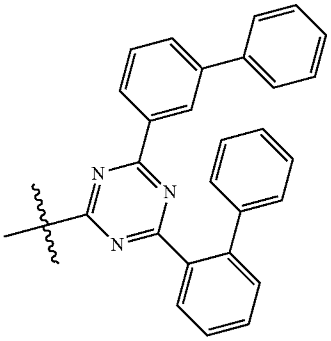
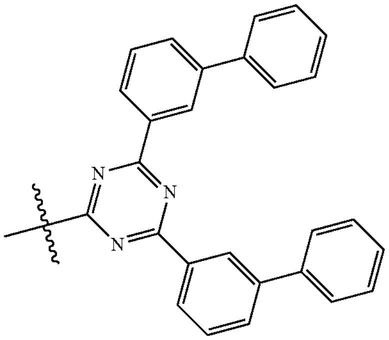
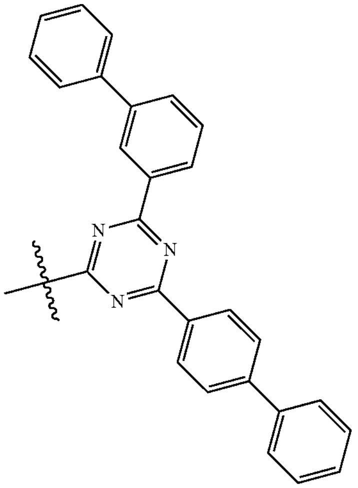

-continued
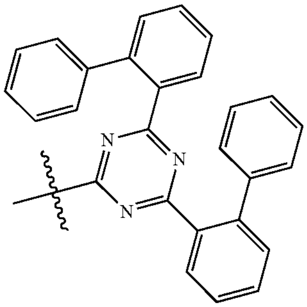
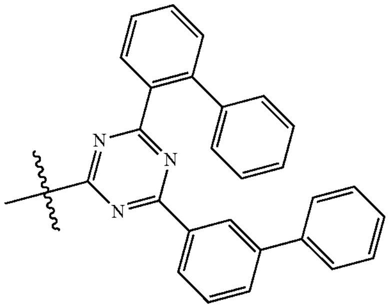
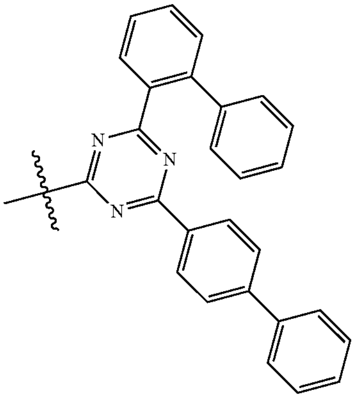 [SMILES: *c1nc(-c2ccc(-c3ccccc3)cc2)nc(-c2ccccc2-c2ccccc2)n1]
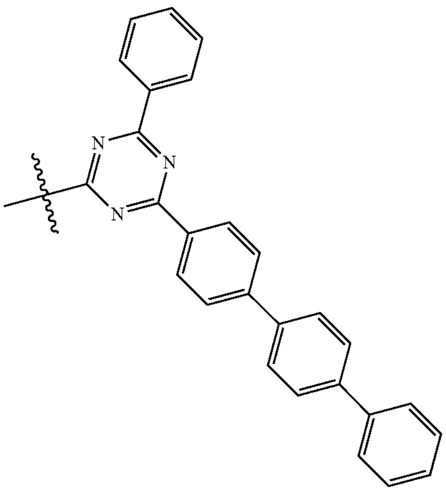
-continued
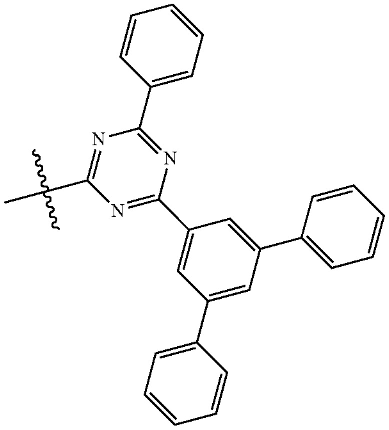
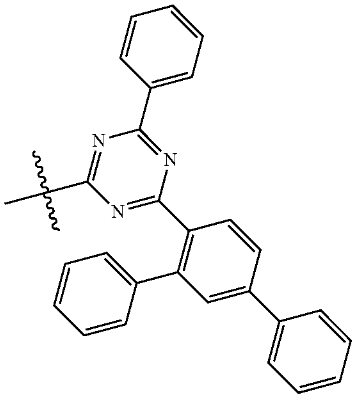
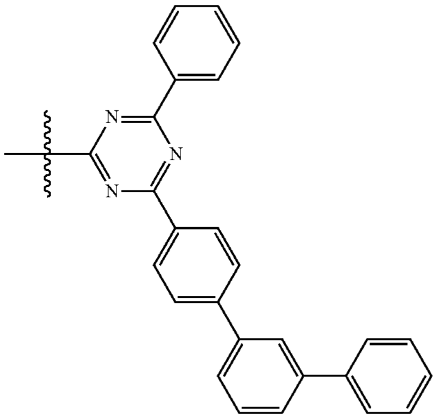

-continued
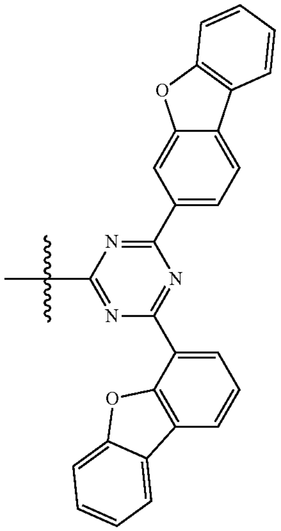
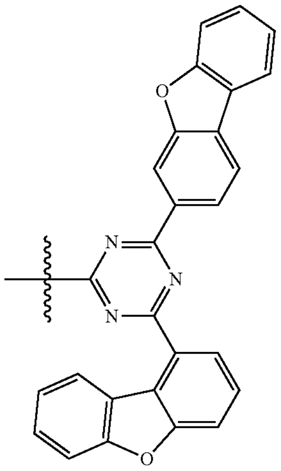
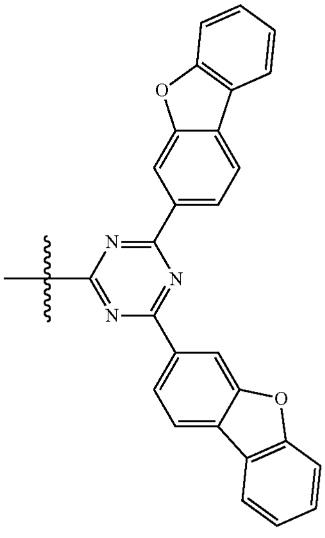
-continued
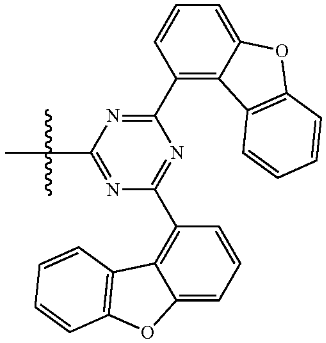 [SMILES: *c1nc(-c2cccc3oc4ccccc4c23)nc(-c2cccc3oc4ccccc4c23)n1]
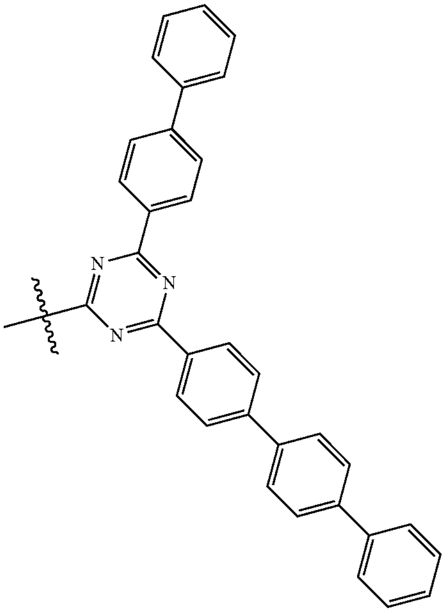
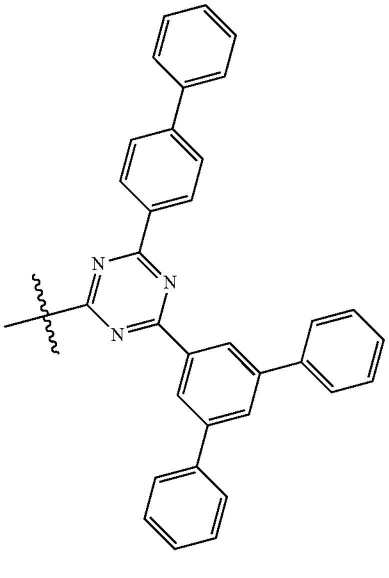

-continued
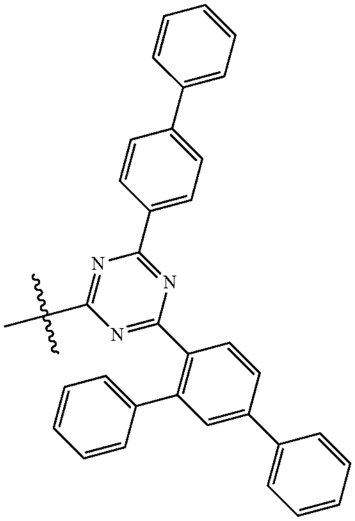
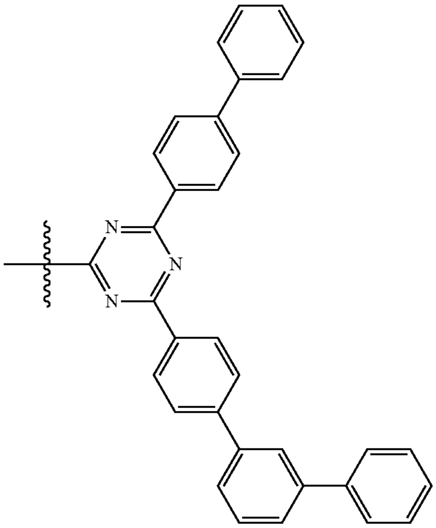
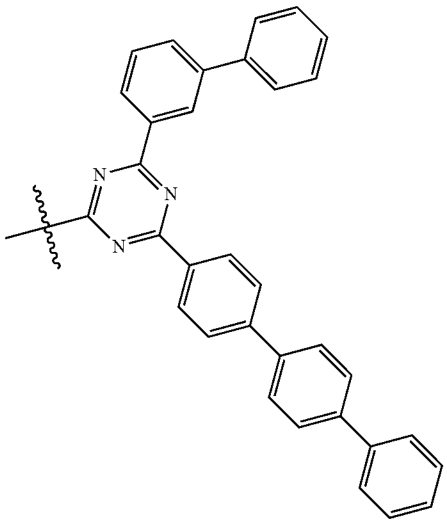
-continued
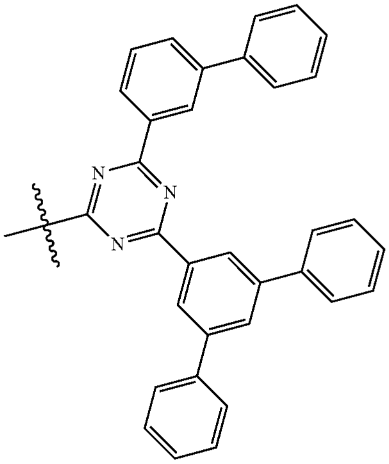
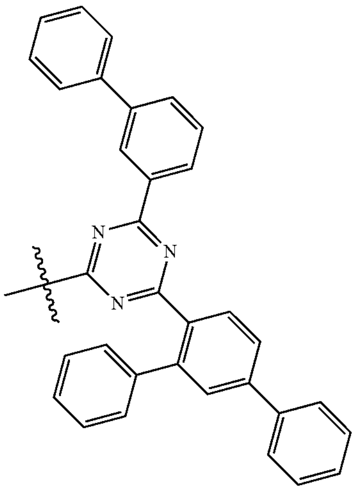
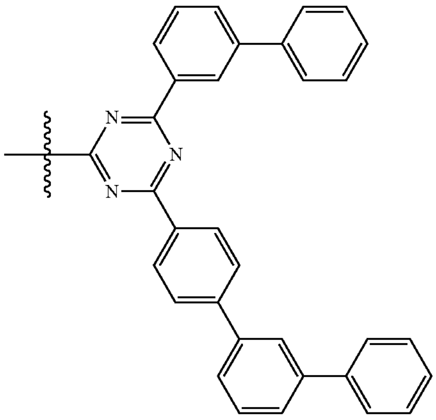

-continued
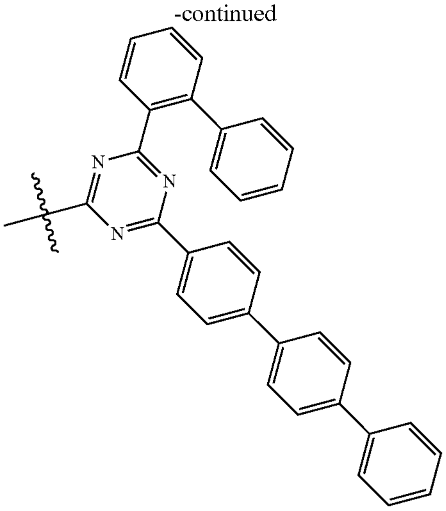
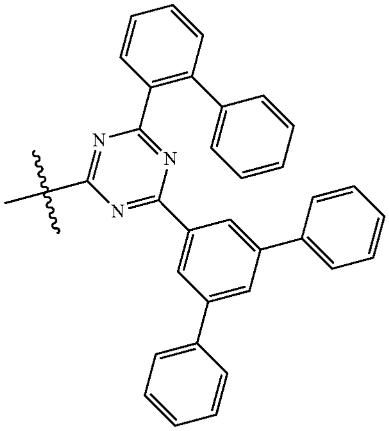
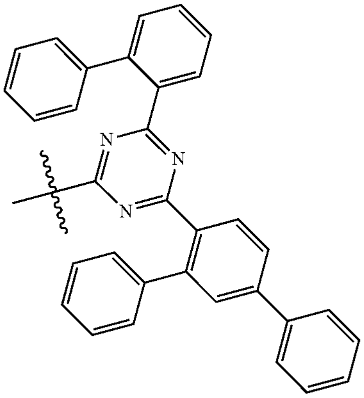
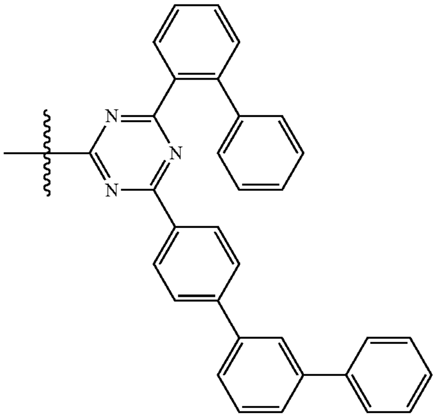
-continued
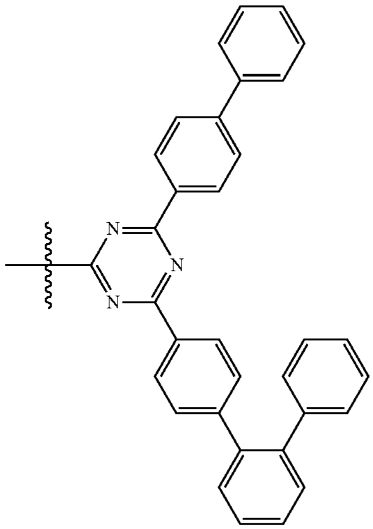
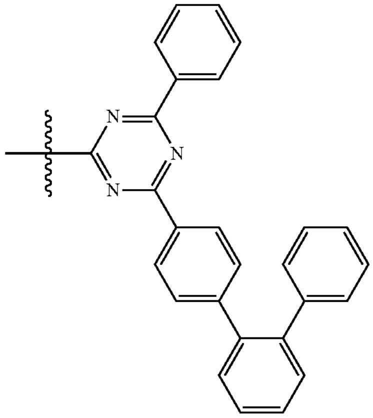
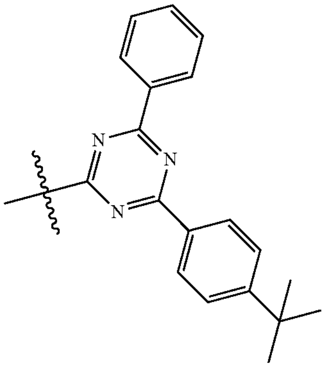
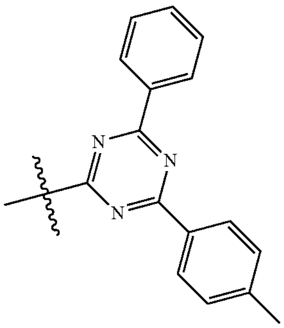

-continued
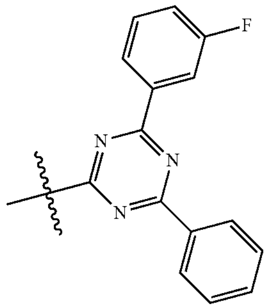
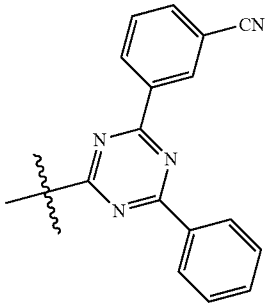
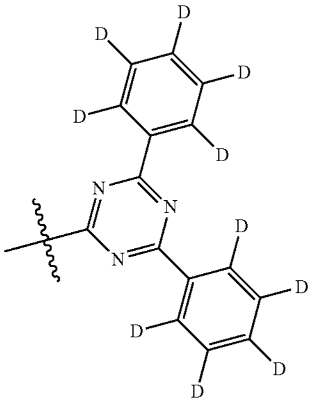
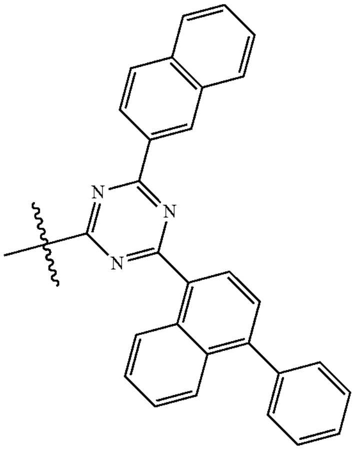
-continued
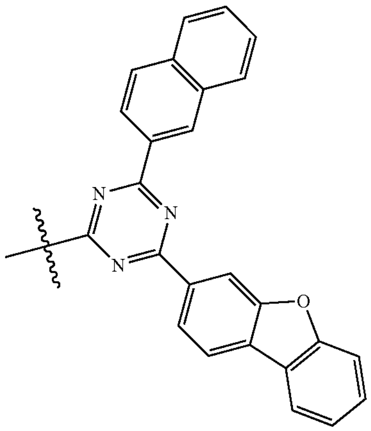
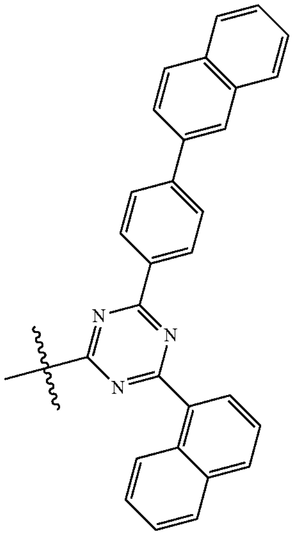
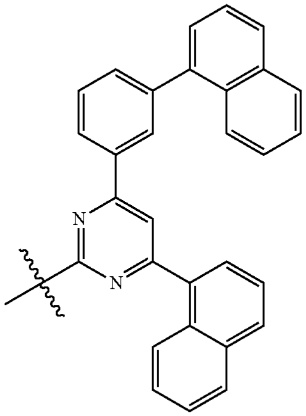

-continued
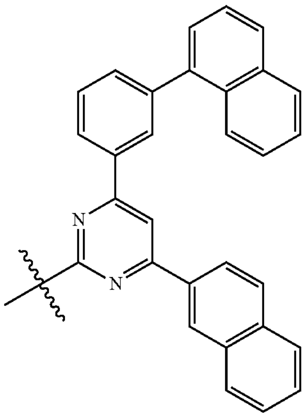
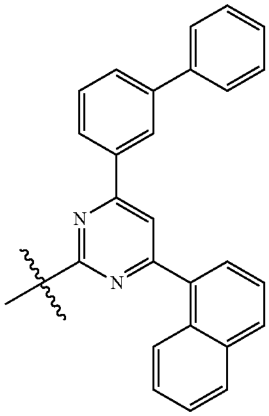
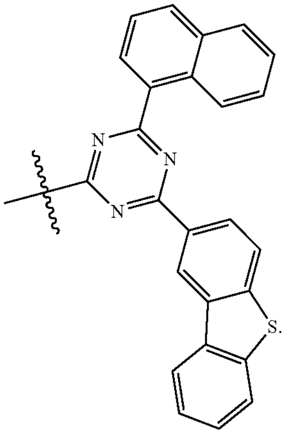 [SMILES: *c1nc(-c2ccc3sc4ccccc4c3c2)nc(-c2cccc3ccccc23)n1]
in the formula 1 is selected from the group consisting of:
In some embodiments of the present disclosure, the organic compound is selected from the group consisting of the following compounds:
A1
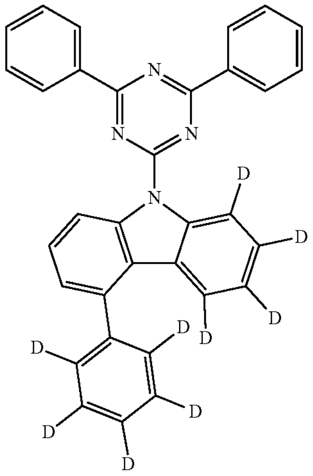
A2
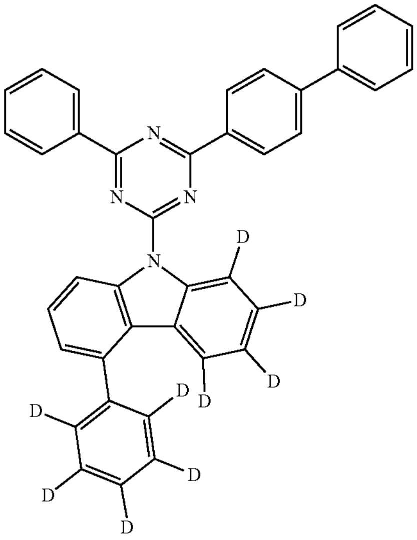
A3
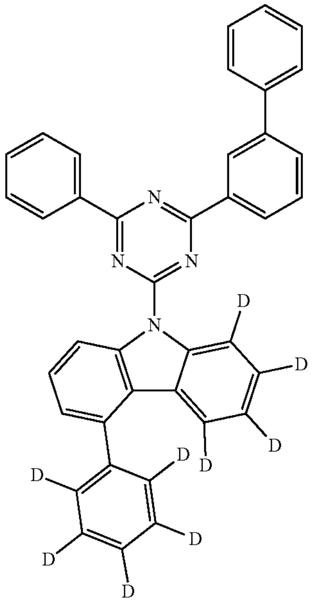

-continued
A4
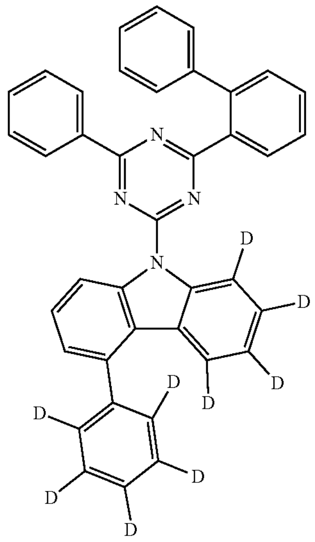
A5
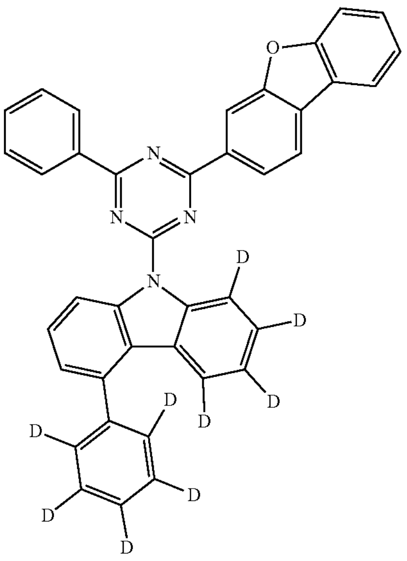
A6
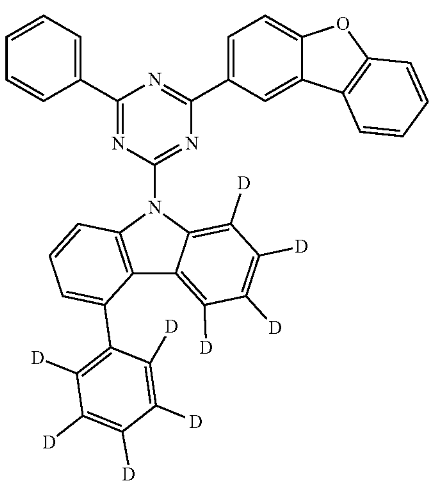
-continued
A7
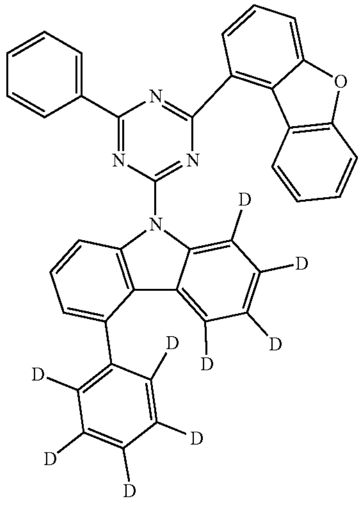
A8
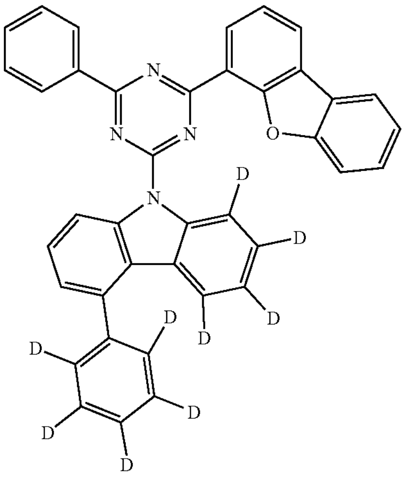
A9
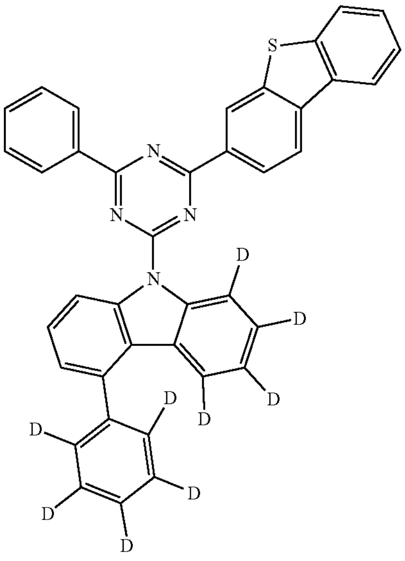

-continued
A10
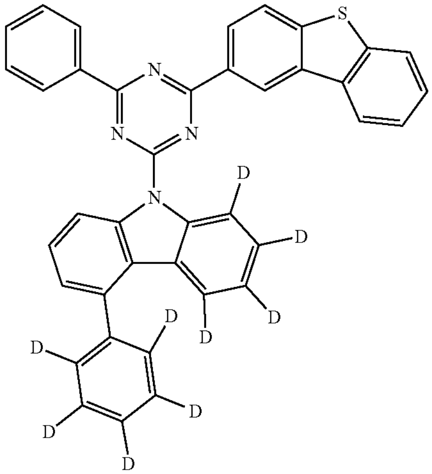
A11
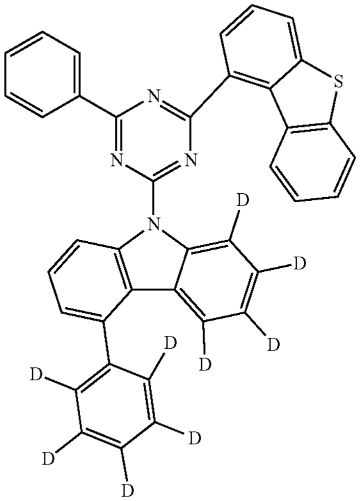
A12
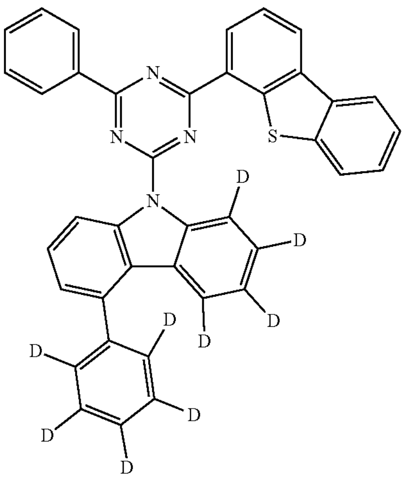
-continued
A13
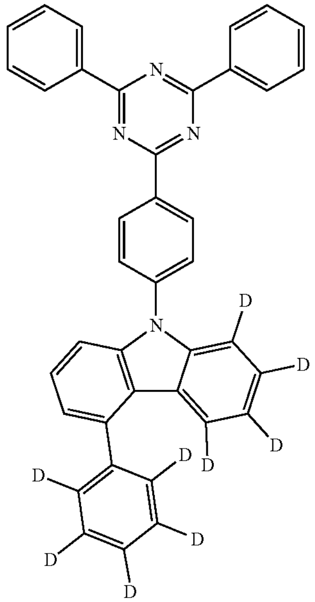
A14
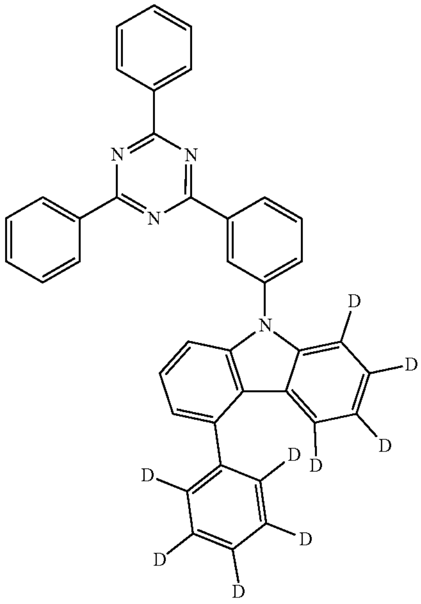
A15
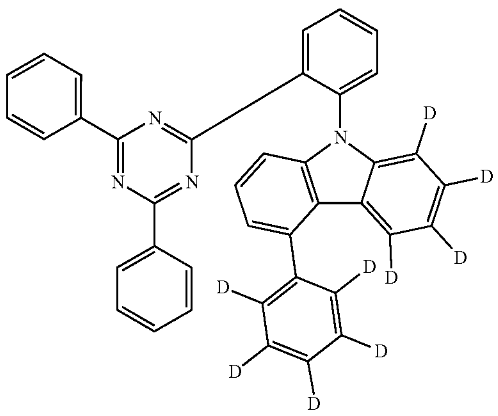

-continued
A16
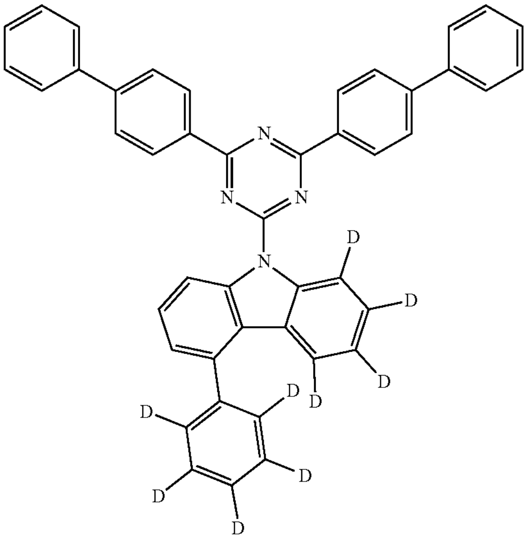
A17
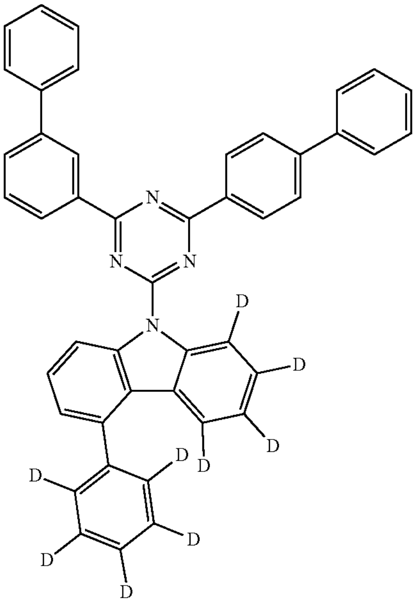
-continued
A18
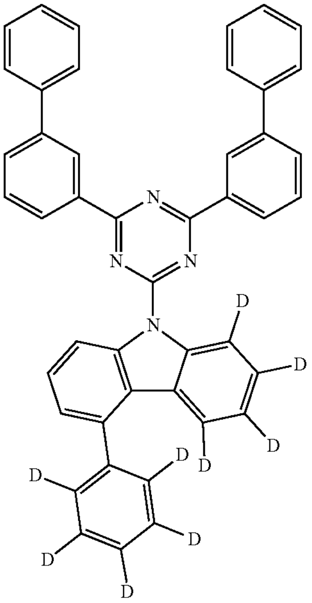
A19
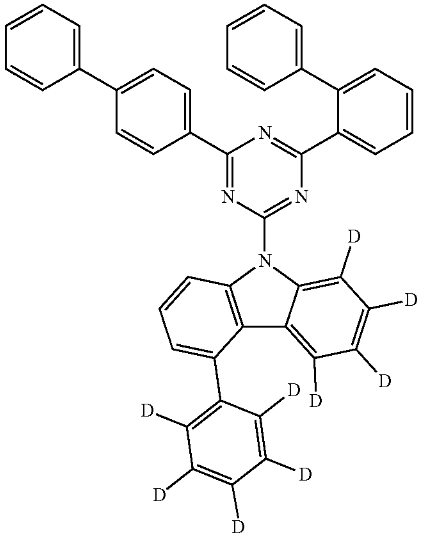

-continued
A20
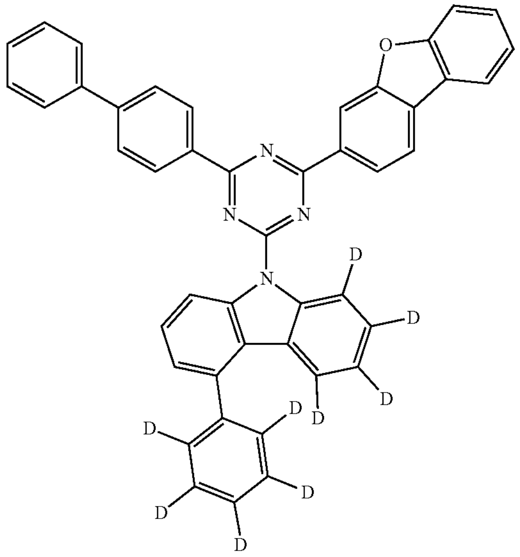
A21
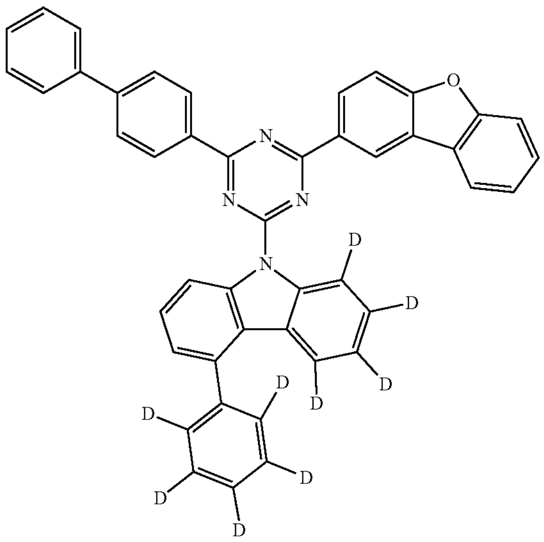
-continued
A22
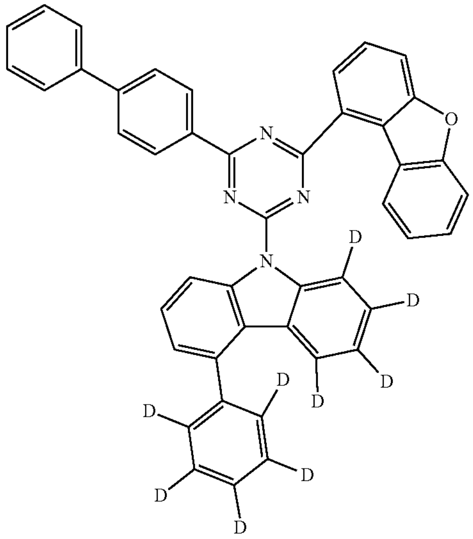
A23
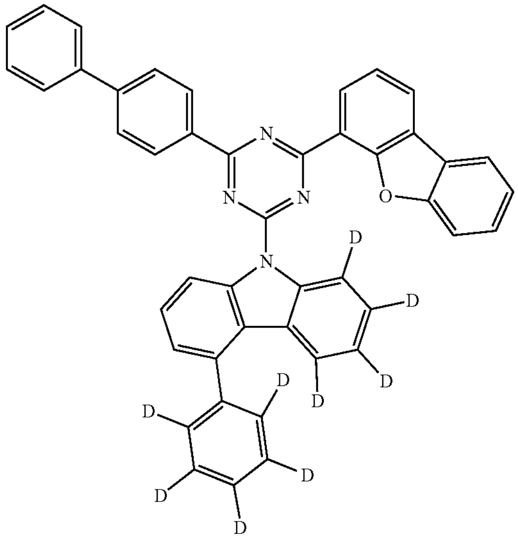

-continued
A24
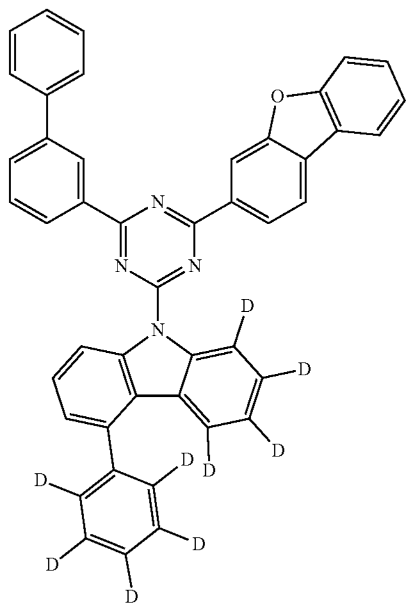
A25
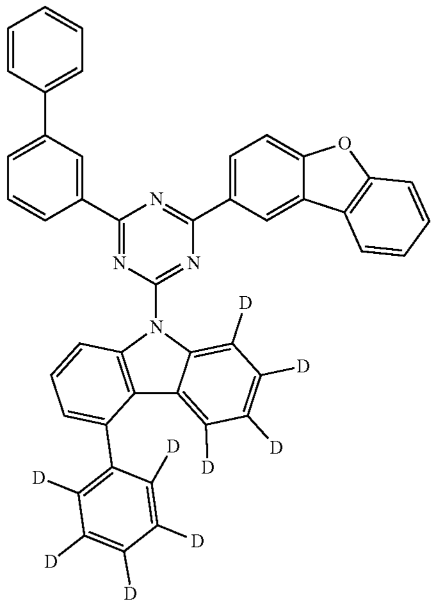
-continued
A26
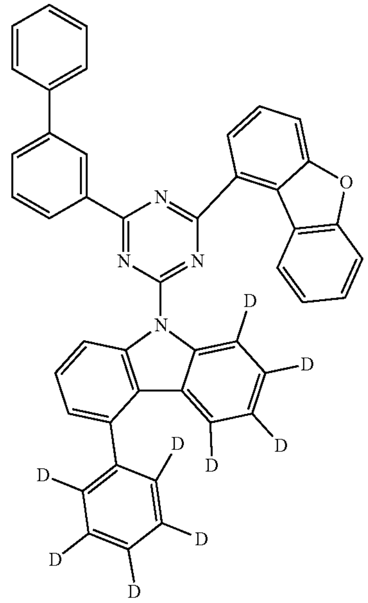
A27
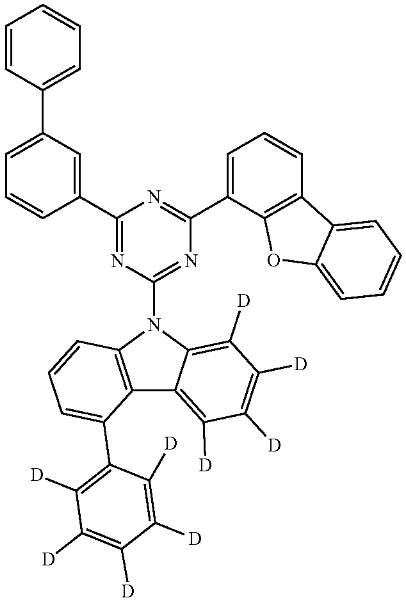

-continued
A28
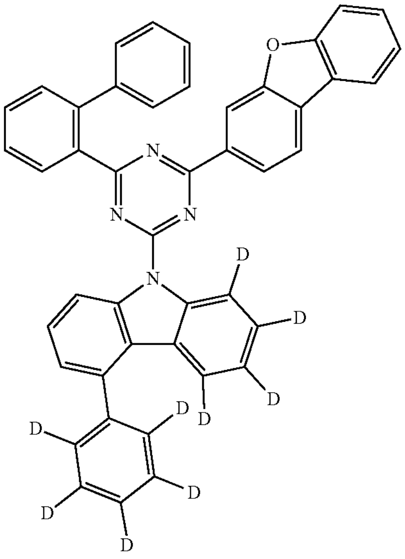
A29
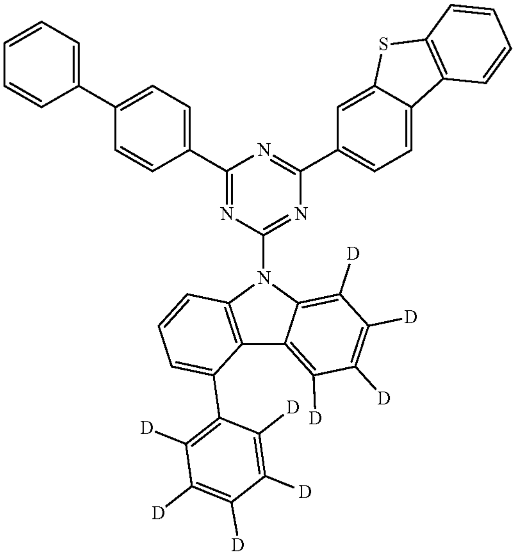
-continued
A30
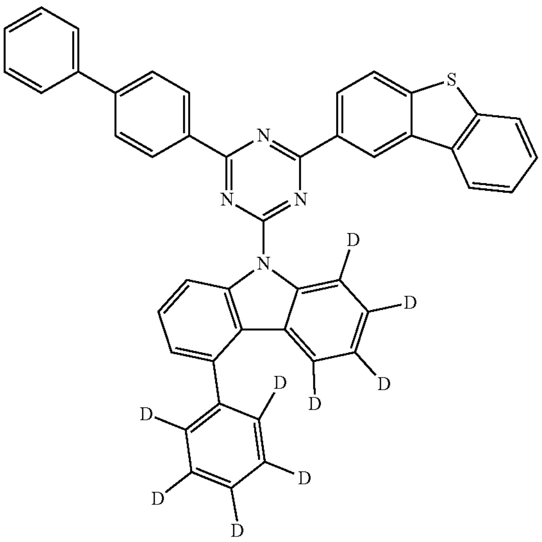
A31
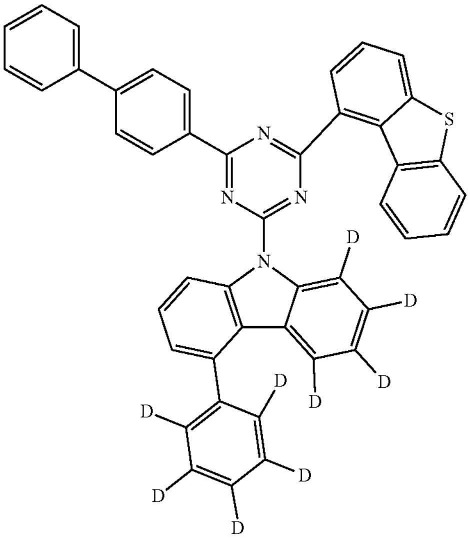
A32
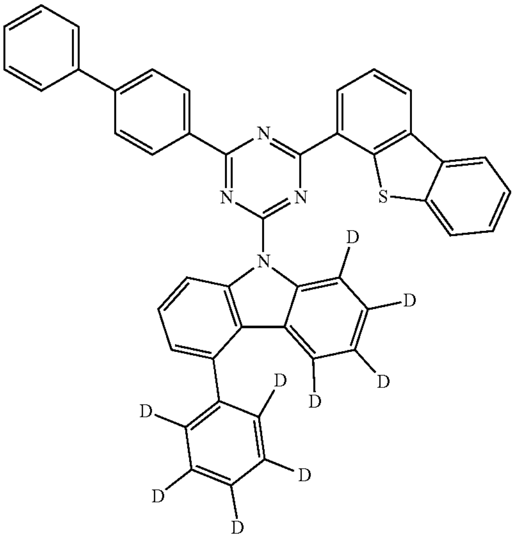

-continued
A33
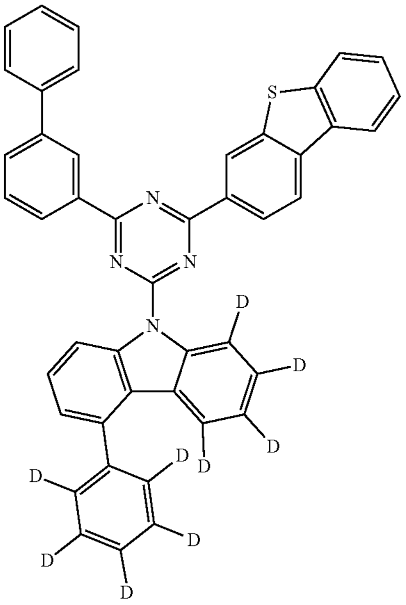
A34
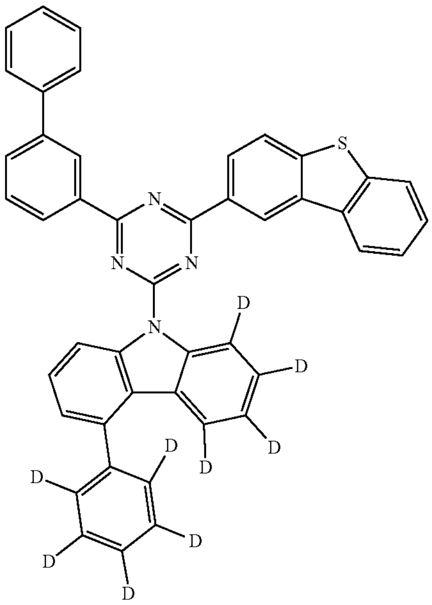
-continued
A35
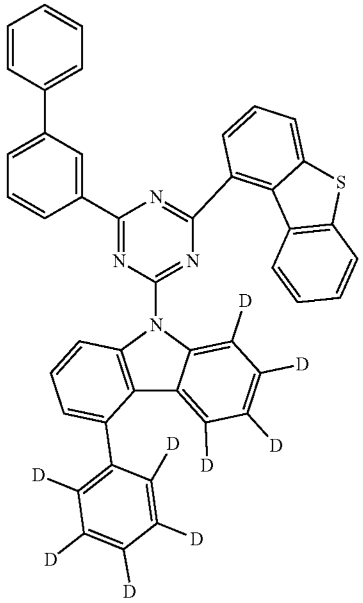
A36
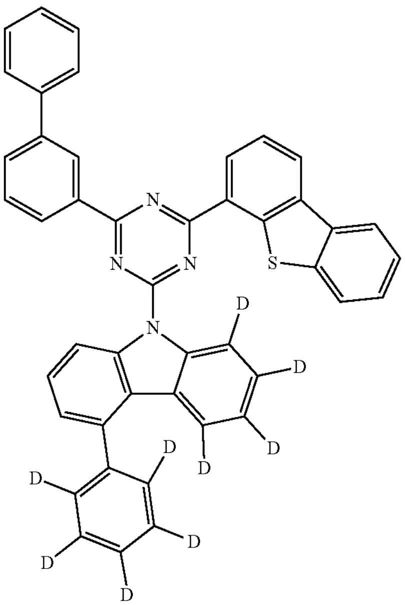

-continued
A37
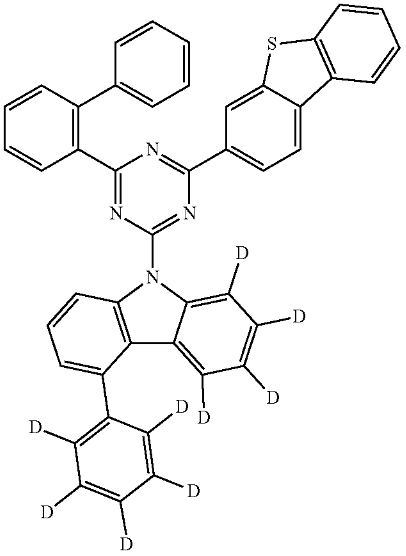
A38
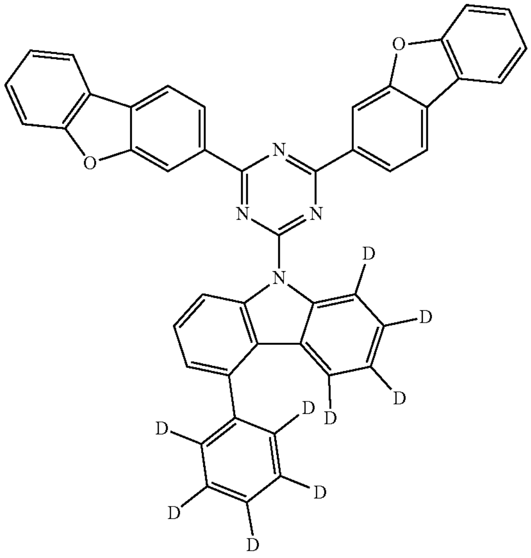
A39
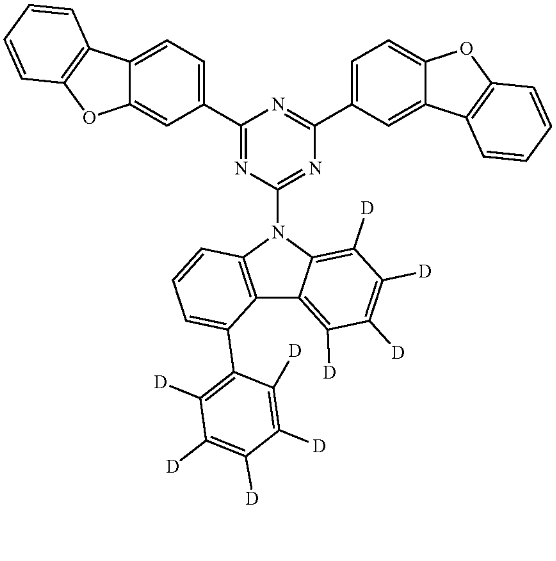
-continued
A40
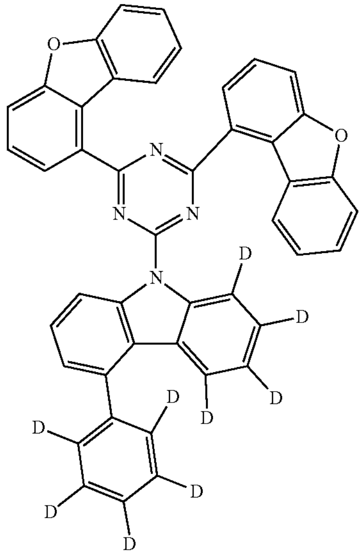
A41
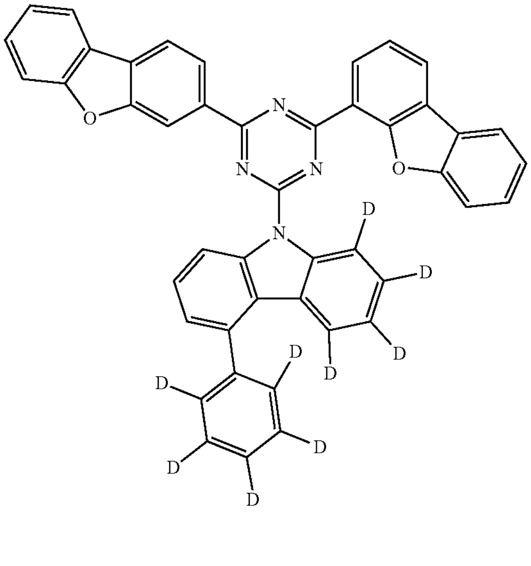

-continued
A42
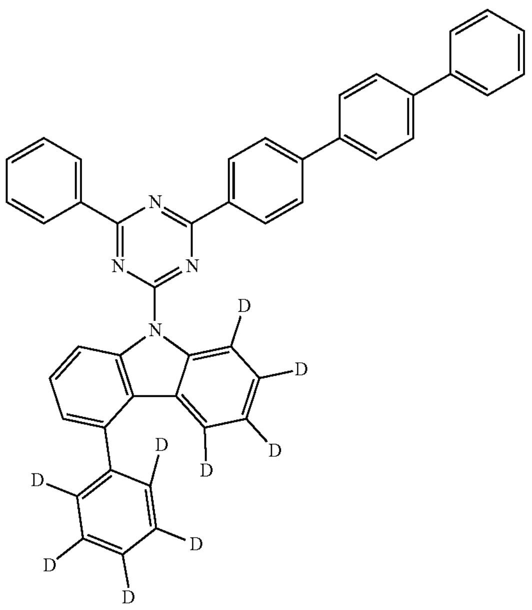
A43
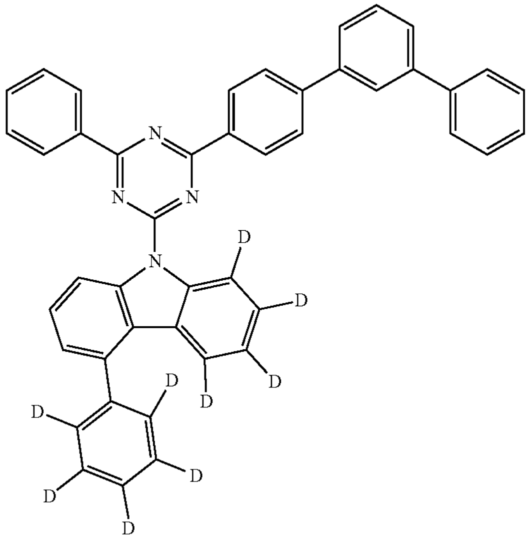
-continued
A44
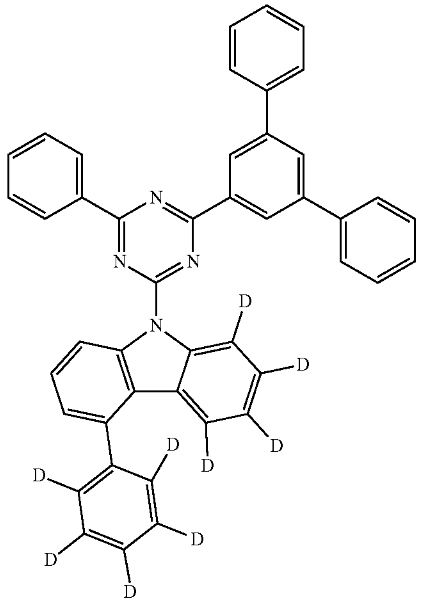
A45
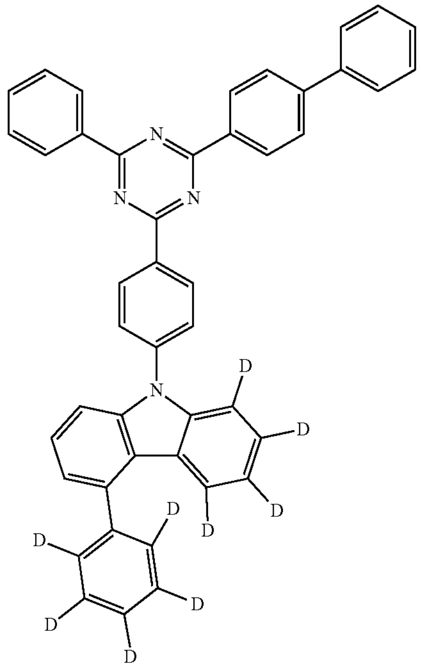

-continued
A46
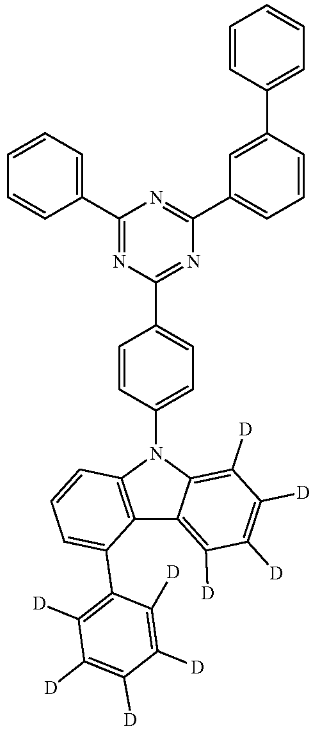
A47
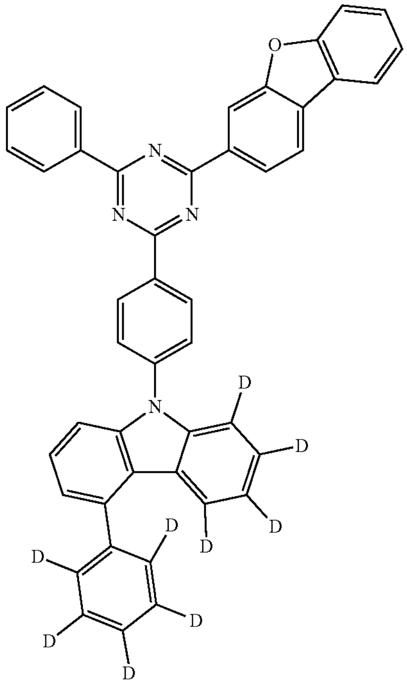
-continued
A48
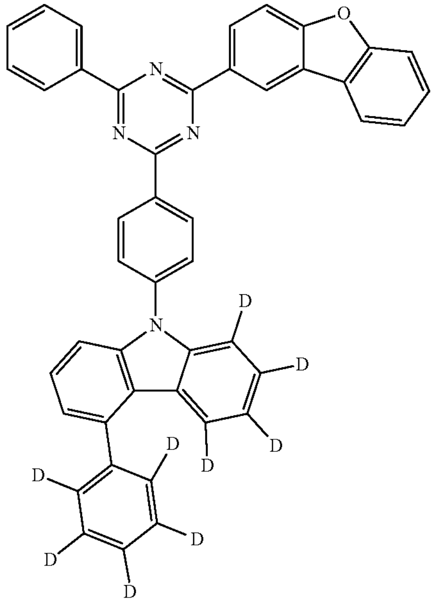
A49
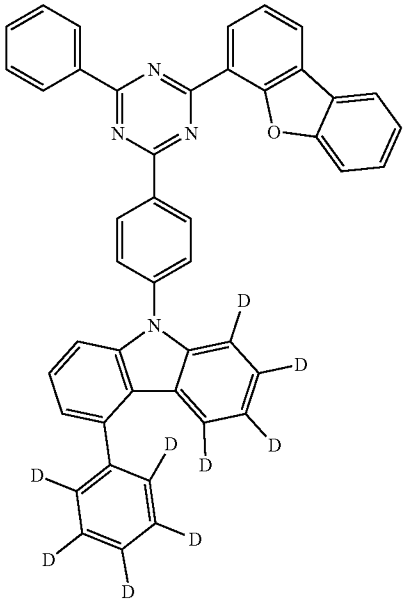

A50
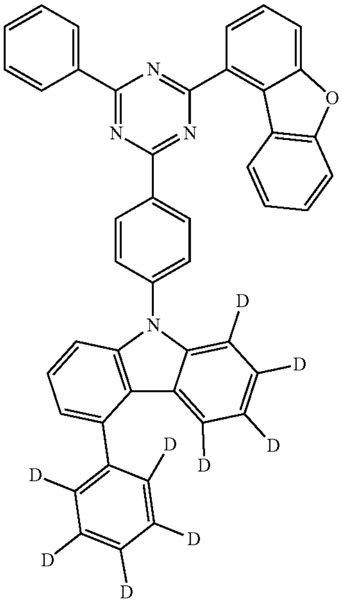
A51
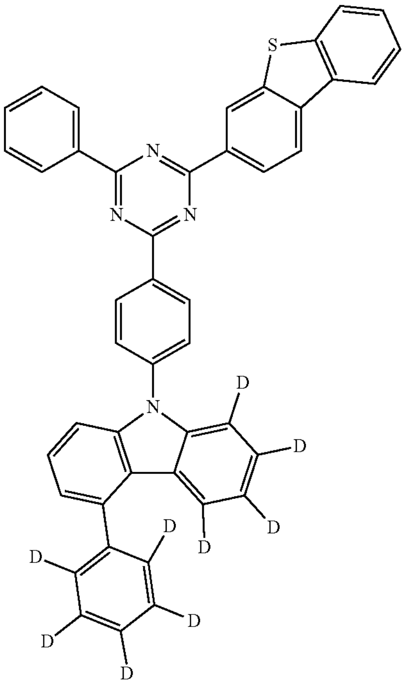
A52
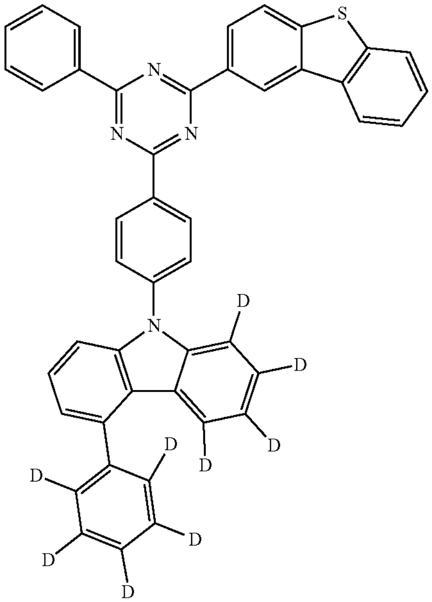
A53
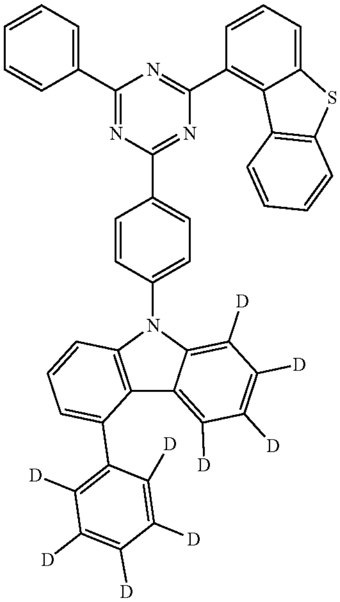

-continued
A54
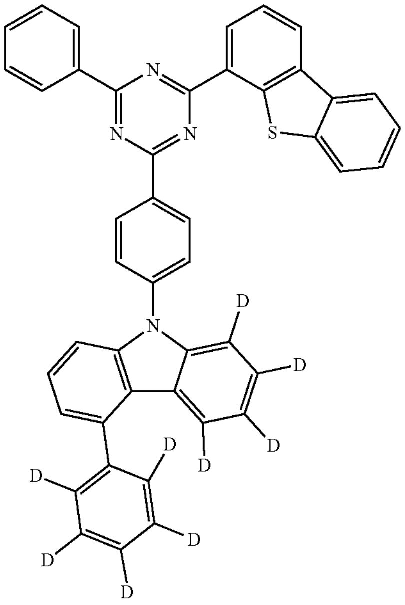
A55
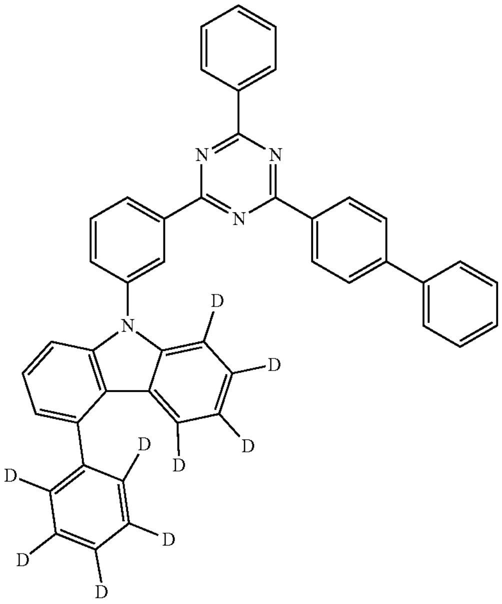
-continued
A56
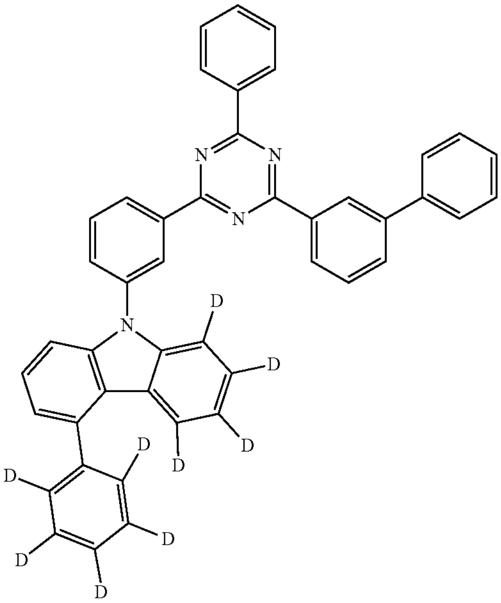
A57
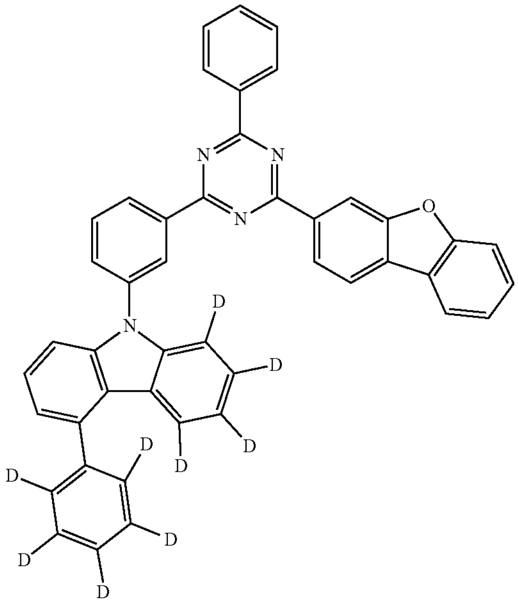

-continued
A58
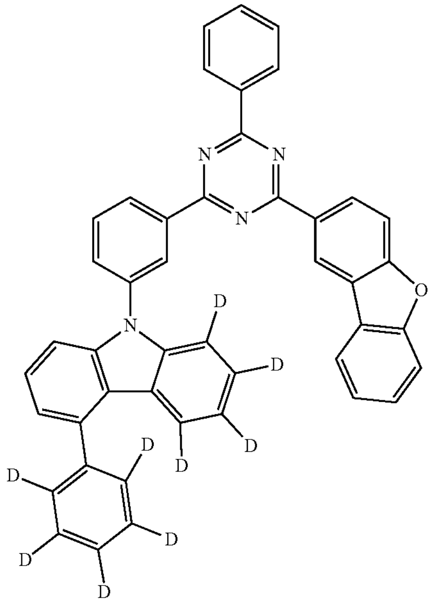
A59
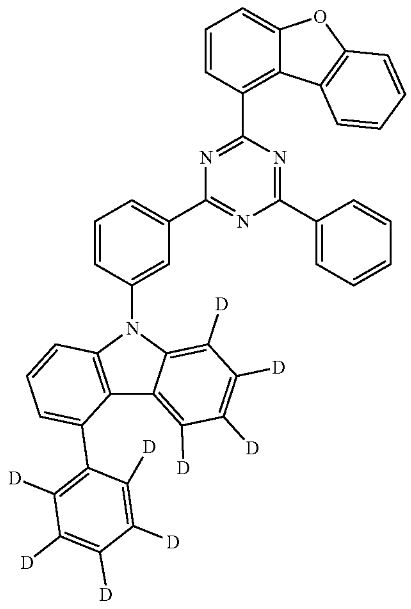
-continued
A60
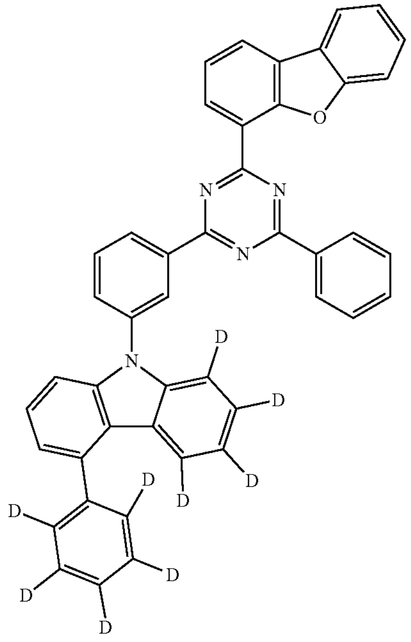
A61
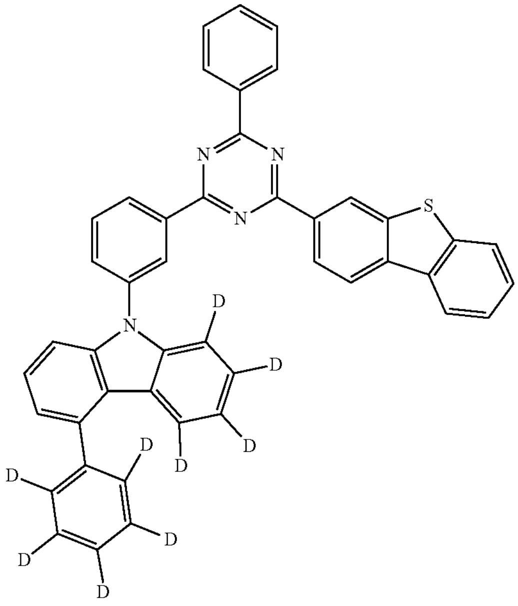

-continued
A62
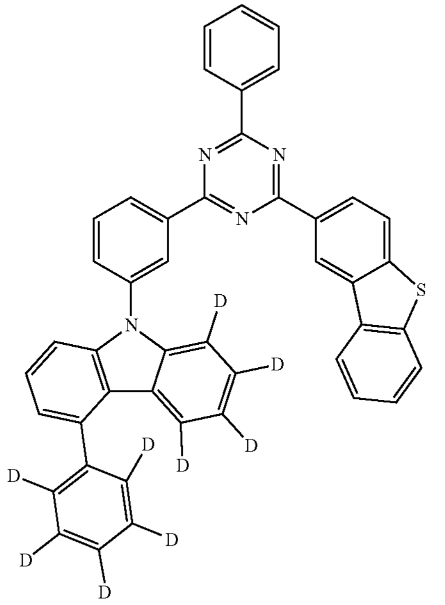
A63
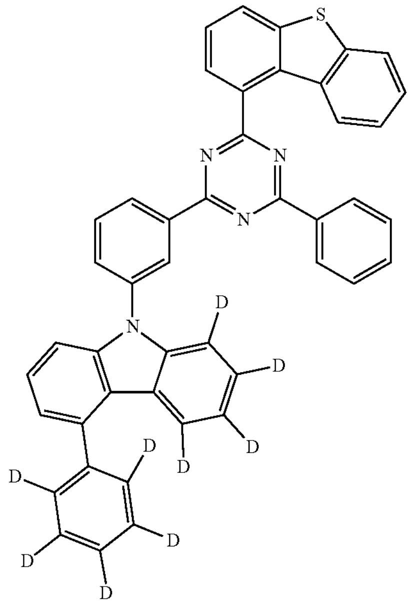
-continued
A64
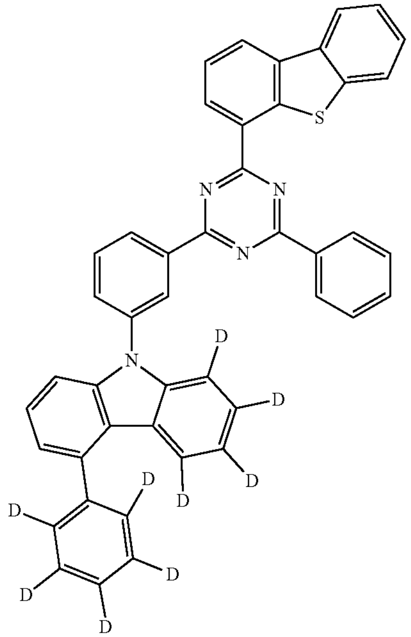
A65
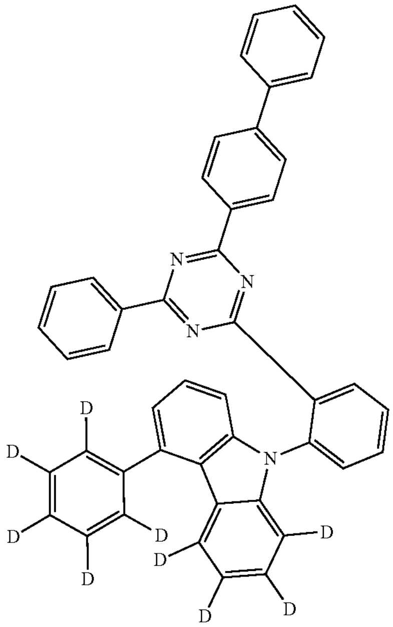

-continued
A66
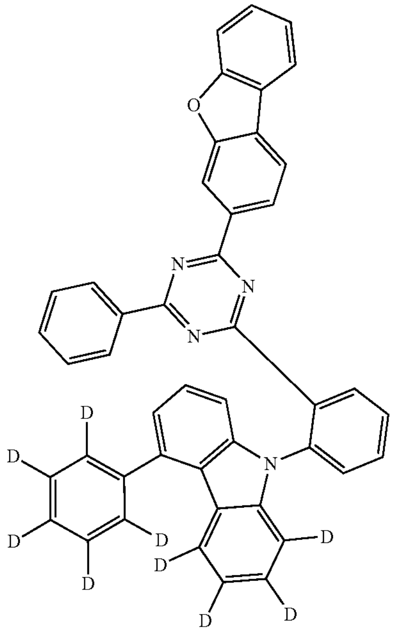
A67
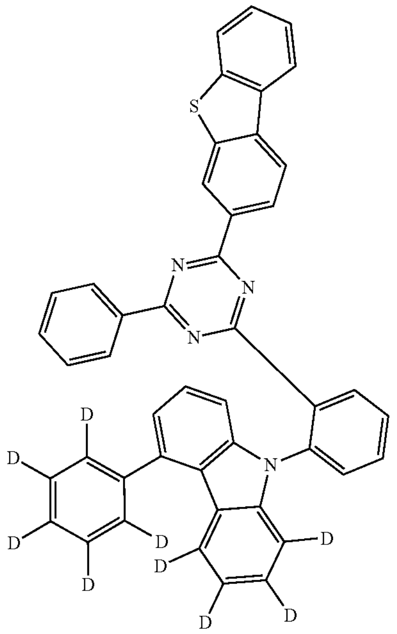
-continued
A68
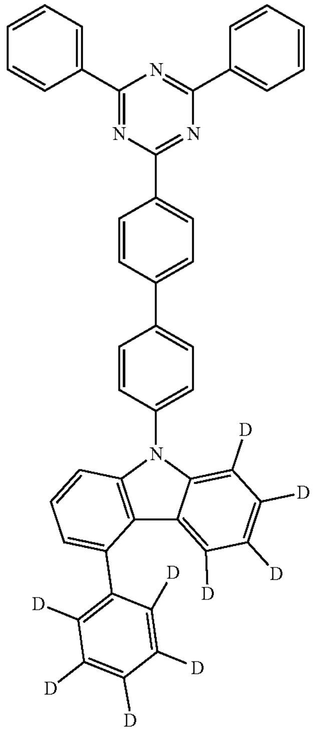
A69
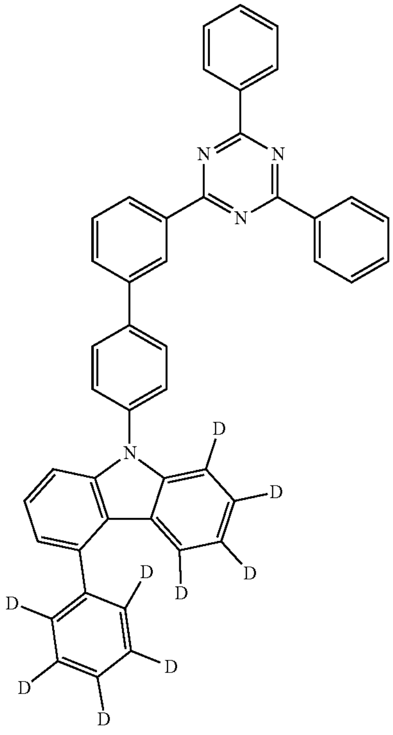

-continued
A70
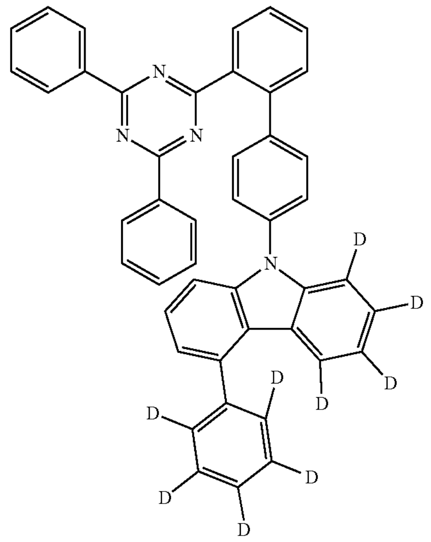
A71
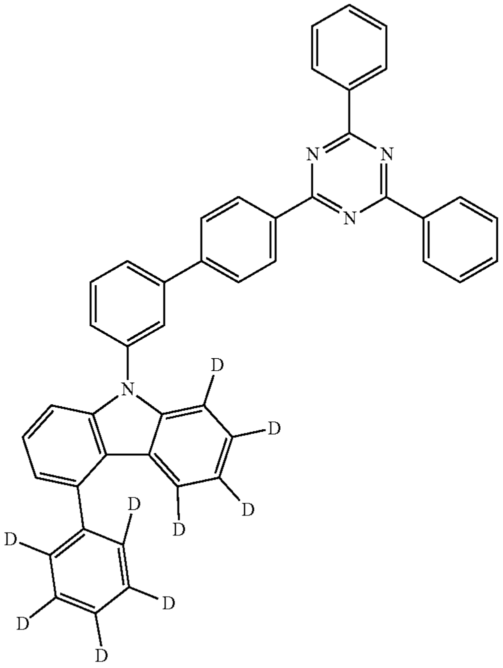
-continued
A72
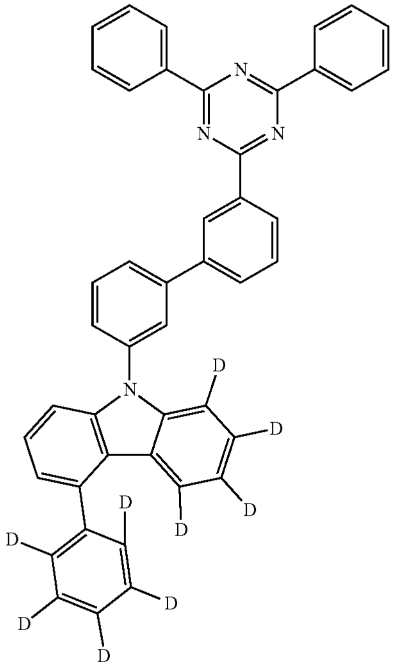
A73
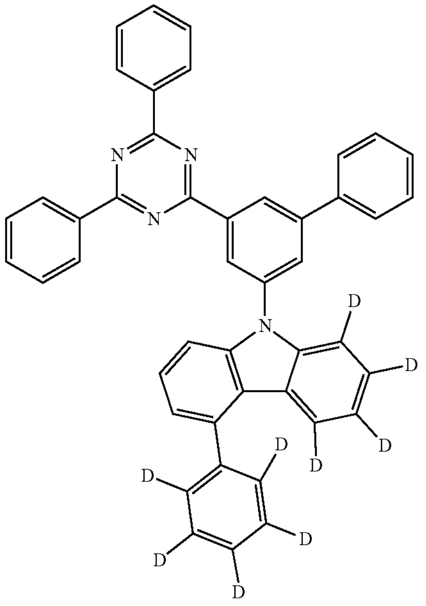

A74
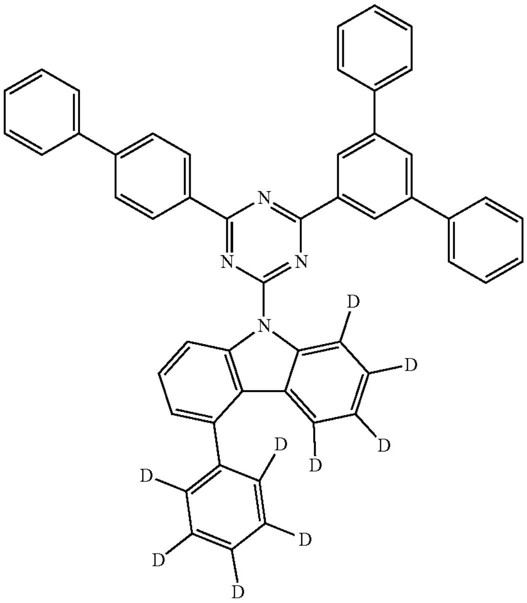
A75
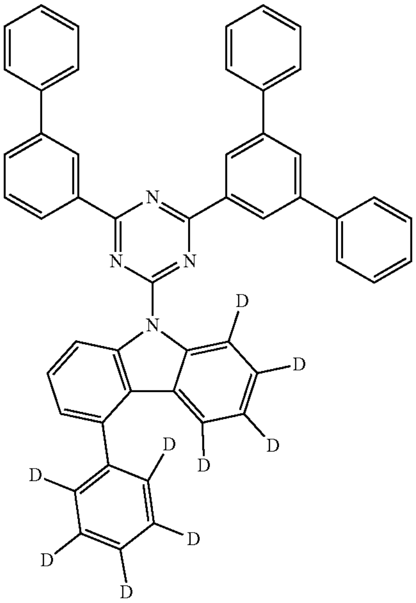
A76
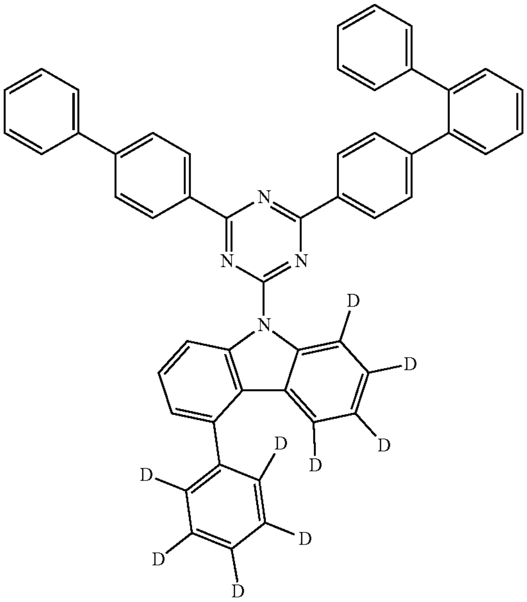
A77
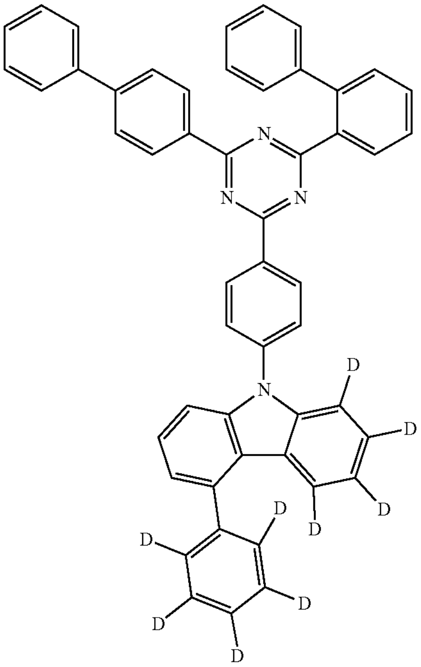

-continued
A78
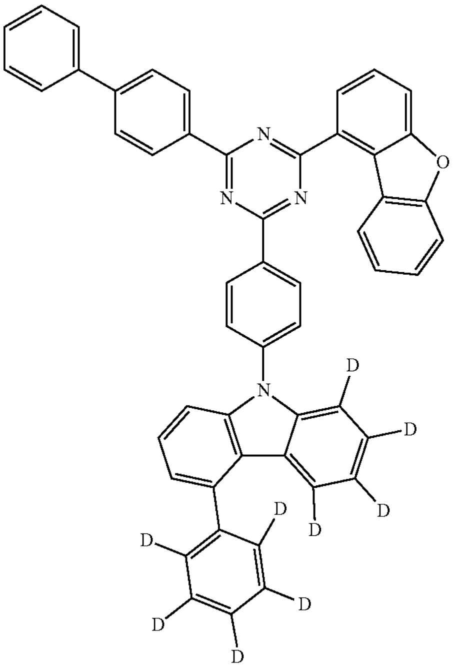
A79
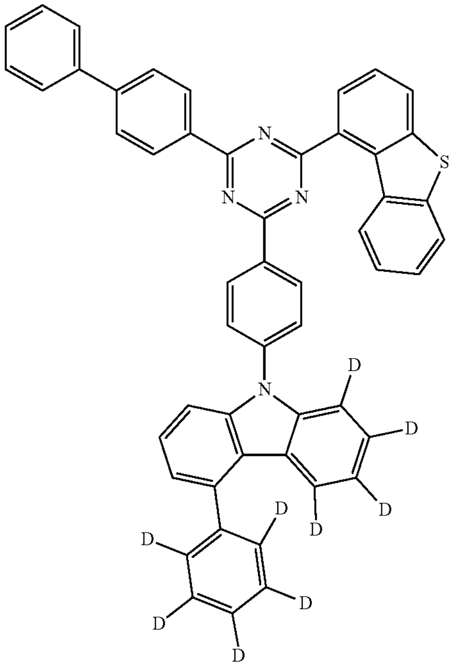
-continued
A80
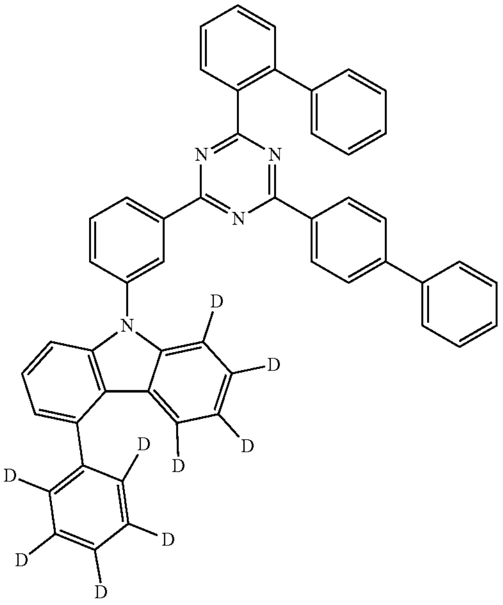
A81
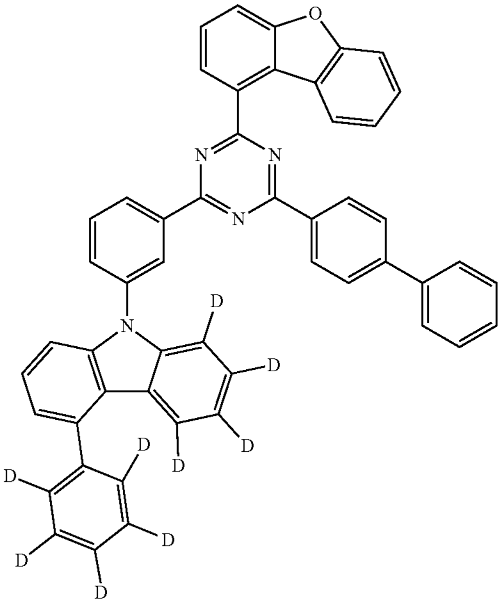

-continued
A82
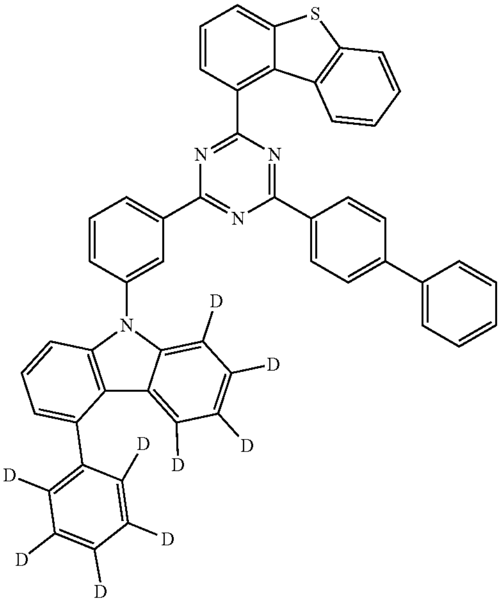
A83
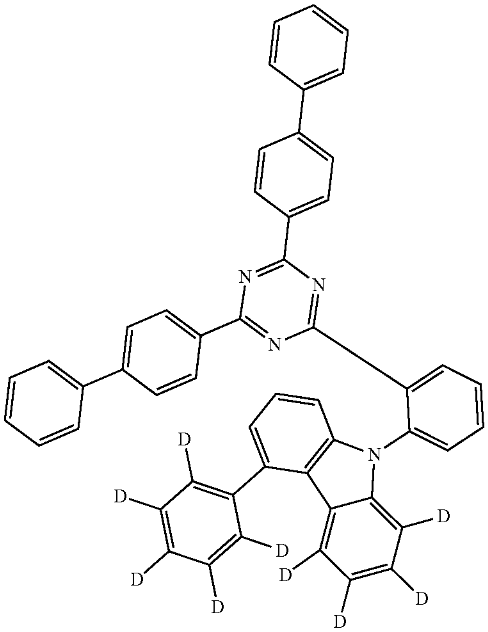
-continued
A84
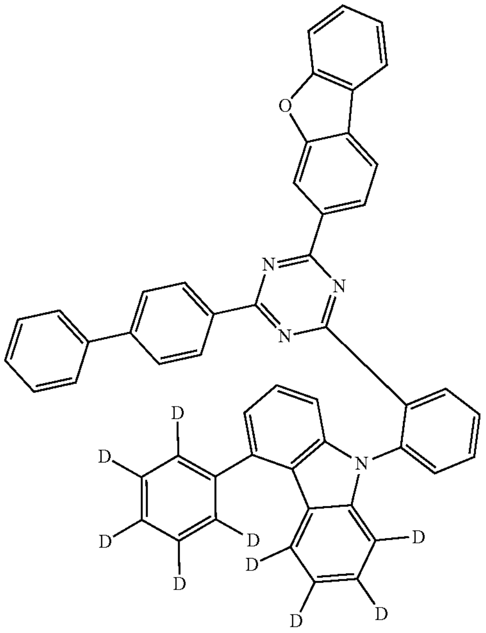
A85
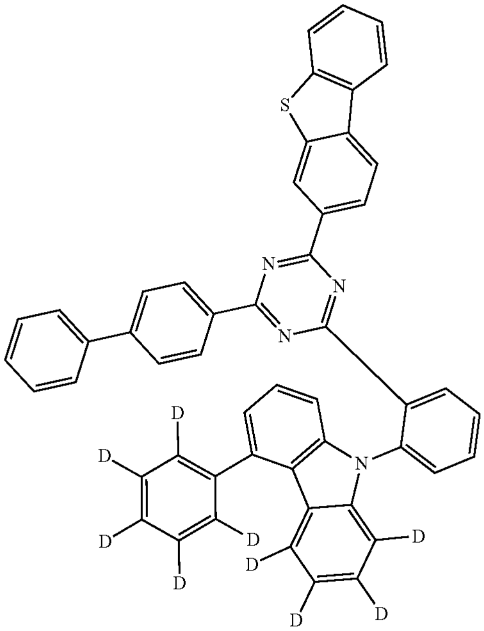

-continued
A86
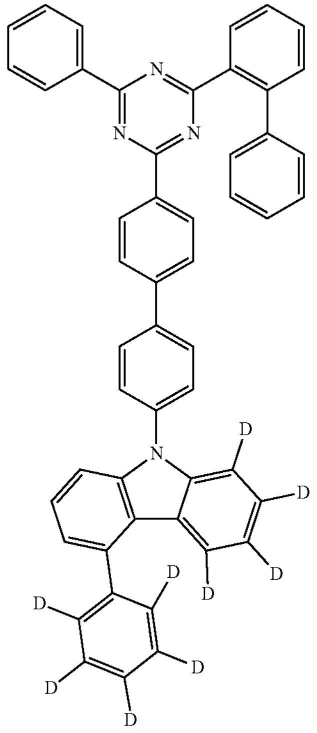
A87
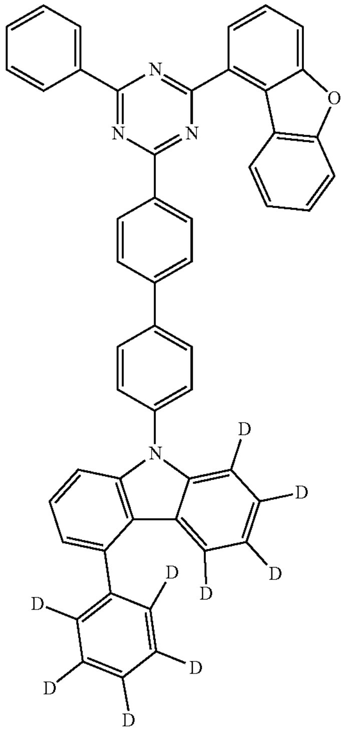
-continued
A88
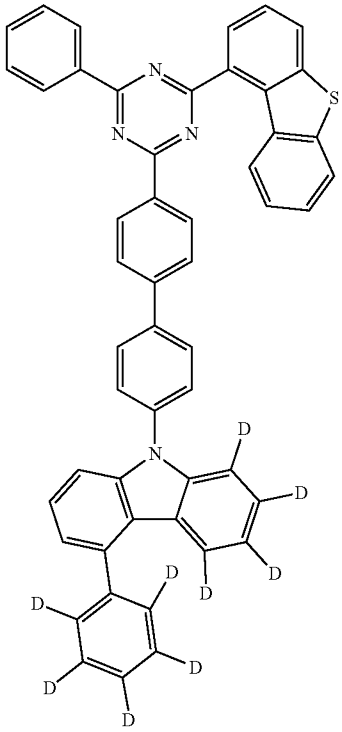
A89
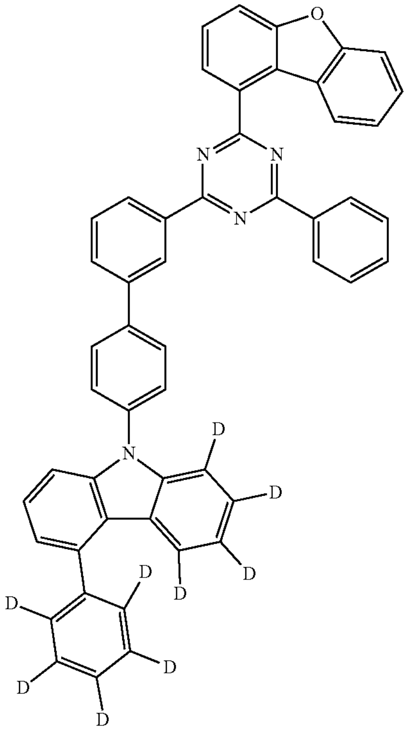

-continued
A90
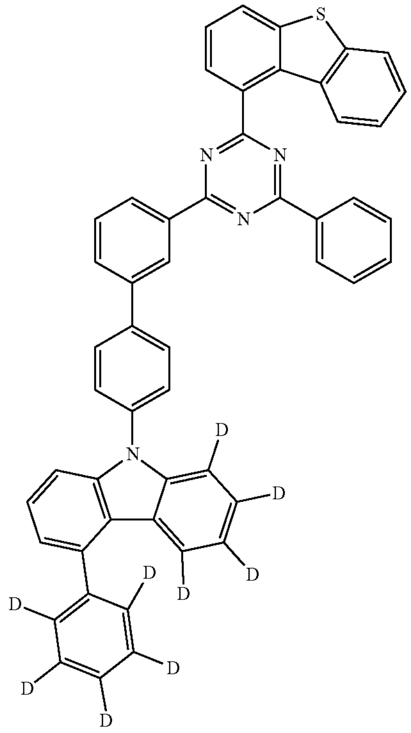
A91
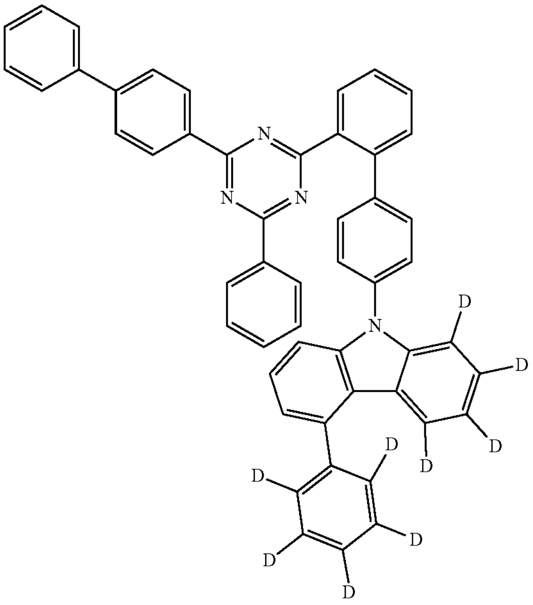
-continued
A92
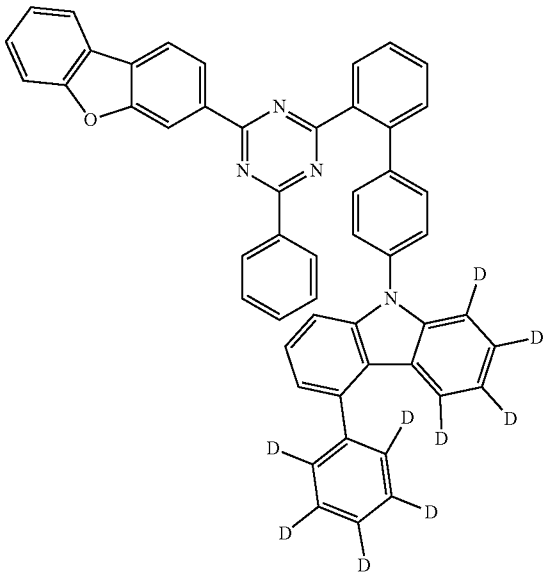
A93
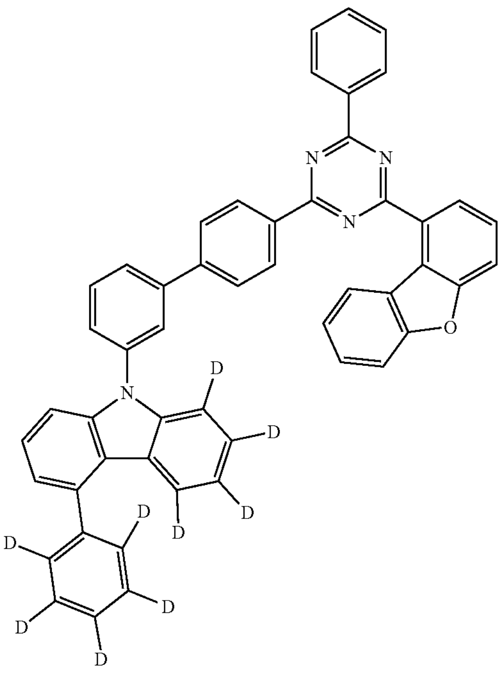

-continued
A94
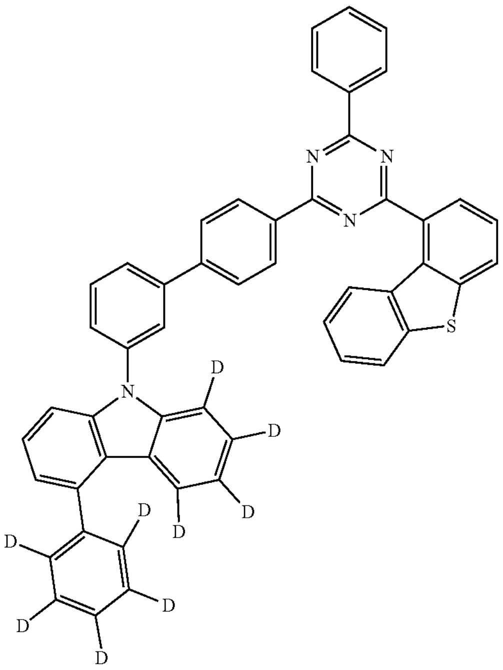
A95
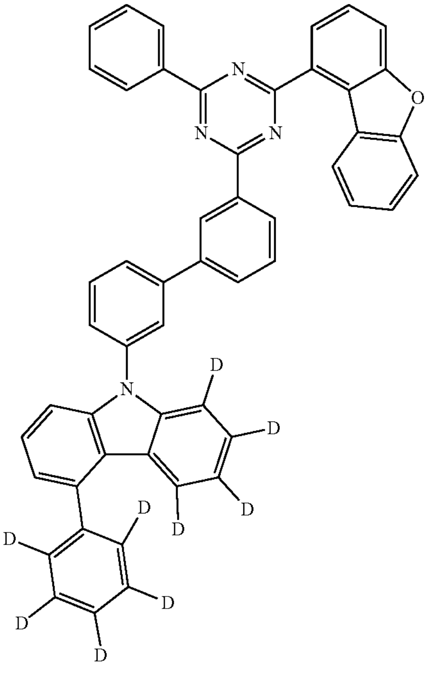
-continued
A96
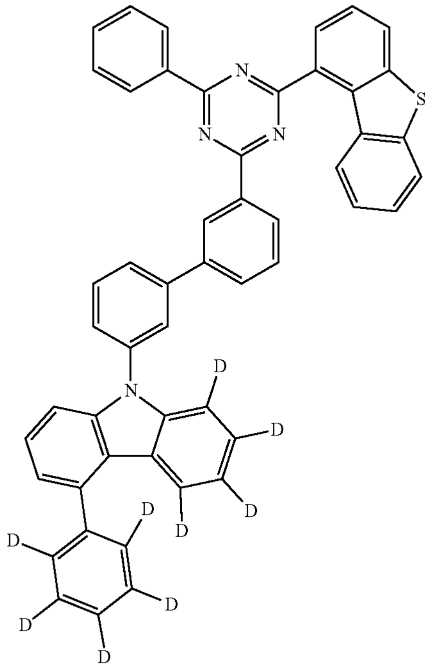
A97
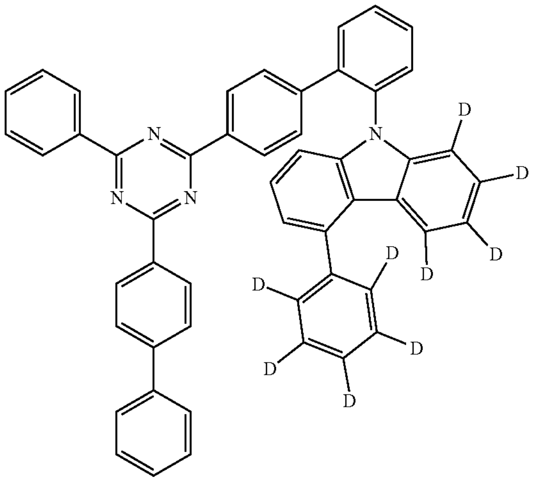
A98
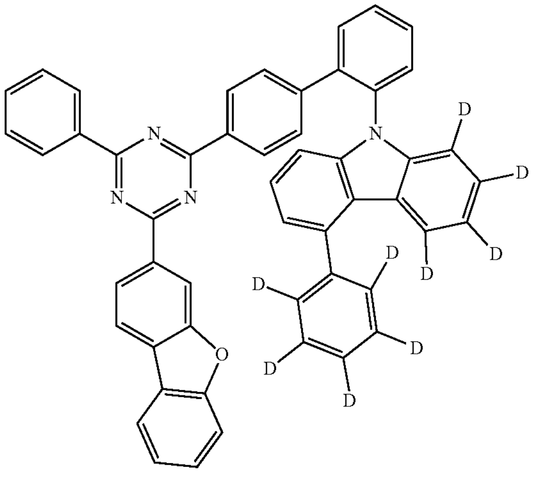

-continued
A99
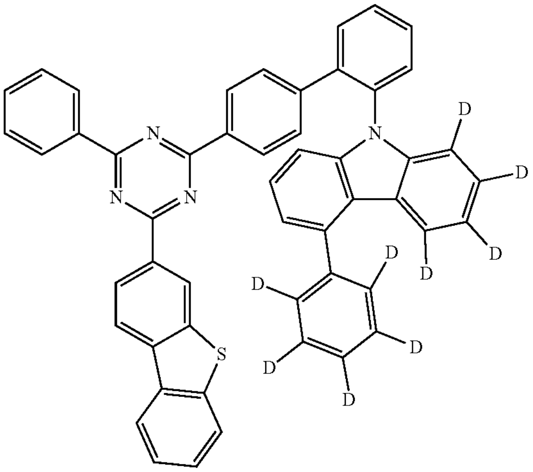
A100
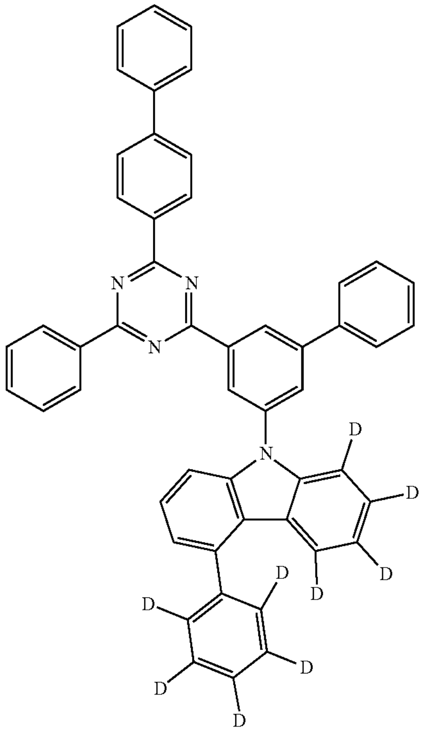
-continued
A101
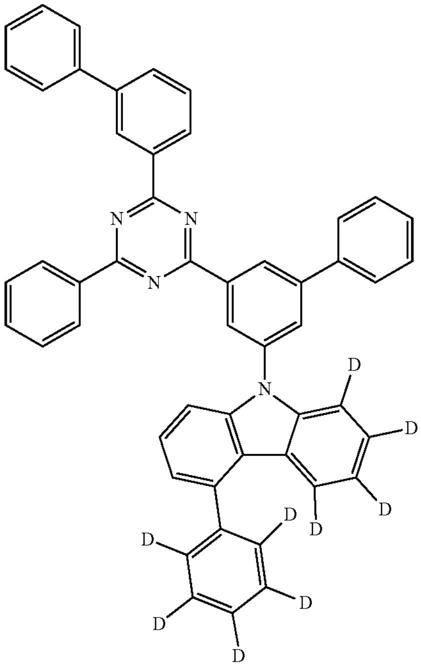
A102
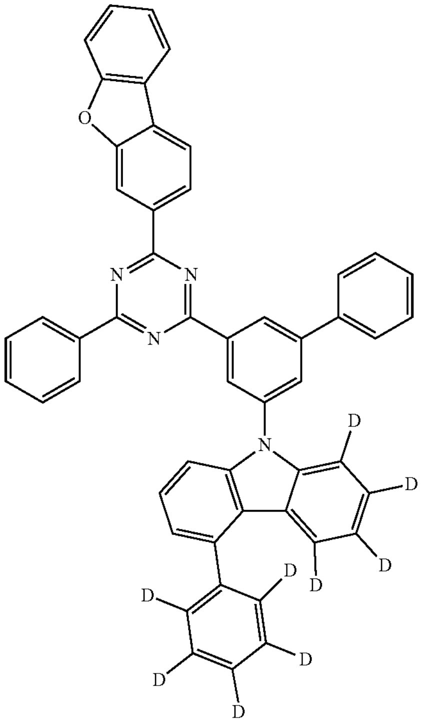

-continued
A103
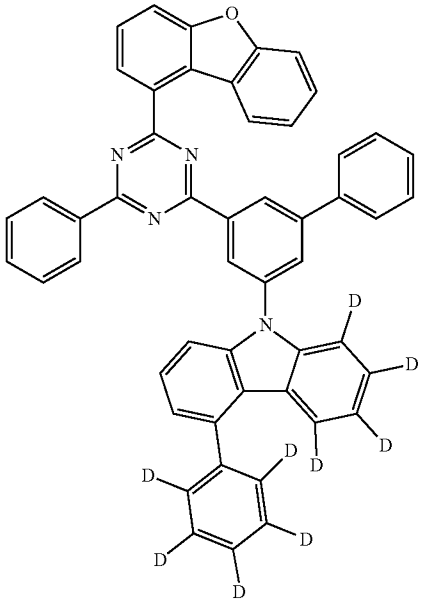
A104
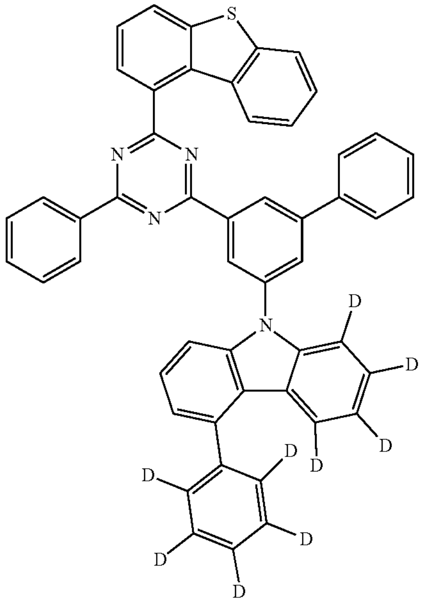
-continued
A105
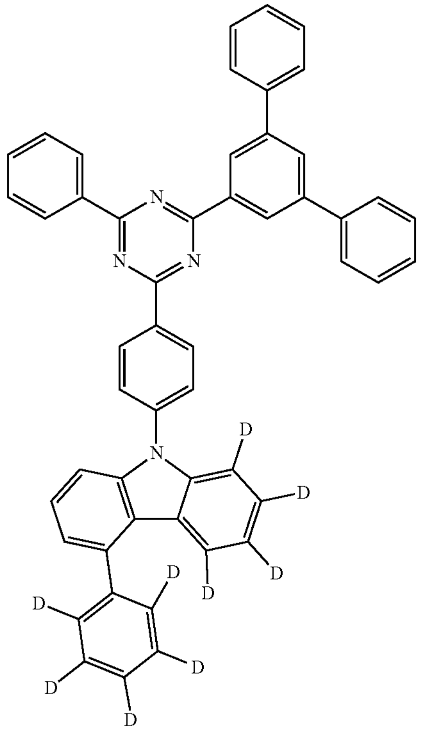
A106
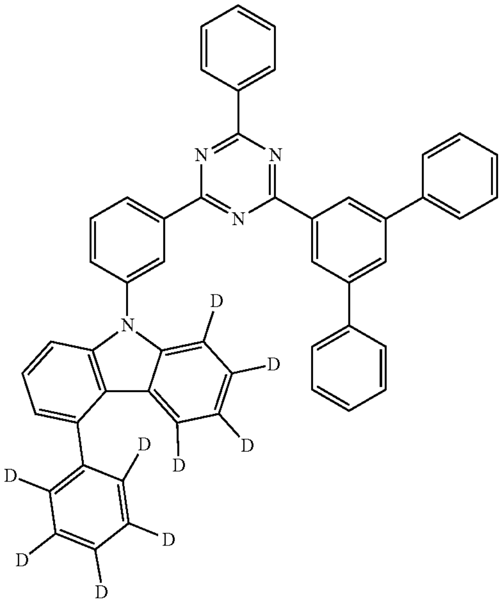

-continued
A107
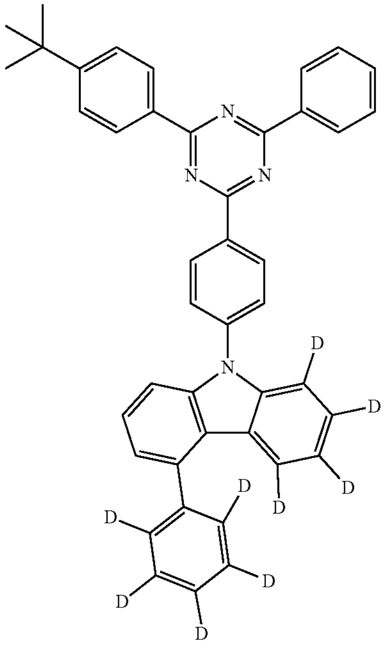
A108
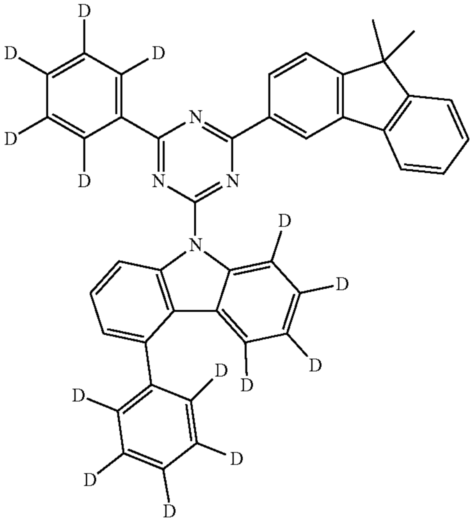
A109
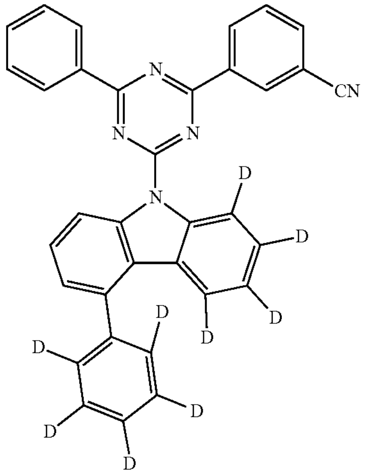
-continued
A220
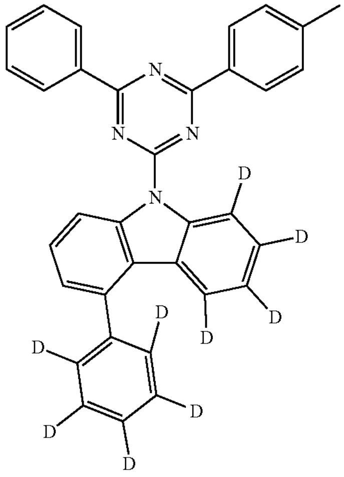
A221
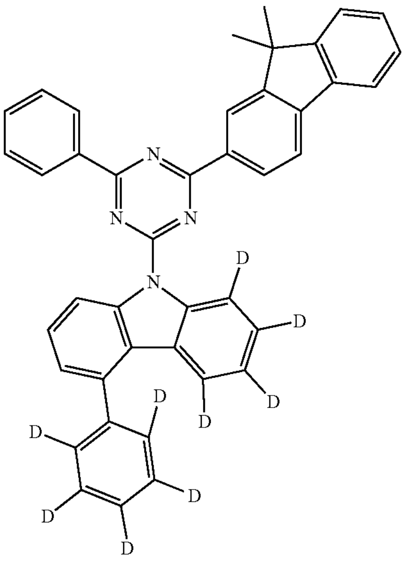
A222
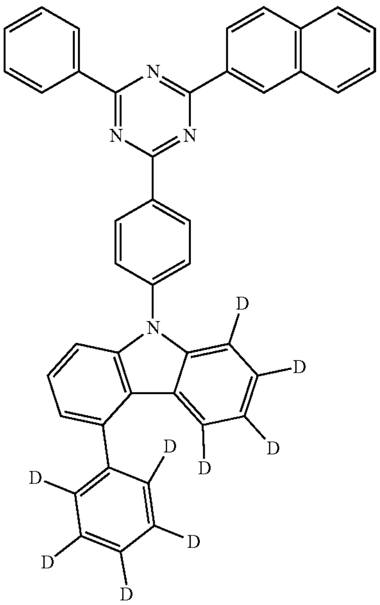

-continued
B1
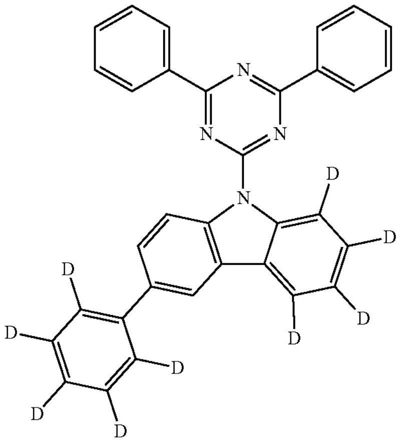
B2
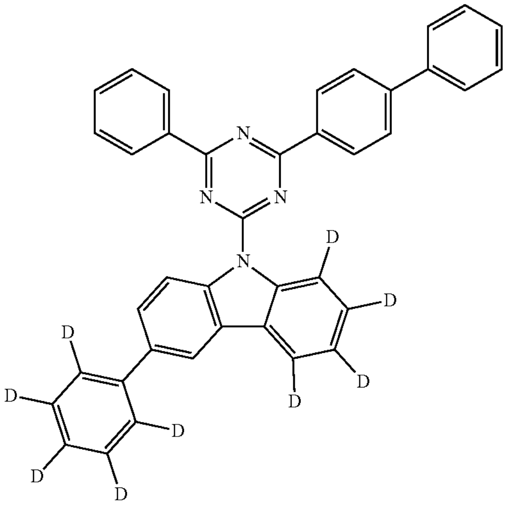
B3
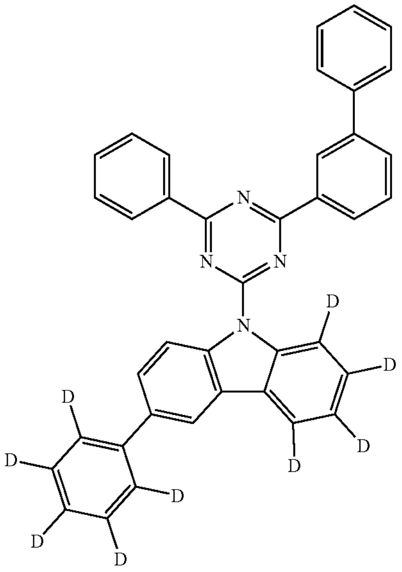
-continued
B4
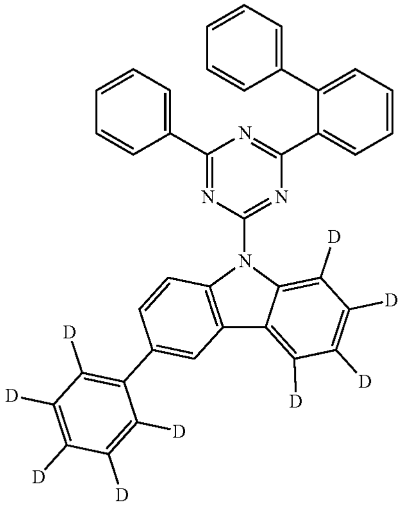
B5
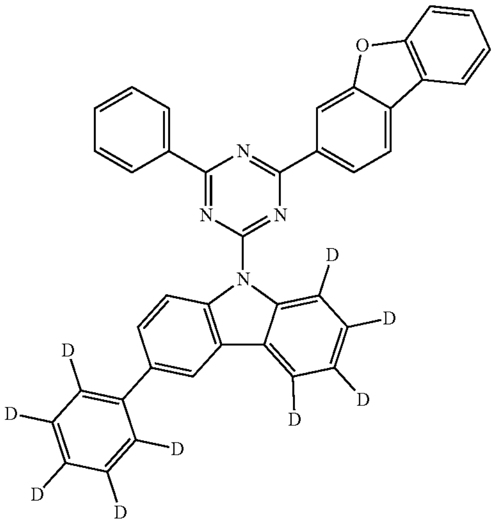
B6
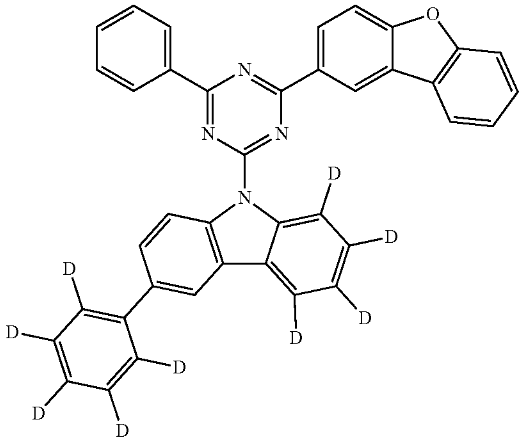

-continued
B7
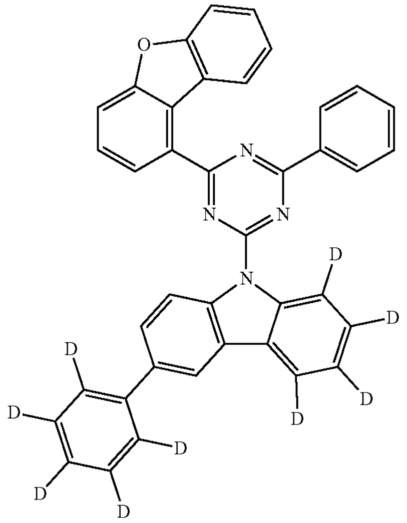
B8
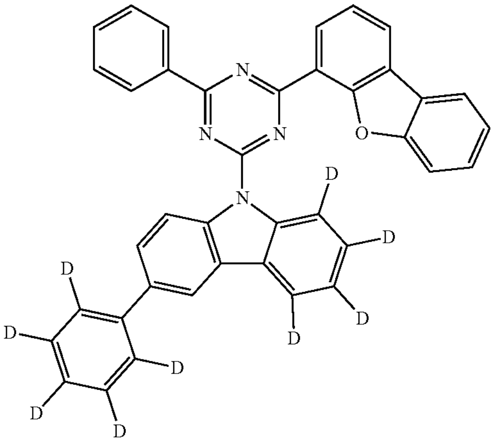
B9
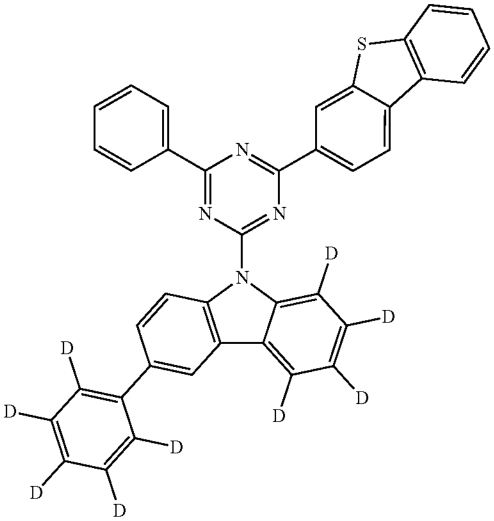
-continued
B10
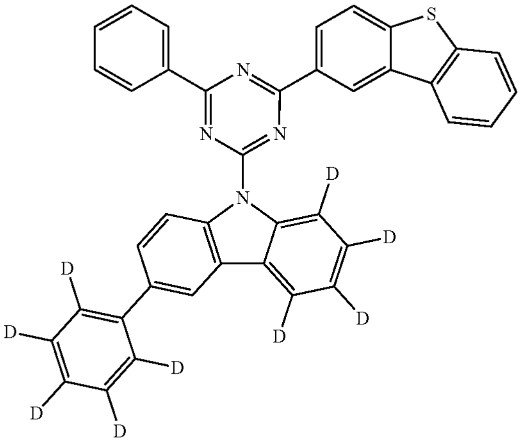
B11
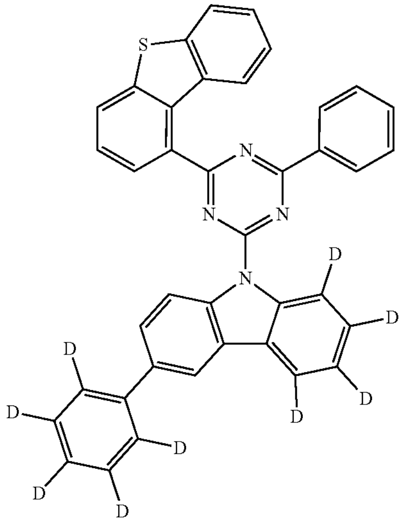
B12
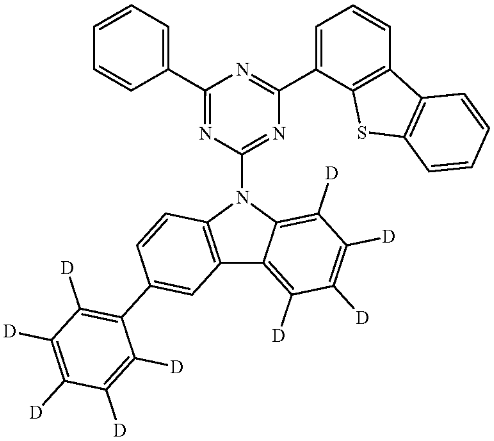

-continued
B13
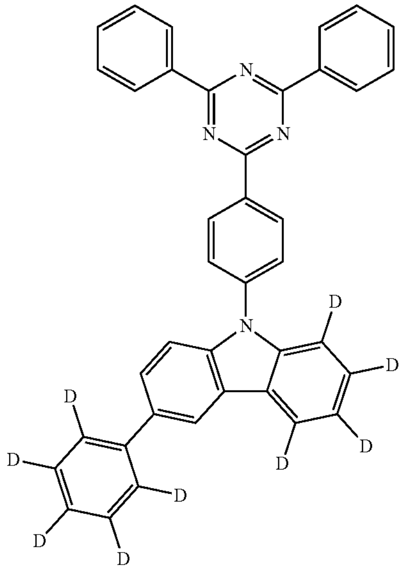
B14
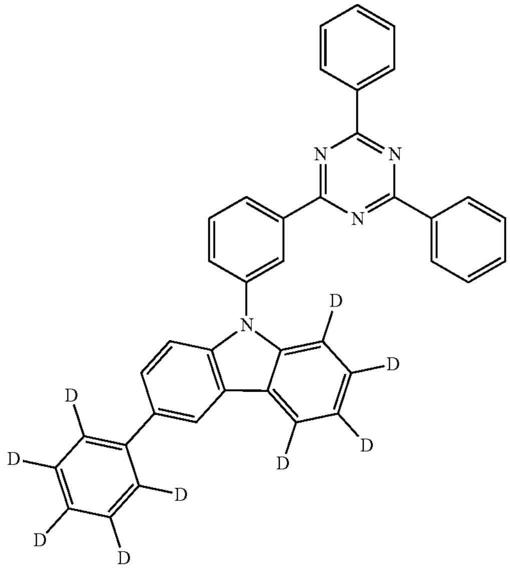
B15
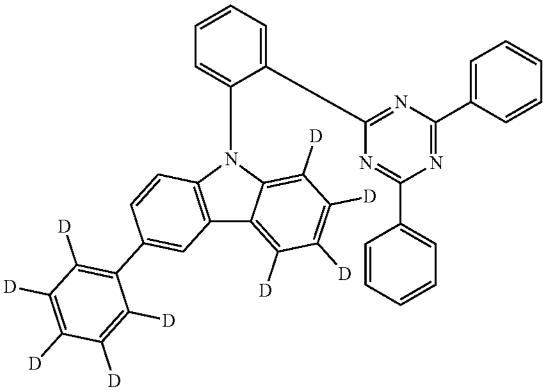
-continued
B16
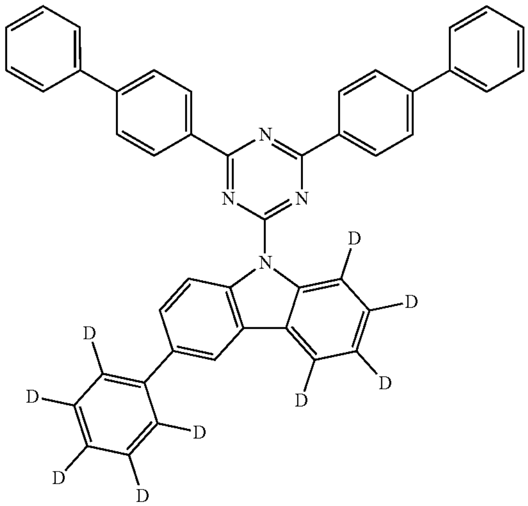
B17
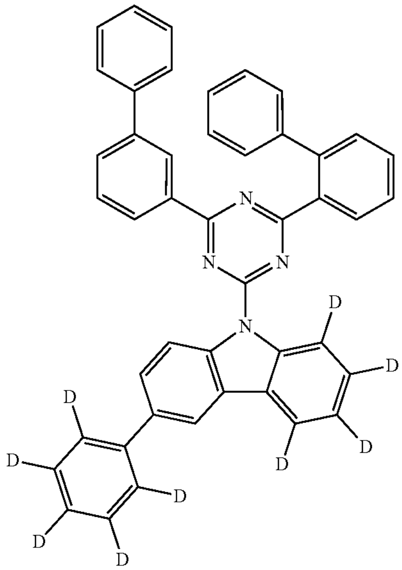
B18
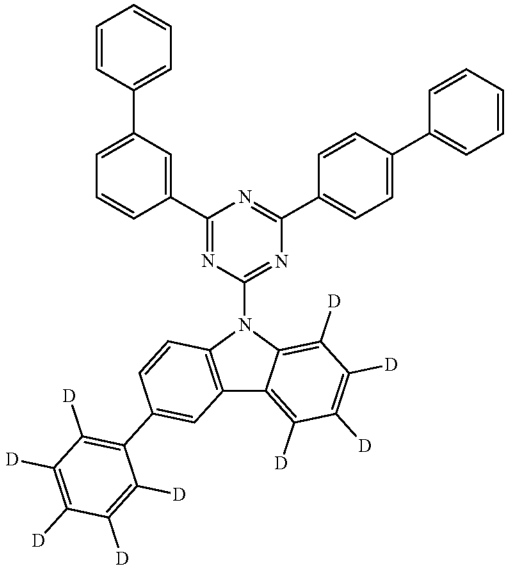

B19
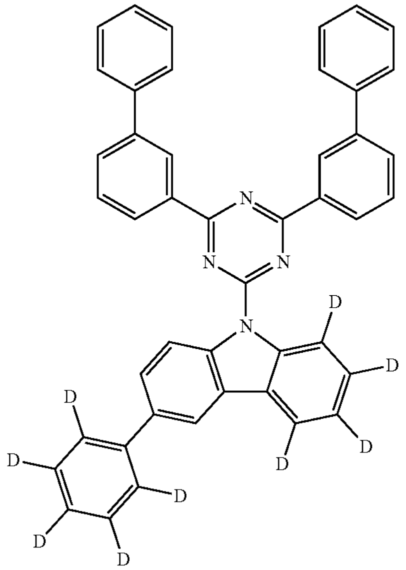
B20
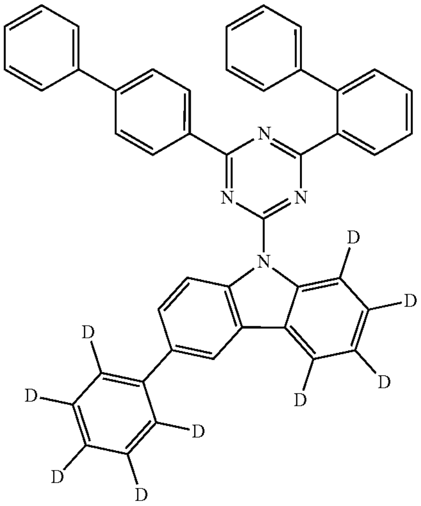
B21
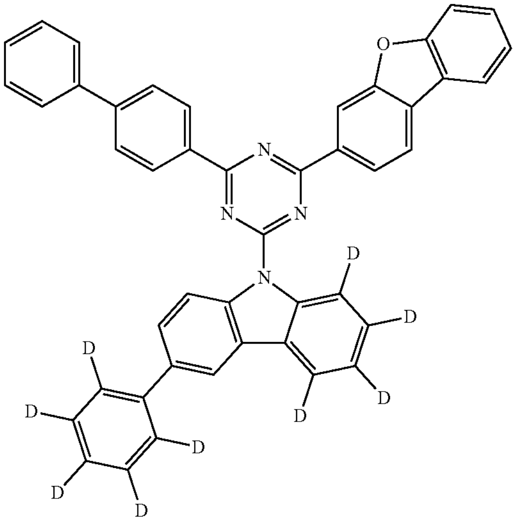
B22
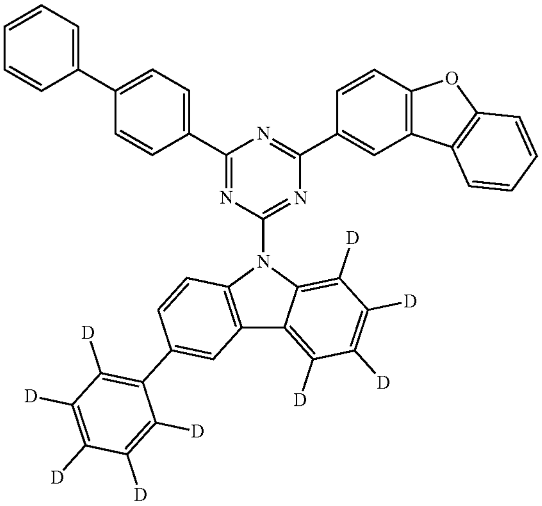
B23
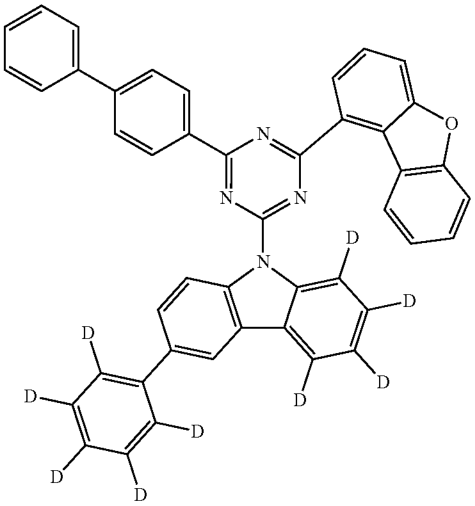
B24
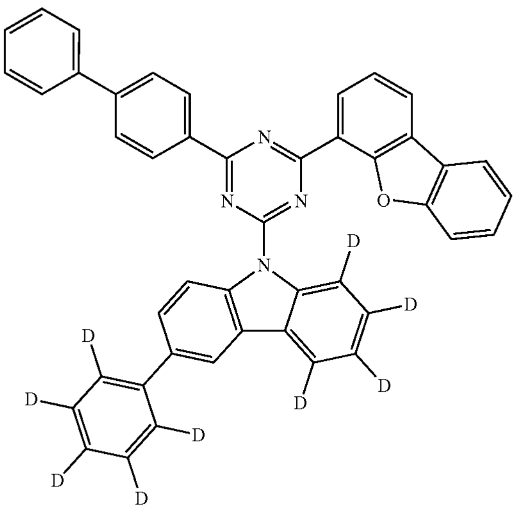

-continued
B25
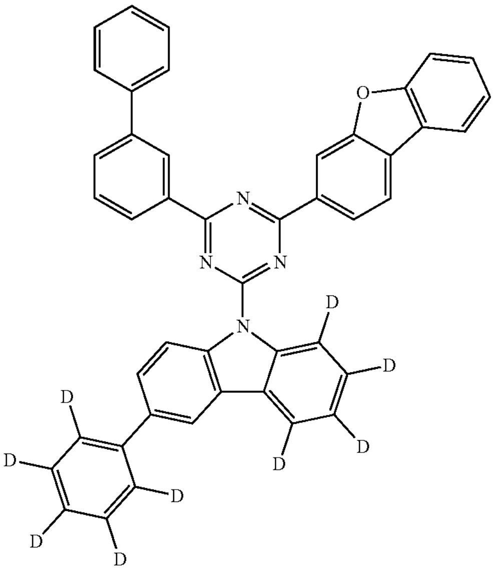
B26
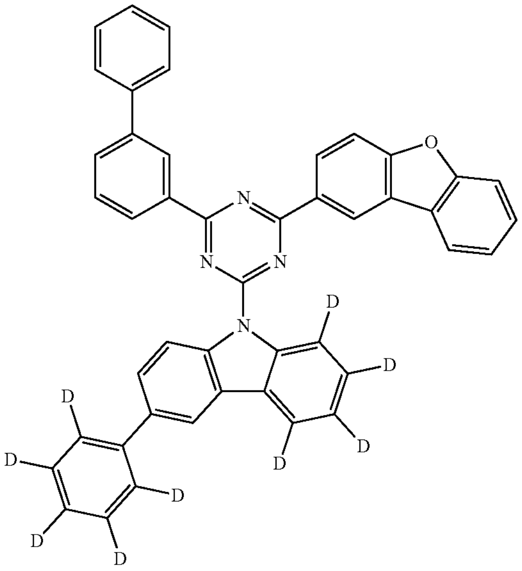
-continued
B27
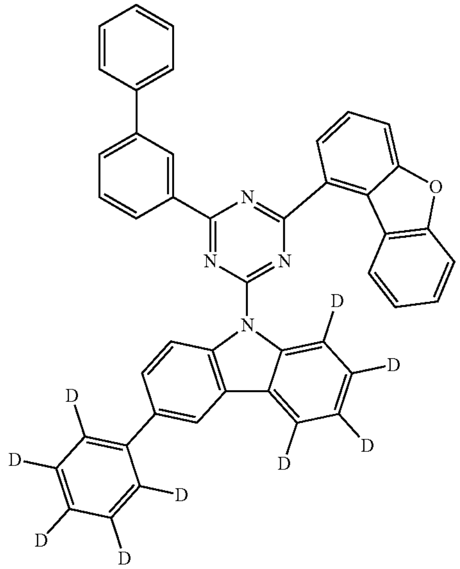
B28
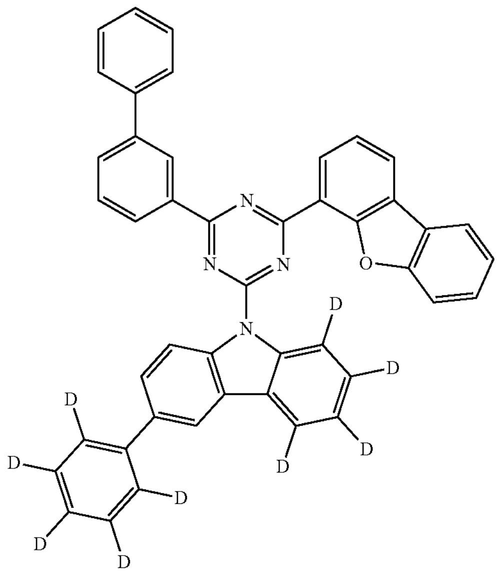
B29
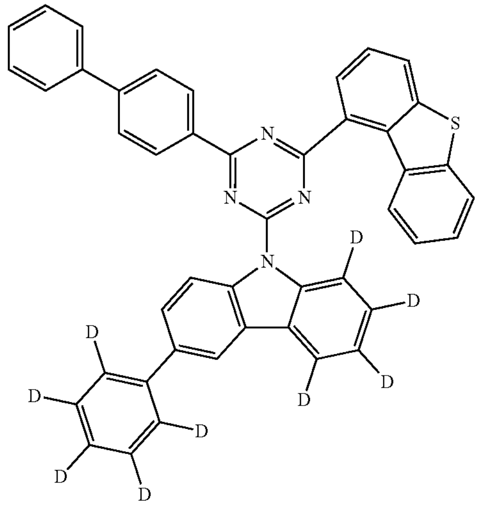

-continued
B30
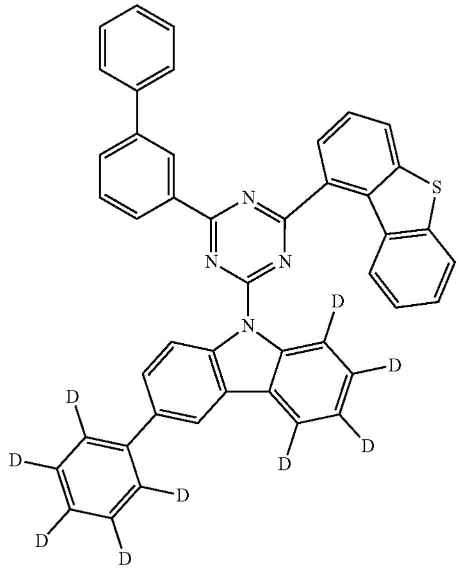
B31
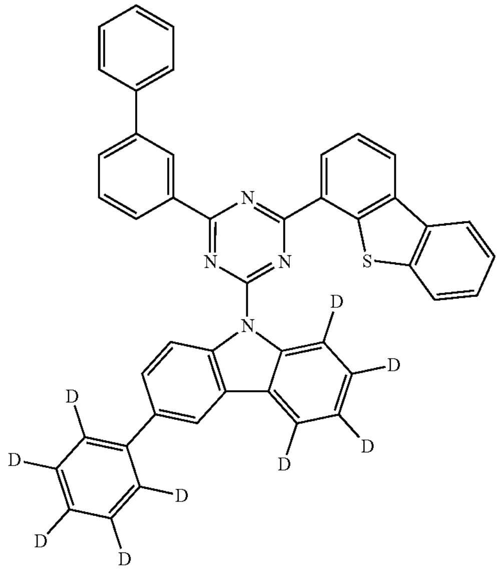
-continued
B32
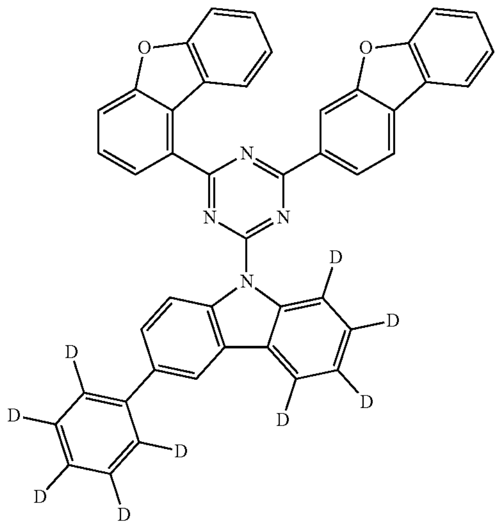
B33
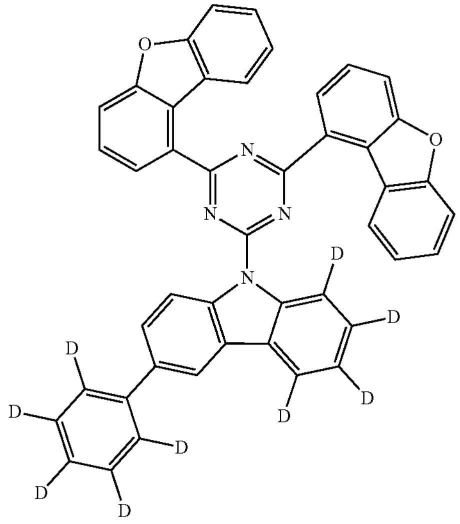
B34
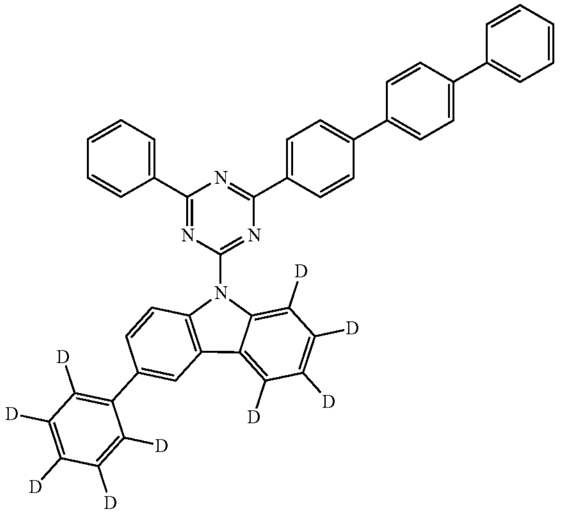

-continued
B35
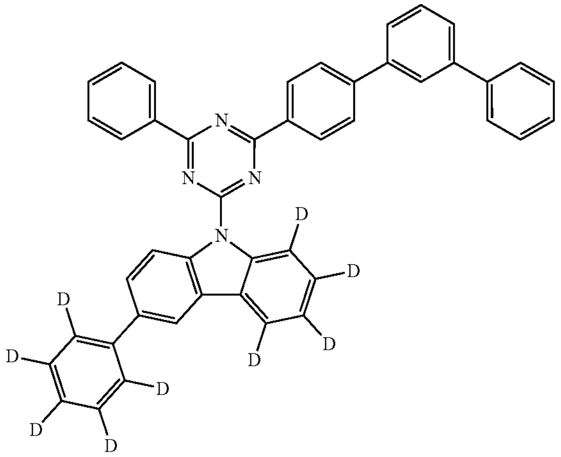
B36
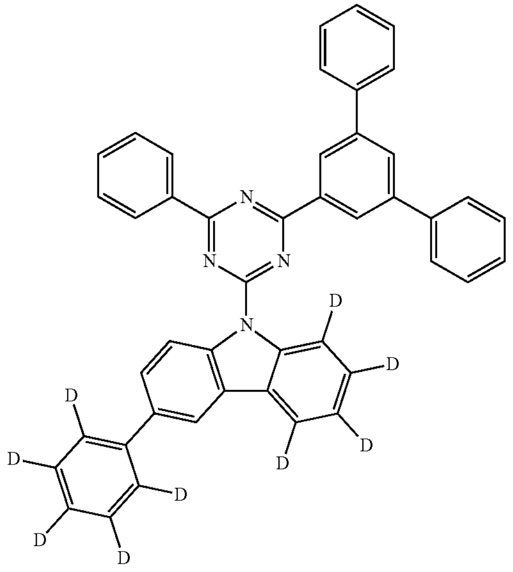
-continued
B37
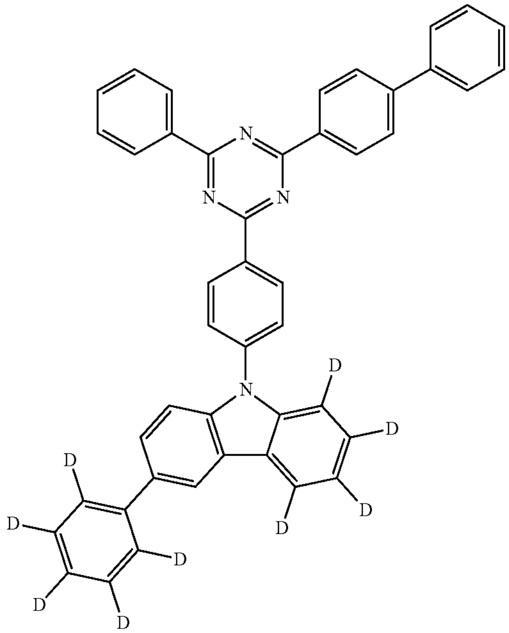
B38
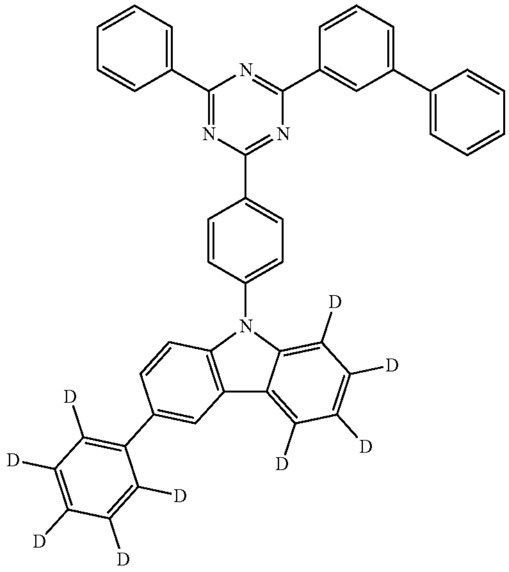

-continued
B39
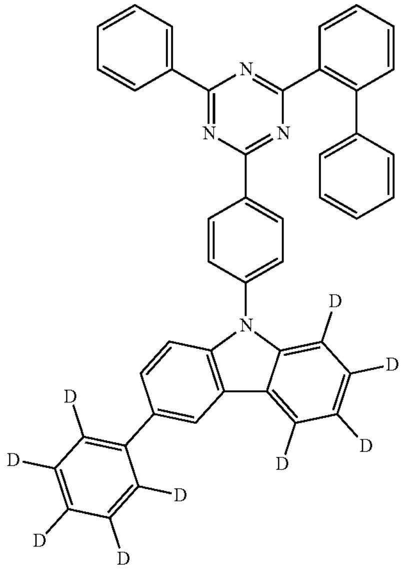
B40
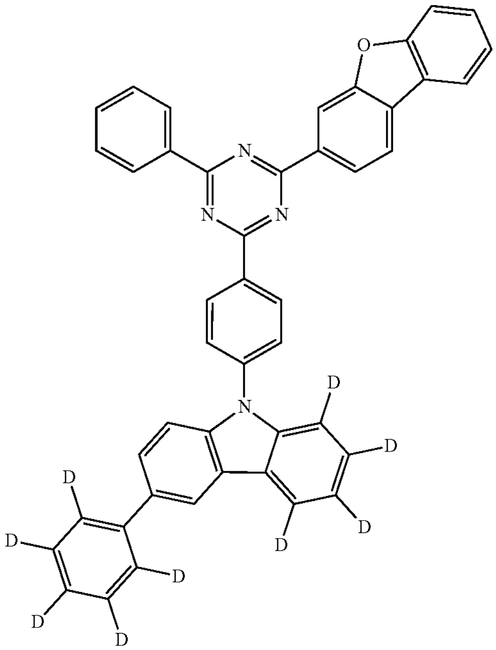
-continued
B41
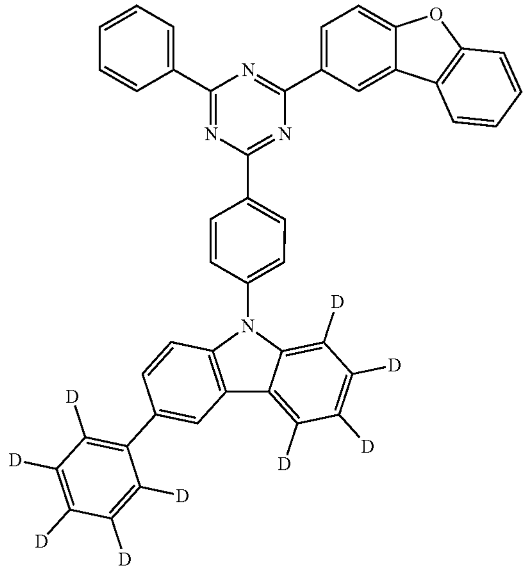
B42
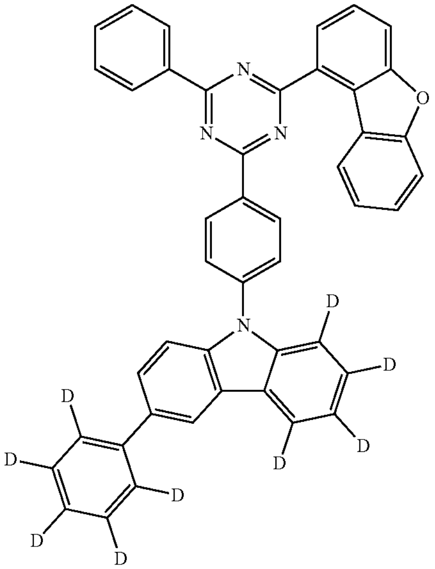

-continued
B43
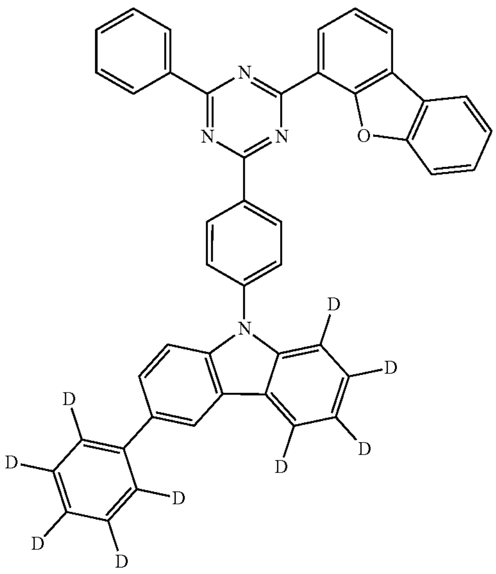
B44
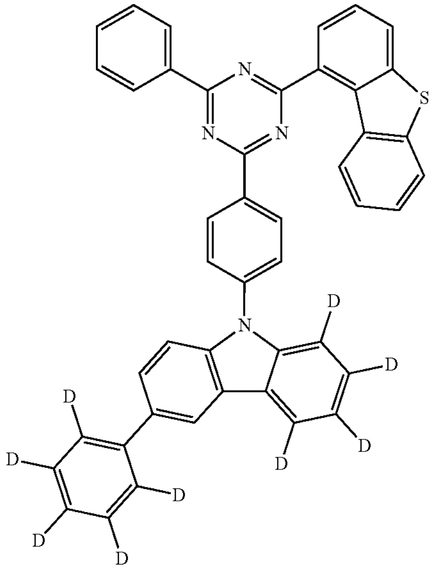
-continued
B45
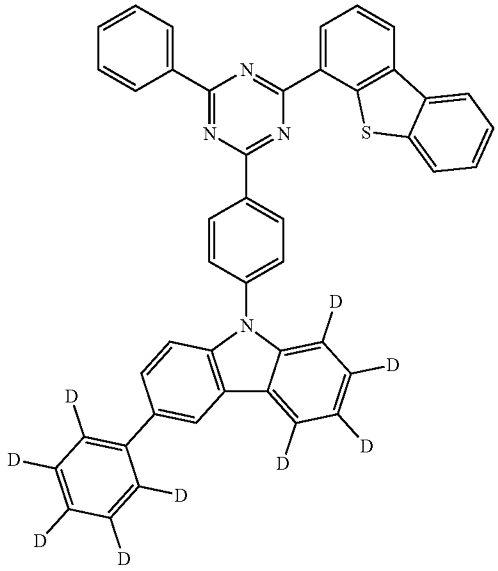
B46
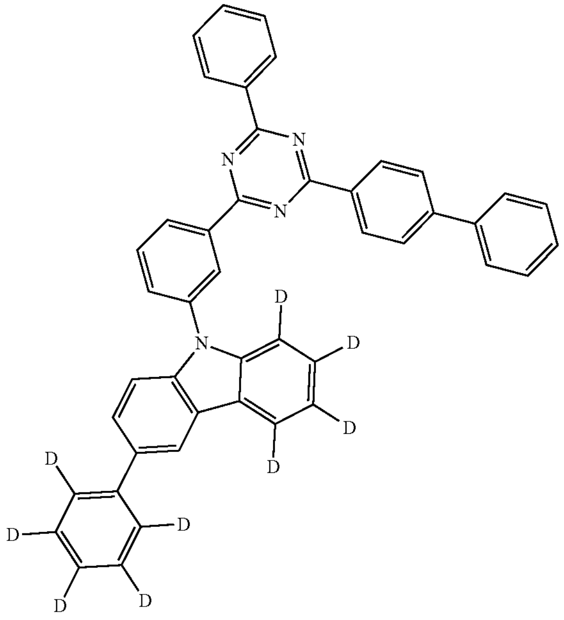

B47
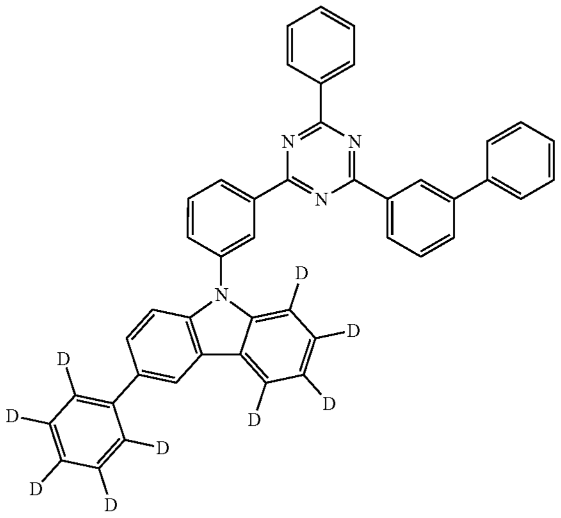
B48
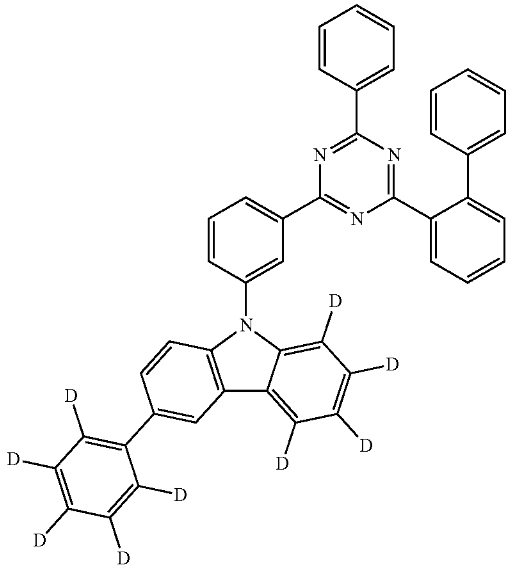
B49
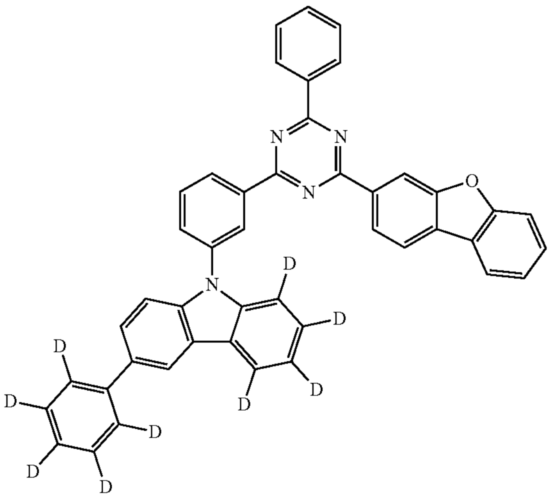
B50
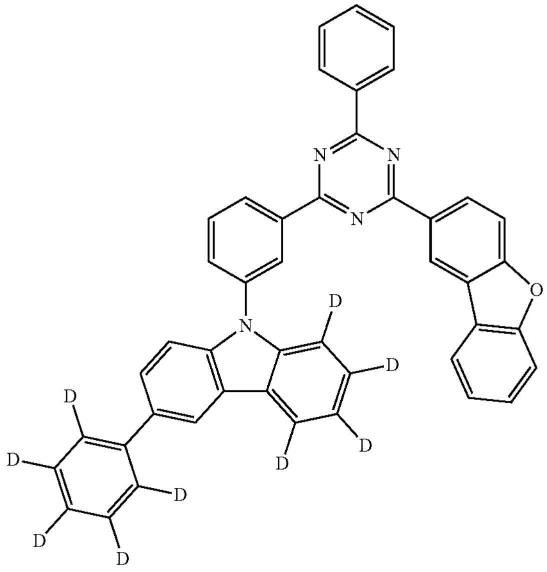
B51
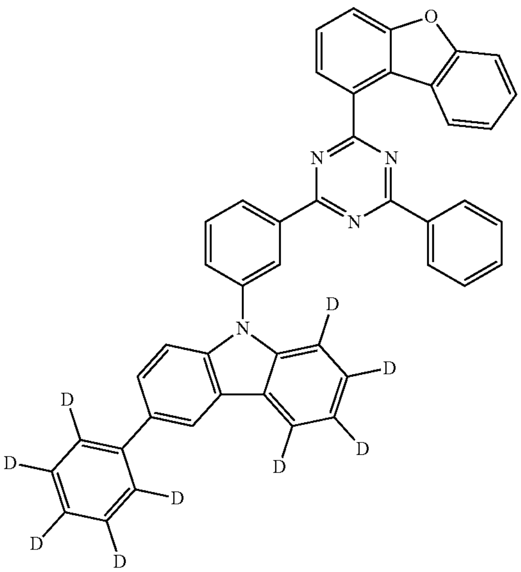

-continued
B52
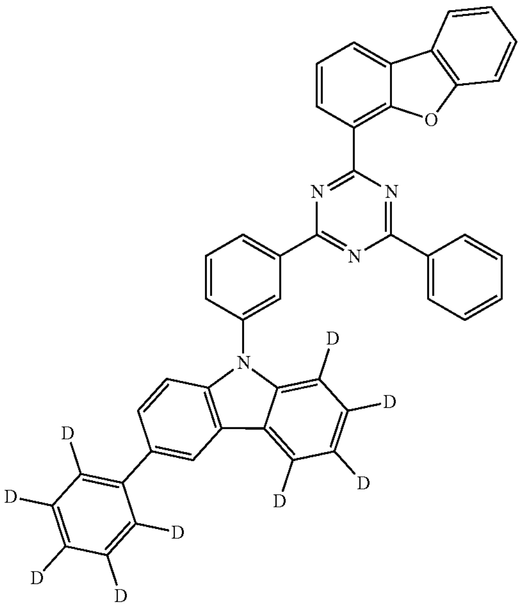
B53
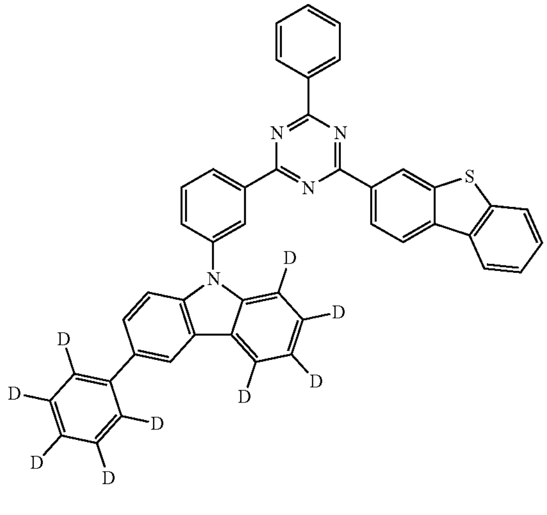
-continued
B54
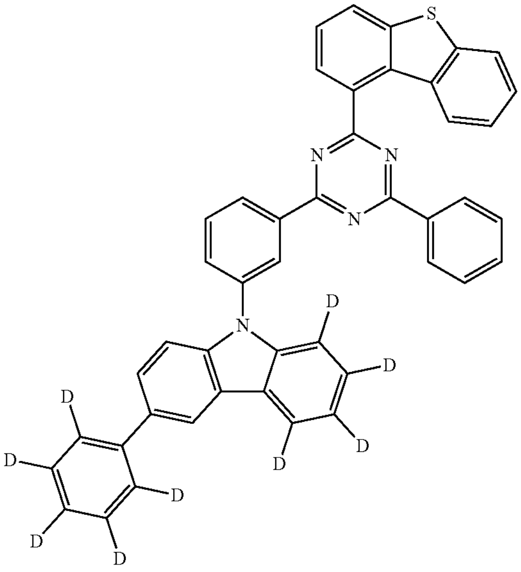
B55
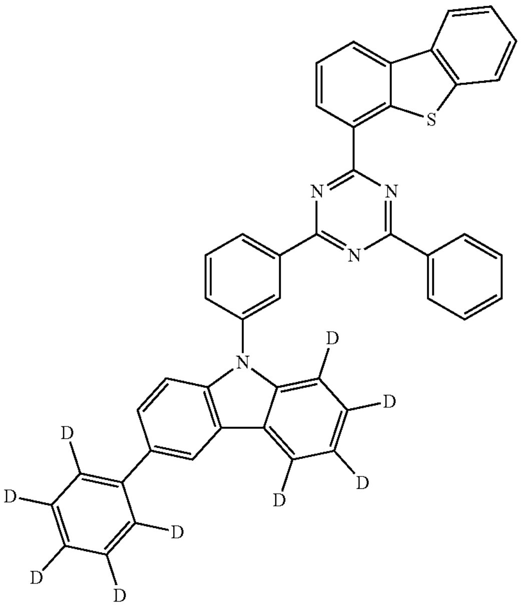

-continued
B56
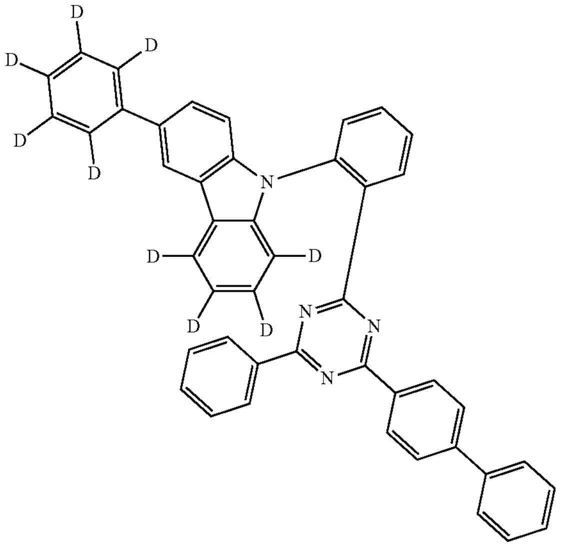
B57
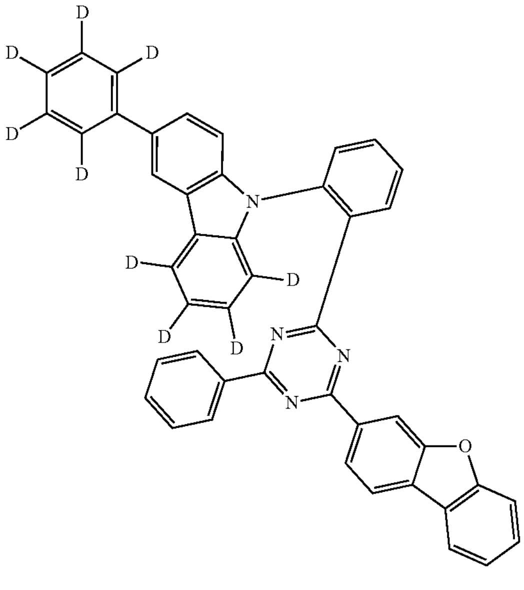
-continued
B58
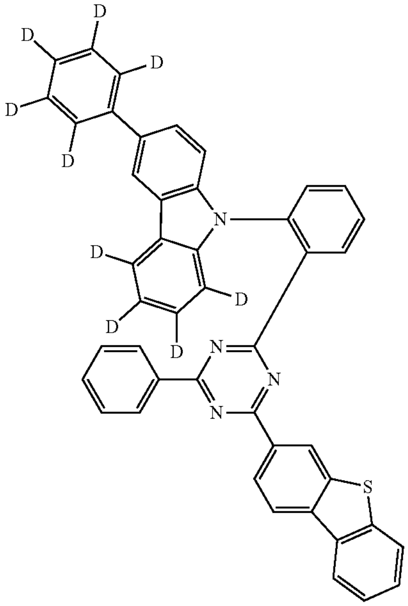
B59
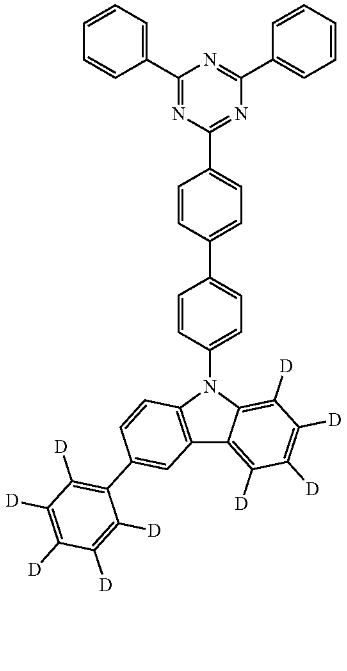

-continued
B60
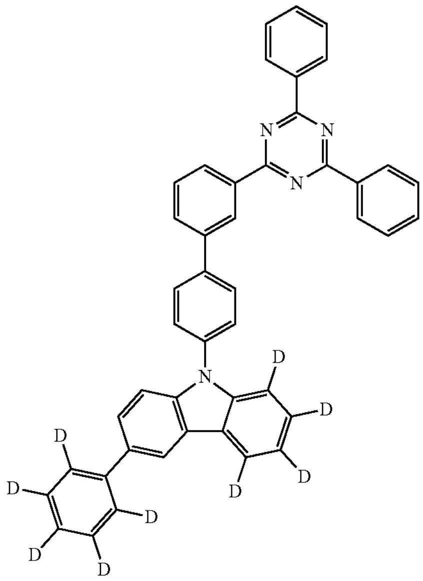
B61
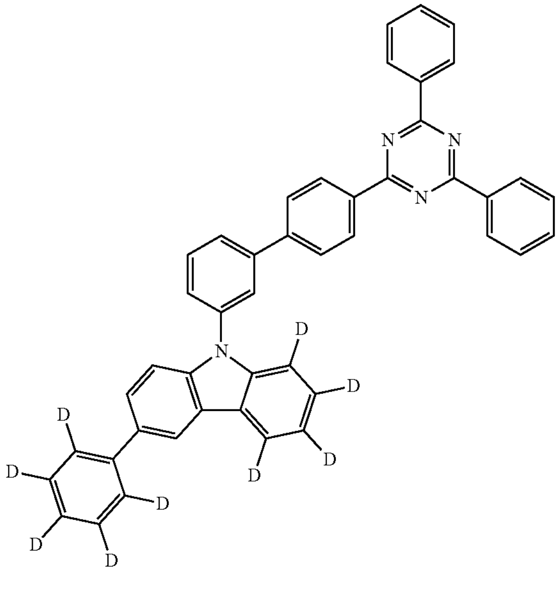
-continued
B62
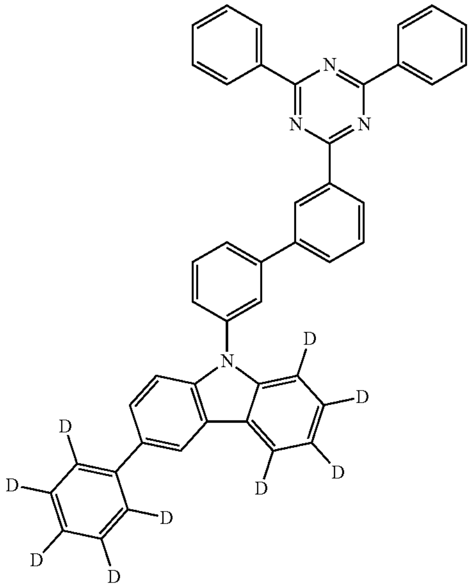
B63
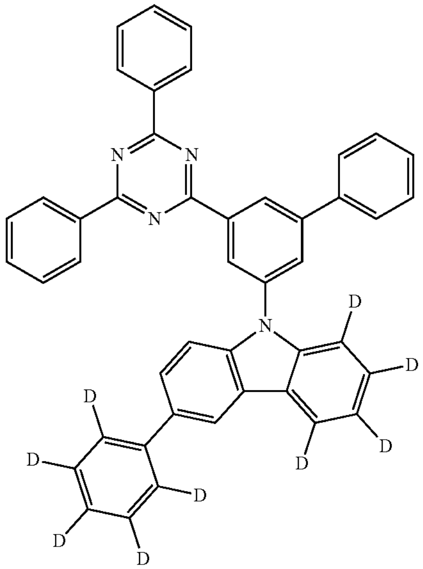
B64
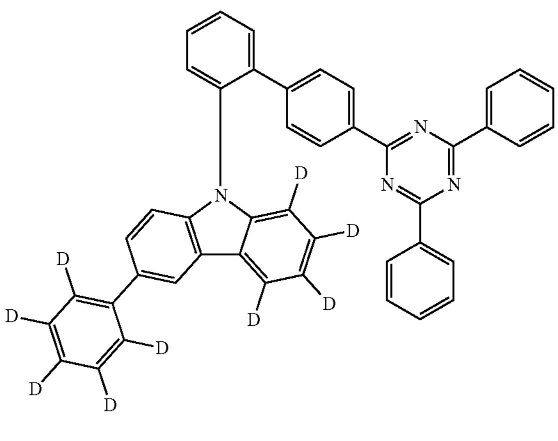

-continued
B65
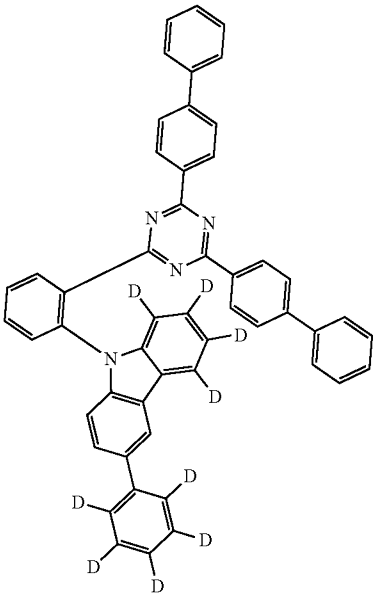
B66
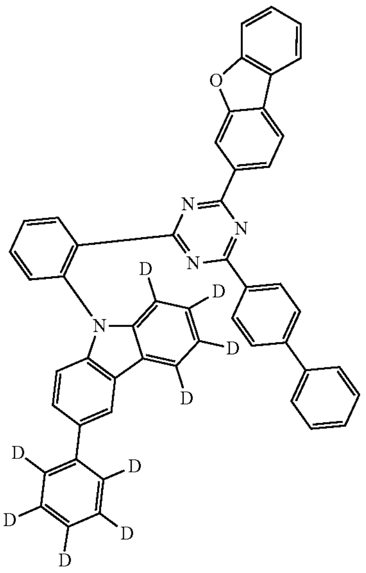
-continued
B67
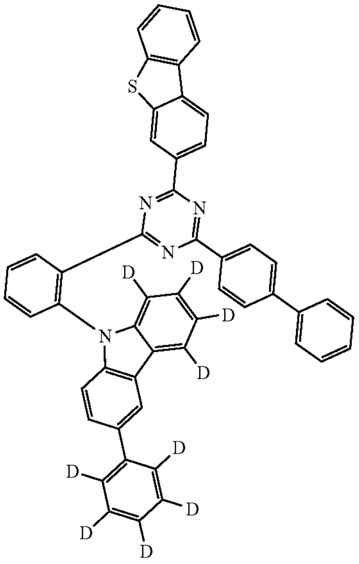
B68
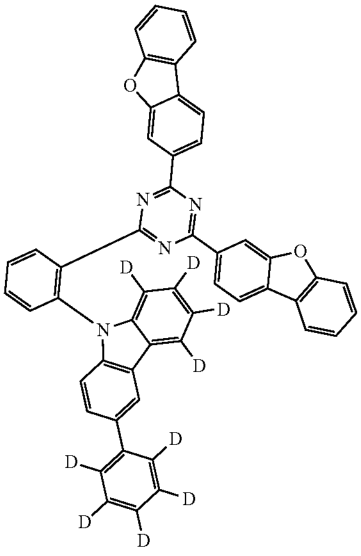

B69
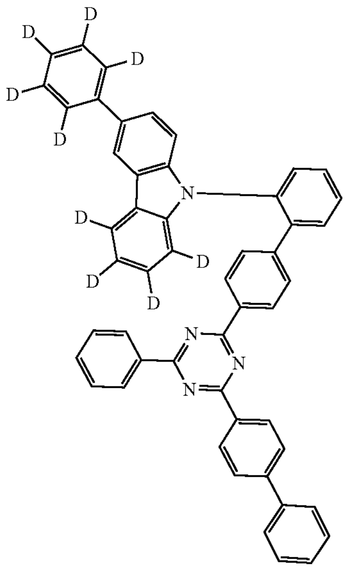
B70
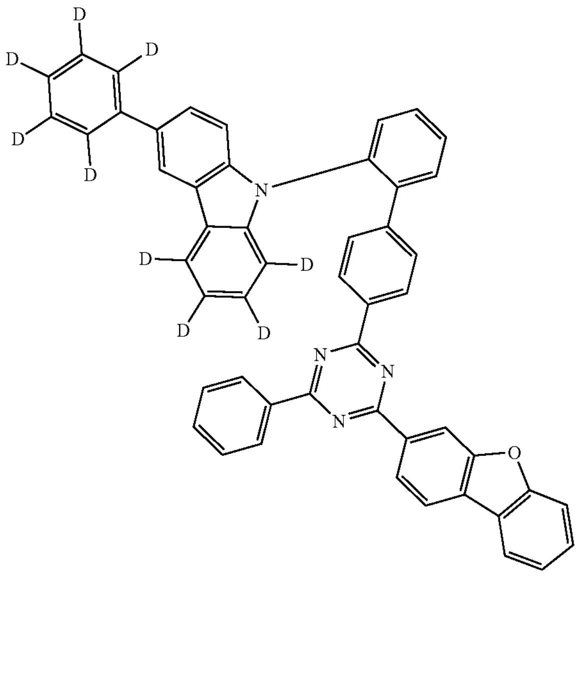
B71
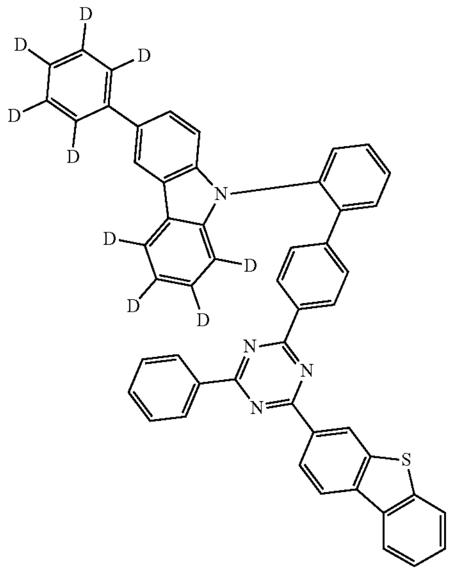
B72
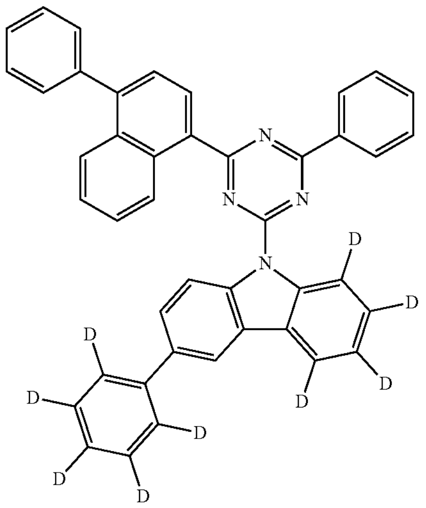
C1
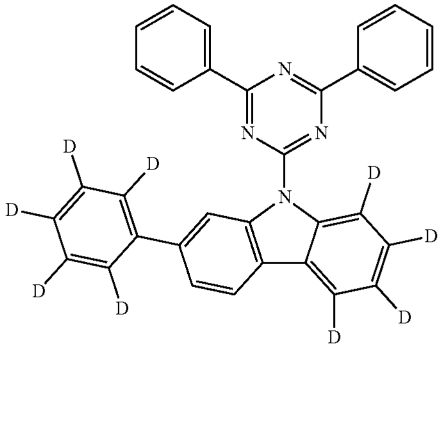

-continued
C2
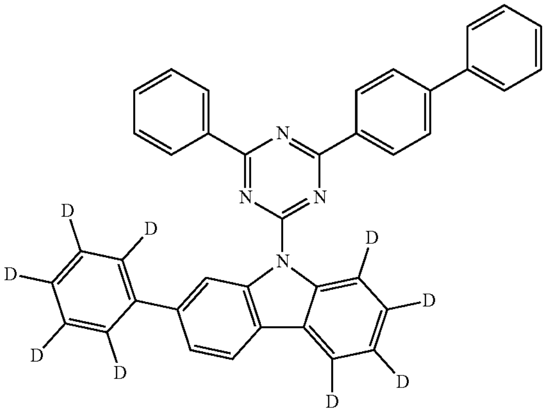
C3
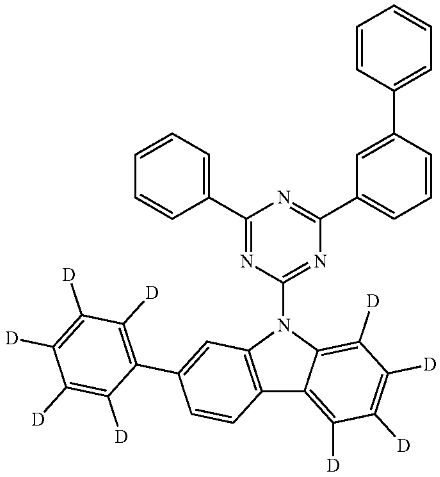
C4
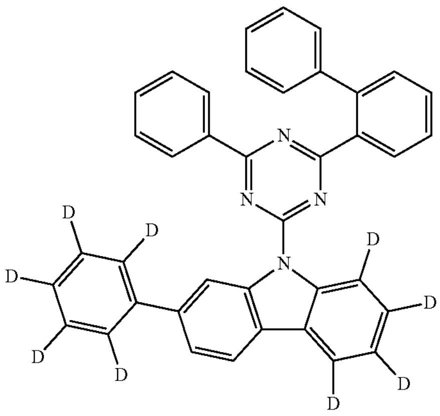
-continued
C5
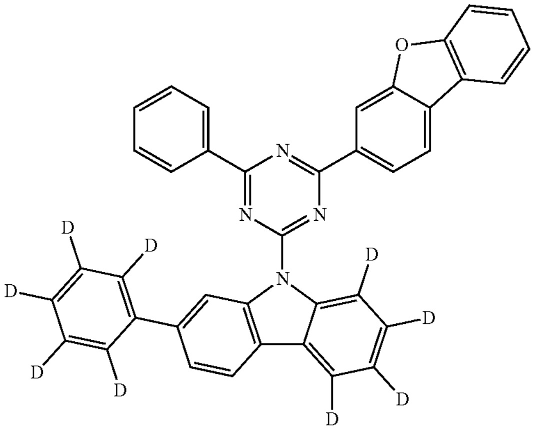
C6
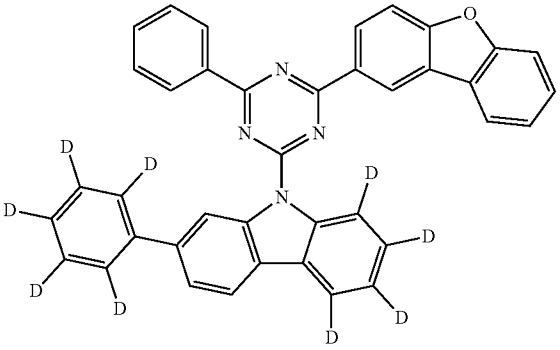
C7
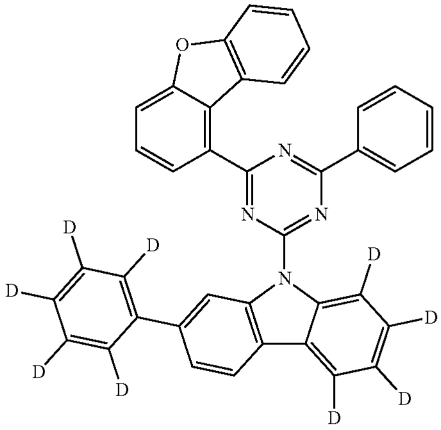
C8
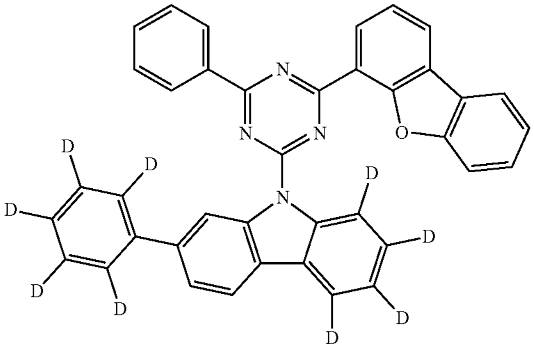

C9
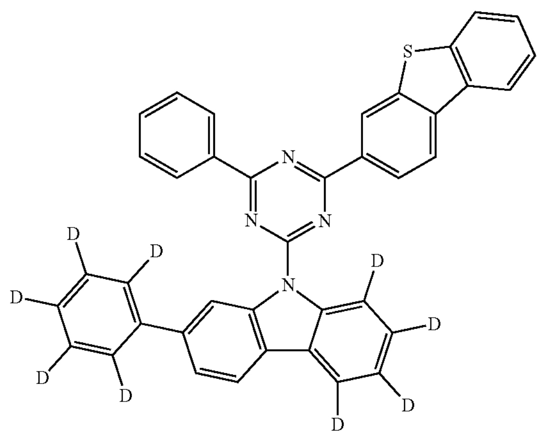
C10
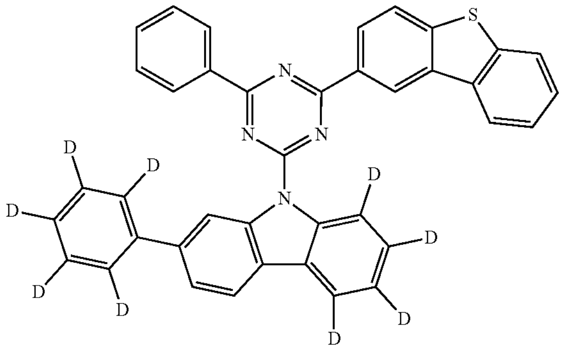
C11
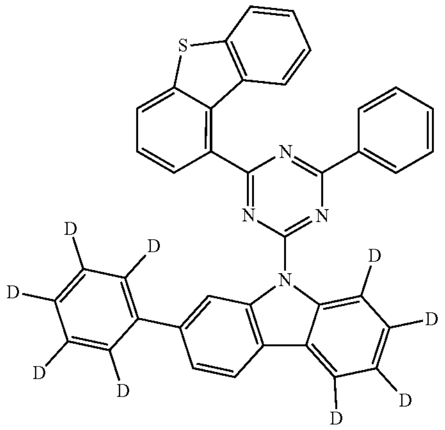
C12
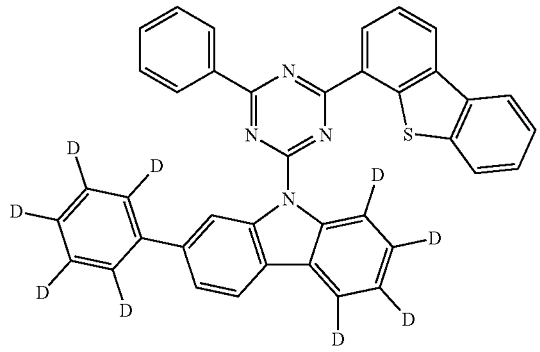
C13
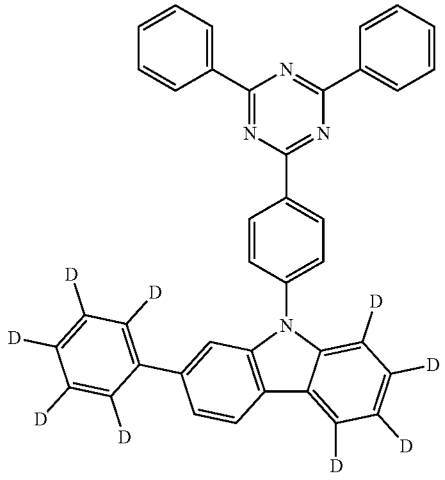
C14
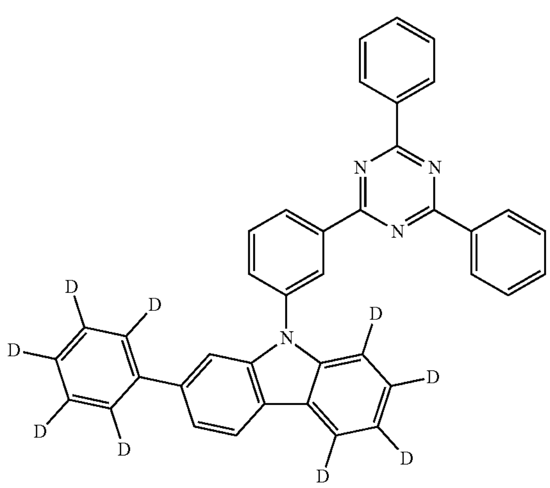
C15
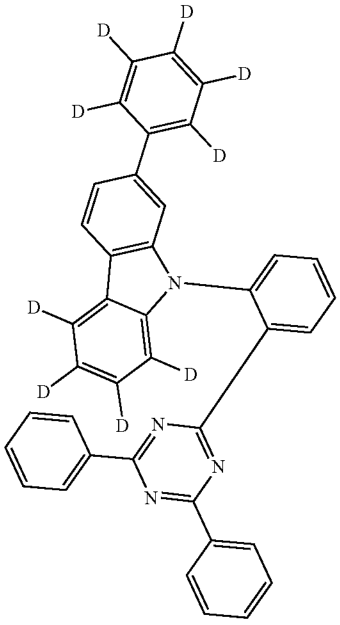

-continued
C16
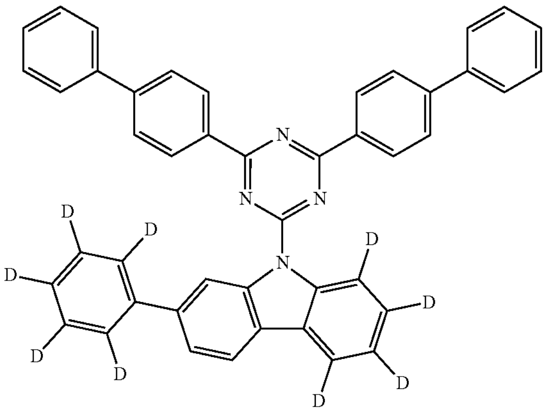
C17
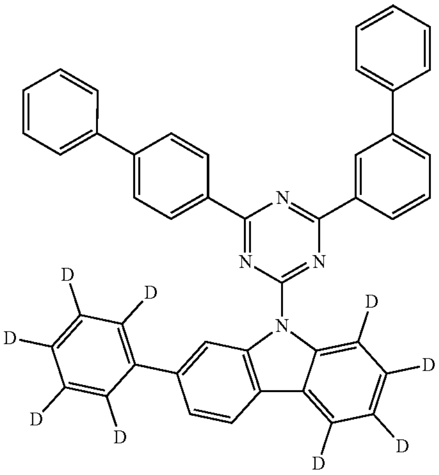
C18
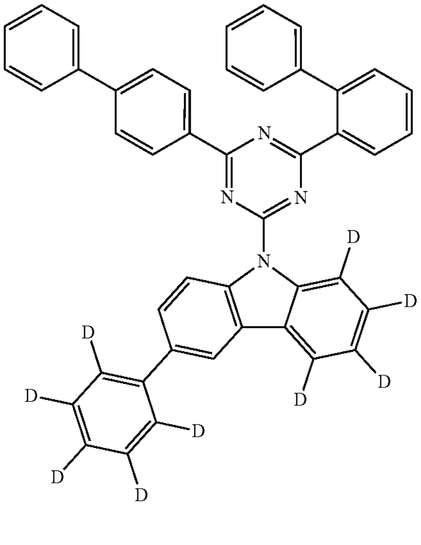
-continued
C19
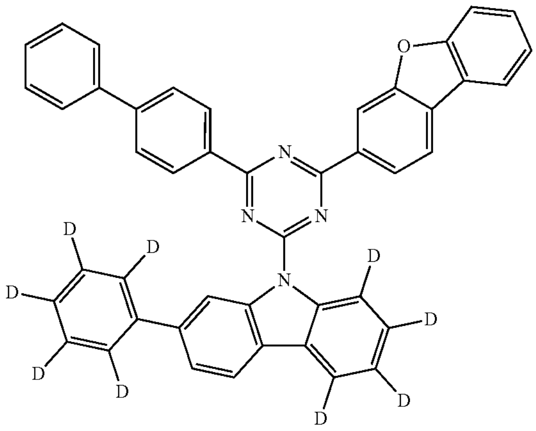
C20
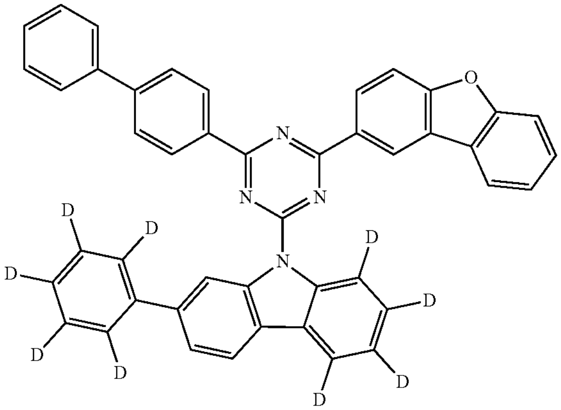
C21
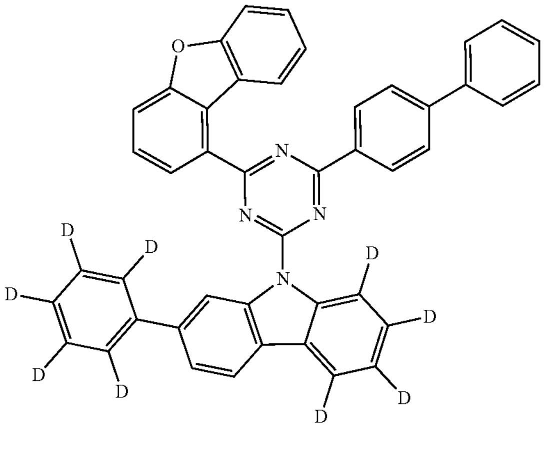

-continued
C22
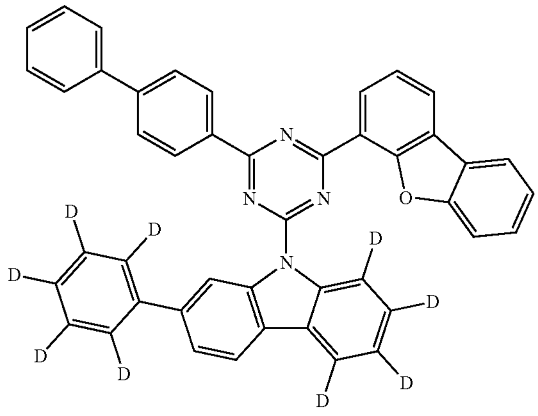
C23
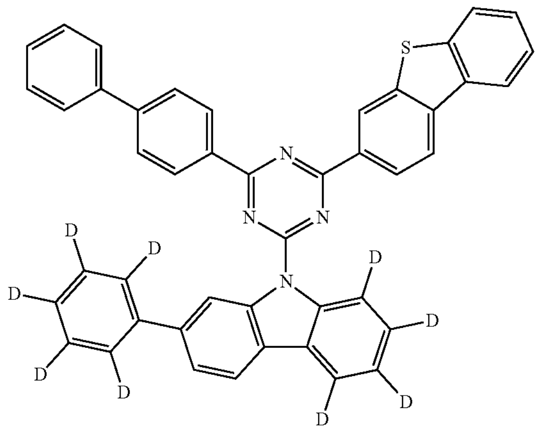
C24
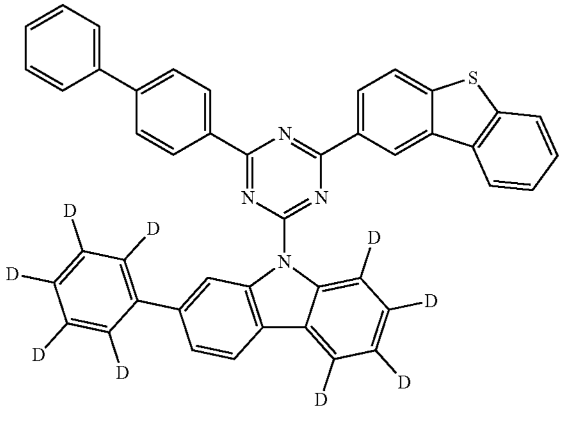
-continued
C25
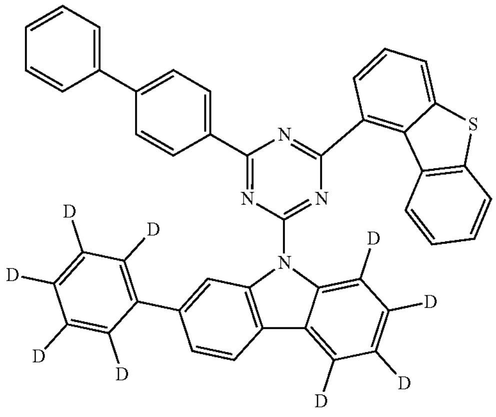
C26
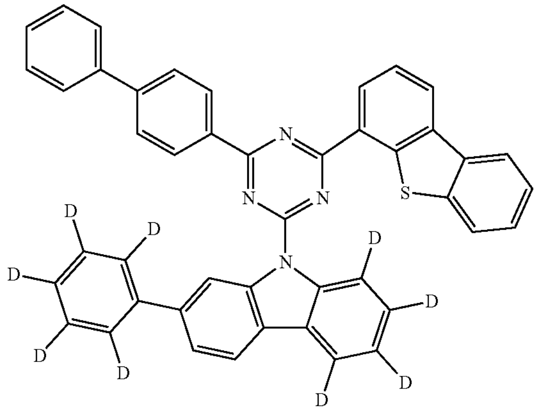
C27
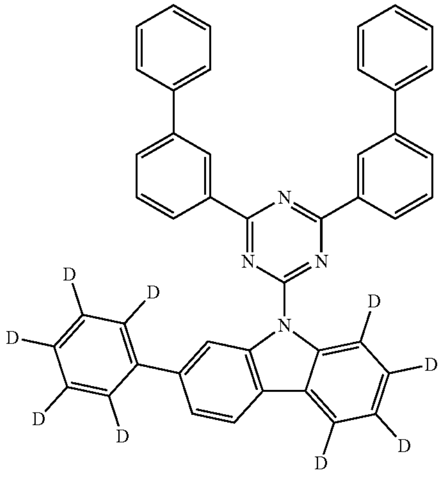

-continued
C28
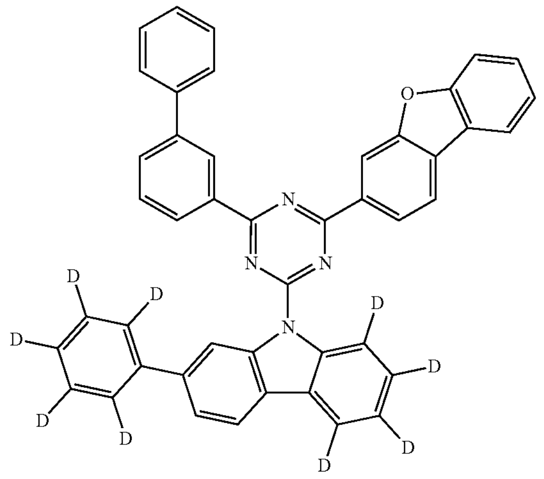
C29
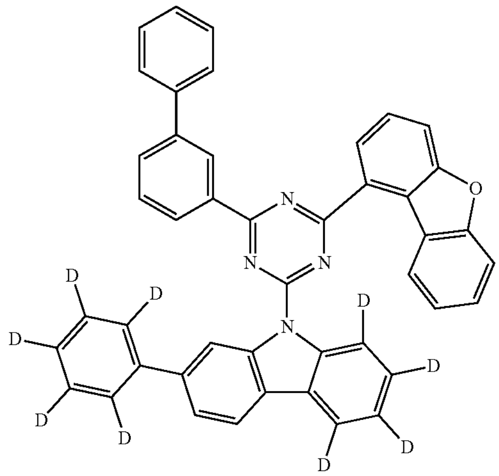
C30
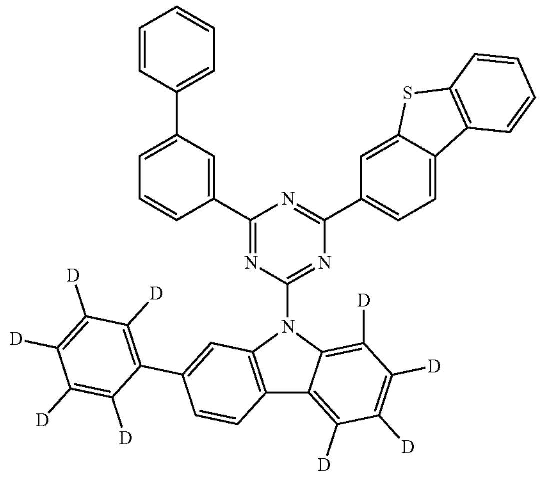
-continued
C31
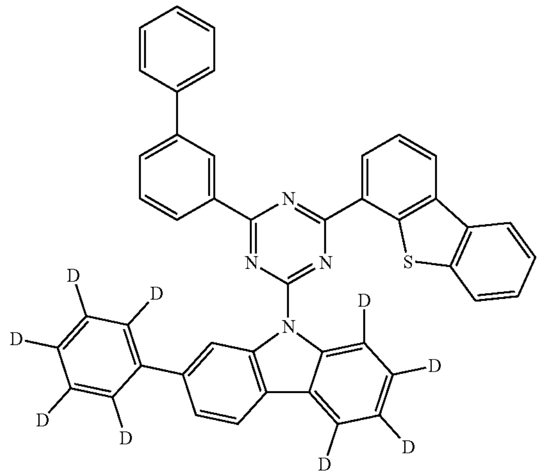
C32
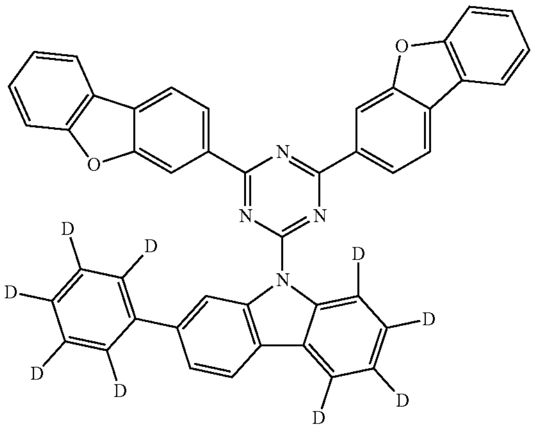
C33
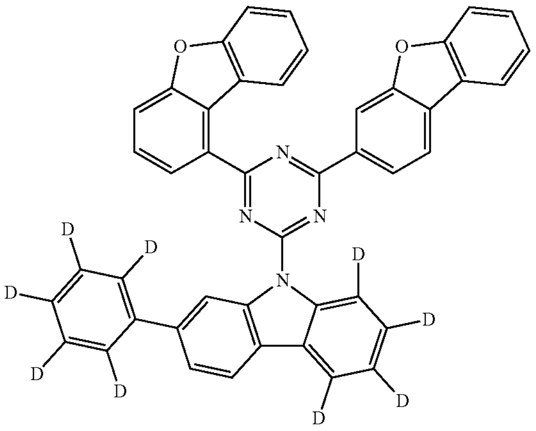

C34
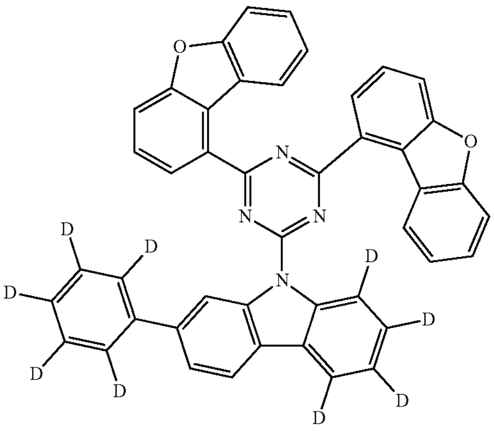
C35
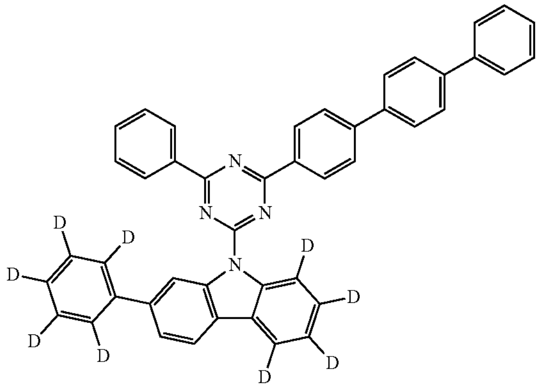
C36
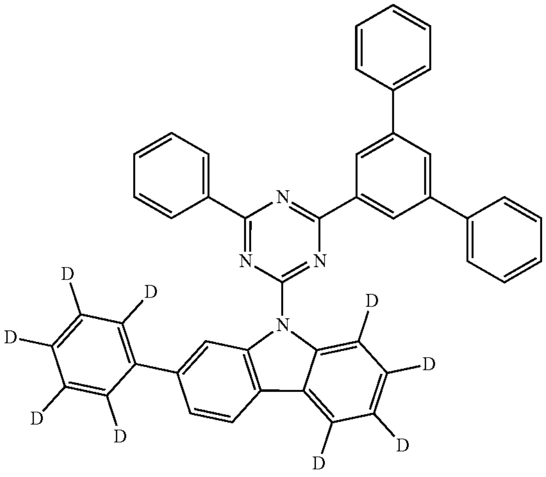
C37
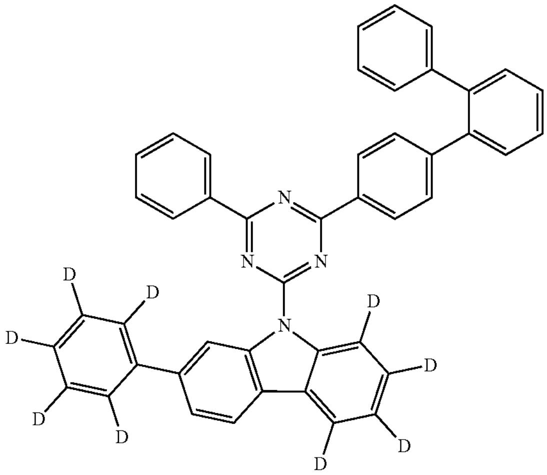
C38
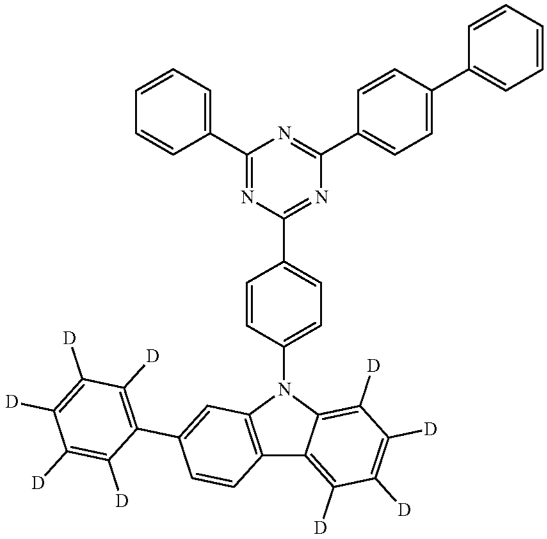
C39
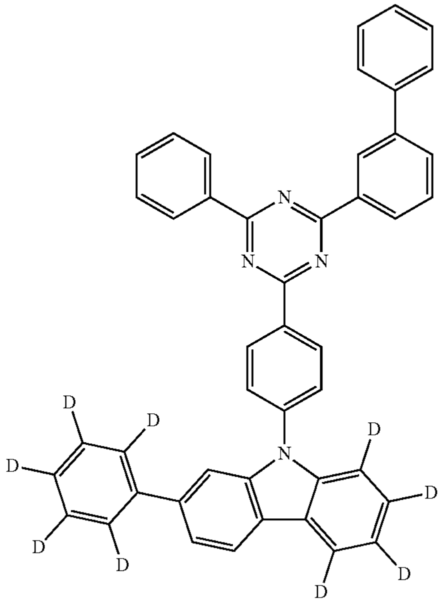

-continued
C40
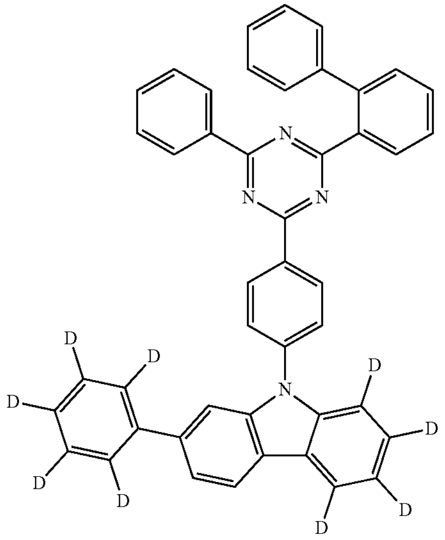
C41
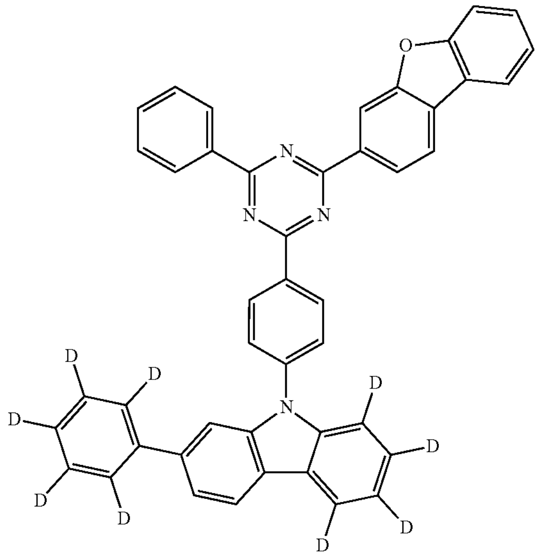
C42
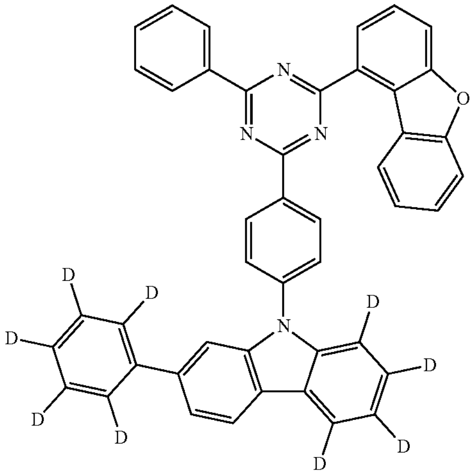
-continued
C43
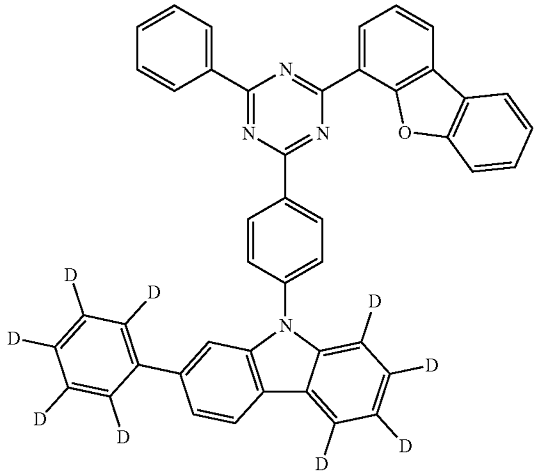
C44
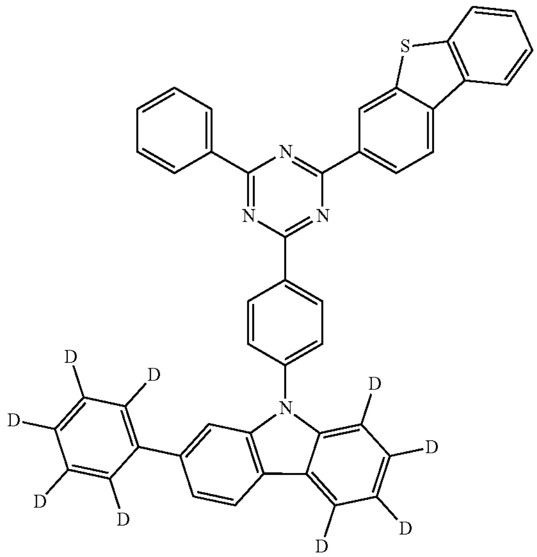
C45
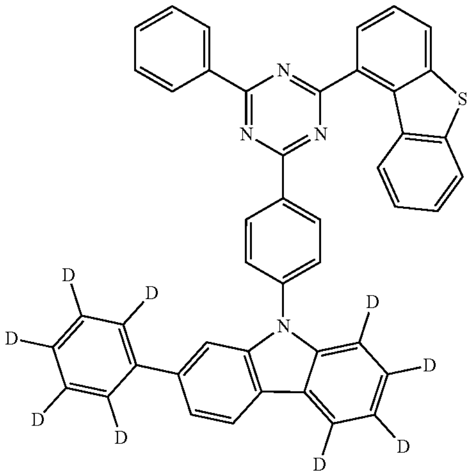

-continued
C46
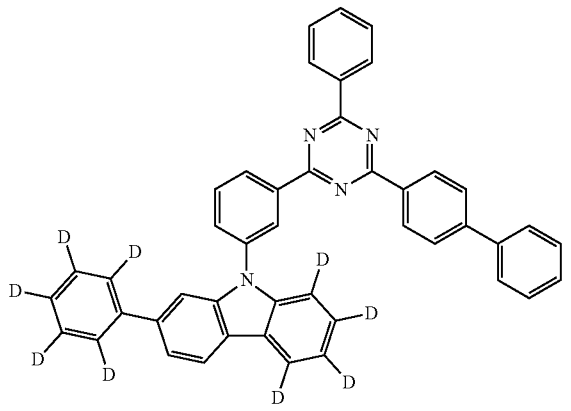
C47
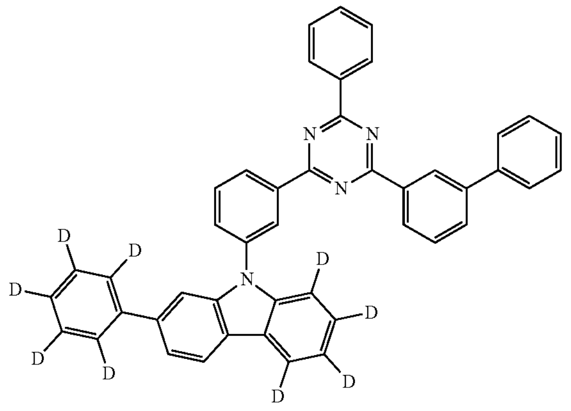
C48
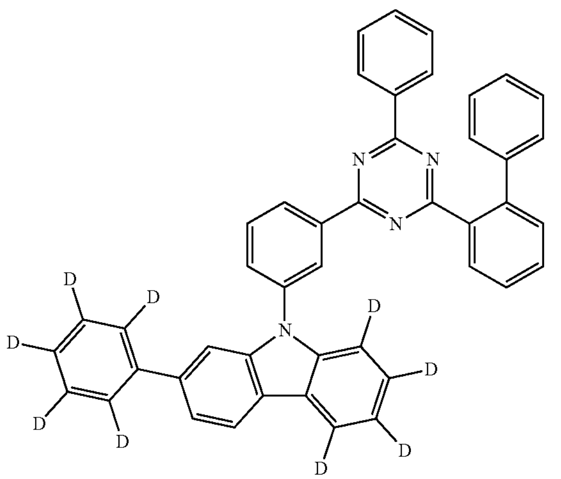
-continued
C49
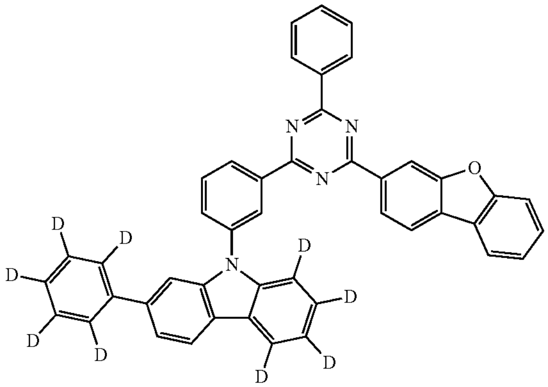
C50
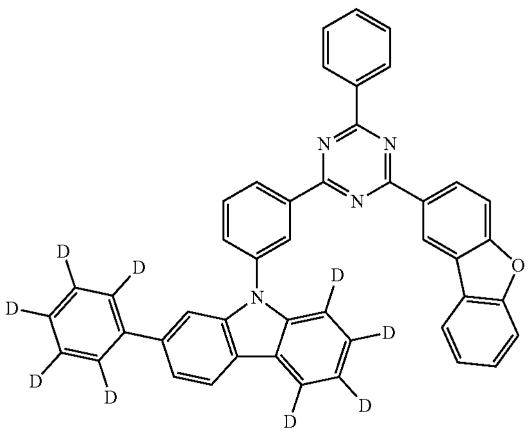
C51
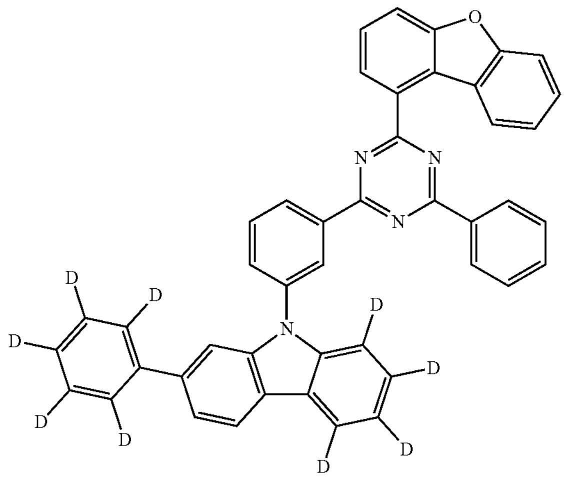

-continued
C52
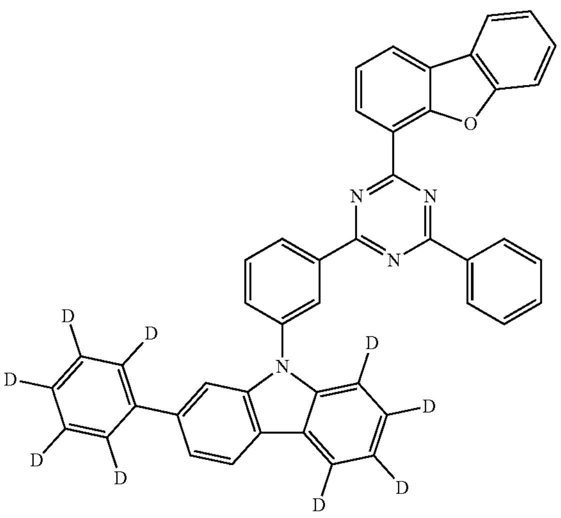
C53
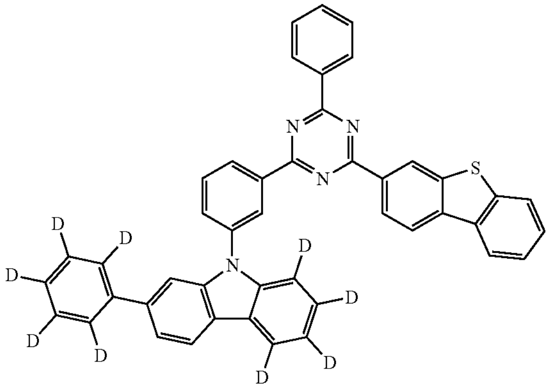
C54
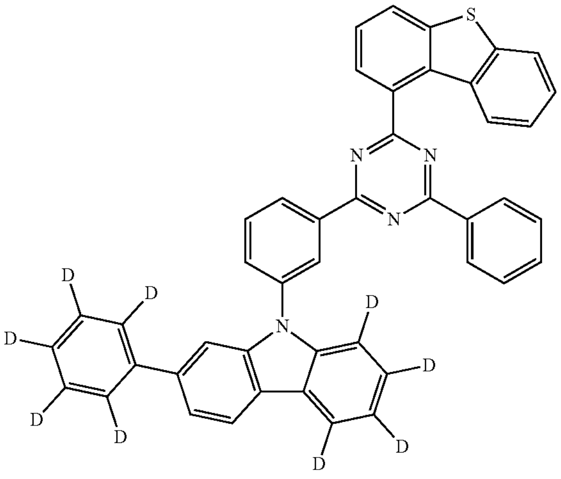
-continued
C55
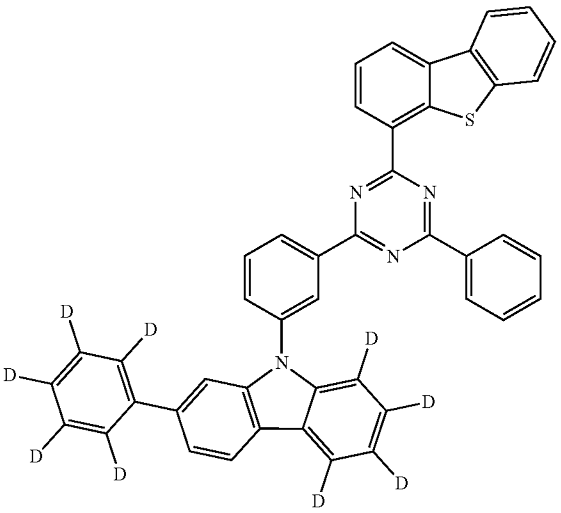
C56
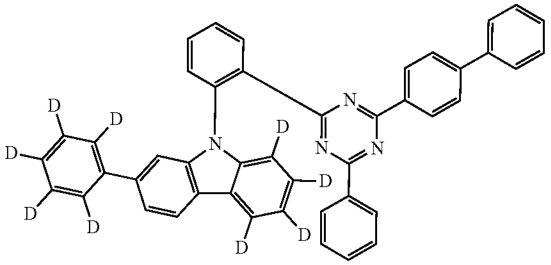
C57
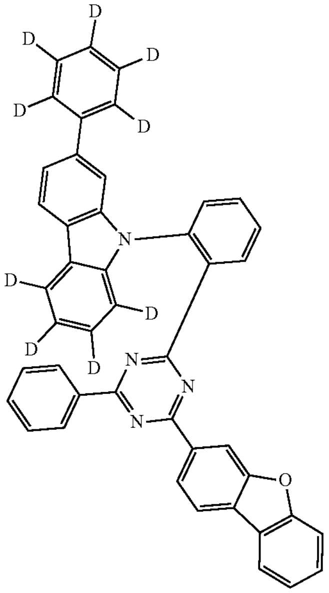

-continued
C58
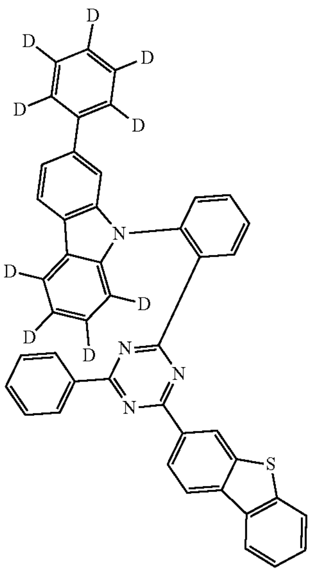
C59
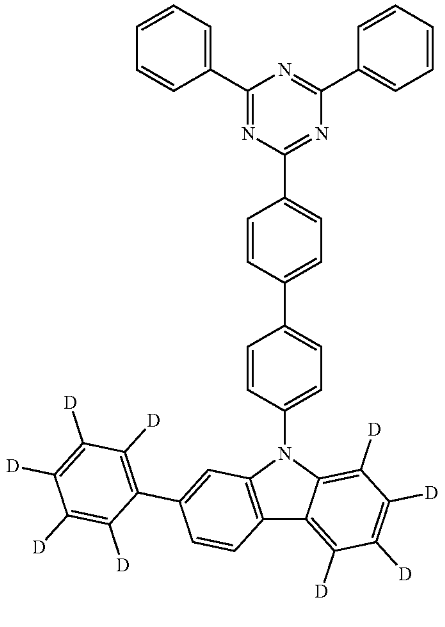
-continued
C60
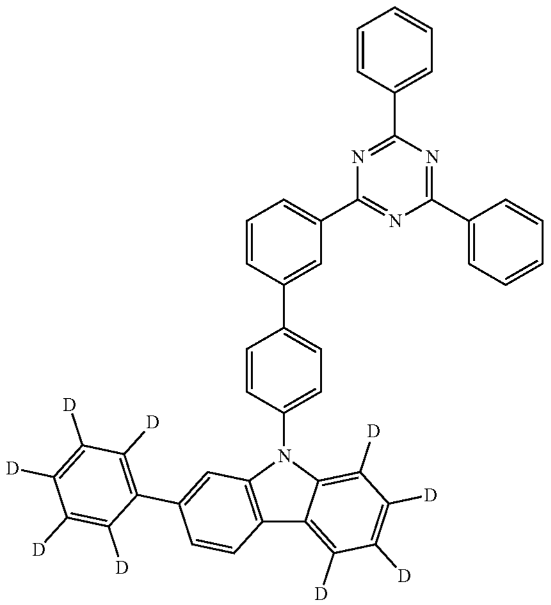
C61
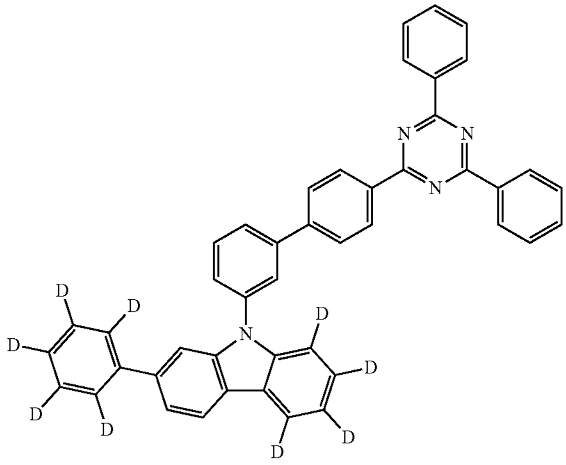
C62
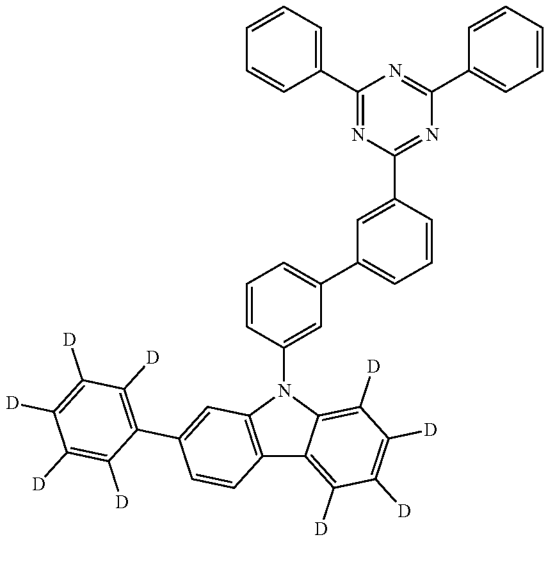

-continued
C63
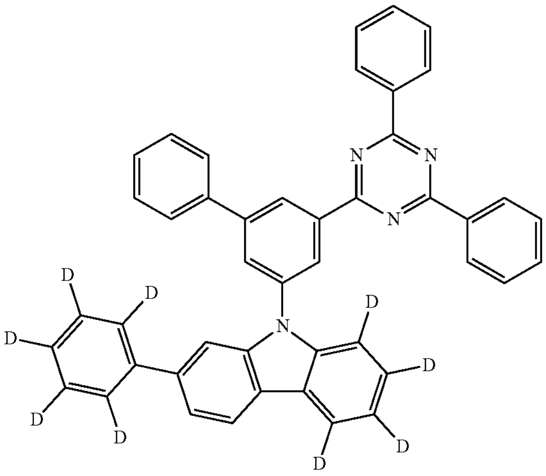
C64
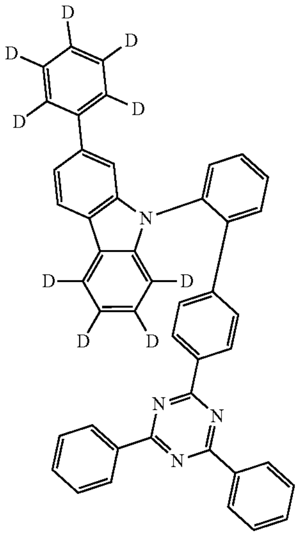
C65
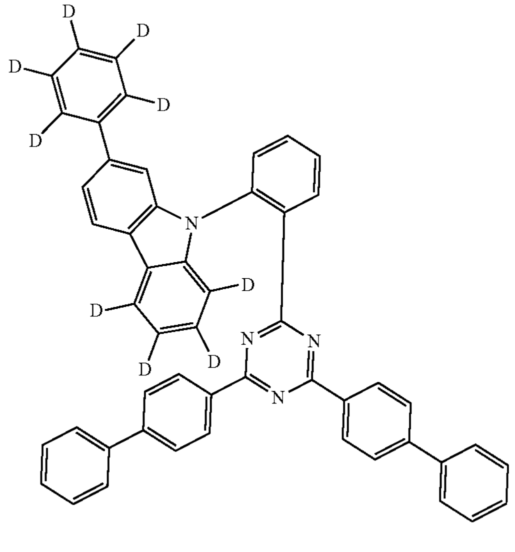
-continued
C66
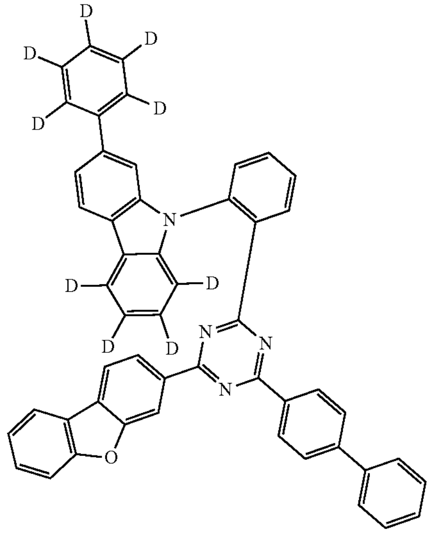
C67
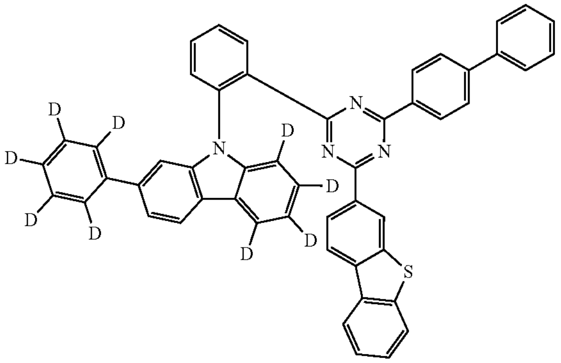
C68
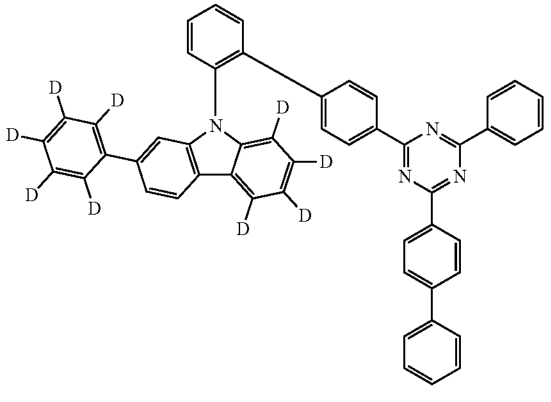

-continued
C69
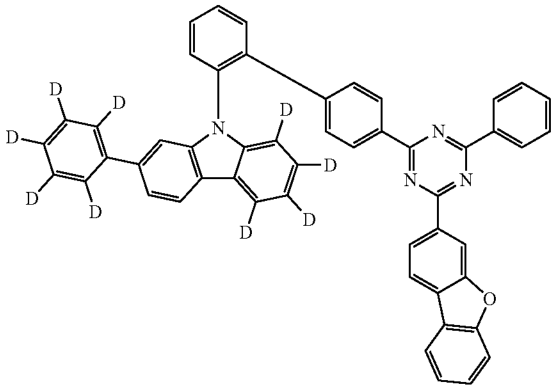
C70
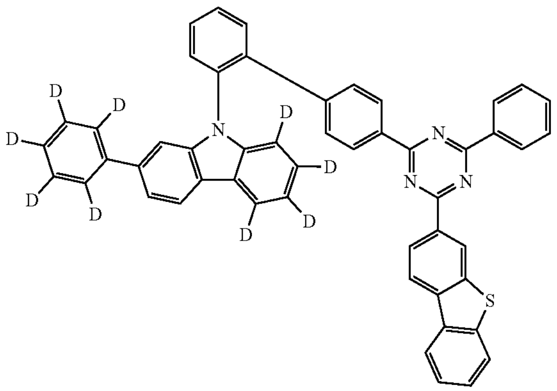
C71
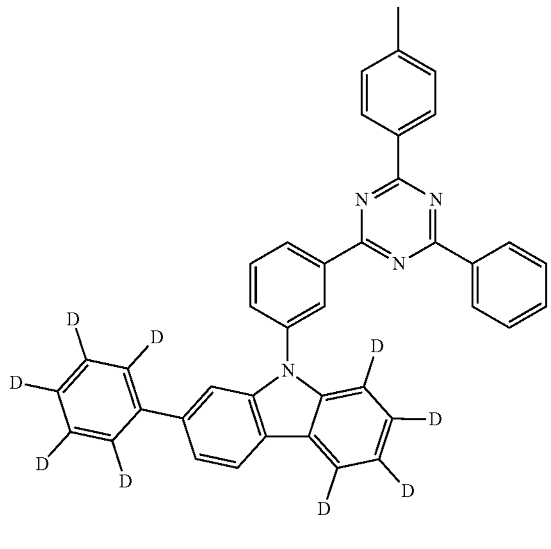
-continued
C72
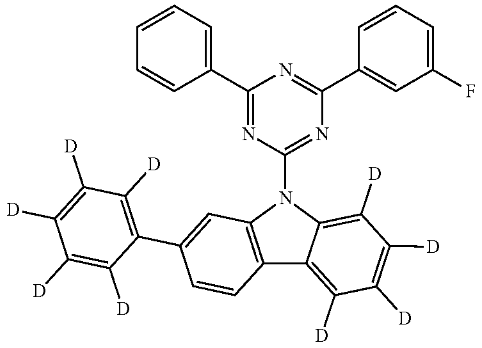
D1
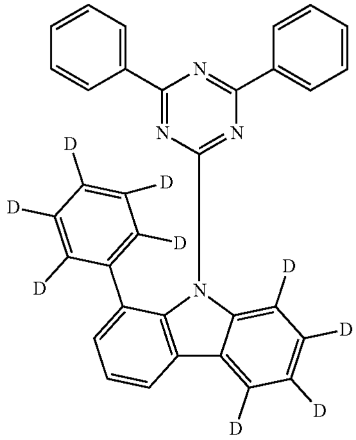
D2
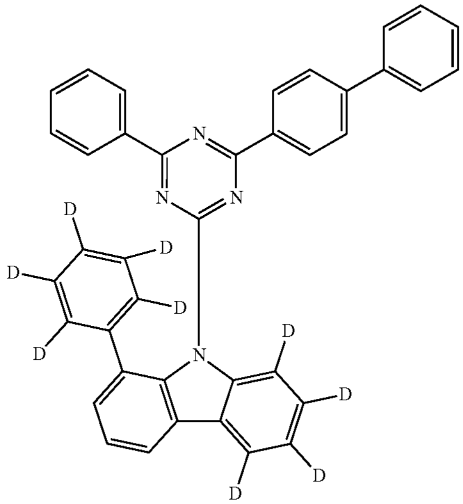

D3
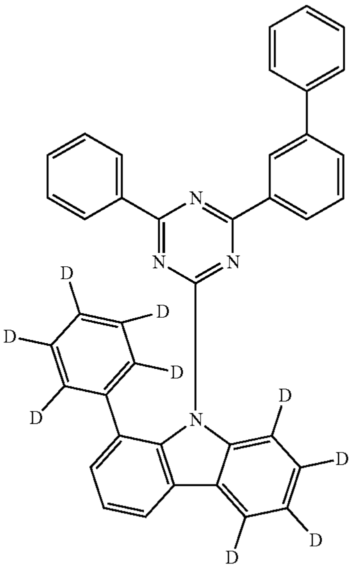
D4
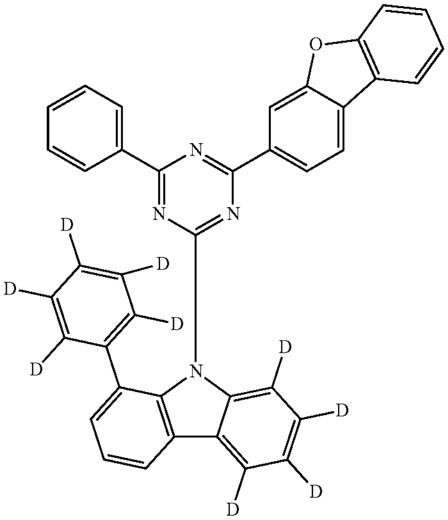
D5
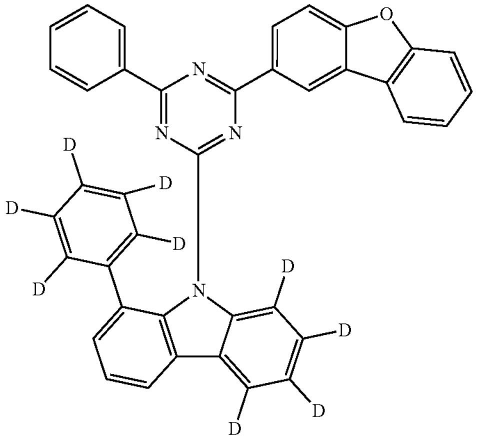
D6
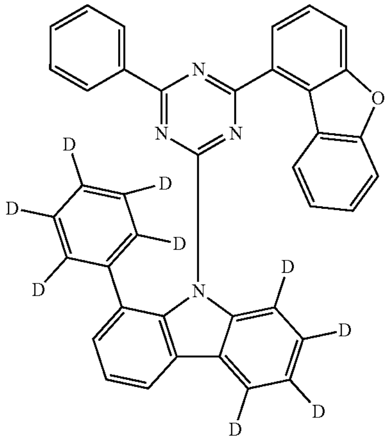
D7
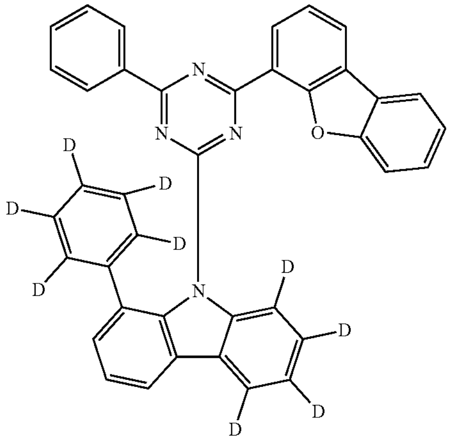
D8
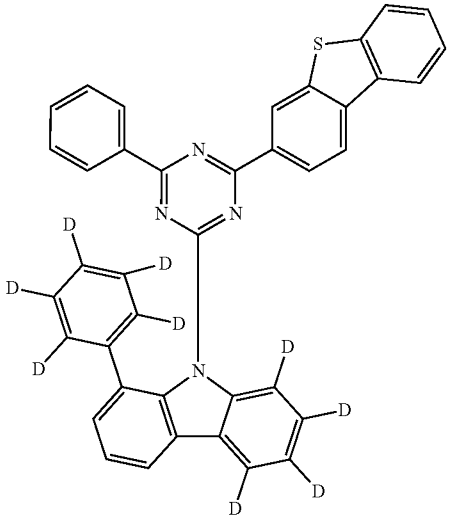

-continued
D9
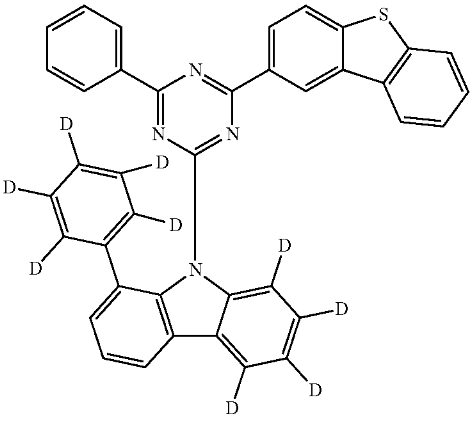
D10
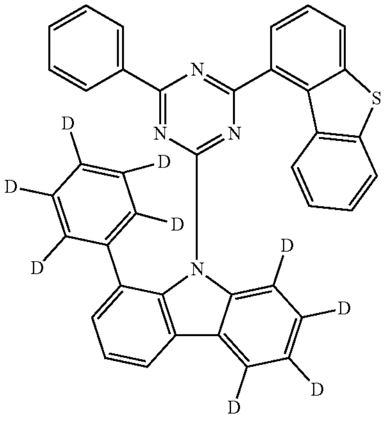
D11
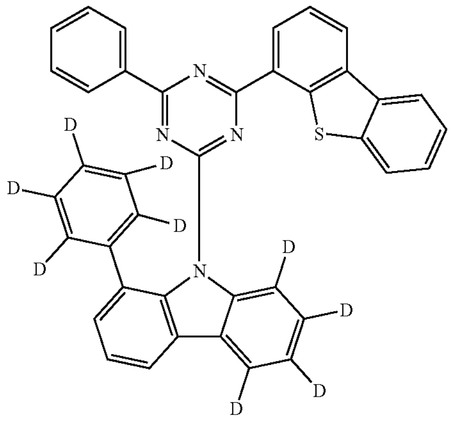
D12
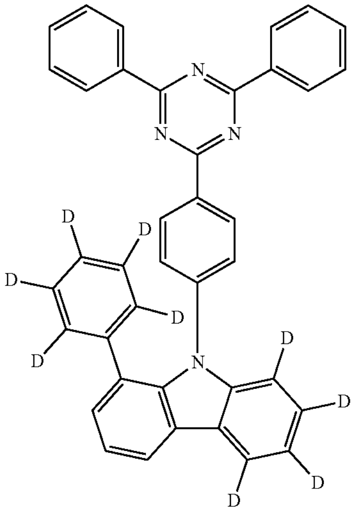
D13
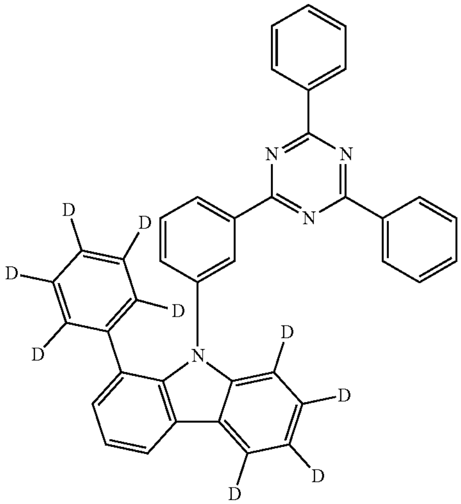
D14
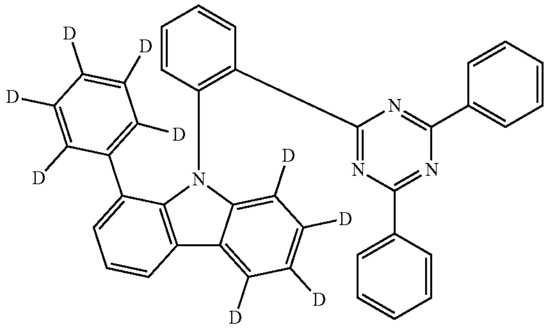

-continued
D15
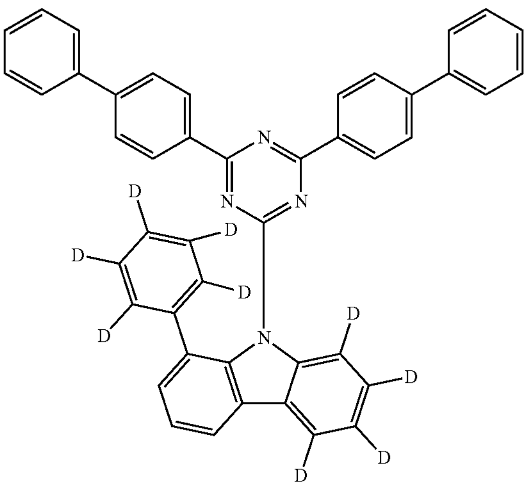
D16
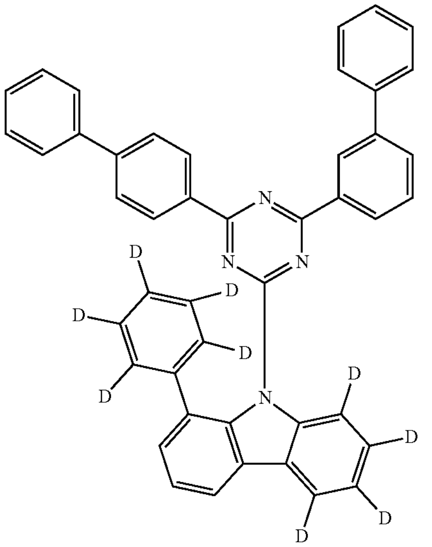
D17
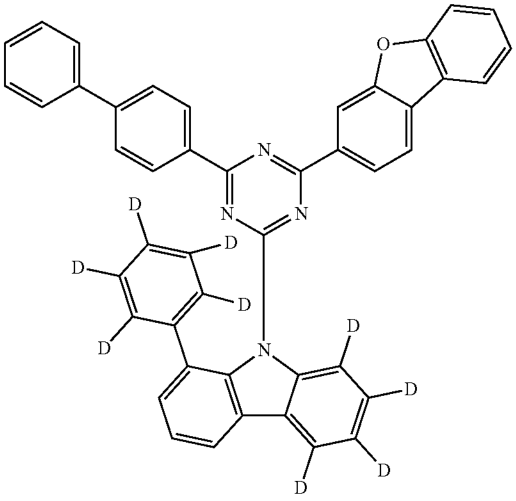
-continued
D18
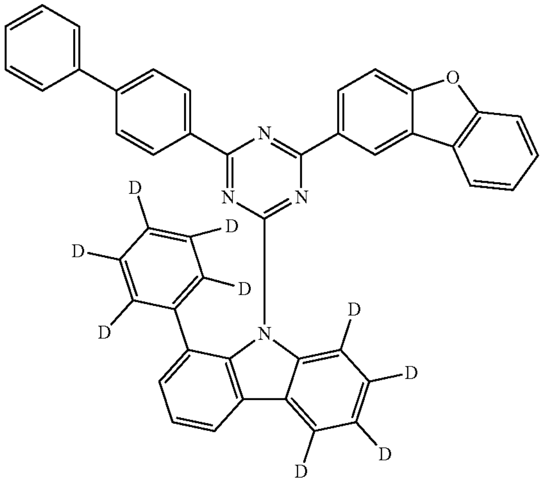
D19
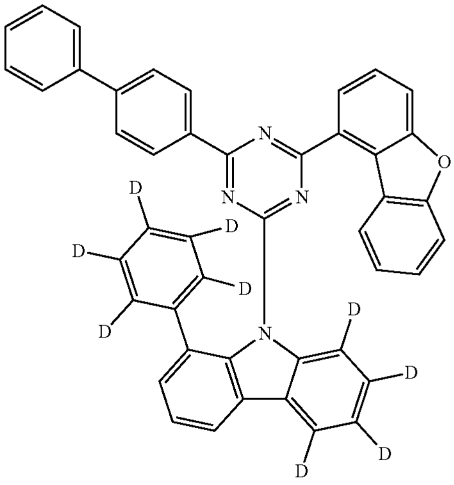
D20
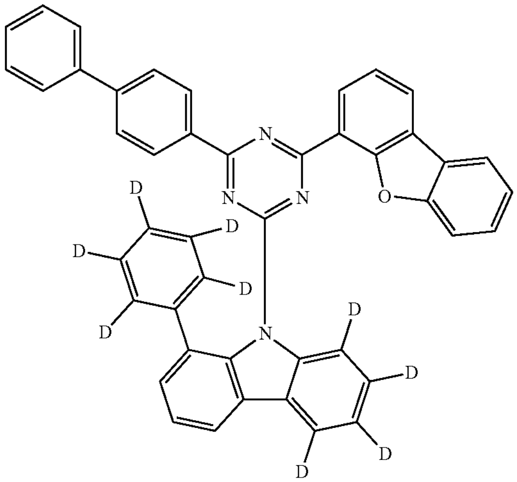

-continued
D21
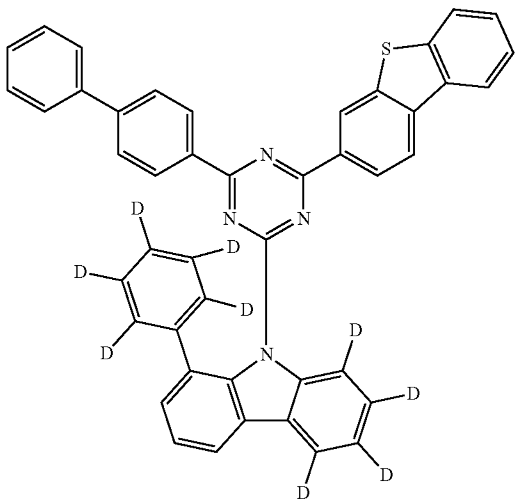
D22
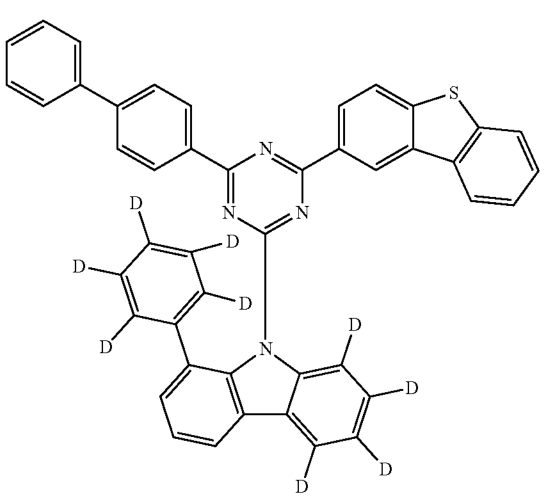
D23
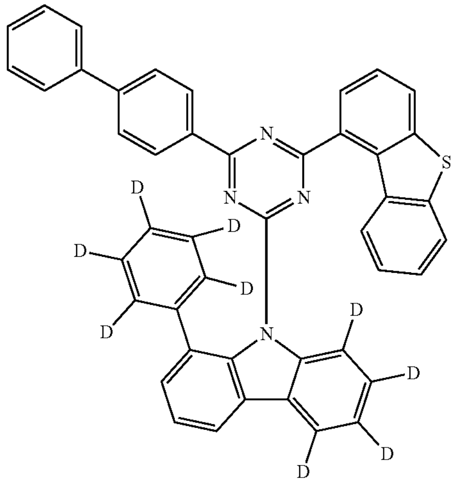
-continued
D24
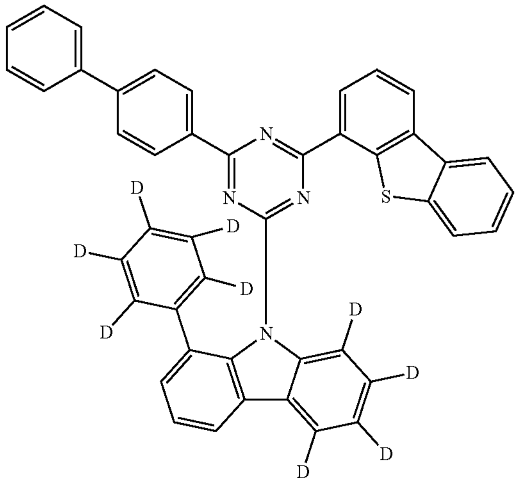
D25
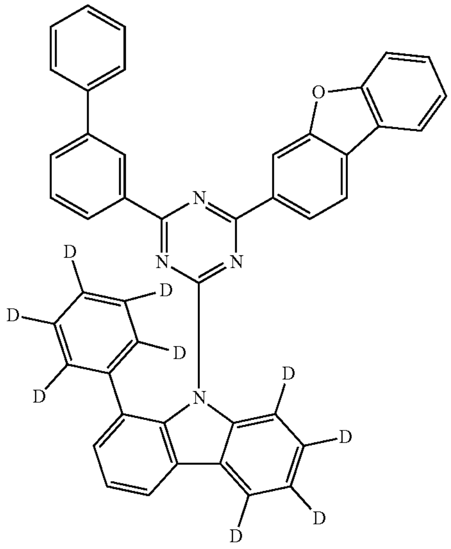
D26
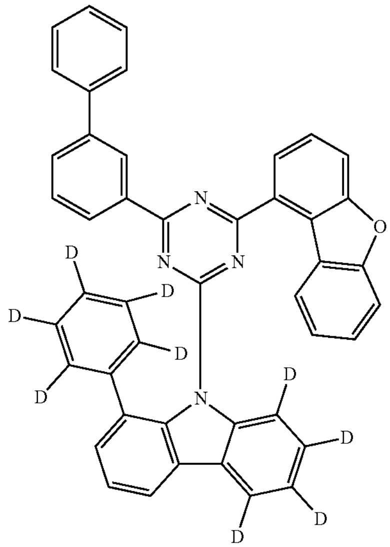

-continued
D27
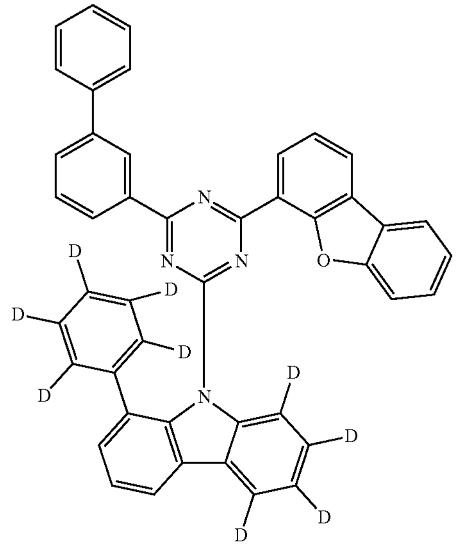
D28
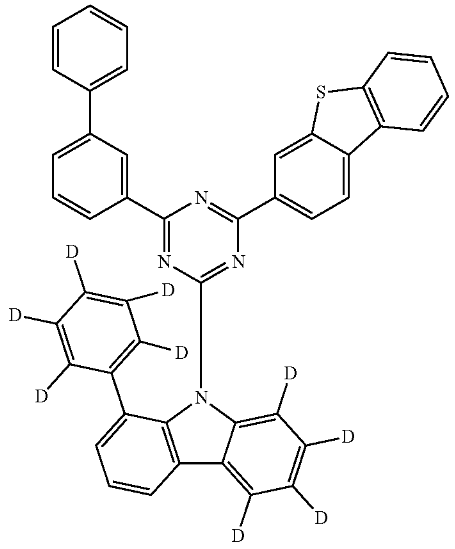
D29
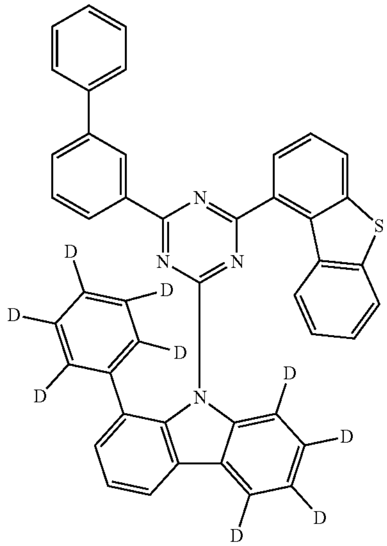
-continued
D30
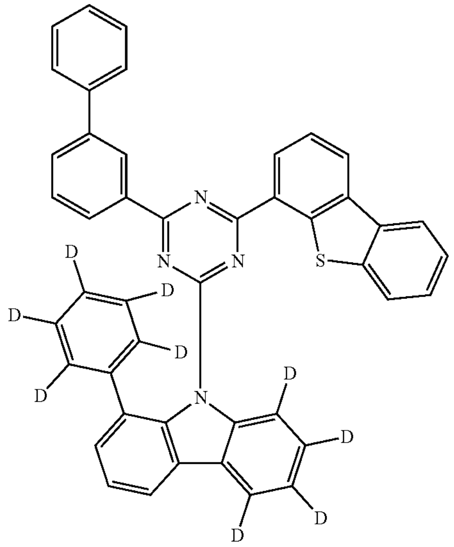
D31
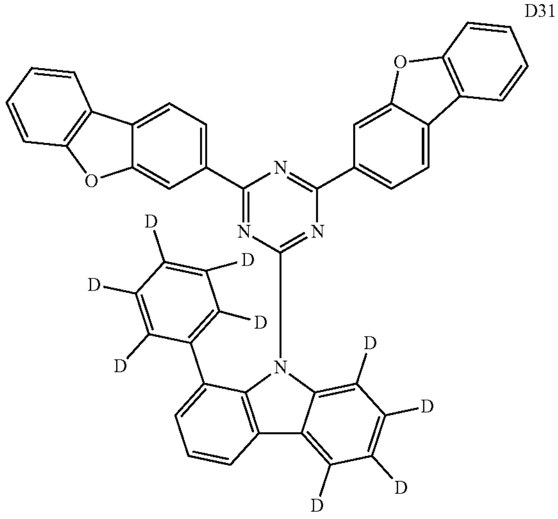
D32
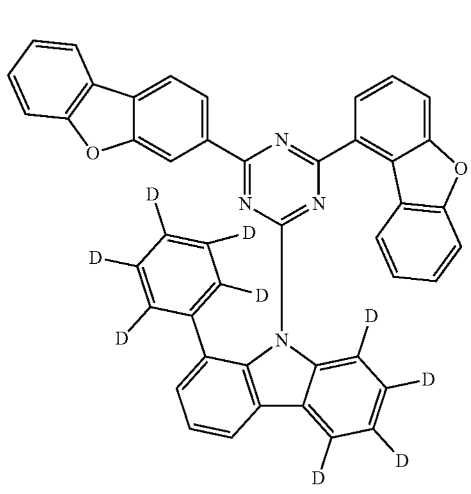

-continued
D33
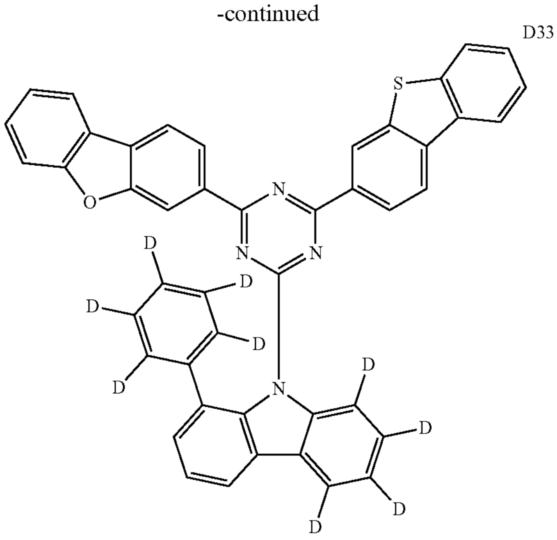
D34
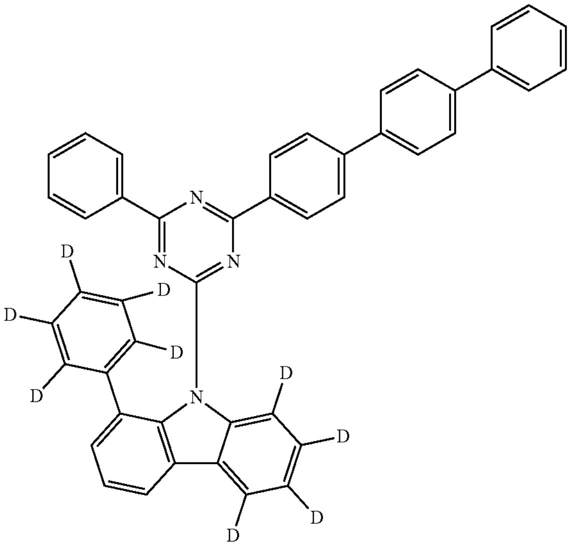
D35
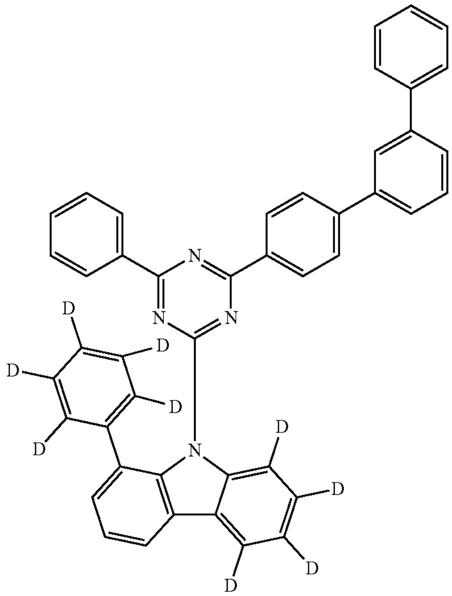
-continued
D36
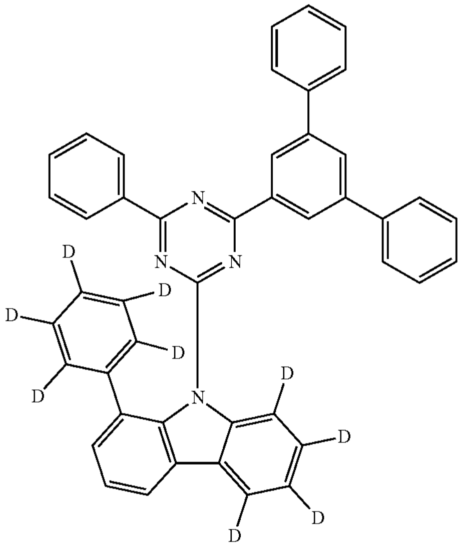
D37
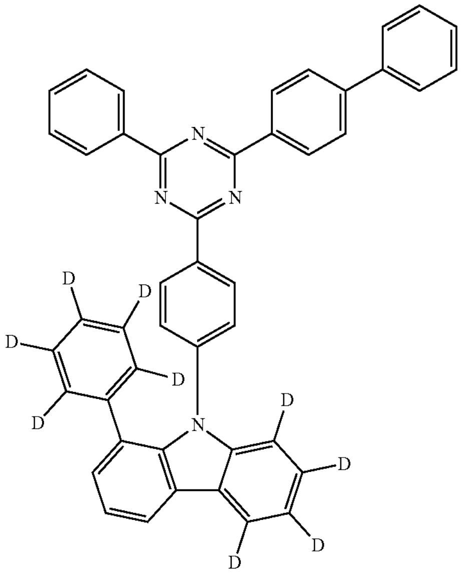

-continued
D38
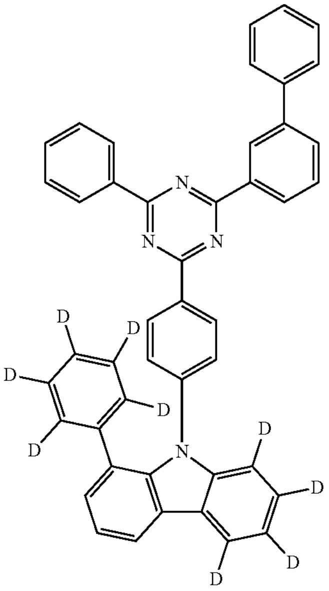
D39
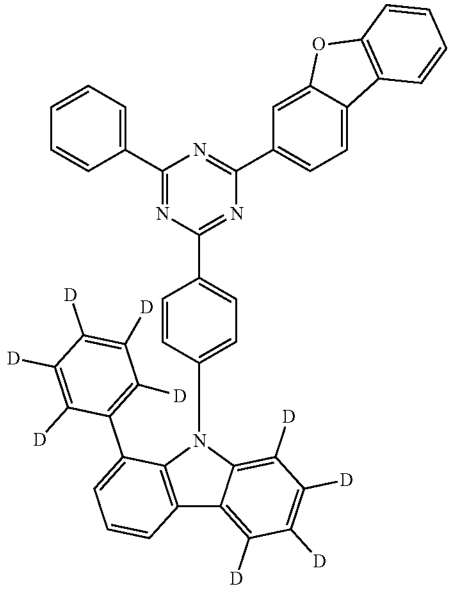
-continued
D40
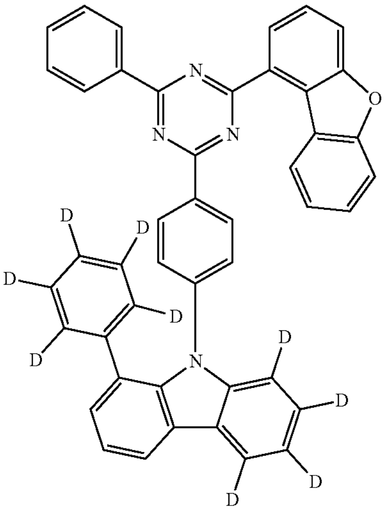
D41
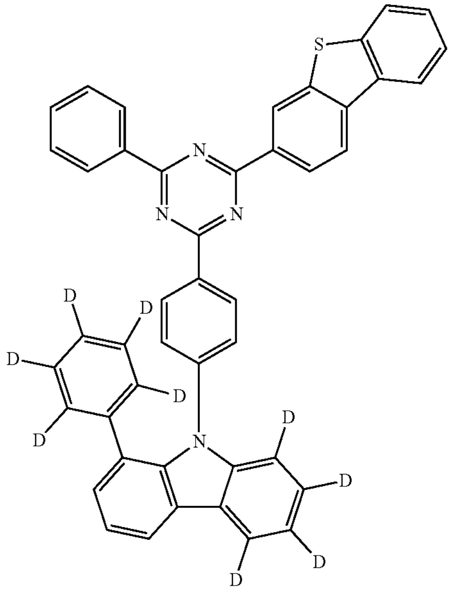
D42
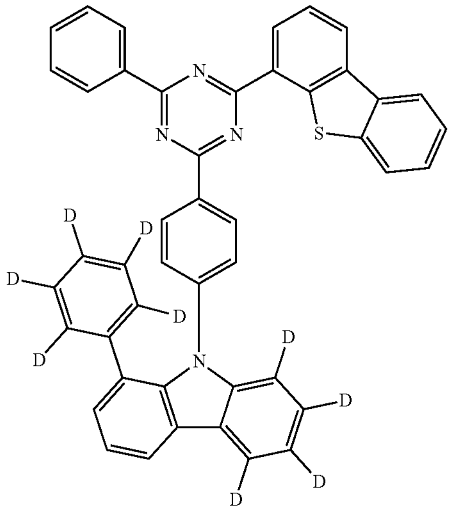

-continued
D43
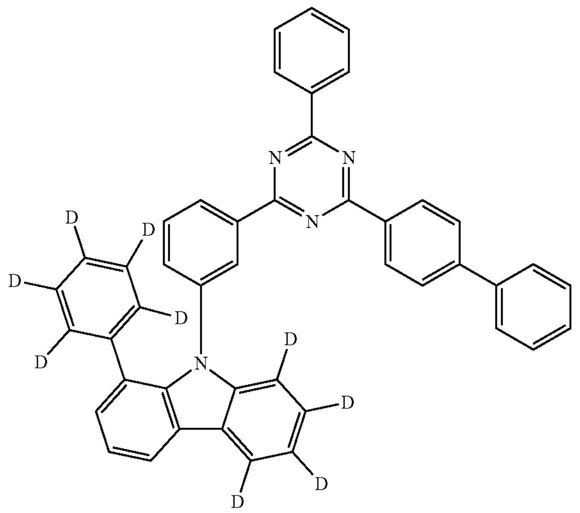
D44
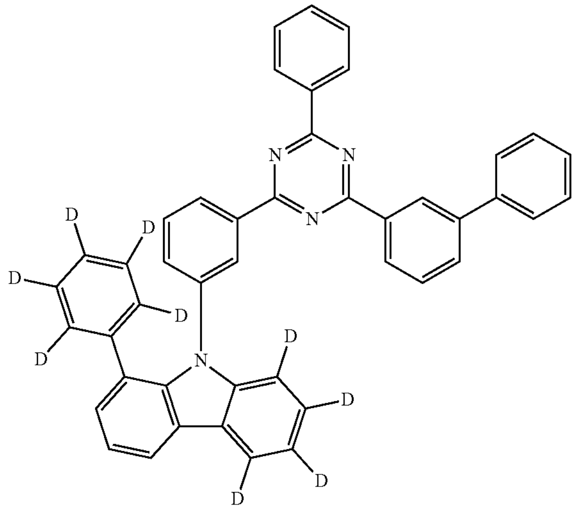
D45
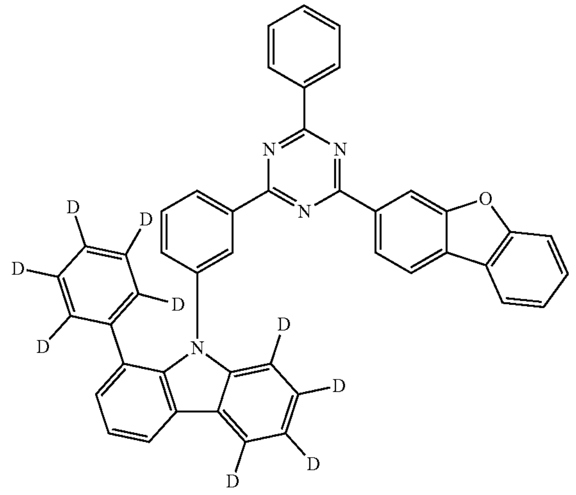
-continued
D46
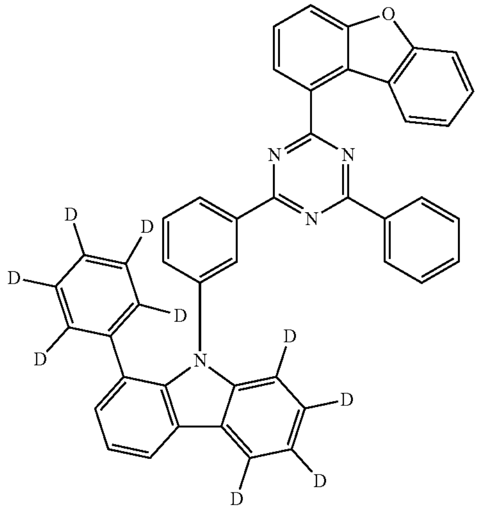
D47
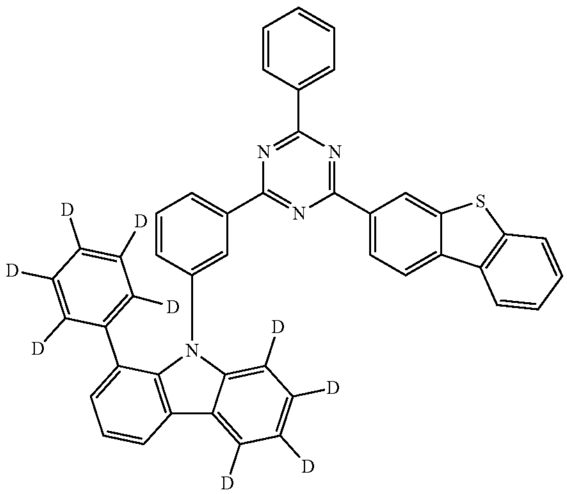
D48
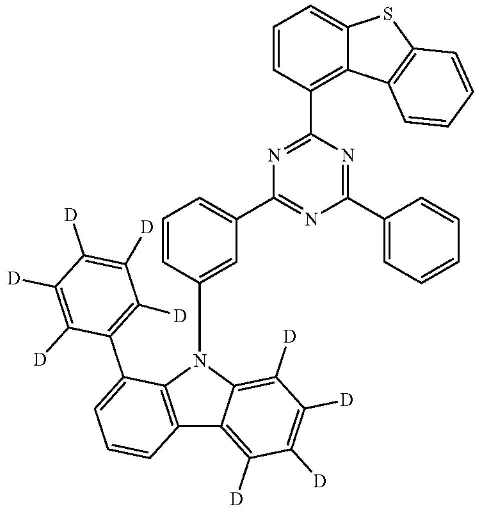

-continued
D49
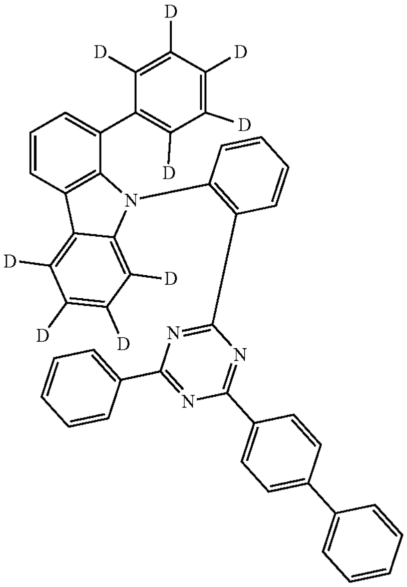
D50
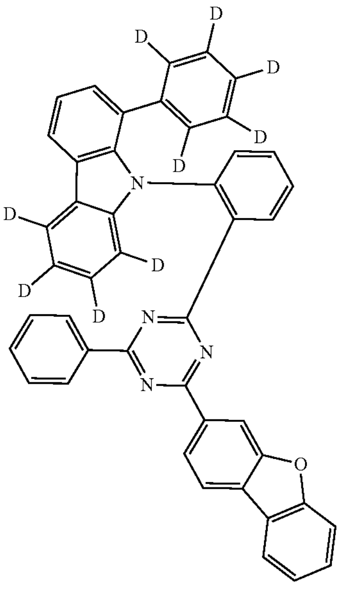
-continued
D51
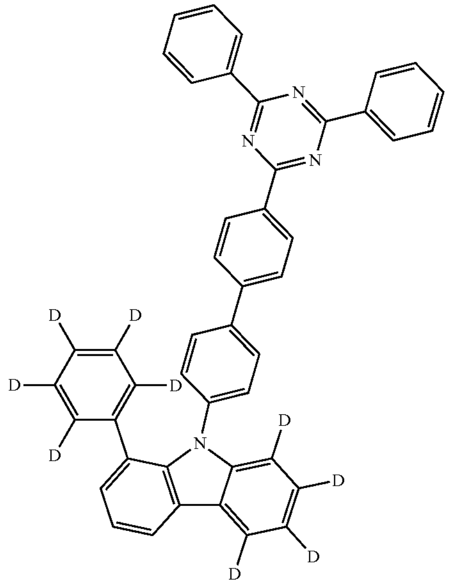
D52
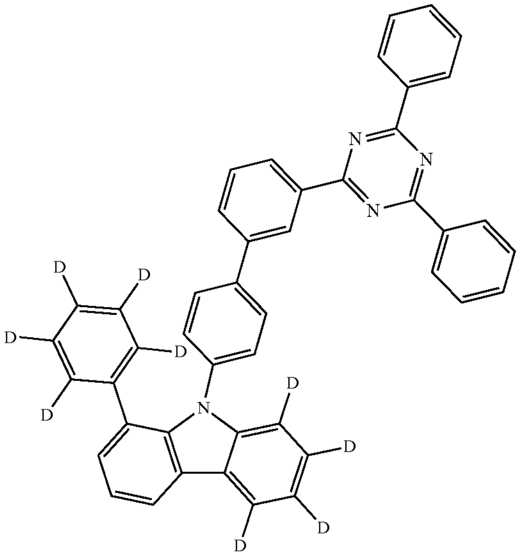
D53
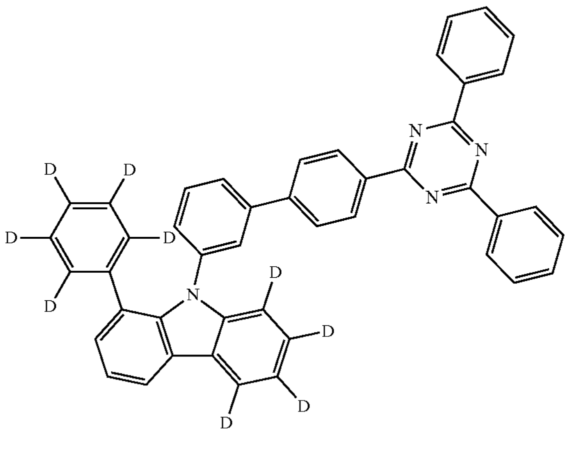

-continued
D54
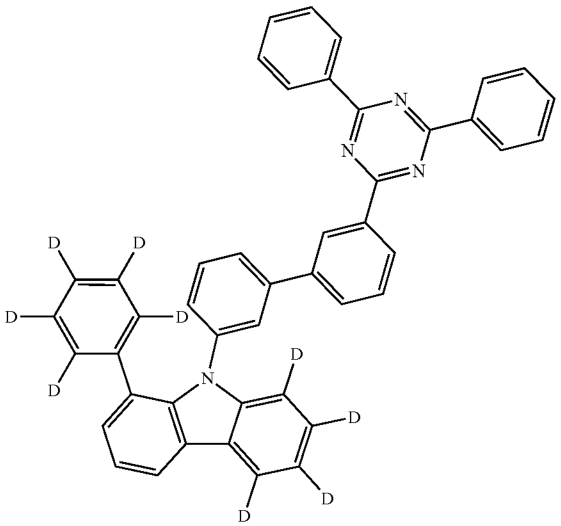
D55
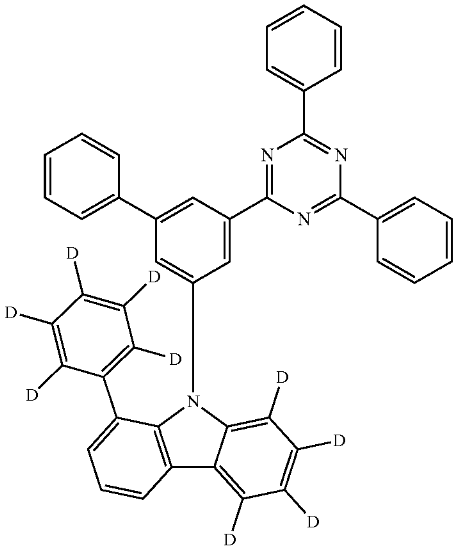
D56
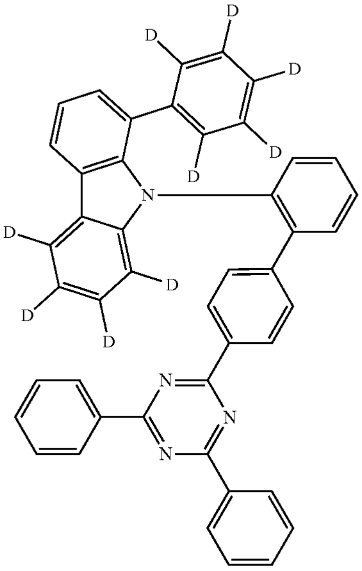
-continued
D57
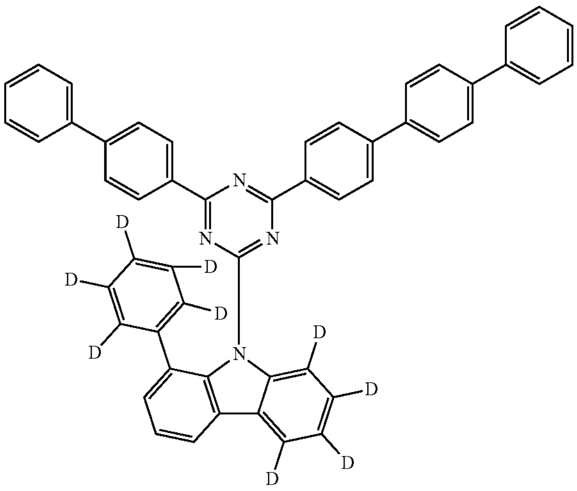
D58
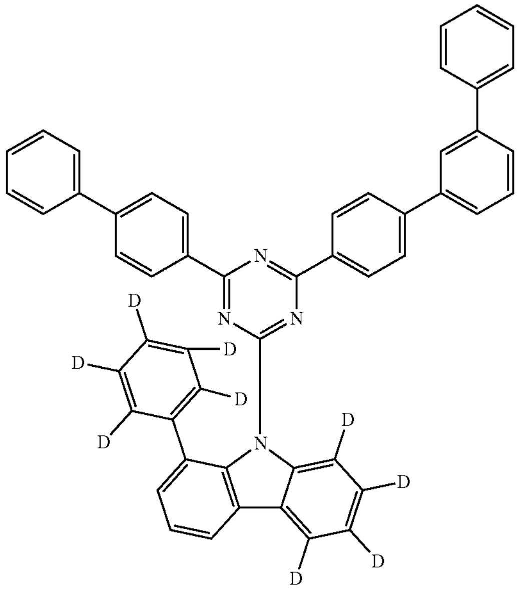

-continued
D59
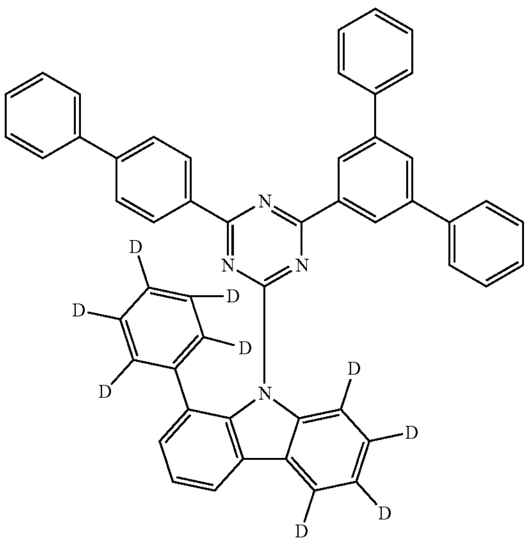
D60
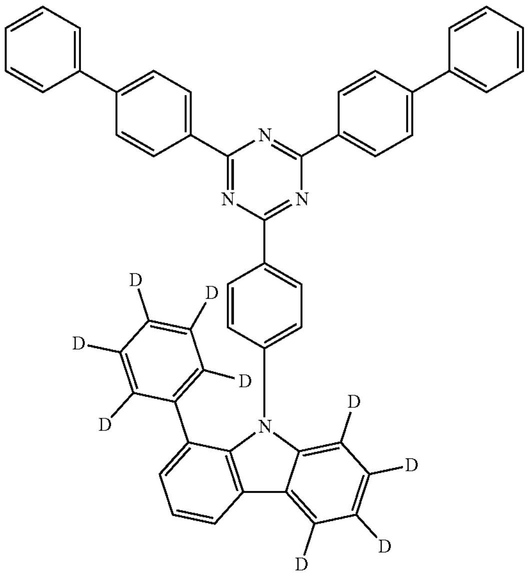
-continued
D61
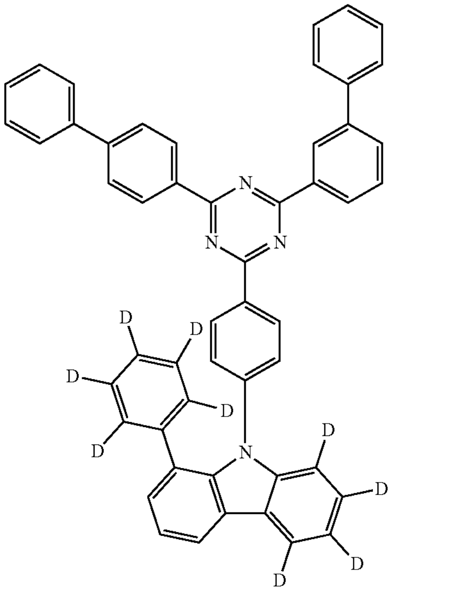
D62
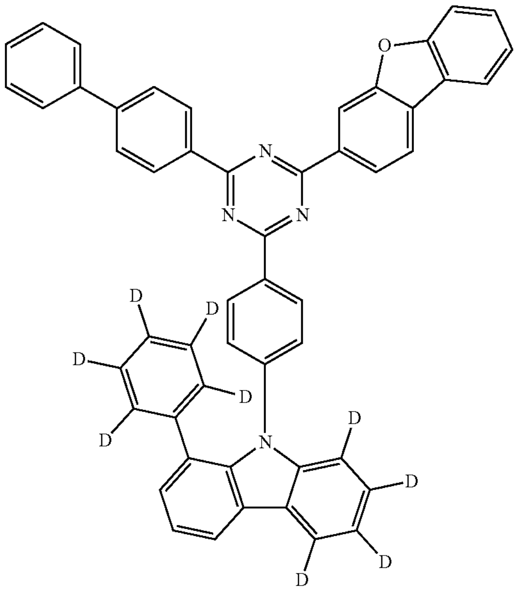

-continued
D63
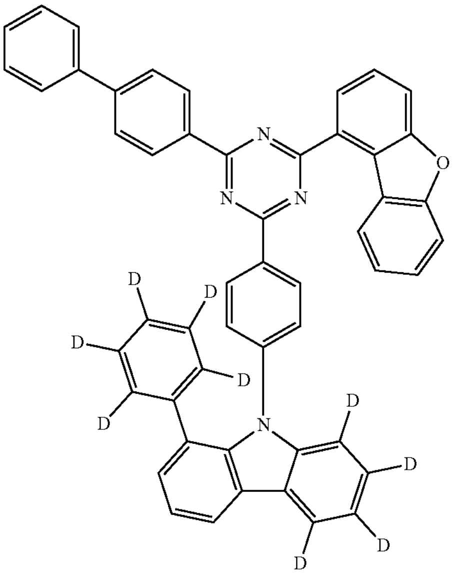
D64
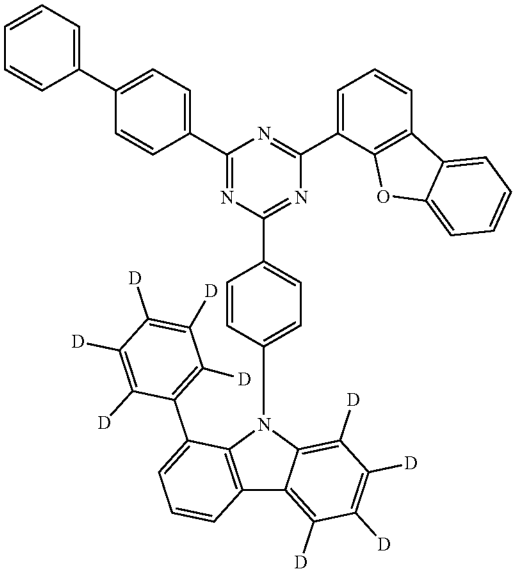
-continued
D65
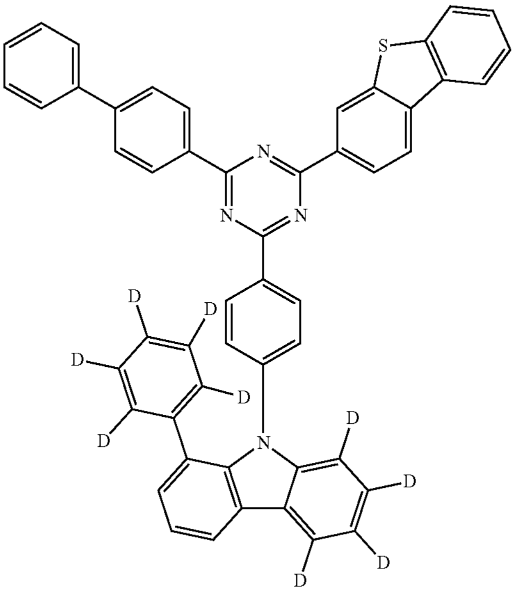
D66
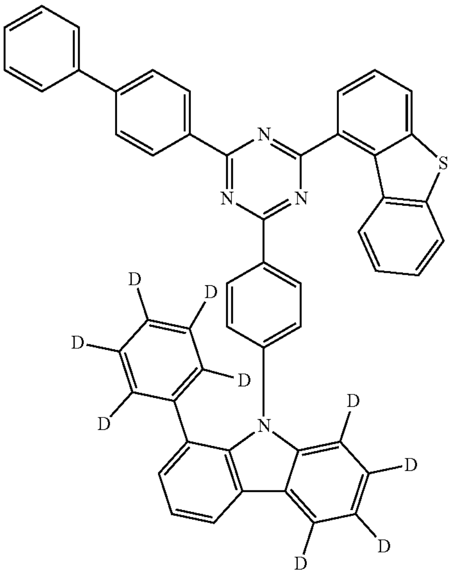

-continued
D67
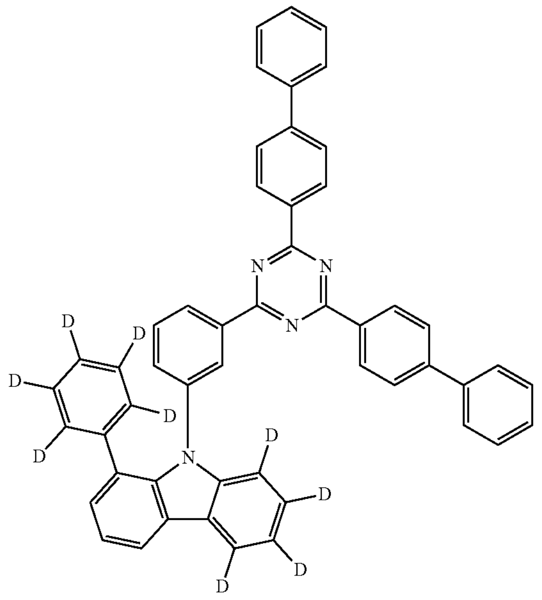
D68
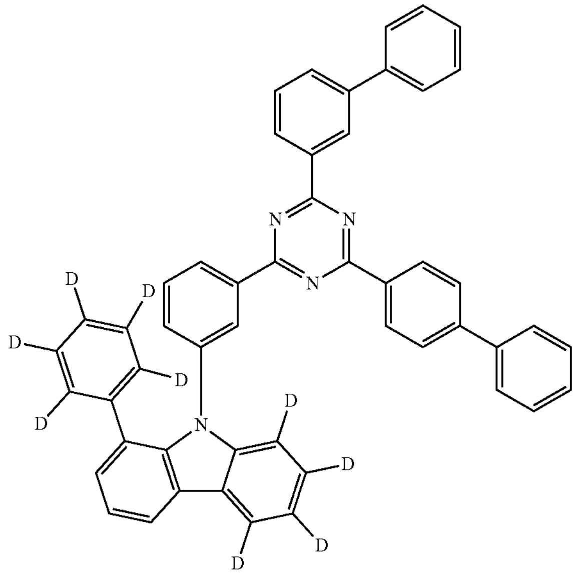
-continued
D69
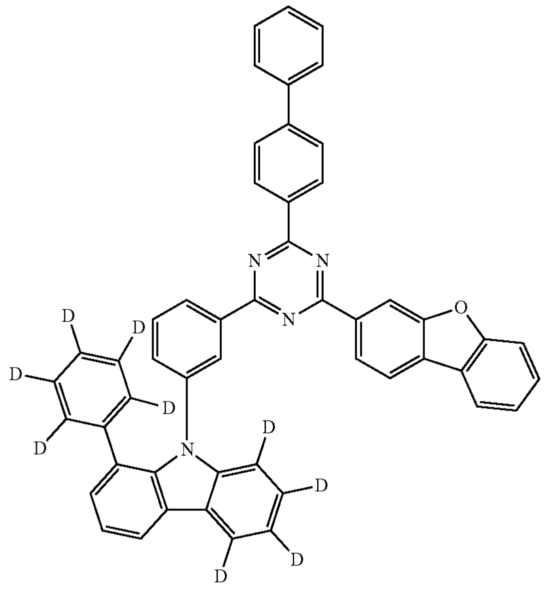
D70
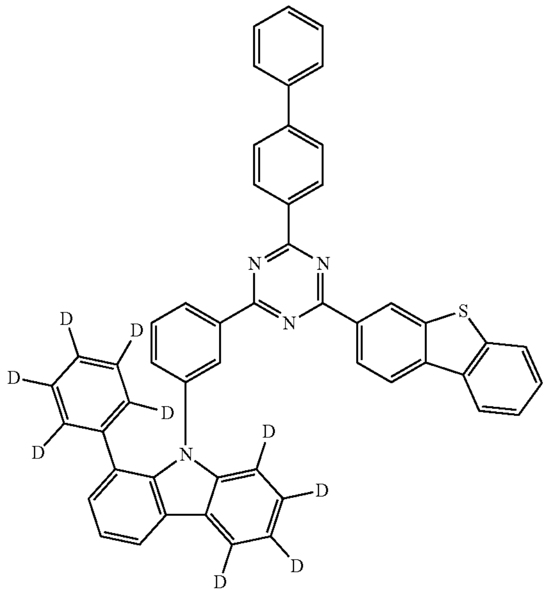

-continued
D71
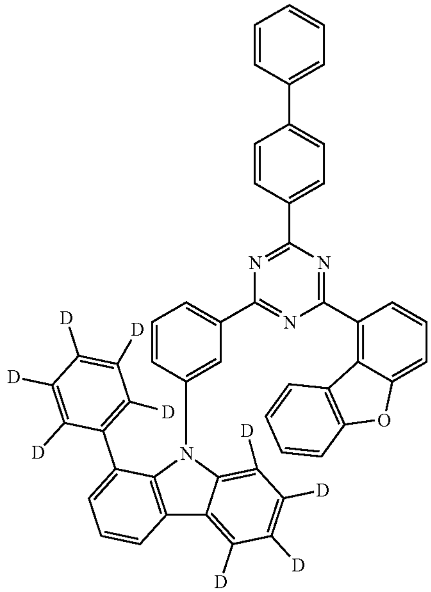
D72
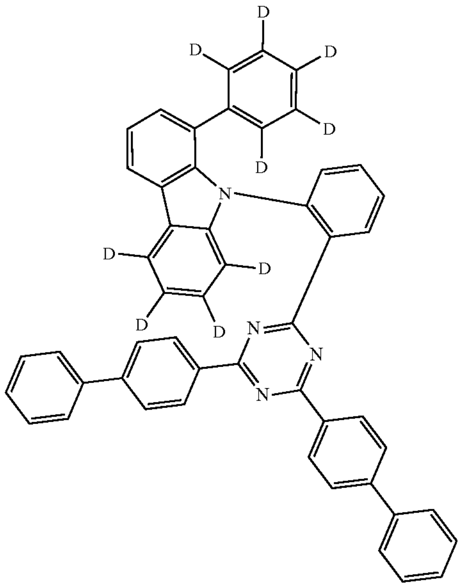
D73
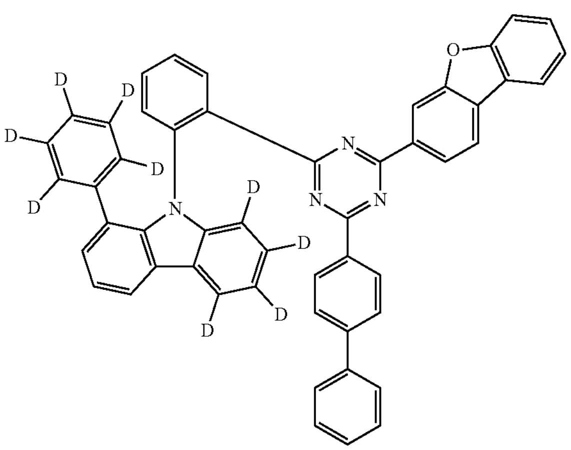
-continued
D74
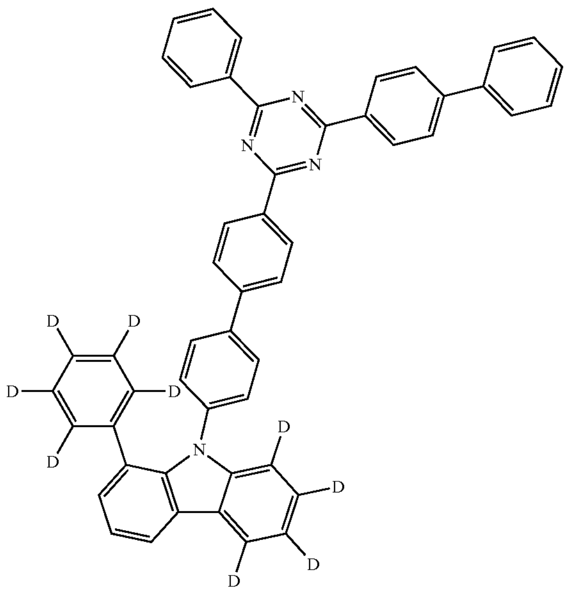
D75
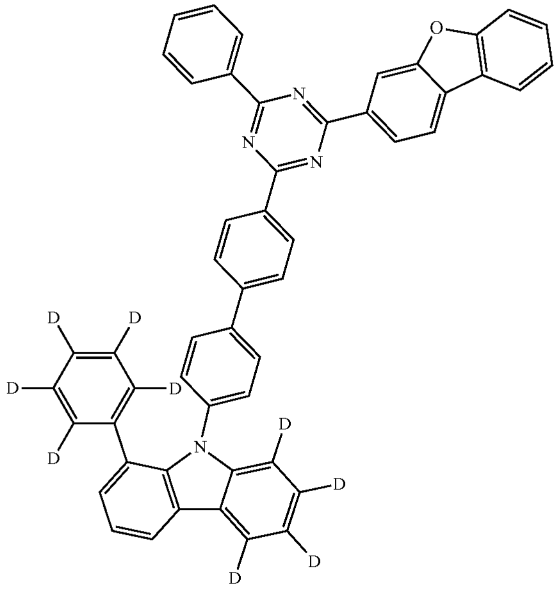

-continued
D76
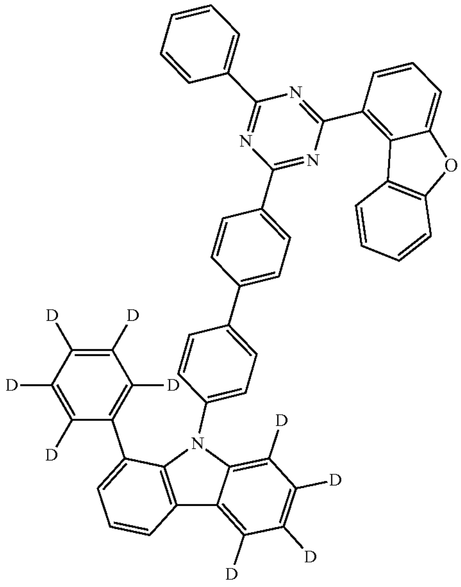
D77
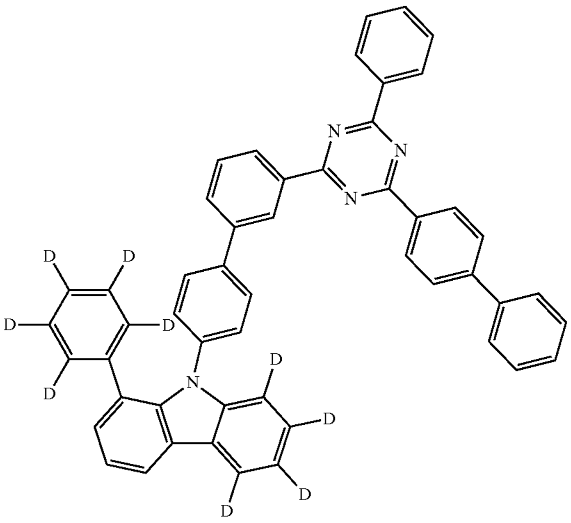
D78
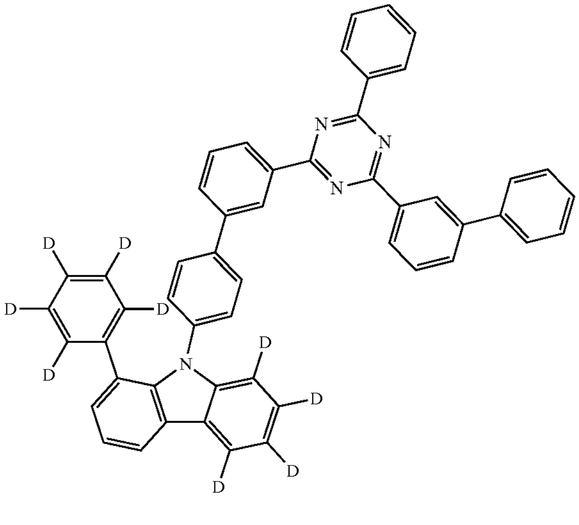
-continued
D79
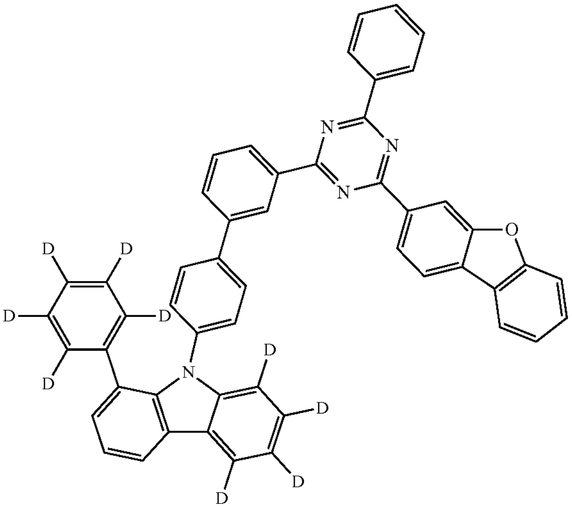
D80
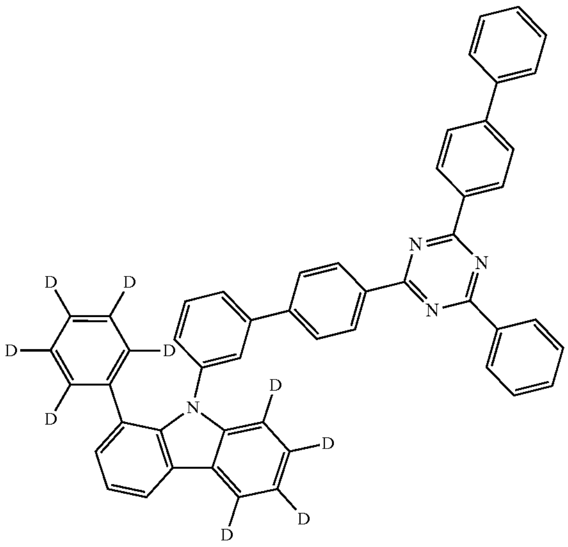
D81
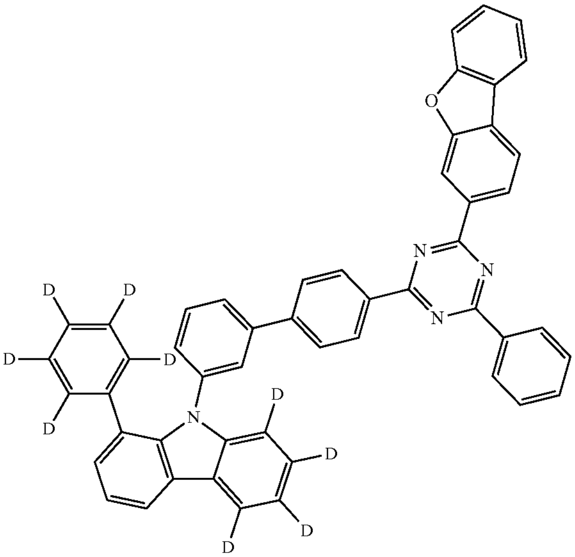

-continued
D82
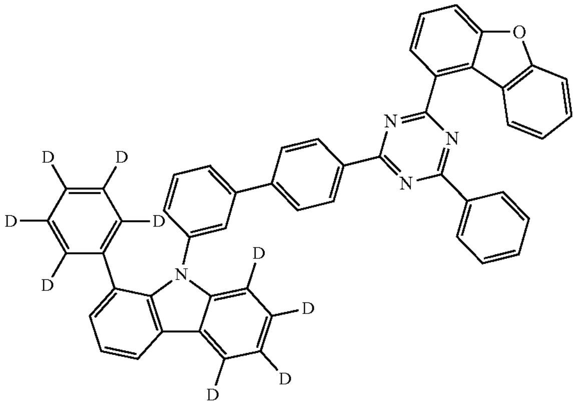
D83
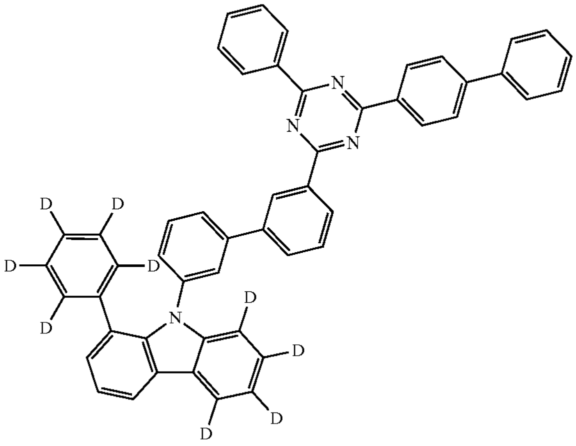
D84
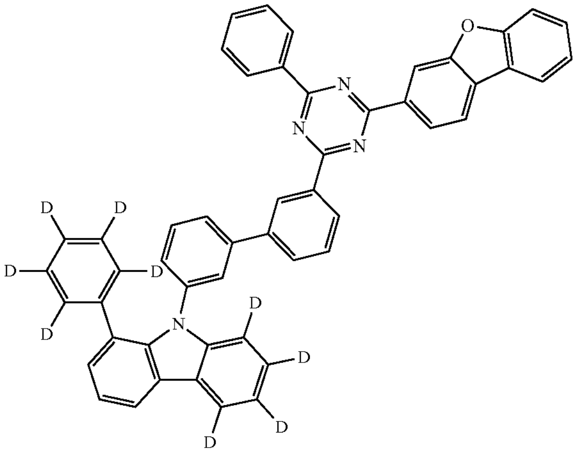
-continued
D85
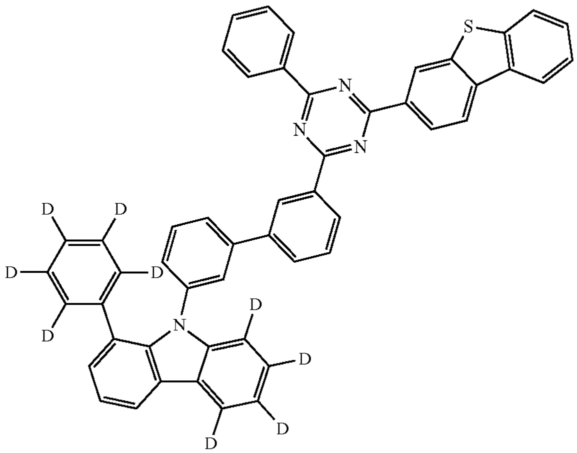
D86
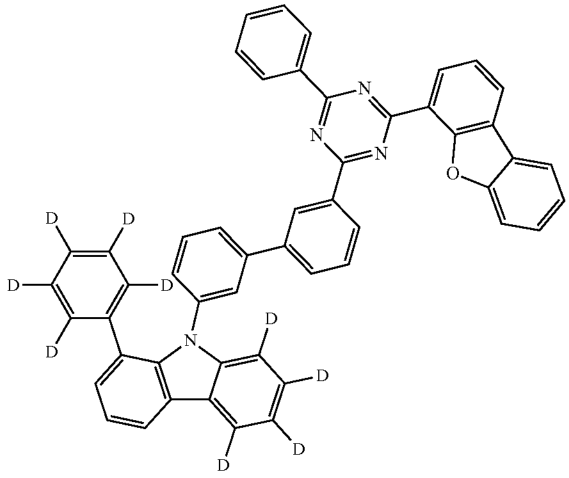
D87
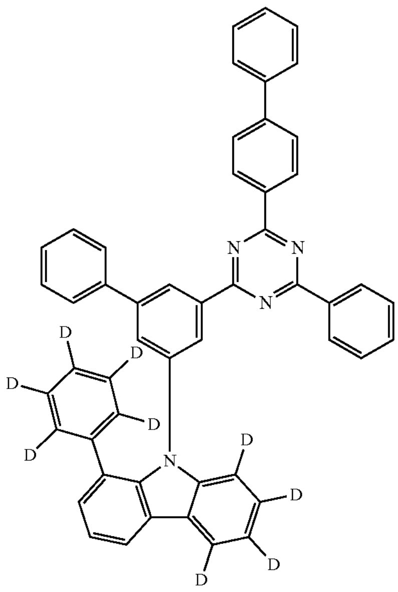

-continued
D88
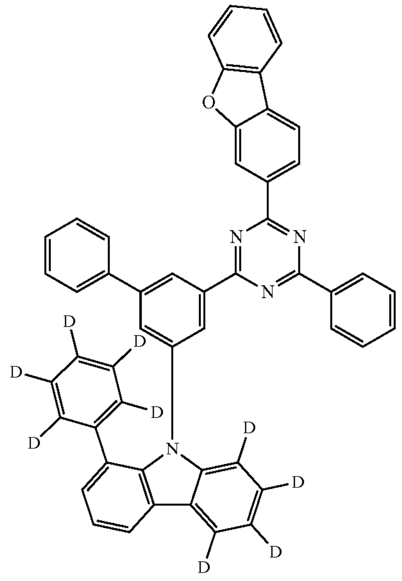
D89
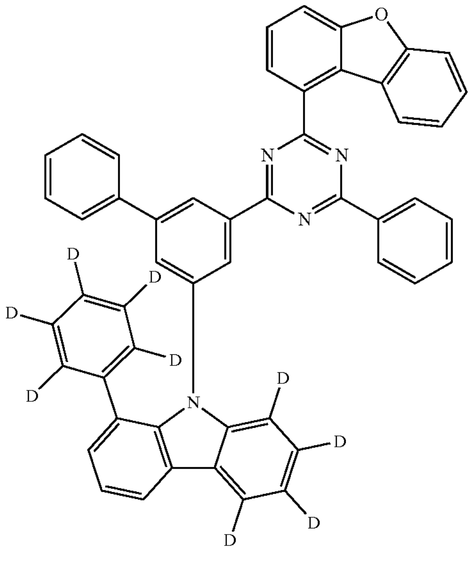
-continued
D90
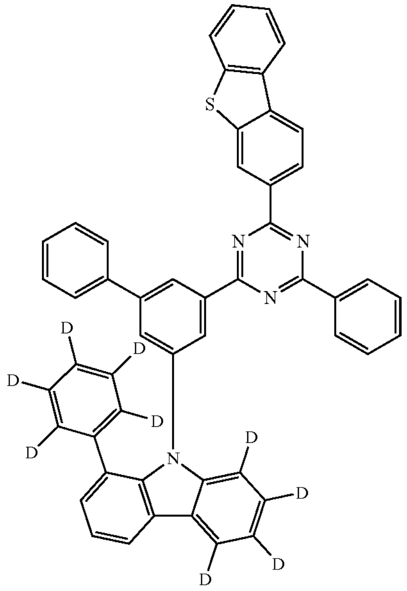
D91
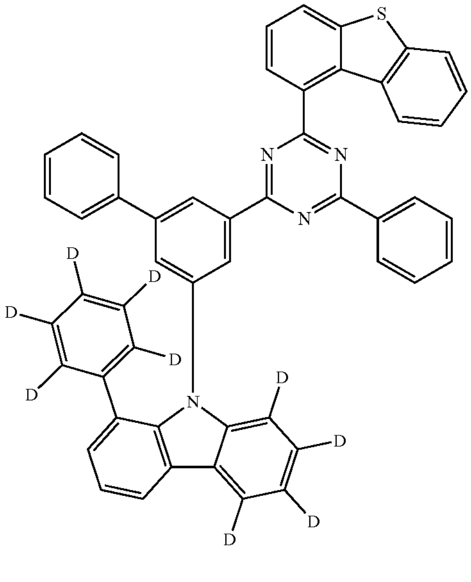

-continued
D92
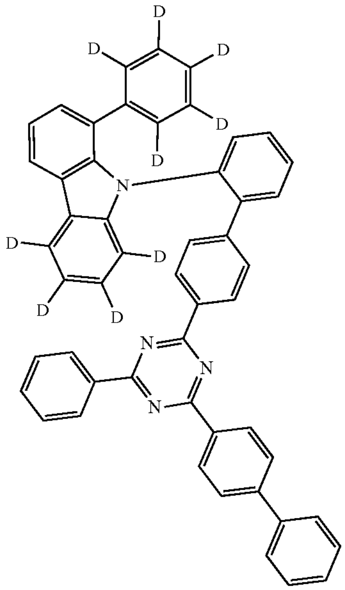
D93
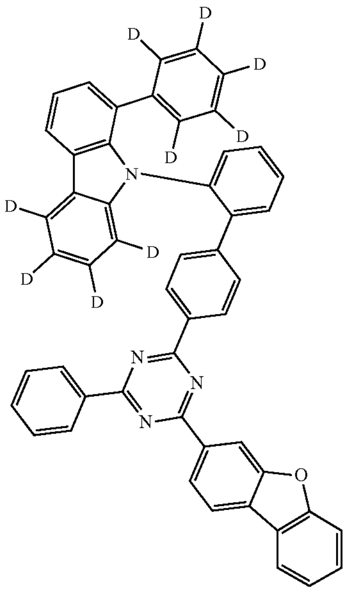
-continued
D94
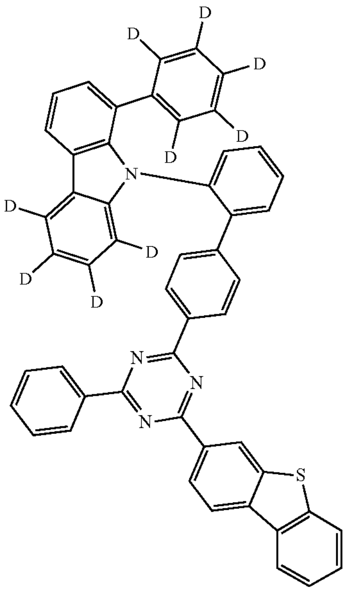
A224
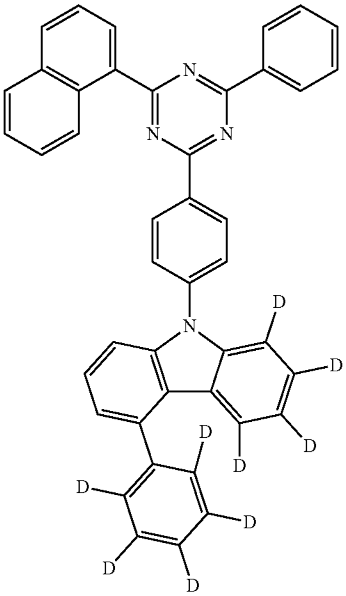

-continued
A225
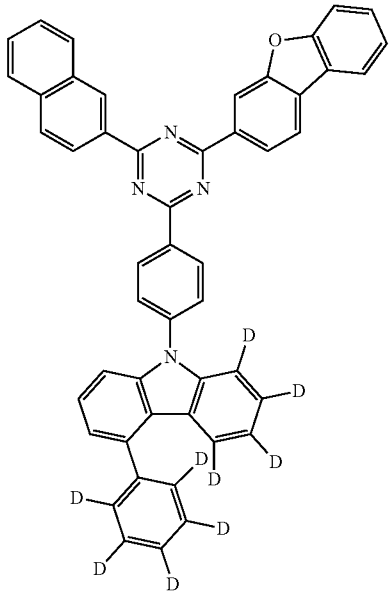
A226
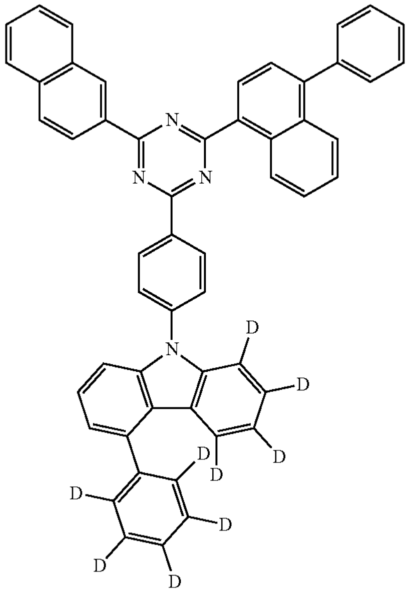
-continued
A227
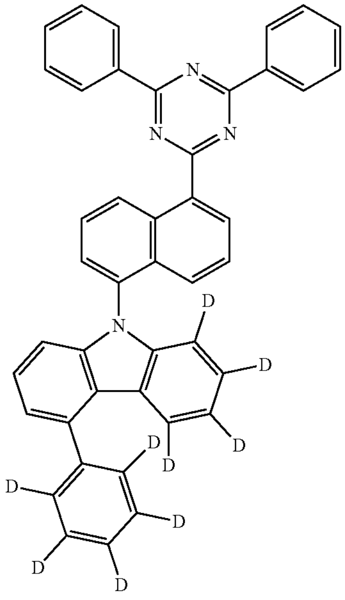
A228
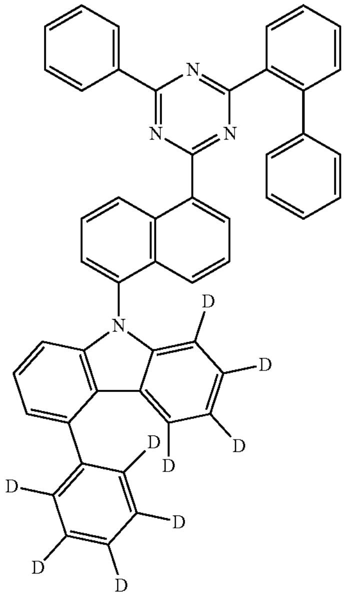

-continued
A229
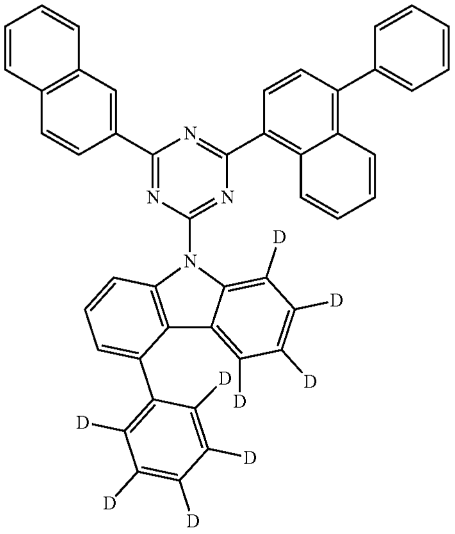
A230
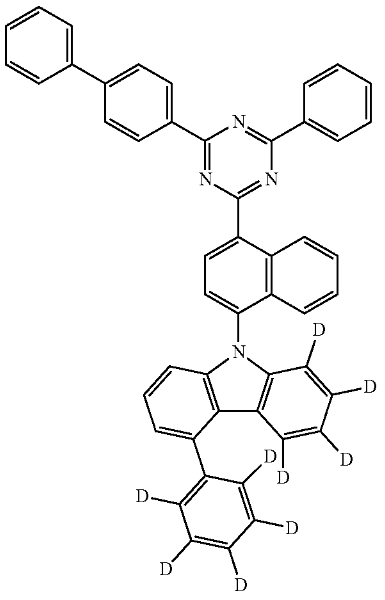
-continued
A231
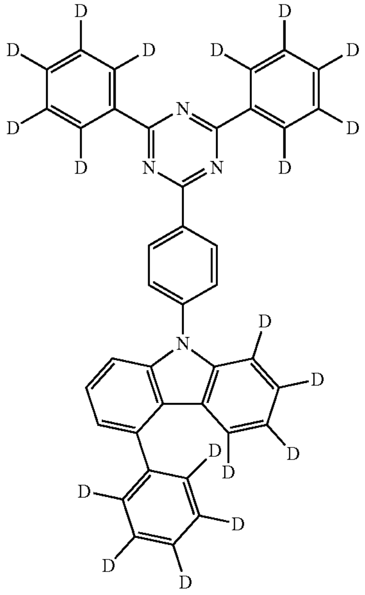
B73
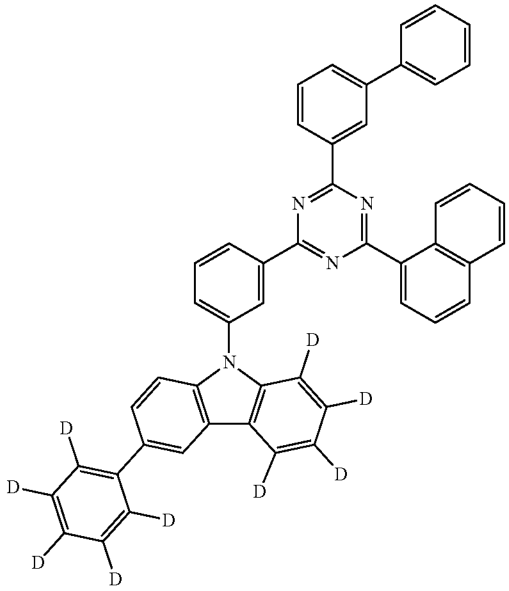

-continued
B74
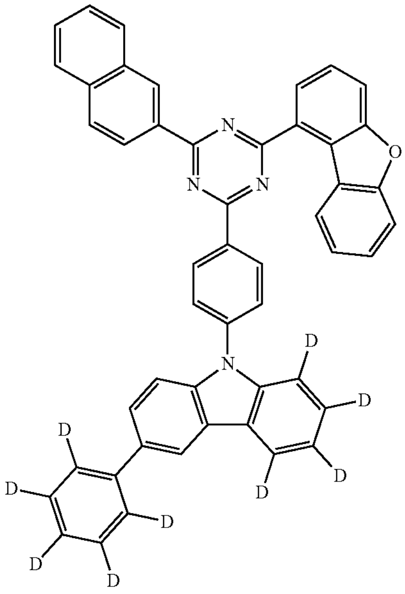
B75
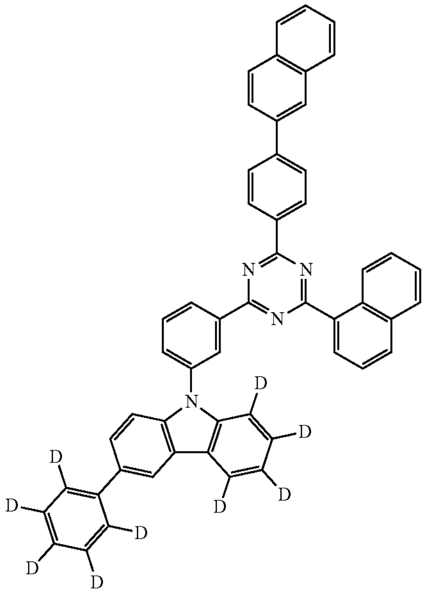
-continued
B76
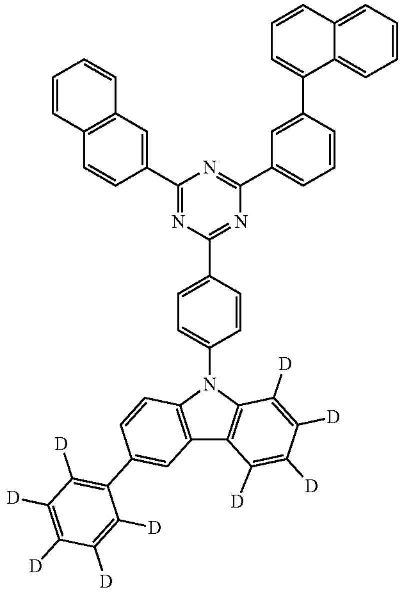
B77
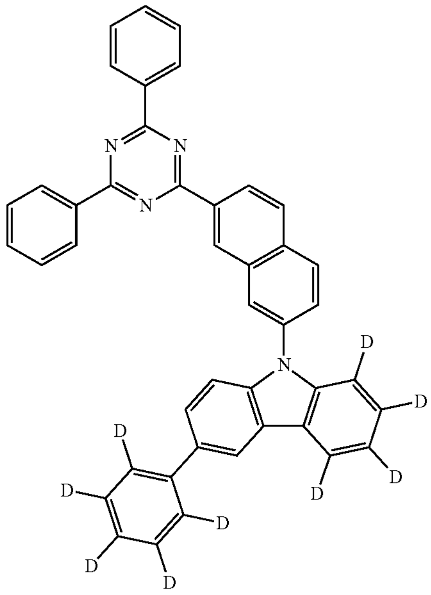

-continued
B78
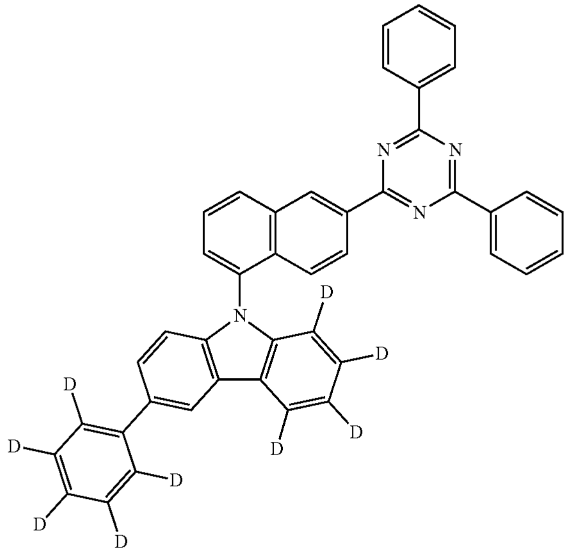
B79
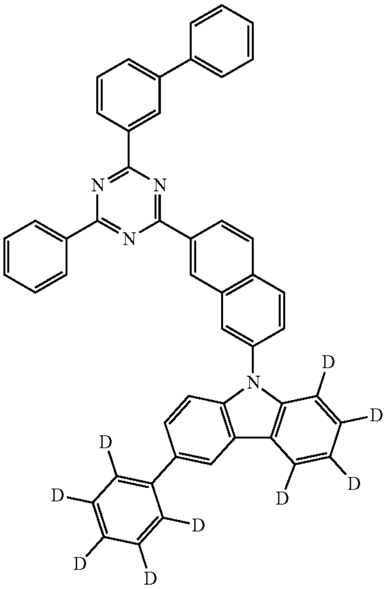
-continued
B80
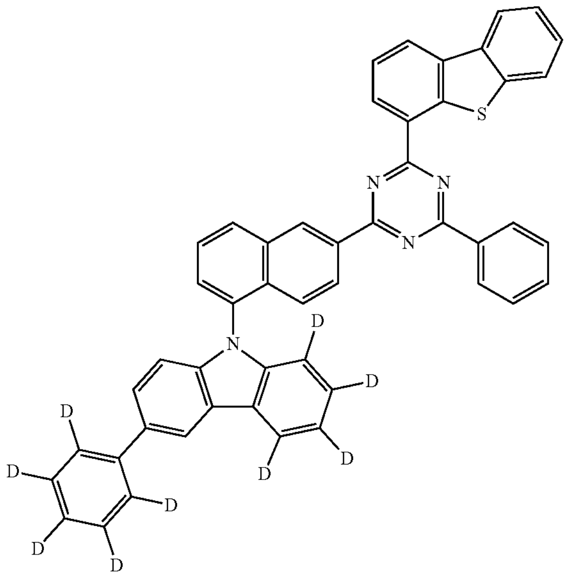
B81
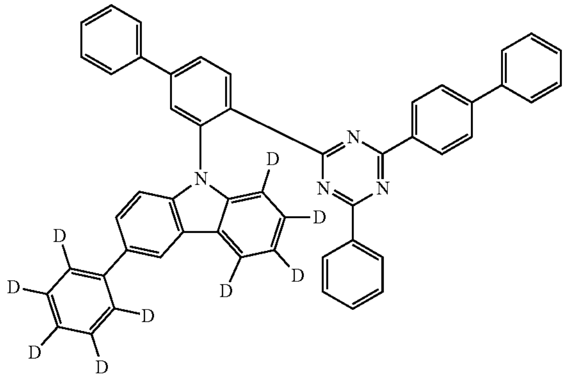
B82
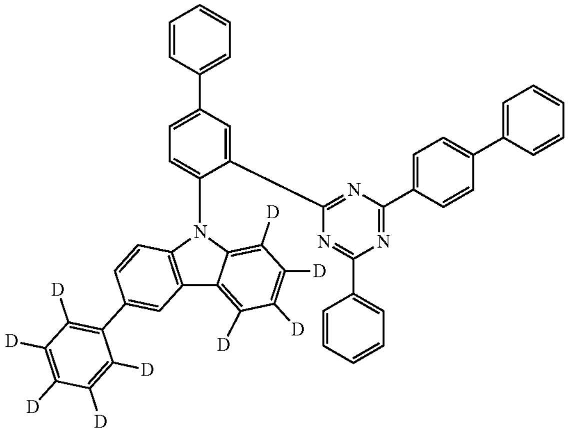

-continued
B83
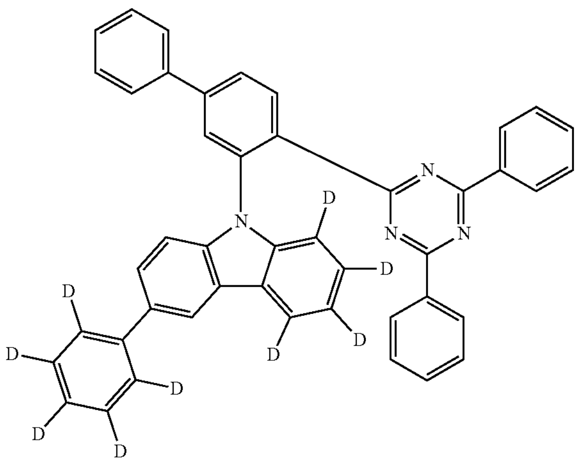
B84
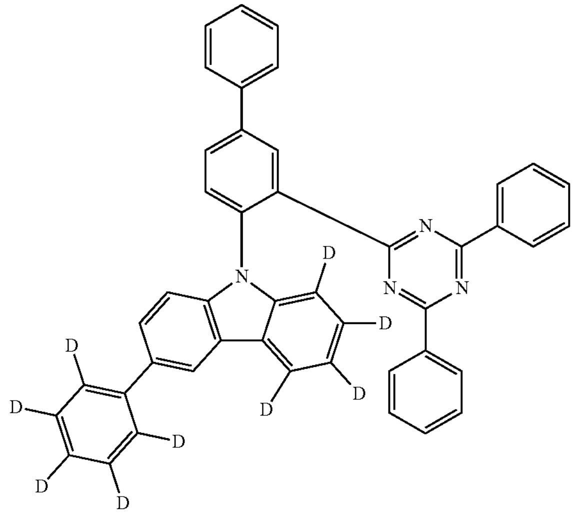
C73
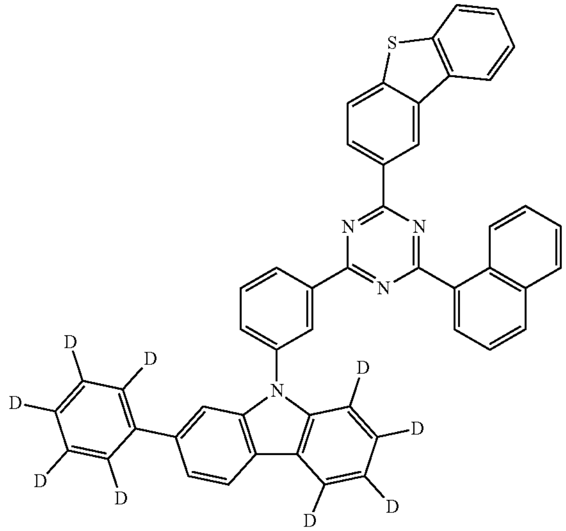
-continued
C74
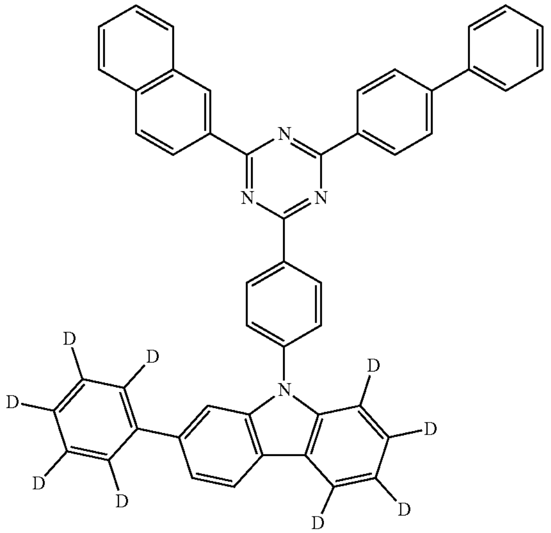
C75
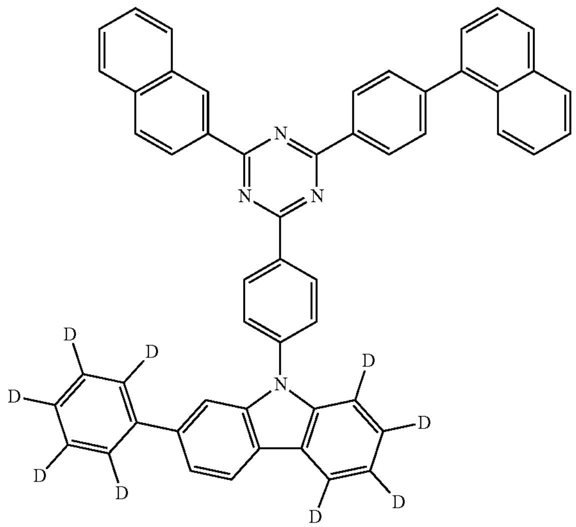

-continued
C76
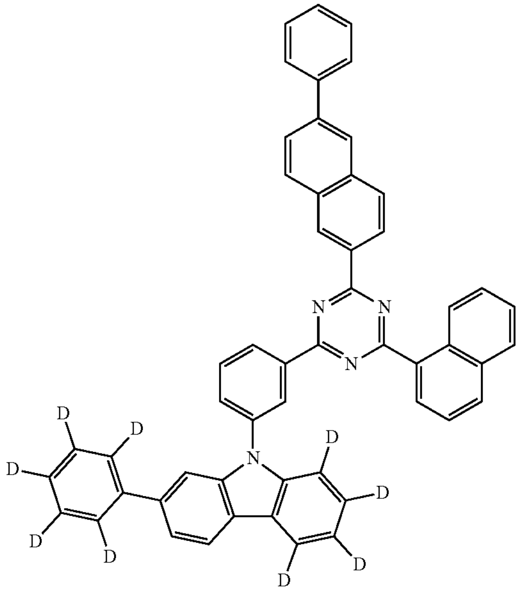
C77
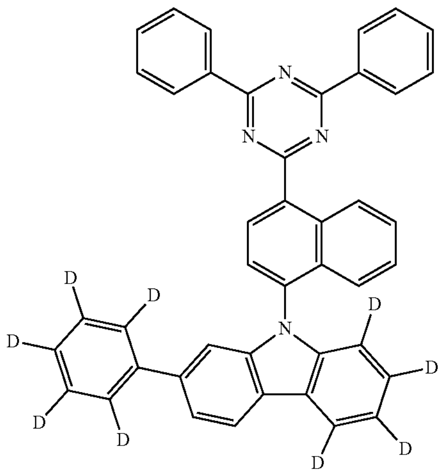
C78
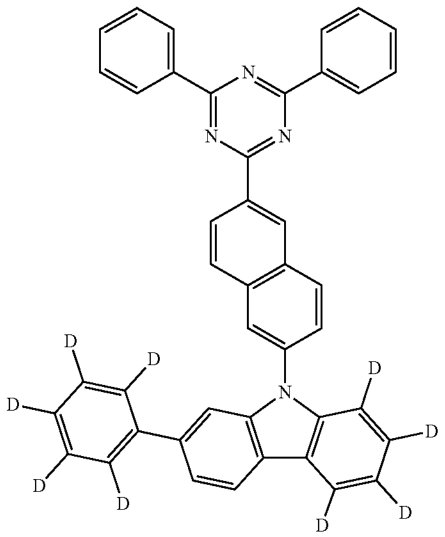
-continued
C79
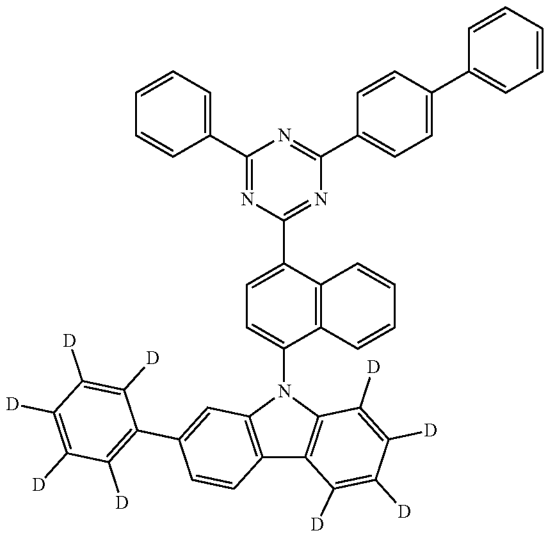
C80
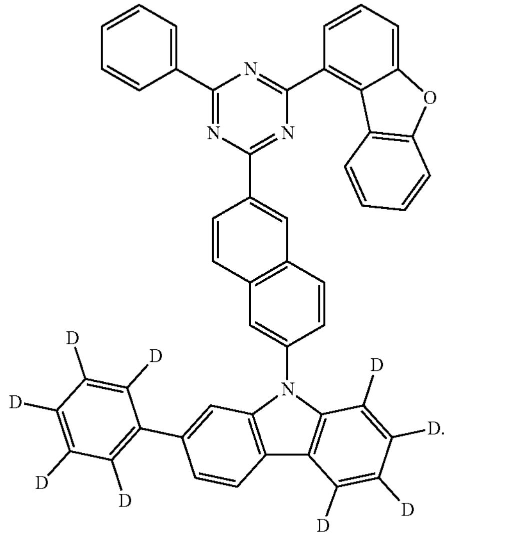
In a second aspect of the present disclosure, also provided is a composition, including a first compound and a second compound, where
the first compound has the structure shown in the formula 1, and the second compound has a structure shown in a formula 2:

Formula 2

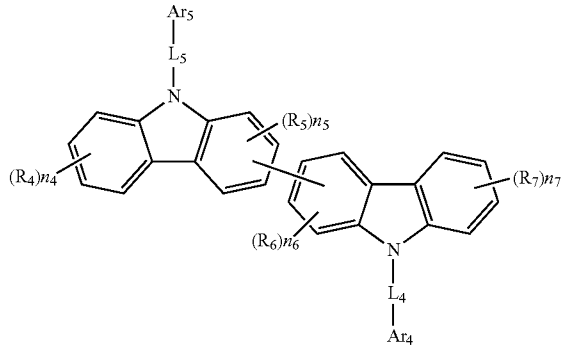

where each $R_4$, each $R_5$, each $R_6$, and each $R_7$ are respectively and independently selected from hydrogen, deuterium, a halogen group, a cyano, an aryl with 6 to 20 carbon atoms, a deuteroaryl with 6 to 20 carbon atoms, an alkyl with 1 to 10 carbon atoms, a deuteroalkyl with 1 to 10 carbon atoms, a haloalkyl with 1 to 10 carbon atoms, or a cycloalkyl with 3 to 10 carbon atoms;

$n_4$ represents the number of substituents $R_4$, $n_4$ is selected from 1, 2, 3 or 4, and when $n_4$ is greater than 1, any two $R_4$ are the same or different;

$n_5$ represents the number of substituents $R_5$, $n_5$ is selected from 1, 2 or 3, and when $n_5$ is greater than 1, any two $R_5$ are the same or different;

$n_6$ represents the number of substituents $R_6$, $n_6$ is selected from 1, 2 or 3, and when no is greater than 1, any two $R_6$ are the same or different;

$n_7$ represents the number of substituents $R_7$, $n_7$ is selected from 1, 2, 3 or 4, and when $n_7$ is greater than 1, any two $R_7$ are the same or different;

$L_4$ and $L_5$ are the same or different, and are respectively and independently selected from a single bond, a substituted or unsubstituted arylene with 6 to 30 carbon atoms, or a substituted or unsubstituted heteroarylene with 3 to 30 carbon atoms;

$Ar_4$ and $Ar_5$ are the same or different, and are respectively and independently selected from a substituted or unsubstituted aryl with 6 to 30 carbon atoms or a substituted or unsubstituted heteroaryl with 3 to 30 carbon atoms; and substituent(s) in $L_4$, $L_5$, $Ar_4$ and $Ar_5$ are the same or different, and are respectively and independently selected from deuterium, a halogen group, a cyano, a heteroaryl with 3 to 20 carbon atoms, an aryl with 6 to 20 carbon atoms, a deuteroaryl with 6 to 20 carbon atoms, a trialkylsilyl with 3 to 12 carbon atoms, an alkyl with 1 to 10 carbon atoms, a deuteroalkyl with 1 to 10 carbon atoms, a haloalkyl with 1 to 10 carbon atoms, a cycloalkyl with 3 to 10 carbon atoms, a heterocycloalkyl with 2 to 10 carbon atoms, or an alkoxy with 1 to 10 carbon atoms.

In some embodiments of the present disclosure, the second compound has a structure represented by a Formula 2-3-3:

Formula 2-3-3

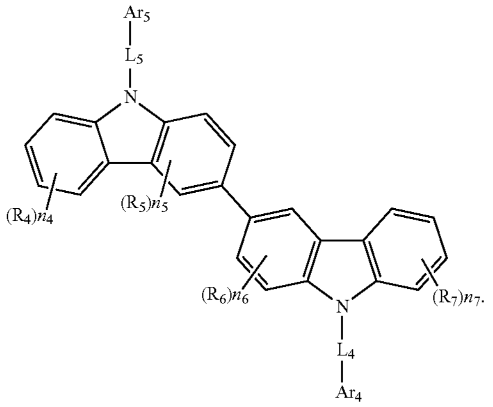

In some embodiments of the present disclosure, in the second compound, each $R_4$, each $R_5$, each $R_6$, and each $R_7$ are respectively and independently selected from hydrogen, deuterium, a fluorine, a methyl, an ethyl, a n-propyl, an isopropyl, a tert-butyl, a phenyl, a naphthyl, a biphenyl, or a pentadeuterophenyl.

In some embodiments of the present disclosure, in the second compound, each $R_4$, each $R_5$, each $R_6$, and each $R_7$ are respectively and independently selected from hydrogen, deuterium, a fluorine, a cyano, a methyl, an ethyl, an-propyl, an isopropyl, a tert-butyl, a the group consisting of:

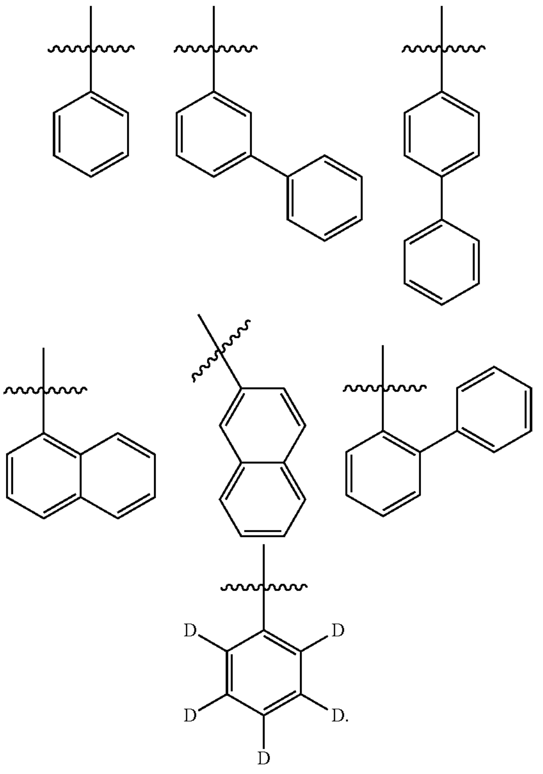

In some embodiments of the present disclosure, in the second compound, $L_4$ and $L_5$ are respectively and independently selected from a single bond, a substituted or unsubstituted arylene with 6 to 20 carbon atoms, or a substituted or unsubstituted heteroarylene with 12 to 20 carbon atoms.

Optionally, substituent(s) in $L_4$ and $L_5$ are respectively and independently selected from deuterium, a halogen group, a cyano, an alkyl with 1 to 5 carbon atoms, or a phenyl.

In other embodiments of the present disclosure, in the second compound, $L_4$ and $L_5$ are respectively and independently selected from a single bond, a substituted or unsubstituted phenylene, a substituted or substituted naphthylene, a substituted or unsubstituted biphenylene, a substituted or unsubstituted dibenzofurylene, a substituted or unsubstituted dibenzothienylene, or a substituted or unsubstituted carbazolylene.

Optionally, substituent(s) in $L_4$ and $L_5$ are respectively and independently selected from deuterium, a fluorine, a cyano, a methyl, an ethyl, an-propyl, an isopropyl, a tert-butyl or a phenyl.

In some embodiments of the present disclosure, in the second compound, $L_4$ and $L_5$ are respectively and independently selected from a single bond, or a substituted or unsubstituted group U, where the unsubstituted group U is selected from the group consisting of:

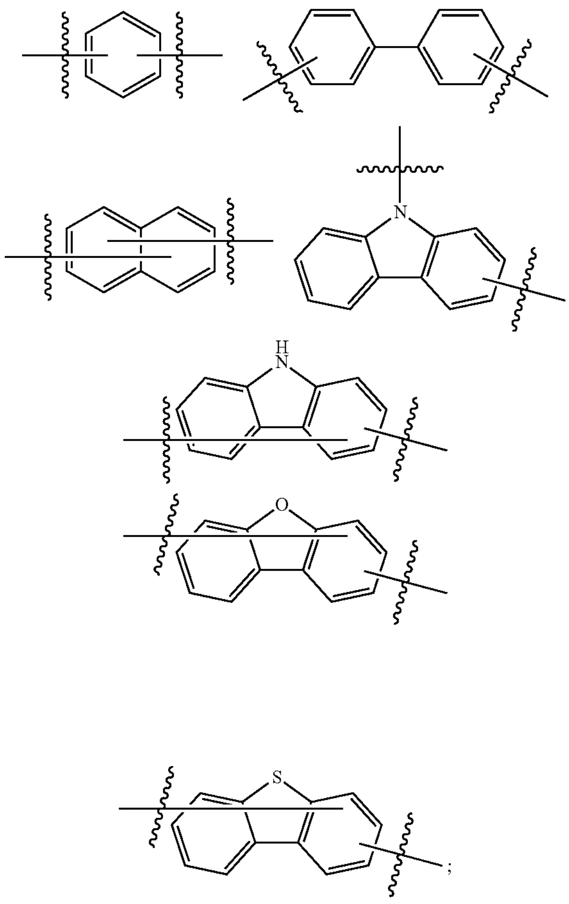

;

where ⸾ represents a chemical bond; the substituted group U has one or more substituents each independently selected from deuterium, cyano, fluorine, methyl, ethyl, n-propyl, isopropyl, tert-butyl, or phenyl; and when the number of substituents on U is greater than 1, the substituents are the same or different.

Optionally, $L_4$ and $L_5$ are respectively and independently selected from a single bond or the group consisting of:

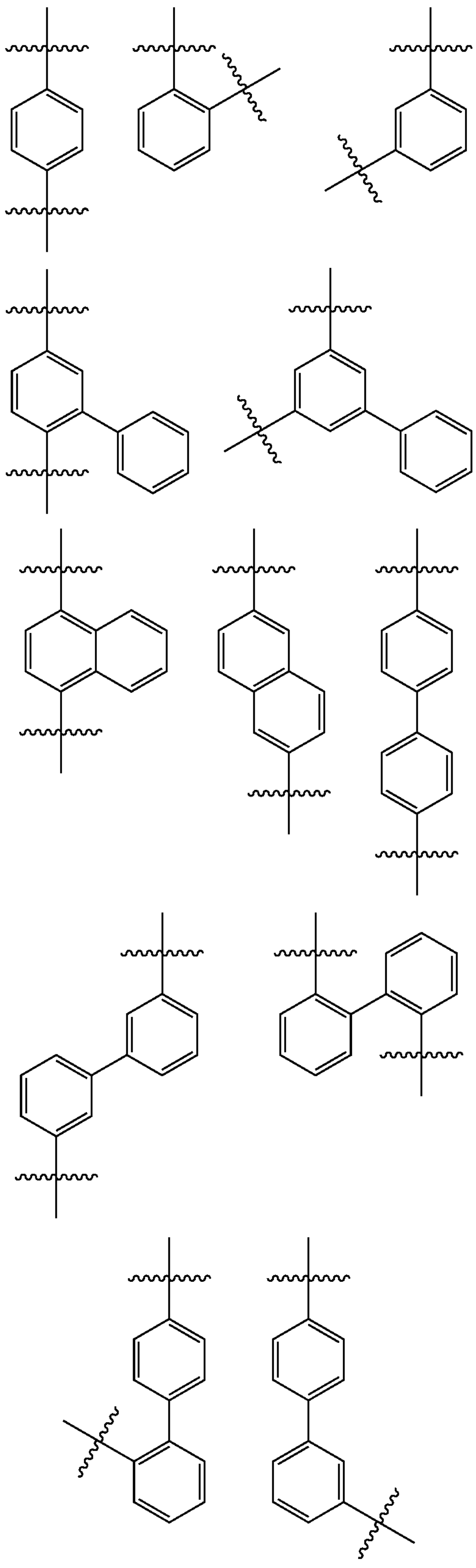

-continued

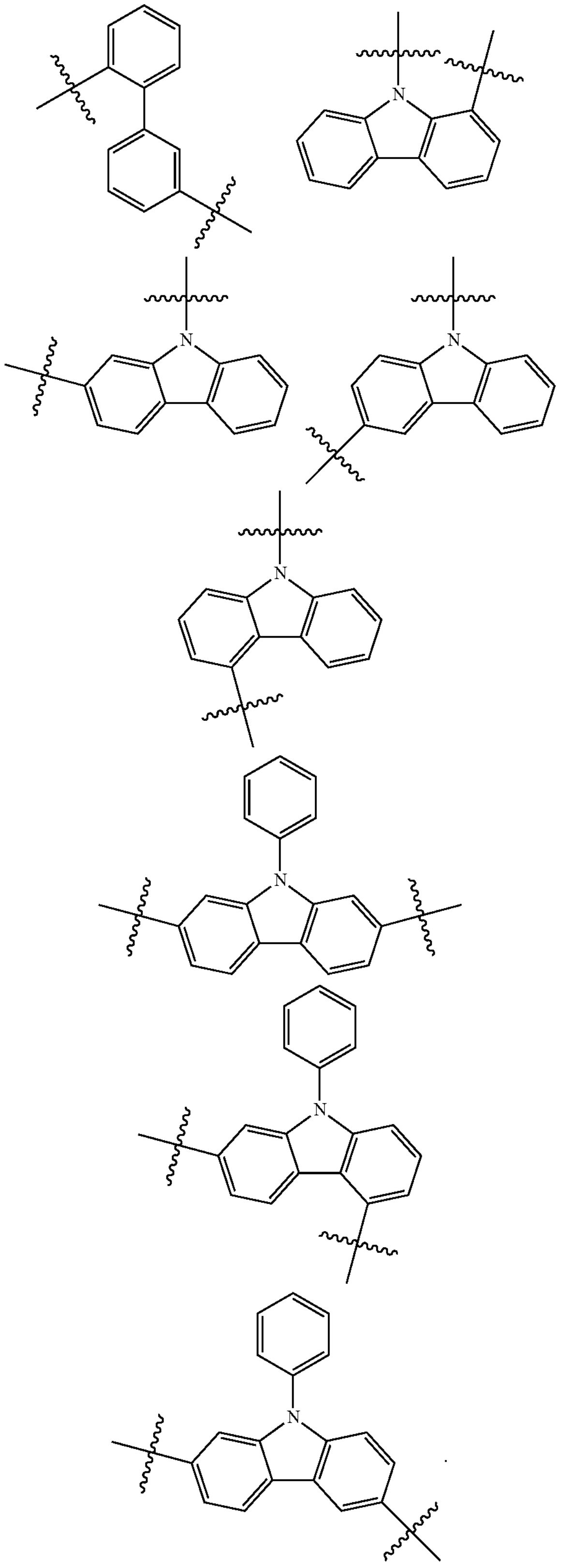

In some embodiments of the present disclosure, in the second compound, $Ar_4$ and $Ar_5$ are respectively and independently selected from a substituted or unsubstituted aryl with 6 to 20 carbon atoms or a substituted or unsubstituted heteroaryl with 12 to 20 carbon atoms.

Optionally, substituent(s) in $Ar_4$ and $Ar_5$ are respectively and independently selected from deuterium, a halogen group, an alkyl with 1 to 5 carbon atoms, a phenyl, or a pentadeuterophenyl.

In other embodiments of the present disclosure, in the second compound, $Ar_4$ and $Ar_5$ are respectively and independently selected from a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted dibenzofuranyl, a substituted or unsubstituted dibenzothienyl, a substituted or unsubstituted carbazolyl, or a substituted or unsubstituted triphenylene.

Optionally, substituent(s) in $Ar_4$ and $Ar_5$ are respectively and independently selected from deuterium, a fluorine, a cyano, a halogen group, a methyl, an ethyl, a n-propyl, an isopropyl, a tert-butyl, a phenyl, or a pentadeuterophenyl.

In some embodiments of the present disclosure, in the second compound, $Ar_4$ and $Ar_5$ are respectively and independently selected from a substituted or unsubstituted group G, where the unsubstituted group G is selected from the group consisting of:

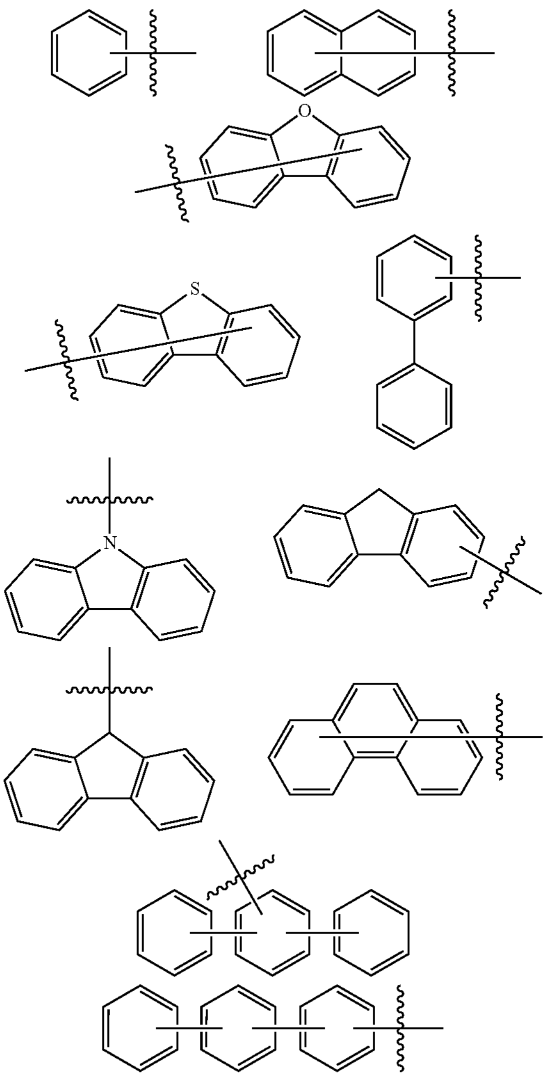

-continued

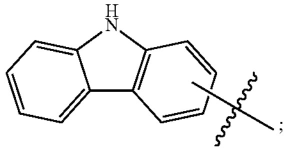

where ⌇ represents a chemical bond; the substituted group G has one or more substituents each independently selected from deuterium, cyano, fluorine, methyl, ethyl, n-propyl, isopropyl, tert-butyl, phenyl, or pentadeuterophenyl; and when the number of substituents on G is greater than 1, the substituents are the same or different.

Optionally, in the second compound, $Ar_4$ and $Ar_5$ are respectively and independently selected from the group consisting of:

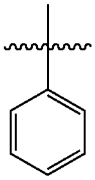
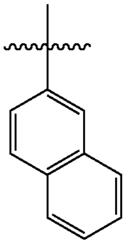
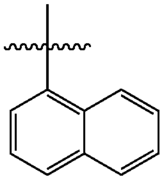
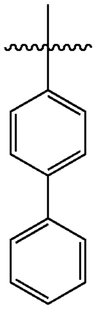
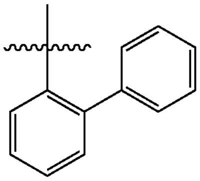
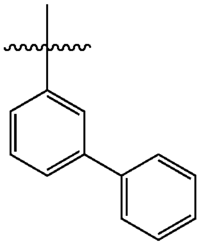
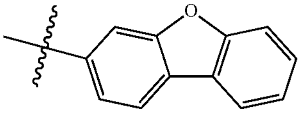
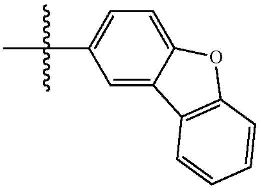
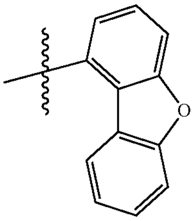
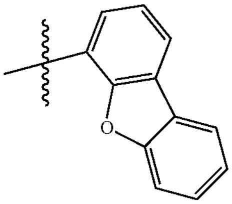
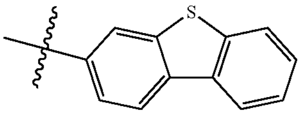
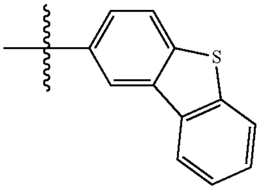

-continued

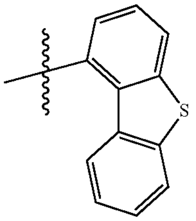
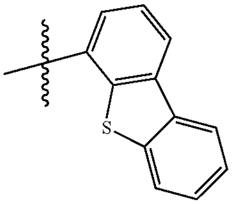
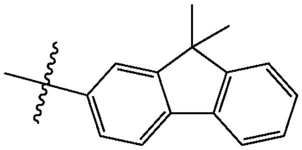
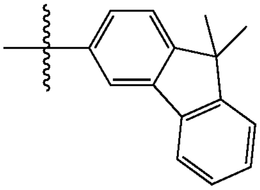
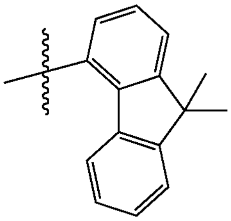
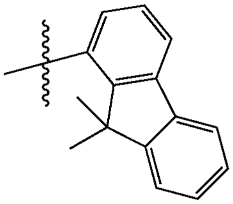
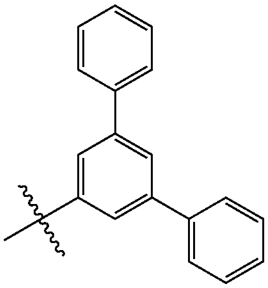
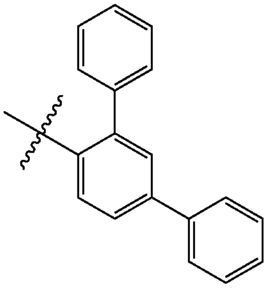
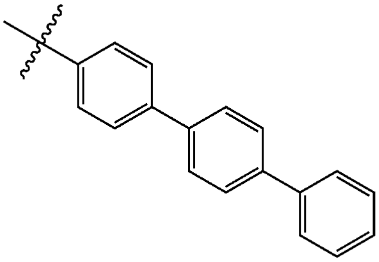
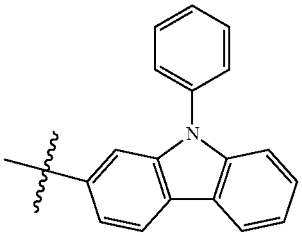
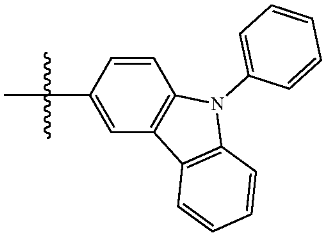

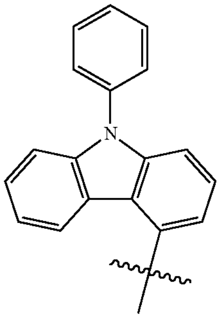
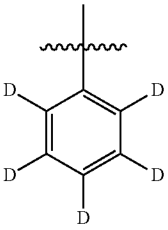
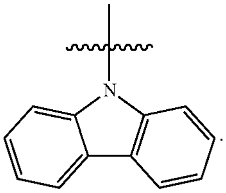
In some embodiments of the present disclosure,
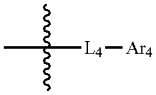 and 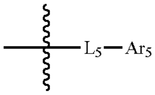
are respectively and independently selected from the group consisting of:
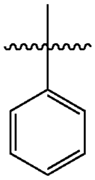
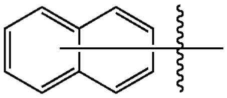
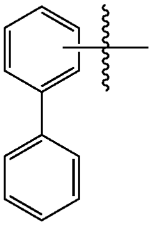
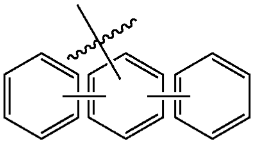
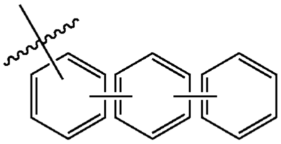
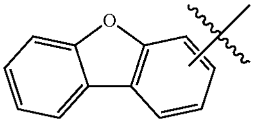
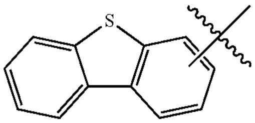
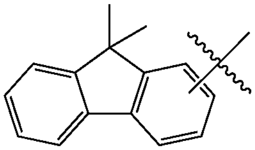
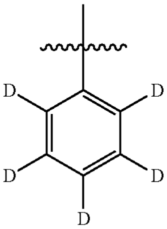
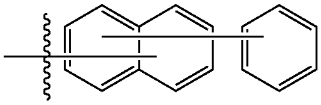
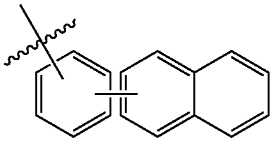
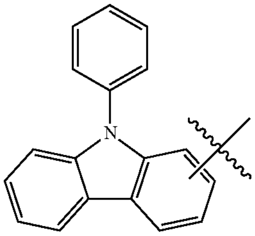
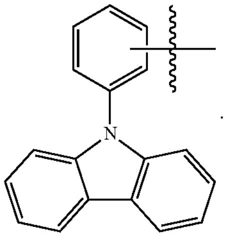
In particular,
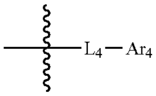 and 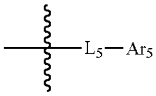
are respectively and independently selected from the group consisting of:
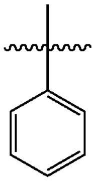
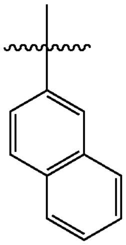
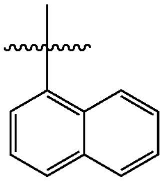
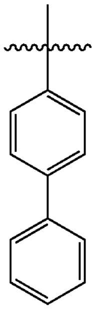
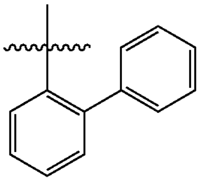
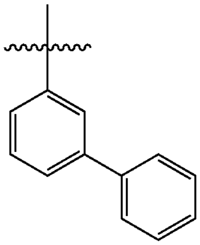

-continued
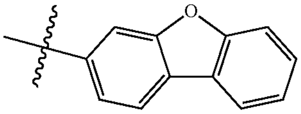
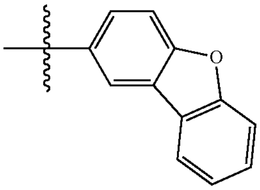
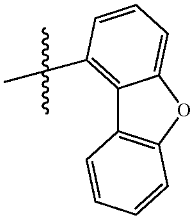
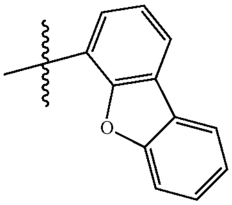
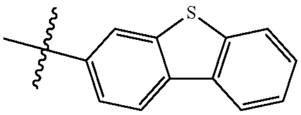
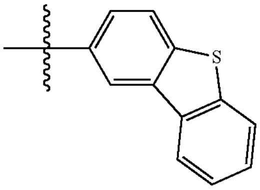
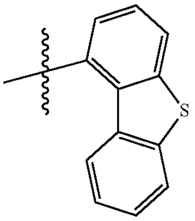
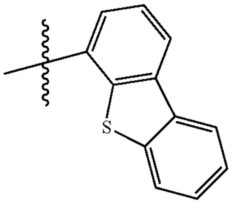
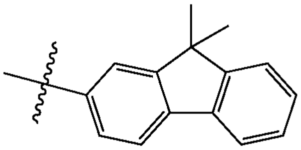
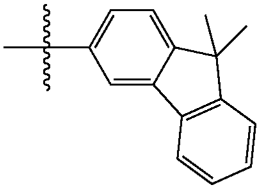
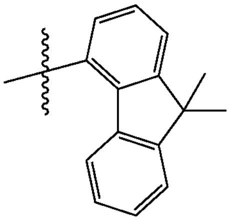
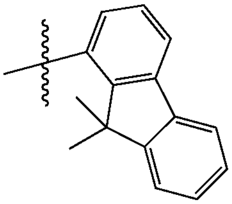
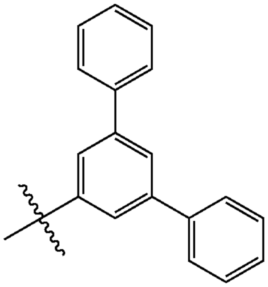
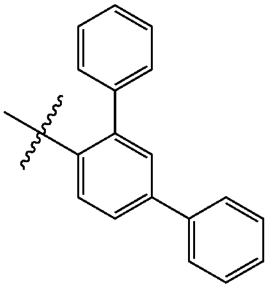
-continued
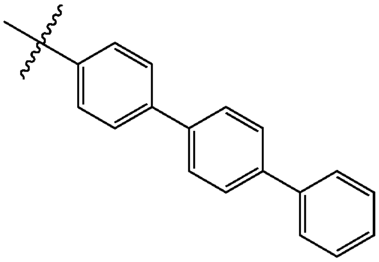
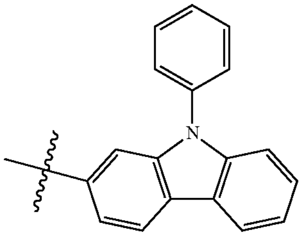
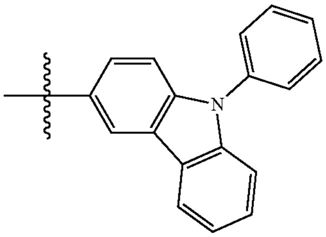
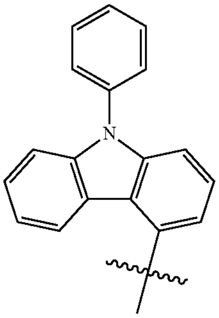
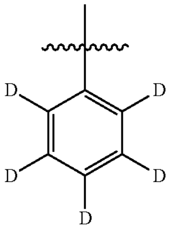
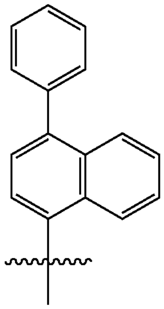
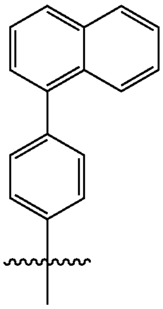

-continued
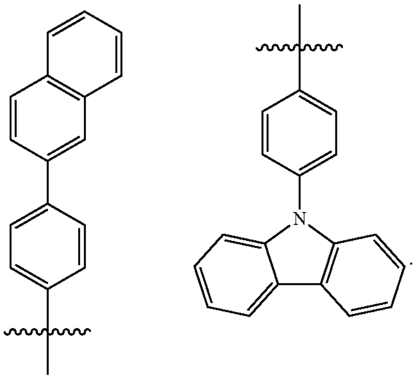
In some embodiments of the present disclosure, the second compound is selected from the group consisting of the following compounds:
1
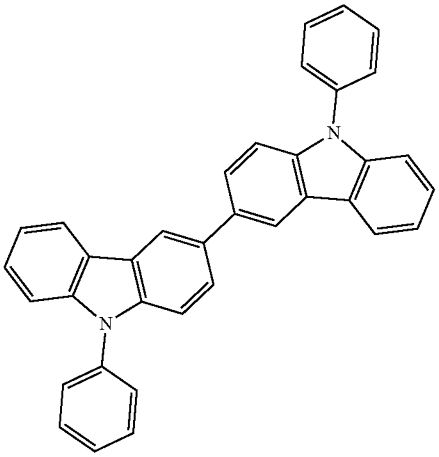
2
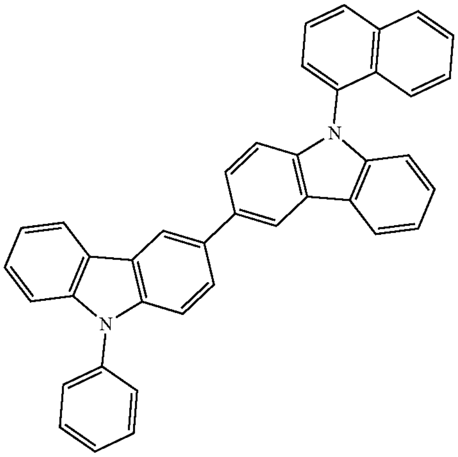
-continued
3
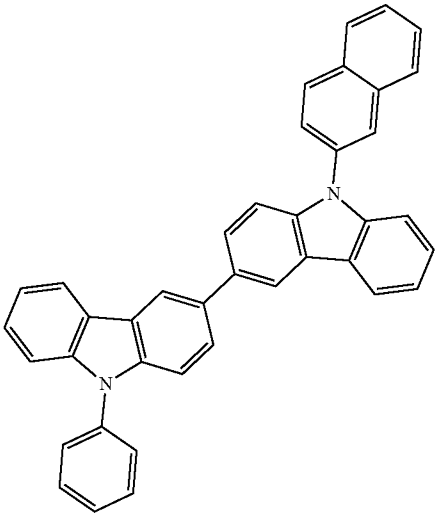
4
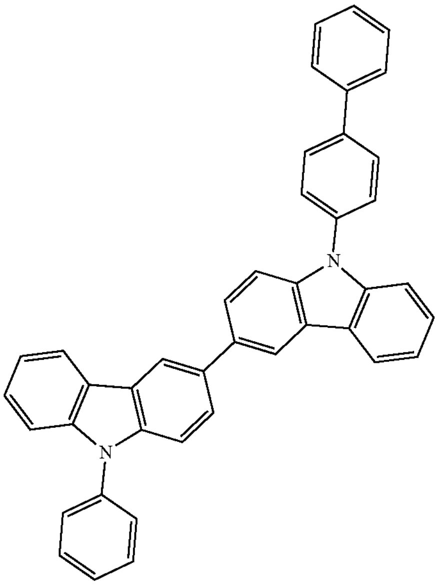

-continued
5
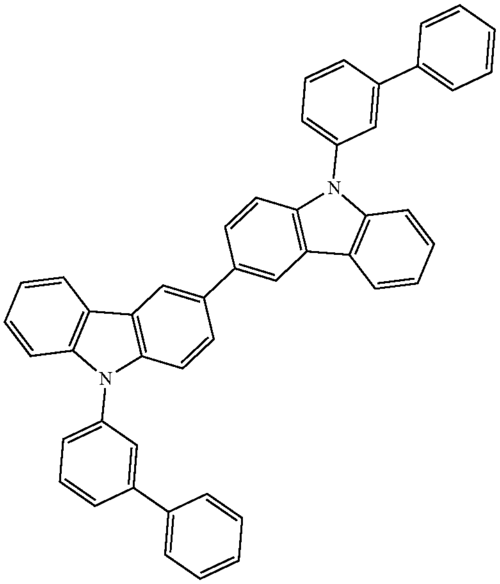
6
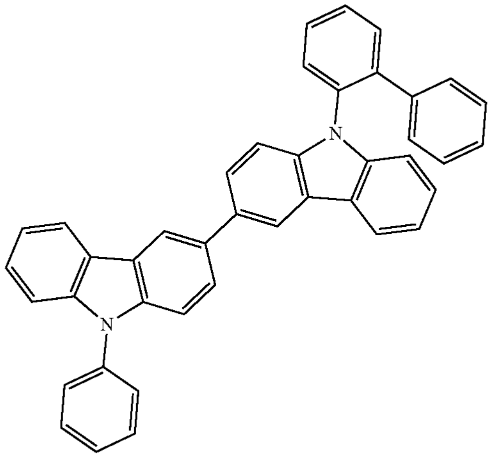
7
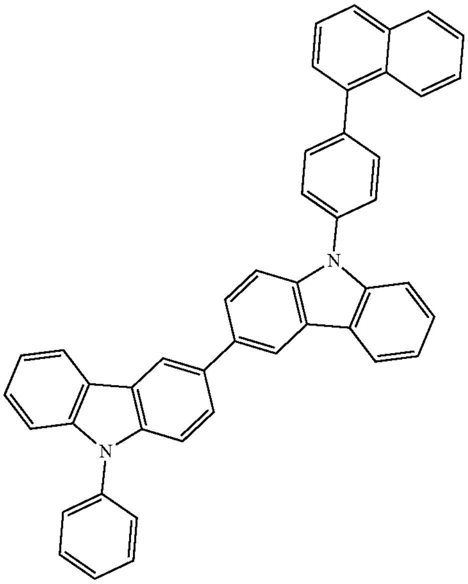
-continued
8
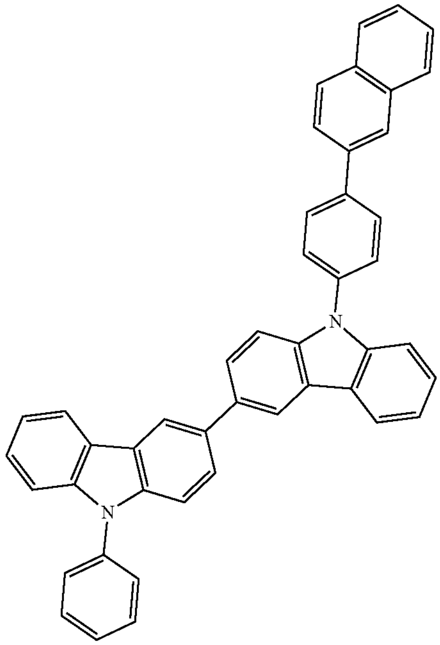
9
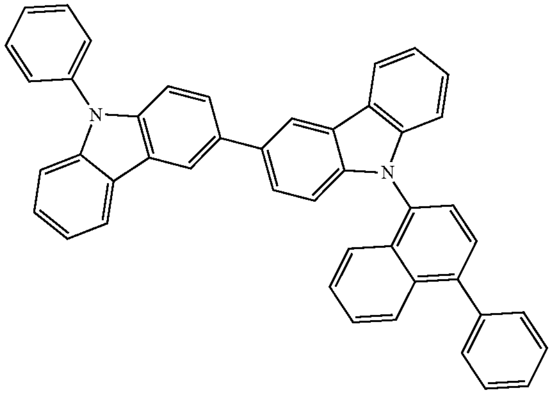
10
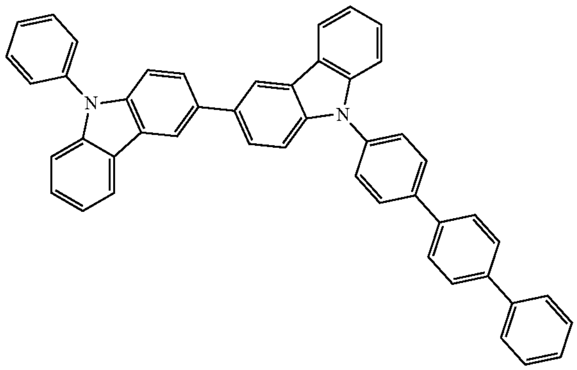

-continued
11
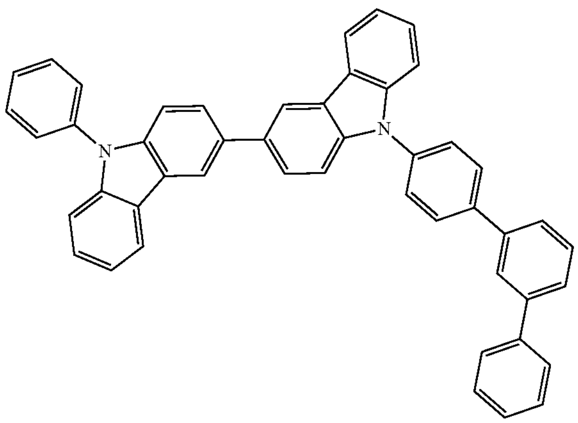
12
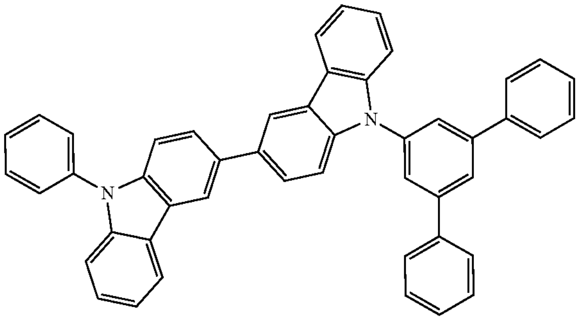
13
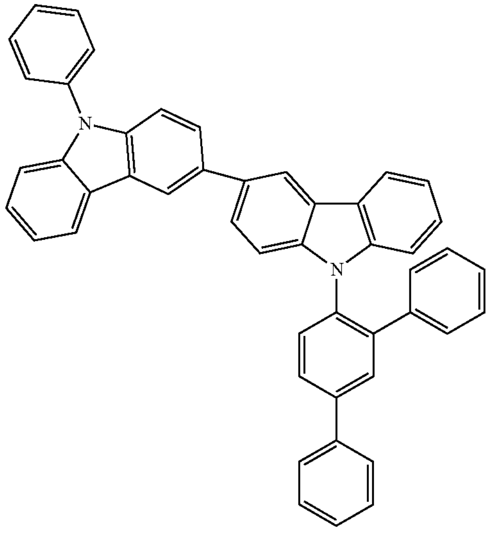
-continued
14
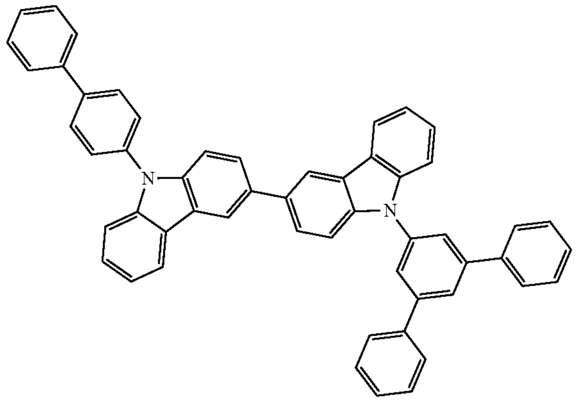
15
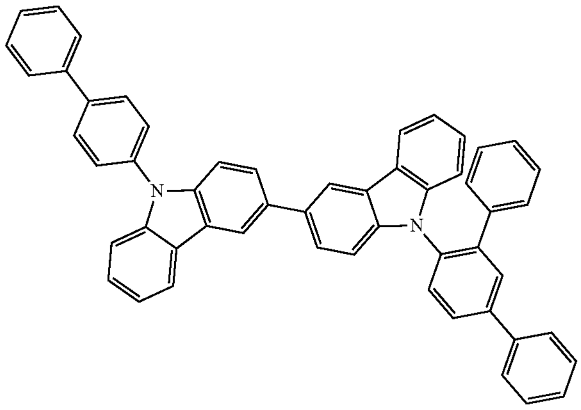
16
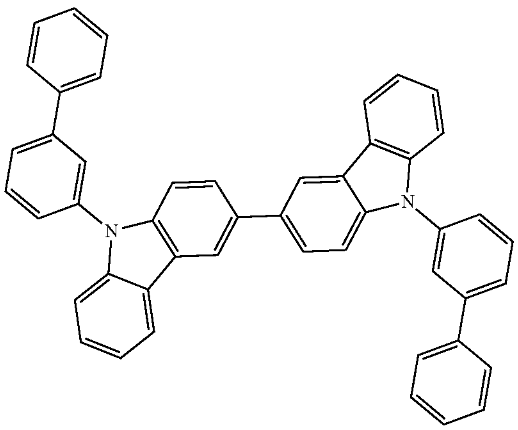

-continued
17
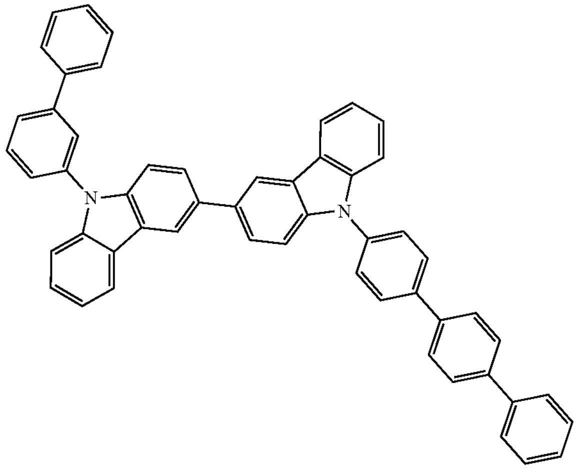
18
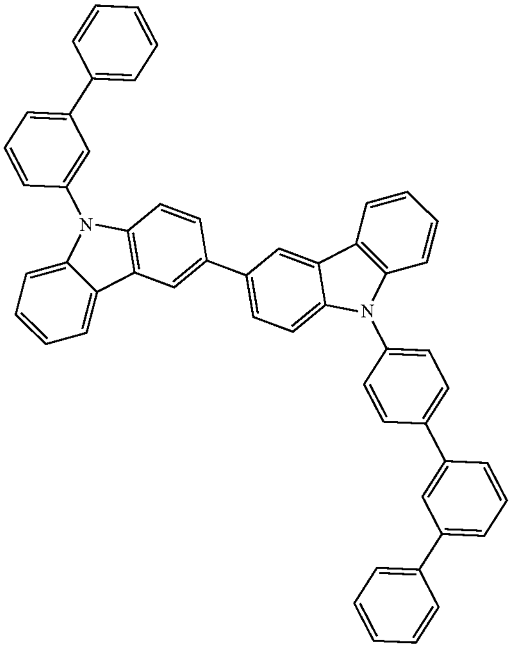
-continued
19
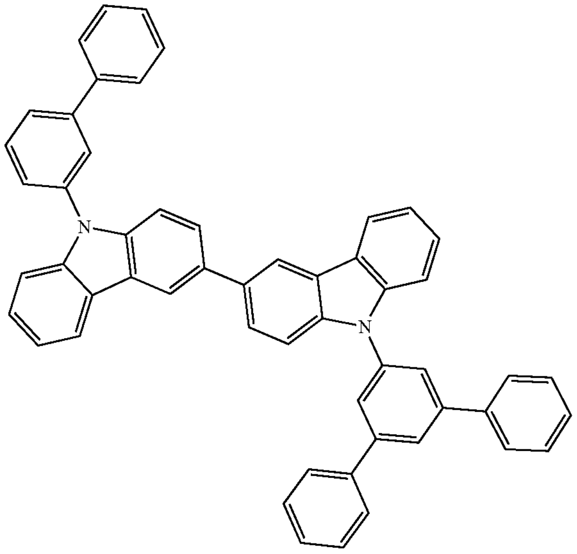
20
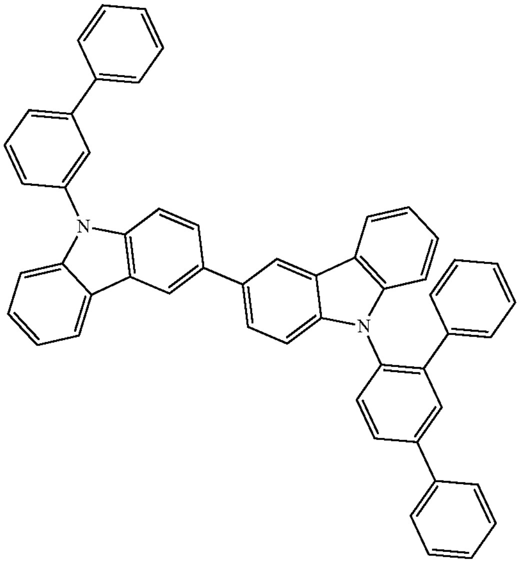

-continued
21
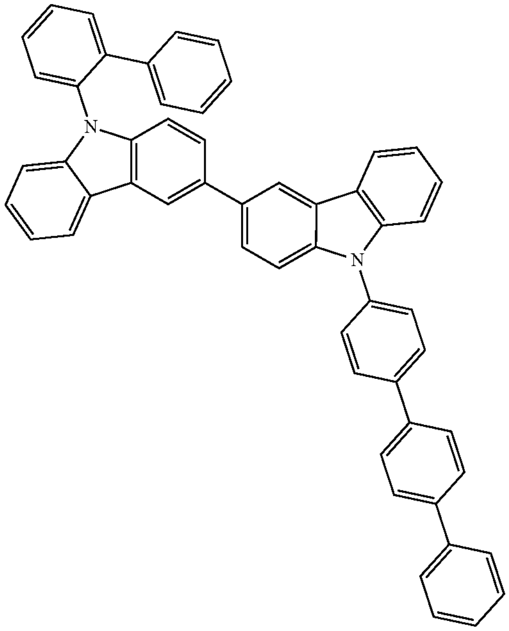
22
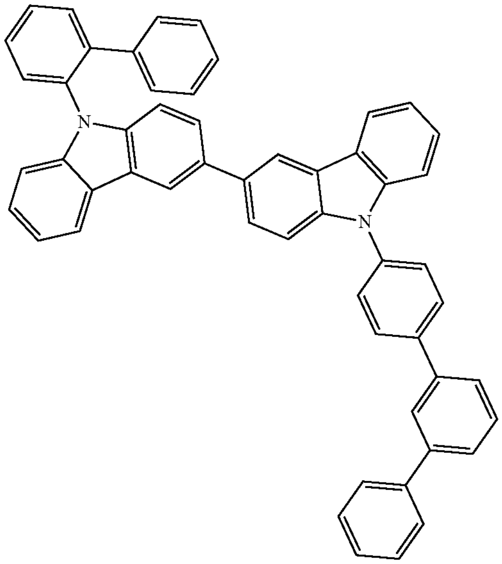
-continued
23
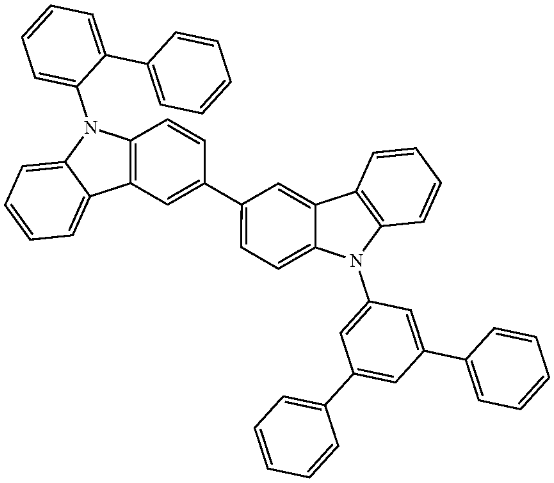
24
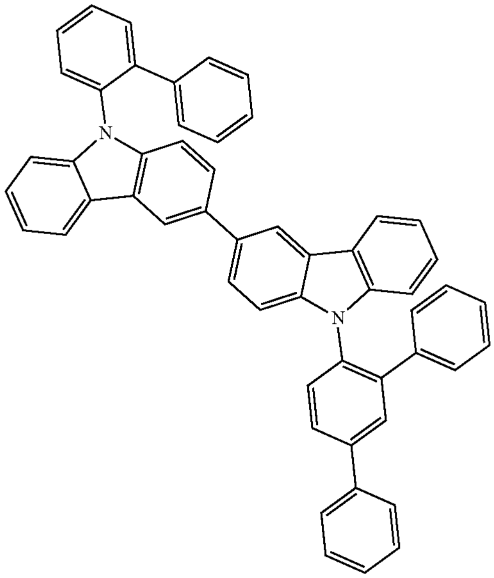
25
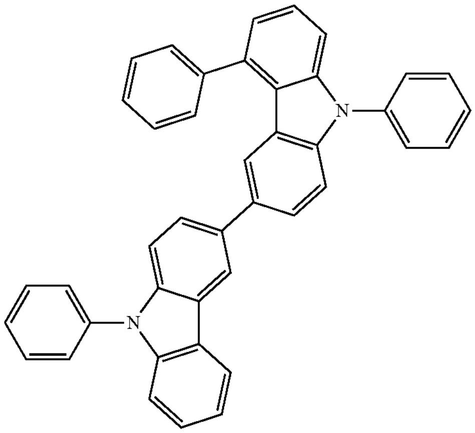

-continued
26
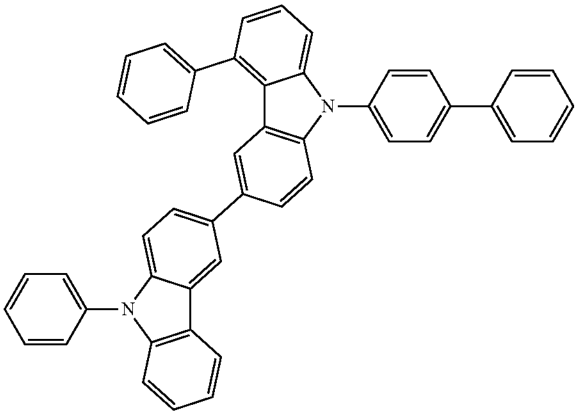
27
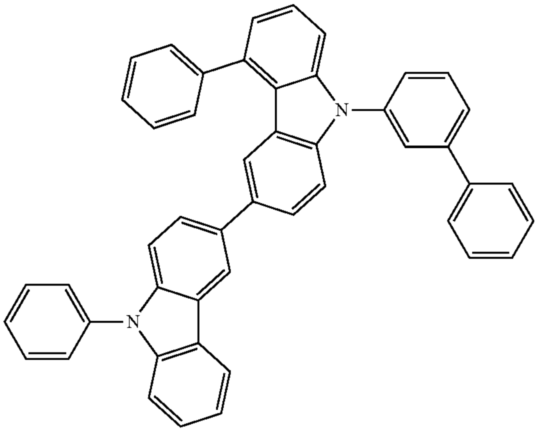
28
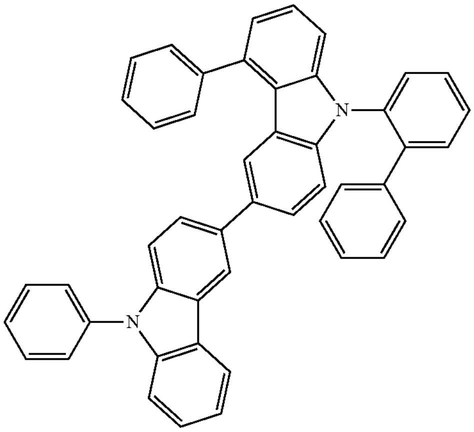
-continued
29
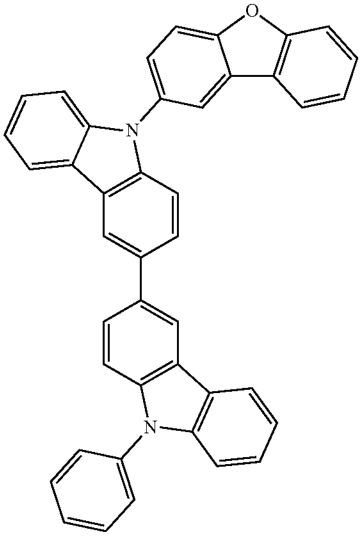
30
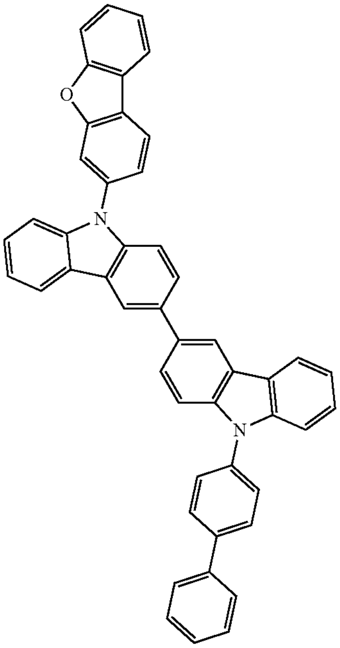

31
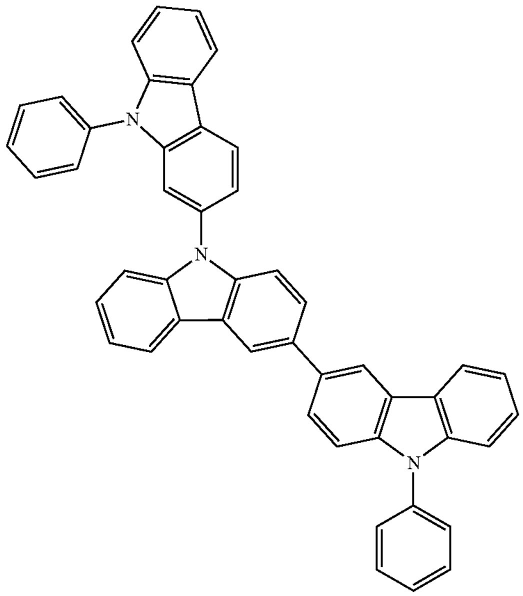
32
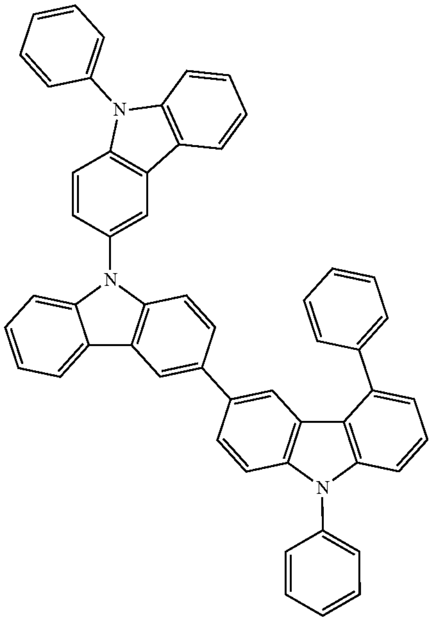
33
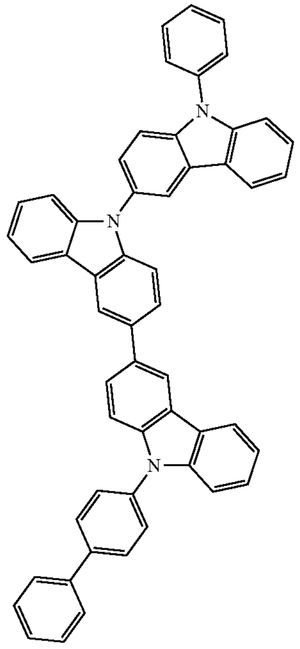
34
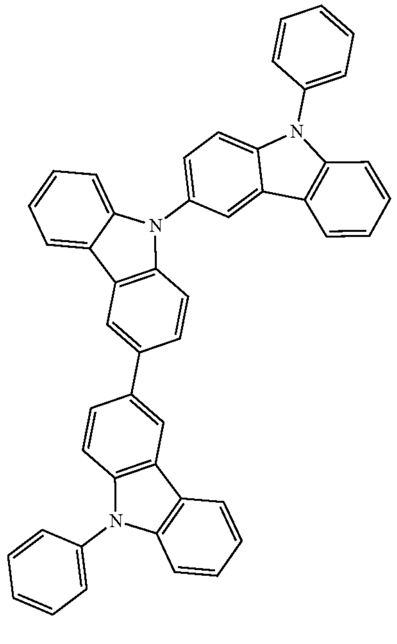

-continued
35
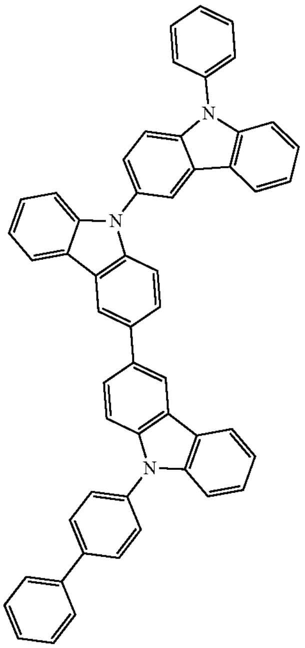
36
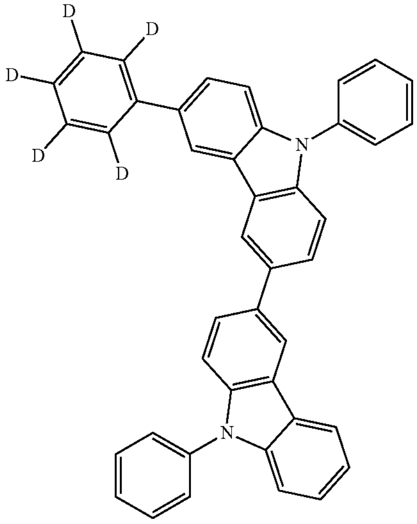
-continued
37
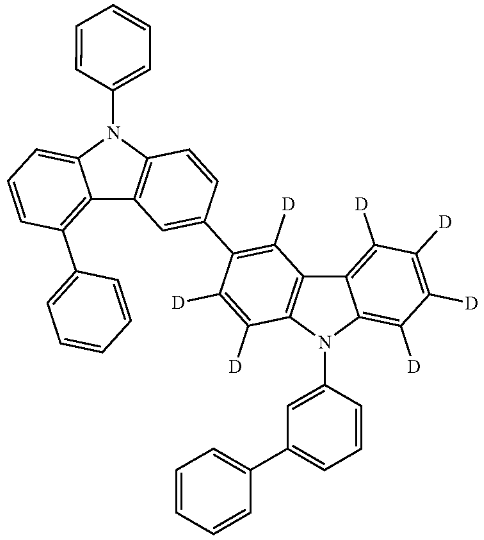
38
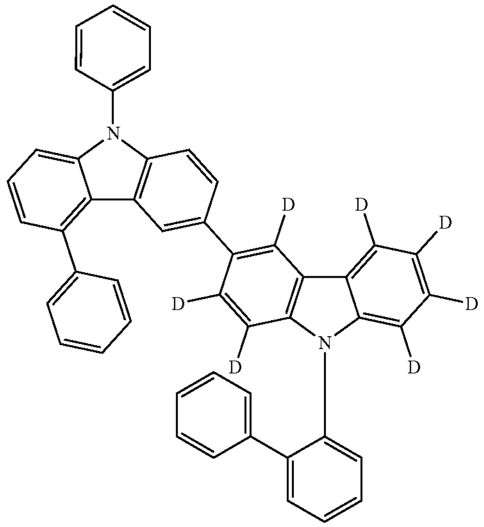
39
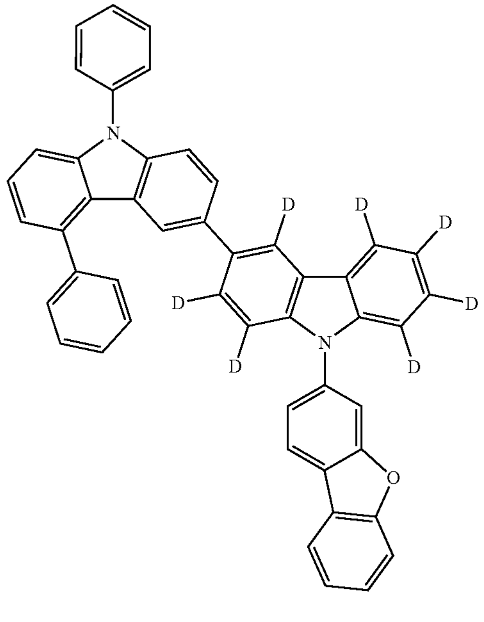

-continued
40
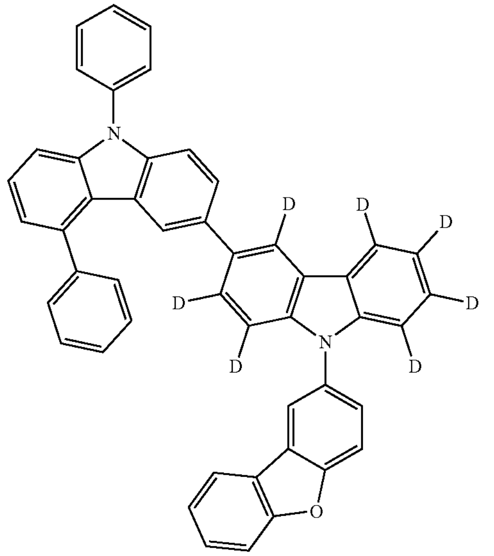
41
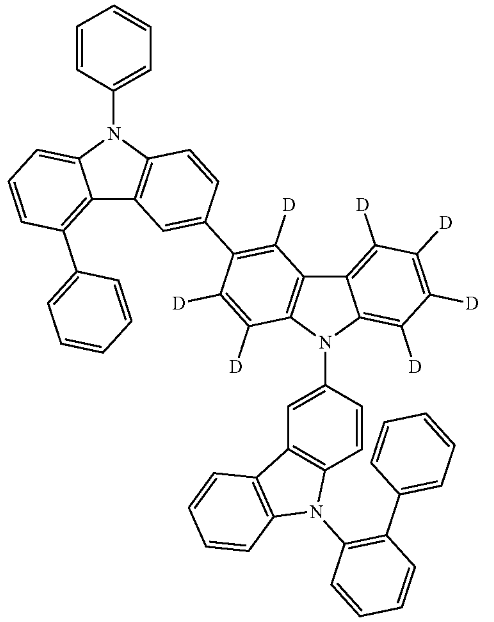
-continued
42
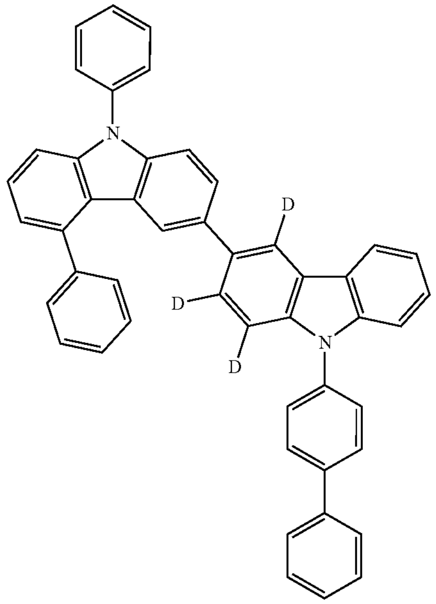
43
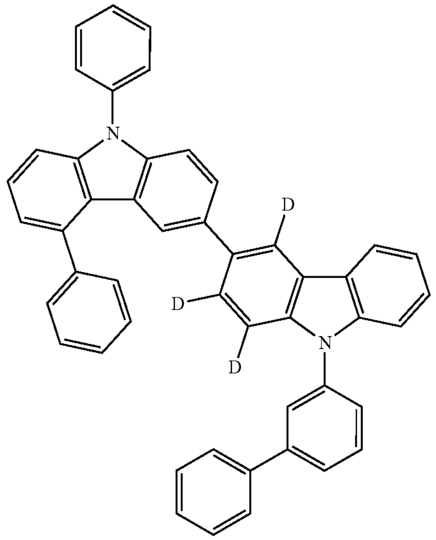
44
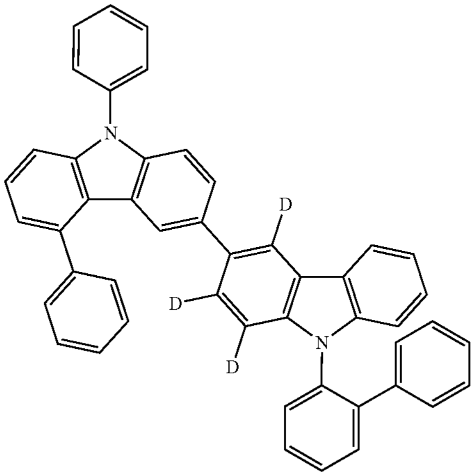

-continued
45
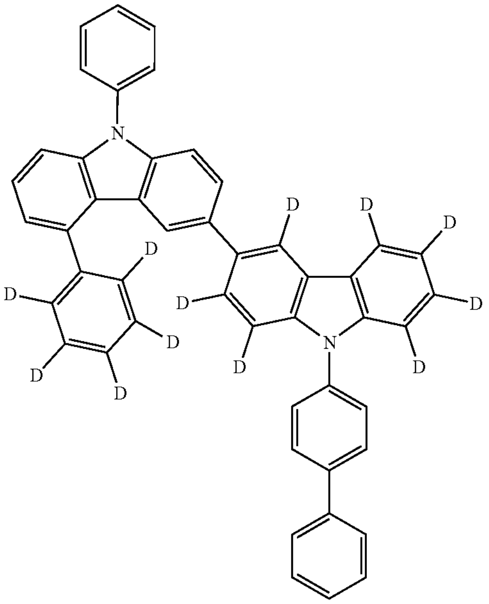
46
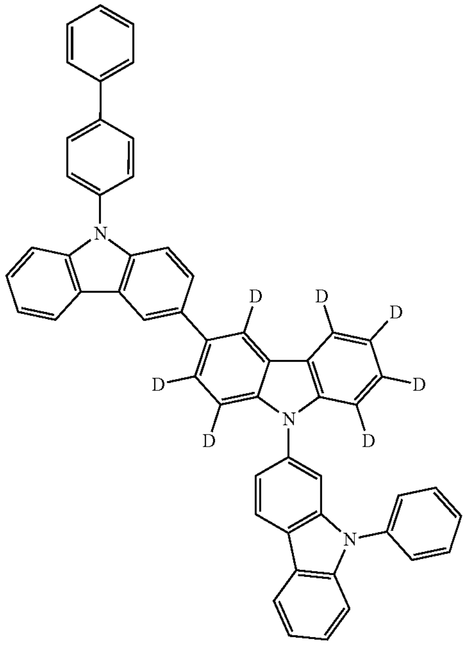
-continued
47
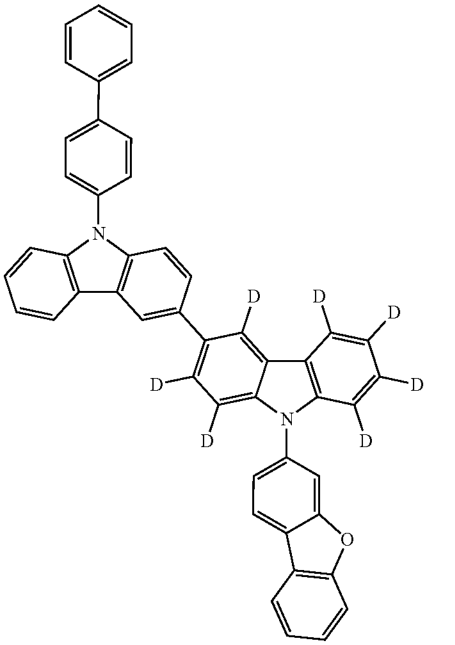
48
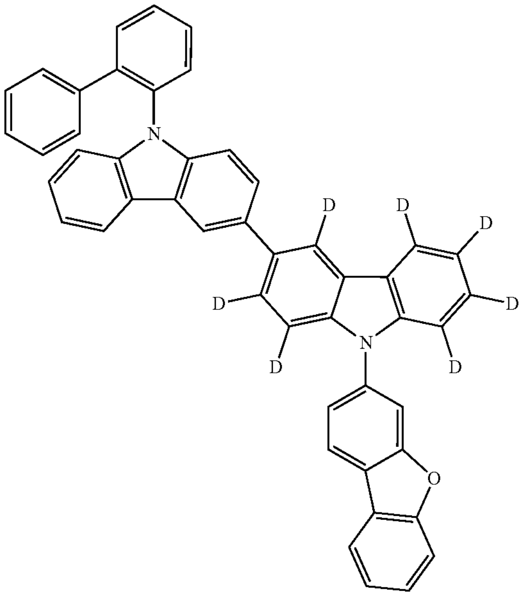

-continued
49
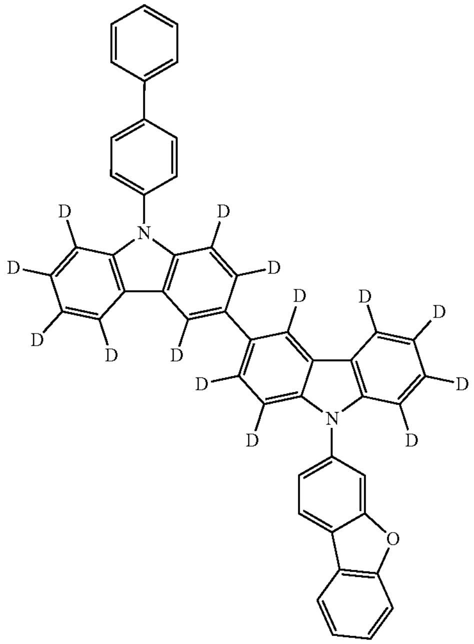
50
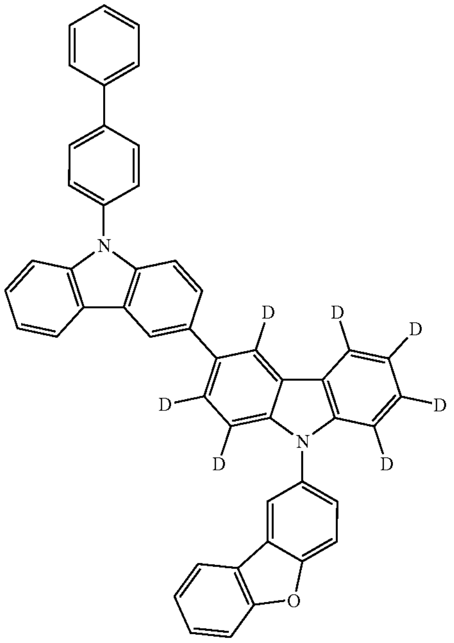
-continued
51
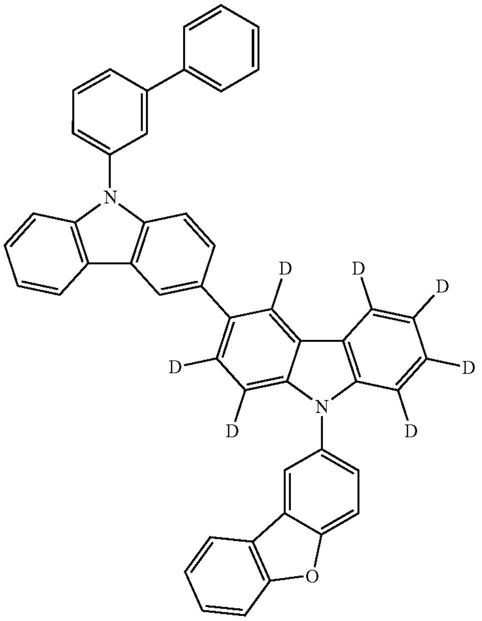
52
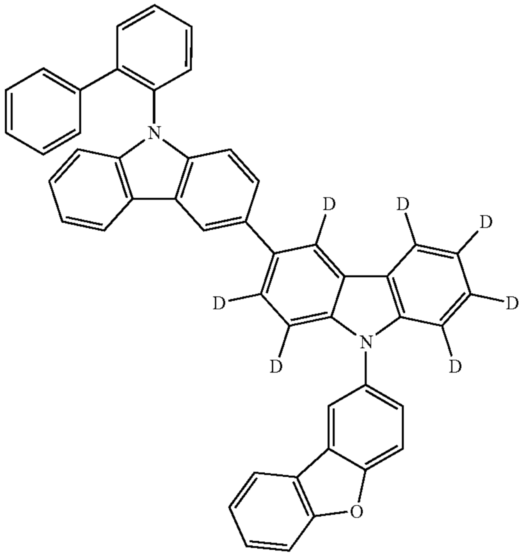

-continued
53
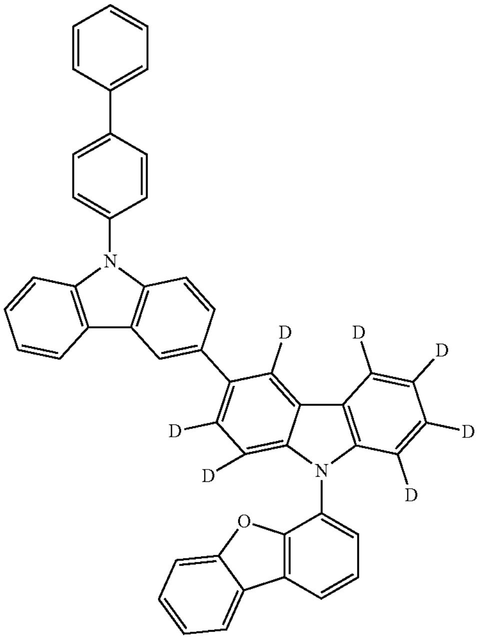
55
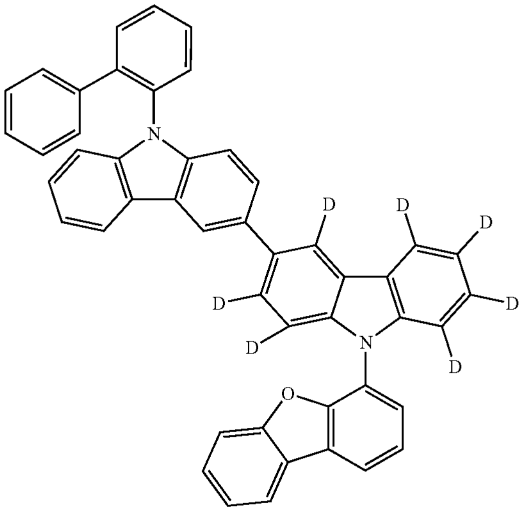
54
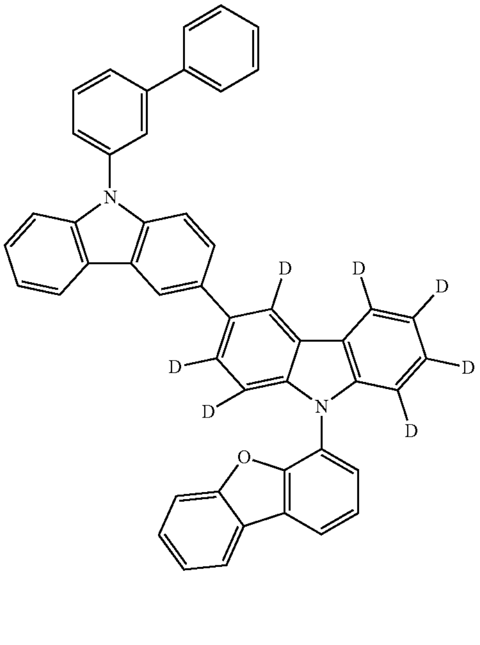
56
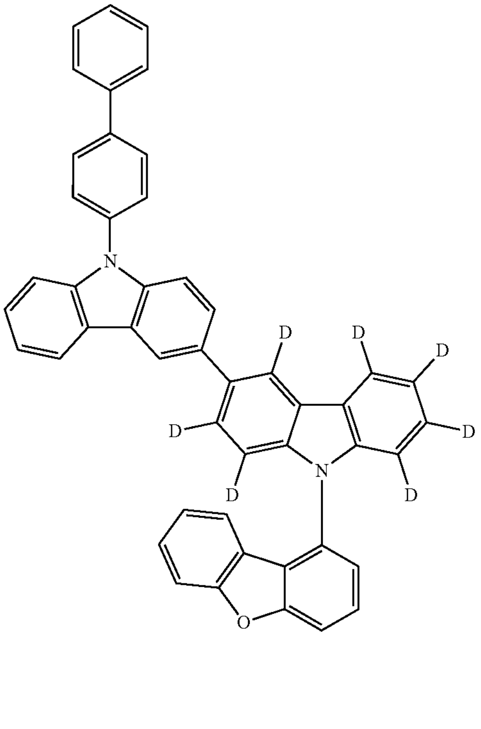

-continued
57
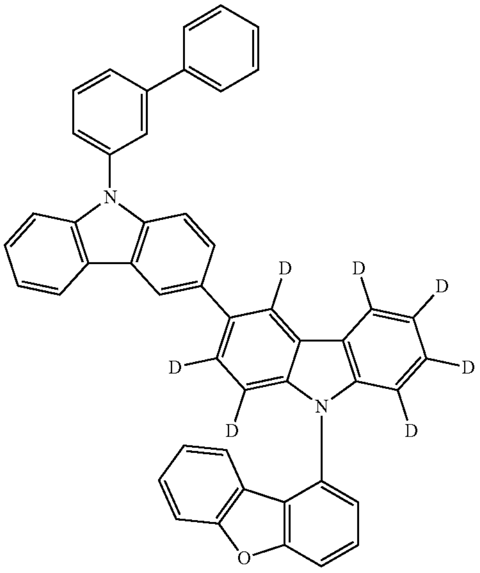
58
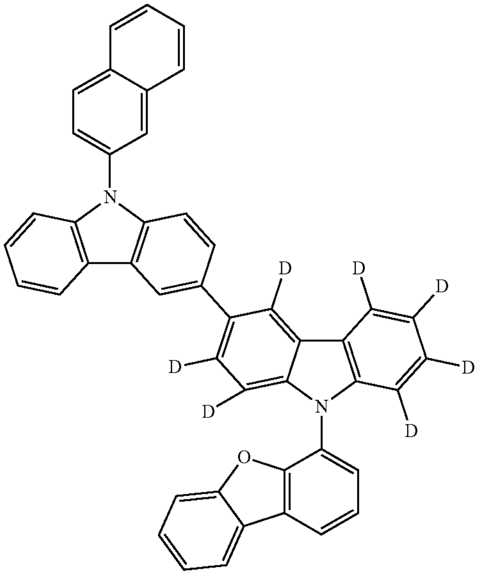
-continued
59
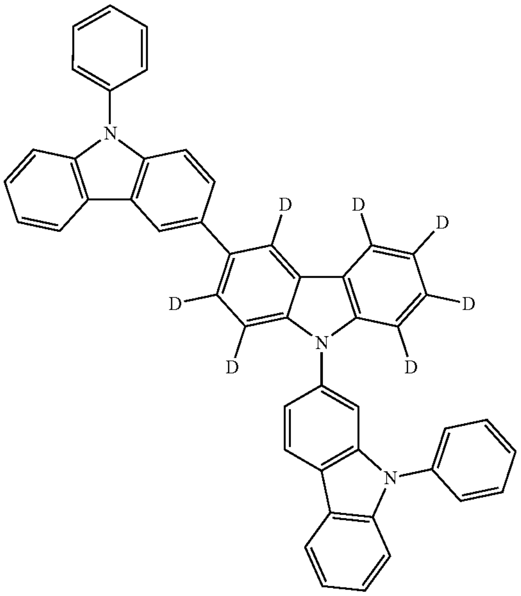
60
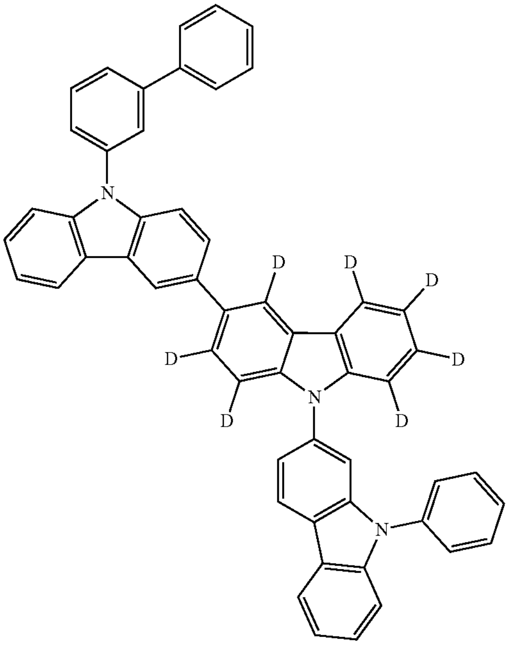

-continued
61
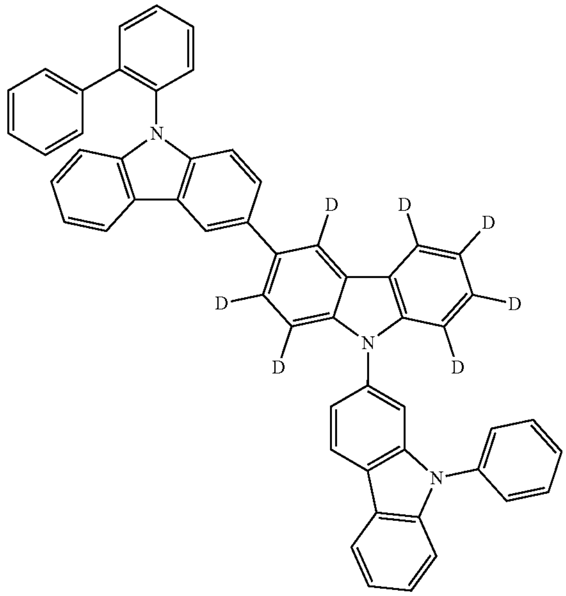
62
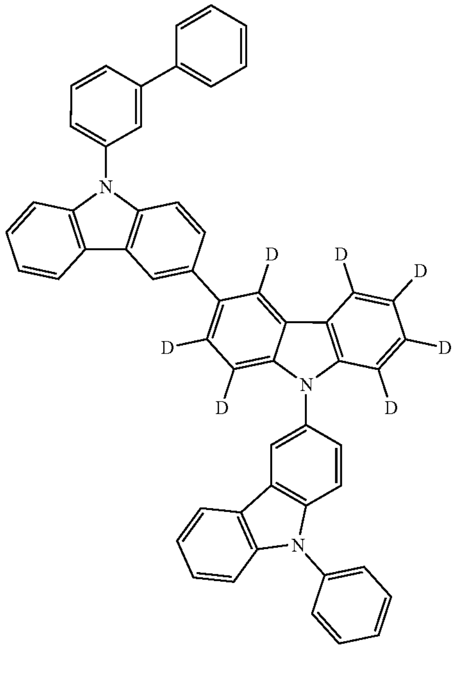
-continued
63
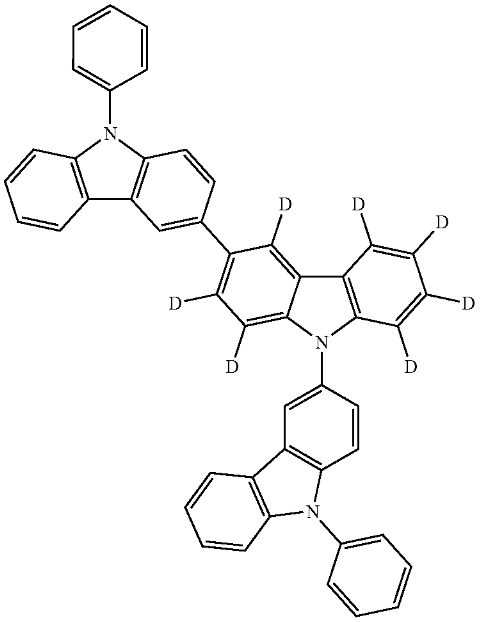
64
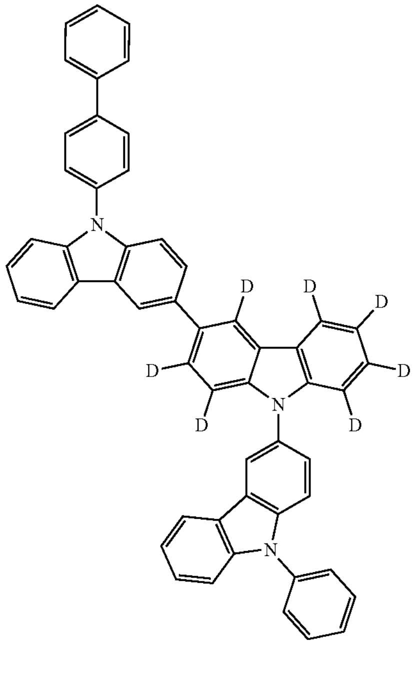

-continued
65
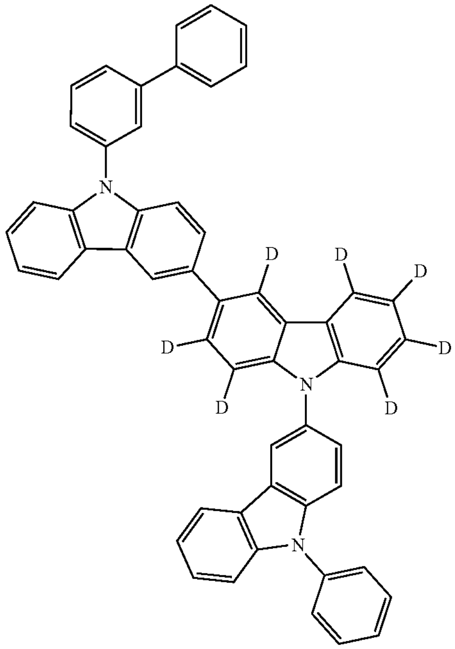
66
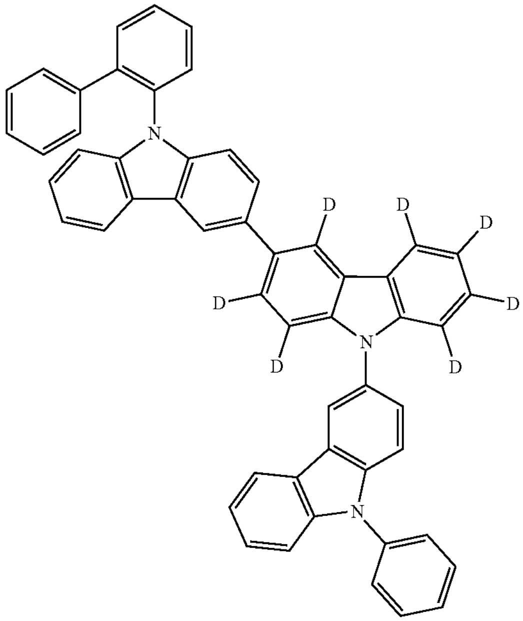
-continued
67
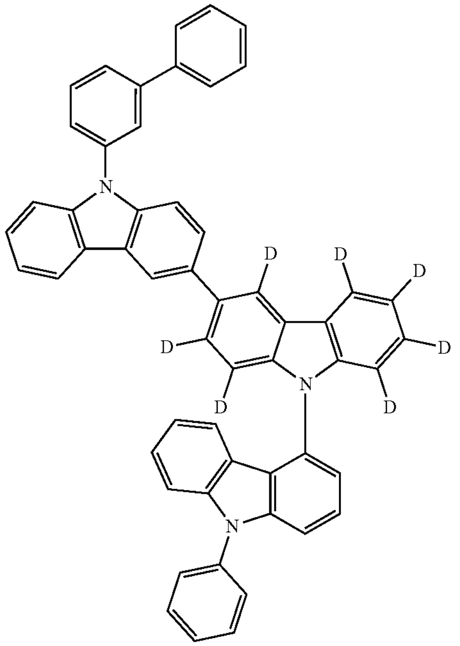
68
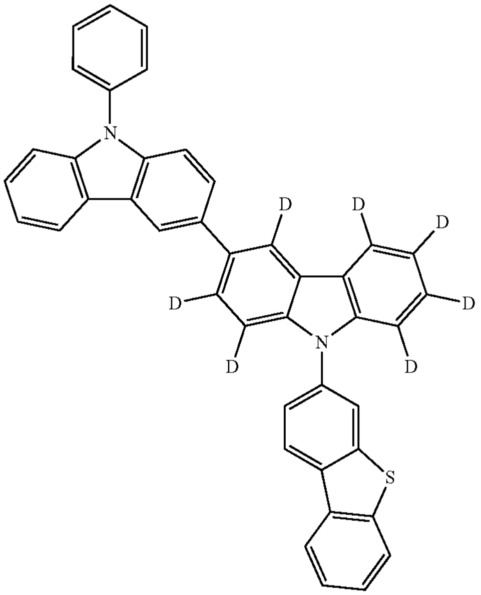

-continued
69
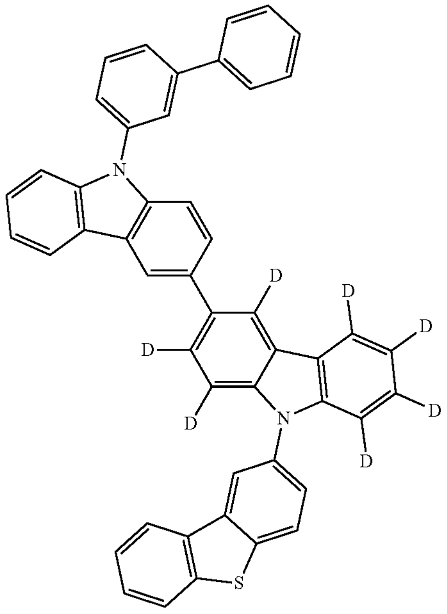
70
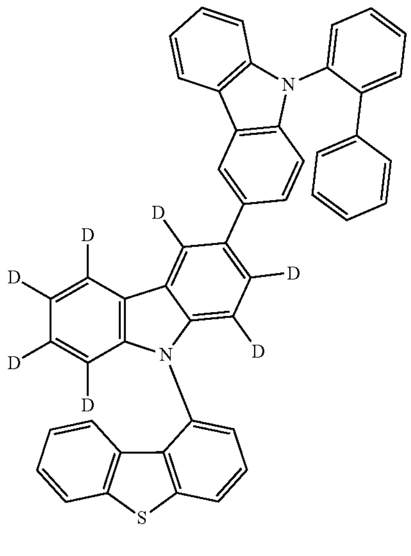
-continued
71
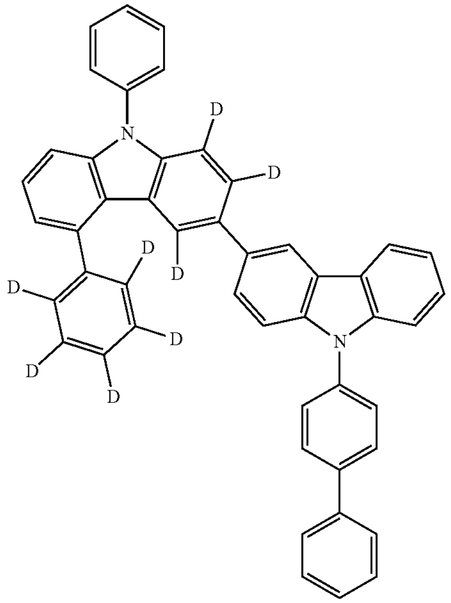
72
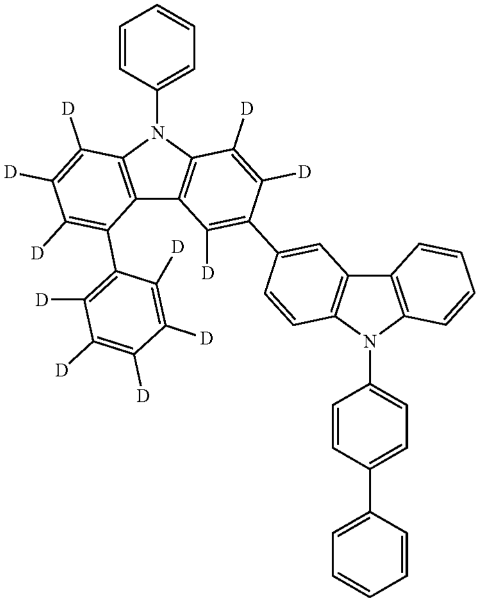

73
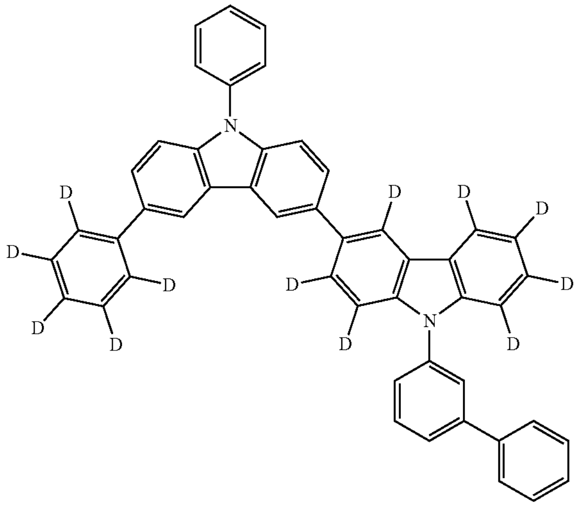
74
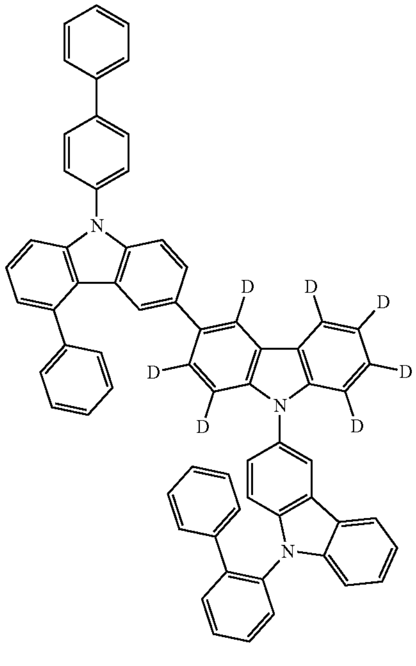
75
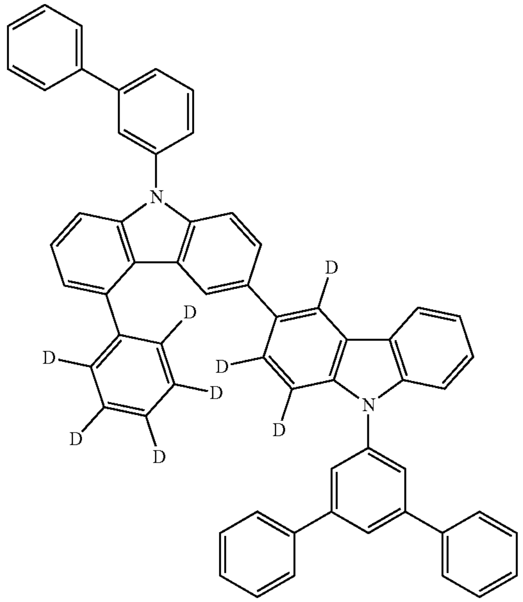
76
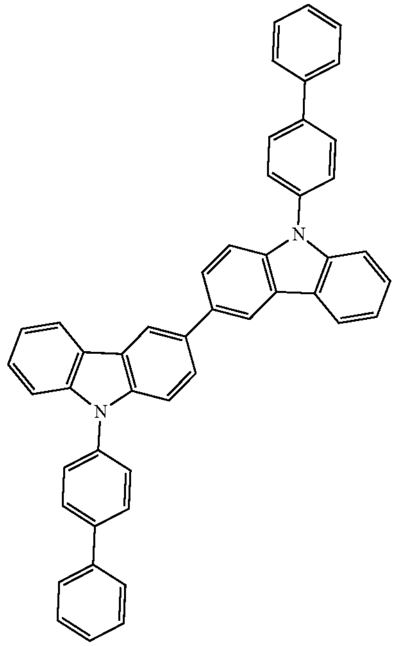

-continued

77

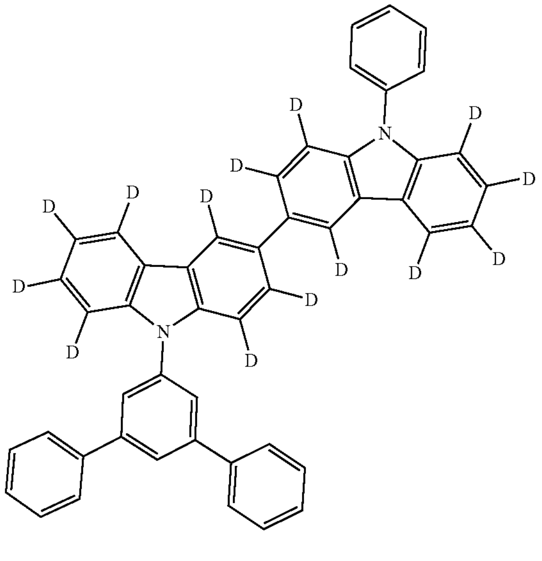

78

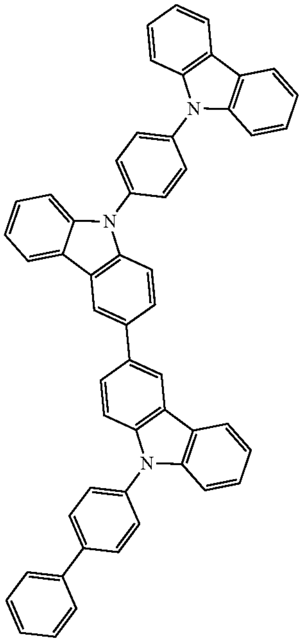

-continued

79

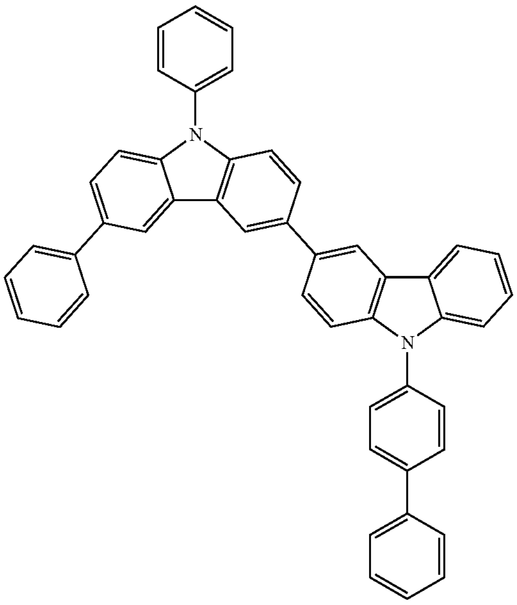

80

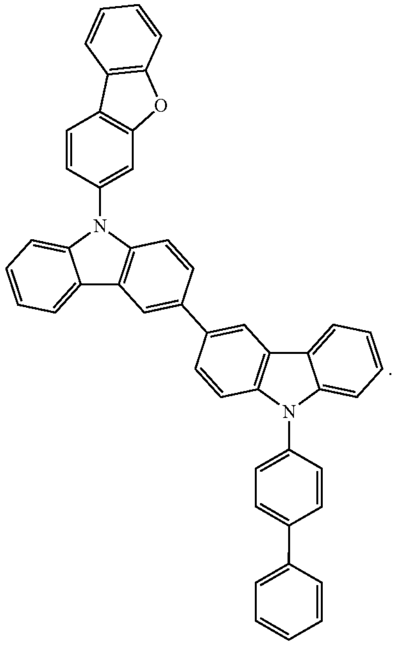

Optionally, the composition is a mixture of the first compound and the second compound. For example, the mixture may be formed by uniformly mixing the first compound with the second compound through mechanical stirring.

The relative amounts of the two types of compounds in the composition are not particularly limited in the present disclosure and can be selected according to the specific application of the organic electroluminescent device. Typically, the mass percentage of the first compound may be 1% to 99% and the mass percentage of the second compound may be 1% to 99% based on the total weight of the composition. For example, a mass ratio of the first compound to the second compound in the composition may be 1:99, 20:80, 30:70, 40:60, 45:65, 50:50, 55:45, 60:40, 70:30, 80:20, 99:1 or the like.

In some embodiments of the present disclosure, the composition consists of the first compound and the second compound, where the mass percentage of the first compound is 20% to 80% and the mass percentage of the second compound is 20% to 80% based on the total weight of the composition.

In some preferred embodiments, in the composition, the mass percentage of the first compound is 30% to 60% and the mass percentage of the second compound is 40% to 70% based on the total weight of the composition, and in this case, when the composition is applied to an organic electroluminescent device, the device can have both high luminous efficiency and long service life. Preferably, the mass percentage of the first compound is 40% to 60% and the mass percentage of the second compound is 40% to 60% based on the total weight of the composition. More preferably, the mass percentage of the first compound is 40% to 50% and the mass percentage of the second compound is 50% to 60%.

The present disclosure also provides use of the composition as a host material for a light-emitting layer of an organic electroluminescent device.

In a third aspect of the present disclosure, also provided is an organic electroluminescent device, including an anode and a cathode which are oppositely disposed, and at least one functional layer between the anode and the cathode, the functional layer including the organic compound shown in the formula 1 according to the present disclosure or the composition containing the first compound and the second compound.

In one embodiment of the present disclosure, the functional layer includes an organic light-emitting layer including the organic compound shown in the formula 1 according to the present disclosure.

In one embodiment of the present disclosure, the functional layer includes an organic light-emitting layer including the composition containing the first compound and the second compound provided in the present disclosure.

In one embodiment of the present disclosure, the organic electroluminescent device is a phosphorescent device.

In one specific embodiment of the present disclosure, the organic electroluminescent device is a green organic electroluminescent device.

In some embodiments of the present disclosure, the organic electroluminescent device sequentially includes an anode (an ITO substrate), a hole transport layer, a hole auxiliary layer, an organic light-emitting layer, an electron transport layer, an electron injection layer, a cathode (a Mg—Ag mixture), and an organic capping layer.

In one specific embodiment of the present disclosure, as shown in FIG. 1, the organic electroluminescent device of the present disclosure includes an anode 100, a cathode 200, and at least one functional layer 300 between an anode layer and a cathode layer, the functional layer 300 including a hole injection layer 310, a hole transport layer 320, a hole auxiliary layer 330, an organic light-emitting layer 340, an electron transport layer 350, and an electron injection layer 360.

Optionally, the anode 100 includes the following anode materials which are optionally materials having a large work function that facilitate hole injection into the functional layer. Specific examples of the anode materials include metals such as nickel, platinum, vanadium, chromium, copper, zinc, and gold, or an alloy of them; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, but are not limited to this. A transparent electrode including indium tin oxide (ITO) as the anode is preferably included.

Optionally, the hole transport layer 320 may include one or more hole transport materials, and the hole transport materials may be selected from carbazole multimers, carbazole-linked triarylamine compounds, or other types of compounds, which are not particularly limited in the present disclosure. For example, in some embodiments of the present disclosure, the hole transport layer 320 consists of HT-01.

Optionally, the hole auxiliary layer 330 may include one or more hole transport materials, and the hole transport materials may be selected from carbazole multimers, carbazole-linked triarylamine compounds, or other types of compounds, which are not particularly limited in the present disclosure. For example, in some embodiments of the present disclosure, the hole auxiliary layer 330 consists of HT-02. The hole auxiliary layer is also referred to as a second hole transport layer, a hole buffer layer, a hole adjustment layer, or an electron blocking layer.

Optionally, the organic light-emitting layer 340 may consist of a single light-emitting material or may include a host material and a guest material. Optionally, the organic light-emitting layer 340 is composed of the host material and the guest material, and holes and electrons which are injected into the organic light-emitting layer 340 may be recombined in the organic light-emitting layer 340 to form excitons, and the excitons transfer energy to the host material, and the host material transfers energy to the guest material, thus enabling the guest material to emit light.

The guest material of the organic light-emitting layer 340 may be a compound having a condensed aryl ring or its derivative, a compound having a heteroaryl ring or its derivative, an aromatic amine derivative, or other materials, which is not particularly limited in the present disclosure.

In some embodiments of the present disclosure, in the green organic electroluminescent device, the organic light-emitting layer 340 includes the organic compound described in the present disclosure, the second compound, and a guest material $Ir(ppy)_3$.

The electron transport layer 350 may have a single-layer structure or a multi-layer structure, and may include one or more electron transport materials, and the electron transport materials may be selected from a benzimidazole derivative, an oxadiazole derivative, a quinoxaline derivative, or other electron transport materials, which are not particularly limited in the present disclosure. For example, in some embodiments of the present disclosure, the electron transport layer 350 may consist of ET-01 and LiQ.

Optionally, the cathode 200 includes a cathode material which is a material having a small work function that facilitates electron injection into the functional layer. Specific examples of the cathode material include: metals such as magnesium, calcium, sodium, potassium, titanium, indium, yttrium, lithium, gadolinium, aluminum, silver, tin and lead or an alloy of them; or multilayer materials such as LiF/Al, Liq/Al, $LiO_2$/Al, LiF/Ca, LiF/Al and $BaF_2$/Ca, but are not limited to this. A metal electrode including silver and magnesium is preferably included as the cathode.

Optionally, the hole injection layer 310 may also be disposed between the anode 100 and the hole transport layer 320 to enhance the ability to inject holes into the hole transport layer 320. The hole injection layer 310 may be made of a benzidine derivative, a starburst arylamine compound, a phthalocyanine derivative, or other materials, which is not particularly limited in the present disclosure. In some embodiments of the present disclosure, the hole injection layer 310 may consist of CuPC and HT-01.

Optionally, the electron injection layer 360 may also be disposed between the cathode 200 and the electron transport layer 350 to enhance the ability to inject electrons into the electron transport layer 350. The electron injection layer 360 may include an inorganic material such as an alkali metal sulfide or an alkali metal halide, or may include a complex of an alkali metal and an organic substance. In some embodiments of the present disclosure, the electron injection layer 360 may include ytterbium (Yb).

In a fourth aspect of the present disclosure, also provided is an electronic apparatus, including the organic electroluminescent device described in the present disclosure.

Figure 2:
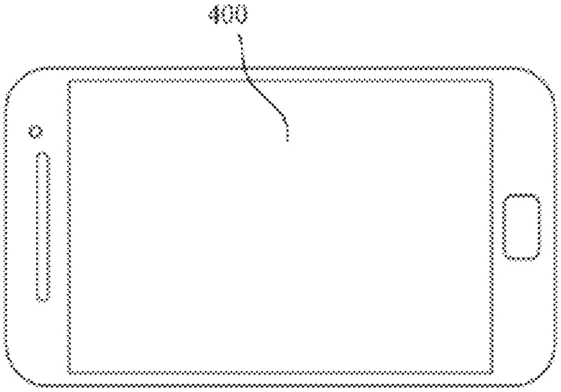
FIG. 2 is a structural schematic diagram of an electronic apparatus according to the present disclosure.

For example, as shown in FIG. 2, the electronic apparatus provided in the present disclosure is a first electronic apparatus 400 that includes any one of the organic electroluminescent devices described in the above embodiments of the organic electroluminescent device. The electronic apparatus may be a display device, a lighting device, an optical communication device, or other types of electronic devices, and may include, for example, but is not limited to, a computer screen, a mobile phone screen, a television, electronic paper, an emergency light, a light module, and the like. Since the first electronic apparatus 400 is provided with the above organic electroluminescent device, the first electronic apparatus 400 has the same beneficial effects, which is not described in detail here in the present disclosure.

The present disclosure will be described in detail below in conjunction with the examples, but the following description is intended to explain the present disclosure, and not to limit the scope of the present disclosure in any way.

Synthesis of Intermediate IM-a-no

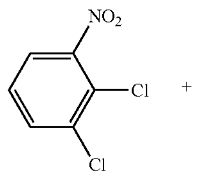

-continued

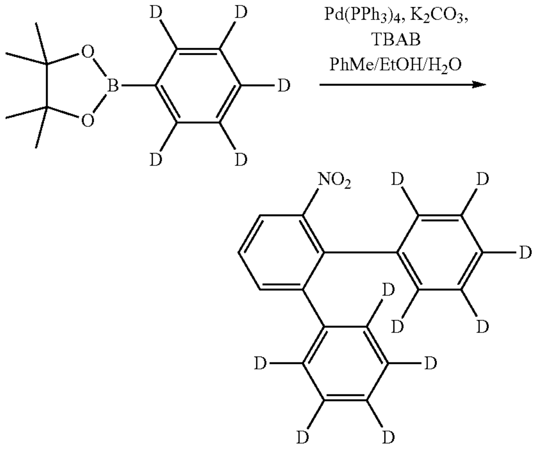

IM-a-no

Under nitrogen protection, 2,3-dichloronitrobenzene (20.0 g; 104.2 mmol), d5-pinacol phenylboronate (47.9 g; 229.2 mmol), tetrakis(triphenylphosphine) palladium (4.8 g; 4.2 mmol), potassium carbonate (57.6 g; 416.7 mmol), tetrabutylammonium bromide (13.4 g; 41.2 mmol), toluene (320 mL), ethanol (80 mL), and deionized water (80 mL) were added into a round bottom flask, a mixed solution was heated to 75° C. to 80° C., and a reaction was carried out under stirring for 72 hours. The reaction solution was cooled to room temperature, deionized water was added into the reaction solution, liquid separation was performed, an organic phase was washed with water and dried over anhydrous magnesium sulfate, and a solvent was removed under reduced pressure; and the obtained crude product was purified by silica gel column chromatography using a dichloromethane/n-heptane mixed solvent as an eluent to obtain an Intermediate IM-a-no (17.7 g; yield: 60%) as a colorless oily substance.

Referring to the synthesis method for the Intermediate IM-a-no, by substituting a Reactant A for 2,3-dichloronitrobenzene, intermediates shown in Table 1 below were synthesized:

TABLE 1

| Intermediate No. | Reactant A | Structure | Yield (%) |
|---|---|---|---|
| IM-b-no | 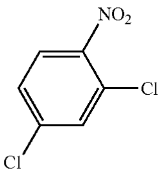 [SMILES: O=[N+]([O-])c1ccc(Cl)cc1Cl] | 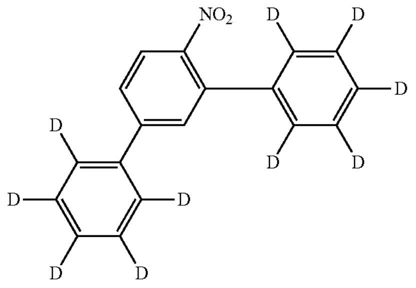 [SMILES: [2H]c1c([2H])c([2H])c(-c2ccc([N+](=O)[O-])c(-c3c([2H])c([2H])c([2H])c([2H])c3[2H])c2)c([2H])c1[2H]] | 75 |

TABLE 1-continued

| Inter-mediate No. | Reactant A | Structure | Yield (%) |
|---|---|---|---|
| IM-c-no | 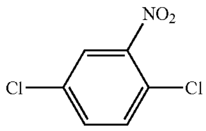 [SMILES: O=[N+]([O-])c1cc(Cl)ccc1Cl] | 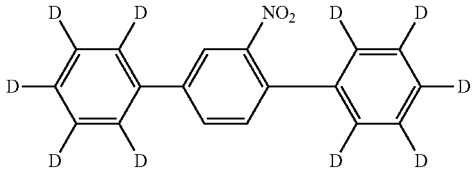 [SMILES: [2H]c1c([2H])c([2H])c(-c2ccc(-c3c([2H])c([2H])c([2H])c([2H])c3[2H])c([N+](=O)[O-])c2)c([2H])c1[2H]] | 71 |
| IM-d-no | 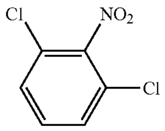 [SMILES: O=[N+]([O-])c1c(Cl)cccc1Cl] | 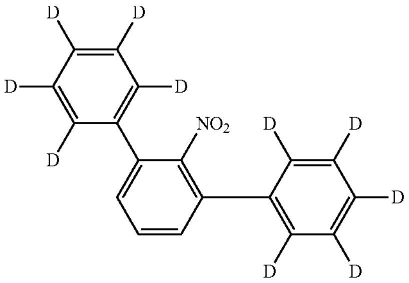 [SMILES: [2H]c1c([2H])c([2H])c(-c2cccc(-c3c([2H])c([2H])c([2H])c([2H])c3[2H])c2[N+](=O)[O-])c([2H])c1[2H]] | 70 |

Synthesis of Intermediate IM-a-nh

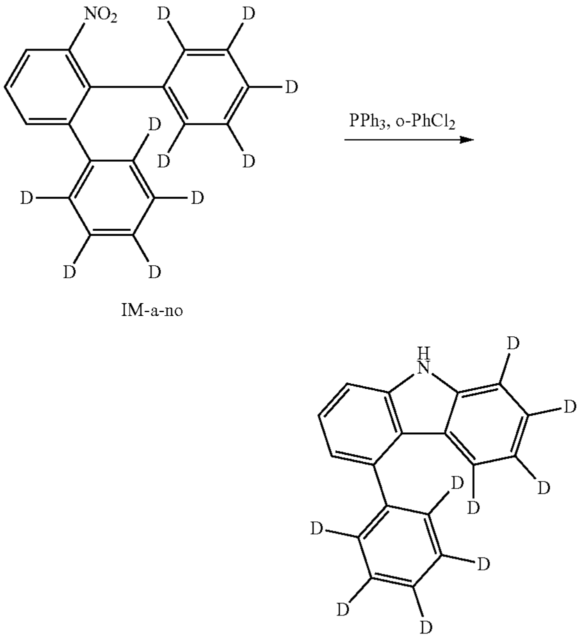

IM-a-no

IM-a-nh

Under nitrogen protection, the Intermediate IM-a-no (16.0 g; 56.1 mmol), triphenylphosphine (36.8 g; 140.2 mmol), and o-dichlorobenzene (150 mL) were added into a round bottom flask, a mixed solution was heated to 175° C. to 180° C. with stirring, and a reaction was carried out for 36 hours. The reaction solution was cooled to room temperature, deionized water was added into the reaction solution, liquid separation was performed, an organic phase was washed with water and dried over anhydrous magnesium sulfate, and a solvent was removed under reduced pressure at a high temperature; and the obtained crude product was purified by silica gel column chromatography using a dichloromethane/n-heptane mixed solvent as an eluent to obtain an Intermediate IM-a-nh (9.2 g; yield: 65%) as a white solid.

Referring to the same method as that for the Intermediate IM-a-nh, intermediates shown in Table 2 below were synthesized by substituting a Reactant B for the Intermediate IM-a-no:

TABLE 2
| Intermediate No. | Reactant B | Structure | Yield (%) |
|---|---|---|---|
| IM-b-nh | 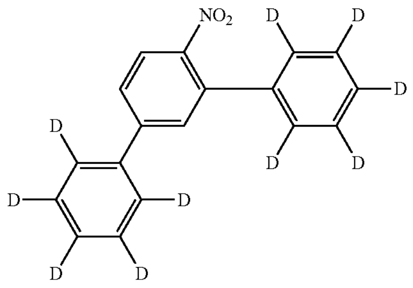 [SMILES: [2H]c1c([2H])c([2H])c(-c2ccc([N+](=O)[O-])c(-c3c([2H])c([2H])c([2H])c([2H])c3[2H])c2)c([2H])c1[2H]] | 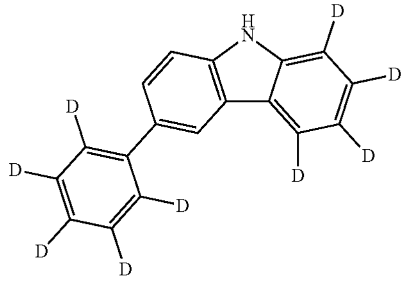 [SMILES: [2H]c1c([2H])c([2H])c(-c2ccc3[nH]c4c([2H])c([2H])c([2H])c([2H])c4c3c2)c([2H])c1[2H]] | 80 |
| IM-c-nh | 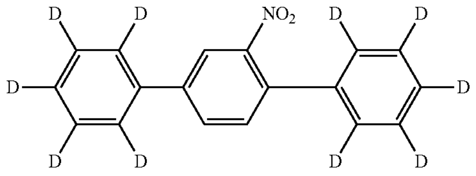 [SMILES: [2H]c1c([2H])c([2H])c(-c2ccc(-c3c([2H])c([2H])c([2H])c([2H])c3[2H])c([N+](=O)[O-])c2)c([2H])c1[2H]] | 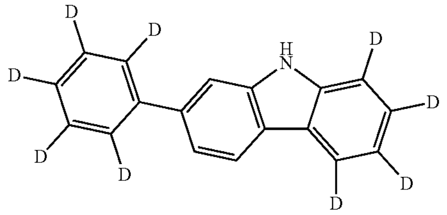 [SMILES: [2H]c1c([2H])c([2H])c(-c2ccc3c(c2)[nH]c2c([2H])c([2H])c([2H])c([2H])c23)c([2H])c1[2H]] | 76 |
| IM-d-nh | 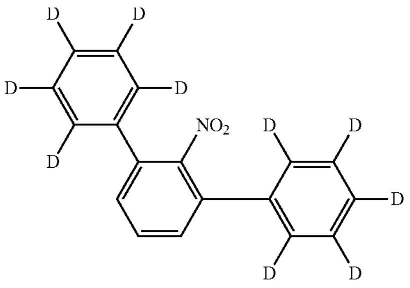 [SMILES: [2H]c1c([2H])c([2H])c(-c2cccc(-c3c([2H])c([2H])c([2H])c([2H])c3[2H])c2[N+](=O)[O-])c([2H])c1[2H]] | 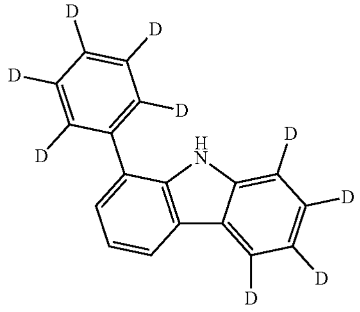 [SMILES: [2H]c1c([2H])c([2H])c(-c2cccc3c2[nH]c2c([2H])c([2H])c([2H])c([2H])c23)c([2H])c1[2H]] | 67 |
Synthesis of Compound A5
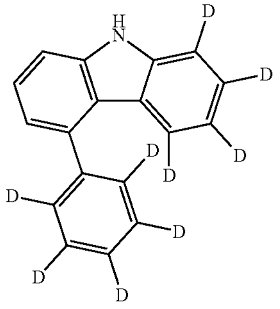
IM-a-nh
+
-continued
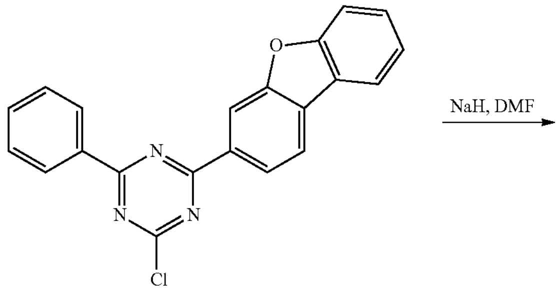

-continued

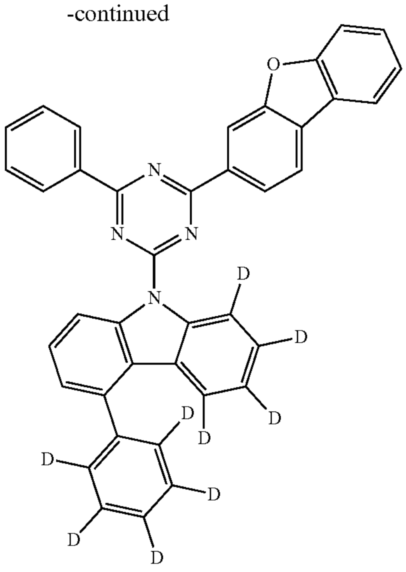

A5

Under nitrogen protection, the Intermediate IM-a-nh (5.0 g; 19.8 mmol), 2-chloro-4-(dibenzofuran-3-yl)-6-phenyl-1,3,5-triazine (10.6 g; 29.7 mmol) and N,N-dimethylformamide (50 mL) were added into a round bottom flask, a mixed solution was cooled to −5° C. to 0° C. with stirring, and sodium hydride (0.6 g; 23.4 mmol) was added, and a reaction was carried out under stirring at −5° C. to 0° C. for 1 hour, then the temperature was raised to 20° C. to 25° C., and a reaction was carried out for 24 hours. The reaction was stopped, the reaction solution was washed with water, and liquid separation was performed, an organic phase was dried over anhydrous magnesium sulfate, and a solvent was removed under reduced pressure to obtain a crude product; and the crude product was purified by silica gel column chromatography using a dichloromethane/n-heptane mixed solvent as an eluent, and then purified by recrystallization using a toluene/n-heptane mixed solvent to obtain a Compound A5 (8.0 g; yield: 70%) as a white solid.

Referring to the synthesis method for the Compound A5, by substituting a Reactant C for the Intermediate IM-a-nh and substituting a Reactant D for 2-chloro-4-(dibenzofuran-3-yl)-6-phenyl-1,3,5-triazine, compounds shown in Table 3 below were synthesized:

TABLE 3

| Compound No. | Reactant C | Reactant D |
|---|---|---|
| A9 | 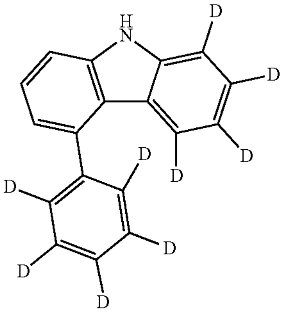 [SMILES: [2H]c1c([2H])c([2H])c(-c2cccc3[nH]c4c([2H])c([2H])c([2H])c([2H])c4c23)c([2H])c1[2H]] | 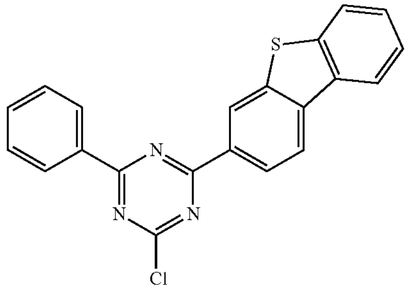 [SMILES: Clc1nc(-c2ccccc2)nc(-c2ccc3c(c2)sc2ccccc23)n1] |
| A16 | 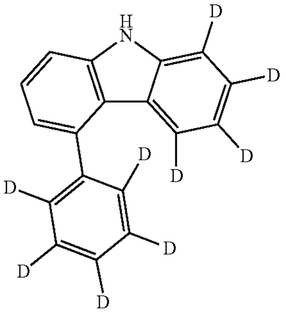 [SMILES: [2H]c1c([2H])c([2H])c(-c2cccc3[nH]c4c([2H])c([2H])c([2H])c([2H])c4c23)c([2H])c1[2H]] | 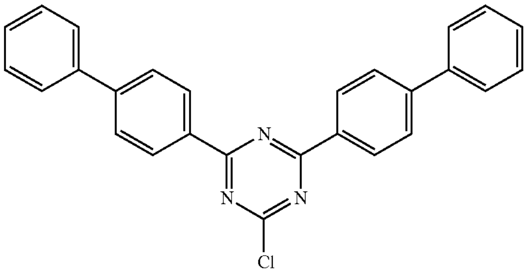 [SMILES: Clc1nc(-c2ccc(-c3ccccc3)cc2)nc(-c2ccc(-c3ccccc3)cc2)n1] |

TABLE 3-continued
| | | |
|---|---|---|
| A17 | 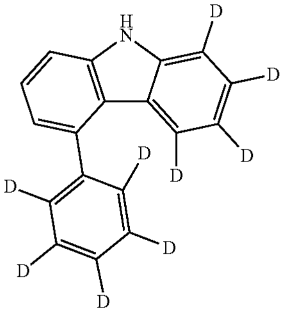 [SMILES: [2H]c1c([2H])c([2H])c(-c2cccc3[nH]c4c([2H])c([2H])c([2H])c([2H])c4c23)c([2H])c1[2H]] | 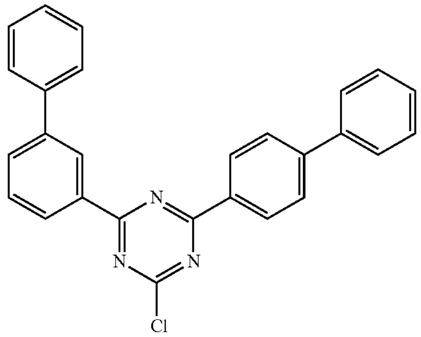 [SMILES: Clc1nc(-c2ccc(-c3ccccc3)cc2)nc(-c2cccc(-c3ccccc3)c2)n1] |
| A20 | 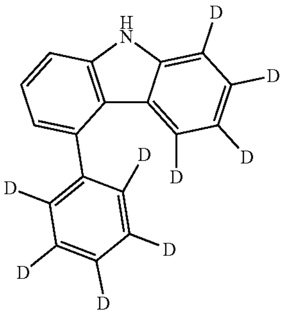 [SMILES: [2H]c1c([2H])c([2H])c(-c2cccc3[nH]c4c([2H])c([2H])c([2H])c([2H])c4c23)c([2H])c1[2H]] | 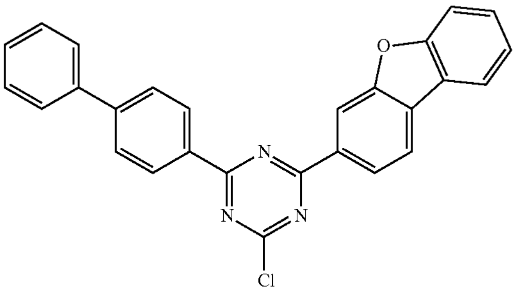 [SMILES: Clc1nc(-c2ccc(-c3ccccc3)cc2)nc(-c2ccc3c(c2)oc2ccccc23)n1] |
| A22 | 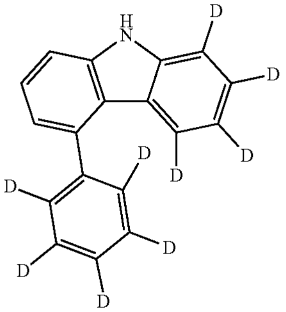 [SMILES: [2H]c1c([2H])c([2H])c(-c2cccc3[nH]c4c([2H])c([2H])c([2H])c([2H])c4c23)c([2H])c1[2H]] | 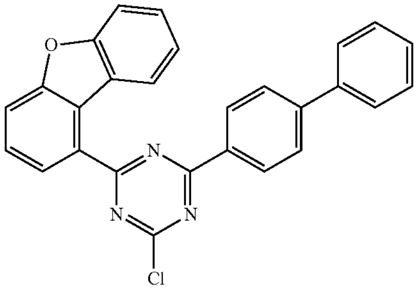 [SMILES: Clc1nc(-c2ccc(-c3ccccc3)cc2)nc(-c2cccc3oc4ccccc4c23)n1] |
| A24 | 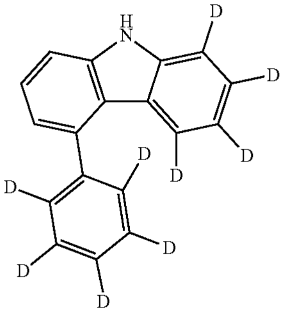 [SMILES: [2H]c1c([2H])c([2H])c(-c2cccc3[nH]c4c([2H])c([2H])c([2H])c([2H])c4c23)c([2H])c1[2H]] | 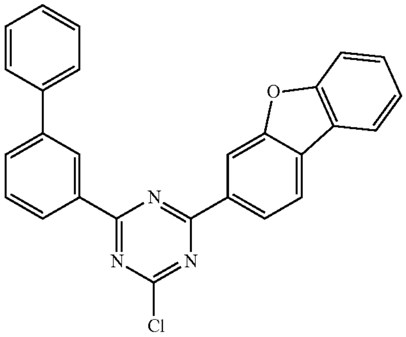 [SMILES: Clc1nc(-c2cccc(-c3ccccc3)c2)nc(-c2ccc3c(c2)oc2ccccc23)n1] |
| B2 | 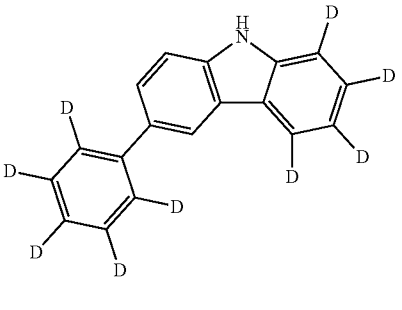 [SMILES: [2H]c1c([2H])c([2H])c(-c2ccc3[nH]c4c([2H])c([2H])c([2H])c([2H])c4c3c2)c([2H])c1[2H]] | 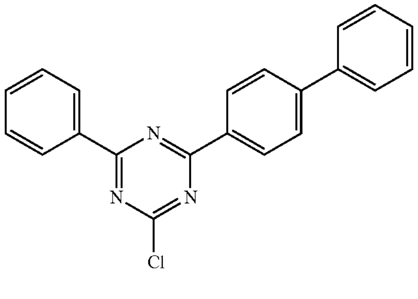 [SMILES: Clc1nc(-c2ccccc2)nc(-c2ccc(-c3ccccc3)cc2)n1] |

TABLE 3-continued
B5
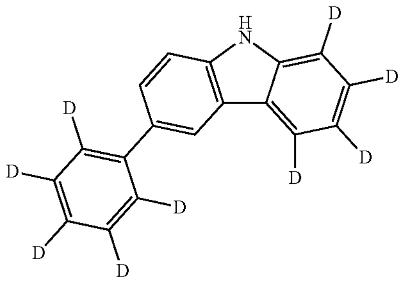 [SMILES: [2H]c1c([2H])c([2H])c(-c2ccc3[nH]c4c([2H])c([2H])c([2H])c([2H])c4c3c2)c([2H])c1[2H]]
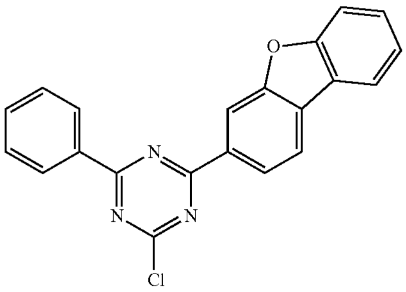 [SMILES: Clc1nc(-c2ccccc2)nc(-c2ccc3c(c2)oc2ccccc23)n1]
B7
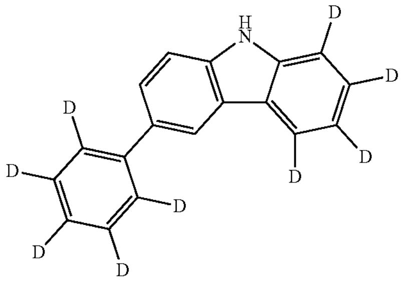 [SMILES: [2H]c1c([2H])c([2H])c(-c2ccc3[nH]c4c([2H])c([2H])c([2H])c([2H])c4c3c2)c([2H])c1[2H]]
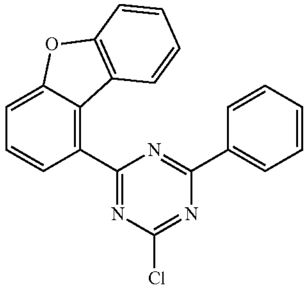 [SMILES: Clc1nc(-c2ccccc2)nc(-c2cccc3oc4ccccc4c23)n1]
B9
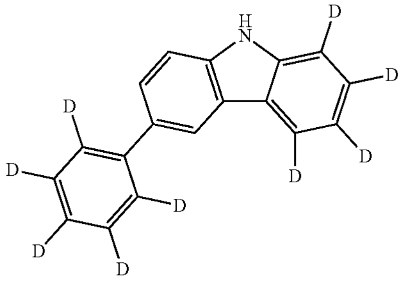 [SMILES: [2H]c1c([2H])c([2H])c(-c2ccc3[nH]c4c([2H])c([2H])c([2H])c([2H])c4c3c2)c([2H])c1[2H]]
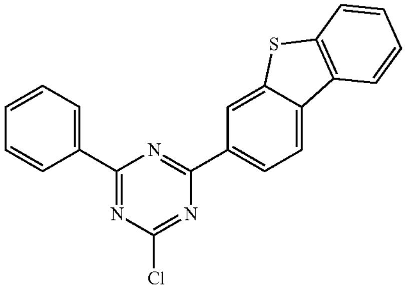 [SMILES: Clc1nc(-c2ccccc2)nc(-c2ccc3c(c2)sc2ccccc23)n1]
B16
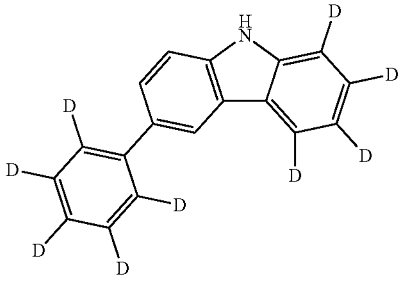 [SMILES: [2H]c1c([2H])c([2H])c(-c2ccc3[nH]c4c([2H])c([2H])c([2H])c([2H])c4c3c2)c([2H])c1[2H]]
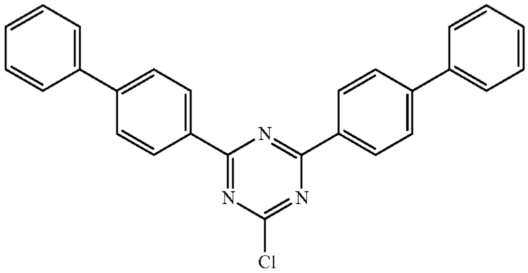 [SMILES: Clc1nc(-c2ccc(-c3ccccc3)cc2)nc(-c2ccc(-c3ccccc3)cc2)n1]
B18
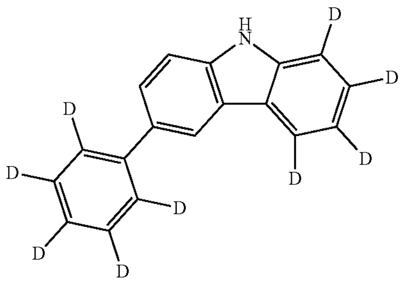 [SMILES: [2H]c1c([2H])c([2H])c(-c2ccc3[nH]c4c([2H])c([2H])c([2H])c([2H])c4c3c2)c([2H])c1[2H]]
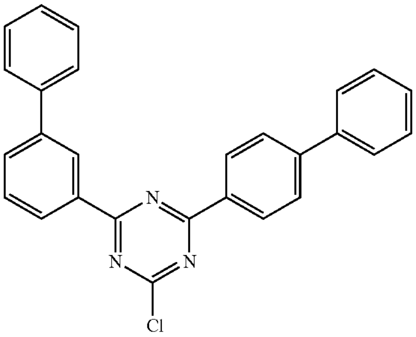 [SMILES: Clc1nc(-c2ccc(-c3ccccc3)cc2)nc(-c2cccc(-c3ccccc3)c2)n1]

TABLE 3-continued
B23
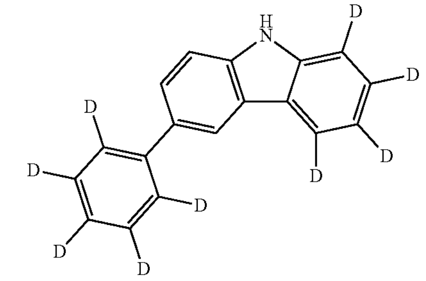 [SMILES: [2H]c1c([2H])c([2H])c(-c2ccc3[nH]c4c([2H])c([2H])c([2H])c([2H])c4c3c2)c([2H])c1[2H]]
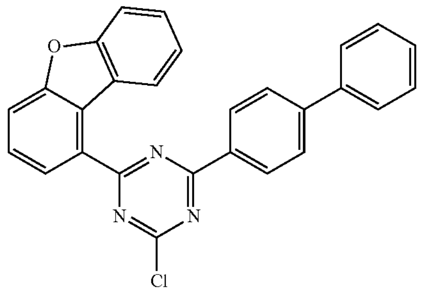
B36
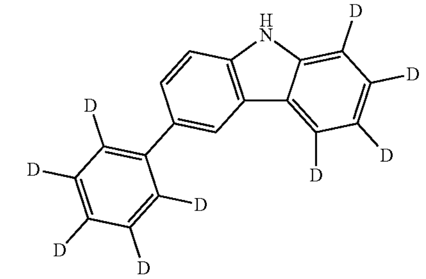 [SMILES: [2H]c1c([2H])c([2H])c(-c2ccc3[nH]c4c([2H])c([2H])c([2H])c([2H])c4c3c2)c([2H])c1[2H]]
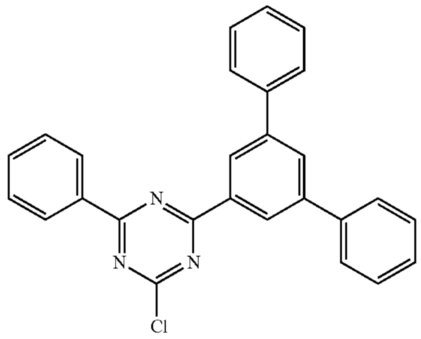 [SMILES: Clc1nc(-c2ccccc2)nc(-c2cc(-c3ccccc3)cc(-c3ccccc3)c2)n1]
C2
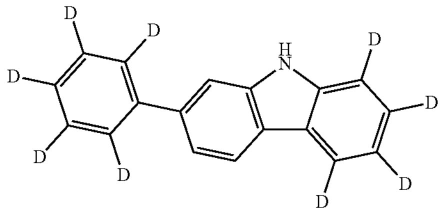 [SMILES: [2H]c1c([2H])c([2H])c(-c2ccc3c(c2)[nH]c2c([2H])c([2H])c([2H])c([2H])c23)c([2H])c1[2H]]
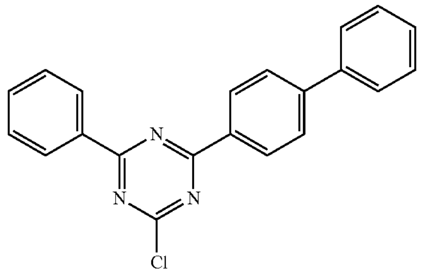 [SMILES: Clc1nc(-c2ccccc2)nc(-c2ccc(-c3ccccc3)cc2)n1]
C5
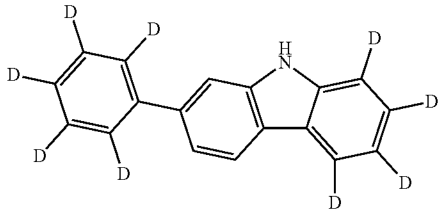 [SMILES: [2H]c1c([2H])c([2H])c(-c2ccc3c(c2)[nH]c2c([2H])c([2H])c([2H])c([2H])c23)c([2H])c1[2H]]
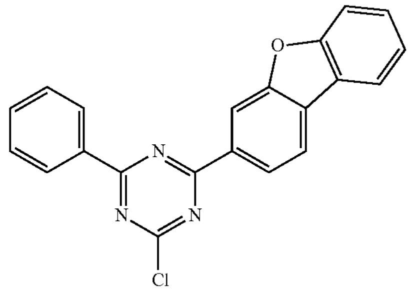
C9
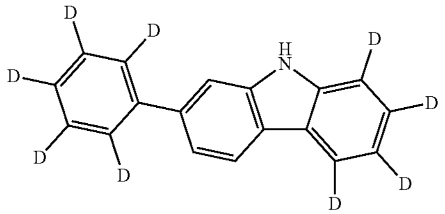 [SMILES: [2H]c1c([2H])c([2H])c(-c2ccc3c(c2)[nH]c2c([2H])c([2H])c([2H])c([2H])c23)c([2H])c1[2H]]
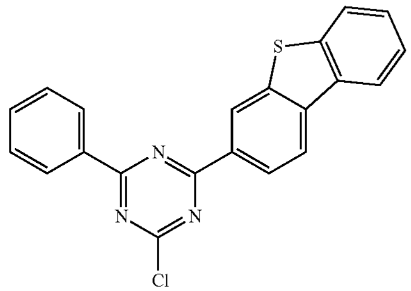

TABLE 3-continued
C16
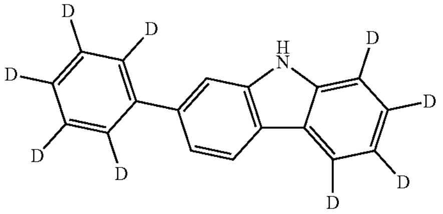 [SMILES: [2H]c1c([2H])c([2H])c(-c2ccc3c(c2)[nH]c2c([2H])c([2H])c([2H])c([2H])c23)c([2H])c1[2H]]
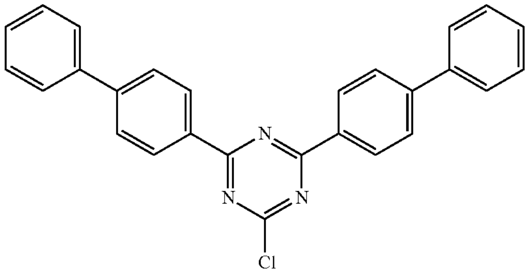 [SMILES: Clc1nc(-c2ccc(-c3ccccc3)cc2)nc(-c2ccc(-c3ccccc3)cc2)n1]
C17
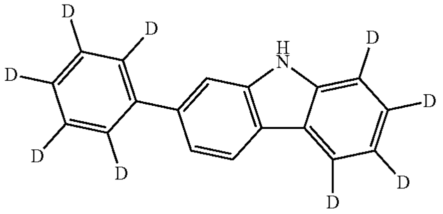 [SMILES: [2H]c1c([2H])c([2H])c(-c2ccc3c(c2)[nH]c2c([2H])c([2H])c([2H])c([2H])c23)c([2H])c1[2H]]
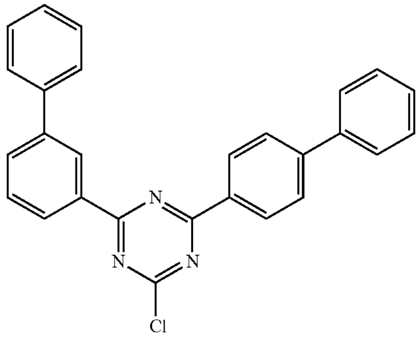 [SMILES: Clc1nc(-c2ccc(-c3ccccc3)cc2)nc(-c2cccc(-c3ccccc3)c2)n1]
C22
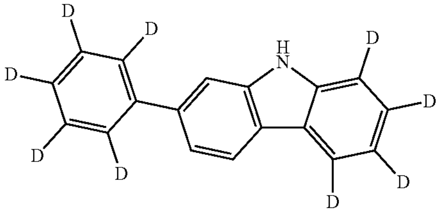 [SMILES: [2H]c1c([2H])c([2H])c(-c2ccc3c(c2)[nH]c2c([2H])c([2H])c([2H])c([2H])c23)c([2H])c1[2H]]
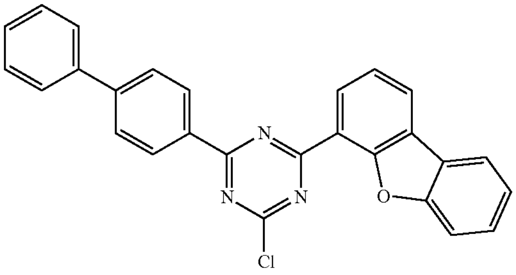 [SMILES: Clc1nc(-c2ccc(-c3ccccc3)cc2)nc(-c2cccc3c2oc2ccccc23)n1]
C25
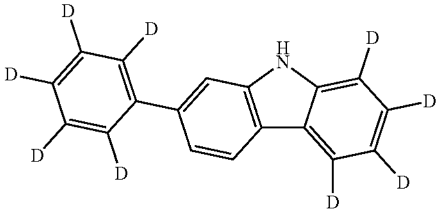 [SMILES: [2H]c1c([2H])c([2H])c(-c2ccc3c(c2)[nH]c2c([2H])c([2H])c([2H])c([2H])c23)c([2H])c1[2H]]
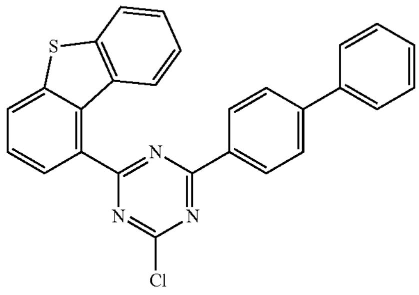
D8
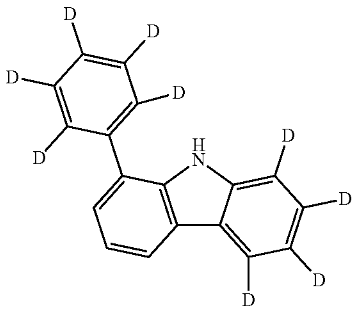 [SMILES: [2H]c1c([2H])c([2H])c(-c2cccc3c2[nH]c2c([2H])c([2H])c([2H])c([2H])c23)c([2H])c1[2H]]
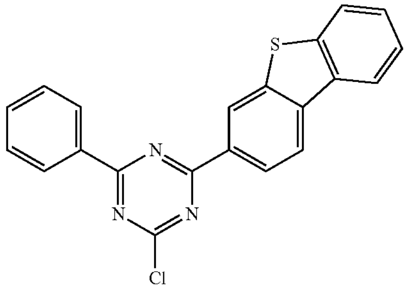

TABLE 3-continued
D15
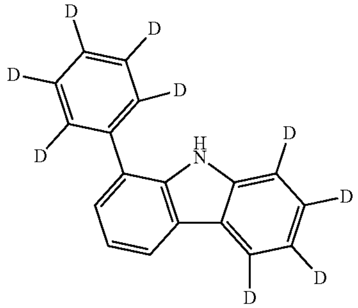 [SMILES: [2H]c1c([2H])c([2H])c(-c2cccc3c2[nH]c2c([2H])c([2H])c([2H])c([2H])c23)c([2H])c1[2H]]
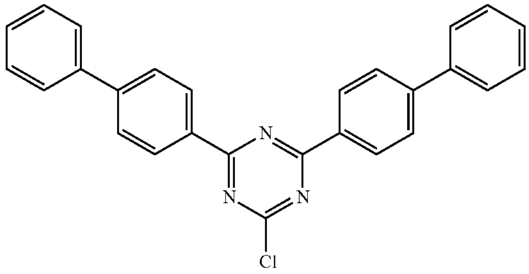 [SMILES: Clc1nc(-c2ccc(-c3ccccc3)cc2)nc(-c2ccc(-c3ccccc3)cc2)n1]
D16
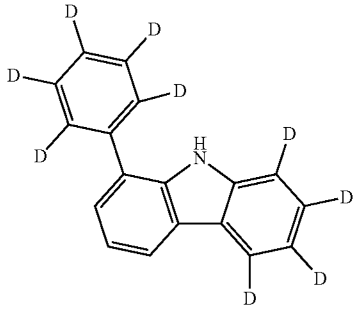 [SMILES: [2H]c1c([2H])c([2H])c(-c2cccc3c2[nH]c2c([2H])c([2H])c([2H])c([2H])c23)c([2H])c1[2H]]
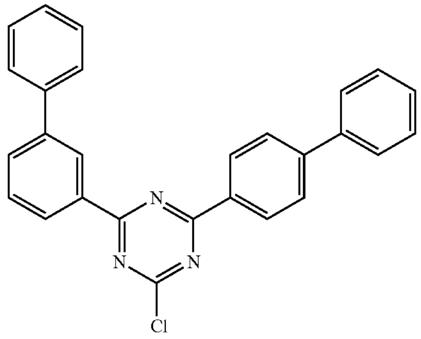 [SMILES: Clc1nc(-c2ccc(-c3ccccc3)cc2)nc(-c2cccc(-c3ccccc3)c2)n1]
D17
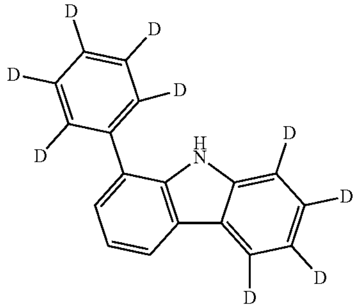 [SMILES: [2H]c1c([2H])c([2H])c(-c2cccc3c2[nH]c2c([2H])c([2H])c([2H])c([2H])c23)c([2H])c1[2H]]
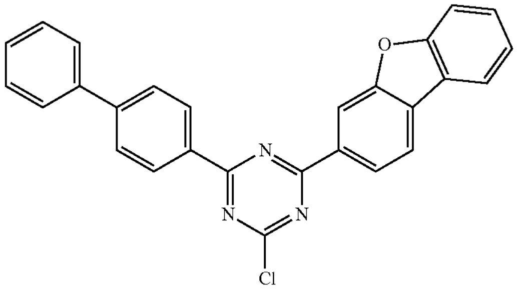 [SMILES: Clc1nc(-c2ccc(-c3ccccc3)cc2)nc(-c2ccc3c(c2)oc2ccccc23)n1]
D34
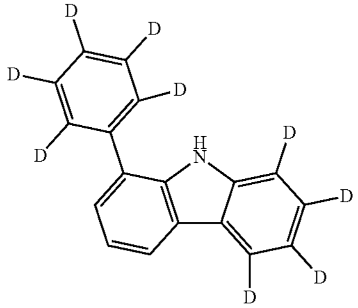 [SMILES: [2H]c1c([2H])c([2H])c(-c2cccc3c2[nH]c2c([2H])c([2H])c([2H])c([2H])c23)c([2H])c1[2H]]
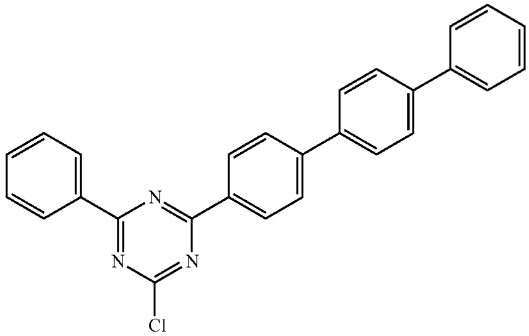 [SMILES: Clc1nc(-c2ccccc2)nc(-c2ccc(-c3ccc(-c4ccccc4)cc3)cc2)n1]

TABLE 3-continued
| Compound No. | Structure | Yield (%) |
|---|---|---|
| A9 | 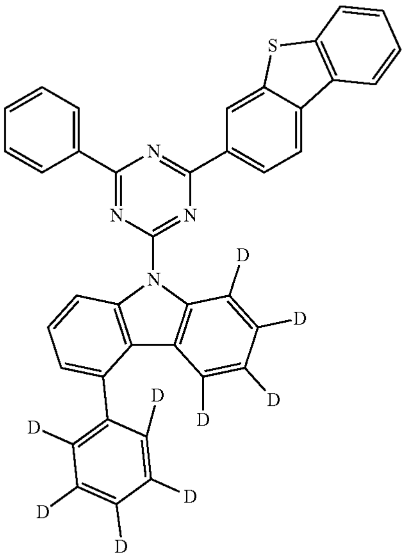 [SMILES: [2H]c1c([2H])c([2H])c(-c2cccc3c2c2c([2H])c([2H])c([2H])c([2H])c2n3-c2nc(-c3ccccc3)nc(-c3ccc4c(c3)sc3ccccc34)n2)c([2H])c1[2H]] | 74 |
| A16 | 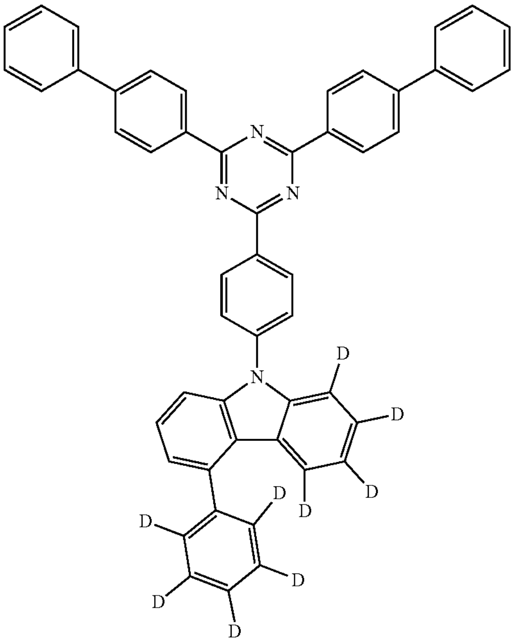 [SMILES: [2H]c1c([2H])c([2H])c(-c2cccc3c2c2c([2H])c([2H])c([2H])c([2H])c2n3-c2ccc(-c3nc(-c4ccc(-c5ccccc5)cc4)nc(-c4ccc(-c5ccccc5)cc4)n3)cc2)c([2H])c1[2H]] | 60 |

TABLE 3-continued
A17
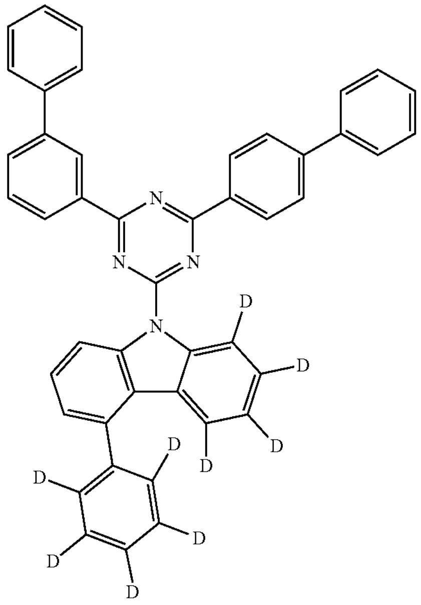 [SMILES: [2H]c1c([2H])c([2H])c(-c2cccc3c2c2c([2H])c([2H])c([2H])c([2H])c2n3-c2nc(-c3ccc(-c4ccccc4)cc3)nc(-c3cccc(-c4ccccc4)c3)n2)c([2H])c1[2H]]
58
A20
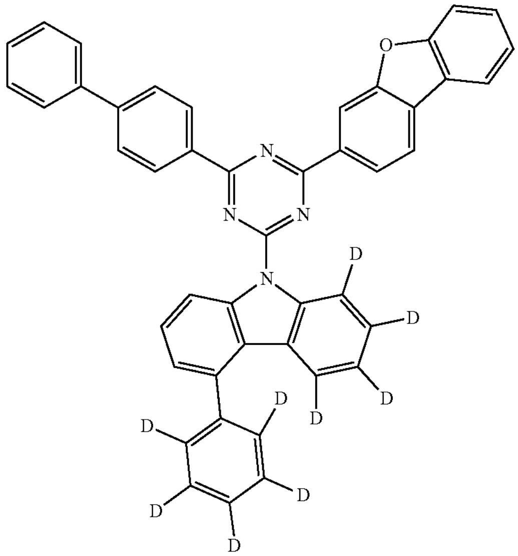 [SMILES: [2H]c1c([2H])c([2H])c(-c2cccc3c2c2c([2H])c([2H])c([2H])c([2H])c2n3-c2nc(-c3ccc(-c4ccccc4)cc3)nc(-c3ccc4c(c3)oc3ccccc34)n2)c([2H])c1[2H]]
61

TABLE 3-continued
| | | |
|---|---|---|
| A22 | 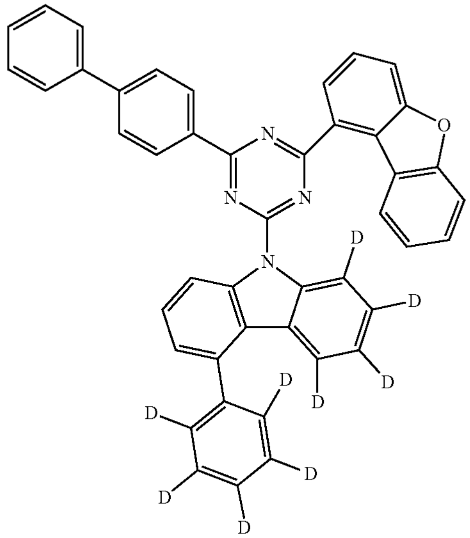 [SMILES: [2H]c1c([2H])c([2H])c(-c2cccc3c2c2c([2H])c([2H])c([2H])c([2H])c2n3-c2nc(-c3ccc(-c4ccccc4)cc3)nc(-c3cccc4oc5ccccc5c34)n2)c([2H])c1[2H]] | 49 |
| A24 | 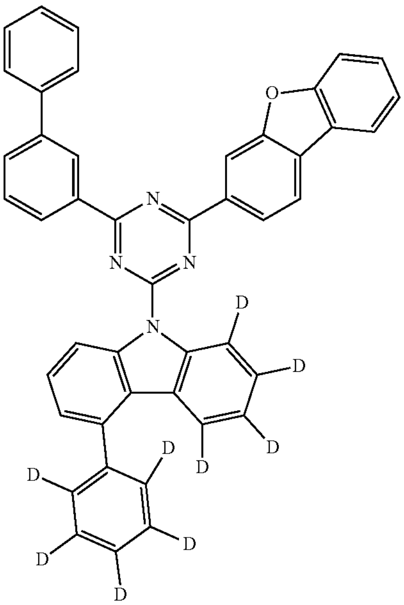 [SMILES: [2H]c1c([2H])c([2H])c(-c2cccc3c2c2c([2H])c([2H])c([2H])c([2H])c2n3-c2nc(-c3cccc(-c4ccccc4)c3)nc(-c3ccc4c(c3)oc3ccccc34)n2)c([2H])c1[2H]] | 72 |
| B2 | 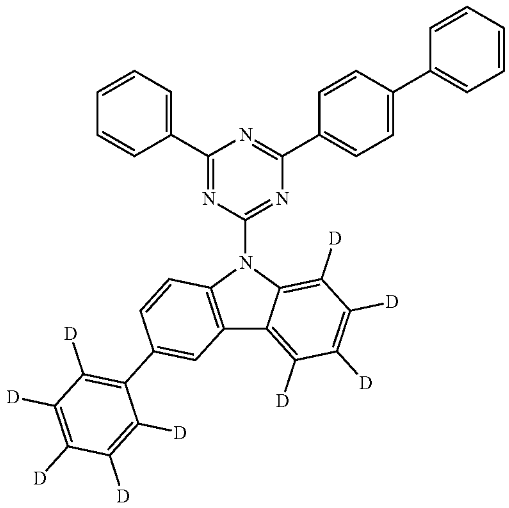 [SMILES: [2H]c1c([2H])c([2H])c(-c2ccc3c(c2)c2c([2H])c([2H])c([2H])c([2H])c2n3-c2nc(-c3ccccc3)nc(-c3ccc(-c4ccccc4)cc3)n2)c([2H])c1[2H]] | 66 |

TABLE 3-continued
B5 58
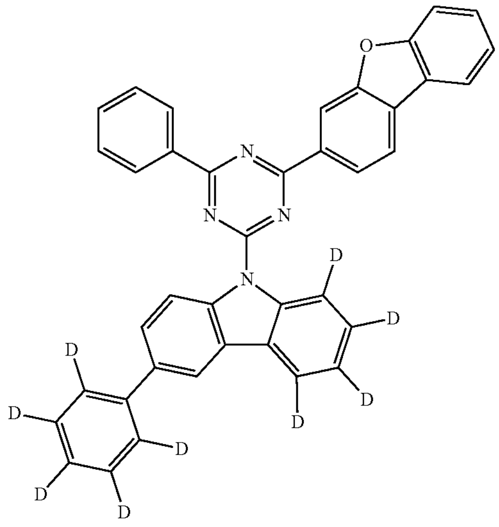 [SMILES: [2H]c1c([2H])c([2H])c(-c2ccc3c(c2)c2c([2H])c([2H])c([2H])c([2H])c2n3-c2nc(-c3ccccc3)nc(-c3ccc4c(c3)oc3ccccc34)n2)c([2H])c1[2H]]
B7 56
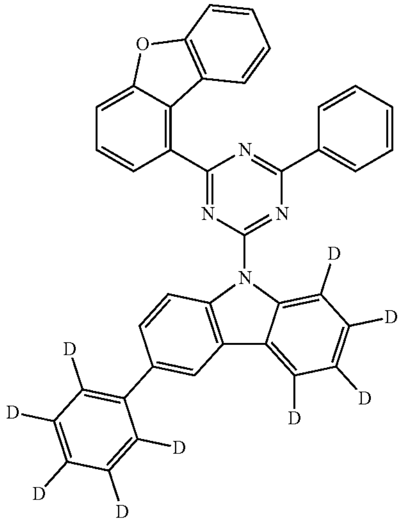 [SMILES: [2H]c1c([2H])c([2H])c(-c2ccc3c(c2)c2c([2H])c([2H])c([2H])c([2H])c2n3-c2nc(-c3ccccc3)nc(-c3cccc4oc5ccccc5c34)n2)c([2H])c1[2H]]
B9 74
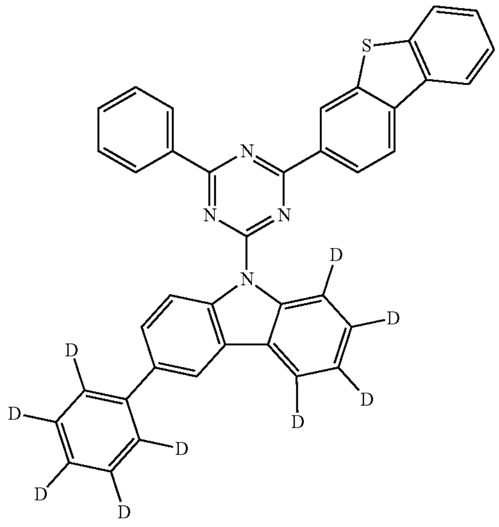

TABLE 3-continued
| | | |
|---|---|---|
| B16 | 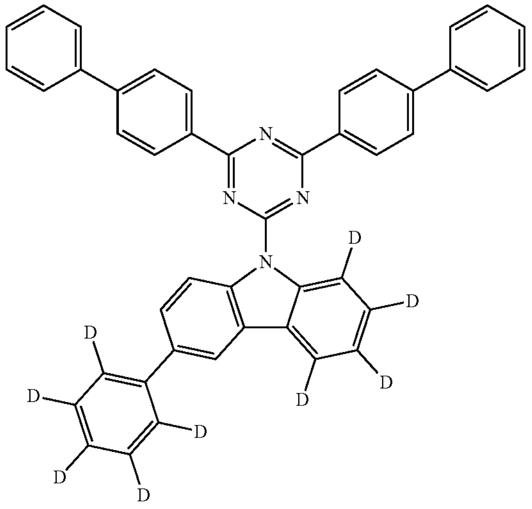 [SMILES: [2H]c1c([2H])c([2H])c(-c2ccc3c(c2)c2c([2H])c([2H])c([2H])c([2H])c2n3-c2nc(-c3ccc(-c4ccccc4)cc3)nc(-c3ccc(-c4ccccc4)cc3)n2)c([2H])c1[2H]] | 66 |
| B18 | 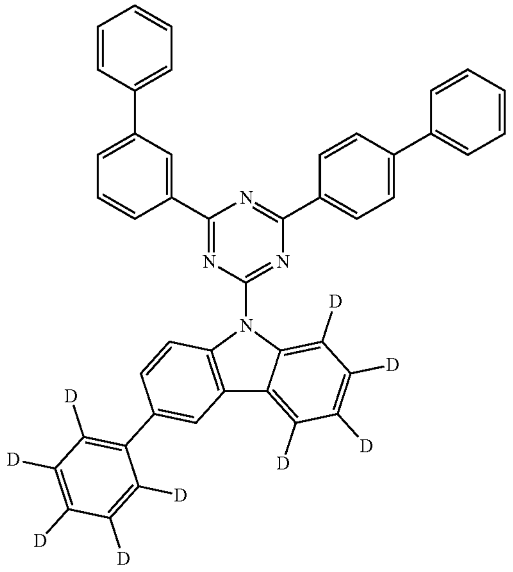 [SMILES: [2H]c1c([2H])c([2H])c(-c2ccc3c(c2)c2c([2H])c([2H])c([2H])c([2H])c2n3-c2nc(-c3ccc(-c4ccccc4)cc3)nc(-c3cccc(-c4ccccc4)c3)n2)c([2H])c1[2H]] | 70 |
| B23 | 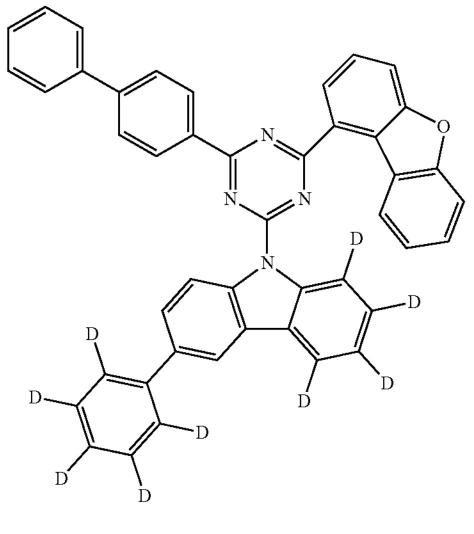 [SMILES: [2H]c1c([2H])c([2H])c(-c2ccc3c(c2)c2c([2H])c([2H])c([2H])c([2H])c2n3-c2nc(-c3ccc(-c4ccccc4)cc3)nc(-c3cccc4oc5ccccc5c34)n2)c([2H])c1[2H]] | 51 |

TABLE 3-continued
| | | |
|---|---|---|
| B36 | 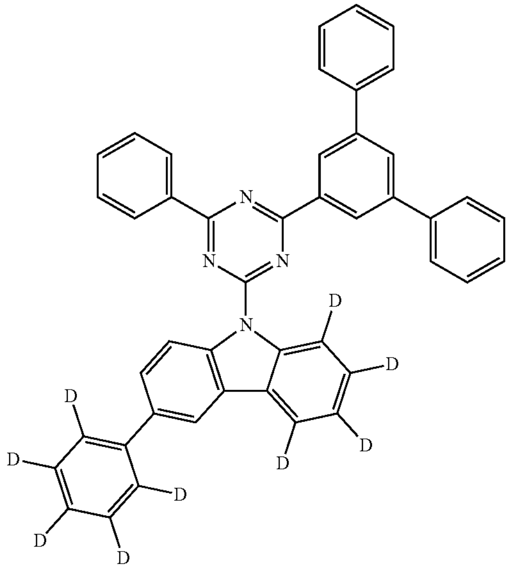 [SMILES: [2H]c1c([2H])c([2H])c(-c2ccc3c(c2)c2c([2H])c([2H])c([2H])c([2H])c2n3-c2nc(-c3ccccc3)nc(-c3cc(-c4ccccc4)cc(-c4ccccc4)c3)n2)c([2H])c1[2H]] | 60 |
| C2 | 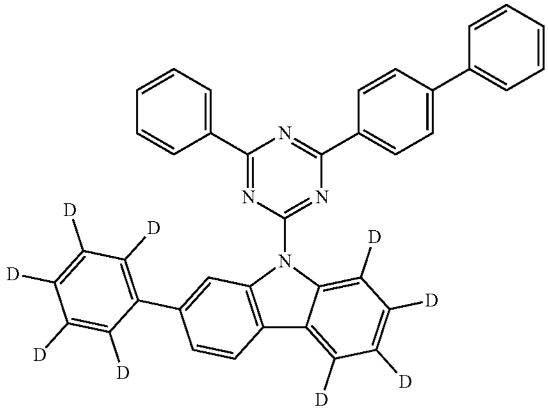 [SMILES: [2H]c1c([2H])c([2H])c(-c2ccc3c4c([2H])c([2H])c([2H])c([2H])c4n(-c4nc(-c5ccccc5)nc(-c5ccc(-c6ccccc6)cc5)n4)c3c2)c([2H])c1[2H]] | 72 |
| C5 | 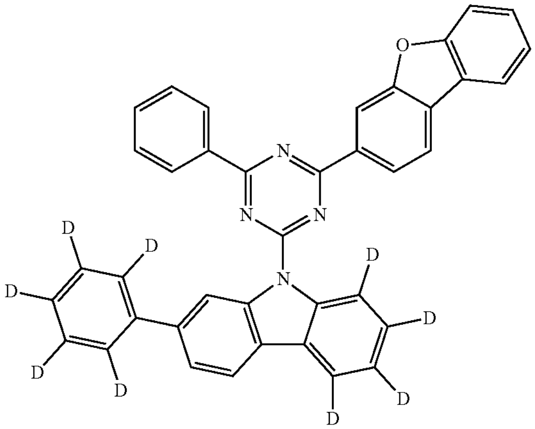 [SMILES: [2H]c1c([2H])c([2H])c(-c2ccc3c4c([2H])c([2H])c([2H])c([2H])c4n(-c4nc(-c5ccccc5)nc(-c5ccc6c(c5)oc5ccccc56)n4)c3c2)c([2H])c1[2H]] | 62 |

TABLE 3-continued
C9 61
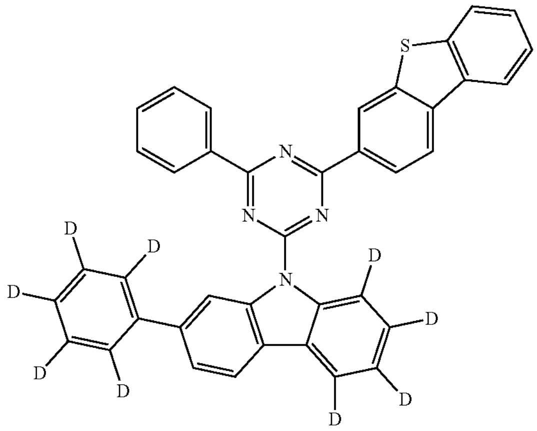 [SMILES: [2H]c1c([2H])c([2H])c(-c2ccc3c4c([2H])c([2H])c([2H])c([2H])c4n(-c4nc(-c5ccccc5)nc(-c5ccc6c(c5)sc5ccccc56)n4)c3c2)c([2H])c1[2H]]
C16 59
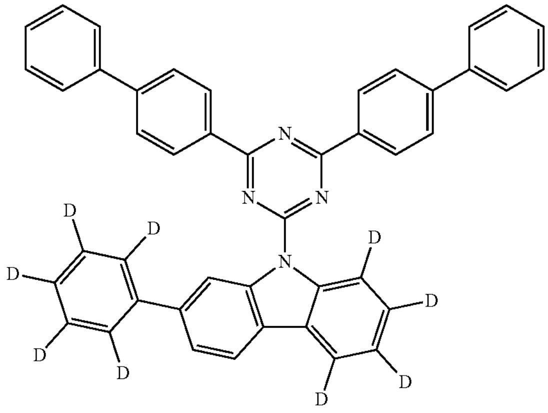 [SMILES: [2H]c1c([2H])c([2H])c(-c2ccc3c4c([2H])c([2H])c([2H])c([2H])c4n(-c4nc(-c5ccc(-c6ccccc6)cc5)nc(-c5ccc(-c6ccccc6)cc5)n4)c3c2)c([2H])c1[2H]]
C17 67
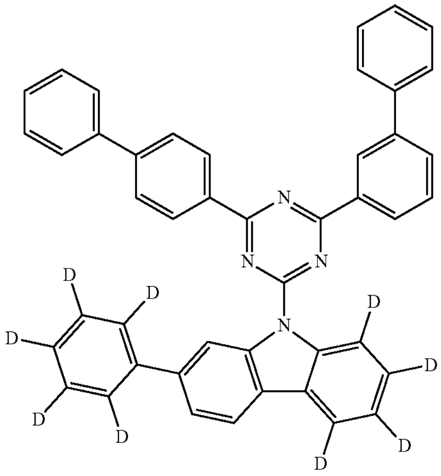 [SMILES: [2H]c1c([2H])c([2H])c(-c2ccc3c4c([2H])c([2H])c([2H])c([2H])c4n(-c4nc(-c5ccc(-c6ccccc6)cc5)nc(-c5cccc(-c6ccccc6)c5)n4)c3c2)c([2H])c1[2H]]

TABLE 3-continued
| | | |
|---|---|---|
| C22 | 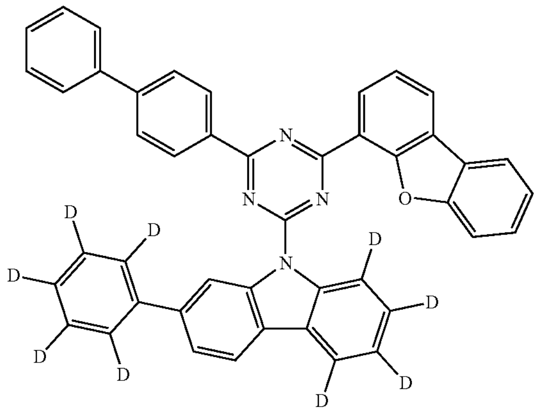 [SMILES: [2H]c1c([2H])c([2H])c(-c2ccc3c4c([2H])c([2H])c([2H])c([2H])c4n(-c4nc(-c5ccc(-c6ccccc6)cc5)nc(-c5cccc6c5oc5ccccc56)n4)c3c2)c([2H])c1[2H]] | 57 |
| C25 | 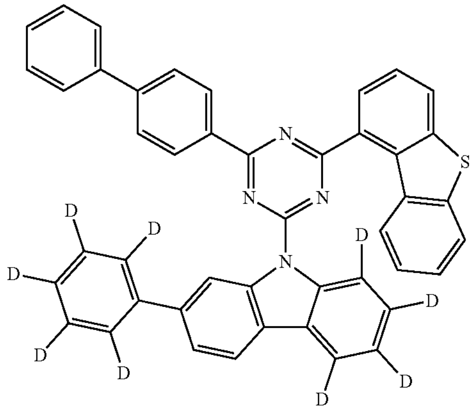 [SMILES: [2H]c1c([2H])c([2H])c(-c2ccc3c4c([2H])c([2H])c([2H])c([2H])c4n(-c4nc(-c5ccc(-c6ccccc6)cc5)nc(-c5cccc6sc7ccccc7c56)n4)c3c2)c([2H])c1[2H]] | 50 |
| D8 | 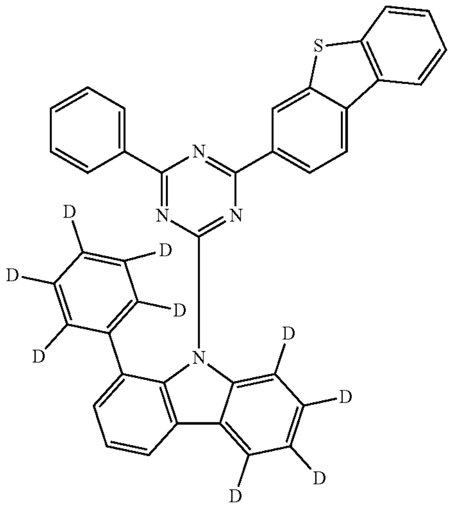 [SMILES: [2H]c1c([2H])c([2H])c(-c2cccc3c4c([2H])c([2H])c([2H])c([2H])c4n(-c4nc(-c5ccccc5)nc(-c5ccc6c(c5)sc5ccccc56)n4)c23)c([2H])c1[2H]] | 36 |

TABLE 3-continued
| | | |
|---|---|---|
| D15 | 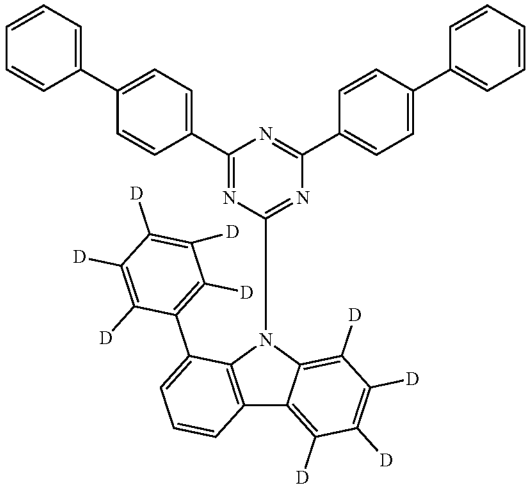 [SMILES: [2H]c1c([2H])c([2H])c(-c2cccc3c4c([2H])c([2H])c([2H])c([2H])c4n(-c4nc(-c5ccc(-c6ccccc6)cc5)nc(-c5ccc(-c6ccccc6)cc5)n4)c23)c([2H])c1[2H]] | 41 |
| D16 | 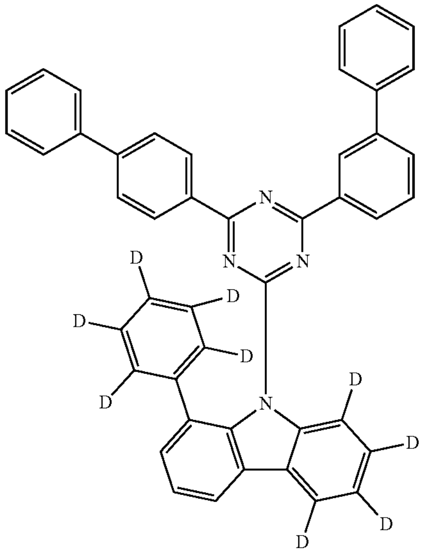 [SMILES: [2H]c1c([2H])c([2H])c(-c2cccc3c4c([2H])c([2H])c([2H])c([2H])c4n(-c4nc(-c5ccc(-c6ccccc6)cc5)nc(-c5cccc(-c6ccccc6)c5)n4)c23)c([2H])c1[2H]] | 42 |
| D17 | 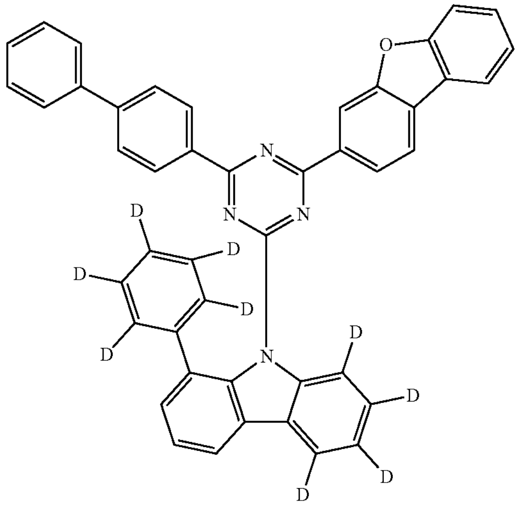 [SMILES: [2H]c1c([2H])c([2H])c(-c2cccc3c4c([2H])c([2H])c([2H])c([2H])c4n(-c4nc(-c5ccc(-c6ccccc6)cc5)nc(-c5ccc6c(c5)oc5ccccc56)n4)c23)c([2H])c1[2H]] | 36 |

TABLE 3-continued

| | | |
|---|---|---|
| D34 | 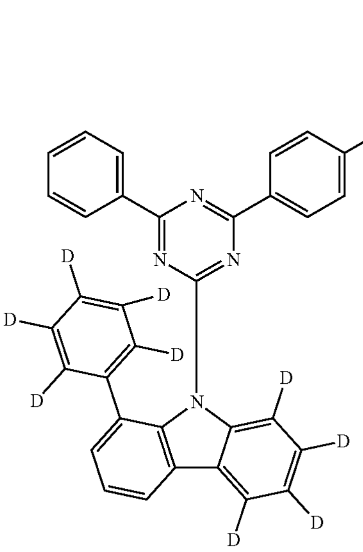 | 45 |

Synthesis of Compound A45

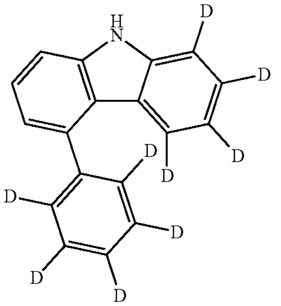

IM-a-nh

+

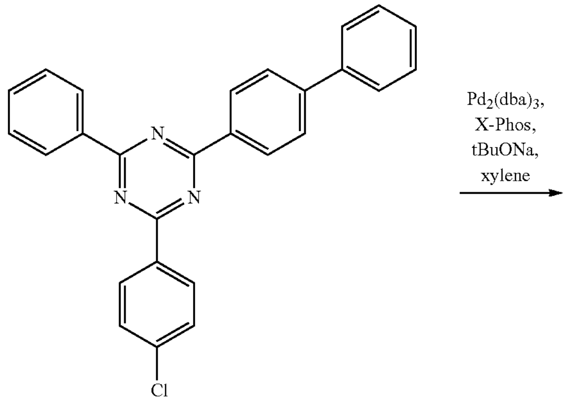

-continued

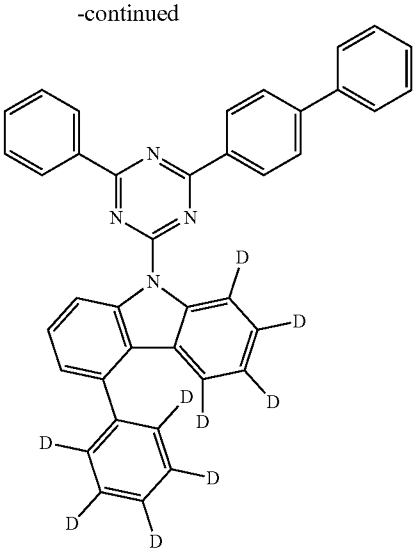

A45

Under nitrogen protection, the Intermediate IM-a-nh (5.0 g; 19.8 mmol), 2-(biphenyl-4-yl)-4-(4-chlorophenyl)-6-phenyl-1,3,5-triazine (8.7 g; 20.8 mmol), tris(dibenzylideneacetone) dipalladium (0.2 g; 0.2 mmol), 2-dicyclohexylphosphine-2',4',6'-triisopropylbiphenyl (0.4 g; 0.2 mmol), sodium tert-butoxide (2.9 g; 29.7 mmol) and xylene (50 mL) were added into a round bottom flask, and a mixed solution was subjected to a reaction under stirring at 135° C. to 140° C. for 16 hours. The reaction solution was cooled to room temperature, the reaction solution was washed with water, liquid separation was performed, an organic phase was dried over anhydrous magnesium sulfate, and a solvent was removed under reduced pressure to obtain a crude product; and the crude product was purified by silica gel column chromatography using a dichloromethane/n-heptane mixed solvent as an eluent, and then purified by recrystallization using a toluene/n-heptane mixed solvent to obtain a Compound A45 (9.4 g; yield: 75%) as a white solid.

Referring to a method similar to that of the Compound A45, compounds shown in Table 4 below were synthesized by using a Reactant E in the table below instead of the Intermediate IM-a-nh and using a Reactant F in the table below instead of 2-(biphenyl-4-yl)-4-(4-chlorophenyl)-6-phenyl-1,3,5-triazine:
TABLE 4
| Compound No. | Reactant E | Reactant F |
|---|---|---|
| A47 | 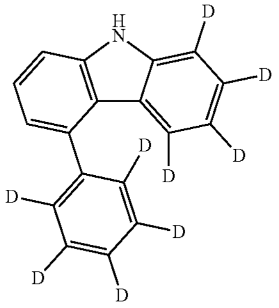 [SMILES: [2H]c1c([2H])c([2H])c(-c2cccc3[nH]c4c([2H])c([2H])c([2H])c([2H])c4c23)c([2H])c1[2H]] | 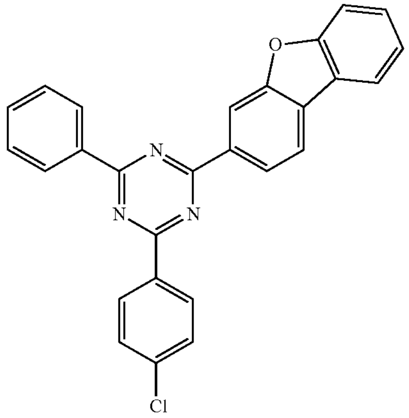 [SMILES: Clc1ccc(-c2nc(-c3ccccc3)nc(-c3ccc4c(c3)oc3ccccc34)n2)cc1] |
| A51 | 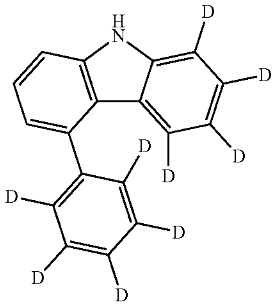 [SMILES: [2H]c1c([2H])c([2H])c(-c2cccc3[nH]c4c([2H])c([2H])c([2H])c([2H])c4c23)c([2H])c1[2H]] | 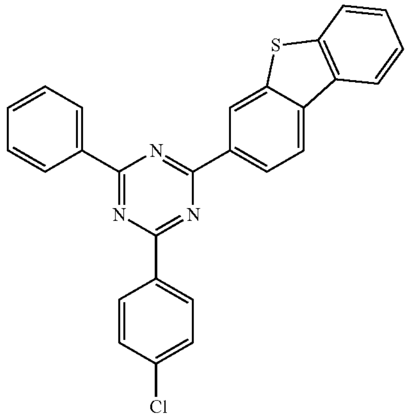 |
| A55 | 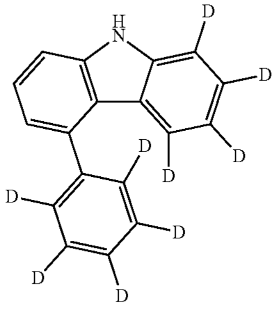 [SMILES: [2H]c1c([2H])c([2H])c(-c2cccc3[nH]c4c([2H])c([2H])c([2H])c([2H])c4c23)c([2H])c1[2H]] | 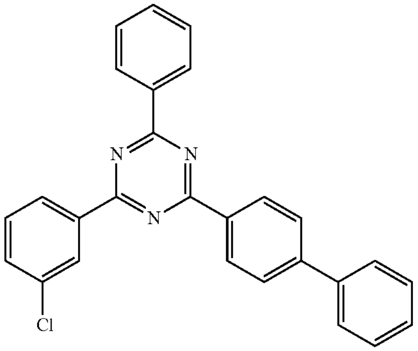 [SMILES: Clc1cccc(-c2nc(-c3ccccc3)nc(-c3ccc(-c4ccccc4)cc3)n2)c1] |

TABLE 4-continued
A57
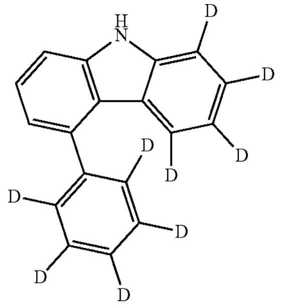 [SMILES: [2H]c1c([2H])c([2H])c(-c2cccc3[nH]c4c([2H])c([2H])c([2H])c([2H])c4c23)c([2H])c1[2H]]
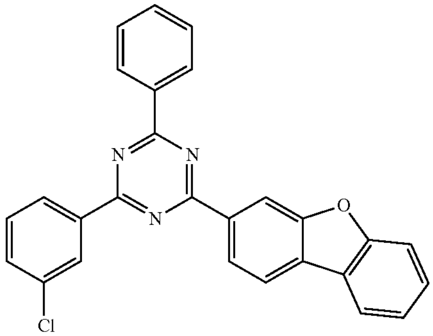
A60
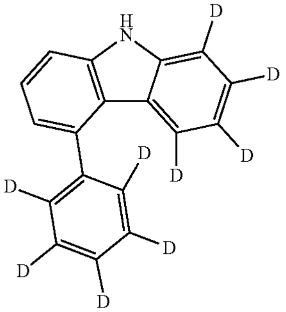 [SMILES: [2H]c1c([2H])c([2H])c(-c2cccc3[nH]c4c([2H])c([2H])c([2H])c([2H])c4c23)c([2H])c1[2H]]
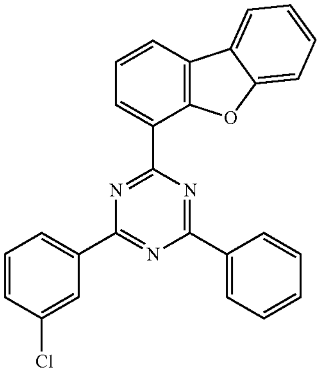 [SMILES: Clc1cccc(-c2nc(-c3ccccc3)nc(-c3cccc4c3oc3ccccc34)n2)c1]
A68
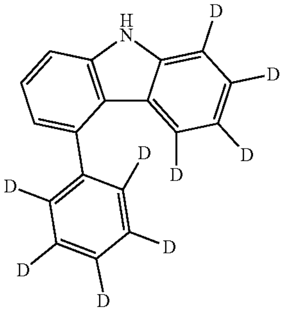 [SMILES: [2H]c1c([2H])c([2H])c(-c2cccc3[nH]c4c([2H])c([2H])c([2H])c([2H])c4c23)c([2H])c1[2H]]
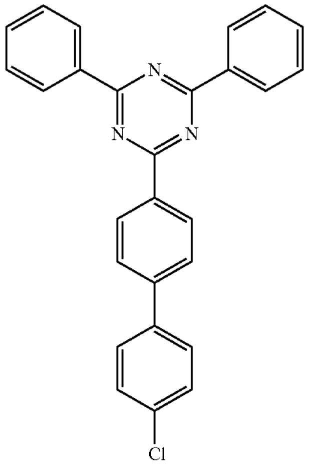 [SMILES: Clc1ccc(-c2ccc(-c3nc(-c4ccccc4)nc(-c4ccccc4)n3)cc2)cc1]
A69
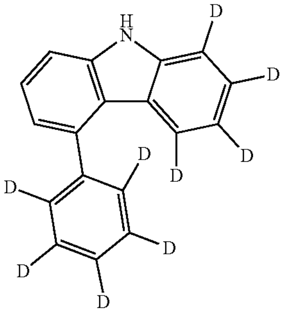 [SMILES: [2H]c1c([2H])c([2H])c(-c2cccc3[nH]c4c([2H])c([2H])c([2H])c([2H])c4c23)c([2H])c1[2H]]
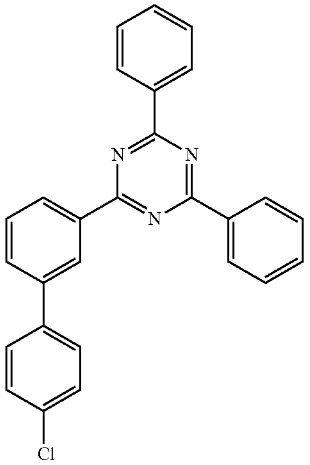 [SMILES: Clc1ccc(-c2cccc(-c3nc(-c4ccccc4)nc(-c4ccccc4)n3)c2)cc1]

TABLE 4-continued
A71
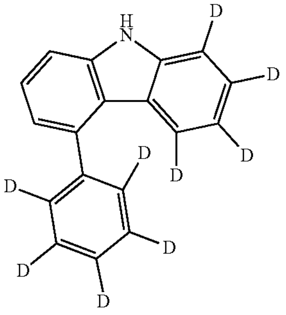 [SMILES: [2H]c1c([2H])c([2H])c(-c2cccc3[nH]c4c([2H])c([2H])c([2H])c([2H])c4c23)c([2H])c1[2H]]
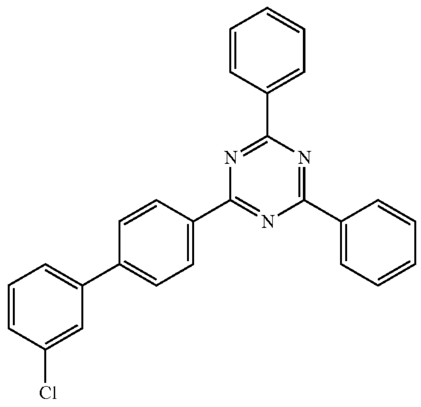 [SMILES: Clc1cccc(-c2ccc(-c3nc(-c4ccccc4)nc(-c4ccccc4)n3)cc2)c1]
A72
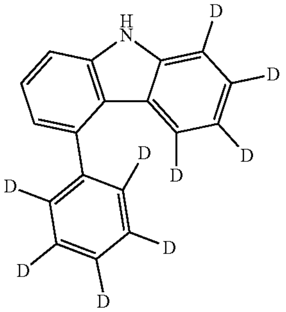 [SMILES: [2H]c1c([2H])c([2H])c(-c2cccc3[nH]c4c([2H])c([2H])c([2H])c([2H])c4c23)c([2H])c1[2H]]
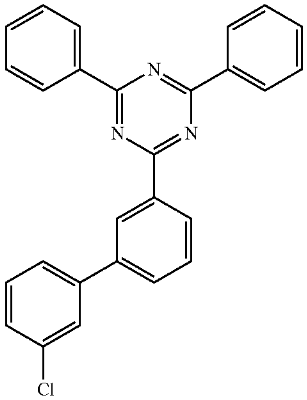 [SMILES: Clc1cccc(-c2cccc(-c3nc(-c4ccccc4)nc(-c4ccccc4)n3)c2)c1]
A81
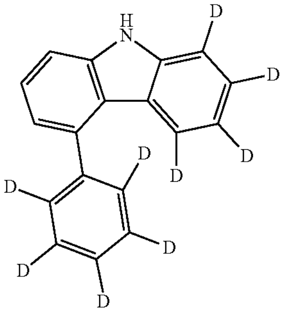 [SMILES: [2H]c1c([2H])c([2H])c(-c2cccc3[nH]c4c([2H])c([2H])c([2H])c([2H])c4c23)c([2H])c1[2H]]
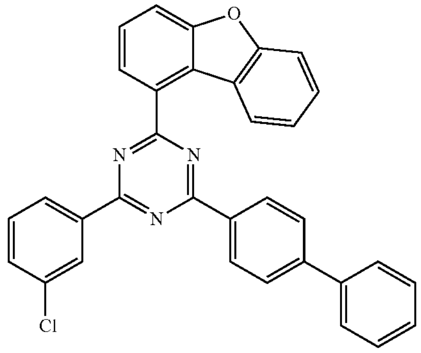 [SMILES: Clc1cccc(-c2nc(-c3ccc(-c4ccccc4)cc3)nc(-c3cccc4oc5ccccc5c34)n2)c1]

TABLE 4-continued
| | | |
|---|---|---|
| A97 | 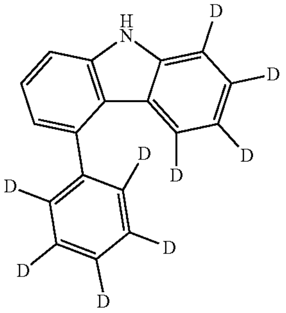 [SMILES: [2H]c1c([2H])c([2H])c(-c2cccc3[nH]c4c([2H])c([2H])c([2H])c([2H])c4c23)c([2H])c1[2H]] | 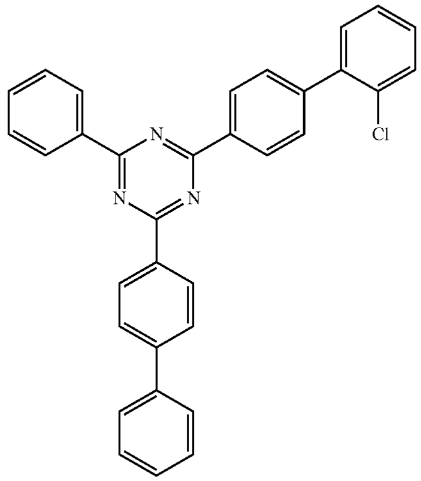 [SMILES: Clc1ccccc1-c1ccc(-c2nc(-c3ccccc3)nc(-c3ccc(-c4ccccc4)cc3)n2)cc1] |
| A104 | 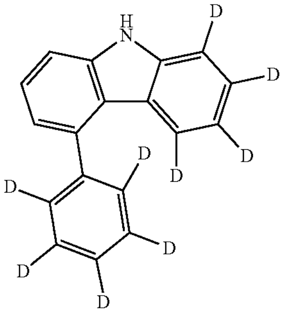 [SMILES: [2H]c1c([2H])c([2H])c(-c2cccc3[nH]c4c([2H])c([2H])c([2H])c([2H])c4c23)c([2H])c1[2H]] | 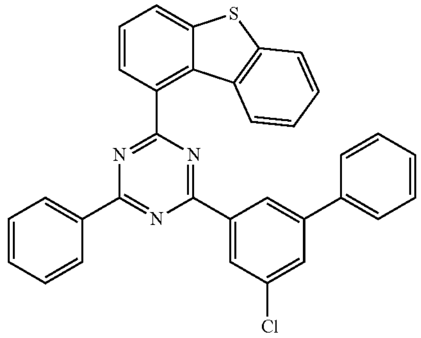 [SMILES: Clc1cc(-c2ccccc2)cc(-c2nc(-c3ccccc3)nc(-c3cccc4sc5ccccc5c34)n2)c1] |
| B13 | 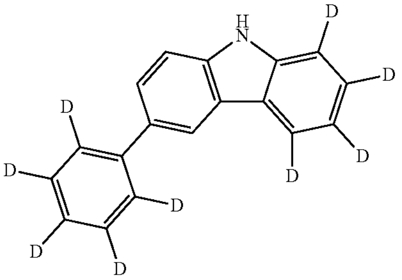 [SMILES: [2H]c1c([2H])c([2H])c(-c2ccc3[nH]c4c([2H])c([2H])c([2H])c([2H])c4c3c2)c([2H])c1[2H]] | 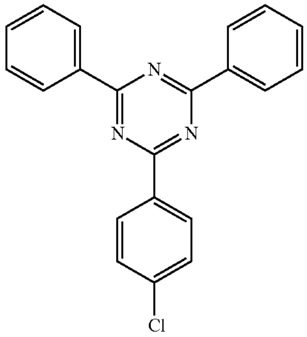 [SMILES: Clc1ccc(-c2nc(-c3ccccc3)nc(-c3ccccc3)n2)cc1] |
| B14 | 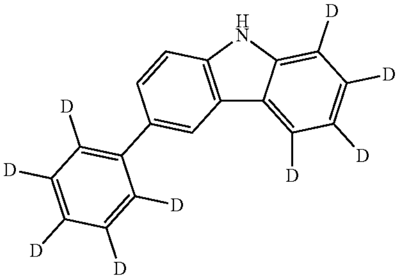 [SMILES: [2H]c1c([2H])c([2H])c(-c2ccc3[nH]c4c([2H])c([2H])c([2H])c([2H])c4c3c2)c([2H])c1[2H]] | 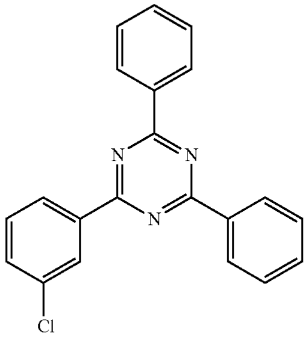 [SMILES: Clc1cccc(-c2nc(-c3ccccc3)nc(-c3ccccc3)n2)c1] |

TABLE 4-continued
B37
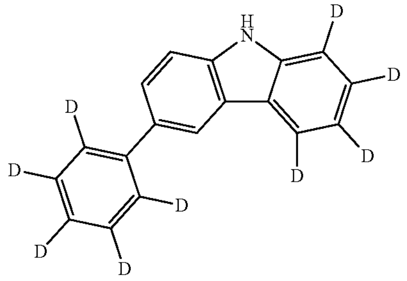 [SMILES: [2H]c1c([2H])c([2H])c(-c2ccc3[nH]c4c([2H])c([2H])c([2H])c([2H])c4c3c2)c([2H])c1[2H]]
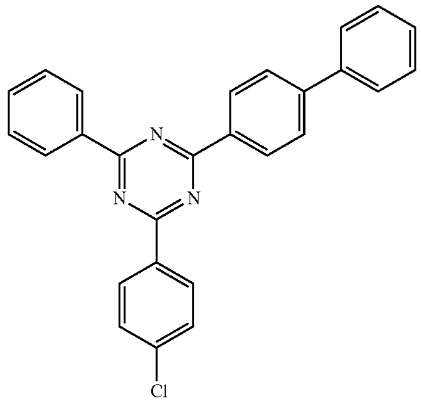 [SMILES: Clc1ccc(-c2nc(-c3ccccc3)nc(-c3ccc(-c4ccccc4)cc3)n2)cc1]
B40
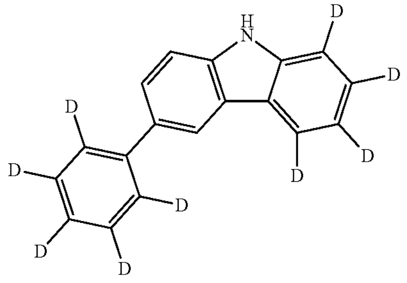 [SMILES: [2H]c1c([2H])c([2H])c(-c2ccc3[nH]c4c([2H])c([2H])c([2H])c([2H])c4c3c2)c([2H])c1[2H]]
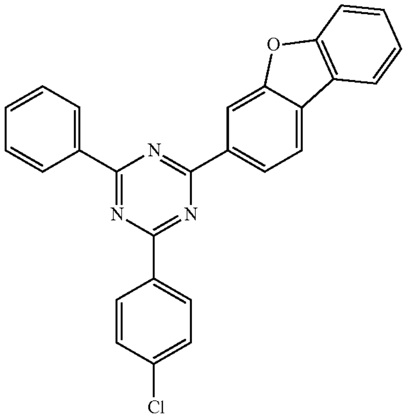 [SMILES: Clc1ccc(-c2nc(-c3ccccc3)nc(-c3ccc4c(c3)oc3ccccc34)n2)cc1]
B46
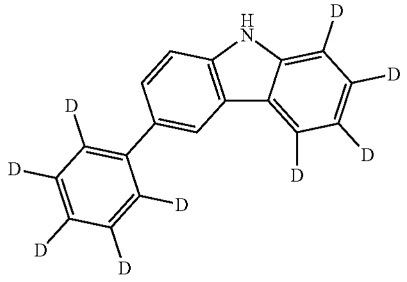 [SMILES: [2H]c1c([2H])c([2H])c(-c2ccc3[nH]c4c([2H])c([2H])c([2H])c([2H])c4c3c2)c([2H])c1[2H]]
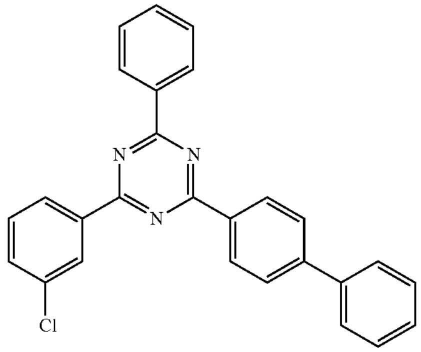 [SMILES: Clc1cccc(-c2nc(-c3ccccc3)nc(-c3ccc(-c4ccccc4)cc3)n2)c1]
B49
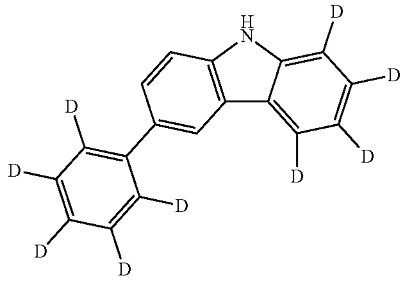 [SMILES: [2H]c1c([2H])c([2H])c(-c2ccc3[nH]c4c([2H])c([2H])c([2H])c([2H])c4c3c2)c([2H])c1[2H]]
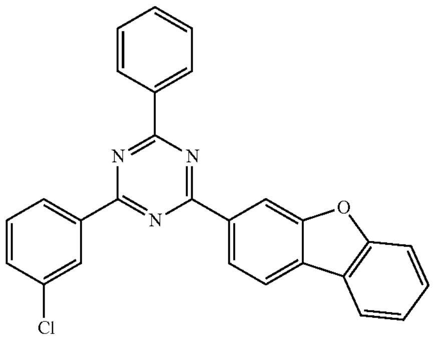 [SMILES: Clc1cccc(-c2nc(-c3ccccc3)nc(-c3ccc4c(c3)oc3ccccc34)n2)c1]

TABLE 4-continued
B59
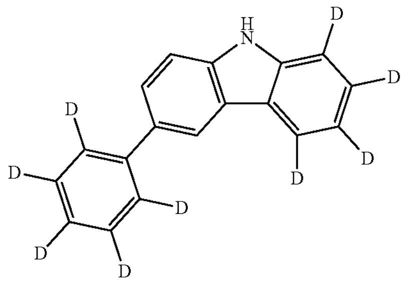 [SMILES: [2H]c1c([2H])c([2H])c(-c2ccc3[nH]c4c([2H])c([2H])c([2H])c([2H])c4c3c2)c([2H])c1[2H]]
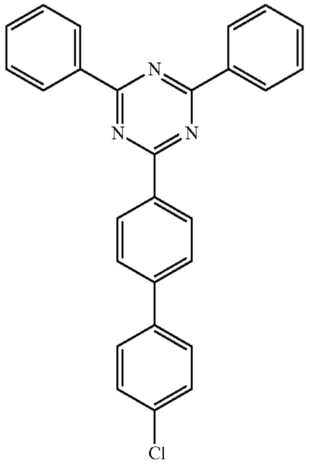 [SMILES: Clc1ccc(-c2ccc(-c3nc(-c4ccccc4)nc(-c4ccccc4)n3)cc2)cc1]
B60
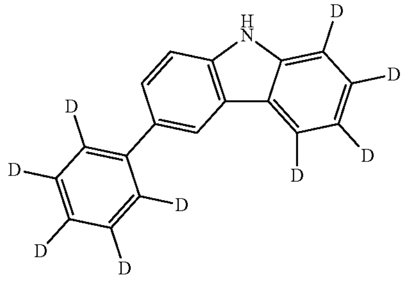 [SMILES: [2H]c1c([2H])c([2H])c(-c2ccc3[nH]c4c([2H])c([2H])c([2H])c([2H])c4c3c2)c([2H])c1[2H]]
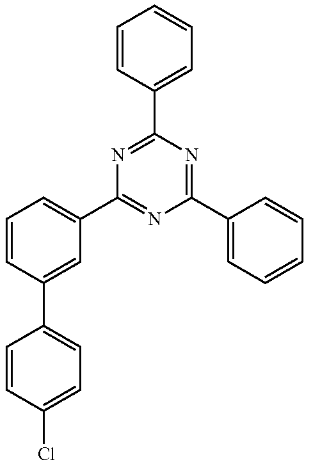 [SMILES: Clc1ccc(-c2cccc(-c3nc(-c4ccccc4)nc(-c4ccccc4)n3)c2)cc1]
B61
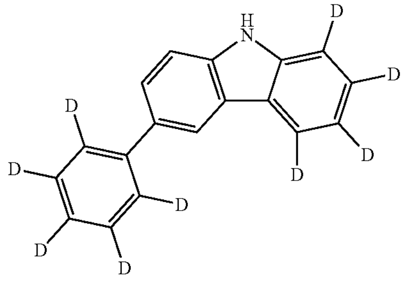 [SMILES: [2H]c1c([2H])c([2H])c(-c2ccc3[nH]c4c([2H])c([2H])c([2H])c([2H])c4c3c2)c([2H])c1[2H]]
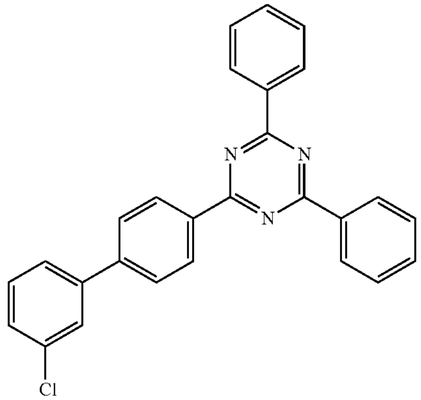 [SMILES: Clc1cccc(-c2ccc(-c3nc(-c4ccccc4)nc(-c4ccccc4)n3)cc2)c1]

TABLE 4-continued
| | | |
|---|---|---|
| B62 | 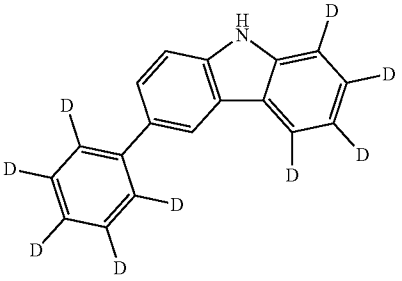 [SMILES: [2H]c1c([2H])c([2H])c(-c2ccc3[nH]c4c([2H])c([2H])c([2H])c([2H])c4c3c2)c([2H])c1[2H]] | 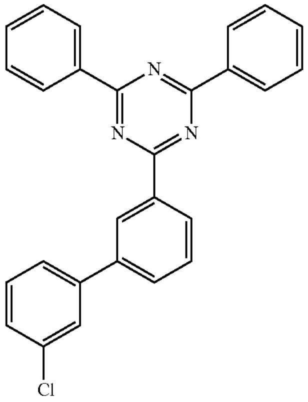 [SMILES: Clc1cccc(-c2cccc(-c3nc(-c4ccccc4)nc(-c4ccccc4)n3)c2)c1] |
| B64 | 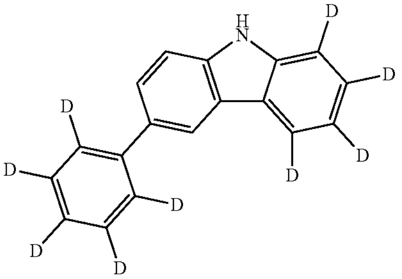 [SMILES: [2H]c1c([2H])c([2H])c(-c2ccc3[nH]c4c([2H])c([2H])c([2H])c([2H])c4c3c2)c([2H])c1[2H]] | 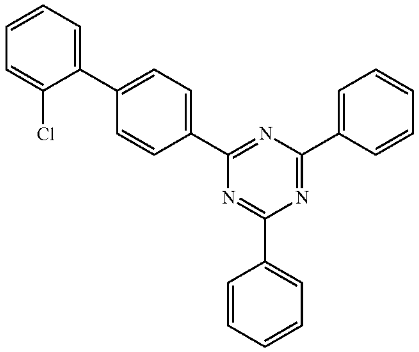 [SMILES: Clc1ccccc1-c1ccc(-c2nc(-c3ccccc3)nc(-c3ccccc3)n2)cc1] |
| B65 | 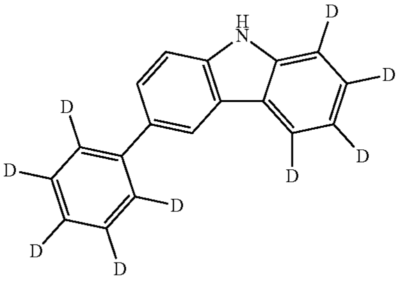 [SMILES: [2H]c1c([2H])c([2H])c(-c2ccc3[nH]c4c([2H])c([2H])c([2H])c([2H])c4c3c2)c([2H])c1[2H]] | 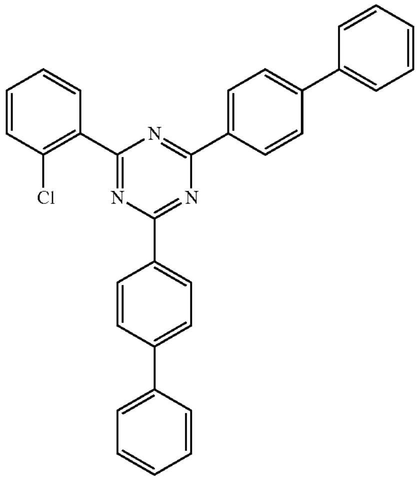 [SMILES: Clc1ccccc1-c1nc(-c2ccc(-c3ccccc3)cc2)nc(-c2ccc(-c3ccccc3)cc2)n1] |
| C13 | 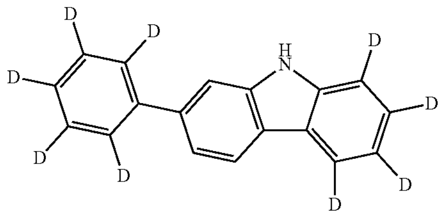 [SMILES: [2H]c1c([2H])c([2H])c(-c2ccc3c(c2)[nH]c2c([2H])c([2H])c([2H])c([2H])c23)c([2H])c1[2H]] | 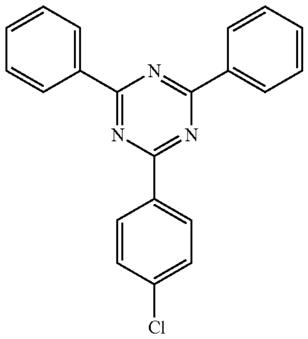 [SMILES: Clc1ccc(-c2nc(-c3ccccc3)nc(-c3ccccc3)n2)cc1] |

TABLE 4-continued
| | | |
|---|---|---|
| C14 | 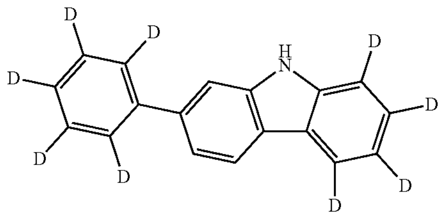 [SMILES: [2H]c1c([2H])c([2H])c(-c2ccc3c(c2)[nH]c2c([2H])c([2H])c([2H])c([2H])c23)c([2H])c1[2H]] | 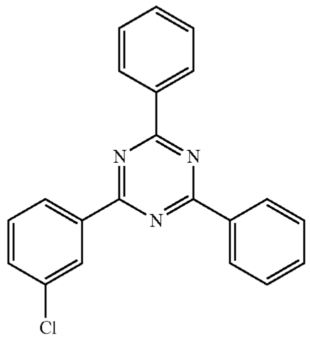 [SMILES: Clc1cccc(-c2nc(-c3ccccc3)nc(-c3ccccc3)n2)c1] |
| C38 | 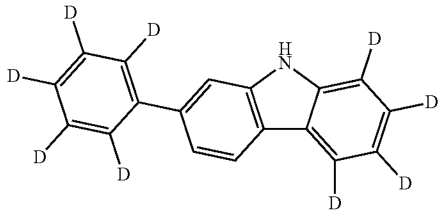 [SMILES: [2H]c1c([2H])c([2H])c(-c2ccc3c(c2)[nH]c2c([2H])c([2H])c([2H])c([2H])c23)c([2H])c1[2H]] | 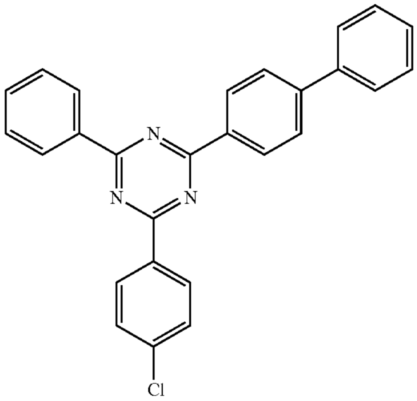 [SMILES: Clc1ccc(-c2nc(-c3ccccc3)nc(-c3ccc(-c4ccccc4)cc3)n2)cc1] |
| C41 | 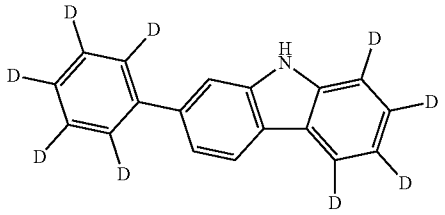 [SMILES: [2H]c1c([2H])c([2H])c(-c2ccc3c(c2)[nH]c2c([2H])c([2H])c([2H])c([2H])c23)c([2H])c1[2H]] | 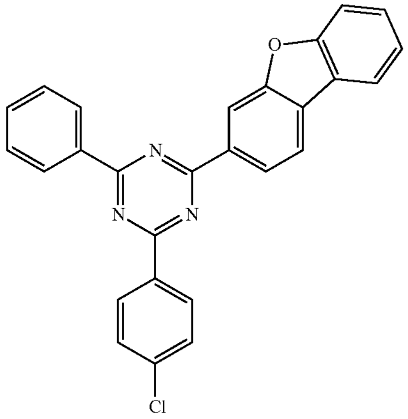 [SMILES: Clc1ccc(-c2nc(-c3ccccc3)nc(-c3ccc4c(c3)oc3ccccc34)n2)cc1] |
| C46 | 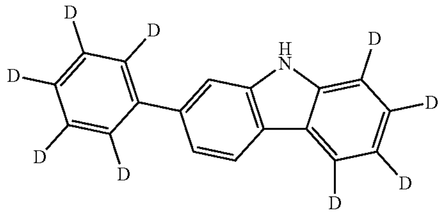 [SMILES: [2H]c1c([2H])c([2H])c(-c2ccc3c(c2)[nH]c2c([2H])c([2H])c([2H])c([2H])c23)c([2H])c1[2H]] | 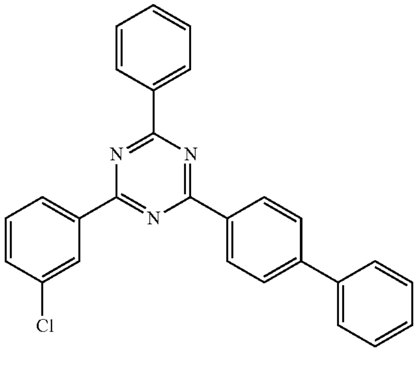 [SMILES: Clc1cccc(-c2nc(-c3ccccc3)nc(-c3ccc(-c4ccccc4)cc3)n2)c1] |

TABLE 4-continued
| | | |
|---|---|---|
| C49 | 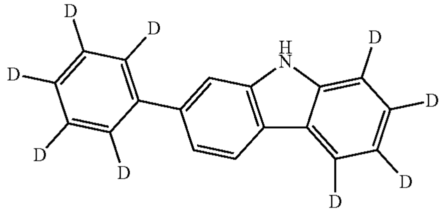 [SMILES: [2H]c1c([2H])c([2H])c(-c2ccc3c(c2)[nH]c2c([2H])c([2H])c([2H])c([2H])c23)c([2H])c1[2H]] | 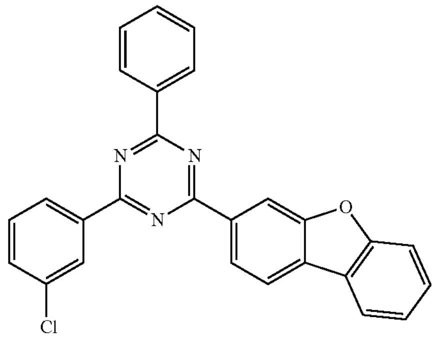 [SMILES: Clc1cccc(-c2nc(-c3ccccc3)nc(-c3ccc4c(c3)oc3ccccc34)n2)c1] |
| C51 | 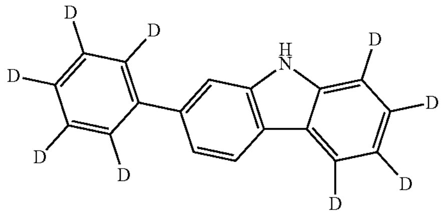 [SMILES: [2H]c1c([2H])c([2H])c(-c2ccc3c(c2)[nH]c2c([2H])c([2H])c([2H])c([2H])c23)c([2H])c1[2H]] | 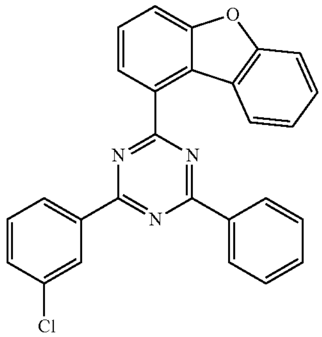 [SMILES: Clc1cccc(-c2nc(-c3ccccc3)nc(-c3cccc4oc5ccccc5c34)n2)c1] |
| C59 | 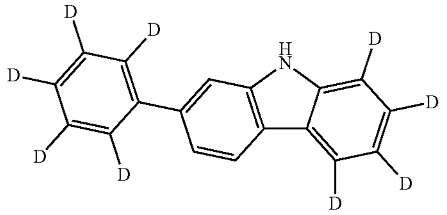 [SMILES: [2H]c1c([2H])c([2H])c(-c2ccc3c(c2)[nH]c2c([2H])c([2H])c([2H])c([2H])c23)c([2H])c1[2H]] | 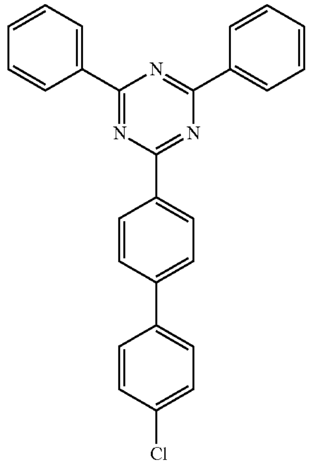 [SMILES: Clc1ccc(-c2ccc(-c3nc(-c4ccccc4)nc(-c4ccccc4)n3)cc2)cc1] |
| C60 | 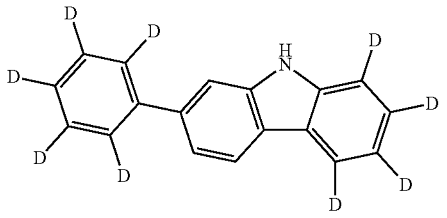 [SMILES: [2H]c1c([2H])c([2H])c(-c2ccc3c(c2)[nH]c2c([2H])c([2H])c([2H])c([2H])c23)c([2H])c1[2H]] | 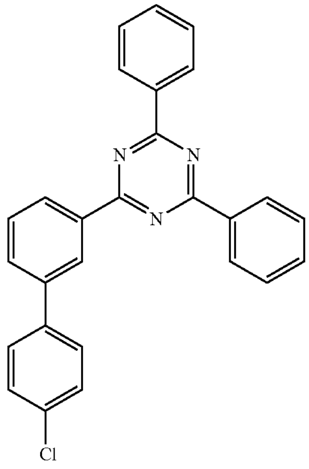 [SMILES: Clc1ccc(-c2cccc(-c3nc(-c4ccccc4)nc(-c4ccccc4)n3)c2)cc1] |

TABLE 4-continued
C61
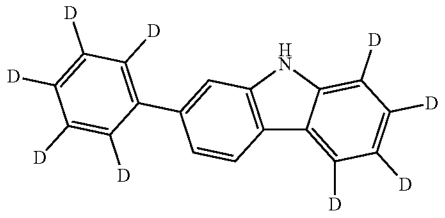 [SMILES: [2H]c1c([2H])c([2H])c(-c2ccc3c(c2)[nH]c2c([2H])c([2H])c([2H])c([2H])c23)c([2H])c1[2H]]
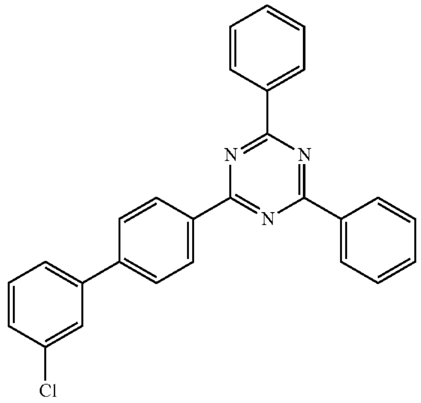 [SMILES: Clc1cccc(-c2ccc(-c3nc(-c4ccccc4)nc(-c4ccccc4)n3)cc2)c1]
C62
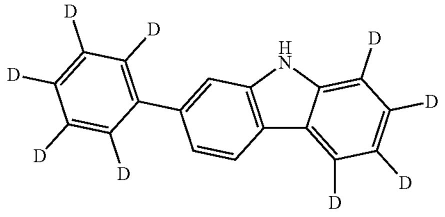 [SMILES: [2H]c1c([2H])c([2H])c(-c2ccc3c(c2)[nH]c2c([2H])c([2H])c([2H])c([2H])c23)c([2H])c1[2H]]
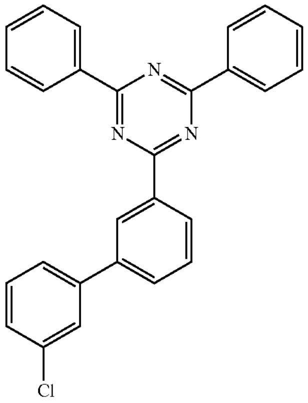 [SMILES: Clc1cccc(-c2cccc(-c3nc(-c4ccccc4)nc(-c4ccccc4)n3)c2)c1]
C63
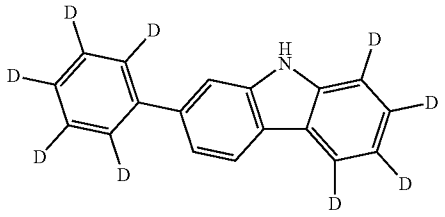 [SMILES: [2H]c1c([2H])c([2H])c(-c2ccc3c(c2)[nH]c2c([2H])c([2H])c([2H])c([2H])c23)c([2H])c1[2H]]
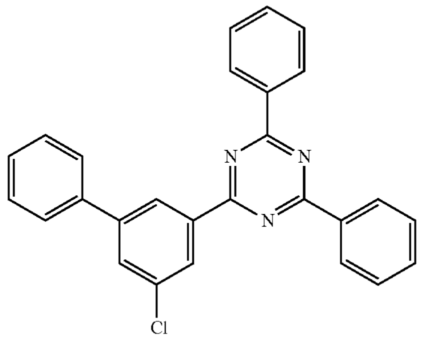 [SMILES: Clc1cc(-c2ccccc2)cc(-c2nc(-c3ccccc3)nc(-c3ccccc3)n2)c1]
C69
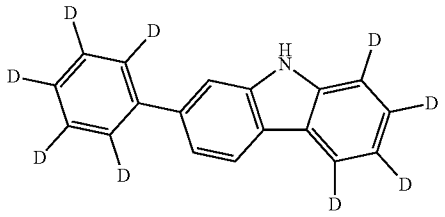 [SMILES: [2H]c1c([2H])c([2H])c(-c2ccc3c(c2)[nH]c2c([2H])c([2H])c([2H])c([2H])c23)c([2H])c1[2H]]
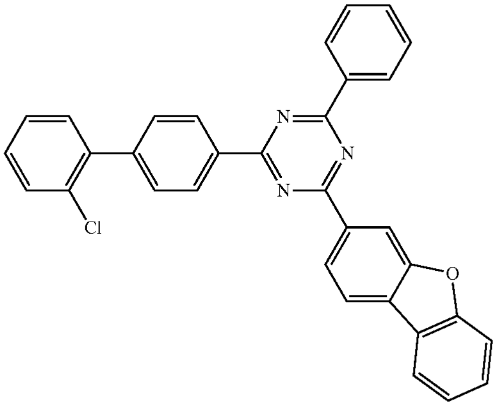 [SMILES: Clc1ccccc1-c1ccc(-c2nc(-c3ccccc3)nc(-c3ccc4c(c3)oc3ccccc34)n2)cc1]

TABLE 4-continued
| | | |
|---|---|---|
| D37 | 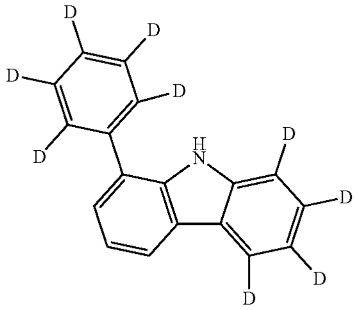 [SMILES: [2H]c1c([2H])c([2H])c(-c2cccc3c2[nH]c2c([2H])c([2H])c([2H])c([2H])c23)c([2H])c1[2H]] | 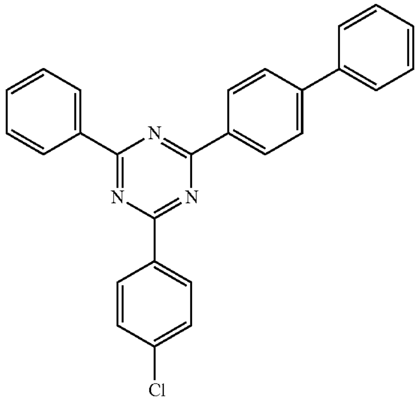 [SMILES: Clc1ccc(-c2nc(-c3ccccc3)nc(-c3ccc(-c4ccccc4)cc3)n2)cc1] |
| D38 | 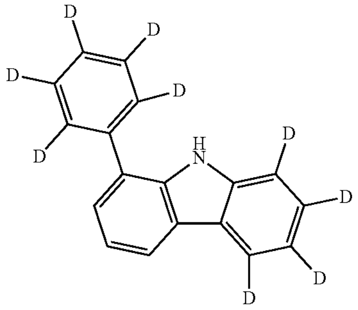 [SMILES: [2H]c1c([2H])c([2H])c(-c2cccc3c2[nH]c2c([2H])c([2H])c([2H])c([2H])c23)c([2H])c1[2H]] | 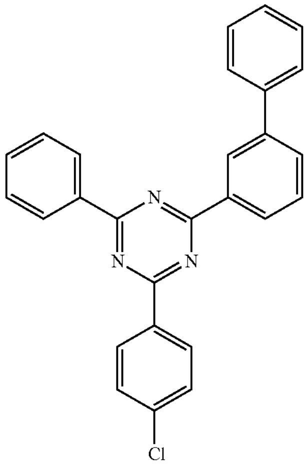 [SMILES: Clc1ccc(-c2nc(-c3ccccc3)nc(-c3cccc(-c4ccccc4)c3)n2)cc1] |
| D39 | 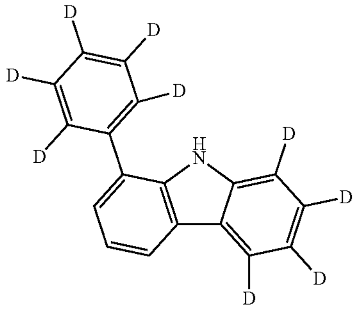 [SMILES: [2H]c1c([2H])c([2H])c(-c2cccc3c2[nH]c2c([2H])c([2H])c([2H])c([2H])c23)c([2H])c1[2H]] | 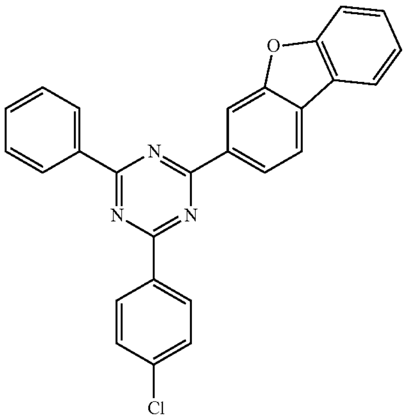 [SMILES: Clc1ccc(-c2nc(-c3ccccc3)nc(-c3ccc4c(c3)oc3ccccc34)n2)cc1] |
| D43 | 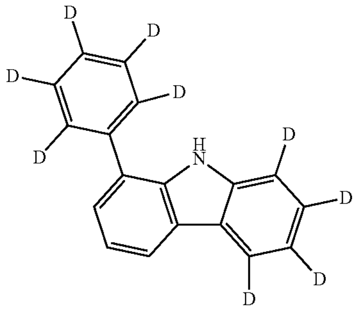 [SMILES: [2H]c1c([2H])c([2H])c(-c2cccc3c2[nH]c2c([2H])c([2H])c([2H])c([2H])c23)c([2H])c1[2H]] | 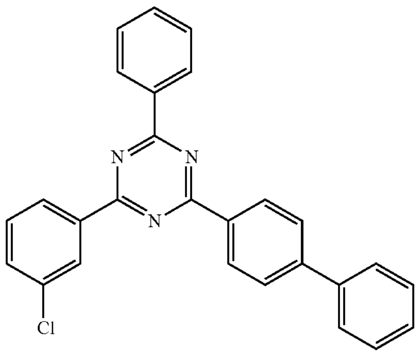 [SMILES: Clc1cccc(-c2nc(-c3ccccc3)nc(-c3ccc(-c4ccccc4)cc3)n2)c1] |

TABLE 4-continued
D45
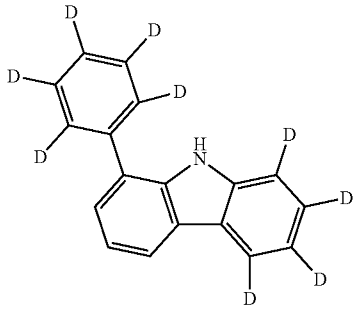 [SMILES: [2H]c1c([2H])c([2H])c(-c2cccc3c2[nH]c2c([2H])c([2H])c([2H])c([2H])c23)c([2H])c1[2H]]
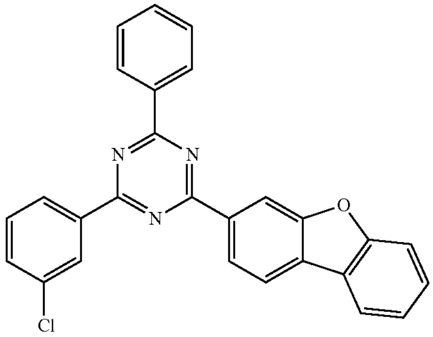 [SMILES: Clc1cccc(-c2nc(-c3ccccc3)nc(-c3ccc4c(c3)oc3ccccc34)n2)c1]
D47
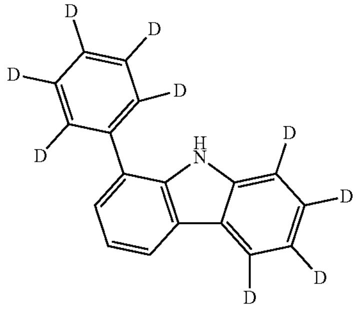 [SMILES: [2H]c1c([2H])c([2H])c(-c2cccc3c2[nH]c2c([2H])c([2H])c([2H])c([2H])c23)c([2H])c1[2H]]
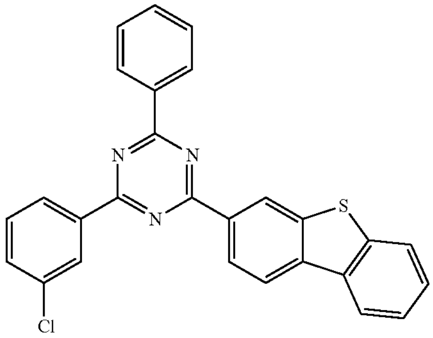
D54
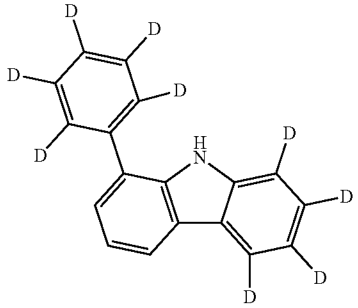 [SMILES: [2H]c1c([2H])c([2H])c(-c2cccc3c2[nH]c2c([2H])c([2H])c([2H])c([2H])c23)c([2H])c1[2H]]
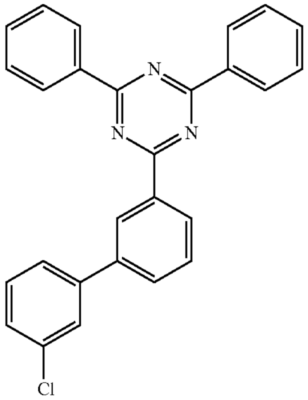 [SMILES: Clc1cccc(-c2cccc(-c3nc(-c4ccccc4)nc(-c4ccccc4)n3)c2)c1]
D61
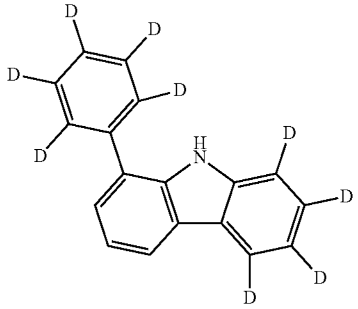 [SMILES: [2H]c1c([2H])c([2H])c(-c2cccc3c2[nH]c2c([2H])c([2H])c([2H])c([2H])c23)c([2H])c1[2H]]
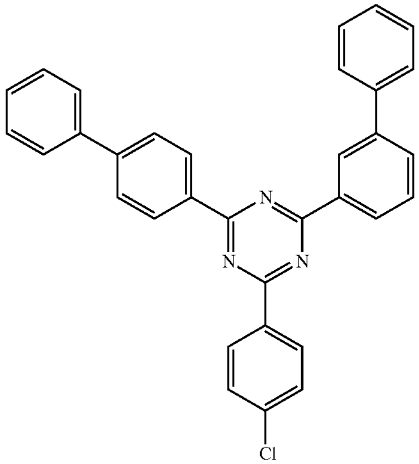 [SMILES: Clc1ccc(-c2nc(-c3ccc(-c4ccccc4)cc3)nc(-c3cccc(-c4ccccc4)c3)n2)cc1]

TABLE 4-continued
D63
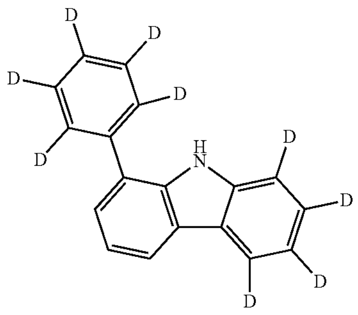 [SMILES: [2H]c1c([2H])c([2H])c(-c2cccc3c2[nH]c2c([2H])c([2H])c([2H])c([2H])c23)c([2H])c1[2H]]
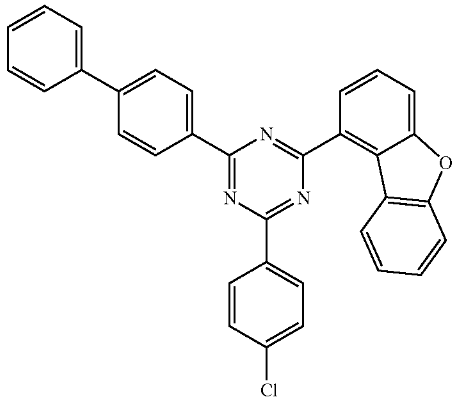 [SMILES: Clc1ccc(-c2nc(-c3ccc(-c4ccccc4)cc3)nc(-c3cccc4oc5ccccc5c34)n2)cc1]
D67
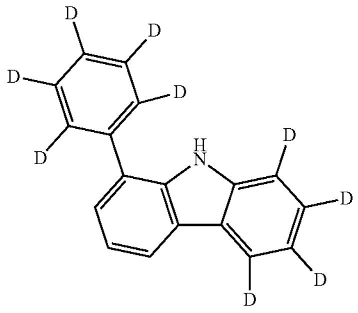 [SMILES: [2H]c1c([2H])c([2H])c(-c2cccc3c2[nH]c2c([2H])c([2H])c([2H])c([2H])c23)c([2H])c1[2H]]
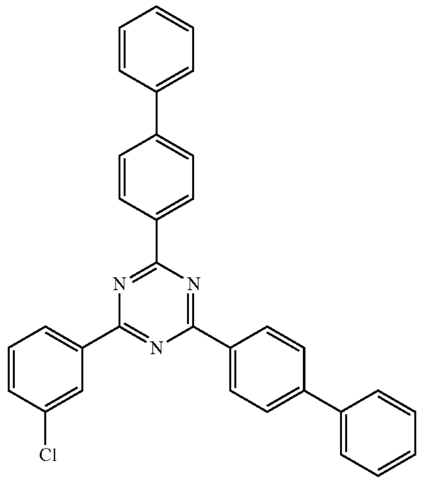 [SMILES: Clc1cccc(-c2nc(-c3ccc(-c4ccccc4)cc3)nc(-c3ccc(-c4ccccc4)cc3)n2)c1]
D71
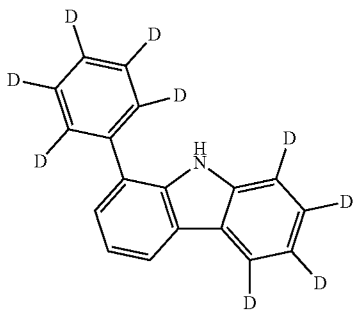 [SMILES: [2H]c1c([2H])c([2H])c(-c2cccc3c2[nH]c2c([2H])c([2H])c([2H])c([2H])c23)c([2H])c1[2H]]
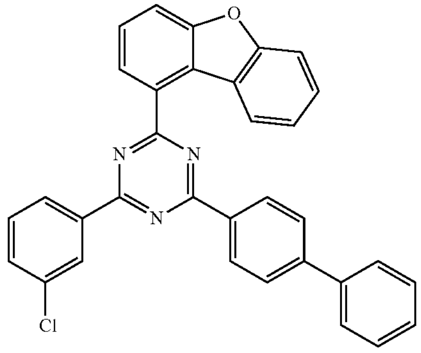 [SMILES: Clc1cccc(-c2nc(-c3ccc(-c4ccccc4)cc3)nc(-c3cccc4oc5ccccc5c34)n2)c1]

TABLE 4-continued
D74
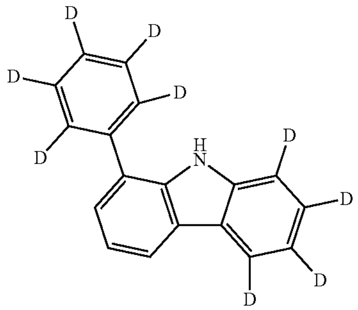 [SMILES: [2H]c1c([2H])c([2H])c(-c2cccc3c2[nH]c2c([2H])c([2H])c([2H])c([2H])c23)c([2H])c1[2H]]
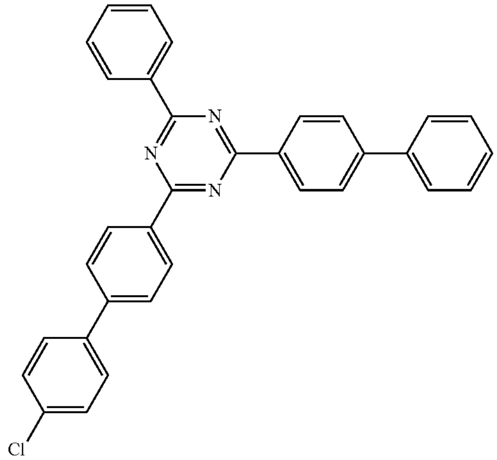 [SMILES: Clc1ccc(-c2ccc(-c3nc(-c4ccccc4)nc(-c4ccc(-c5ccccc5)cc4)n3)cc2)cc1]
D75
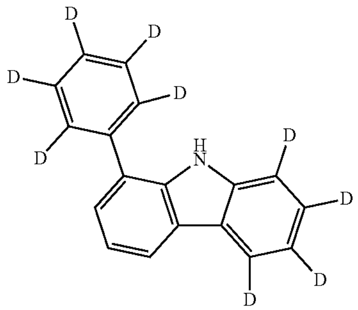 [SMILES: [2H]c1c([2H])c([2H])c(-c2cccc3c2[nH]c2c([2H])c([2H])c([2H])c([2H])c23)c([2H])c1[2H]]
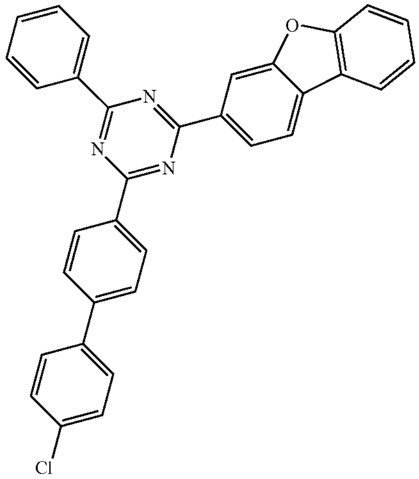 [SMILES: Clc1ccc(-c2ccc(-c3nc(-c4ccccc4)nc(-c4ccc5c(c4)oc4ccccc45)n3)cc2)cc1]
D77
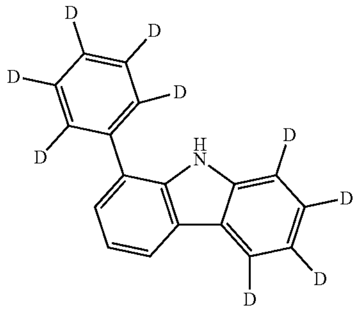 [SMILES: [2H]c1c([2H])c([2H])c(-c2cccc3c2[nH]c2c([2H])c([2H])c([2H])c([2H])c23)c([2H])c1[2H]]
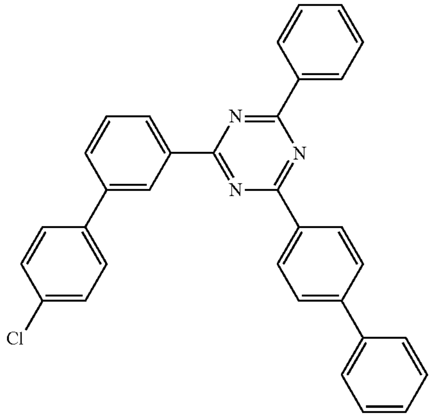 [SMILES: Clc1ccc(-c2cccc(-c3nc(-c4ccccc4)nc(-c4ccc(-c5ccccc5)cc4)n3)c2)cc1]

TABLE 4-continued
D79
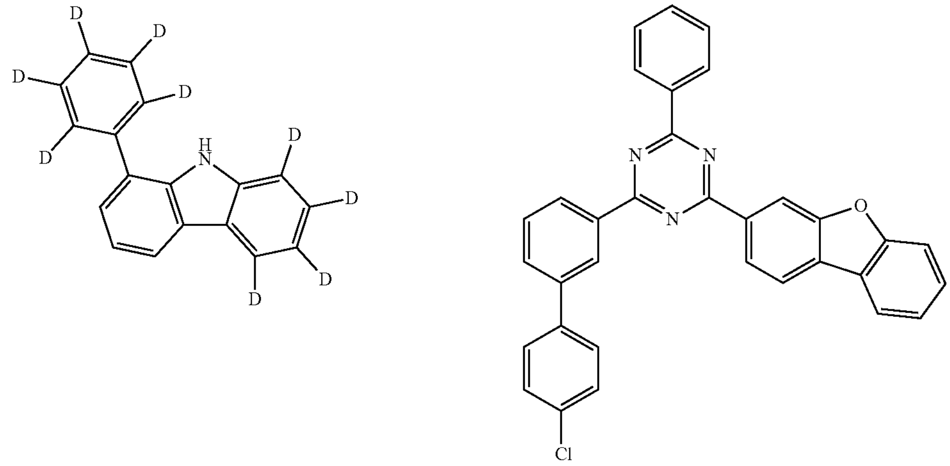
D83
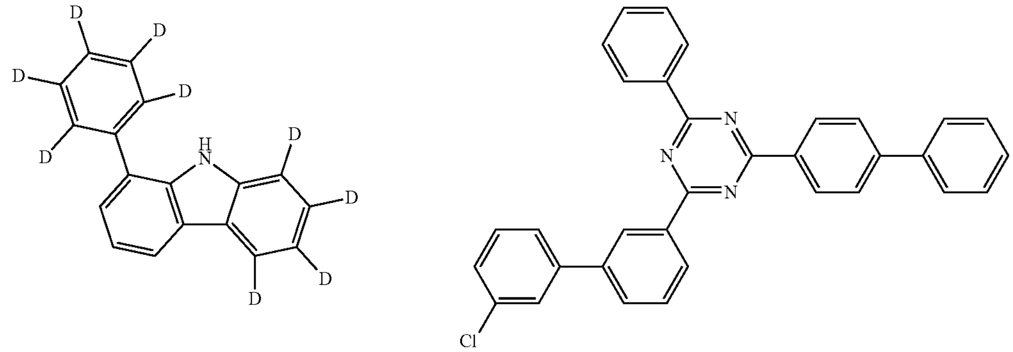
D84
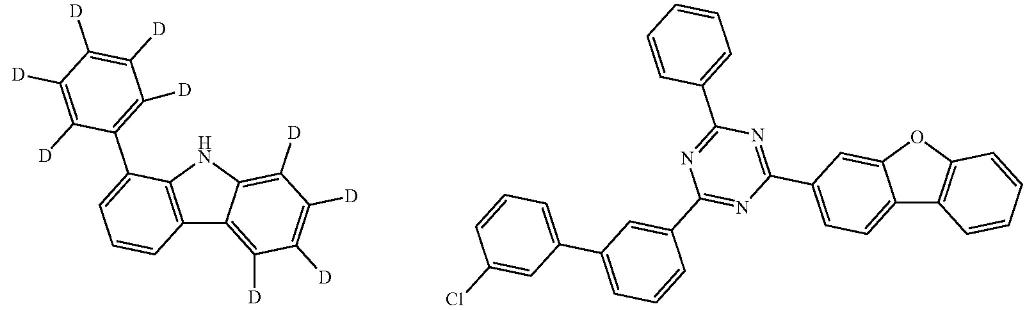
D85
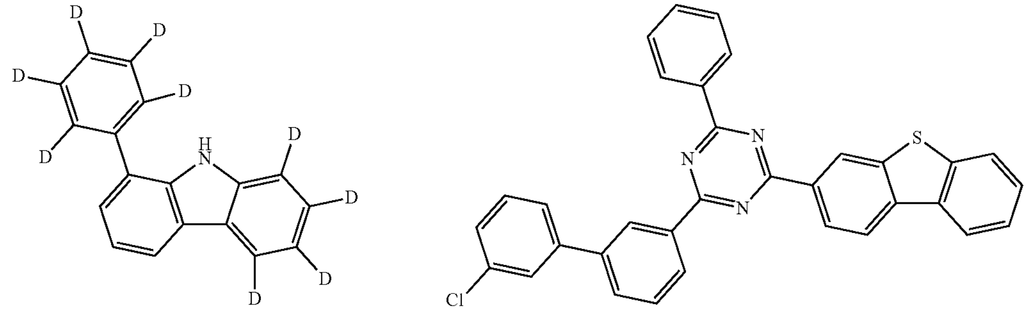

TABLE 4-continued
| | | |
|---|---|---|
| A229 | 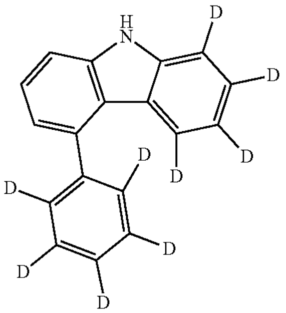 [SMILES: [2H]c1c([2H])c([2H])c(-c2cccc3[nH]c4c([2H])c([2H])c([2H])c([2H])c4c23)c([2H])c1[2H]] | 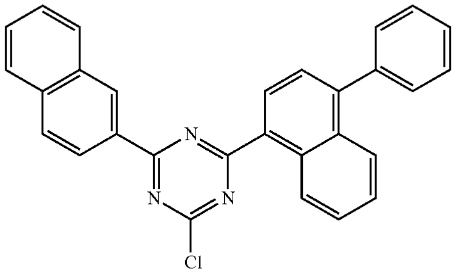 [SMILES: Clc1nc(-c2ccc3ccccc3c2)nc(-c2ccc(-c3ccccc3)c3ccccc23)n1] |
| A230 | 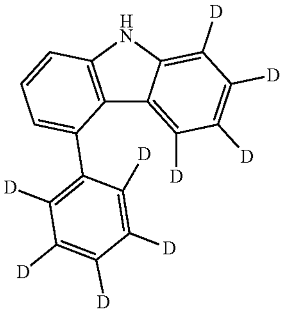 [SMILES: [2H]c1c([2H])c([2H])c(-c2cccc3[nH]c4c([2H])c([2H])c([2H])c([2H])c4c23)c([2H])c1[2H]] | 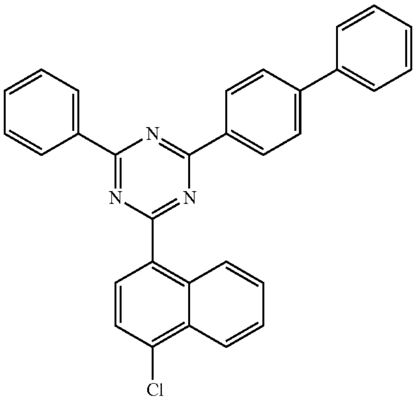 [SMILES: Clc1ccc(-c2nc(-c3ccccc3)nc(-c3ccc(-c4ccccc4)cc3)n2)c2ccccc12] |
| A231 | 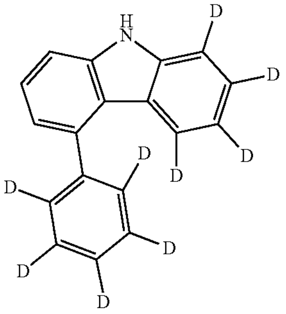 [SMILES: [2H]c1c([2H])c([2H])c(-c2cccc3[nH]c4c([2H])c([2H])c([2H])c([2H])c4c23)c([2H])c1[2H]] | 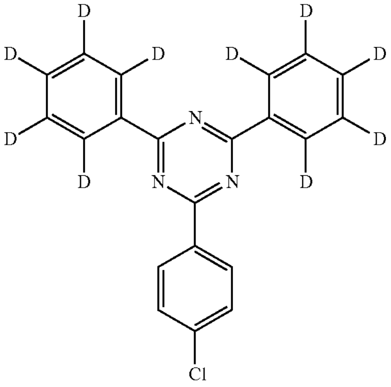 [SMILES: [2H]c1c([2H])c([2H])c(-c2nc(-c3ccc(Cl)cc3)nc(-c3c([2H])c([2H])c([2H])c([2H])c3[2H])n2)c([2H])c1[2H]] |
| B81 | 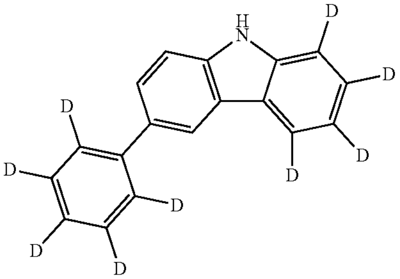 [SMILES: [2H]c1c([2H])c([2H])c(-c2ccc3[nH]c4c([2H])c([2H])c([2H])c([2H])c4c3c2)c([2H])c1[2H]] | 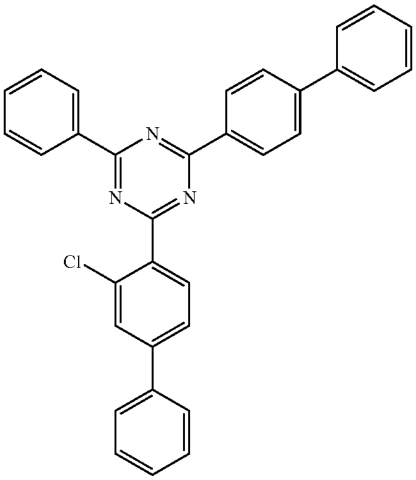 [SMILES: Clc1cc(-c2ccccc2)ccc1-c1nc(-c2ccccc2)nc(-c2ccc(-c3ccccc3)cc2)n1] |

TABLE 4-continued
| Compound No. | Structure | Yield (%) |
|---|---|---|
| A47 | 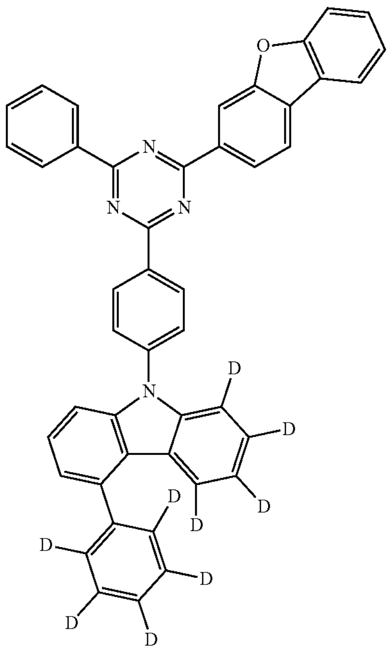 | 75 |
| A51 | 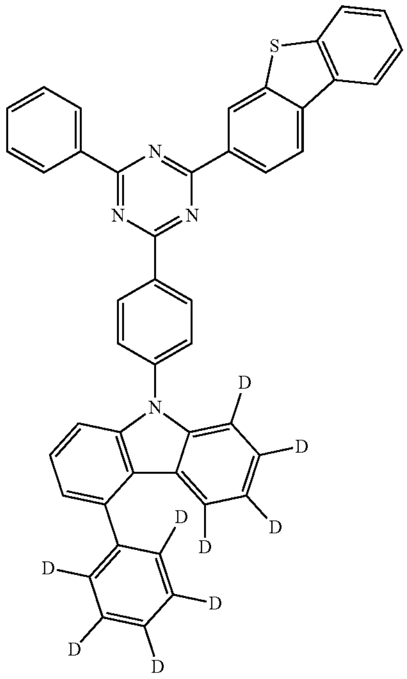 [SMILES: [2H]c1c([2H])c([2H])c(-c2cccc3c2c2c([2H])c([2H])c([2H])c([2H])c2n3-c2ccc(-c3nc(-c4ccccc4)nc(-c4ccc5c(c4)oc4ccccc45)n3)cc2)c([2H])c1[2H]] | 79 |

TABLE 4-continued
A55 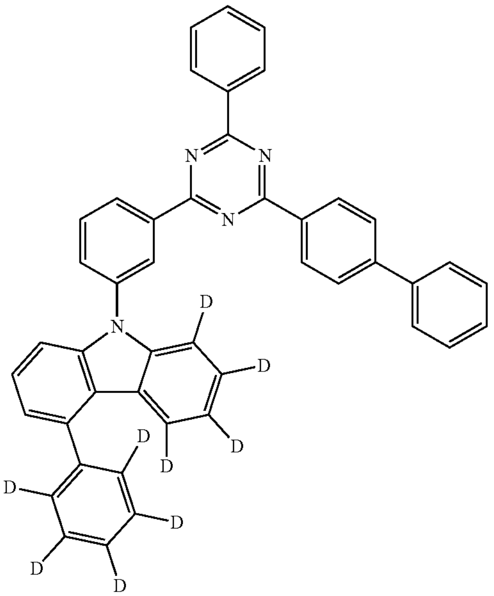 [SMILES: [2H]c1c([2H])c([2H])c(-c2cccc3c2c2c([2H])c([2H])c([2H])c([2H])c2n3-c2cccc(-c3nc(-c4ccccc4)nc(-c4ccc(-c5ccccc5)cc4)n3)c2)c([2H])c1[2H]] 69
A57 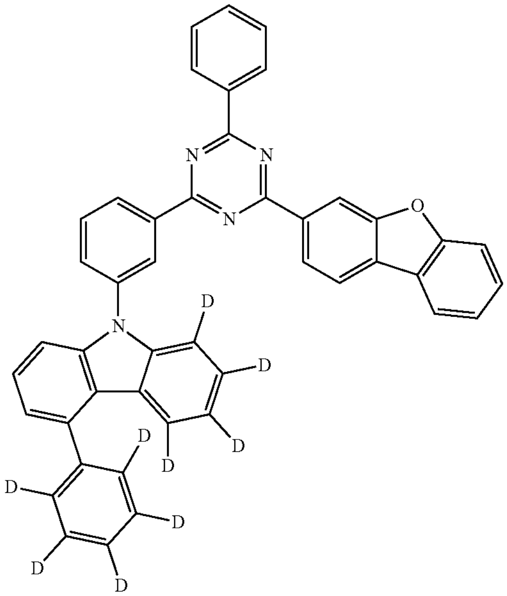 [SMILES: [2H]c1c([2H])c([2H])c(-c2cccc3c2c2c([2H])c([2H])c([2H])c([2H])c2n3-c2cccc(-c3nc(-c4ccccc4)nc(-c4ccc5c(c4)oc4ccccc45)n3)c2)c([2H])c1[2H]] 69

TABLE 4-continued
A60 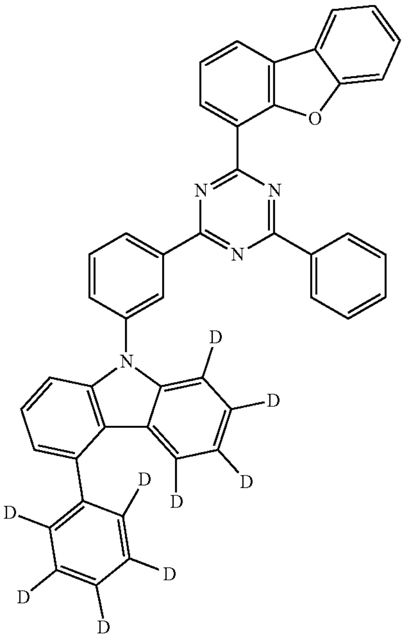 [SMILES: [2H]c1c([2H])c([2H])c(-c2cccc3c2c2c([2H])c([2H])c([2H])c([2H])c2n3-c2cccc(-c3nc(-c4ccccc4)nc(-c4cccc5c4oc4ccccc45)n3)c2)c([2H])c1[2H]] 64
A68 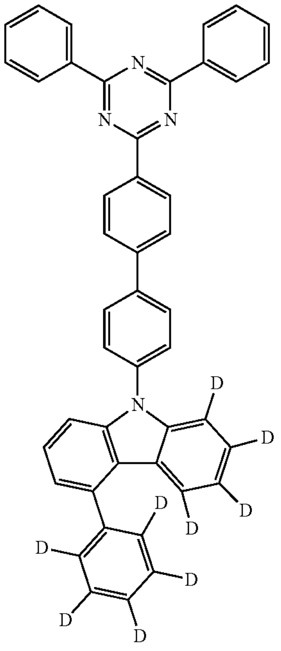 [SMILES: [2H]c1c([2H])c([2H])c(-c2cccc3c2c2c([2H])c([2H])c([2H])c([2H])c2n3-c2ccc(-c3ccc(-c4nc(-c5ccccc5)nc(-c5ccccc5)n4)cc3)cc2)c([2H])c1[2H]] 76

TABLE 4-continued
| | | |
|---|---|---|
| A69 | 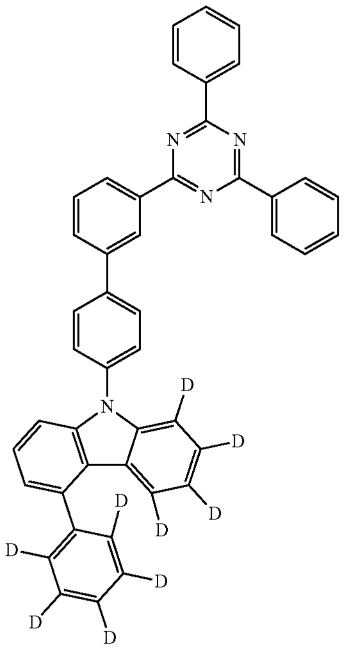 [SMILES: [2H]c1c([2H])c([2H])c(-c2cccc3c2c2c([2H])c([2H])c([2H])c([2H])c2n3-c2ccc(-c3cccc(-c4nc(-c5ccccc5)nc(-c5ccccc5)n4)c3)cc2)c([2H])c1[2H]] | 75 |
| A71 | 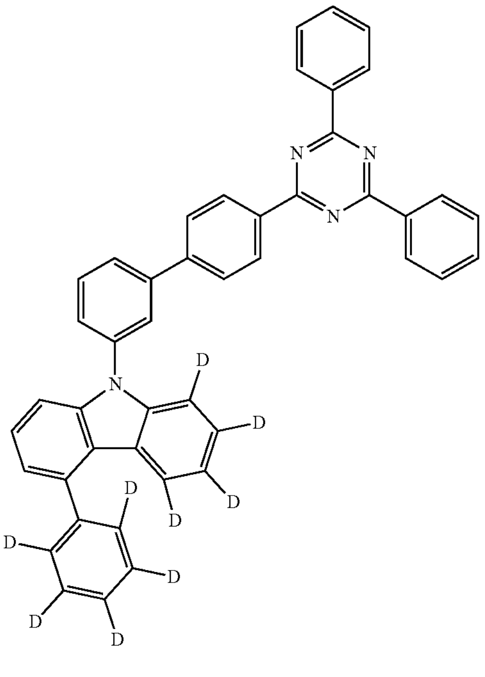 [SMILES: [2H]c1c([2H])c([2H])c(-c2cccc3c2c2c([2H])c([2H])c([2H])c([2H])c2n3-c2cccc(-c3ccc(-c4nc(-c5ccccc5)nc(-c5ccccc5)n4)cc3)c2)c([2H])c1[2H]] | 61 |

TABLE 4-continued
A72 68
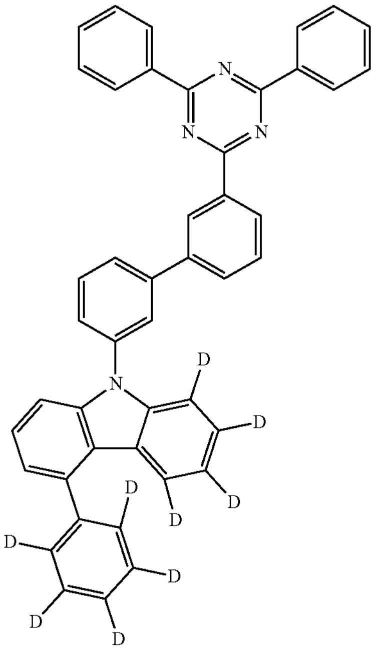 [SMILES: [2H]c1c([2H])c([2H])c(-c2cccc3c2c2c([2H])c([2H])c([2H])c([2H])c2n3-c2cccc(-c3cccc(-c4nc(-c5ccccc5)nc(-c5ccccc5)n4)c3)c2)c([2H])c1[2H]]
A81 56
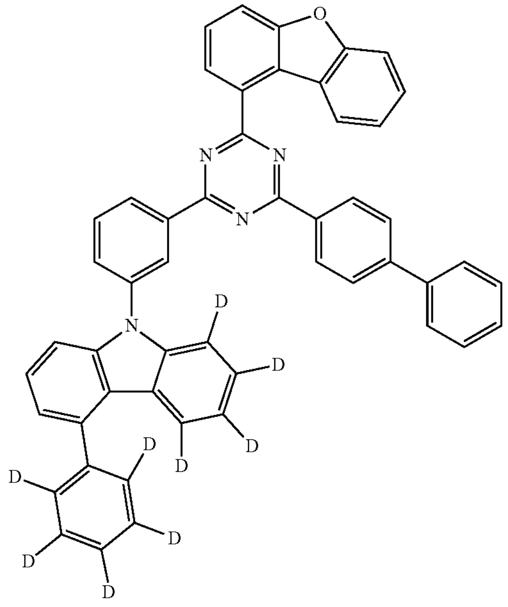 [SMILES: [2H]c1c([2H])c([2H])c(-c2cccc3c2c2c([2H])c([2H])c([2H])c([2H])c2n3-c2cccc(-c3nc(-c4ccc(-c5ccccc5)cc4)nc(-c4cccc5oc6ccccc6c45)n3)c2)c([2H])c1[2H]]

TABLE 4-continued
A97 36
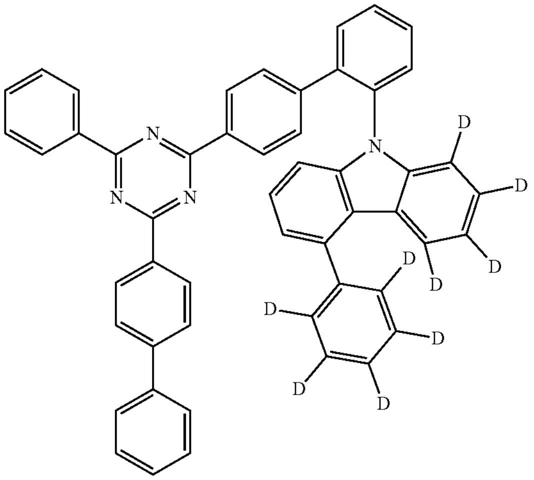 [SMILES: [2H]c1c([2H])c([2H])c(-c2cccc3c2c2c([2H])c([2H])c([2H])c([2H])c2n3-c2ccccc2-c2ccc(-c3nc(-c4ccccc4)nc(-c4ccc(-c5ccccc5)cc4)n3)cc2)c([2H])c1[2H]]
A104 79
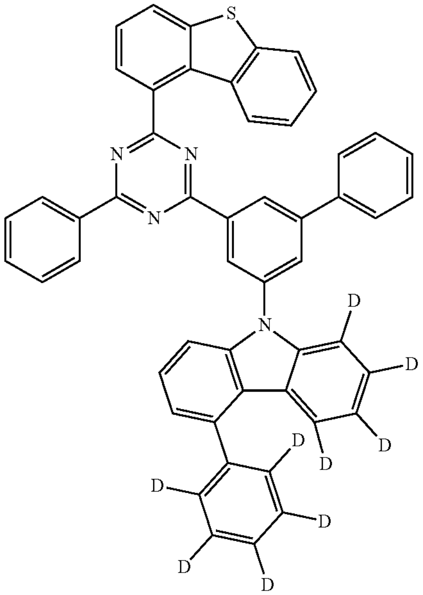 [SMILES: [2H]c1c([2H])c([2H])c(-c2cccc3c2c2c([2H])c([2H])c([2H])c([2H])c2n3-c2cc(-c3ccccc3)cc(-c3nc(-c4ccccc4)nc(-c4cccc5sc6ccccc6c45)n3)c2)c([2H])c1[2H]]
B13 63
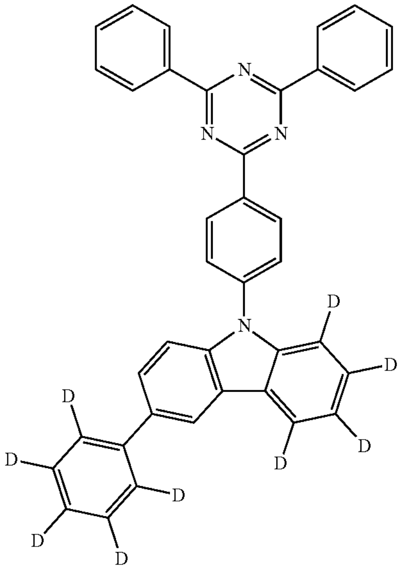 [SMILES: [2H]c1c([2H])c([2H])c(-c2ccc3c(c2)c2c([2H])c([2H])c([2H])c([2H])c2n3-c2ccc(-c3nc(-c4ccccc4)nc(-c4ccccc4)n3)cc2)c([2H])c1[2H]]

TABLE 4-continued
B14 70
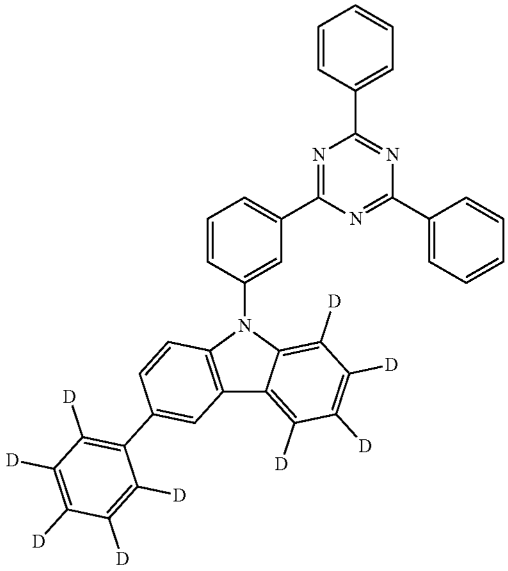 [SMILES: [2H]c1c([2H])c([2H])c(-c2ccc3c(c2)c2c([2H])c([2H])c([2H])c([2H])c2n3-c2cccc(-c3nc(-c4ccccc4)nc(-c4ccccc4)n3)c2)c([2H])c1[2H]]
B37 66
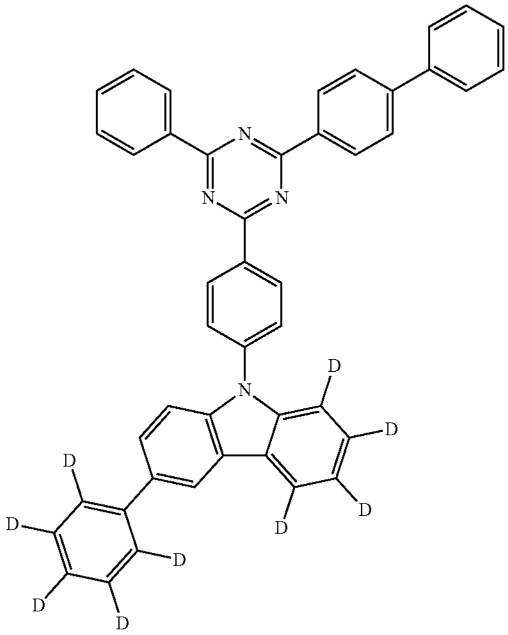 [SMILES: [2H]c1c([2H])c([2H])c(-c2ccc3c(c2)c2c([2H])c([2H])c([2H])c([2H])c2n3-c2ccc(-c3nc(-c4ccccc4)nc(-c4ccc(-c5ccccc5)cc4)n3)cc2)c([2H])c1[2H]]

TABLE 4-continued
B40 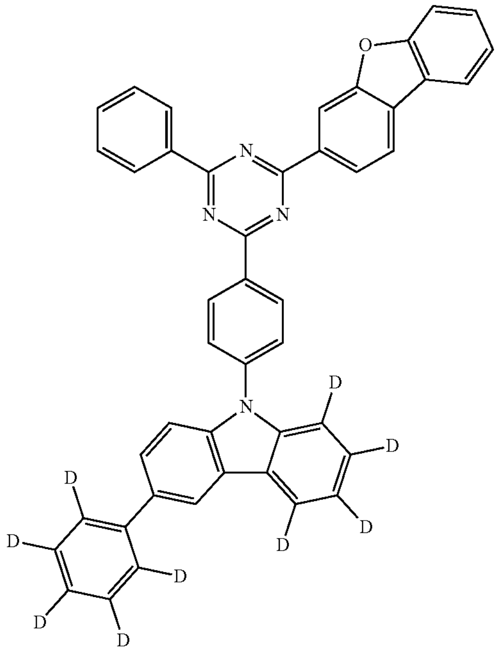 [SMILES: [2H]c1c([2H])c([2H])c(-c2ccc3c(c2)c2c([2H])c([2H])c([2H])c([2H])c2n3-c2ccc(-c3nc(-c4ccccc4)nc(-c4ccc5c(c4)oc4ccccc45)n3)cc2)c([2H])c1[2H]] 77
B46 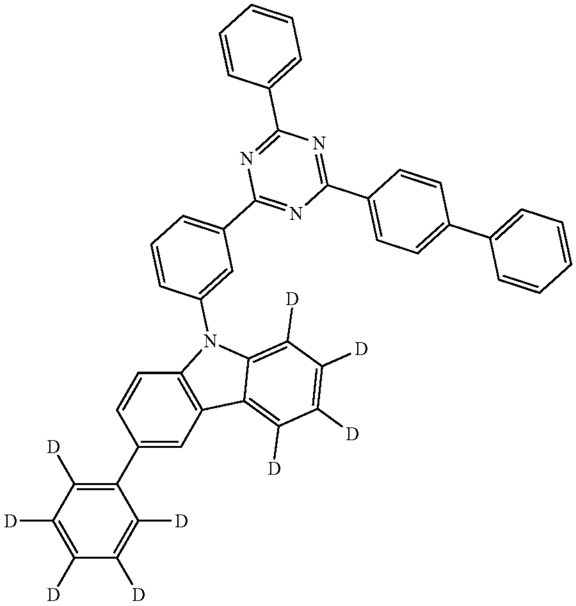 [SMILES: [2H]c1c([2H])c([2H])c(-c2ccc3c(c2)c2c([2H])c([2H])c([2H])c([2H])c2n3-c2cccc(-c3nc(-c4ccccc4)nc(-c4ccc(-c5ccccc5)cc4)n3)c2)c([2H])c1[2H]] 79

TABLE 4-continued
B49
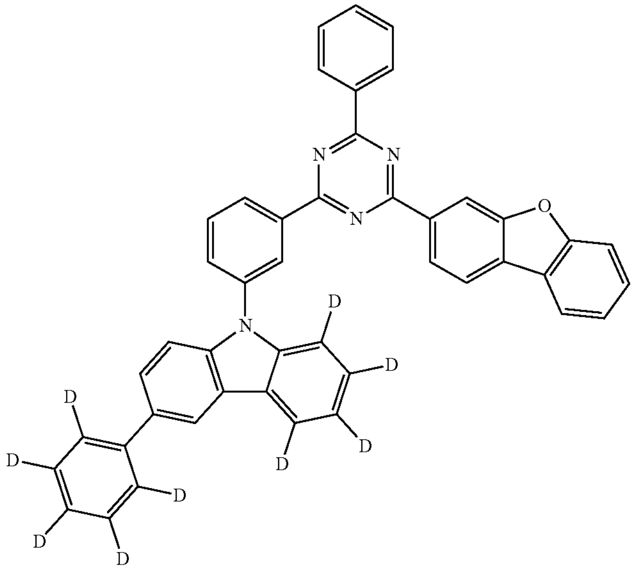 [SMILES: [2H]c1c([2H])c([2H])c(-c2ccc3c(c2)c2c([2H])c([2H])c([2H])c([2H])c2n3-c2cccc(-c3nc(-c4ccccc4)nc(-c4ccc5c(c4)oc4ccccc45)n3)c2)c([2H])c1[2H]]
76
B59
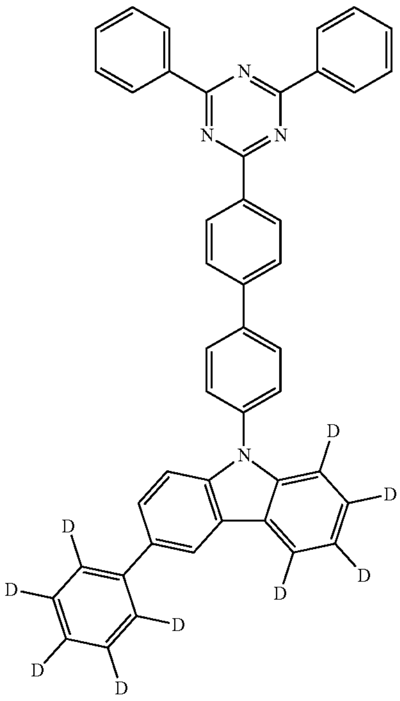 [SMILES: [2H]c1c([2H])c([2H])c(-c2ccc3c(c2)c2c([2H])c([2H])c([2H])c([2H])c2n3-c2ccc(-c3ccc(-c4nc(-c5ccccc5)nc(-c5ccccc5)n4)cc3)cc2)c([2H])c1[2H]]
75

TABLE 4-continued
B60 62
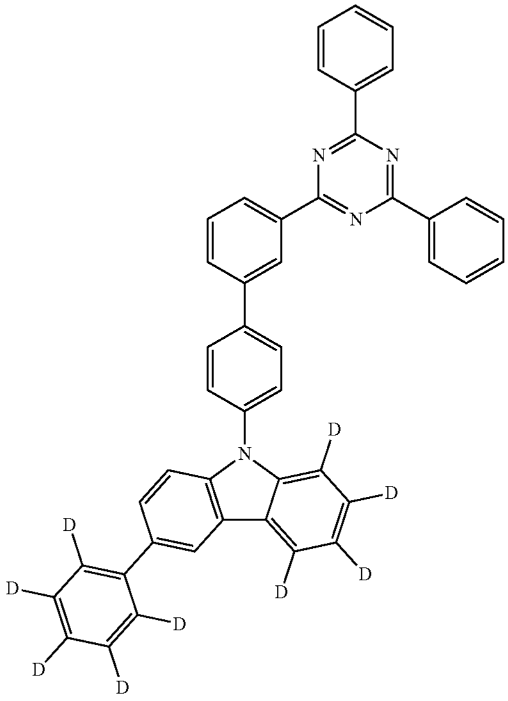 [SMILES: [2H]c1c([2H])c([2H])c(-c2ccc3c(c2)c2c([2H])c([2H])c([2H])c([2H])c2n3-c2ccc(-c3cccc(-c4nc(-c5ccccc5)nc(-c5ccccc5)n4)c3)cc2)c([2H])c1[2H]]
B61 51
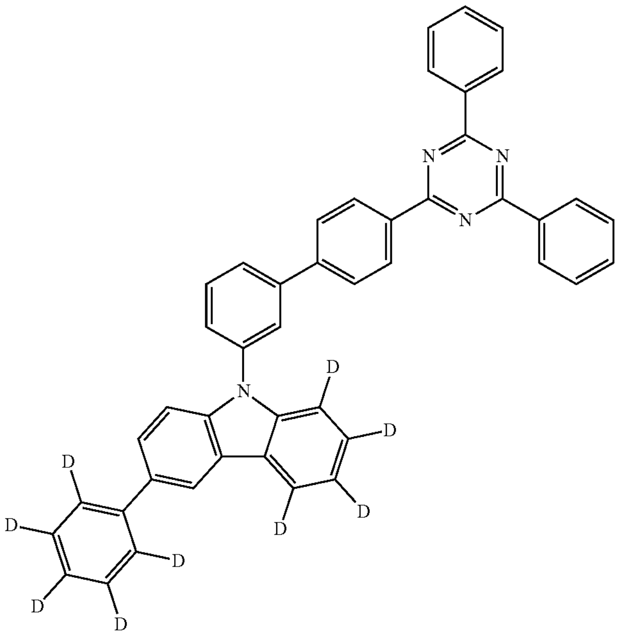 [SMILES: [2H]c1c([2H])c([2H])c(-c2ccc3c(c2)c2c([2H])c([2H])c([2H])c([2H])c2n3-c2cccc(-c3ccc(-c4nc(-c5ccccc5)nc(-c5ccccc5)n4)cc3)c2)c([2H])c1[2H]]

TABLE 4-continued
B62
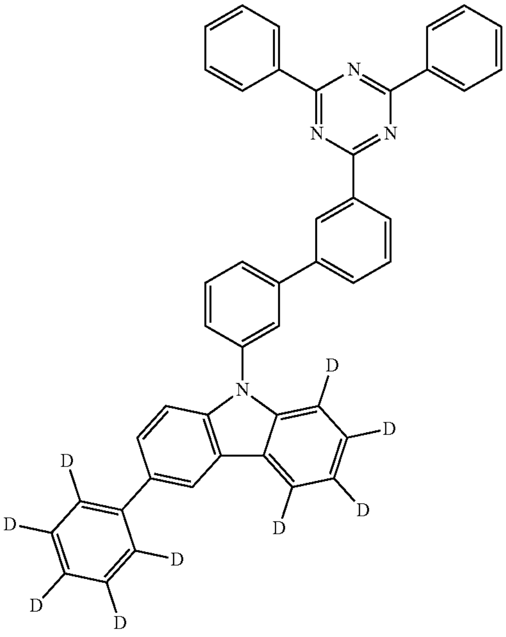 [SMILES: [2H]c1c([2H])c([2H])c(-c2ccc3c(c2)c2c([2H])c([2H])c([2H])c([2H])c2n3-c2cccc(-c3cccc(-c4nc(-c5ccccc5)nc(-c5ccccc5)n4)c3)c2)c([2H])c1[2H]]
69
B64
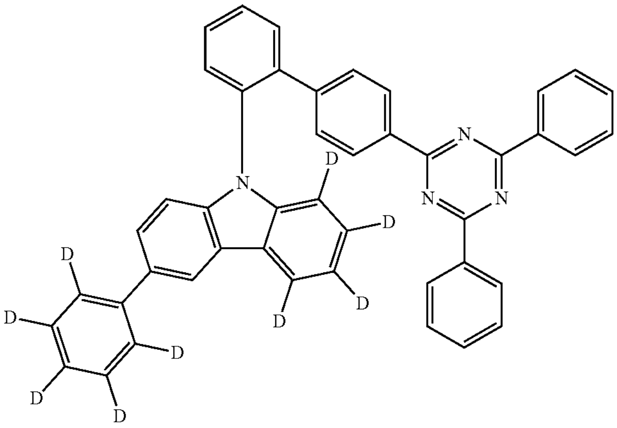 [SMILES: [2H]c1c([2H])c([2H])c(-c2ccc3c(c2)c2c([2H])c([2H])c([2H])c([2H])c2n3-c2ccccc2-c2ccc(-c3nc(-c4ccccc4)nc(-c4ccccc4)n3)cc2)c([2H])c1[2H]]
44

TABLE 4-continued
B65
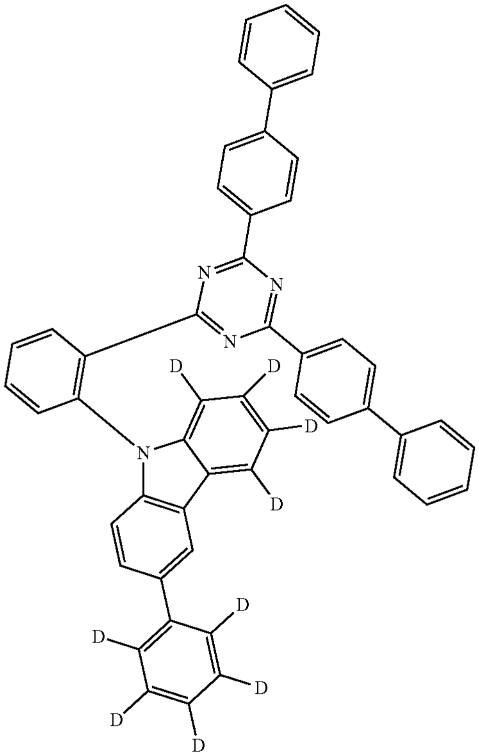 [SMILES: [2H]c1c([2H])c([2H])c(-c2ccc3c(c2)c2c([2H])c([2H])c([2H])c([2H])c2n3-c2ccccc2-c2nc(-c3ccc(-c4ccccc4)cc3)nc(-c3ccc(-c4ccccc4)cc3)n2)c([2H])c1[2H]]
36
C13
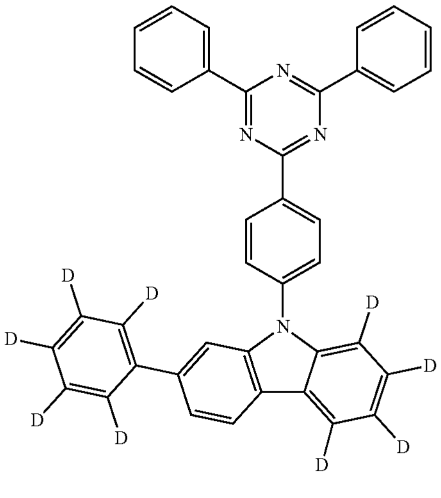 [SMILES: [2H]c1c([2H])c([2H])c(-c2ccc3c4c([2H])c([2H])c([2H])c([2H])c4n(-c4ccc(-c5nc(-c6ccccc6)nc(-c6ccccc6)n5)cc4)c3c2)c([2H])c1[2H]]
65

TABLE 4-continued
C14 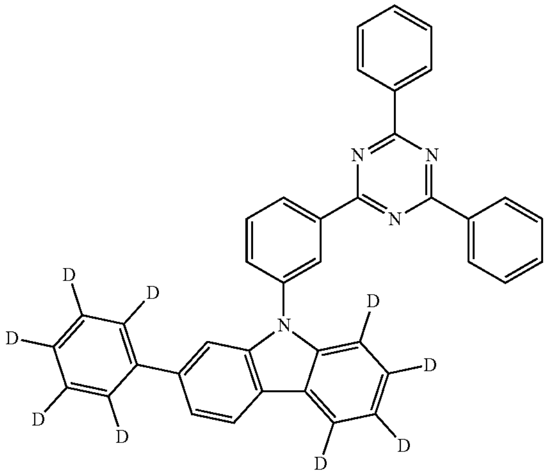 [SMILES: [2H]c1c([2H])c([2H])c(-c2ccc3c4c([2H])c([2H])c([2H])c([2H])c4n(-c4cccc(-c5nc(-c6ccccc6)nc(-c6ccccc6)n5)c4)c3c2)c([2H])c1[2H]] 58
C38 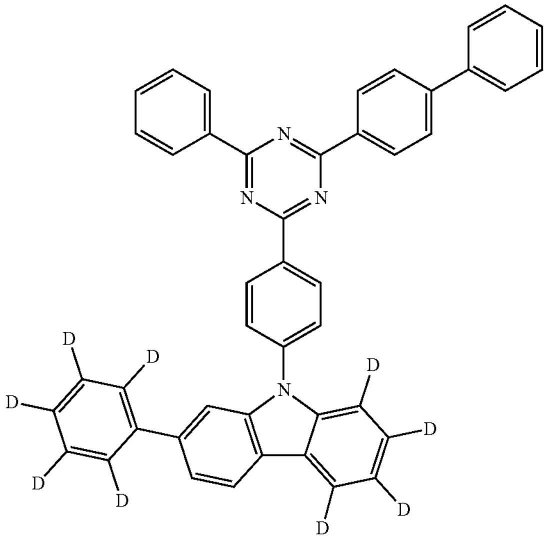 [SMILES: [2H]c1c([2H])c([2H])c(-c2ccc3c4c([2H])c([2H])c([2H])c([2H])c4n(-c4ccc(-c5nc(-c6ccccc6)nc(-c6ccc(-c7ccccc7)cc6)n5)cc4)c3c2)c([2H])c1[2H]] 75
C41 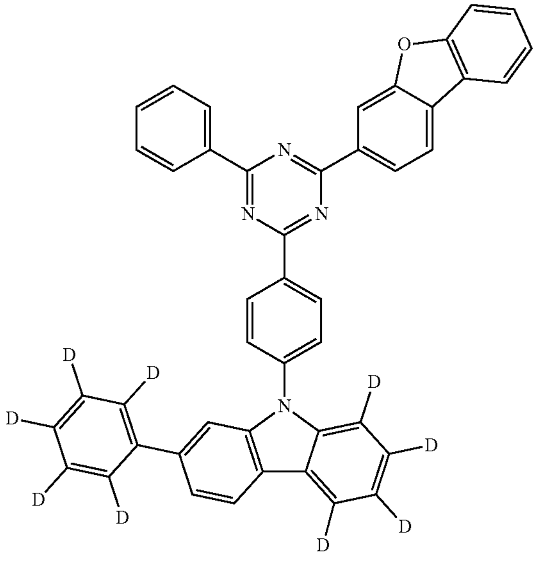 [SMILES: [2H]c1c([2H])c([2H])c(-c2ccc3c4c([2H])c([2H])c([2H])c([2H])c4n(-c4ccc(-c5nc(-c6ccccc6)nc(-c6ccc7c(c6)oc6ccccc67)n5)cc4)c3c2)c([2H])c1[2H]] 76

TABLE 4-continued
C46 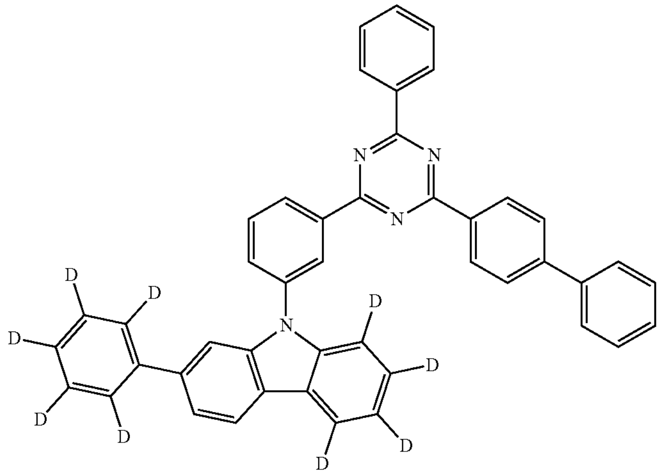 [SMILES: [2H]c1c([2H])c([2H])c(-c2ccc3c4c([2H])c([2H])c([2H])c([2H])c4n(-c4cccc(-c5nc(-c6ccccc6)nc(-c6ccc(-c7ccccc7)cc6)n5)c4)c3c2)c([2H])c1[2H]] 75
C49 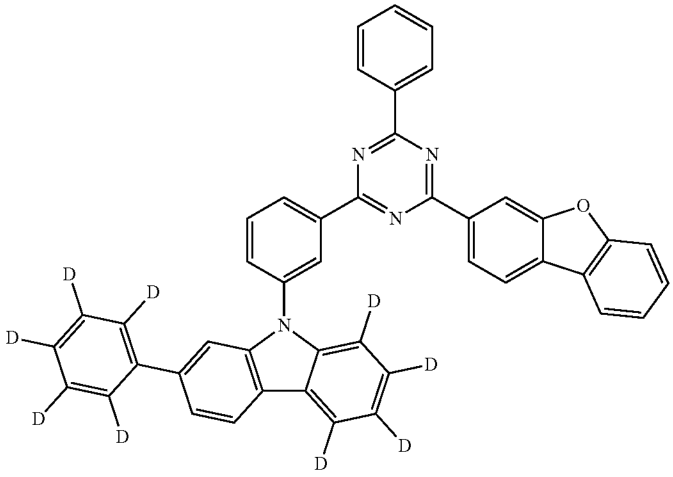 [SMILES: [2H]c1c([2H])c([2H])c(-c2ccc3c4c([2H])c([2H])c([2H])c([2H])c4n(-c4cccc(-c5nc(-c6ccccc6)nc(-c6ccc7c(c6)oc6ccccc67)n5)c4)c3c2)c([2H])c1[2H]] 59
C51 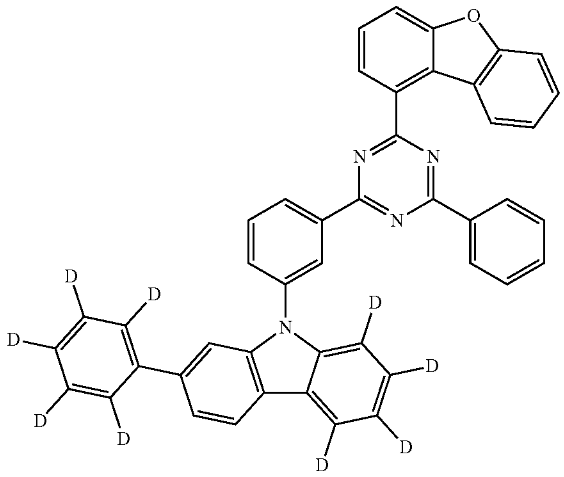 [SMILES: [2H]c1c([2H])c([2H])c(-c2ccc3c4c([2H])c([2H])c([2H])c([2H])c4n(-c4cccc(-c5nc(-c6ccccc6)nc(-c6cccc7oc8ccccc8c67)n5)c4)c3c2)c([2H])c1[2H]] 46

TABLE 4-continued
C59 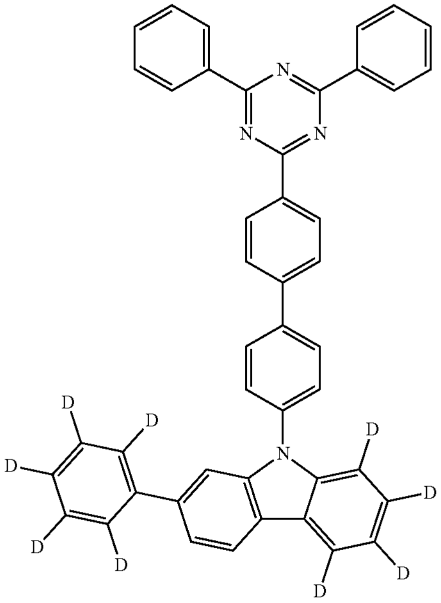 [SMILES: [2H]c1c([2H])c([2H])c(-c2ccc3c4c([2H])c([2H])c([2H])c([2H])c4n(-c4ccc(-c5ccc(-c6nc(-c7ccccc7)nc(-c7ccccc7)n6)cc5)cc4)c3c2)c([2H])c1[2H]] 65
C60 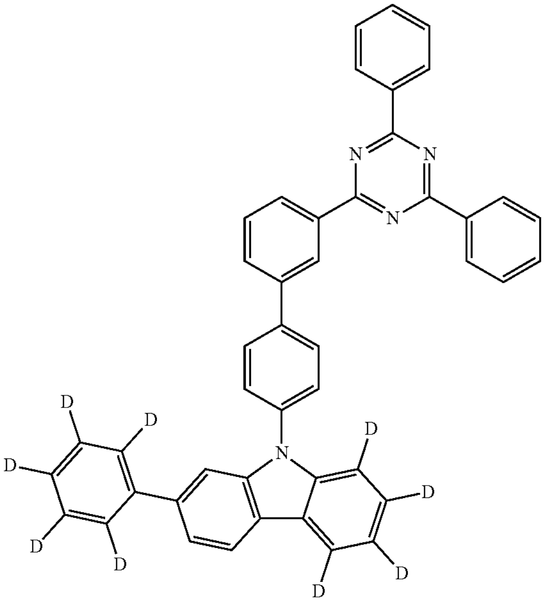 [SMILES: [2H]c1c([2H])c([2H])c(-c2ccc3c4c([2H])c([2H])c([2H])c([2H])c4n(-c4ccc(-c5cccc(-c6nc(-c7ccccc7)nc(-c7ccccc7)n6)c5)cc4)c3c2)c([2H])c1[2H]] 63

TABLE 4-continued
| | | |
|---|---|---|
| C61 | 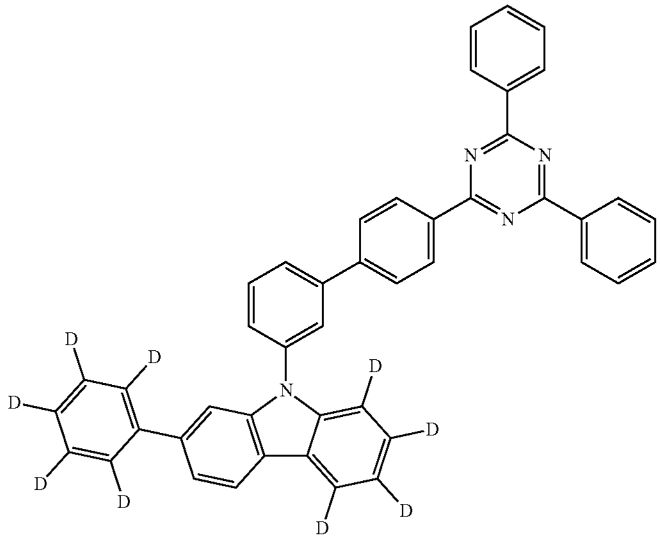 [SMILES: [2H]c1c([2H])c([2H])c(-c2ccc3c4c([2H])c([2H])c([2H])c([2H])c4n(-c4cccc(-c5ccc(-c6nc(-c7ccccc7)nc(-c7ccccc7)n6)cc5)c4)c3c2)c([2H])c1[2H]] | 76 |
| C62 | 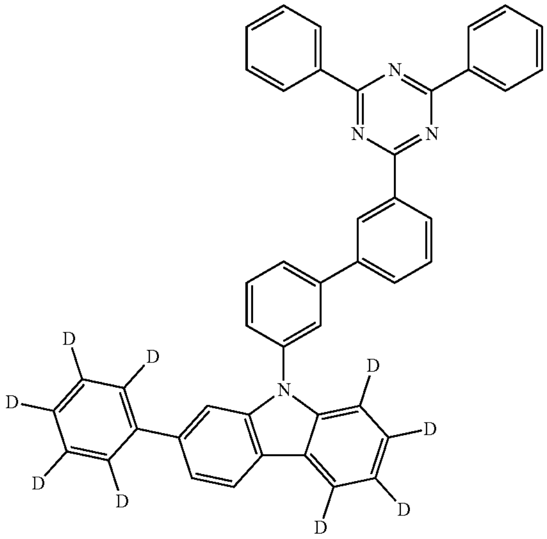 [SMILES: [2H]c1c([2H])c([2H])c(-c2ccc3c4c([2H])c([2H])c([2H])c([2H])c4n(-c4cccc(-c5cccc(-c6nc(-c7ccccc7)nc(-c7ccccc7)n6)c5)c4)c3c2)c([2H])c1[2H]] | 57 |
| C63 | 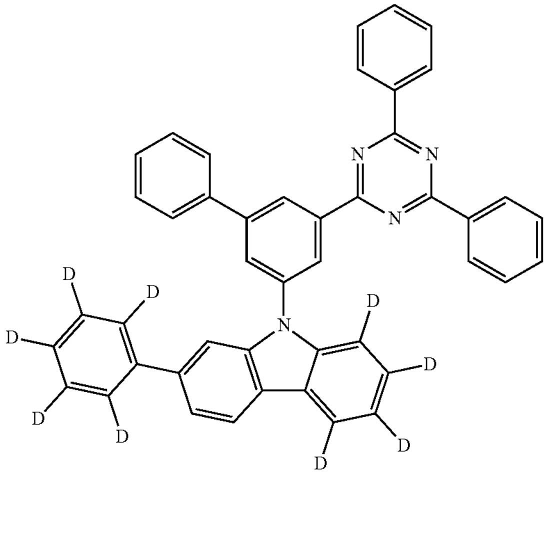 [SMILES: [2H]c1c([2H])c([2H])c(-c2ccc3c4c([2H])c([2H])c([2H])c([2H])c4n(-c4cc(-c5ccccc5)cc(-c5nc(-c6ccccc6)nc(-c6ccccc6)n5)c4)c3c2)c([2H])c1[2H]] | 68 |

TABLE 4-continued
C69 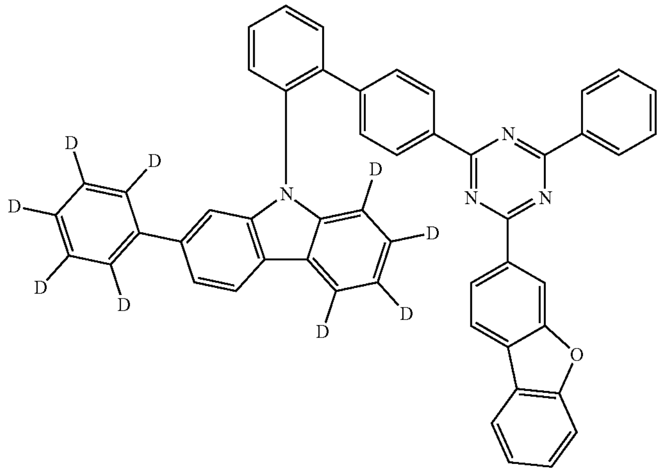 [SMILES: [2H]c1c([2H])c([2H])c(-c2ccc3c4c([2H])c([2H])c([2H])c([2H])c4n(-c4ccccc4-c4ccc(-c5nc(-c6ccccc6)nc(-c6ccc7c(c6)oc6ccccc67)n5)cc4)c3c2)c([2H])c1[2H]] 41
D37 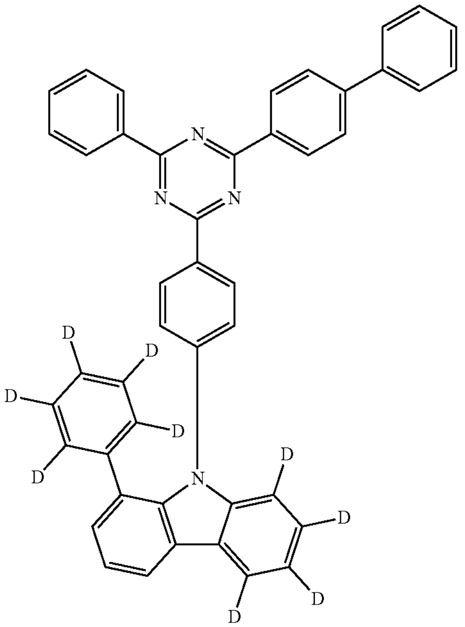 [SMILES: [2H]c1c([2H])c([2H])c(-c2cccc3c4c([2H])c([2H])c([2H])c([2H])c4n(-c4ccc(-c5nc(-c6ccccc6)nc(-c6ccc(-c7ccccc7)cc6)n5)cc4)c23)c([2H])c1[2H]] 47

TABLE 4-continued
| | | |
|---|---|---|
| D38 | 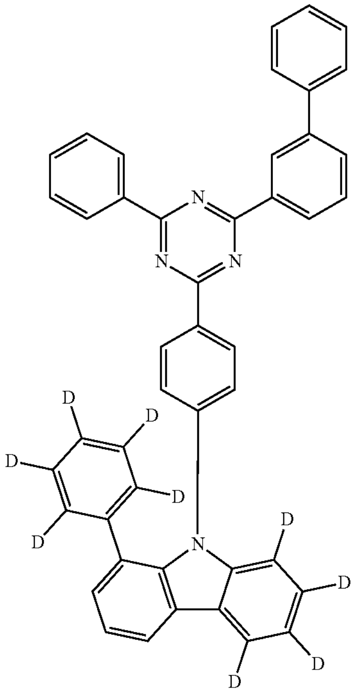 [SMILES: [2H]c1c([2H])c([2H])c(-c2cccc3c4c([2H])c([2H])c([2H])c([2H])c4n(-c4ccc(-c5nc(-c6ccccc6)nc(-c6cccc(-c7ccccc7)c6)n5)cc4)c23)c([2H])c1[2H]] | 43 |
| D39 | 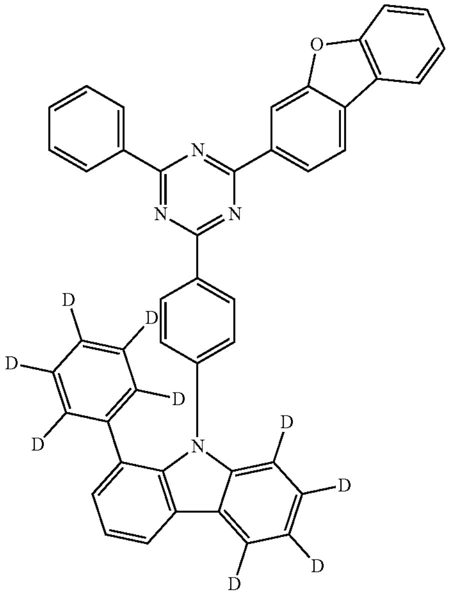 [SMILES: [2H]c1c([2H])c([2H])c(-c2cccc3c4c([2H])c([2H])c([2H])c([2H])c4n(-c4ccc(-c5nc(-c6ccccc6)nc(-c6ccc7c(c6)oc6ccccc67)n5)cc4)c23)c([2H])c1[2H]] | 46 |

TABLE 4-continued
D43 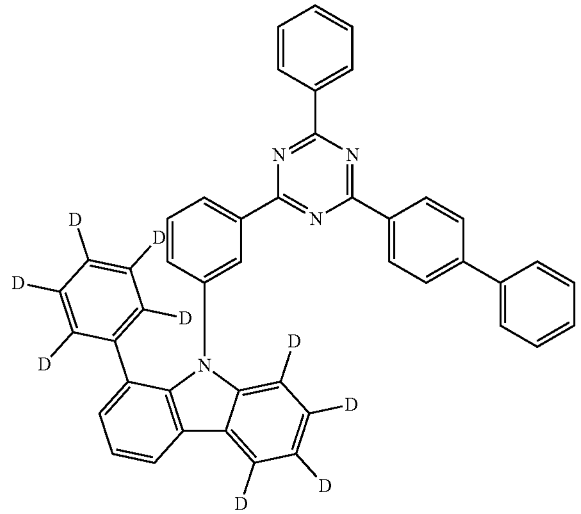 [SMILES: [2H]c1c([2H])c([2H])c(-c2cccc3c4c([2H])c([2H])c([2H])c([2H])c4n(-c4cccc(-c5nc(-c6ccccc6)nc(-c6ccc(-c7ccccc7)cc6)n5)c4)c23)c([2H])c1[2H]] 53
D45 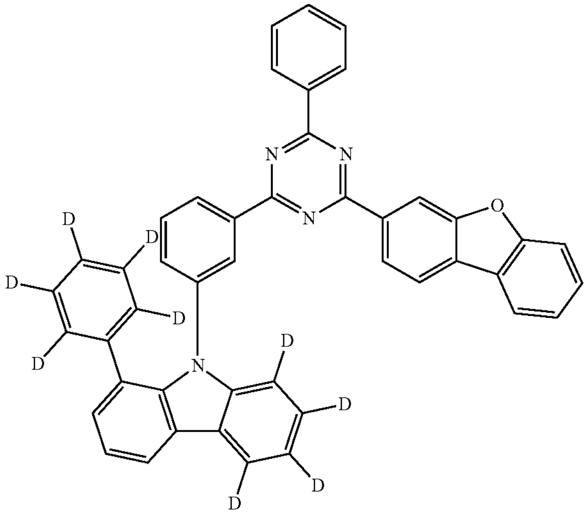 [SMILES: [2H]c1c([2H])c([2H])c(-c2cccc3c4c([2H])c([2H])c([2H])c([2H])c4n(-c4cccc(-c5nc(-c6ccccc6)nc(-c6ccc7c(c6)oc6ccccc67)n5)c4)c23)c([2H])c1[2H]] 36
D47 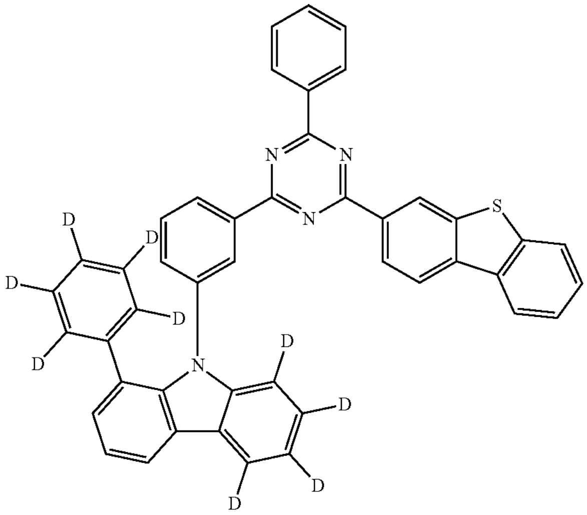 37

TABLE 4-continued
| | | |
|---|---|---|
| D54 | 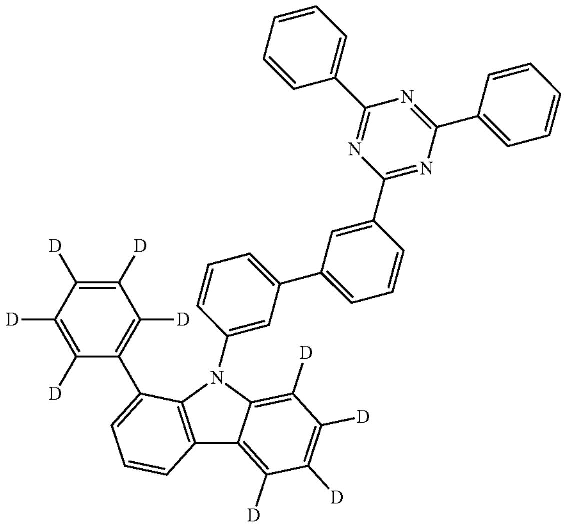 [SMILES: [2H]c1c([2H])c([2H])c(-c2cccc3c4c([2H])c([2H])c([2H])c([2H])c4n(-c4cccc(-c5cccc(-c6nc(-c7ccccc7)nc(-c7ccccc7)n6)c5)c4)c23)c([2H])c1[2H]] | 42 |
| D61 | 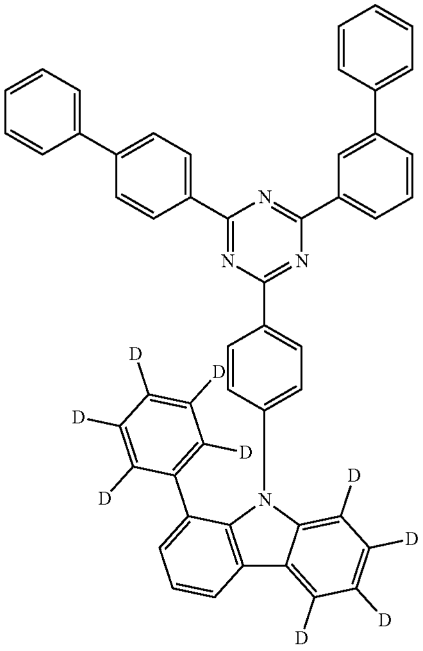 [SMILES: [2H]c1c([2H])c([2H])c(-c2cccc3c4c([2H])c([2H])c([2H])c([2H])c4n(-c4ccc(-c5nc(-c6ccc(-c7ccccc7)cc6)nc(-c6cccc(-c7ccccc7)c6)n5)cc4)c23)c([2H])c1[2H]] | 33 |

TABLE 4-continued
D63
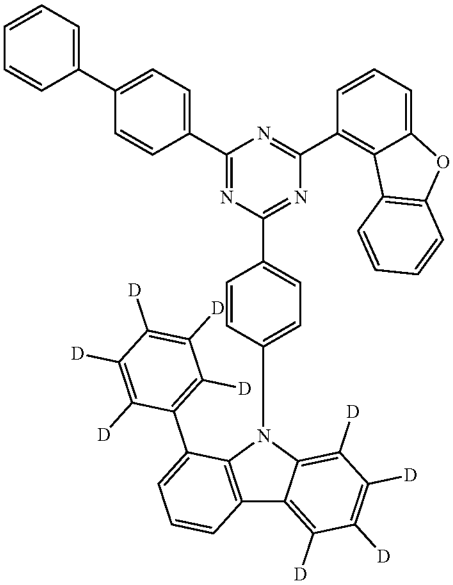 [SMILES: [2H]c1c([2H])c([2H])c(-c2cccc3c4c([2H])c([2H])c([2H])c([2H])c4n(-c4ccc(-c5nc(-c6ccc(-c7ccccc7)cc6)nc(-c6cccc7oc8ccccc8c67)n5)cc4)c23)c([2H])c1[2H]]
37
D67
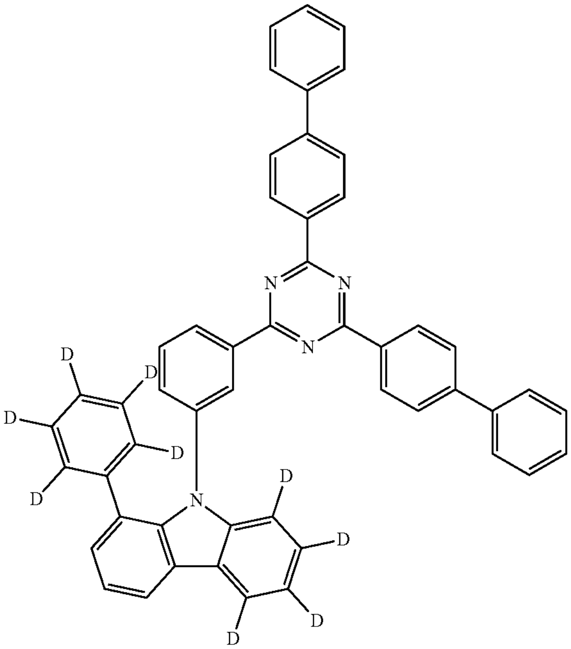 [SMILES: [2H]c1c([2H])c([2H])c(-c2cccc3c4c([2H])c([2H])c([2H])c([2H])c4n(-c4cccc(-c5nc(-c6ccc(-c7ccccc7)cc6)nc(-c6ccc(-c7ccccc7)cc6)n5)c4)c23)c([2H])c1[2H]]
38

TABLE 4-continued
D71 29
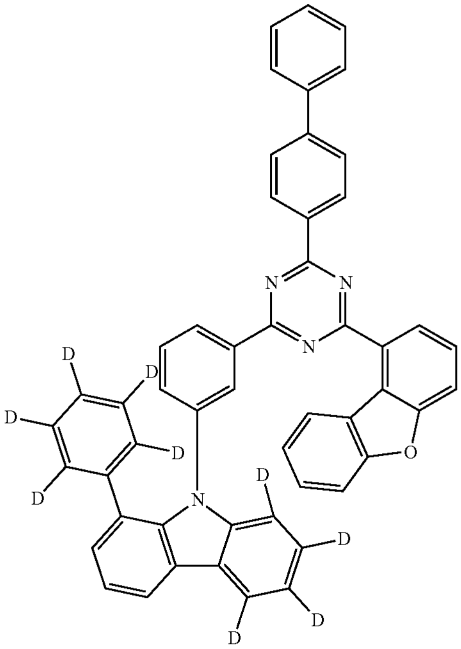 [SMILES: [2H]c1c([2H])c([2H])c(-c2cccc3c4c([2H])c([2H])c([2H])c([2H])c4n(-c4cccc(-c5nc(-c6ccc(-c7ccccc7)cc6)nc(-c6cccc7oc8ccccc8c67)n5)c4)c23)c([2H])c1[2H]]
D74 38
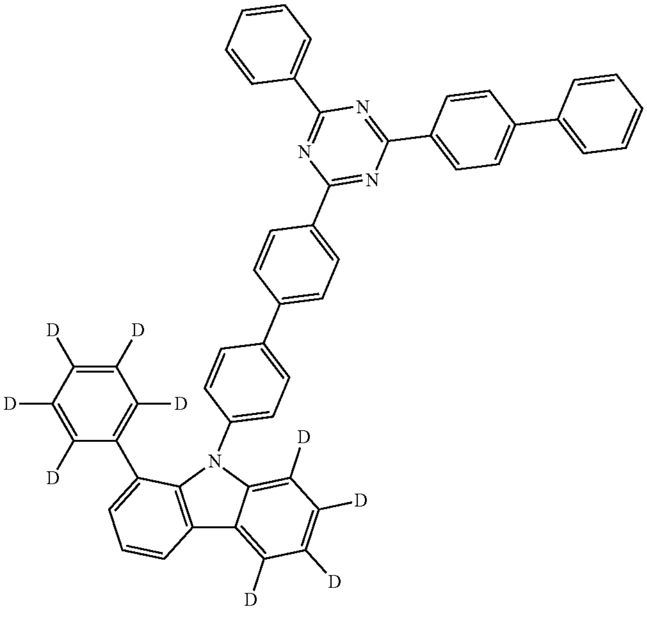 [SMILES: [2H]c1c([2H])c([2H])c(-c2cccc3c4c([2H])c([2H])c([2H])c([2H])c4n(-c4ccc(-c5ccc(-c6nc(-c7ccccc7)nc(-c7ccc(-c8ccccc8)cc7)n6)cc5)cc4)c23)c([2H])c1[2H]]

TABLE 4-continued
| | | |
|---|---|---|
| D75 | 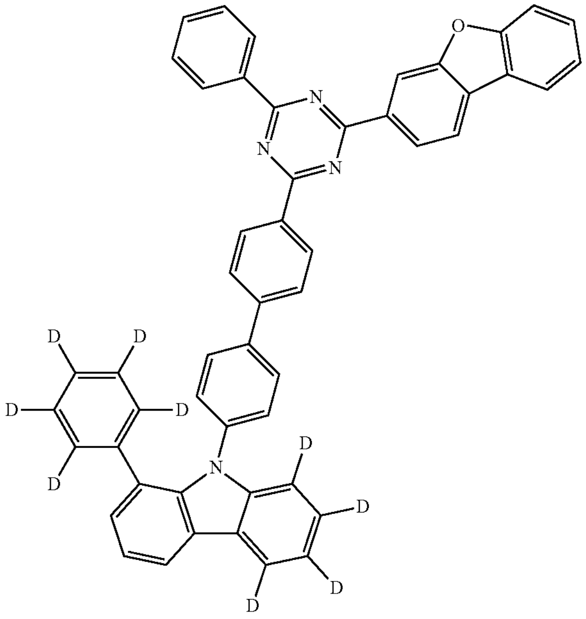 [SMILES: [2H]c1c([2H])c([2H])c(-c2cccc3c4c([2H])c([2H])c([2H])c([2H])c4n(-c4ccc(-c5ccc(-c6nc(-c7ccccc7)nc(-c7ccc8c(c7)oc7ccccc78)n6)cc5)cc4)c23)c([2H])c1[2H]] | 46 |
| D77 | 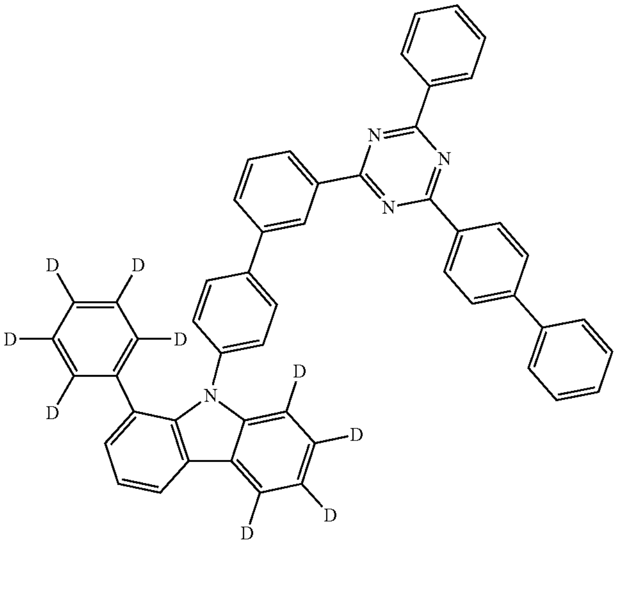 [SMILES: [2H]c1c([2H])c([2H])c(-c2cccc3c4c([2H])c([2H])c([2H])c([2H])c4n(-c4ccc(-c5cccc(-c6nc(-c7ccccc7)nc(-c7ccc(-c8ccccc8)cc7)n6)c5)cc4)c23)c([2H])c1[2H]] | 34 |

TABLE 4-continued
D79 46
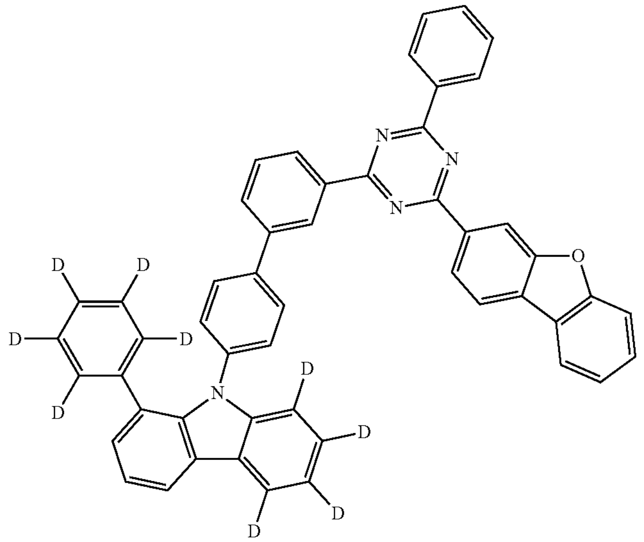 [SMILES: [2H]c1c([2H])c([2H])c(-c2cccc3c4c([2H])c([2H])c([2H])c([2H])c4n(-c4ccc(-c5cccc(-c6nc(-c7ccccc7)nc(-c7ccc8c(c7)oc7ccccc78)n6)c5)cc4)c23)c([2H])c1[2H]]
D83 52
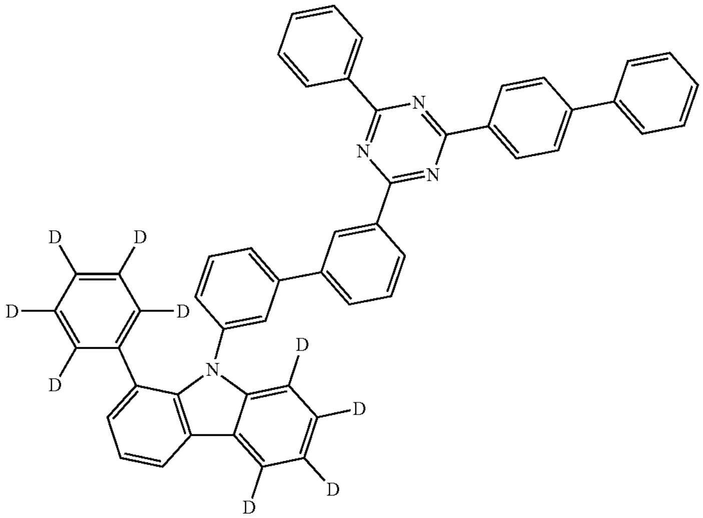 [SMILES: [2H]c1c([2H])c([2H])c(-c2cccc3c4c([2H])c([2H])c([2H])c([2H])c4n(-c4cccc(-c5cccc(-c6nc(-c7ccccc7)nc(-c7ccc(-c8ccccc8)cc7)n6)c5)c4)c23)c([2H])c1[2H]]
D84 49
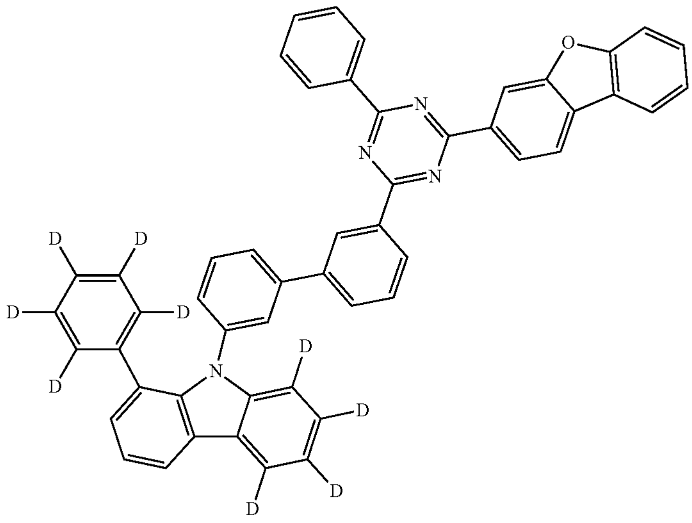 [SMILES: [2H]c1c([2H])c([2H])c(-c2cccc3c4c([2H])c([2H])c([2H])c([2H])c4n(-c4cccc(-c5cccc(-c6nc(-c7ccccc7)nc(-c7ccc8c(c7)oc7ccccc78)n6)c5)c4)c23)c([2H])c1[2H]]

TABLE 4-continued
D85 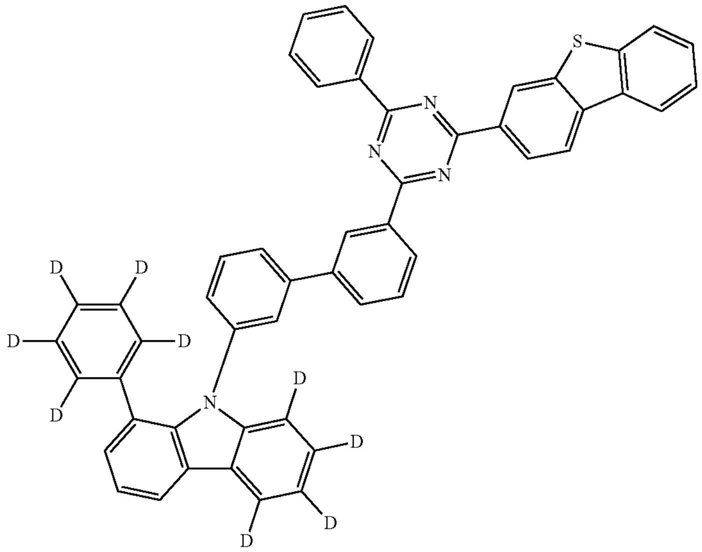 [SMILES: [2H]c1c([2H])c([2H])c(-c2cccc3c4c([2H])c([2H])c([2H])c([2H])c4n(-c4cccc(-c5cccc(-c6nc(-c7ccccc7)nc(-c7ccc8c(c7)sc7ccccc78)n6)c5)c4)c23)c([2H])c1[2H]] 38
A229 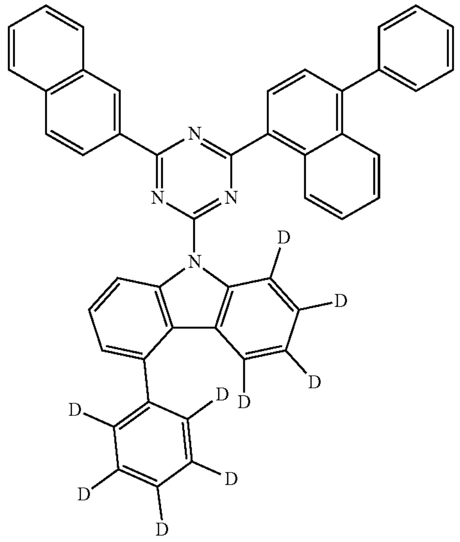 [SMILES: [2H]c1c([2H])c([2H])c(-c2cccc3c2c2c([2H])c([2H])c([2H])c([2H])c2n3-c2nc(-c3ccc4ccccc4c3)nc(-c3ccc(-c4ccccc4)c4ccccc34)n2)c([2H])c1[2H]] 41

TABLE 4-continued
A230 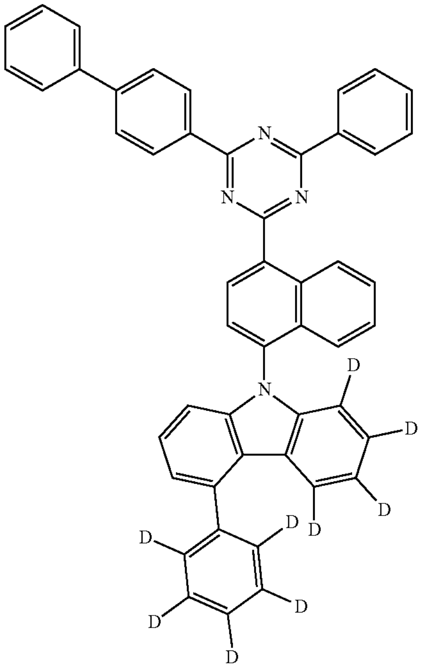 [SMILES: [2H]c1c([2H])c([2H])c(-c2cccc3c2c2c([2H])c([2H])c([2H])c([2H])c2n3-c2ccc(-c3nc(-c4ccccc4)nc(-c4ccc(-c5ccccc5)cc4)n3)c3ccccc23)c([2H])c1[2H]] 52
A231 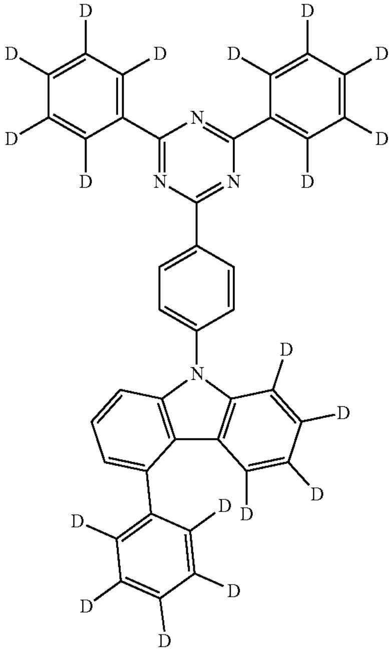 [SMILES: [2H]c1c([2H])c([2H])c(-c2nc(-c3ccc(-n4c5cccc(-c6c([2H])c([2H])c([2H])c([2H])c6[2H])c5c5c([2H])c([2H])c([2H])c([2H])c54)cc3)nc(-c3c([2H])c([2H])c([2H])c([2H])c3[2H])n2)c([2H])c1[2H]] 67

TABLE 4-continued

| | | |
|---|---|---|
| B81 | 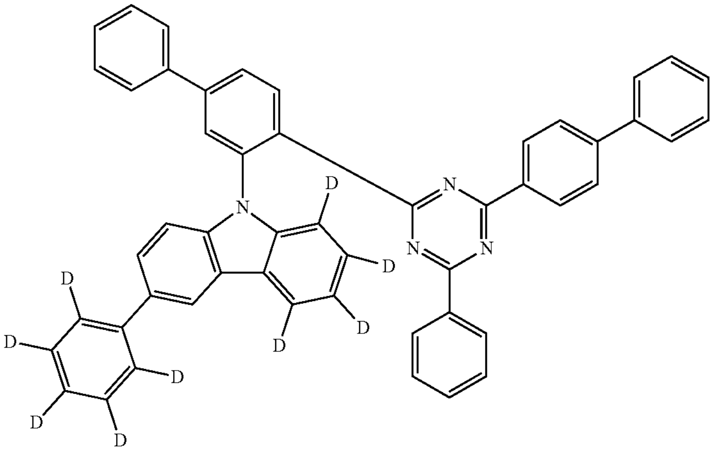 [SMILES: [2H]c1c([2H])c([2H])c(-c2ccc3c(c2)c2c([2H])c([2H])c([2H])c([2H])c2n3-c2cc(-c3ccccc3)ccc2-c2nc(-c3ccccc3)nc(-c3ccc(-c4ccccc4)cc3)n2)c([2H])c1[2H]] | 34 |

Mass spectrum data of some compounds are shown in Table 5 below:

TABLE 5

| Compound | Mass spectrum data | Compound | Mass spectrum data |
|---|---|---|---|
| Compound A5 | m/z = 574.3 (M + H)$^+$ | Compound C9 | m/z = 590.2 (M + H)$^+$ |
| Compound A9 | m/z = 590.2 (M + H)$^+$ | Compound C13 | m/z = 560.3 (M + H)$^+$ |
| Compound A16 | m/z = 636.3 (M + H)$^+$ | Compound C14 | m/z = 560.3 (M + H)$^+$ |
| Compound A17 | m/z = 636.3 (M + H)$^+$ | Compound C16 | m/z = 636.3 (M + H)$^+$ |
| Compound A20 | m/z = 650.3 (M + H)$^+$ | Compound C17 | m/z = 636.3 (M + H)$^+$ |
| Compound A22 | m/z = 650.3 (M + H)$^+$ | Compound C22 | m/z = 650.3 (M + H)$^+$ |
| Compound A24 | m/z = 650.3 (M + H)$^+$ | Compound C25 | m/z = 666.3 (M + H)$^+$ |
| Compound A45 | m/z = 636.3 (M + H)$^+$ | Compound C38 | m/z = 636.3 (M + H)$^+$ |
| Compound A47 | m/z = 650.3 (M + H)$^+$ | Compound C41 | m/z = 650.3 (M + H)$^+$ |
| Compound A51 | m/z = 666.3 (M + H)$^+$ | Compound C46 | m/z = 636.3 (M + H)$^+$ |
| Compound A55 | m/z = 636.3 (M + H)$^+$ | Compound C49 | m/z = 650.3 (M + H)$^+$ |
| Compound A57 | m/z = 650.3 (M + H)$^+$ | Compound C51 | m/z = 650.3 (M + H)$^+$ |
| Compound A60 | m/z = 650.3 (M + H)$^+$ | Compound C59 | m/z = 636.3 (M + H)$^+$ |
| Compound A68 | m/z = 636.3 (M + H)$^+$ | Compound C60 | m/z = 636.3 (M + H)$^+$ |
| Compound A69 | m/z = 636.3 (M + H)$^+$ | Compound C61 | m/z = 636.3 (M + H)$^+$ |
| Compound A71 | m/z = 636.3 (M + H)$^+$ | Compound C62 | m/z = 636.3 (M + H)$^+$ |
| Compound A72 | m/z = 636.3 (M + H)$^+$ | Compound C63 | m/z = 636.3 (M + H)$^+$ |
| Compound A81 | m/z = 726.3 (M + H)$^+$ | Compound C69 | m/z = 726.3 (M + H)$^+$ |
| Compound A97 | m/z = 712.3 (M + H)$^+$ | Compound D8 | m/z = 590.2 (M + H)$^+$ |
| Compound A104 | m/z = 742.3 (M + H)$^+$ | Compound D15 | m/z = 636.3 (M + H)$^+$ |
| Compound B2 | m/z = 560.3 (M + H)$^+$ | Compound D16 | m/z = 636.3 (M + H)$^+$ |
| Compound B5 | m/z = 574.3 (M + H)$^+$ | Compound D17 | m/z = 650.3 (M + H)$^+$ |
| Compound B7 | m/z = 574.3 (M + H)$^+$ | Compound D34 | m/z = 636.3 (M + H)$^+$ |
| Compound B9 | m/z = 590.2 (M + H)$^+$ | Compound D37 | m/z = 636.3 (M + H)$^+$ |
| Compound B13 | m/z = 560.3 (M + H)$^+$ | Compound D38 | m/z = 636.3 (M + H)$^+$ |
| Compound B14 | m/z = 560.3 (M + H)$^+$ | Compound D39 | m/z = 650.3 (M + H)$^+$ |
| Compound B16 | m/z = 636.3 (M + H)$^+$ | Compound D43 | m/z = 636.3 (M + H)$^+$ |
| Compound B18 | m/z = 636.3 (M + H)$^+$ | Compound D45 | m/z = 650.3 (M + H)$^+$ |
| Compound B23 | m/z = 650.3 (M + H)$^+$ | Compound D47 | m/z = 666.3 (M + H)$^+$ |
| Compound B36 | m/z = 636.3 (M + H)$^+$ | Compound D54 | m/z = 636.3 (M + H)$^+$ |
| Compound B37 | m/z = 636.3 (M + H)$^+$ | Compound D61 | m/z = 712.3 (M + H)$^+$ |
| Compound B40 | m/z = 650.3 (M + H)$^+$ | Compound D63 | m/z = 726.3 (M + H)$^+$ |
| Compound B46 | m/z = 636.3 (M + H)$^+$ | Compound D67 | m/z = 712.3 (M + H)$^+$ |
| Compound B49 | m/z = 650.3 (M + H)$^+$ | Compound D71 | m/z = 726.3 (M + H)$^+$ |
| Compound B59 | m/z = 636.3 (M + H)$^+$ | Compound D74 | m/z = 712.3 (M + H)$^+$ |
| Compound B60 | m/z = 636.3 (M + H)$^+$ | Compound D75 | m/z = 726.3 (M + H)$^+$ |
| Compound B61 | m/z = 636.3 (M + H)$^+$ | Compound D77 | m/z = 712.3 (M + H)$^+$ |
| Compound B62 | m/z = 636.3 (M + H)$^+$ | Compound D79 | m/z = 726.3 (M + H)$^+$ |
| Compound B64 | m/z = 636.3 (M + H)$^+$ | Compound D83 | m/z = 712.3 (M + H)$^+$ |
| Compound B65 | m/z = 712.3 (M + H)$^+$ | Compound D84 | m/z = 726.3 (M + H)$^+$ |
| Compound C2 | m/z = 560.3 (M + H)$^+$ | Compound D85 | m/z = 742.3 (M + H)$^+$ |
| Compound C5 | m/z = 574.3 (M + H)$^+$ | Compound A229 | m/z = 660.3 (M + H)$^+$ |
| Compound A230 | m/z = 686.3 (M + H)$^+$ | Compound A231 | m/z = 570.3 (M + H)$^+$ |
| Compound B81 | m/z = 712.3 (M + H)$^+$ | | |

NMR data of some compounds are shown in Table 6 below:

TABLE 6

| Compound | NMR data |
|---|---|
| Compound A47 | $^1$HNMR ($CD_2Cl_2$, 400 MHz): 9.09-9.05 (m, 3H), 8.89-8.84 (m, 3H), 8.18 (d, 1H), 8.08 (d, 1H), 7.86 (d, 2H), 7.68-7.61 (m, 4H), 7.57-7.54 (m, 2H), 7.48 (t, 1H), 7.42 (t, 1H), 7.17 (d, 1H). |
| Compound B61 | $^1$HNMR ($CD_2Cl_2$, 400 MHz): 8.87 (d, 2H), 8.79-8.77 (m, 4H), 8.39 (s, 1H), 7.97 (s, 1H), 7.90 (d, 2H), 7.86 (d, 1H), 7.77 (t, 1H), 7.70 (d, 1H), 7.67-7.56 (m, 8H). |
| Compound C2 | $^1$HNMR ($CD_2Cl_2$, 400 MHz): 9.65 (s, 1H), 8.85 (d, 2H), 8.80 (d, 2H), 8.15 (d, 1H), 7.86 (d, 2H), 7.75-7.72 (m, 3H), 7.70-7.61 (m, 3H), 7.51 (t, 2H), 7.42 (t, 1H). |

Manufacture and Performance Evaluation of Organic Electroluminescent Devices

Example 1

Green Organic Electroluminescent Device

An anode was pretreated by the following process: surface treatment was performed with UV ozone and $O_2$:$N_2$ plasma on an ITO/Ag/ITO substrate with a thickness of 110 Å, 1100 Å, and 100 Å to increase the work function of the anode, and the surface of the ITO substrate was washed with an organic solvent to remove impurities and oil stains from the surface of the ITO substrate.

CuPC and HT-01 were co-evaporated on an experimental substrate (the anode) at an evaporation rate ratio of 2%: 98% to form a hole injection layer (HIL) with a thickness of 110 Å, and then HT-01 was vacuum-evaporated on the hole injection layer to form a hole transport layer with a thickness of 1230 Å.

HT-02 was evaporated on the hole transport layer to form a hole auxiliary layer with a thickness of 360 Å.

A composition GH-1-1 and Ir(ppy)$_3$ were co-evaporated on the hole auxiliary layer at an evaporation rate ratio of 100%: 10% to form an organic light-emitting layer (a green organic light-emitting layer) with a thickness of 300 Å.

ET-01 and LiQ were mixed in a weight ratio of 1:1 and evaporated to form an electron transport layer having a thickness of 340 Å, Yb was evaporated on the electron transport layer to form an electron injection layer with a thickness of 15 Å, and magnesium and silver were co-evaporated on the electron injection layer at an evaporation ratio of 1:9 to form a cathode with a thickness of 120 Å.

In addition, CP-01 was evaporated on the above cathode to form an organic capping layer (CPL) with a thickness of 700 Å, thus realizing the manufacture of an organic light-emitting device.

Examples 2 to 84

When the organic light-emitting layer was formed, by using a host material composition GH—X-Y shown in Table 7 instead of the composition GH-1-1 in Example 1, an organic electroluminescent device was manufactured by the same method as that in Example 1.

Comparative Examples 1 to 6

An organic electroluminescent device was manufactured by the same method as that in Device Example 1 except that GH—X-Y was used when the organic light-emitting layer was formed.

In the above Examples and Comparative examples, the host material composition GH—X-Y used was obtained by mixing a first compound shown in Table 7 below with a second compound shown in Table 7 below, with a specific composition shown in Table 7. A mass ratio refers to a ratio of the mass percent content of the first compound to the mass percent content of the second compound shown in the table. Taking the composition GH-1-1 as an example, it can be seen with reference to Table 7 that GH-1-1 was formed by mixing the compound A5 with a compound 49 in a mass ratio of 40:60; and for another example, a host material GH-D1-1 in Comparative example 1 was formed by mixing a compound I with a compound 5 in a mass ratio of 40:60.

The second compound employed is shown below, and according to the description of a patent document JP3139321B2, Compound 5 was obtained; according to a patent document CN103518271B, Compound 12 was obtained; according to a patent document U.S. Pat. No. 9,564,595B2, Compound 35 was obtained; according to the description of a patent document CN104205393B, Compound 36 was obtained; and according to the description of a patent document KR1020220013910A, Compound 49 was obtained.

5

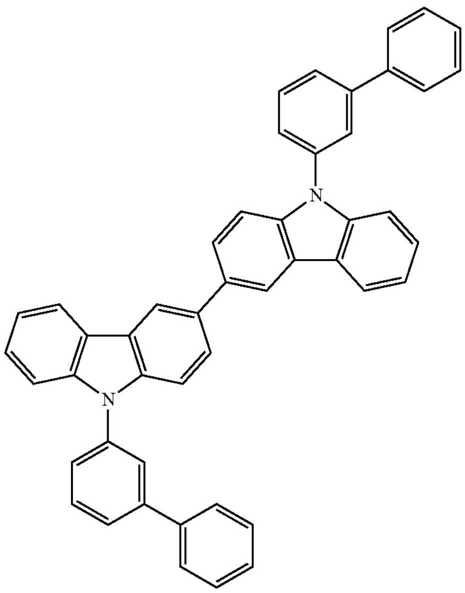

CAS:1353040-89-1

-continued
12
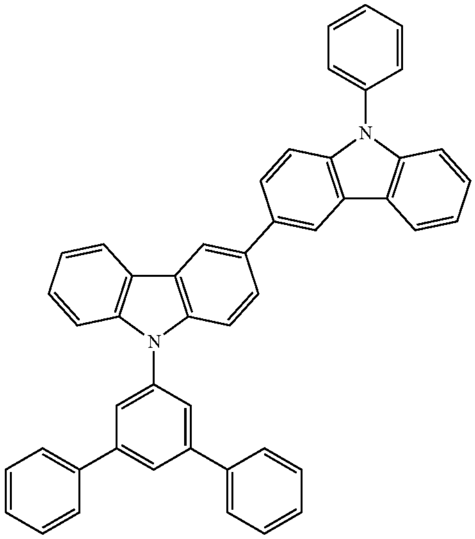
CAS:1410876-33-3
35
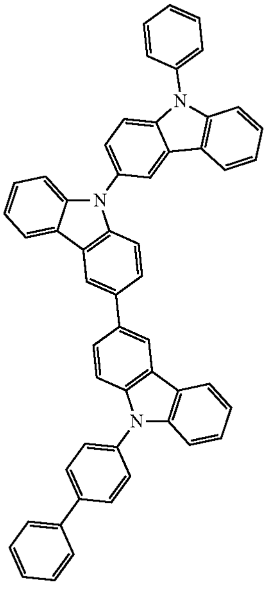
CAS:1643479-54-2
-continued
36
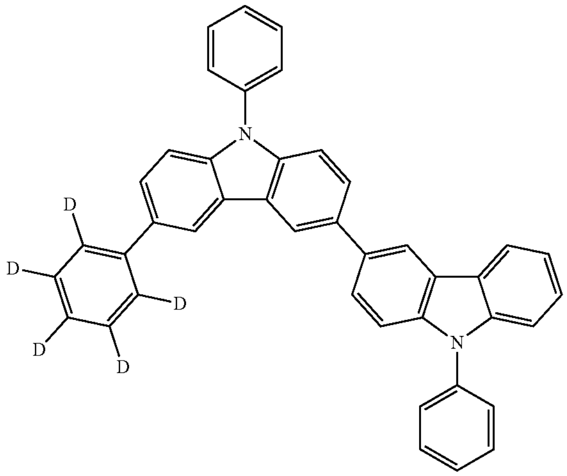
CAS:2763236-01-5
49
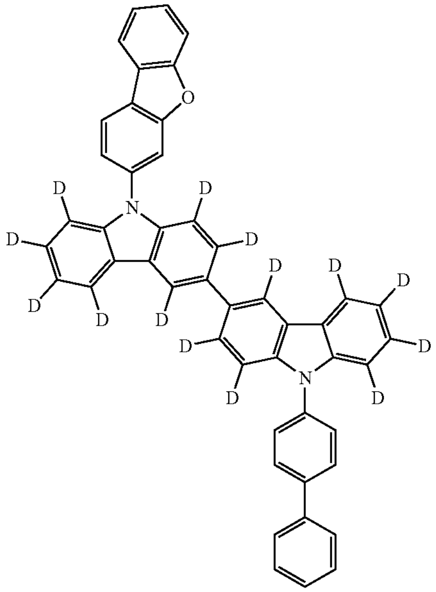
CAS:2760403-16-3
Structural formulas of other main materials employed in Examples 1 to 83 and Comparative examples 1 to 6 are shown below:
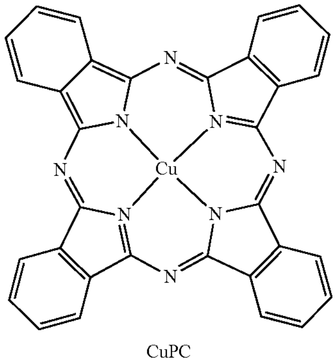
CuPC -continued
HT-01
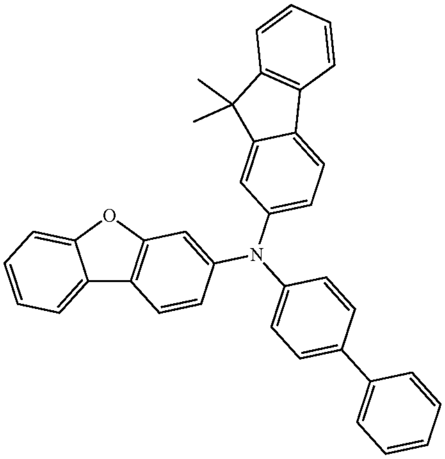
HT-02
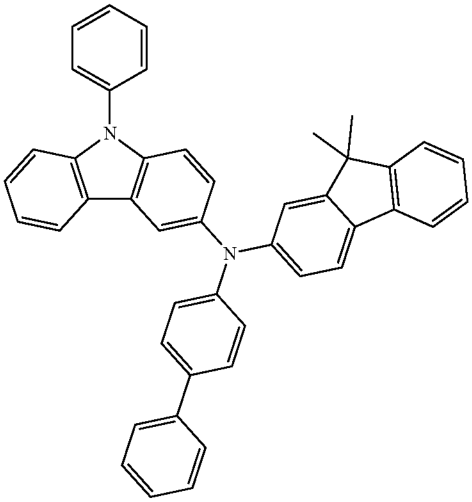
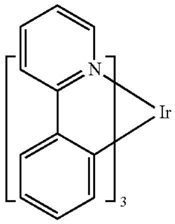
$Ir(ppy)_3$
-continued
ET-01
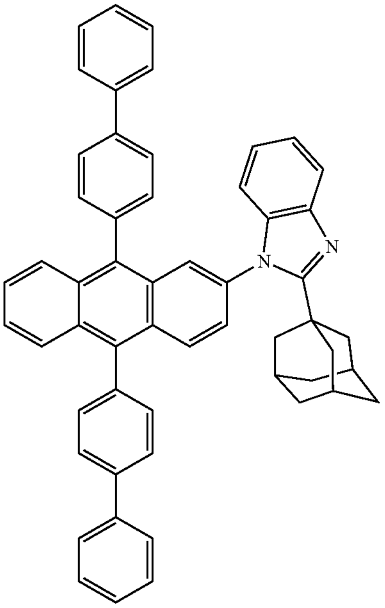
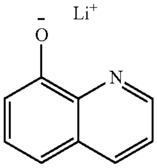
LiQ
CP-01
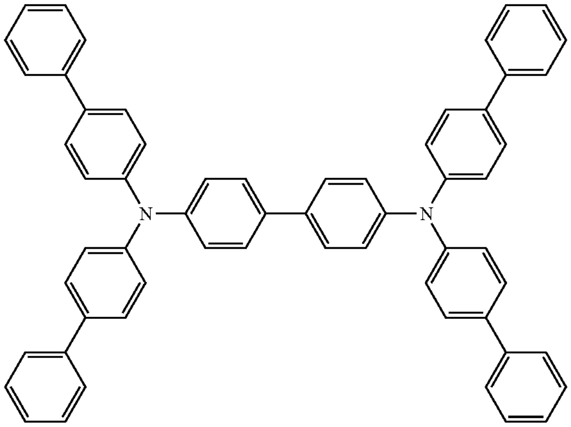
Compound I
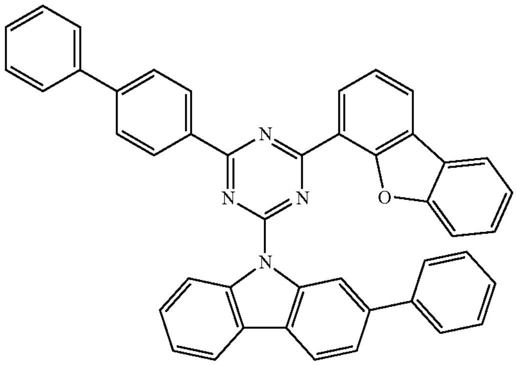

-continued

Compound II

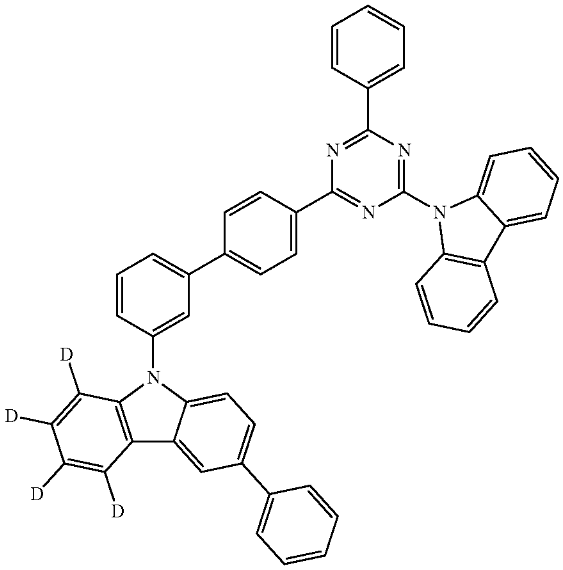

Compound III

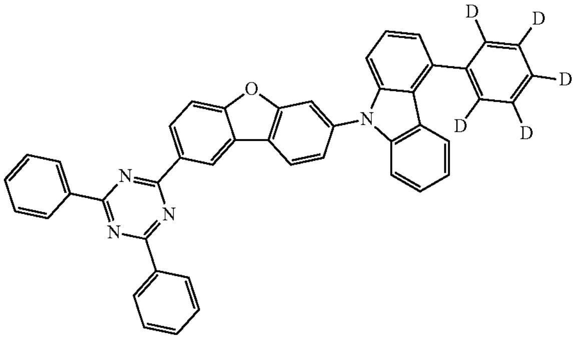

-continued

Compound IV

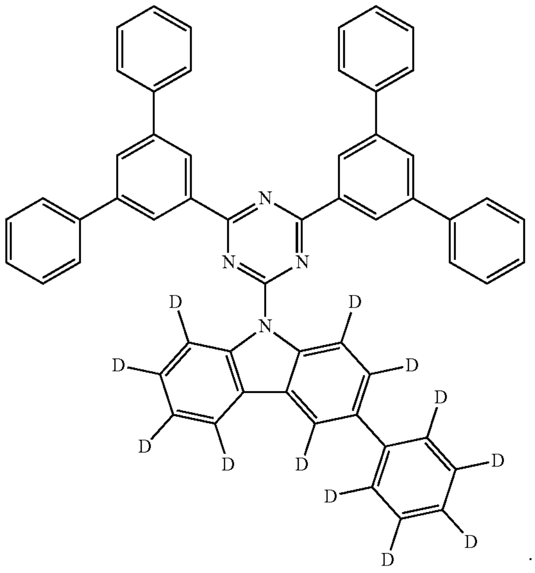

As for the organic electroluminescent devices manufactured above, the current-voltage-luminance (IVL) of the devices was specifically tested under the condition of 10 $mA/cm^2$, and the T95 device service life was tested under the condition of 20 $mA/cm^2$, and the test results are shown in Table 7.

TABLE 7

| Example No. | Composition GH-X-Y: First compound | Composition GH-X-Y: Second compound | Composition GH-X-Y: Mass ratio of first compound to second compound | Driving voltage (V) | Luminous efficiency (Cd/A) | Chromaticity coordinate CIEx, CIEy | External quantum efficiency EQE (%) | T95 (h) @20 $mA/cm^2$ |
|---|---|---|---|---|---|---|---|---|
| Example 1 | GH-1-1 | | | 3.77 | 130.63 | 0.22, 0.73 | 31.35 | 389 |
| | Compound A5 | Compound 49 | 40:60 | | | | | |
| Example 2 | GH-2-1 | | | 3.78 | 130.92 | 0.22, 0.73 | 31.44 | 380 |
| | Compound A9 | Compound 5 | 40:60 | | | | | |
| Example 3 | GH-3-1 | | | 3.73 | 131.92 | 0.22, 0.73 | 31.62 | 388 |
| | Compound A16 | Compound 36 | 40:60 | | | | | |
| Example 4 | GH-4-1 | | | 3.72 | 126.20 | 0.22, 0.73 | 30.32 | 379 |
| | Compound A17 | Compound 35 | 40:60 | | | | | |
| Example 5 | GH-5-1 | | | 3.74 | 126.50 | 0.22, 0.73 | 30.40 | 384 |
| | Compound A22 | Compound 5 | 40:60 | | | | | |

TABLE 7-continued

| Example No. | Composition GH-X-Y First compound | Second compound | Mass ratio of first compound to second compound | Driving voltage (V) | Luminous efficiency (Cd/A) | Chromaticity coordinate CIEx, CIEy | External quantum efficiency EQE (%) | T95 (h) @20 mA/cm$^2$ |
|---|---|---|---|---|---|---|---|---|
| Example 6 | GH-6-1 | | | 3.73 | 128.20 | 0.22, 0.73 | 30.80 | 385 |
| | Compound A24 | Compound 35 | 40:60 | | | | | |
| Example 7 | GH-7-1 | | | 3.75 | 129.22 | 0.22, 0.73 | 31.04 | 387 |
| | Compound A46 | Compound 36 | 40:60 | | | | | |
| Example 8 | GH-8-1 | | | 3.78 | 129.80 | 0.22, 0.73 | 31.20 | 386 |
| | Compound A47 | Compound 49 | 40:60 | | | | | |
| Example 9 | GH-9-1 | | | 3.74 | 130.00 | 0.22, 0.73 | 31.24 | 381 |
| | Compound A51 | Compound 5 | 40:60 | | | | | |
| Example 10 | GH-10-1 | | | 3.77 | 131.40 | 0.22, 0.73 | 31.57 | 382 |
| | Compound A55 | Compound 35 | 40:60 | | | | | |
| Example 11 | GH-11-1 | | | 3.77 | 130.05 | 0.22, 0.73 | 31.26 | 389 |
| | Compound A57 | Compound 36 | 40:60 | | | | | |
| Example 12 | GH-12-1 | | | 3.72 | 126.40 | 0.22, 0.73 | 30.36 | 388 |
| | Compound A60 | Compound 49 | 40:60 | | | | | |
| Example 13 | GH-13-1 | | | 3.73 | 127.20 | 0.22, 0.73 | 30.50 | 379 |
| | Compound A68 | Compound 35 | 40:60 | | | | | |
| Example 14 | GH-14-1 | | | 3.71 | 130.40 | 0.22, 0.73 | 31.32 | 378 |
| | Compound A69 | Compound 49 | 40:60 | | | | | |
| Example 15 | GH-15-1 | | | 3.75 | 130.10 | 0.22, 0.73 | 31.27 | 381 |
| | Compound A71 | Compound 49 | 40:60 | | | | | |
| Example 16 | GH-16-1 | | | 3.71 | 130.84 | 0.22, 0.73 | 31.42 | 387 |
| | Compound A97 | Compound 36 | 40:60 | | | | | |
| Example 17 | GH-17-1 | | | 3.76 | 126.12 | 0.22, 0.73 | 30.29 | 388 |
| | Compound A104 | Compound 36 | 40:60 | | | | | |
| Example 18 | GH-18-1 | | | 3.78 | 130.24 | 0.22, 0.73 | 31.28 | 378 |
| | Compound B2 | Compound 5 | 40:60 | | | | | |
| Example 19 | GH-19-1 | | | 3.75 | 130.80 | 0.22, 0.73 | 31.40 | 388 |
| | Compound B5 | Compound 49 | 40:60 | | | | | |
| Example 20 | GH-20-1 | | | 3.74 | 128.04 | 0.22, 0.73 | 30.75 | 386 |
| | Compound B7 | Compound 35 | 40:60 | | | | | |
| Example 21 | GH-21-1 | | | 3.75 | 129.54 | 0.22, 0.73 | 31.11 | 389 |
| | Compound B9 | Compound 36 | 40:60 | | | | | |
| Example 22 | GH-22-1 | | | 3.75 | 127.40 | 0.22, 0.73 | 30.59 | 389 |
| | Compound B13 | Compound 49 | 40:60 | | | | | |
| Example 23 | GH-23-1 | | | 3.77 | 131.00 | 0.22, 0.73 | 31.45 | 379 |
| | Compound B14 | Compound 36 | 40:60 | | | | | |

TABLE 7-continued

| Example No. | Composition GH-X-Y First compound | Second compound | Mass ratio of first compound to second compound | Driving voltage (V) | Luminous efficiency (Cd/A) | Chromaticity coordinate CIEx, CIEy | External quantum efficiency EQE (%) | T95 (h) @20 mA/$cm^2$ |
|---|---|---|---|---|---|---|---|---|
| Example 24 | GH-24-1 | | | 3.78 | 127.60 | 0.22, 0.73 | 30.61 | 382 |
| | Compound B16 | Compound 35 | 40:60 | | | | | |
| Example 25 | GH-25-1 | | | 3.71 | 125.80 | 0.22, 0.73 | 30.22 | 386 |
| | Compound B18 | Compound 5 | 40:60 | | | | | |
| Example 26 | GH-26-1 | | | 3.76 | 127.84 | 0.22, 0.73 | 30.71 | 381 |
| | Compound B23 | Compound 5 | 40:60 | | | | | |
| Example 27 | GH-27-1 | | | 3.77 | 128.80 | 0.22, 0.73 | 30.90 | 379 |
| | Compound B36 | Compound 5 | 40:60 | | | | | |
| Example 28 | GH-28-1 | | | 3.73 | 126.14 | 0.22, 0.73 | 30.28 | 383 |
| | Compound B37 | Compound 36 | 40:60 | | | | | |
| Example 29 | GH-29-1 | | | 3.78 | 125.70 | 0.22, 0.73 | 30.20 | 386 |
| | Compound B40 | Compound 12 | 40:60 | | | | | |
| Example 30 | GH-30-1 | | | 3.74 | 131.14 | 0.22, 0.73 | 31.51 | 388 |
| | Compound B46 | Compound 36 | 40:60 | | | | | |
| Example 31 | GH-31-1 | | | 3.78 | 129.50 | 0.22, 0.73 | 31.10 | 378 |
| | Compound B49 | Compound 35 | 40:60 | | | | | |
| Example 32 | GH-32-1 | | | 3.72 | 130.72 | 0.22, 0.73 | 31.41 | 378 |
| | Compound B59 | Compound 12 | 40:60 | | | | | |
| Example 33 | GH-33-1 | | | 3.73 | 130.90 | 0.22, 0.73 | 31.43 | 381 |
| | Compound B60 | Compound 49 | 40:60 | | | | | |
| Example 34 | GH-34-1 | | | 3.71 | 131.10 | 0.22, 0.73 | 31.50 | 379 |
| | Compound B61 | Compound 12 | 40:60 | | | | | |
| Example 35 | GH-35-1 | | | 3.77 | 130.20 | 0.22, 0.73 | 31.29 | 383 |
| | Compound B62 | Compound 5 | 40:60 | | | | | |
| Example 36 | GH-36-1 | | | 3.71 | 125.03 | 0.22, 0.73 | 30.01 | 384 |
| | Compound B64 | Compound 35 | 40:60 | | | | | |
| Example 37 | GH-37-1 | | | 3.76 | 127.30 | 0.22, 0.73 | 30.60 | 389 |
| | Compound B65 | Compound 36 | 40:60 | | | | | |
| Example 38 | GH-38-1 | | | 3.77 | 130.67 | 0.22, 0.73 | 31.38 | 359 |
| | Compound C9 | Compound 49 | 40:60 | | | | | |
| Example 39 | GH-39-1 | | | 3.77 | 130.30 | 0.22, 0.73 | 31.30 | 355 |
| | Compound C13 | Compound 12 | 40:60 | | | | | |
| Example 40 | GH-40-1 | | | 3.76 | 126.23 | 0.22, 0.73 | 30.34 | 351 |
| | Compound C14 | Compound 5 | 40:60 | | | | | |
| Example 41 | GH-41-1 | | | 3.78 | 128.10 | 0.22, 0.73 | 30.70 | 341 |
| | Compound C16 | Compound 5 | 40:60 | | | | | |

TABLE 7-continued

| Example No. | Composition GH-X-Y: First compound | Composition GH-X-Y: Second compound | Composition GH-X-Y: Mass ratio of first compound to second compound | Driving voltage (V) | Luminous efficiency (Cd/A) | Chromaticity coordinate CIEx, CIEy | External quantum efficiency EQE (%) | T95 (h) @20 mA/cm$^2$ |
|---|---|---|---|---|---|---|---|---|
| Example 42 | | GH-42-1 | | 3.76 | 125.50 | 0.22, 0.73 | 30.17 | 356 |
| | Compound C17 | Compound 35 | 40:60 | | | | | |
| Example 43 | | GH-43-1 | | 3.76 | 129.60 | 0.22, 0.73 | 31.12 | 354 |
| | Compound C22 | Compound 12 | 40:60 | | | | | |
| Example 44 | | GH-44-1 | | 3.72 | 125.39 | 0.22, 0.73 | 30.08 | 359 |
| | Compound C25 | Compound 49 | 40:60 | | | | | |
| Example 45 | GH-45-1 | | | 3.78 | 128.40 | 0.22, 0.73 | 30.80 | 360 |
| | Compound C38 | Compound 36 | 40:60 | | | | | |
| Example 46 | | GH-46-1 | | 3.76 | 125.00 | 0.22, 0.73 | 29.98 | 344 |
| | Compound C41 | Compound 5 | 40:60 | | | | | |
| Example 47 | | GH-47-1 | | 3.78 | 131.77 | 0.22, 0.73 | 31.59 | 342 |
| | Compound C46 | Compound 12 | 40:60 | | | | | |
| Example 48 | | GH-48-1 | | 3.78 | 131.80 | 0.22, 0.73 | 31.60 | 358 |
| | Compound C49 | Compound 35 | 40:60 | | | | | |
| Example 49 | | GH-49-1 | | 3.75 | 129.30 | 0.22, 0.73 | 31.02 | 359 |
| | Compound C51 | Compound 36 | 40:60 | | | | | |
| Example 50 | | GH-50-1 | | 3.73 | 128.33 | 0.22, 0.73 | 30.82 | 357 |
| | Compound C59 | Compound 49 | 40:60 | | | | | |
| Example 51 | | GH-51-1 | | 3.73 | 129.20 | 0.22, 0.73 | 31.00 | 347 |
| | Compound C60 | Compound 35 | 40:60 | | | | | |
| Example 52 | | GH-52-1 | | 3.72 | 127.78 | 0.22, 0.73 | 30.69 | 342 |
| | Compound C61 | Compound 12 | 40:60 | | | | | |
| Example 53 | | GH-53-1 | | 3.75 | 131.30 | 0.22, 0.73 | 31.54 | 358 |
| | Compound C62 | Compound 5 | 40:60 | | | | | |
| Example 54 | | GH-54-1 | | 3.76 | 130.38 | 0.22, 0.73 | 31.31 | 360 |
| | Compound C63 | Compound 36 | 40:60 | | | | | |
| Example 55 | | GH-55-1 | | 3.73 | 128.30 | 0.22, 0.73 | 30.80 | 352 |
| | Compound C69 | Compound 49 | 40:60 | | | | | |
| Example 56 | | GH-56-1 | | 3.73 | 126.21 | 0.22, 0.73 | 30.31 | 351 |
| | Compound D8 | Compound 12 | 40:60 | | | | | |
| Example 57 | | GH-57-1 | | 3.73 | 125.40 | 0.22, 0.73 | 30.14 | 360 |
| | Compound D15 | Compound 36 | 40:60 | | | | | |
| Example 58 | | GH-58-1 | | 3.74 | 128.00 | 0.22, 0.73 | 30.67 | 347 |
| | Compound D16 | Compound 5 | 40:60 | | | | | |
| Example 59 | | GH-59-1 | | 3.75 | 126.13 | 0.22, 0.73 | 30.30 | 349 |
| | Compound D17 | Compound 12 | 40:60 | | | | | |

TABLE 7-continued

| Example No. | Composition GH-X-Y First compound | Second compound | Mass ratio of first compound to second compound | Driving voltage (V) | Luminous efficiency (Cd/A) | Chromaticity coordinate CIEx, CIEy | External quantum efficiency EQE (%) | T95 (h) @20 mA/cm$^2$ |
|---|---|---|---|---|---|---|---|---|
| Example 60 | GH-60-1 | | | 3.73 | 131.90 | 0.22, 0.73 | 31.61 | 349 |
| | Compound D34 | Compound 35 | 40:60 | | | | | |
| Example 61 | GH-61-1 | | | 3.74 | 125.21 | 0.22, 0.73 | 30.11 | 360 |
| | Compound D37 | Compound 36 | 40:60 | | | | | |
| Example 62 | GH-62-1 | | | 3.77 | 128.60 | 0.22, 0.73 | 30.85 | 358 |
| | Compound D38 | Compound 49 | 40:60 | | | | | |
| Example 63 | GH-63-1 | | | 3.72 | 127.88 | 0.22, 0.73 | 30.64 | 350 |
| | Compound D39 | Compound 5 | 40:60 | | | | | |
| Example 64 | GH-64-1 | | | 3.77 | 126.90 | 0.22, 0.73 | 30.48 | 346 |
| | Compound D43 | Compound 35 | 40:60 | | | | | |
| Example 65 | GH-65-1 | | | 3.74 | 126.10 | 0.22, 0.73 | 30.26 | 344 |
| | Compound D45 | Compound 12 | 40:60 | | | | | |
| Example 66 | GH-66-1 | | | 3.72 | 127.80 | 0.22, 0.73 | 30.62 | 363 |
| | Compound D47 | Compound 36 | 40:60 | | | | | |
| Example 67 | GH-67-1 | | | 3.73 | 129.47 | 0.22, 0.73 | 31.08 | 347 |
| | Compound D54 | Compound 49 | 40:60 | | | | | |
| Example 68 | GH-68-1 | | | 3.74 | 127.90 | 0.22, 0.73 | 30.72 | 360 |
| | Compound D61 | Compound 5 | 40:60 | | | | | |
| Example 69 | GH-69-1 | | | 3.76 | 127.92 | 0.22, 0.73 | 30.73 | 354 |
| | Compound D63 | Compound 35 | 40:60 | | | | | |
| Example 70 | GH-70-1 | | | 3.77 | 126.60 | 0.22, 0.73 | 30.42 | 354 |
| | Compound D67 | Compound 12 | 40:60 | | | | | |
| Example 71 | GH-71-1 | | | 3.74 | 126.00 | 0.22, 0.73 | 30.27 | 358 |
| | Compound D71 | Compound 36 | 40:60 | | | | | |
| Example 72 | GH-72-1 | | | 3.72 | 130.60 | 0.22, 0.73 | 31.37 | 359 |
| | Compound D74 | Compound 49 | 40:60 | | | | | |
| Example 73 | GH-73-1 | | | 3.73 | 125.20 | 0.22, 0.73 | 30.10 | 346 |
| | Compound D75 | Compound 5 | 40:60 | | | | | |
| Example 74 | GH-74-1 | | | 3.72 | 130.71 | 0.22, 0.73 | 31.39 | 343 |
| | Compound D77 | Compound 12 | 40:60 | | | | | |
| Example 75 | GH-75-1 | | | 3.76 | 127.50 | 0.22, 0.73 | 30.57 | 352 |
| | Compound D79 | Compound 35 | 40:60 | | | | | |
| Example 76 | GH-76-1 | | | 3.78 | 125.10 | 0.22, 0.73 | 30.00 | 357 |
| | Compound D83 | Compound 36 | 40:60 | | | | | |
| Example 77 | GH-77-1 | | | 3.72 | 127.42 | 0.22, 0.73 | 30.56 | 360 |
| | Compound D84 | Compound 49 | 40:60 | | | | | |

TABLE 7-continued

| Example No. | Composition GH-X-Y: First compound | Composition GH-X-Y: Second compound | Composition GH-X-Y: Mass ratio of first compound to second compound | Driving voltage (V) | Luminous efficiency (Cd/A) | Chromaticity coordinate CIEx, CIEy | External quantum efficiency EQE (%) | T95 (h) @20 mA/cm$^2$ |
|---|---|---|---|---|---|---|---|---|
| Example 78 | GH-78-1 | | | 3.74 | 130.70 | 0.22, 0.73 | 31.39 | 356 |
| | Compound D85 | Compound 12 | 40:60 | | | | | |
| Example 79 | GH-79-1 | | | 3.75 | 128.89 | 0.22, 0.73 | 30.89 | 382 |
| | Compound A16 | Compound 36 | 50:50 | | | | | |
| Example 80 | GH-80-1 | | | 3.78 | 126.57 | 0.22, 0.73 | 30.33 | 378 |
| | Compound A16 | Compound 36 | 60:40 | | | | | |
| Example 81 | GH-81-1 | | | 3.76 | 126.41 | 0.22, 0.73 | 30.31 | 389 |
| | Compound A229 | Compound 36 | 40:60 | | | | | |
| Example 82 | GH-82-1 | | | 3.73 | 129.73 | 0.22, 0.73 | 31.08 | 387 |
| | Compound A230 | Compound 36 | 40:60 | | | | | |
| Example 83 | GH-83-1 | | | 3.75 | 130.74 | 0.22, 0.73 | 31.33 | 386 |
| | Compound A231 | Compound 49 | 40:60 | | | | | |
| Example 84 | GH-84-1 | | | 3.72 | 130.83 | 0.22, 0.73 | 31.36 | 380 |
| | Compound B81 | Compound 36 | 40:60 | | | | | |
| Comparative | GH-D1-1 | | | 3.76 | 104.20 | 0.22, 0.73 | 25.02 | 245 |
| example 1 | Compound I | Compound 5 | 40:60 | | | | | |
| Comparative | GH-D2-1 | | | 3.75 | 103.42 | 0.22, 0.73 | 24.83 | 255 |
| example 2 | Compound I | Compound 36 | 40:60 | | | | | |
| Comparative | GH-D3-1 | | | 4.05 | 113.00 | 0.22, 0.73 | 27.10 | 287 |
| example 3 | Compound II | Compound 12 | 40:60 | | | | | |
| Comparative | GH-D4-1 | | | 4.07 | 110.20 | 0.22, 0.73 | 26.47 | 294 |
| example 4 | Compound II | Compound 49 | 40:60 | | | | | |
| Comparative | GH-D5-1 | | | 3.77 | 113.56 | 0.22, 0.73 | 27.27 | 250 |
| example 5 | Compound III | Compound 12 | 40:60 | | | | | |
| Comparative | GH-D6-1 | | | 3.75 | 112.50 | 0.22, 0.73 | 27.02 | 280 |
| example 6 | Compound IV | Compound 35 | 40:60 | | | | | |

As can be seen from the above table, the current efficiency of the devices in Examples 1 to 84 was improved by at least 10.1% and the service life of the devices in Examples 1 to 84 was improved by at least 16.0% compared with Comparative examples 1 to 6.

Compared with Comparative examples 1 and 2, when the organic compound shown in the formula 1 according to the present disclosure is used as a green electron type host material, the manufactured device has significantly improved service life characteristics when the driving voltage and the efficiency are close. The reason may be that specific sites in the phenylcarbazole core structure in the compounds of the present disclosure are deuterated, making photoelectric stability of the compounds improved compared with the compound I.

Compared with Comparative examples 3 and 4, when the organic compound shown in the formula 1 according to the present disclosure is used as a green electron type host material, the manufactured device has a remarkably reduced driving voltage and improved luminous efficiency. The reason may be that compared with the carbazole group with hole characteristics in the compound II, the compound of the present disclosure uses a neutral or electronic group to connect the triazine group, so that the molecule has better electron injection and transport characteristics, resulting in enhanced carrier injection and recombination efficiency.

Compared with Comparative example 5, the service life of the device is improved for the compounds of the present disclosure compared with the compound III in Comparative example. The reason may be that compared with the compound III, a specific site in the carbazole group is deuterated in the compound of the present disclosure, thus improving photoelectric stability of the compounds.

Compared with Comparative example 6, both the service life and the efficiency of the device are improved for the compounds of the present disclosure compared with the compound IV in Comparative example. The reason may be that compared with the compound IV, only one of the benzene rings on the carbazole group is perdeuterated in the compounds of the present disclosure, which can effectively control the local symmetry of the molecular structure and reduce the intermolecular force, thus improving the amorphous stability and film-forming properties of the material.

It will be easy for those skilled in the art to think of other embodiments of the present disclosure after considering the specification and practicing the present disclosure disclosed here. The present disclosure is intended to cover any variations, uses, or adaptive changes of the present disclosure, and these variations, uses, or adaptive changes follow the general principles of the present disclosure and include common general knowledge or conventional technical means in the art not disclosed in the present disclosure. The specification and examples are only considered as exemplary, and the true scope and spirit of the present disclosure are indicated by the following claims.

The invention claimed is:

1. An organic compound, having a structure as shown in a formula 1:

Formula 1

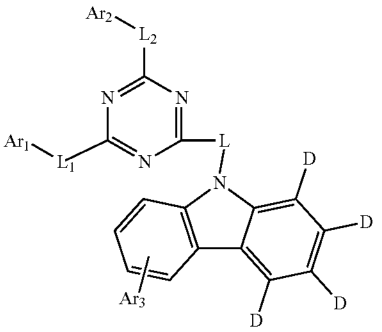

wherein $Ar_1$ is selected from a substituted or unsubstituted phenyl, a substituted or unsubstituted naphthyl, a substituted or unsubstituted biphenyl, a substituted or unsubstituted phenanthryl, a substituted or unsubstituted fluorenyl, a substituted or unsubstituted terphenyl, a substituted or unsubstituted dibenzofuranyl, or a substituted or unsubstituted dibenzothienyl;

$Ar_2$ is selected from a substituted or unsubstituted phenyl, a substituted or unsubstituted naphthyl, or a substituted or unsubstituted biphenyl;

substituent(s) in $Ar_1$ are the same or different, and are respectively and independently selected from deuterium, a fluorine, a cyano, a methyl, an ethyl, a n-propyl, an isopropyl, a tert-butyl, a phenyl, or a pentadeuterophenyl;

substituent(s) in $Ar_2$ are the same or different, and are respectively and independently selected from deuterium, a fluorine, a cyano, a methyl, an ethyl, a n-propyl, an isopropyl, or a tert-butyl;

L, $L_1$ and $L_2$ are the same or different, and are respectively and independently selected from a single bond, a substituted or unsubstituted phenylene, a substituted or unsubstituted naphthylene, or a substituted or unsubstituted biphenylene; and substituent(s) in L, $L_1$ and $L_2$ are the same or different, and are respectively and independently selected from deuterium, a fluorine, a cyano, a methyl, an ethyl, a n-propyl, an isopropyl, a tert-butyl, or a phenyl; and $Ar_3$ is

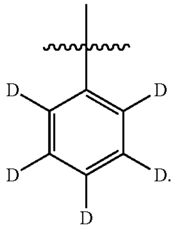

2. The organic compound according to claim 1, wherein

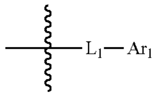

is selected from the group consisting of:

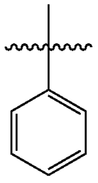
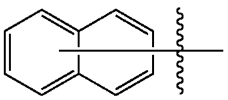
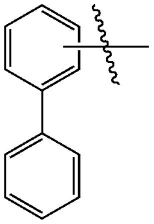
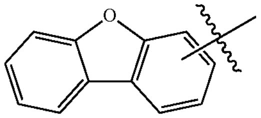
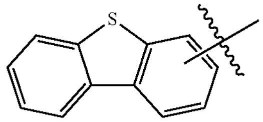
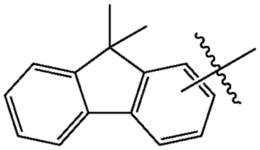
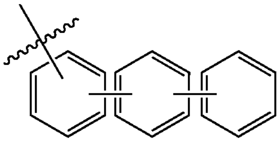
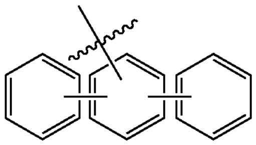
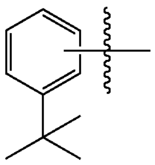
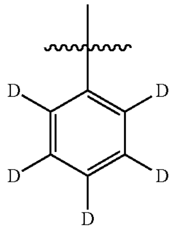
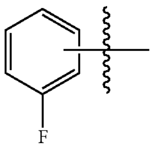
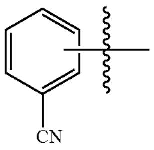

-continued
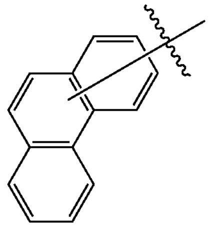
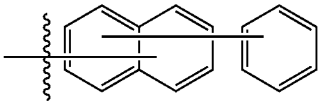
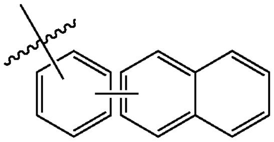
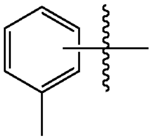
;
and
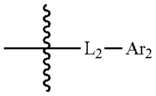
is selected from the group consisting of:
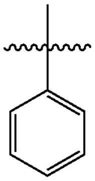
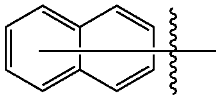
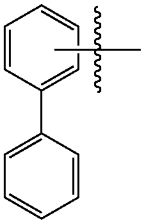
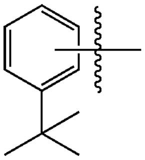
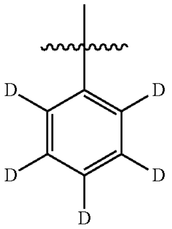
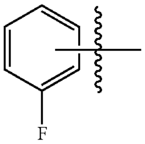
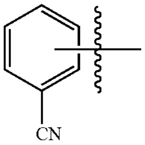
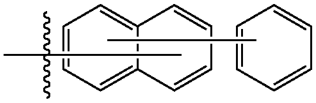
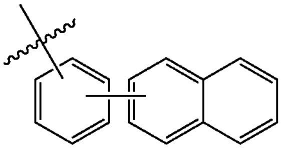
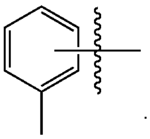
.
3. The organic compound according to claim 1, wherein
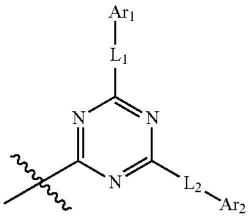
in the formula 1 is selected from the group consisting of:
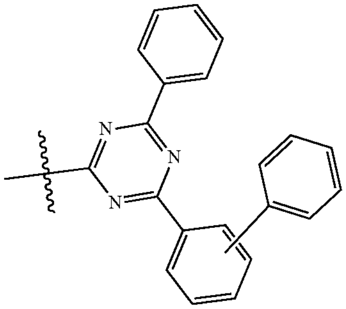
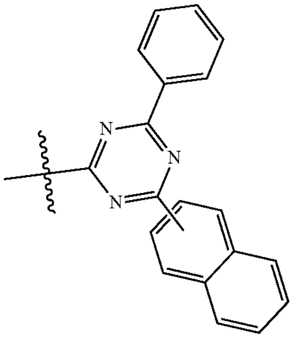
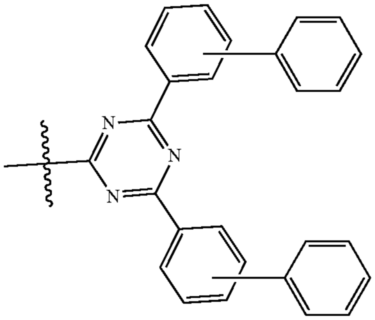
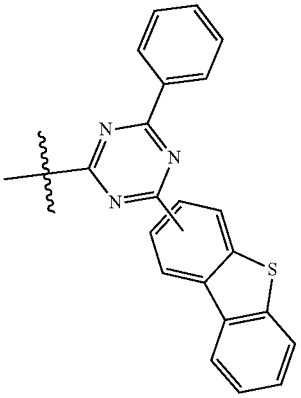

-continued
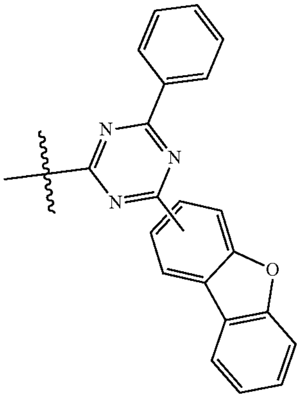
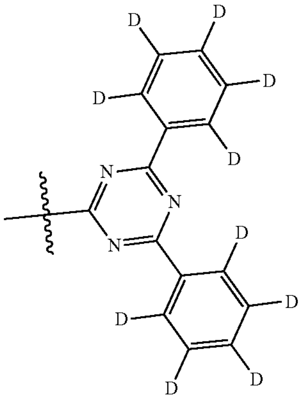
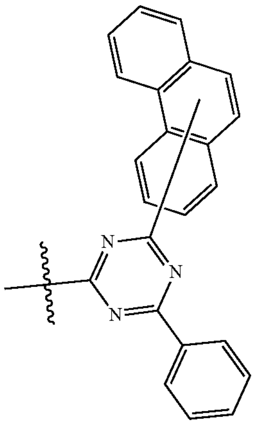
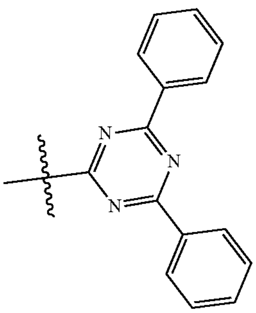
-continued
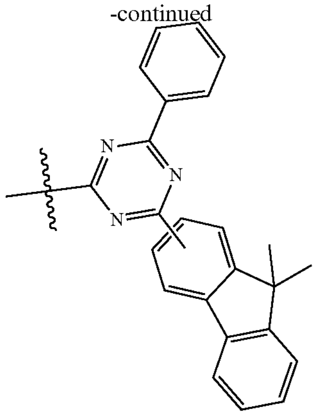
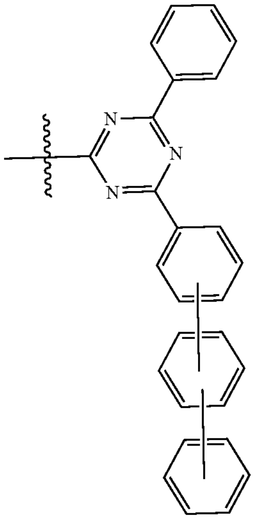
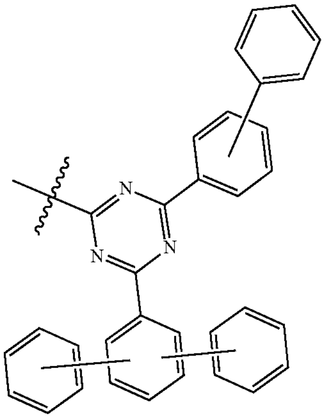
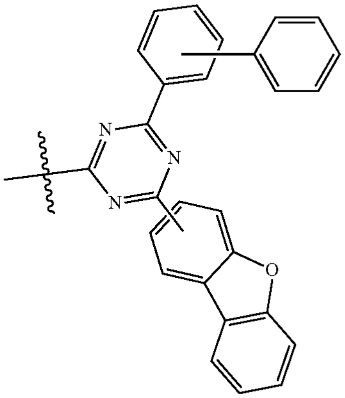

-continued
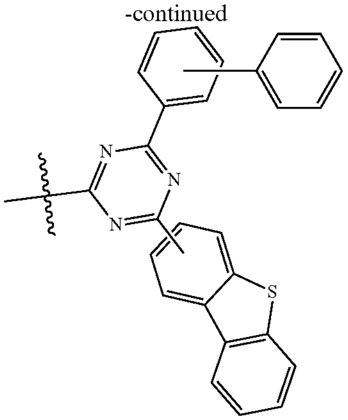
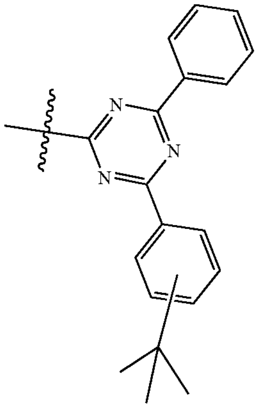
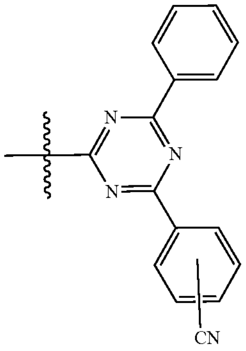
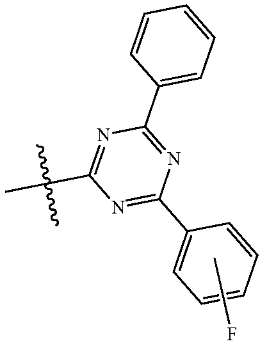
-continued
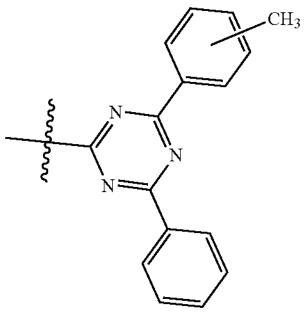
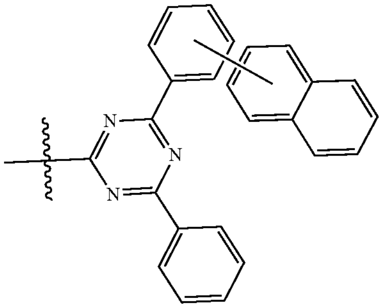
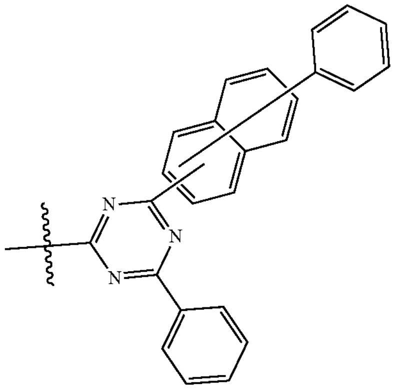
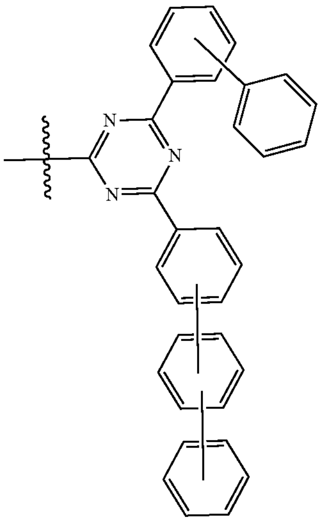

-continued
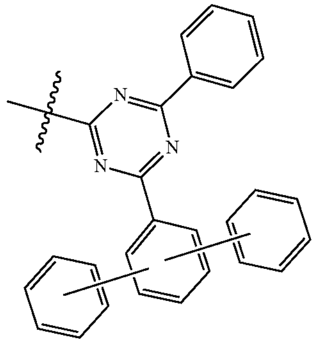
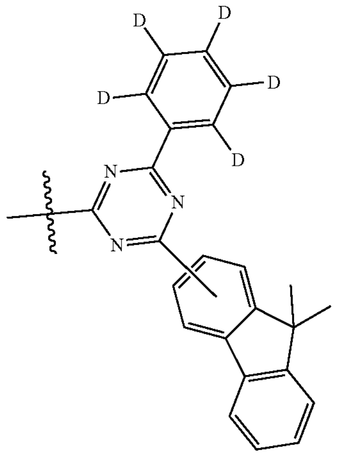
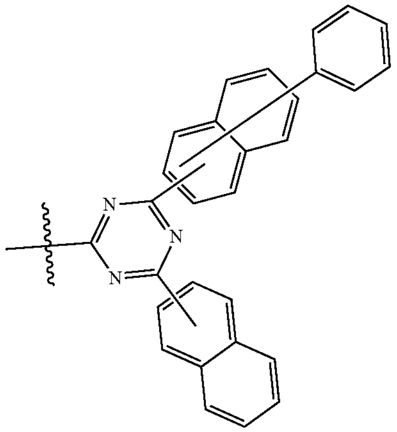
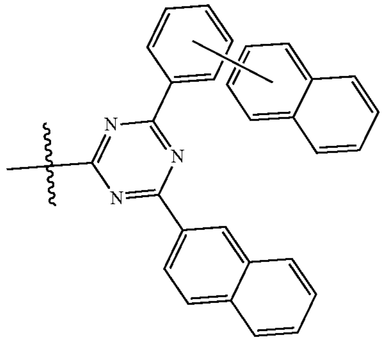
-continued
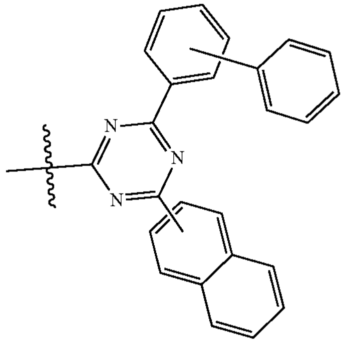
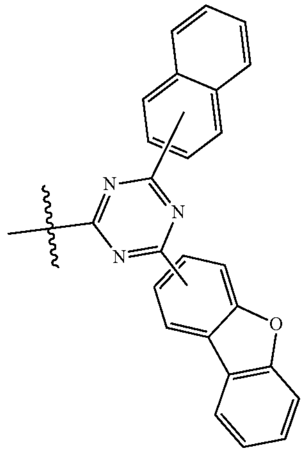
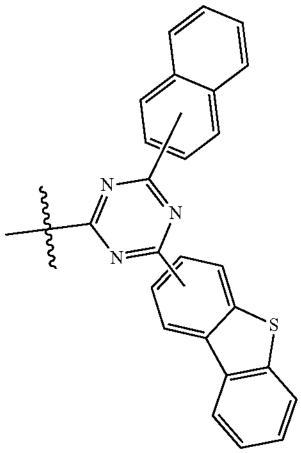
.

4. The organic compound according to claim 1, wherein the organic compound is selected from the group consisting of the following compounds:
A1
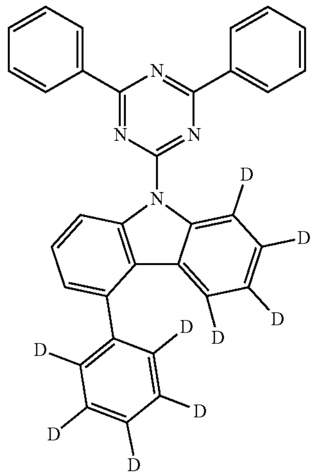
A2
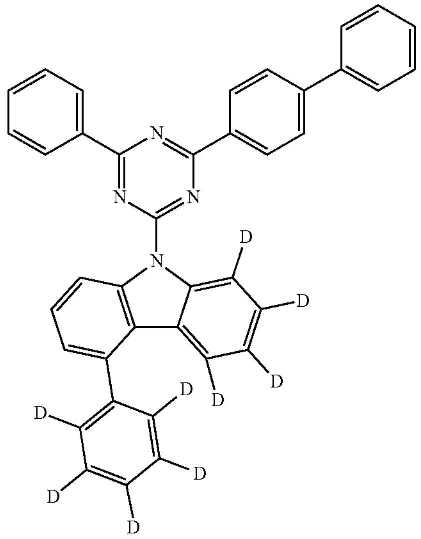
-continued
A3
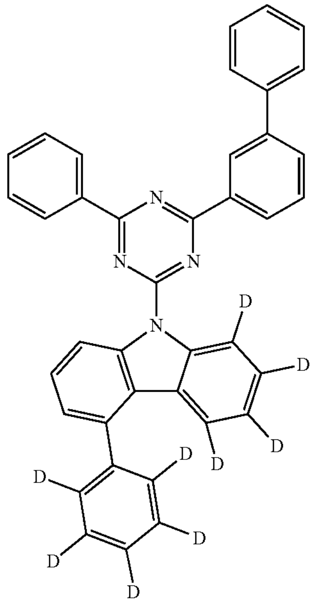
A4
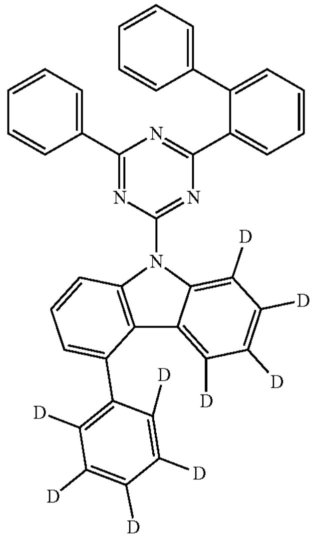

-continued
A5
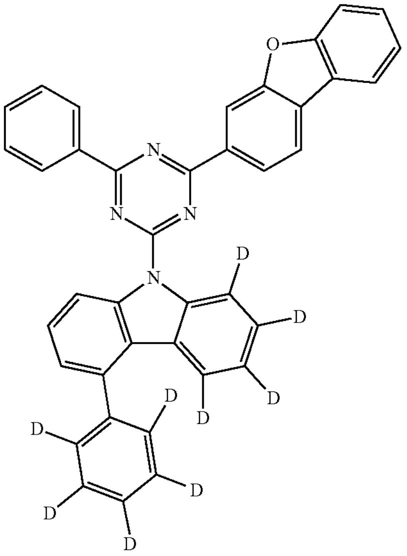
A6
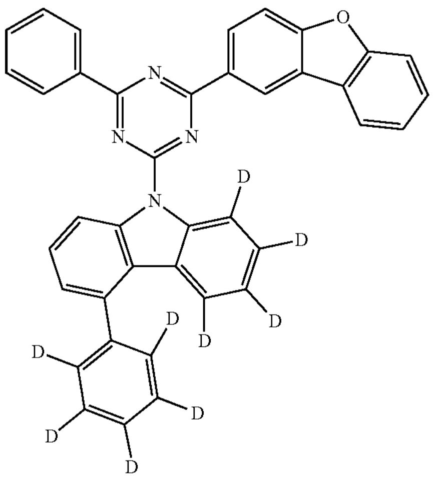
A7
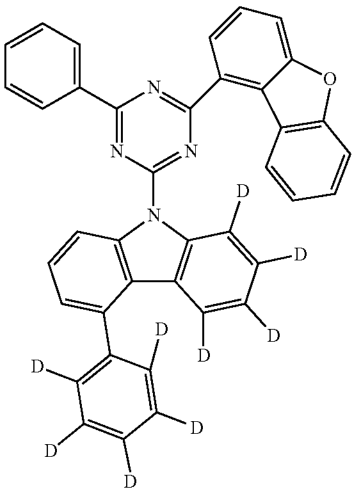
-continued
A8
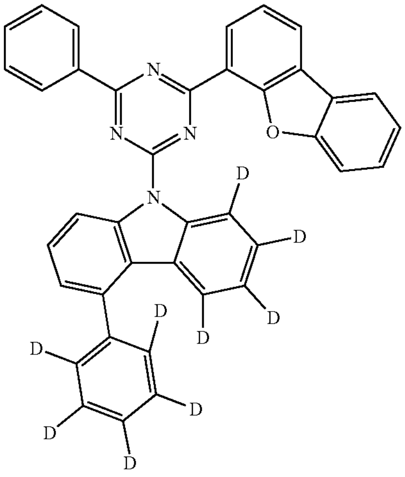
A9
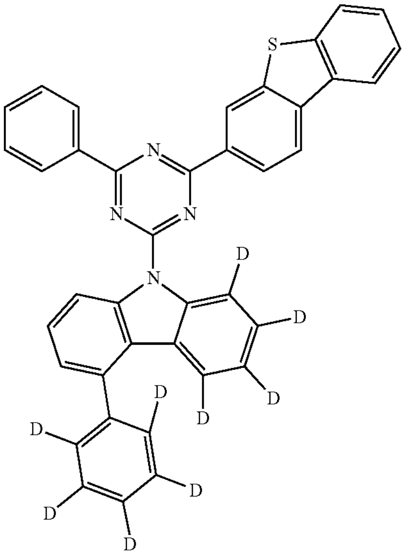
A10
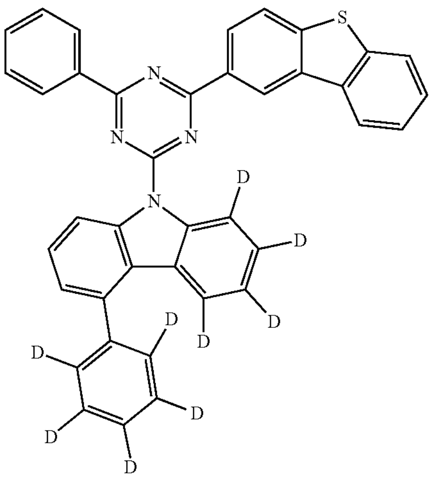

-continued
A11
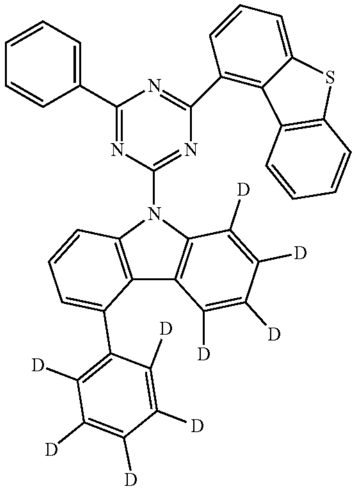
A12
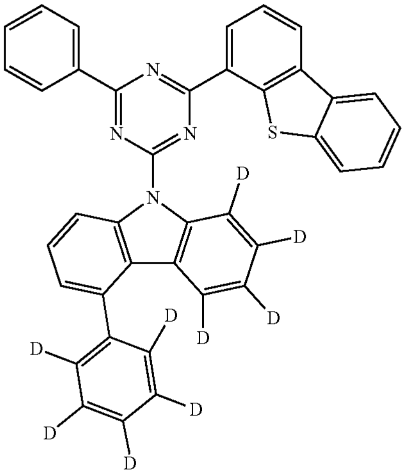
A13
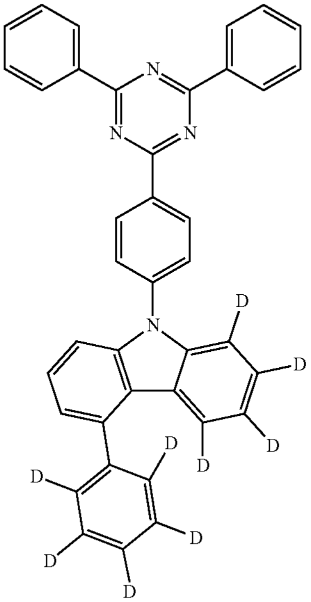
-continued
A14
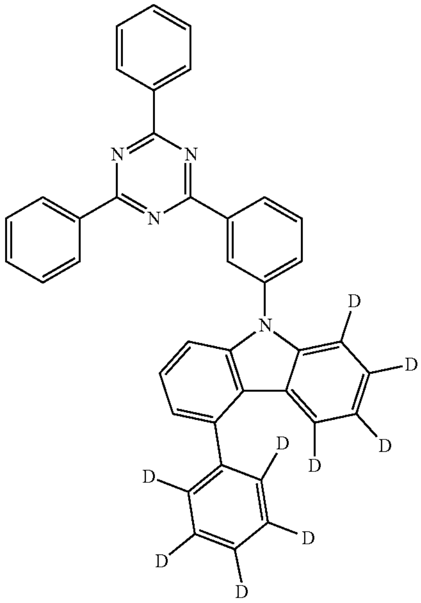
A15
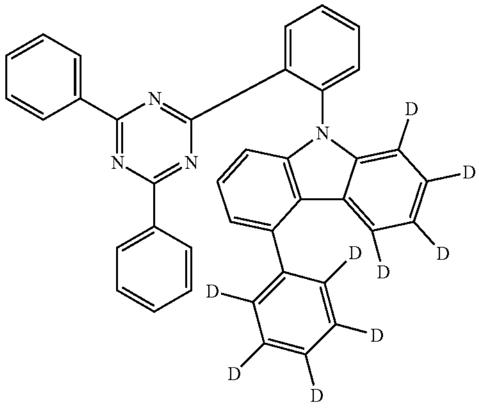
A16
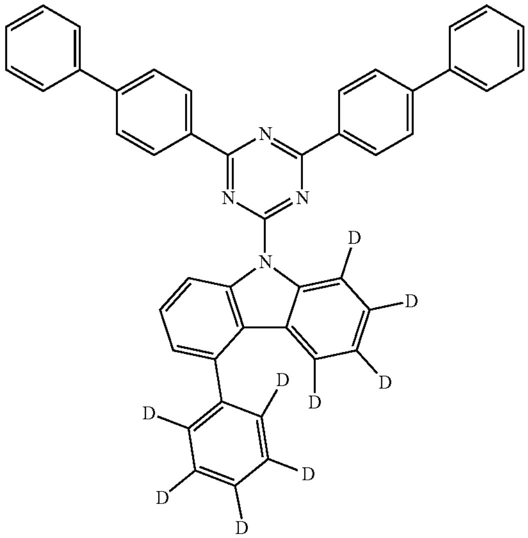

-continued
A17
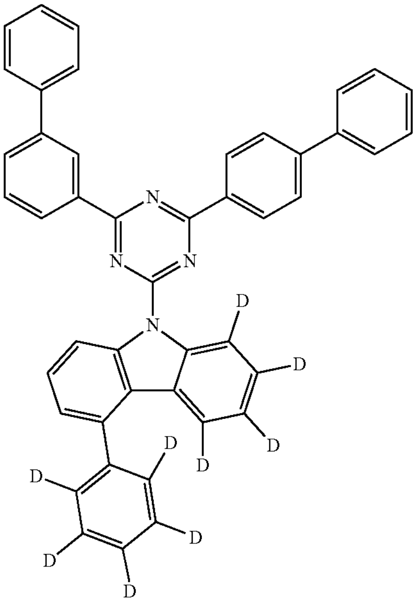
A18
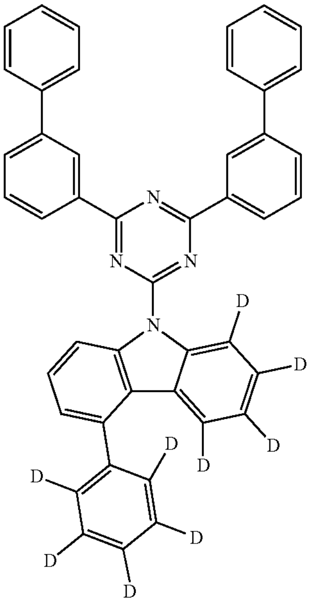
-continued
A19
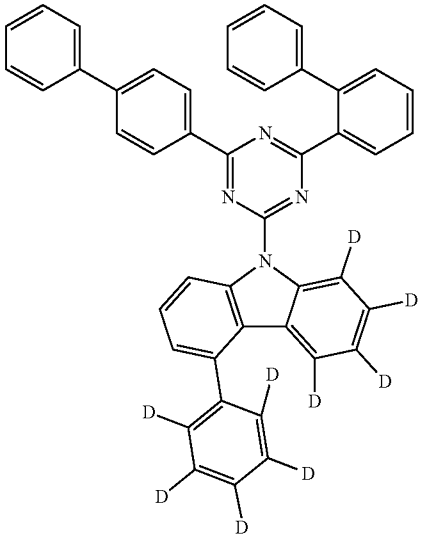
A20
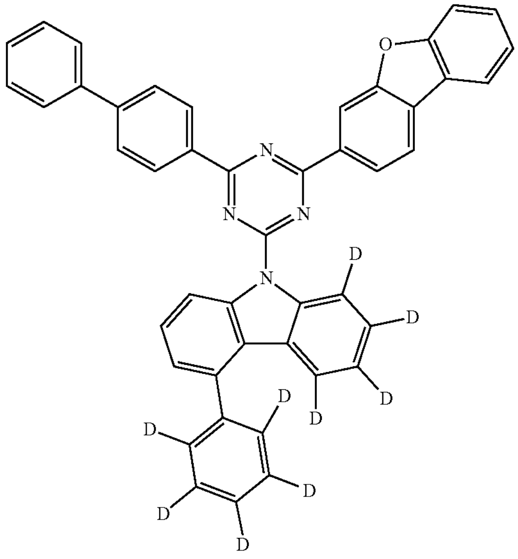

-continued
A21
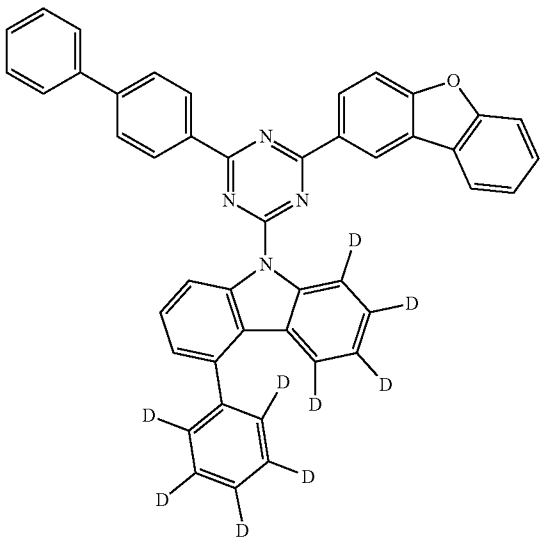
A22
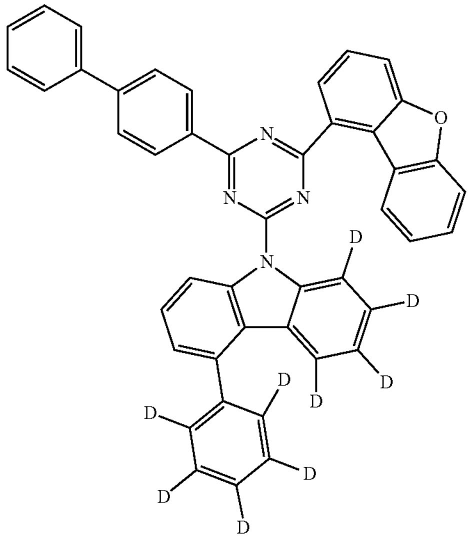
A23
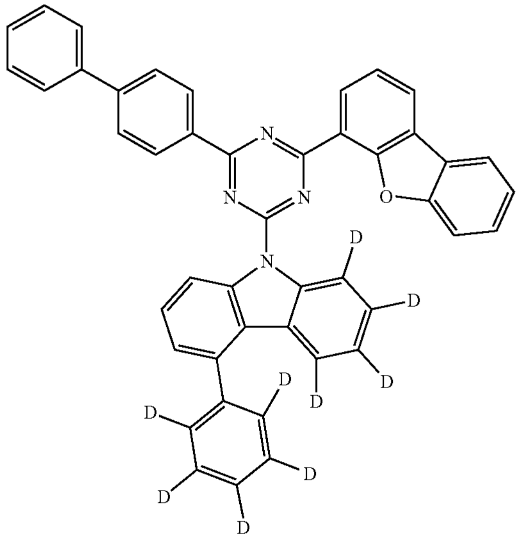
-continued
A24
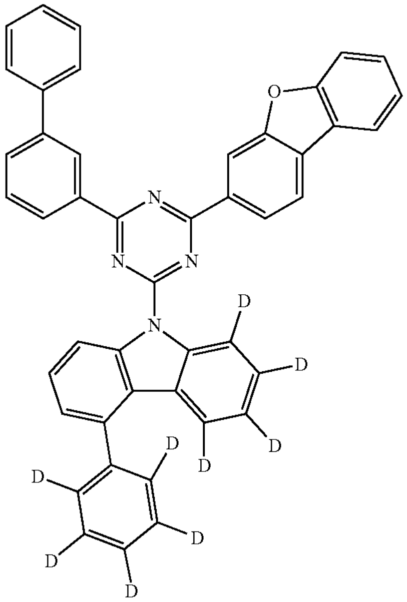
A25
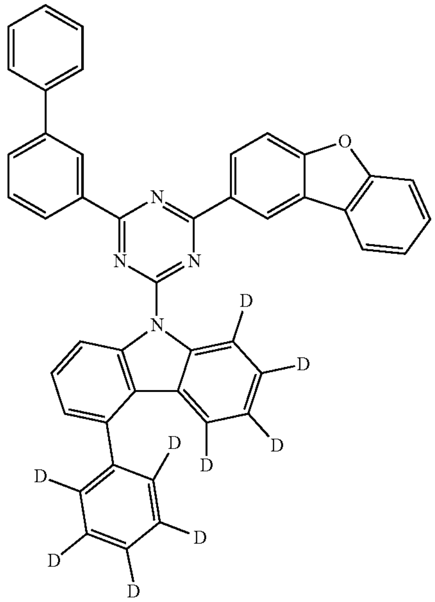

-continued
A26
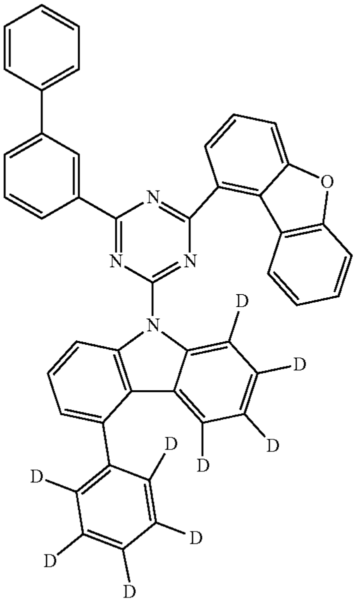
A27
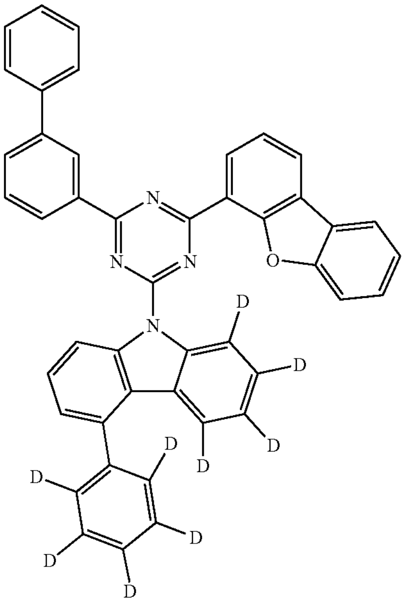
-continued
A28
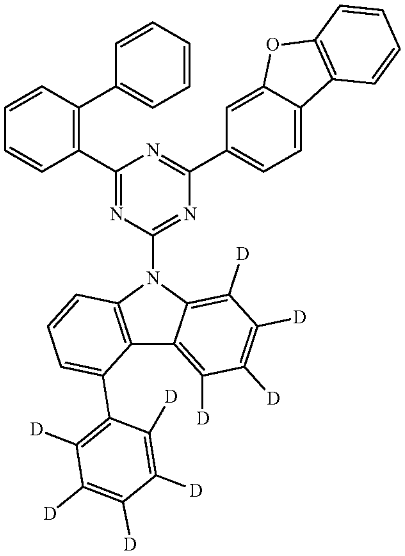
A29
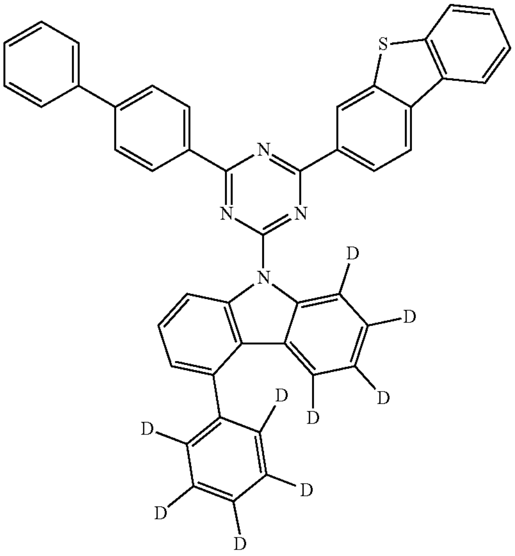

-continued
A30
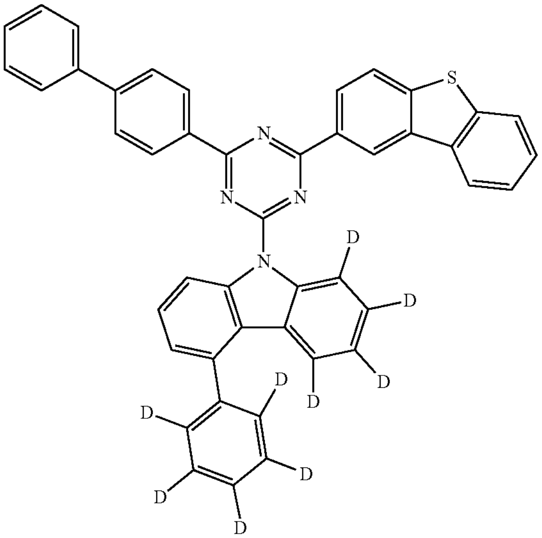
A31
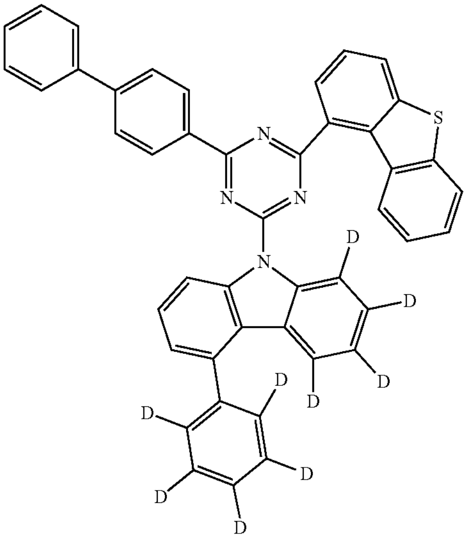
A32
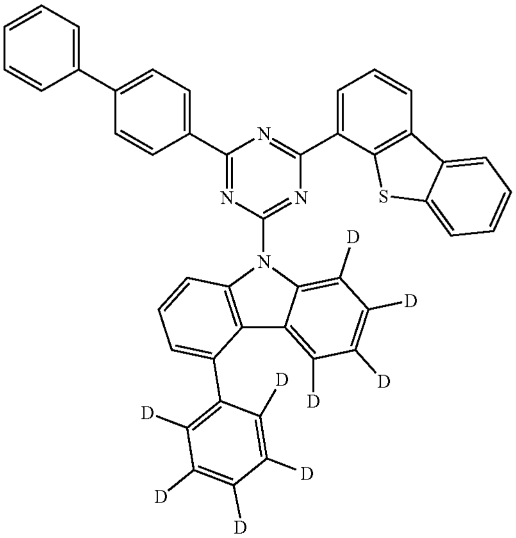
-continued
A33
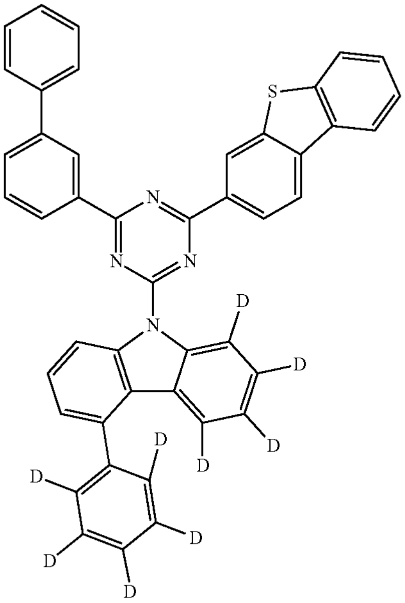
A34
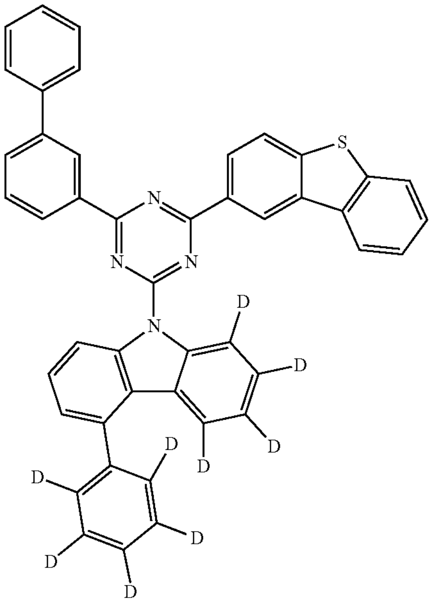

-continued
A35
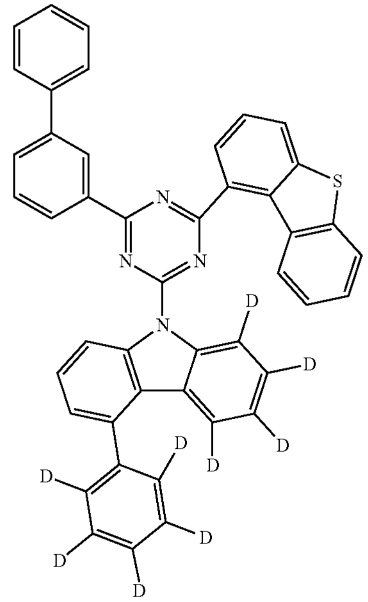
A36
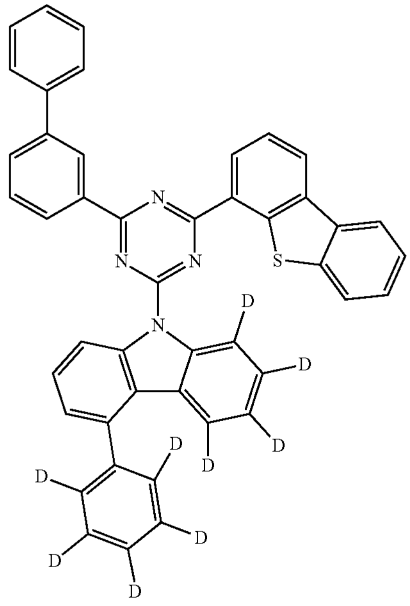
-continued
A37
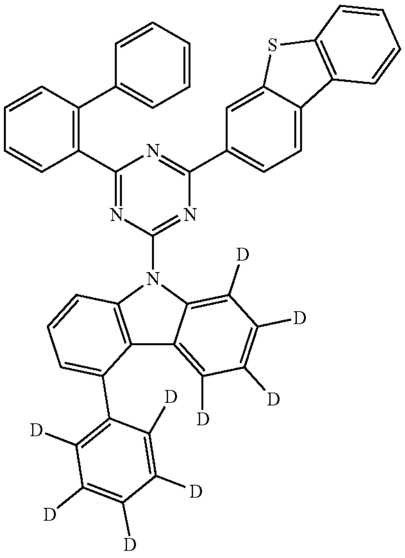
A42
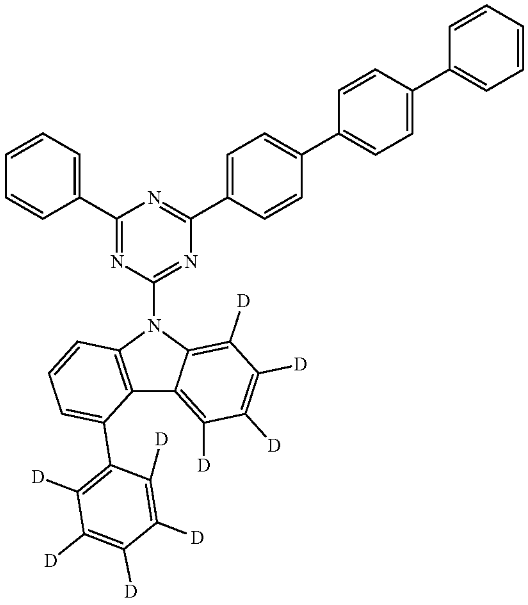

-continued
A43
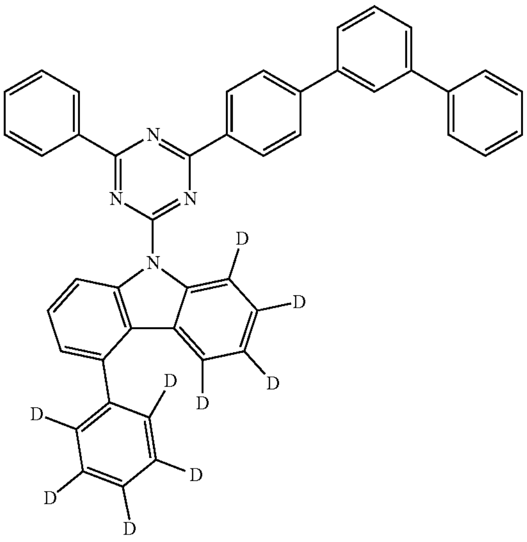
A44
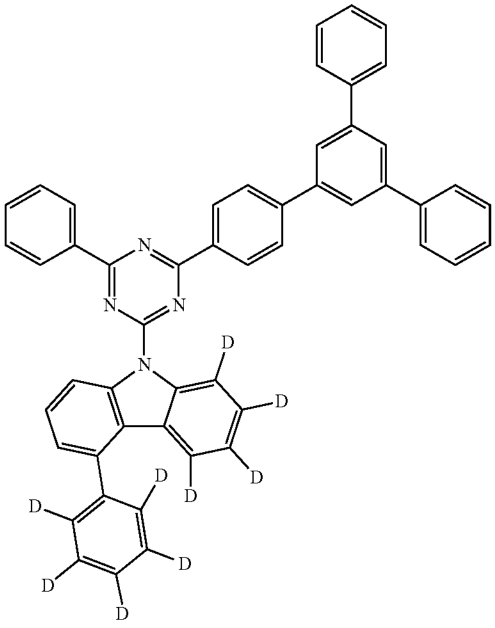
-continued
A45
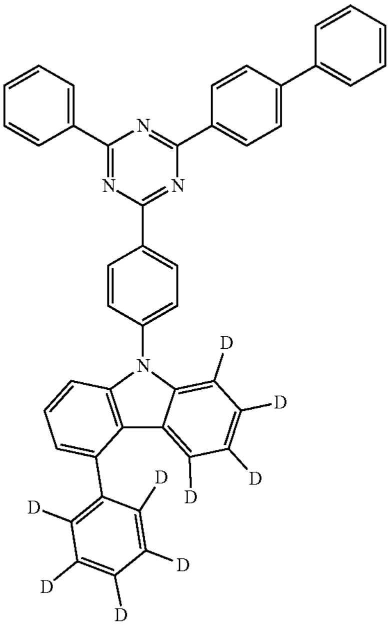
A46
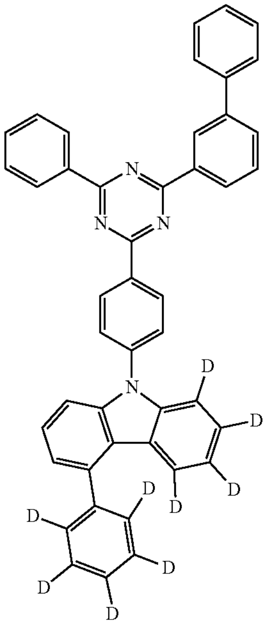

-continued
A47
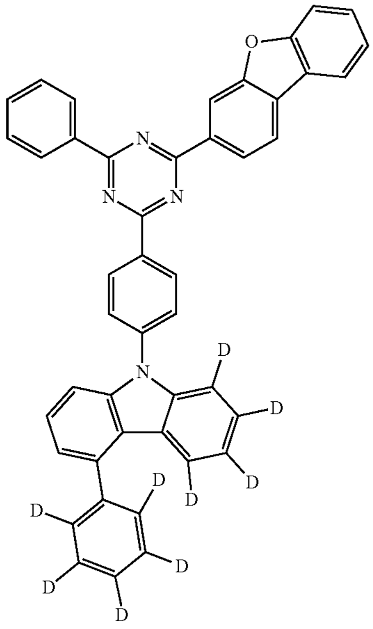
A49
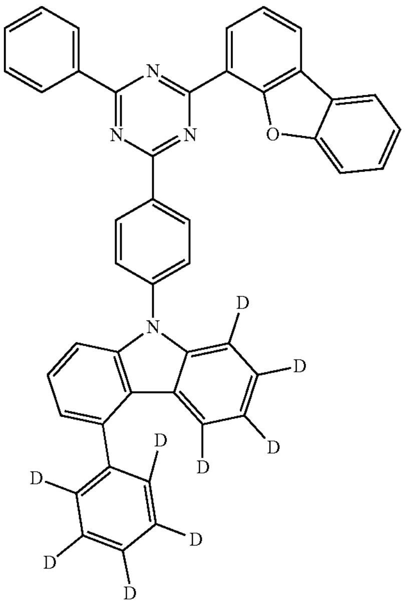
A48
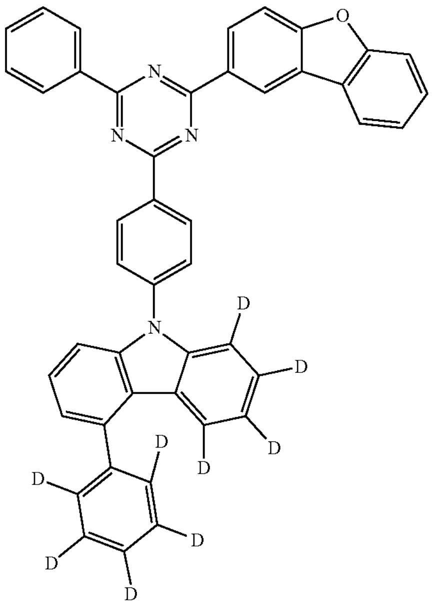
A50
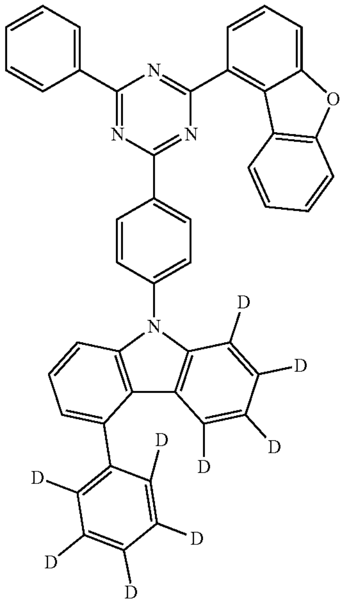

-continued
A51
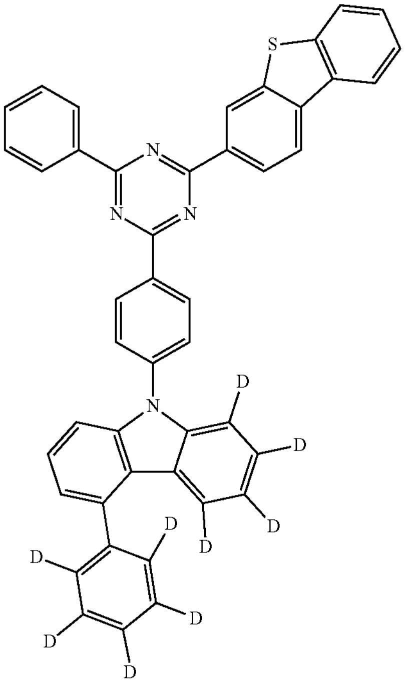
A52
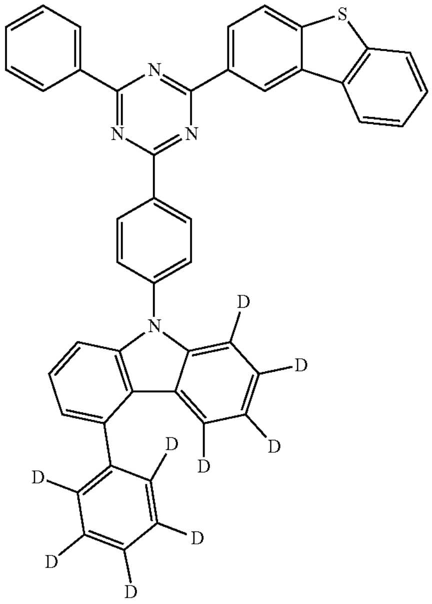
-continued
A53
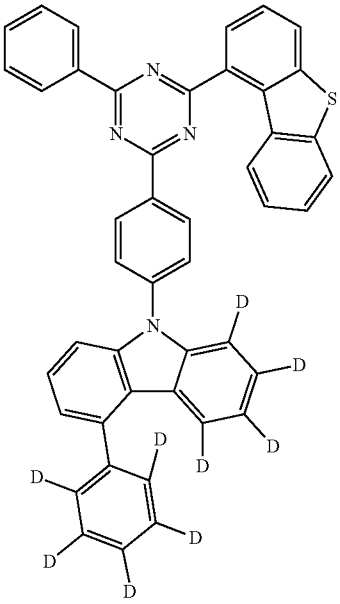
A54
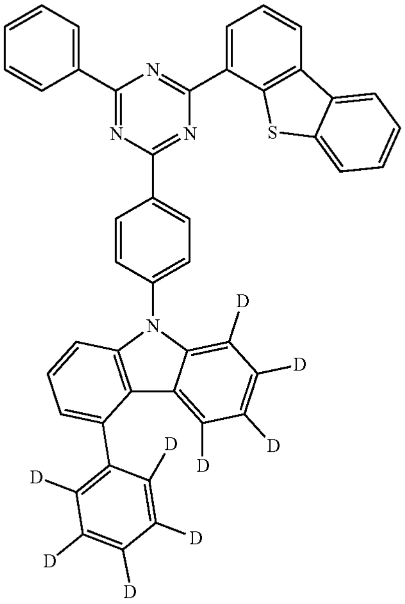

A55
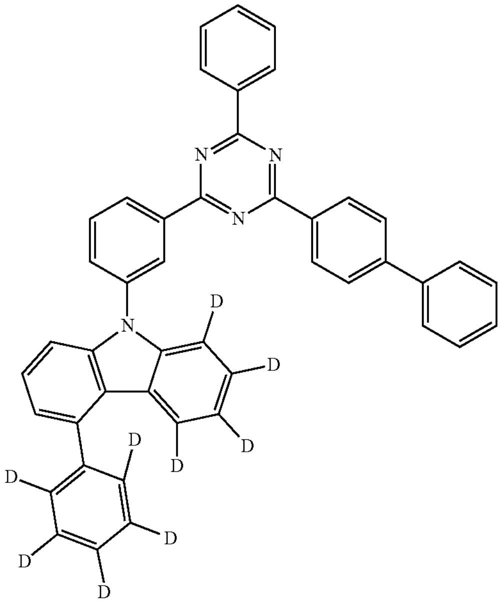
A56
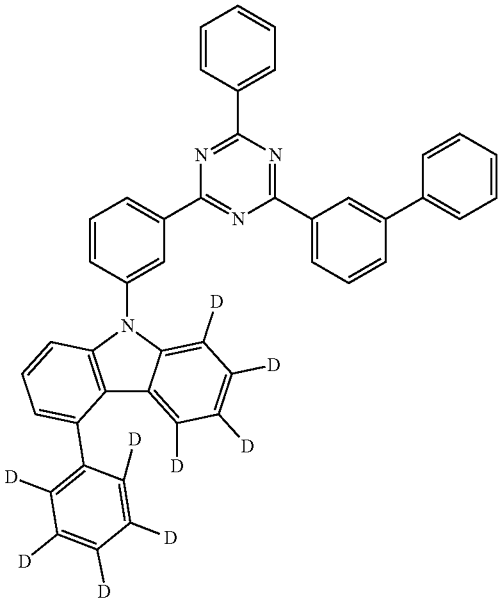
A57
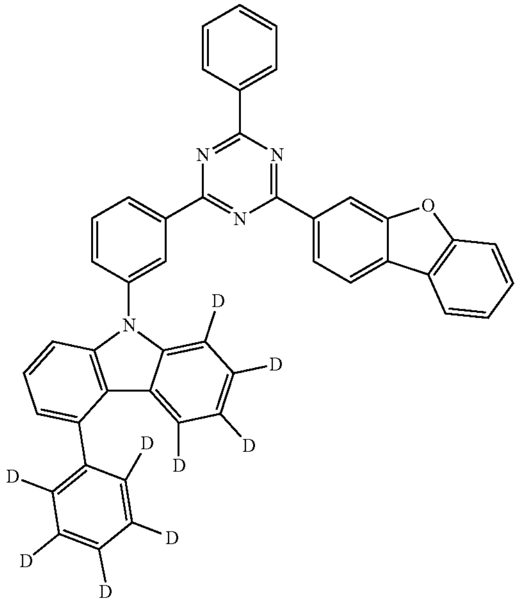
A58
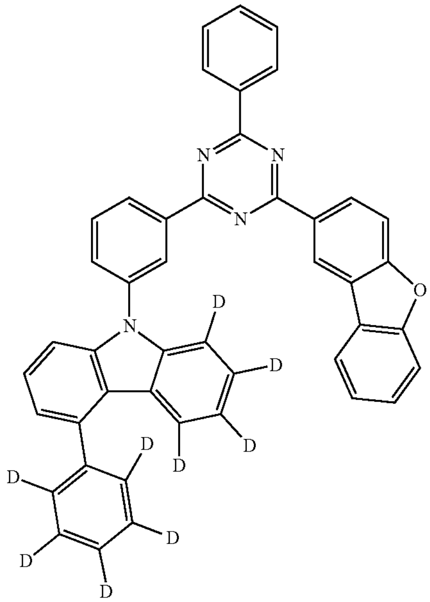

-continued
A59
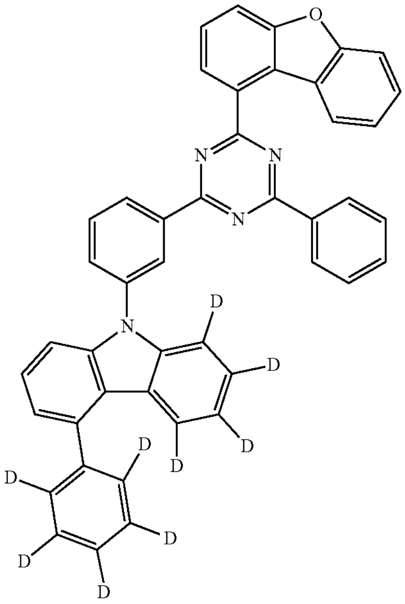
A60
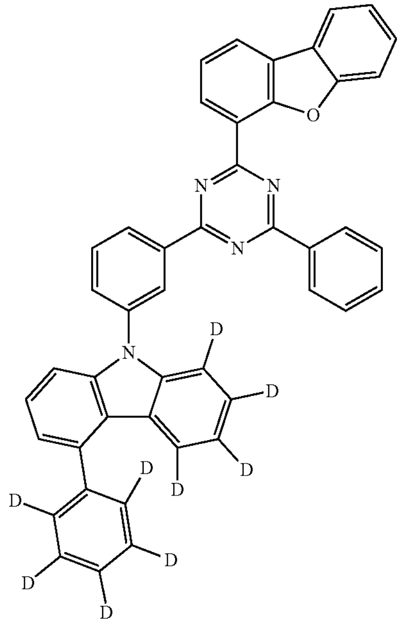
-continued
A61
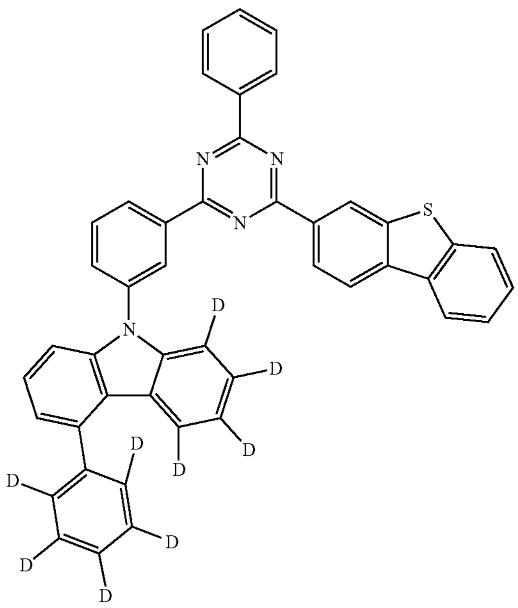
A62
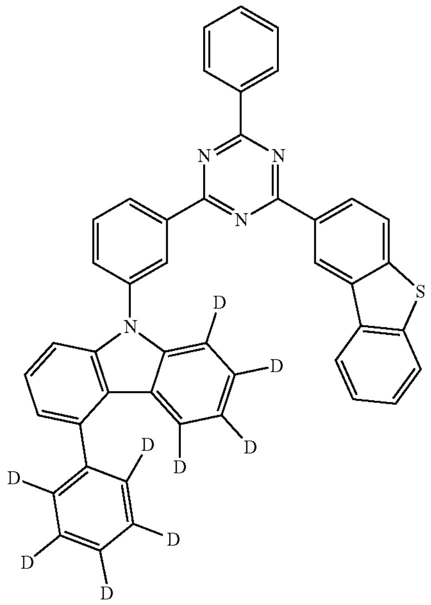

-continued
A63
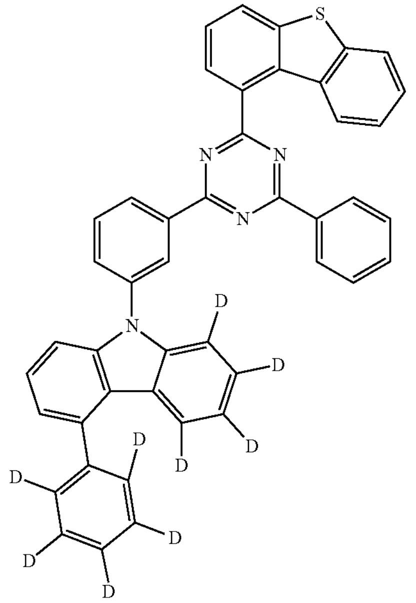
A64
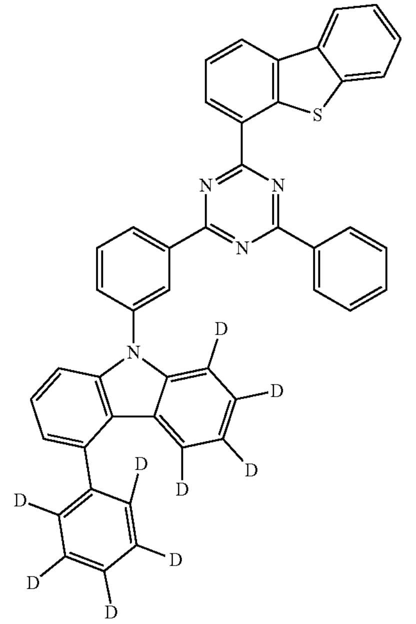
-continued
A65
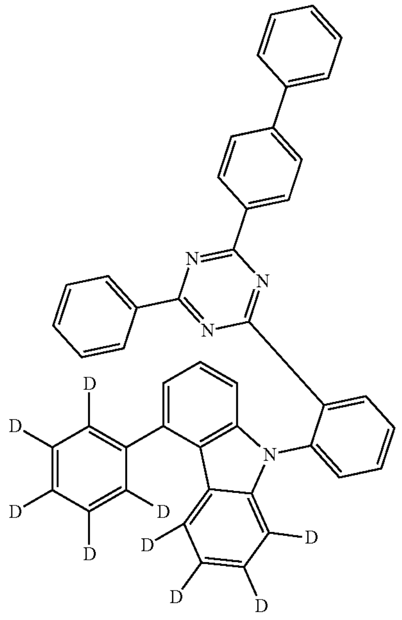
A66
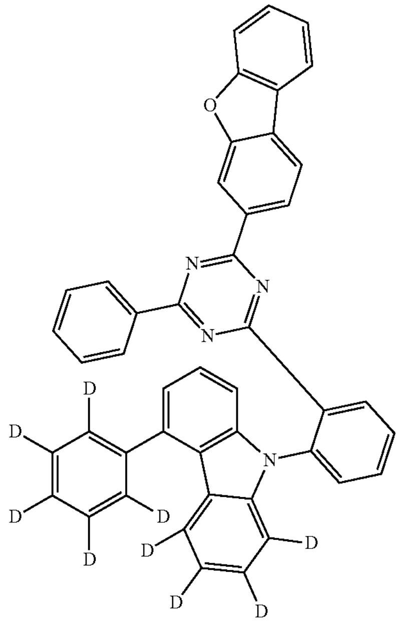

-continued
A67
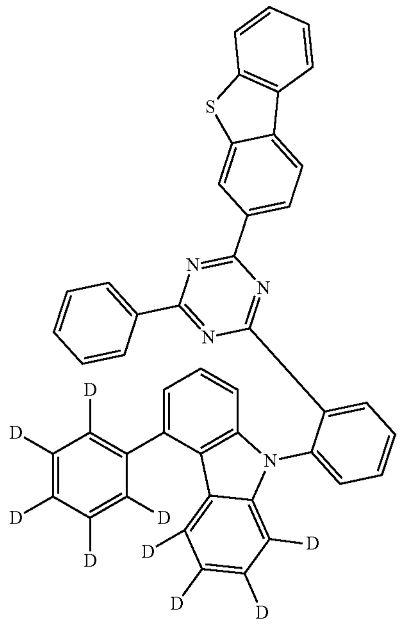
A68
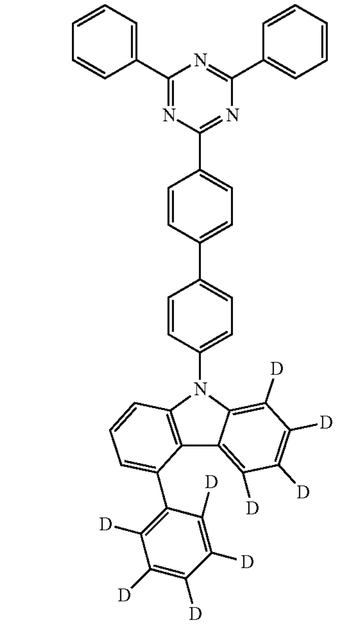
-continued
A69
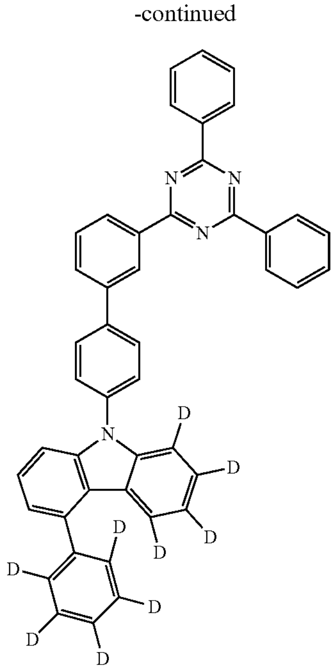
A70
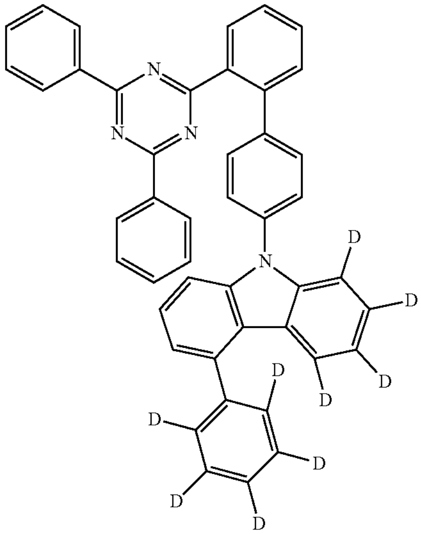

-continued
A71
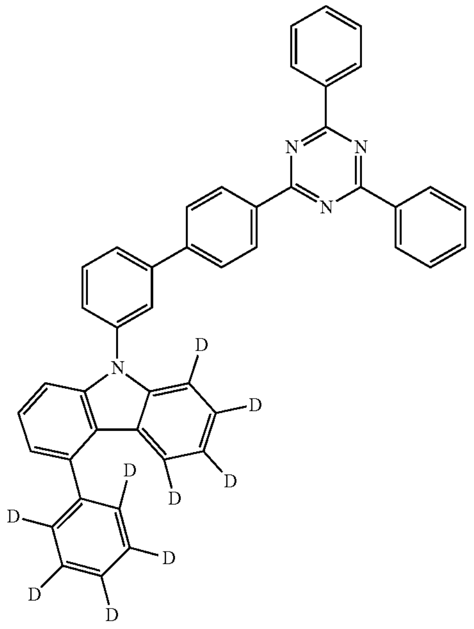
A72
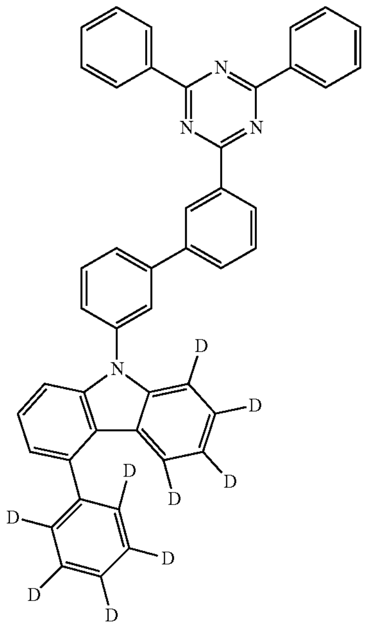
-continued
A73
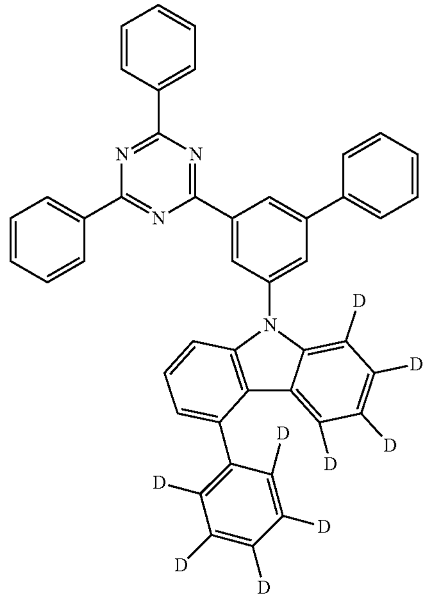
A74
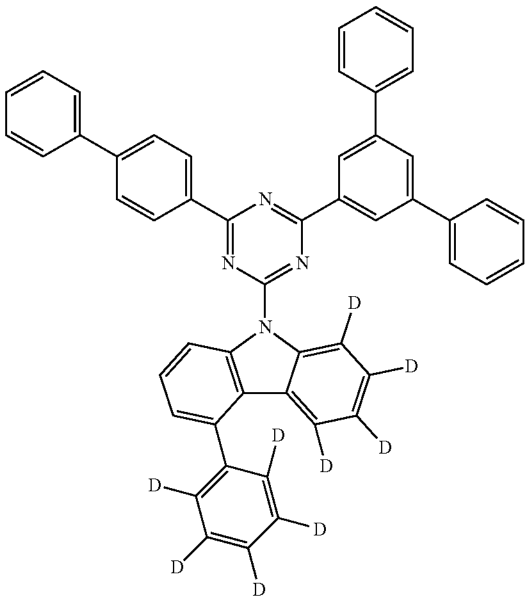

-continued
A75
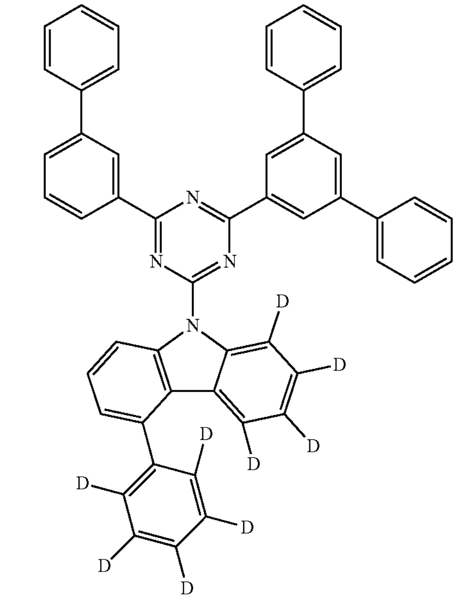
A76
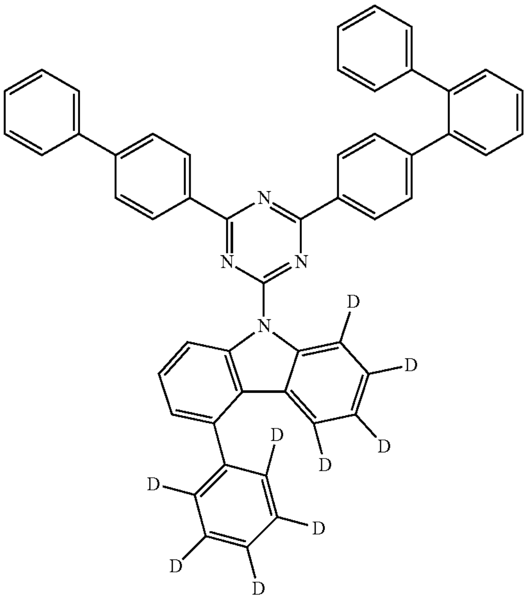
-continued
A77
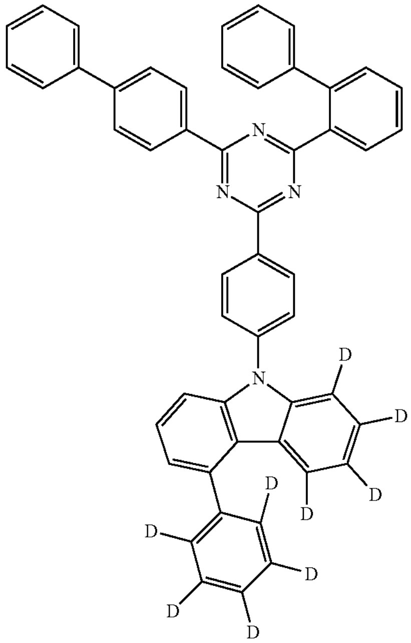
A78
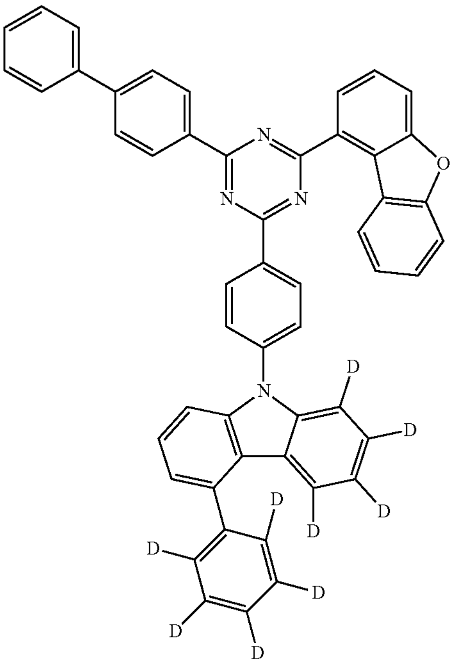

-continued
A79
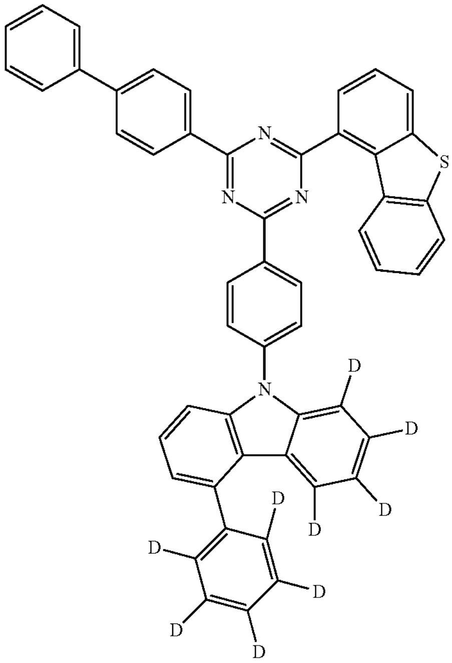
A80
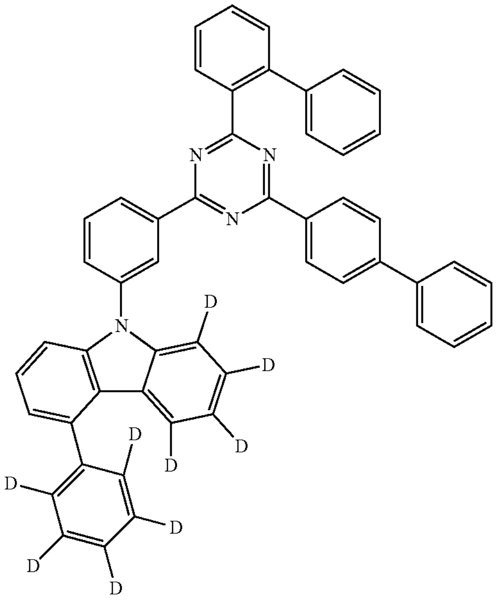
-continued
A81
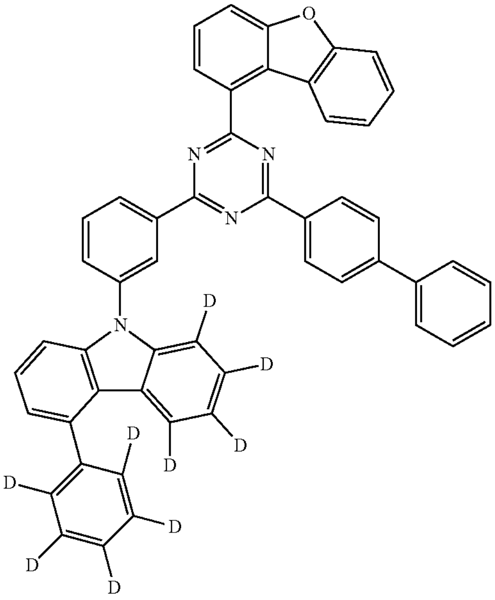
A82
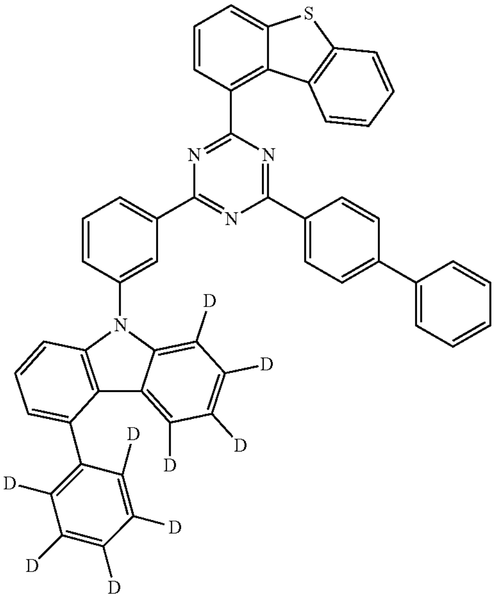

-continued
A83
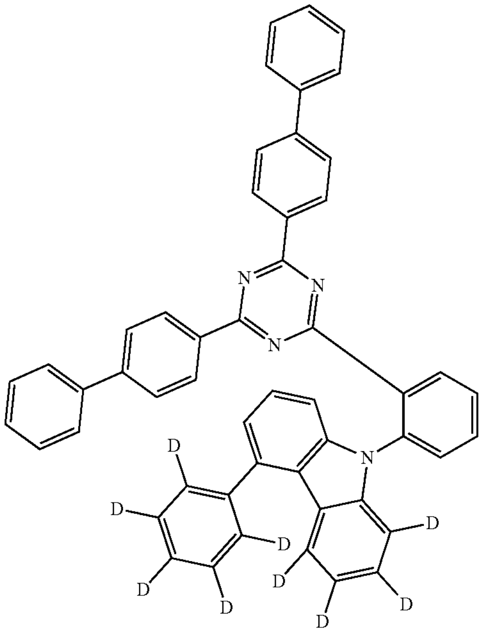
A84
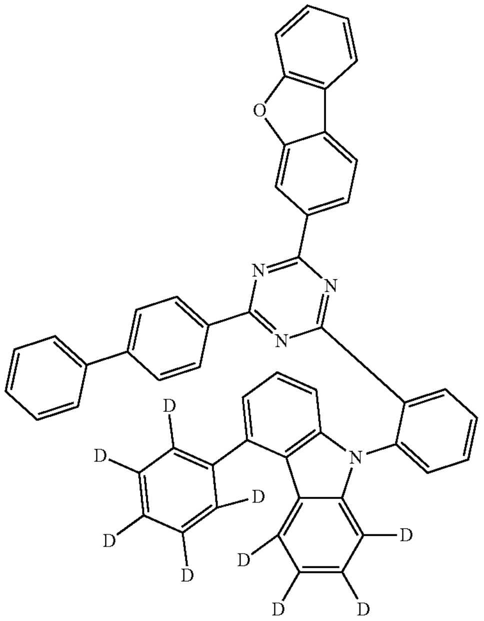
-continued
A85
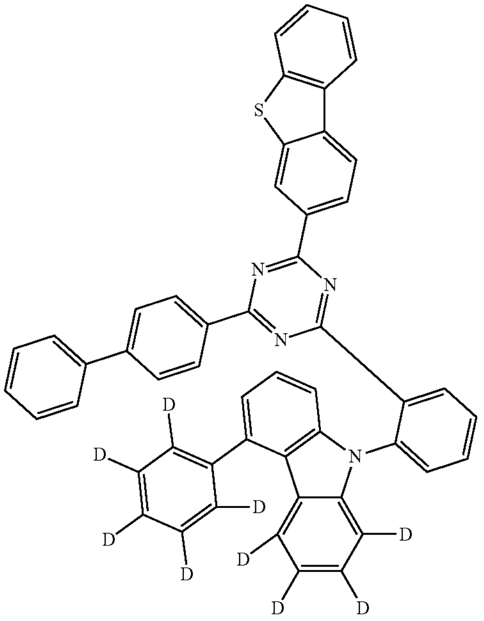
A86
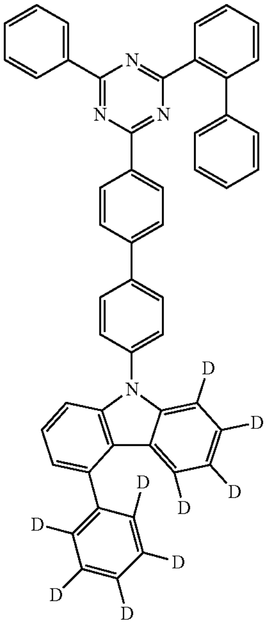

-continued
A87
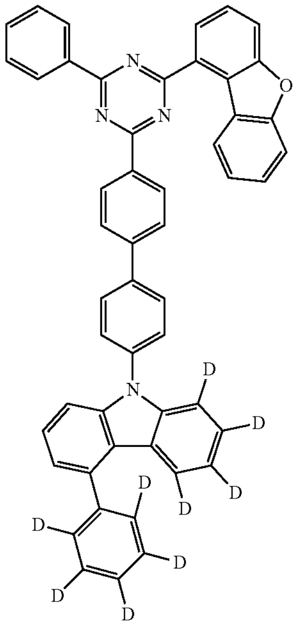
-continued
A89
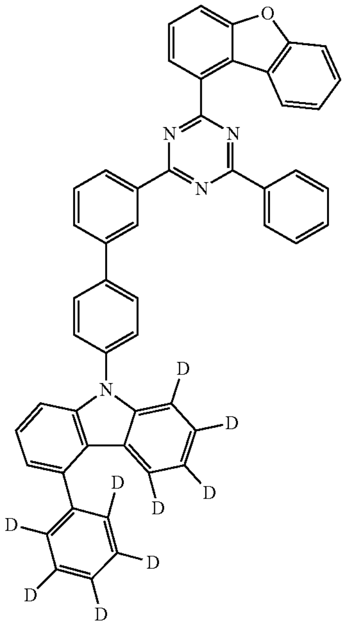
A88
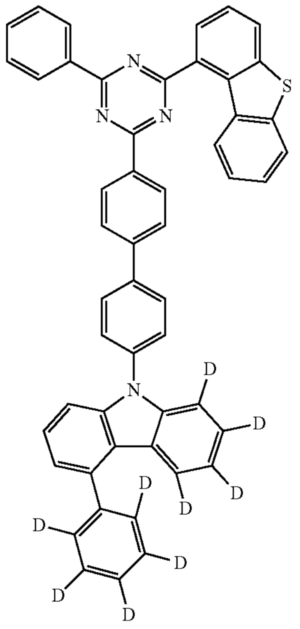
A90
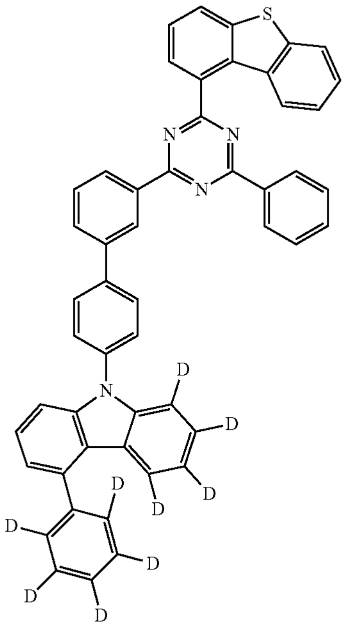

-continued
A91
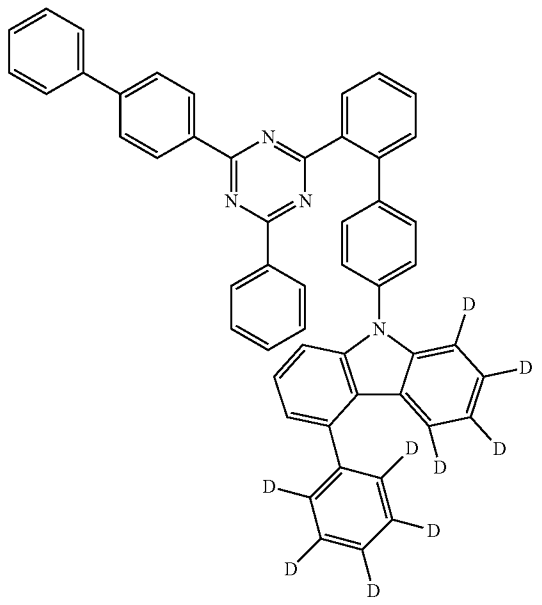
A92
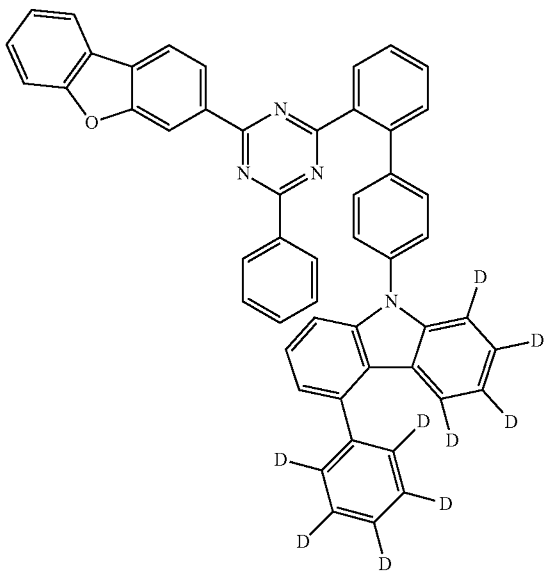
-continued
A93
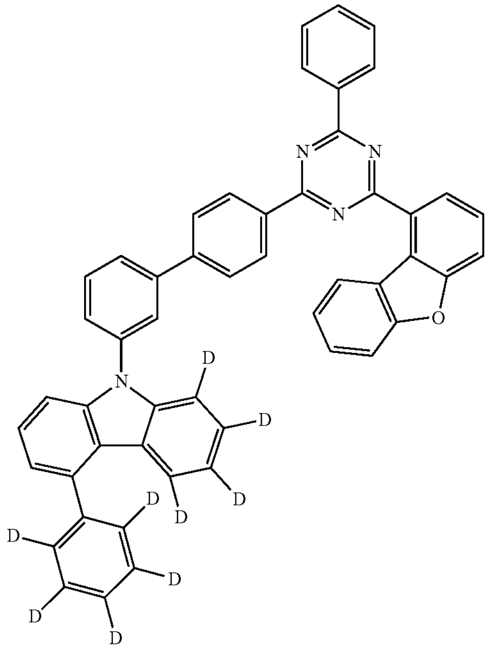
A94
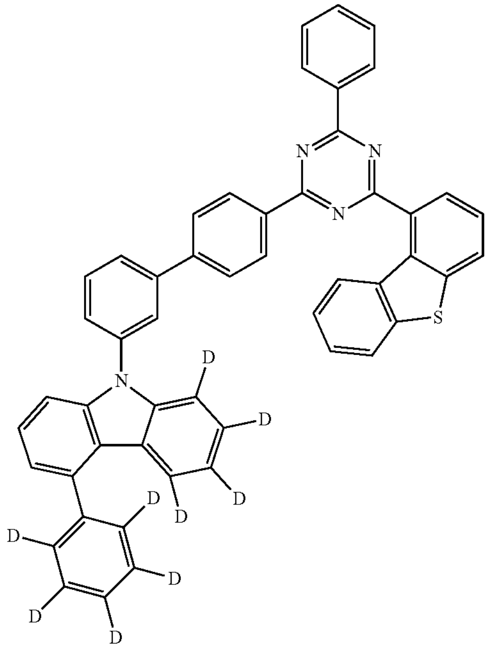

-continued
A95
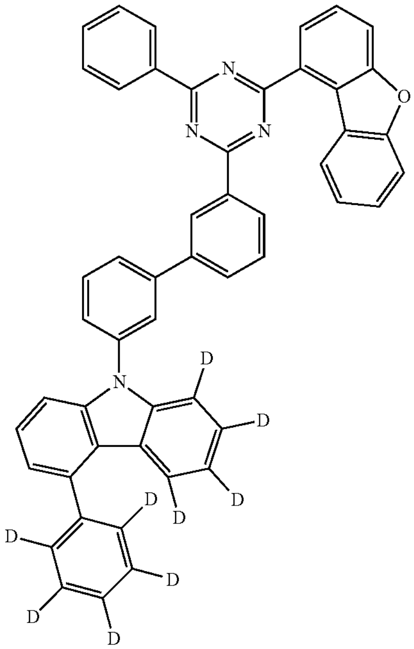
A97
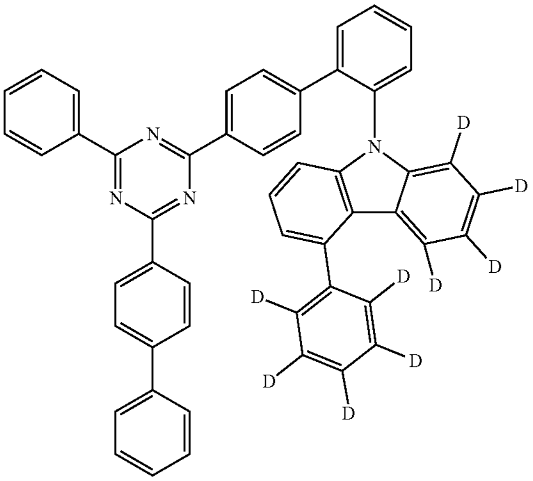
A98
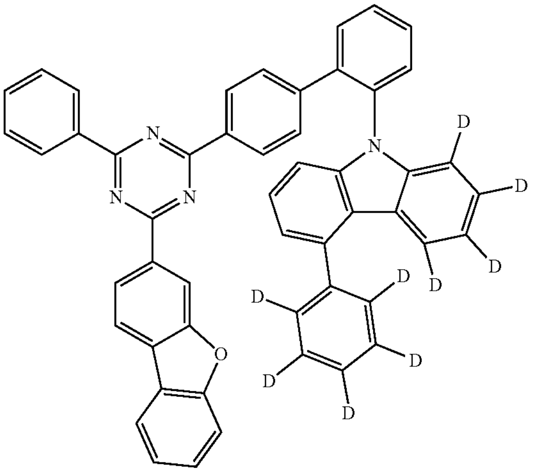
A96
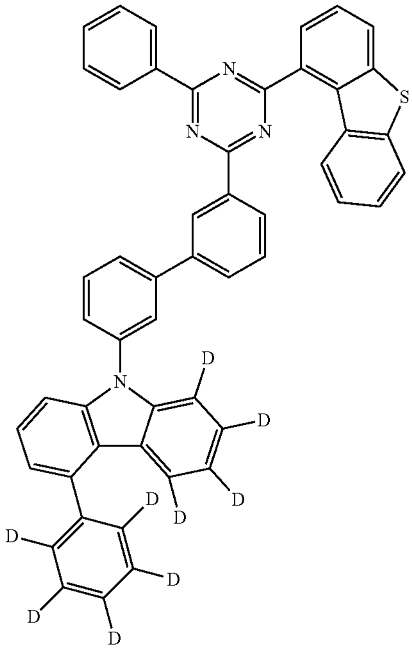
A99
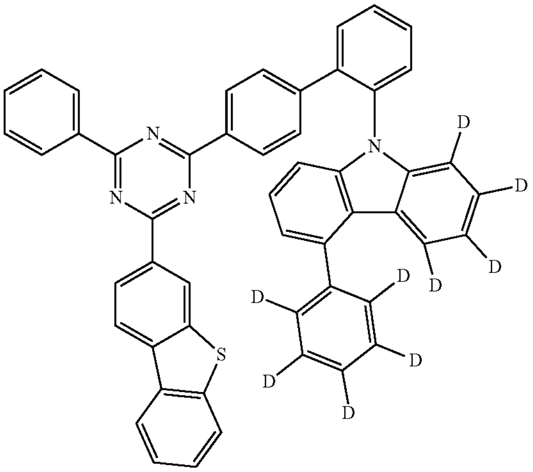

-continued
A100
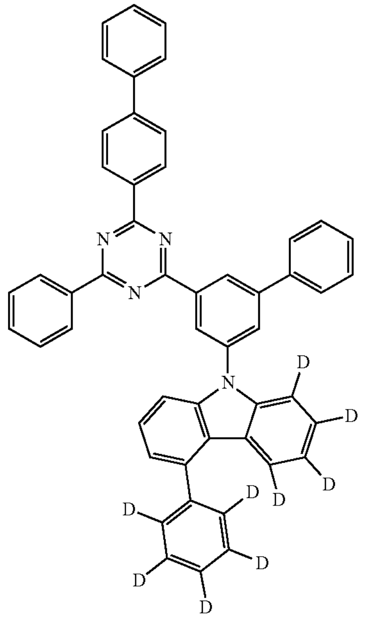
A101
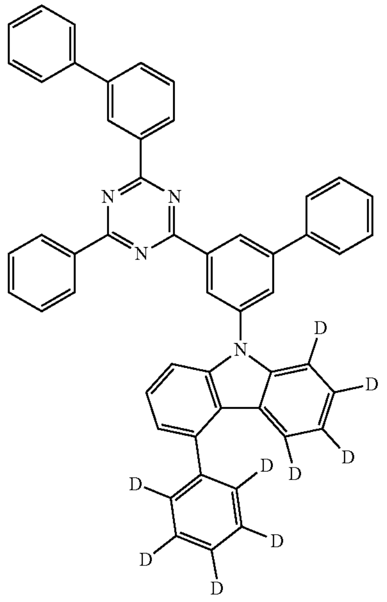
-continued
A102
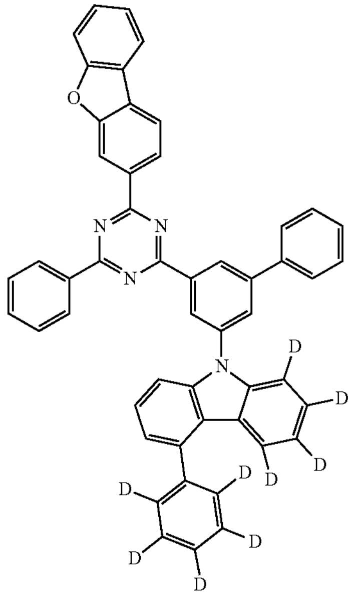
A103
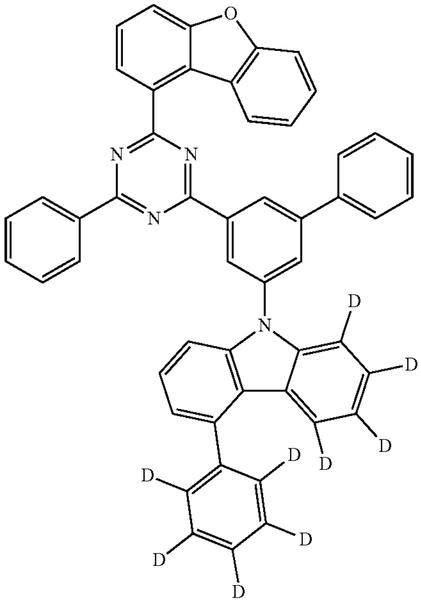

-continued
A104
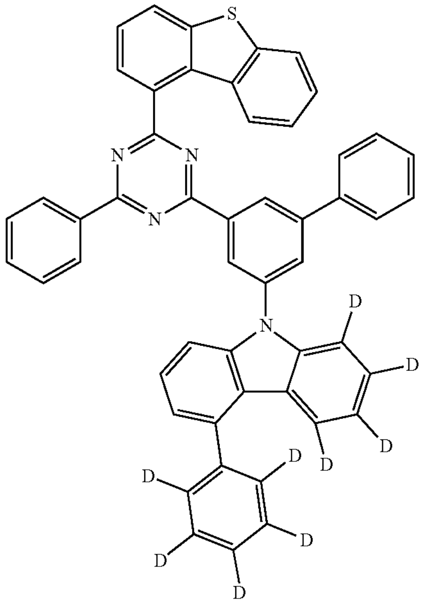
A105
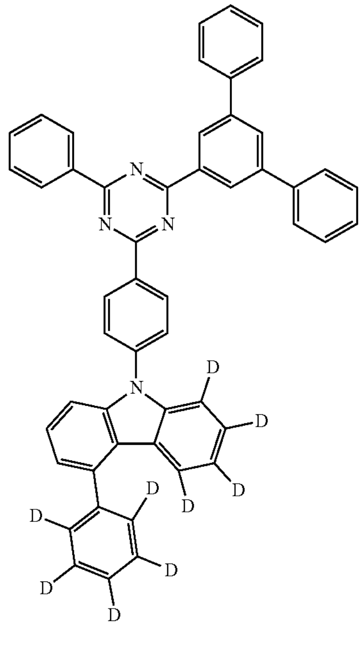
-continued
A106
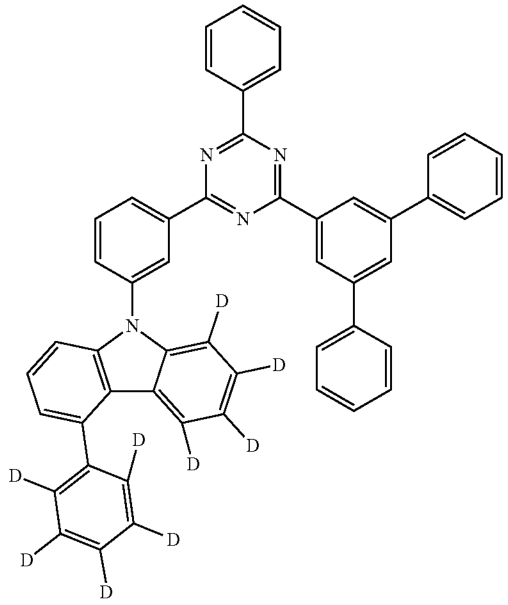
A107
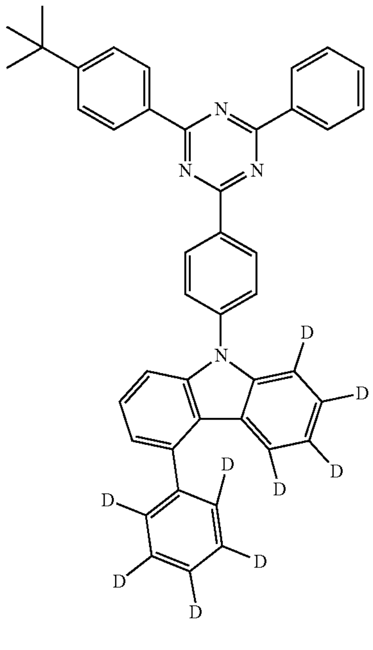

-continued
A108
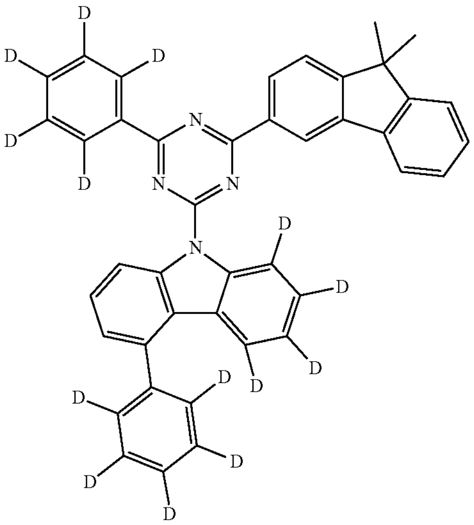
A109
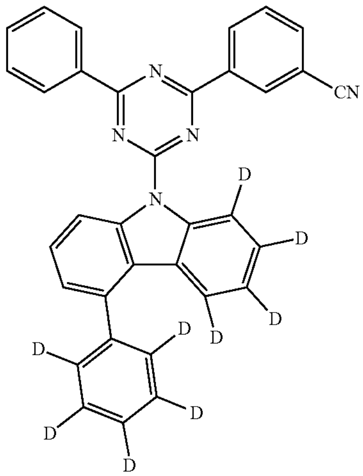
A220
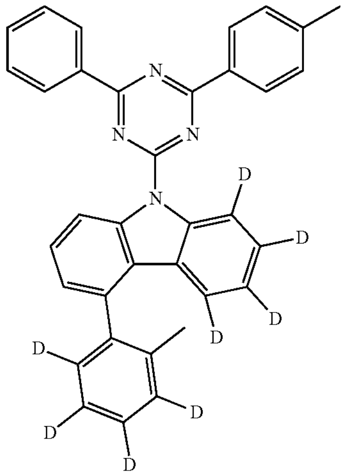
-continued
A221
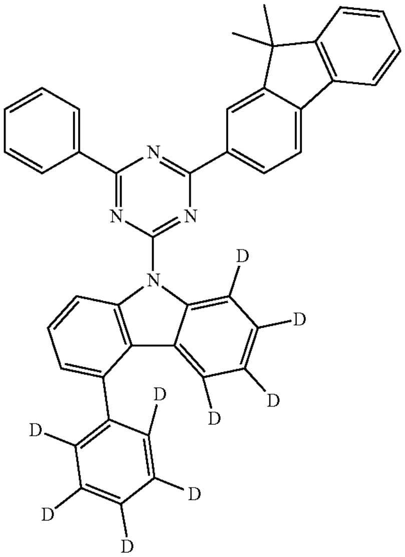
A222
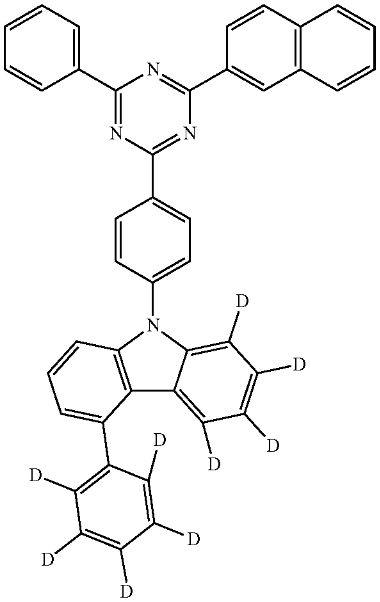
B1
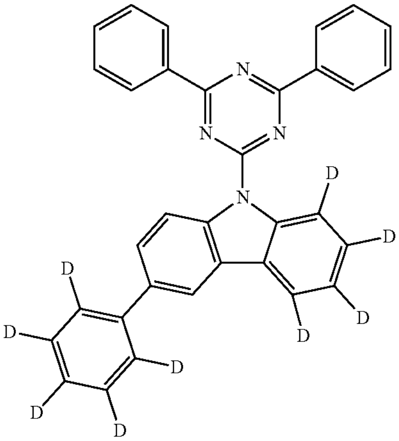

-continued
B2
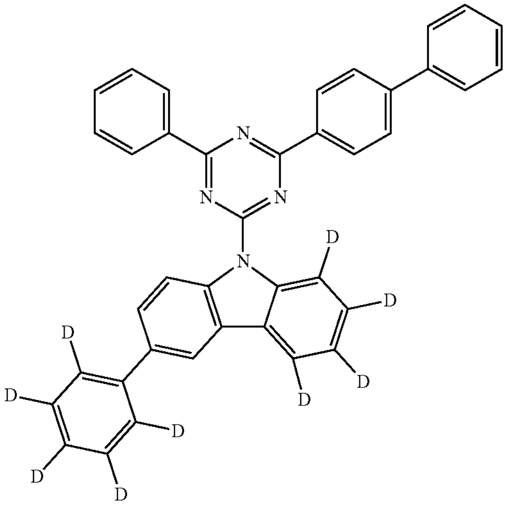
B3
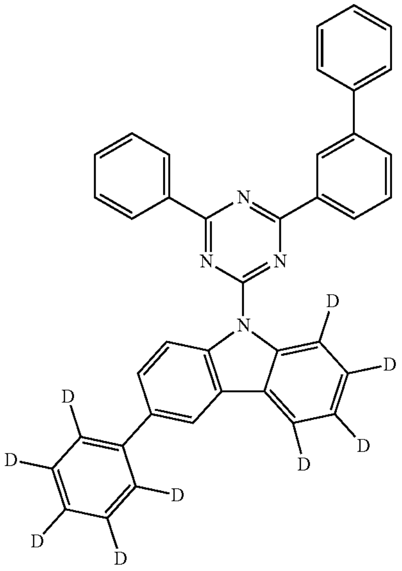
B4
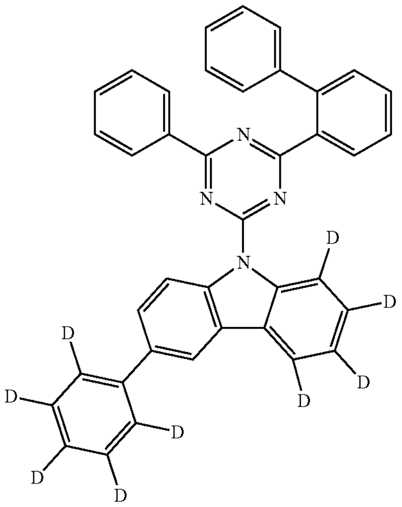
-continued
B5
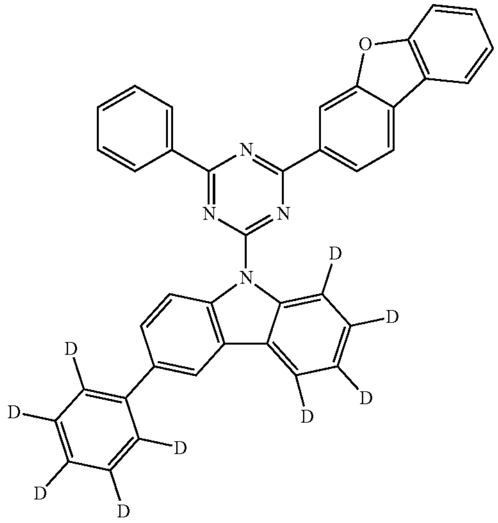
B6
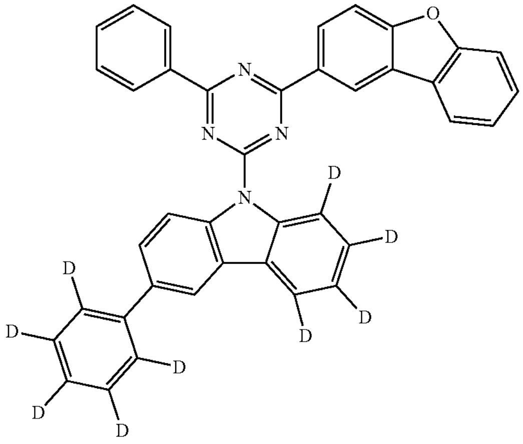
B7
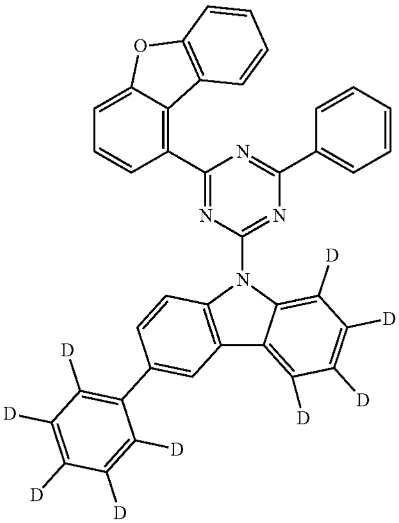

-continued
B8
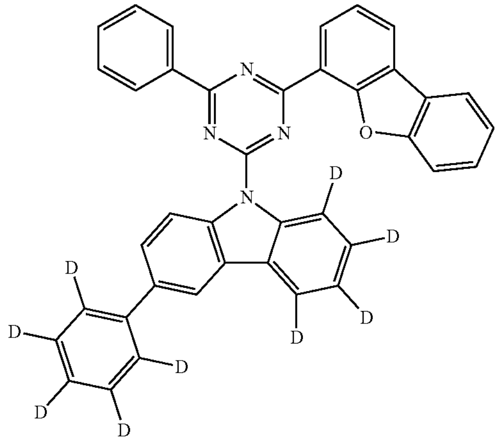
B9
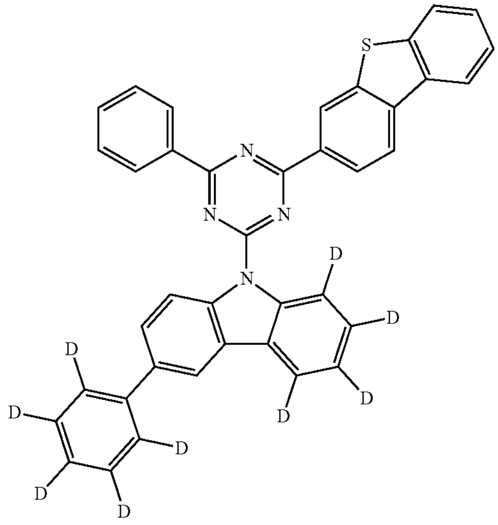
B10
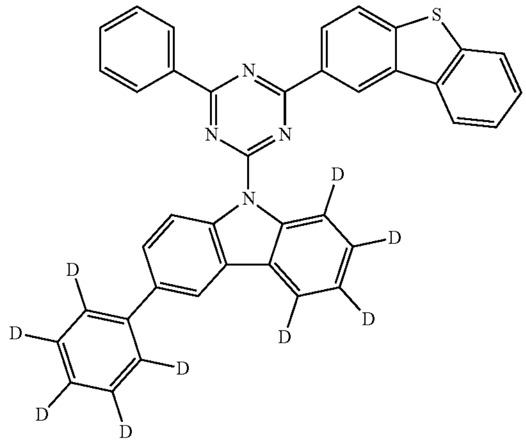
-continued
B11
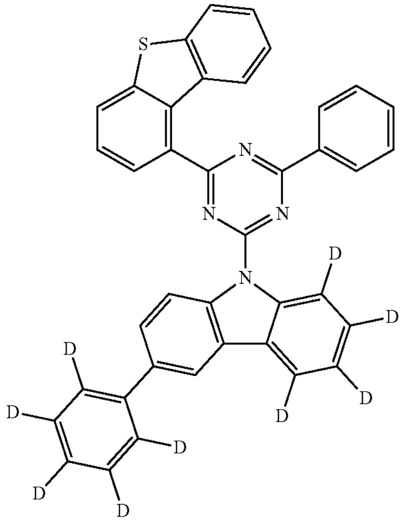
B12
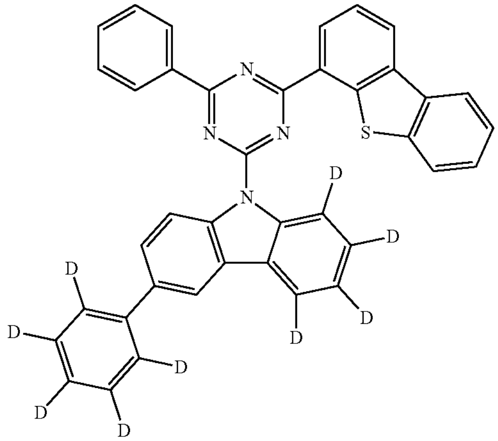
B13
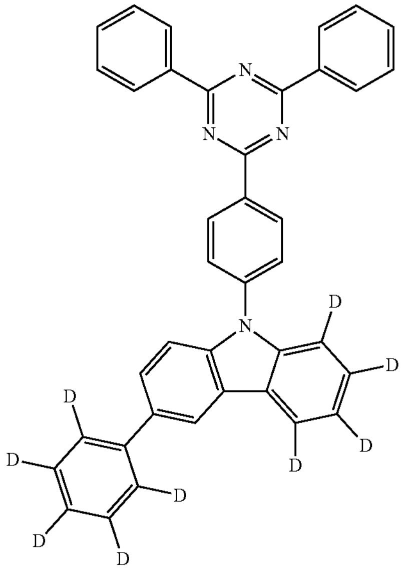

-continued
B14
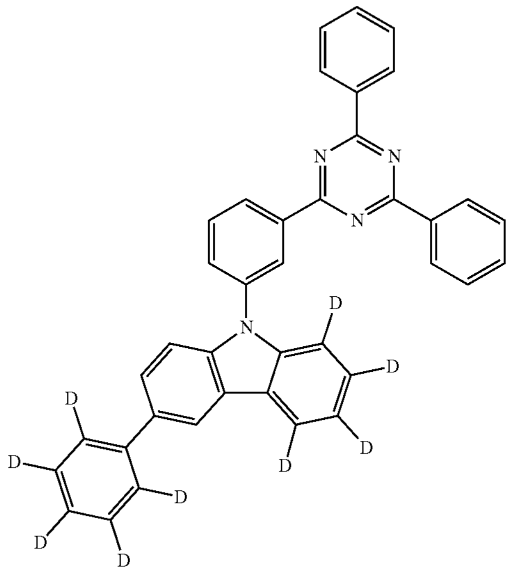
B15
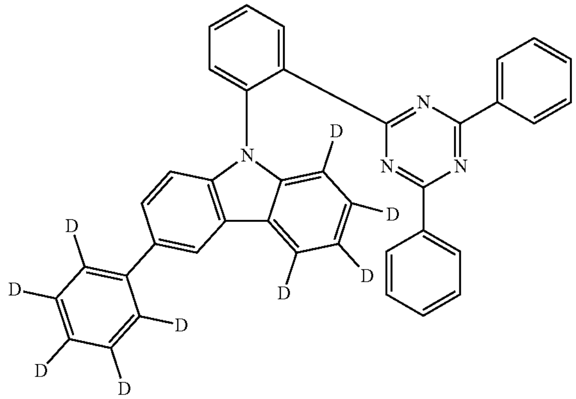
B16
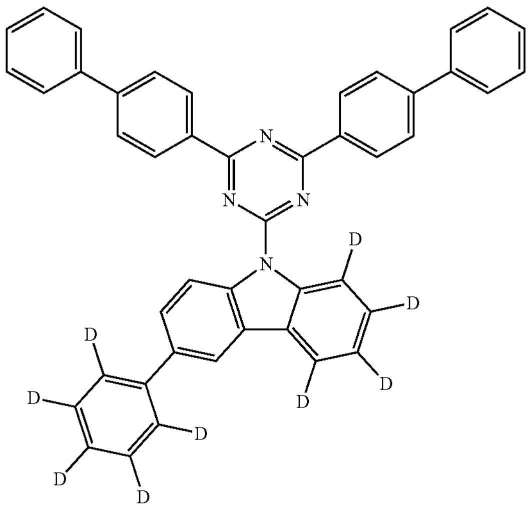
-continued
B17
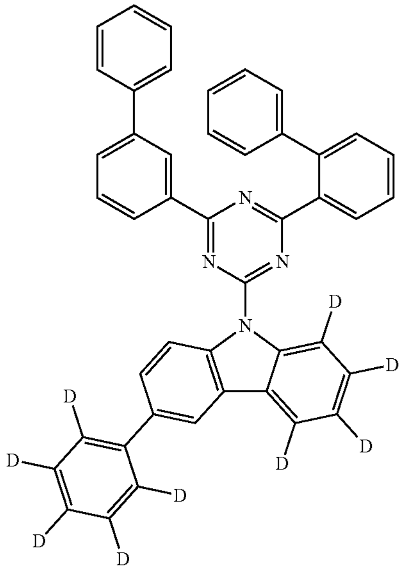
B18
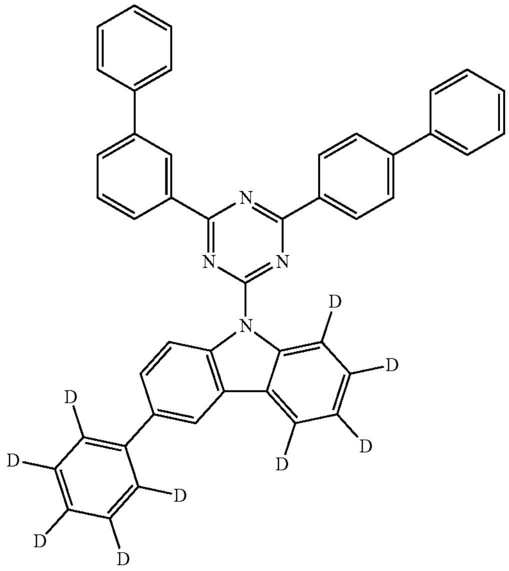

-continued
B19
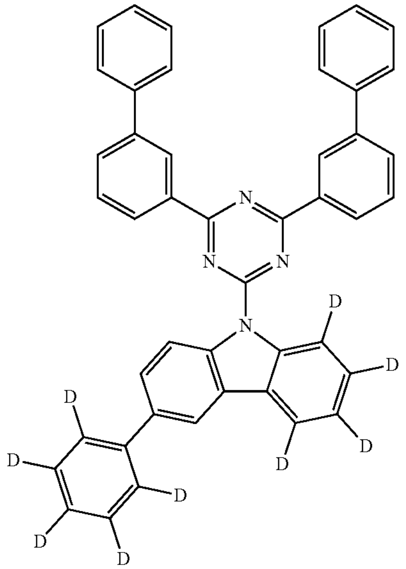
B20
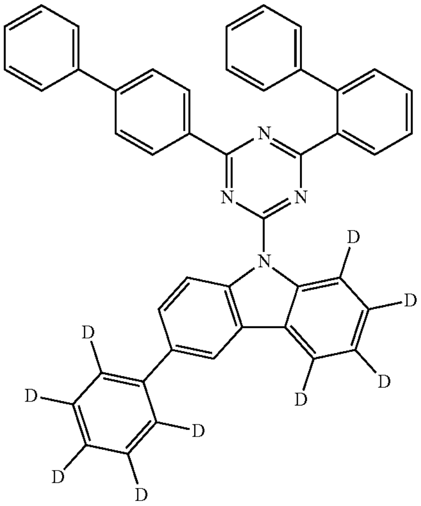
B21
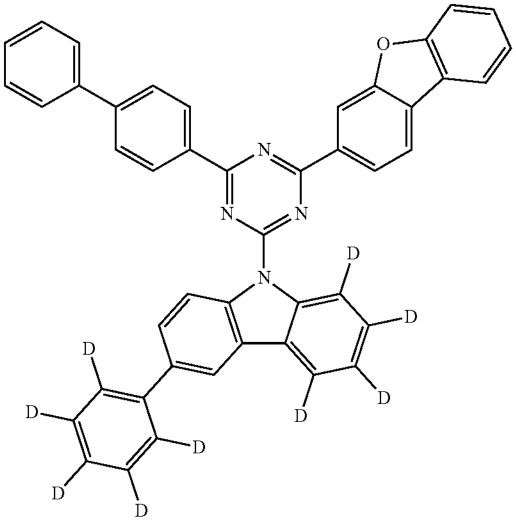
-continued
B22
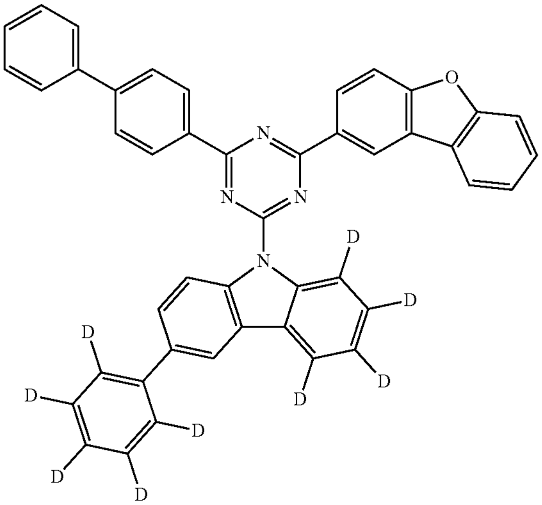
B23
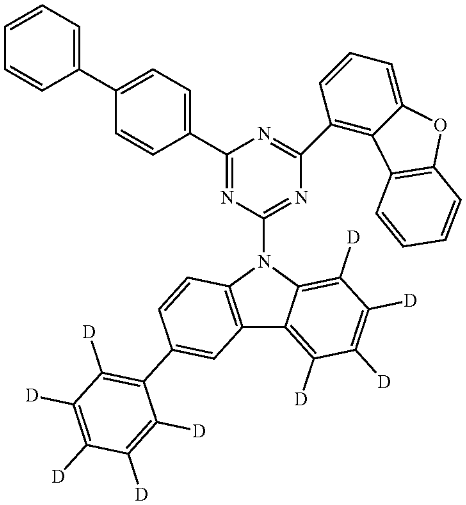
B24
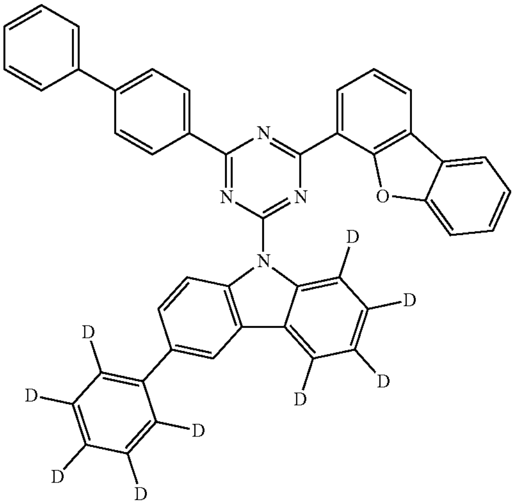

-continued
B25
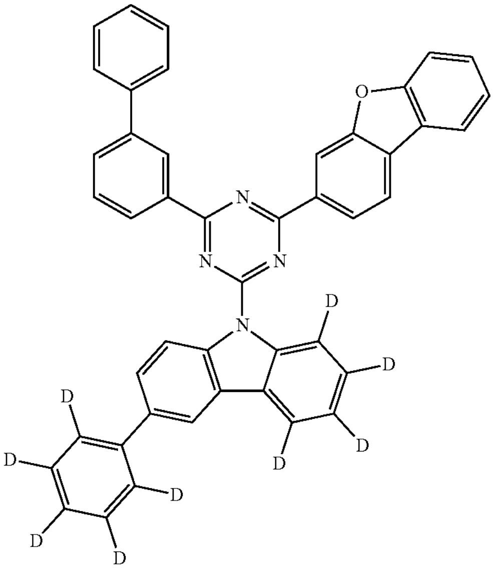
B26
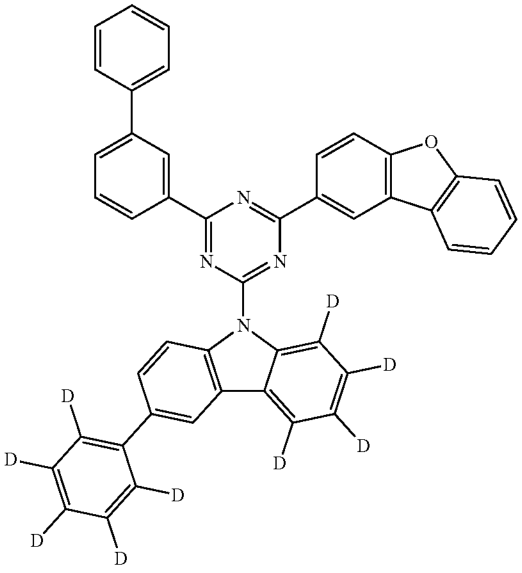
-continued
B27
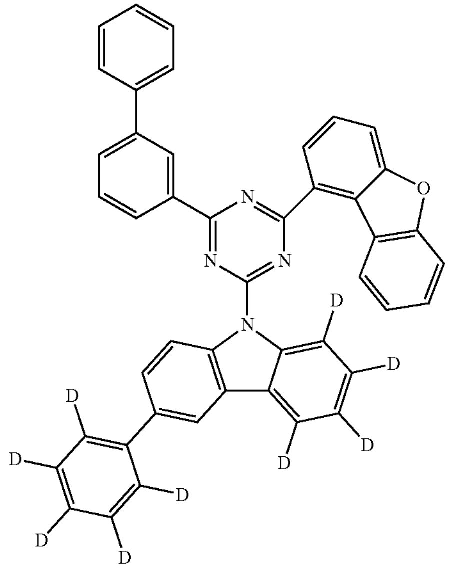
B28
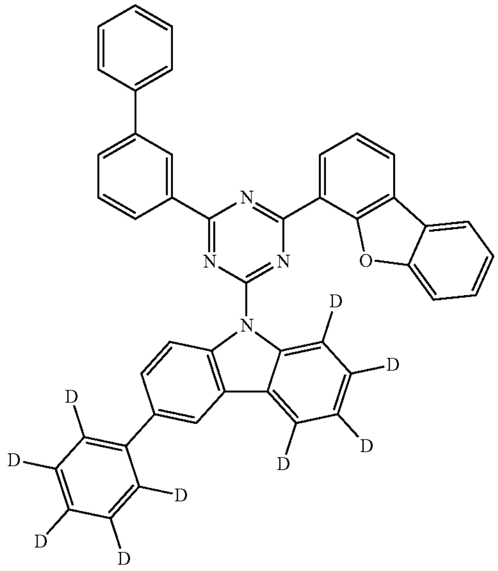
B29
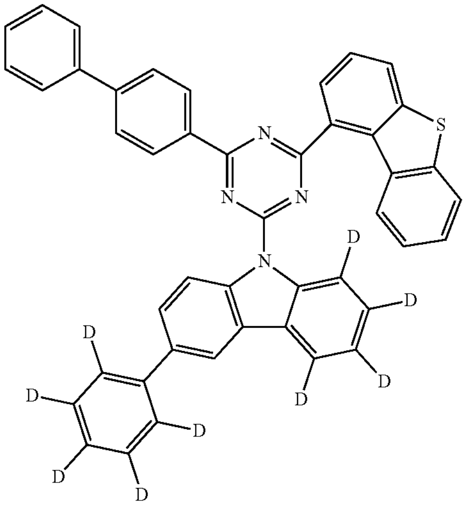

-continued
B30
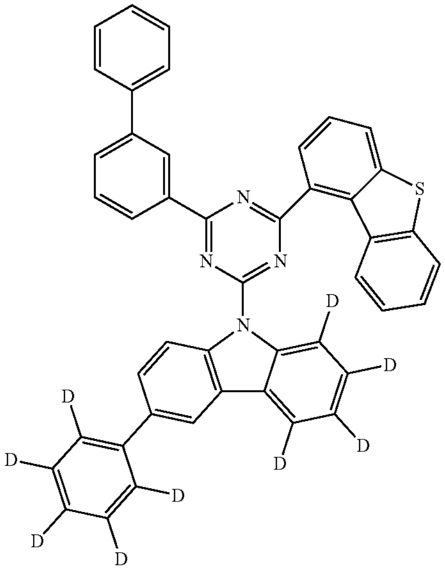
B31
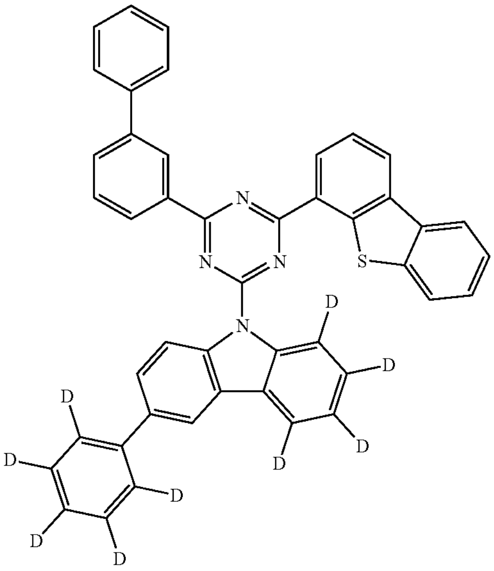
-continued
B34
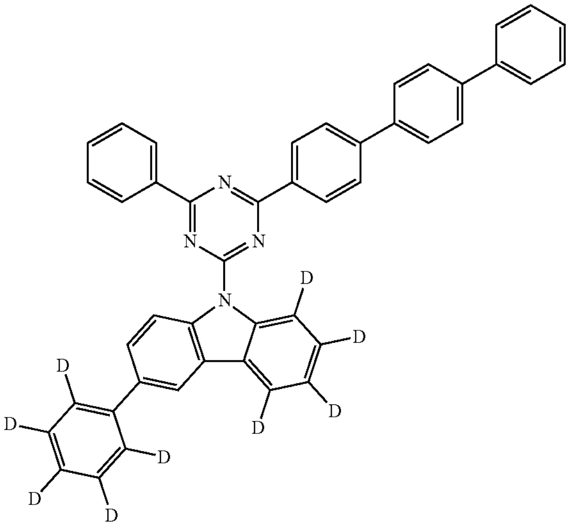
B35
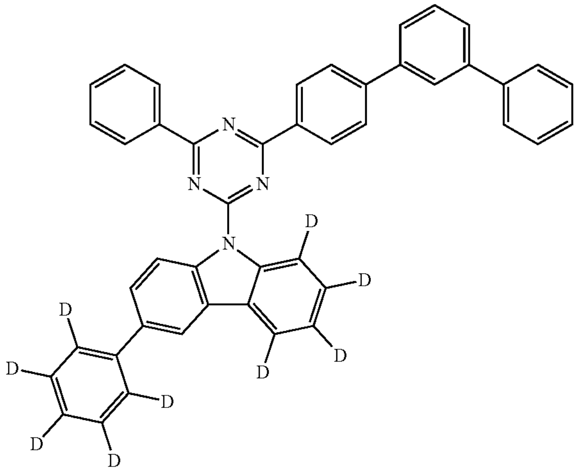
B36
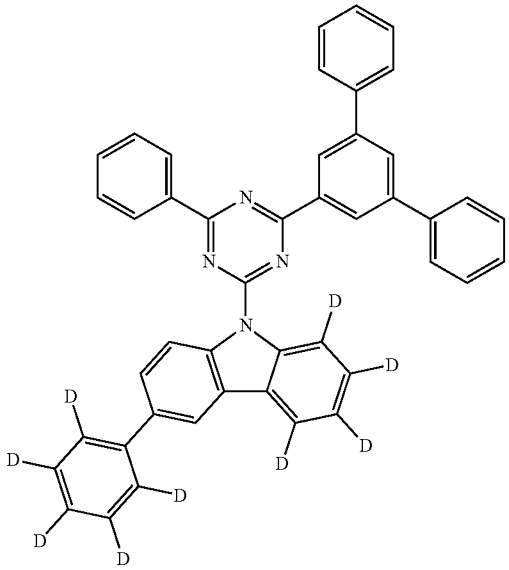

472
-continued
B37
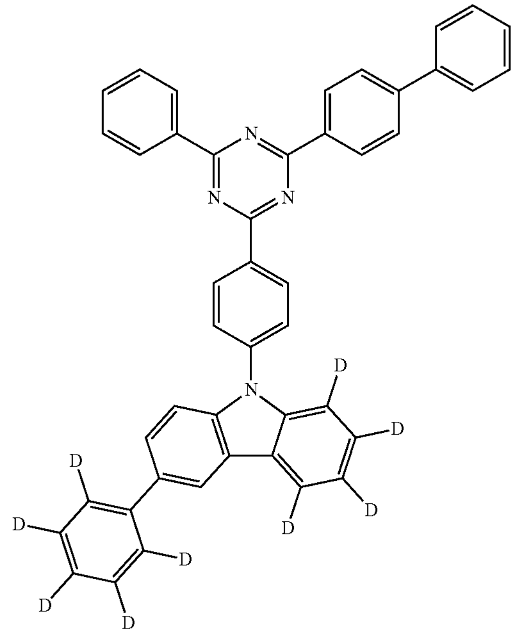
B39
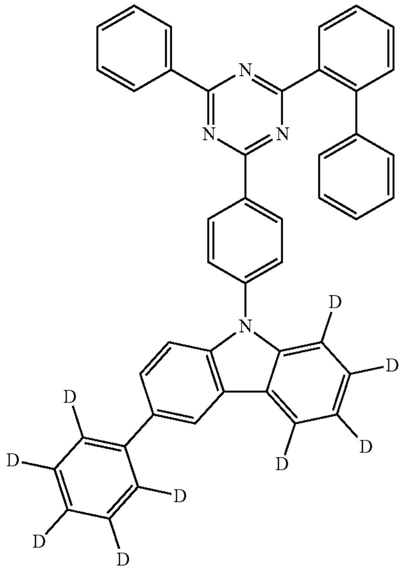
B38
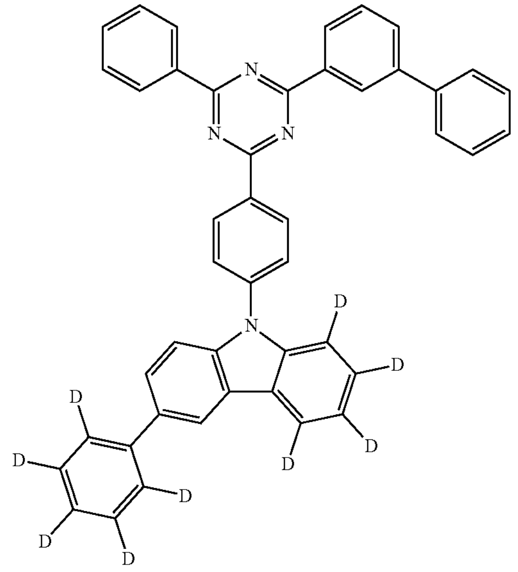
B40
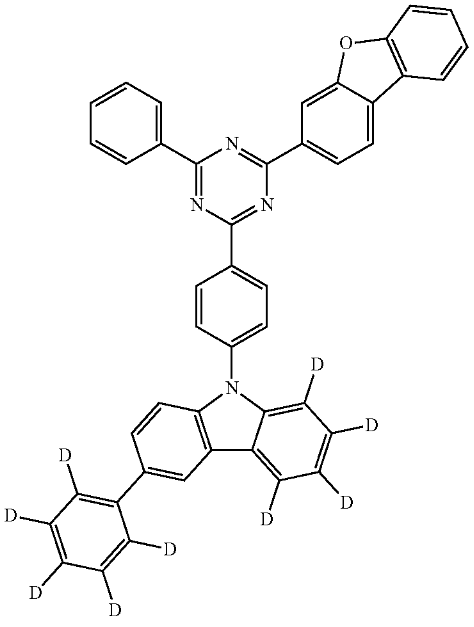

-continued
B41
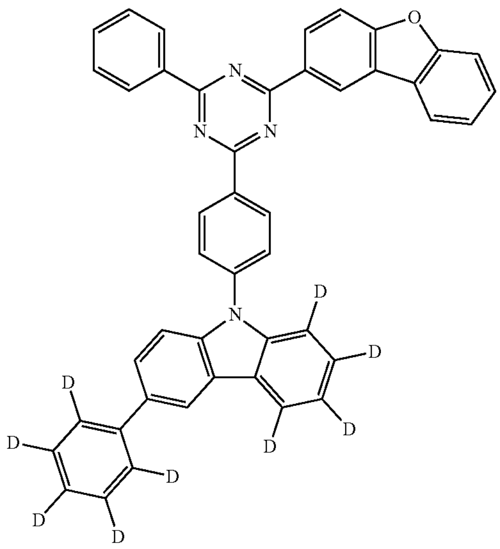
B42
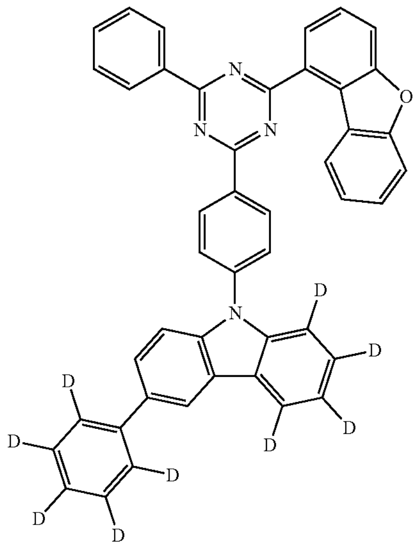
B43
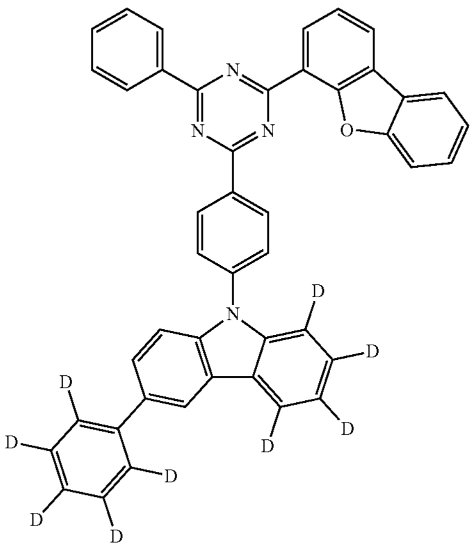
-continued
B44
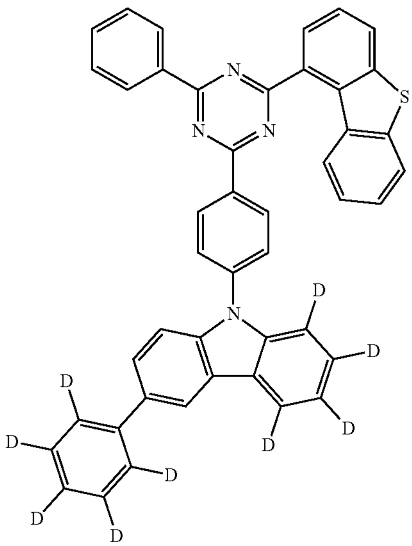
B45
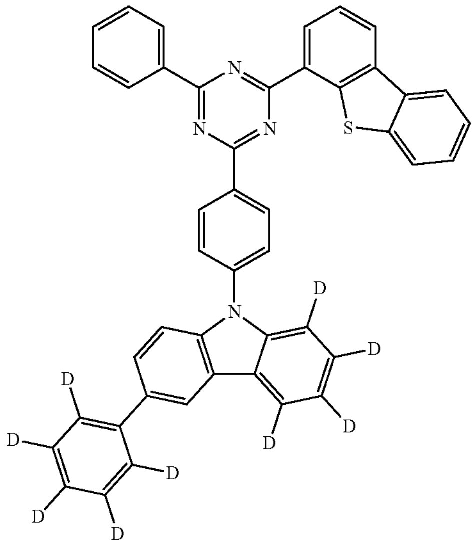

B46
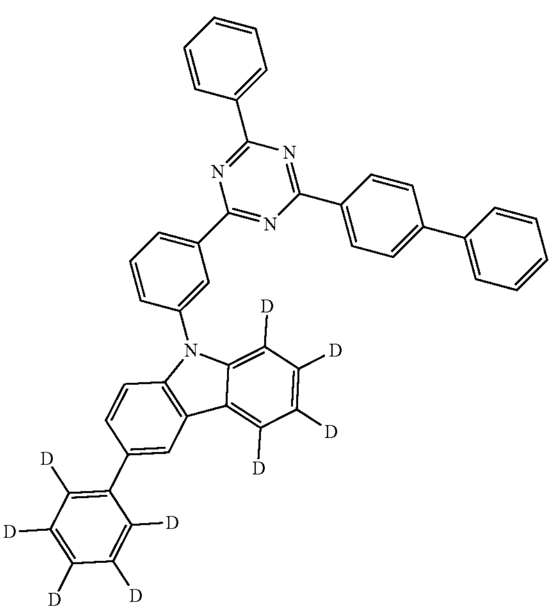
B47
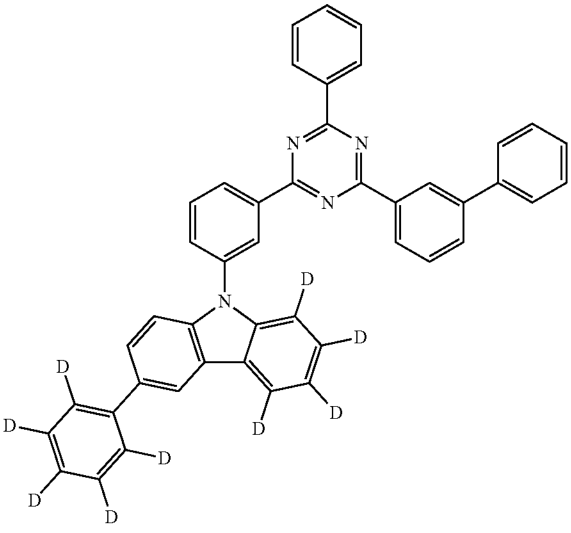
B48
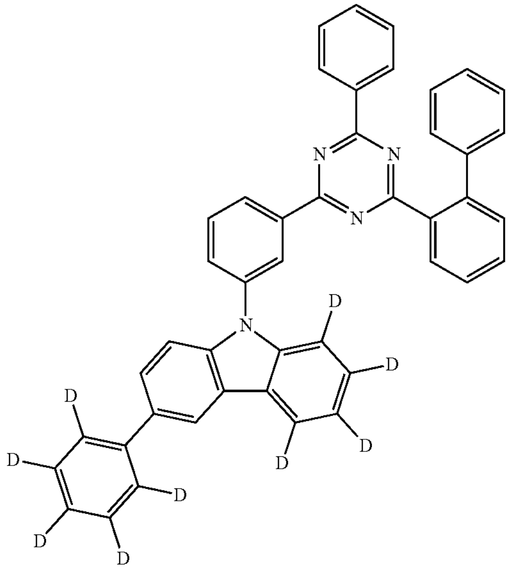
B49
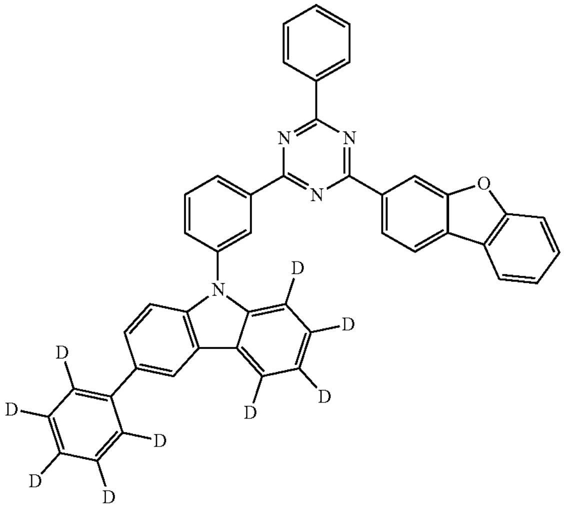

-continued
B50
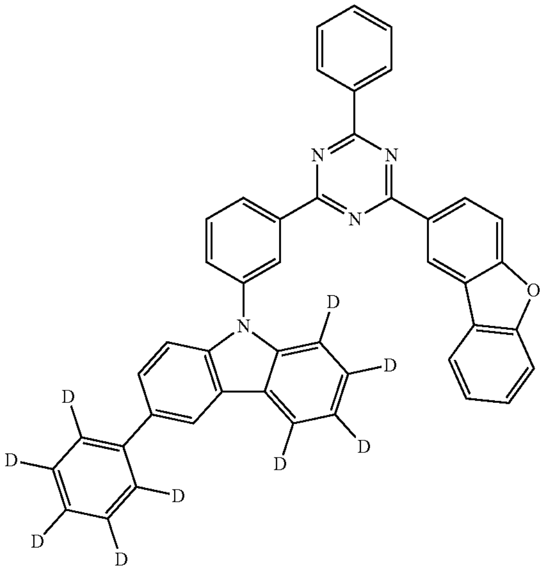
B51
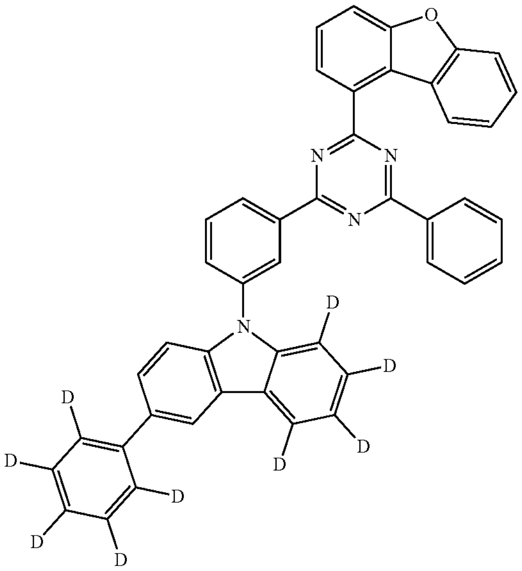
-continued
B52
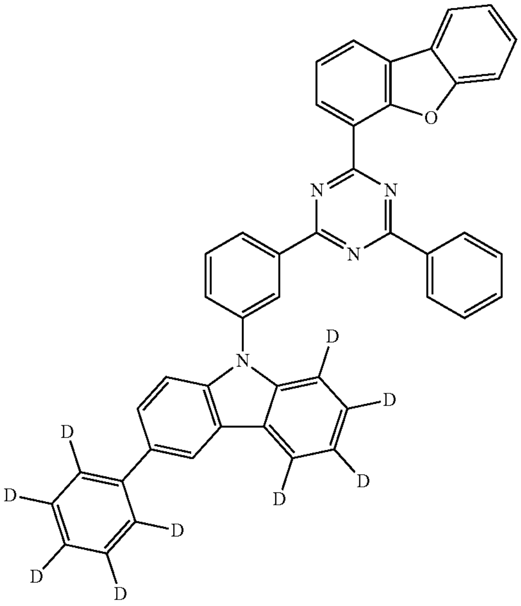
B53
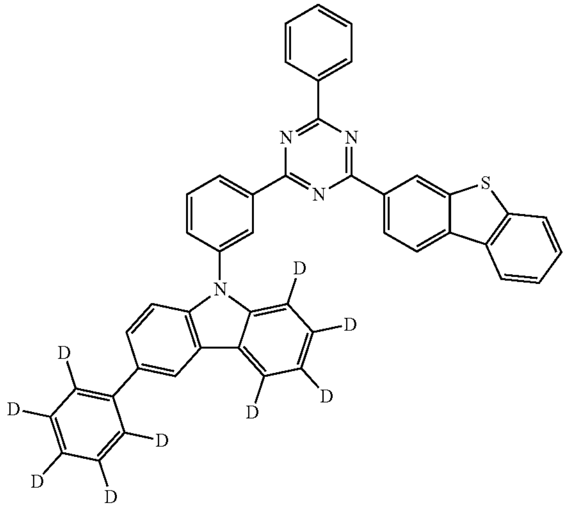

-continued
B54
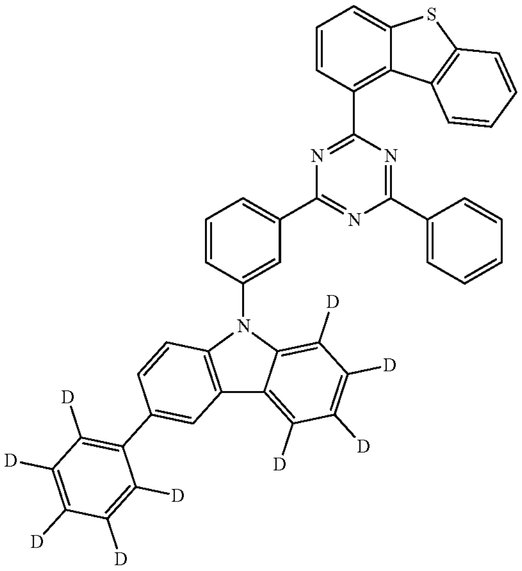
B55
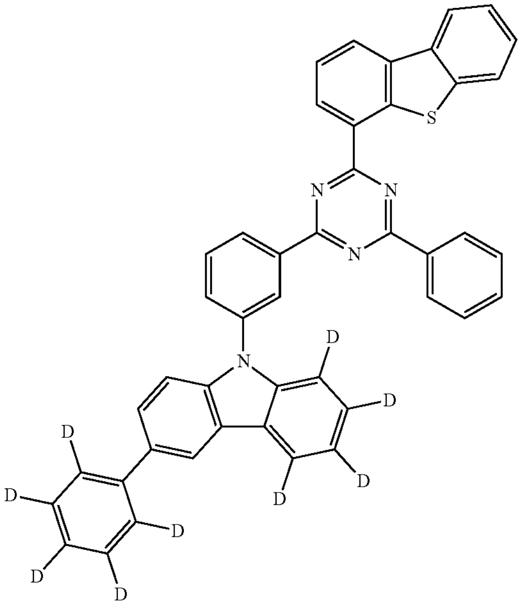
-continued
B56
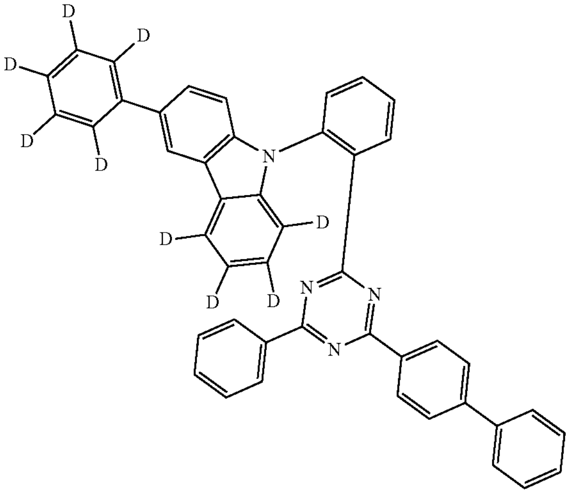
B57
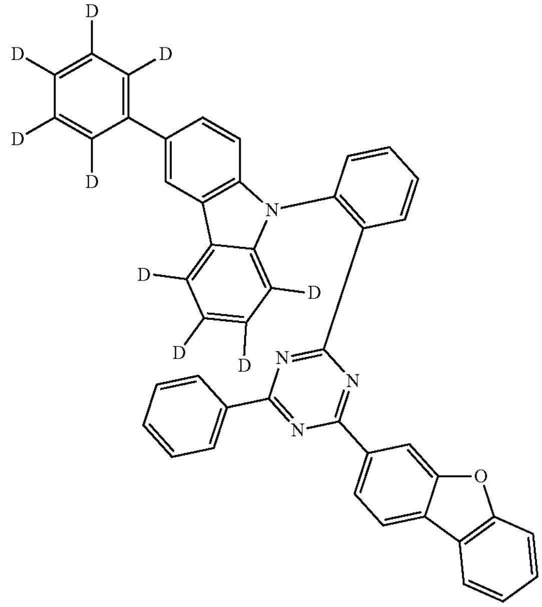

-continued
B58
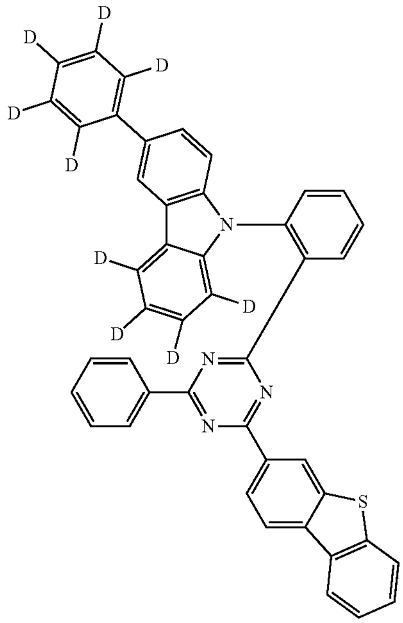
B59
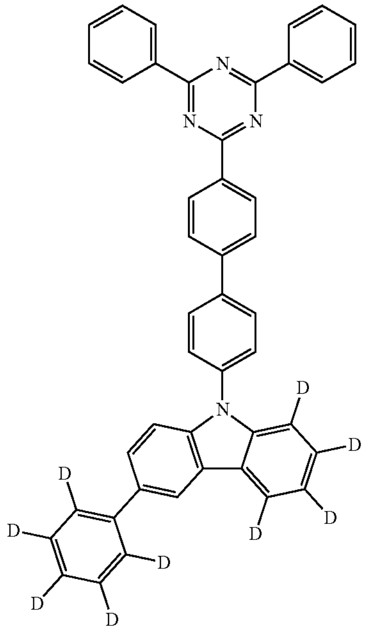
-continued
B60
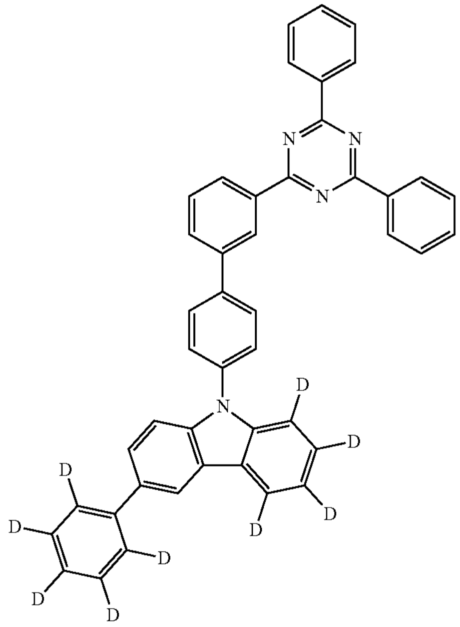
B61
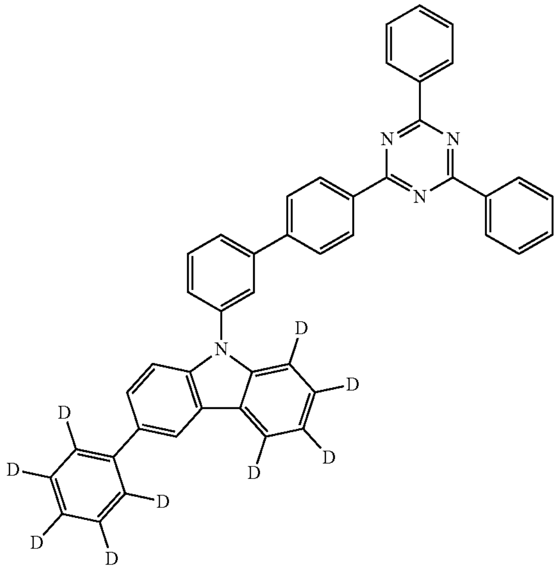

-continued
B62
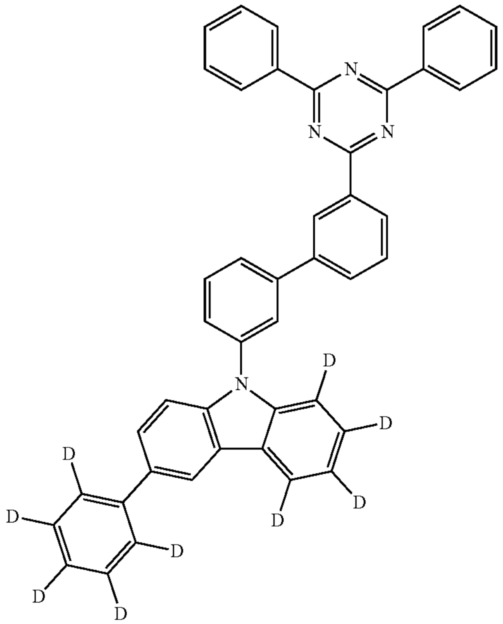
B63
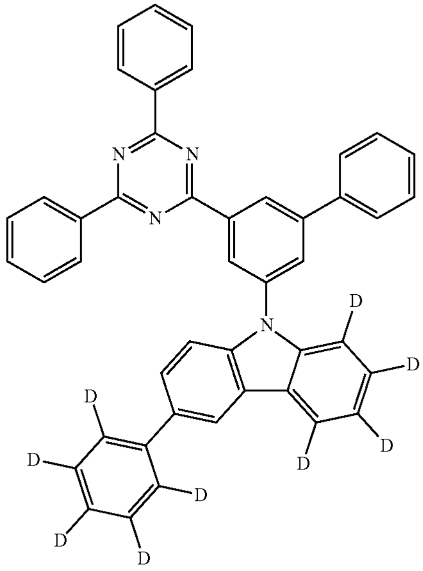
B64
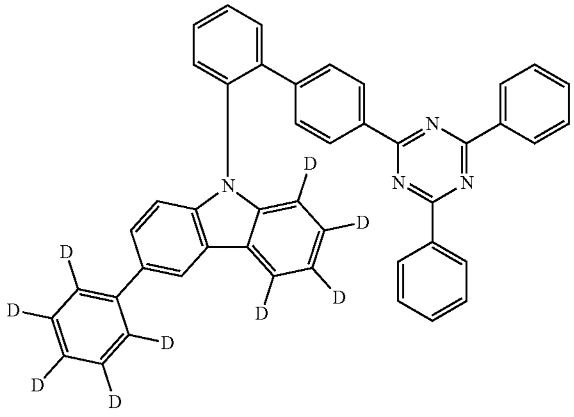
-continued
B65
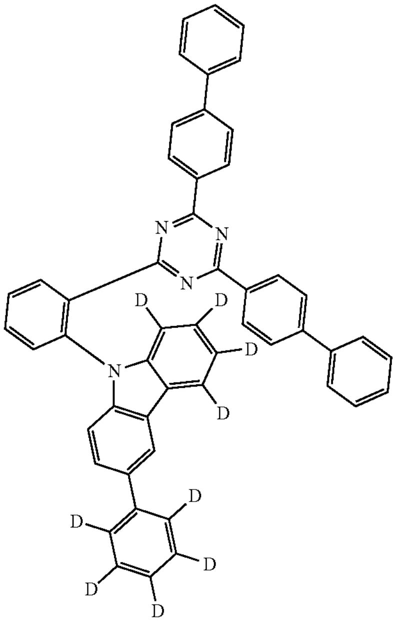
B66
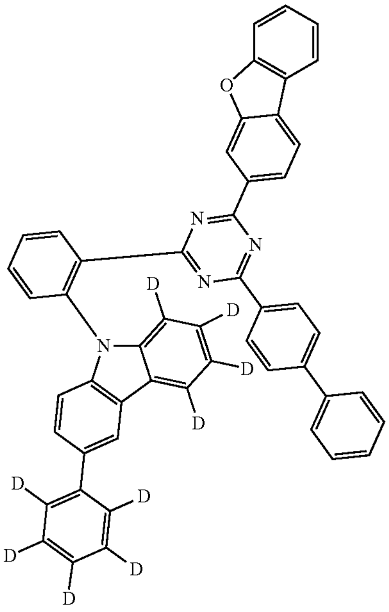

-continued
B67
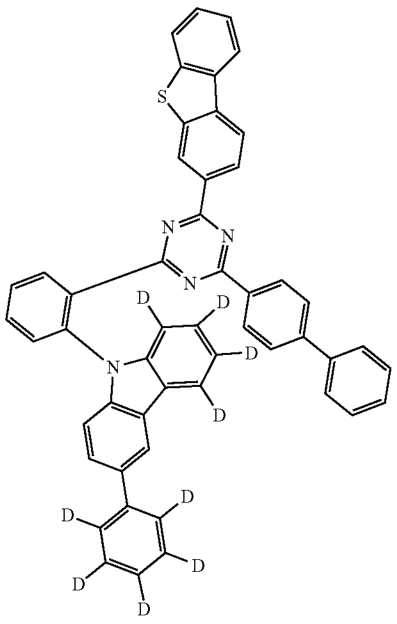
-continued
B70
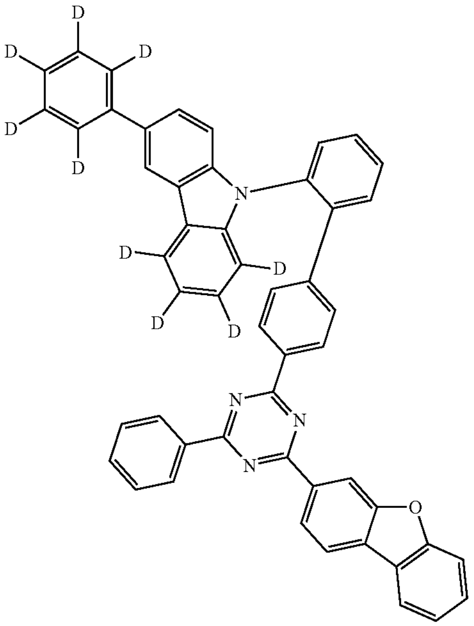
B69
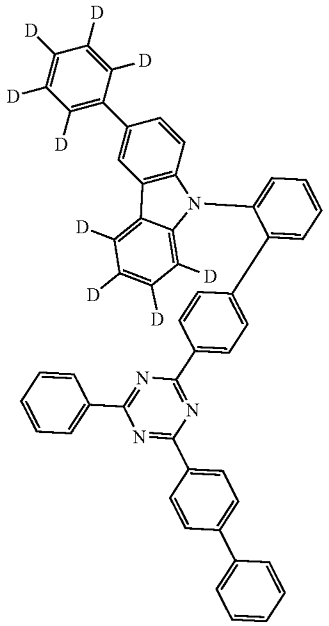
B71
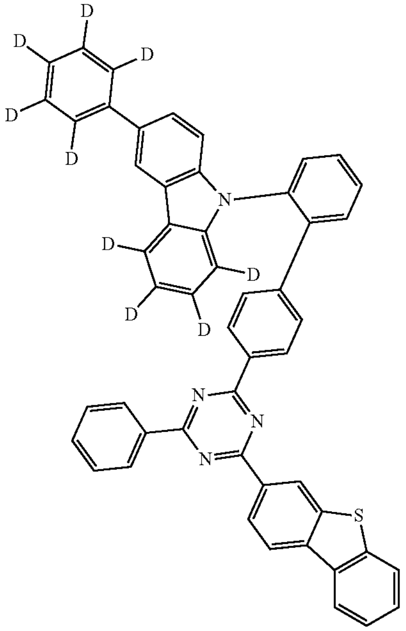

-continued
B72
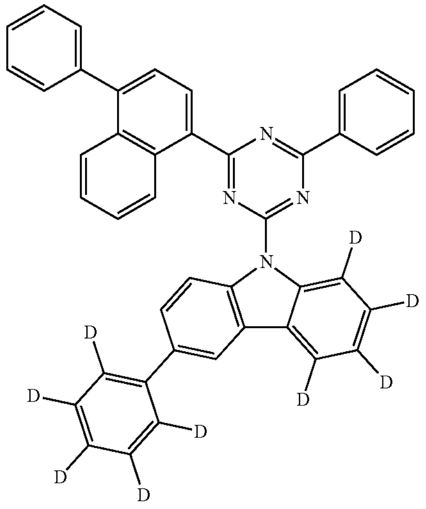
C1
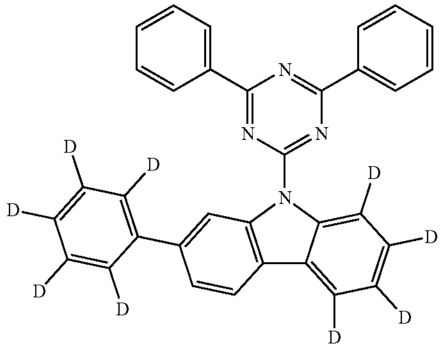
C2
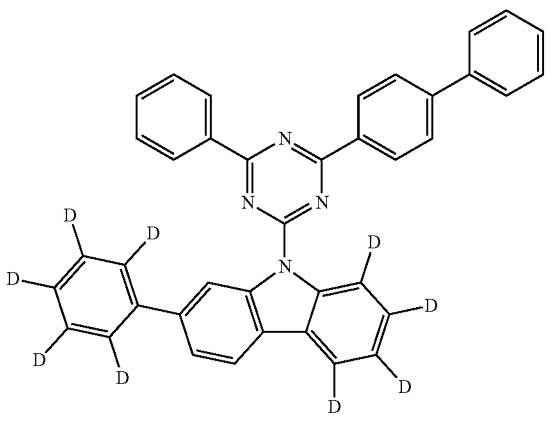
-continued
C3
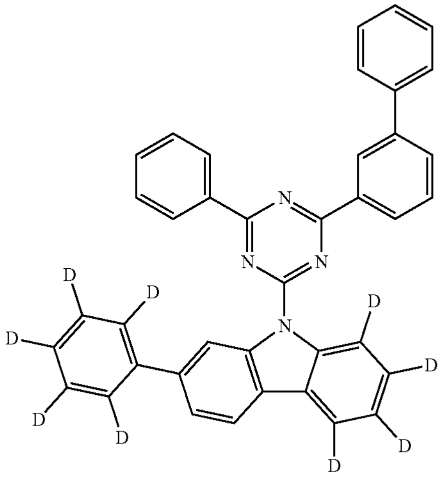
C4
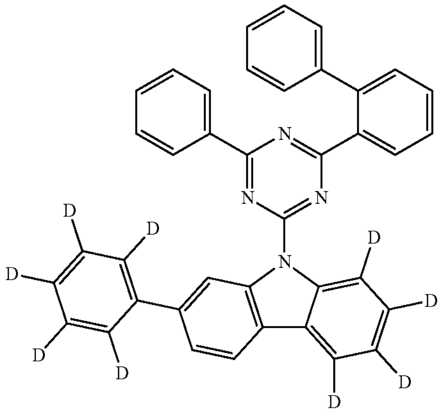
C5
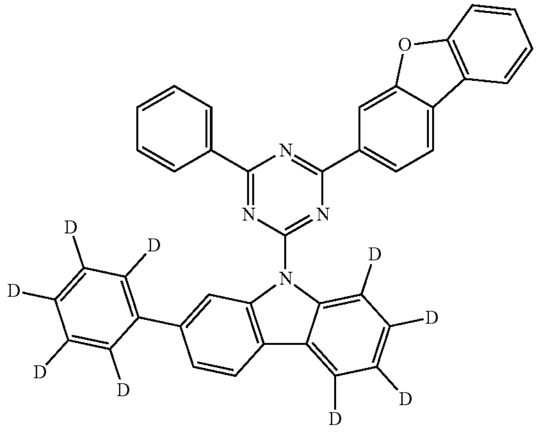

-continued
C6
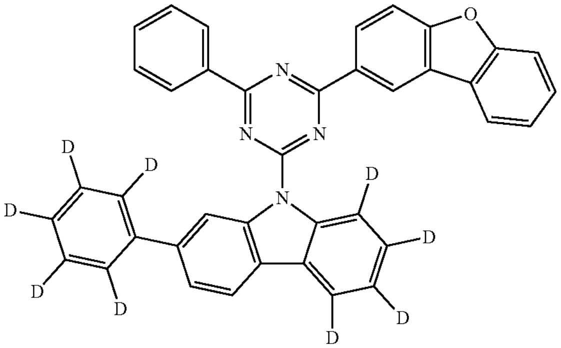
C7
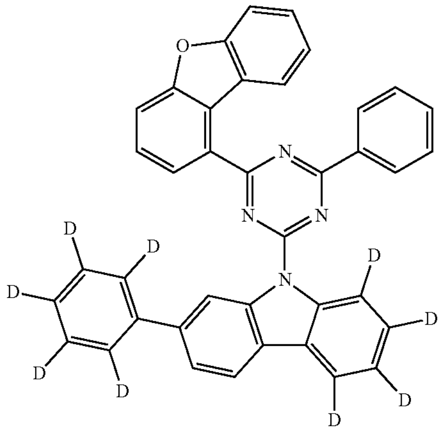
C8
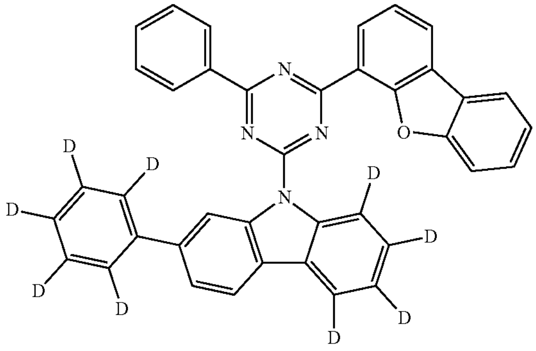
C9
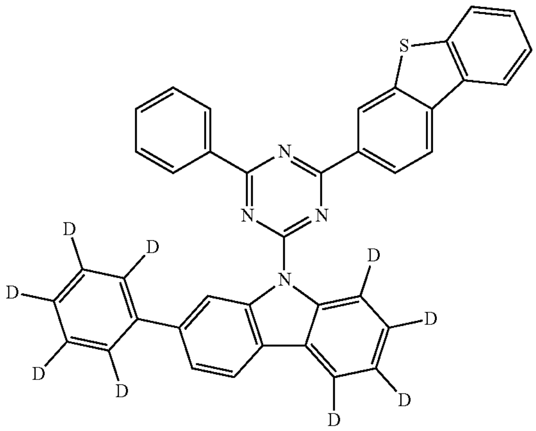
-continued
C10
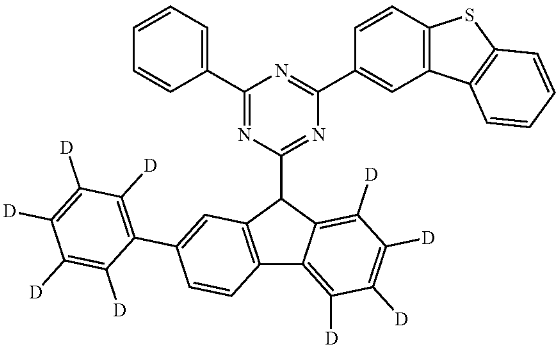
C11
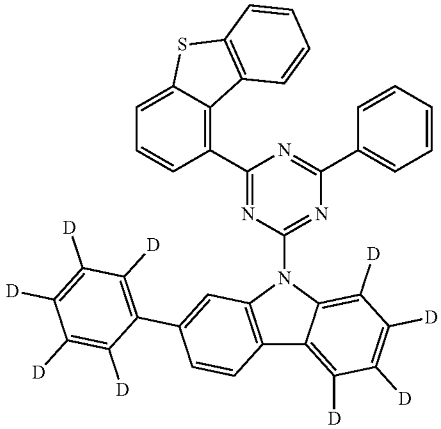
C12
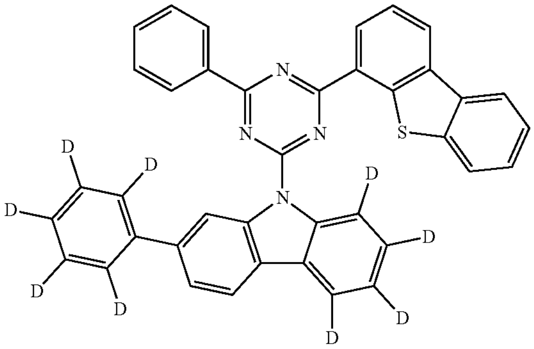
C13
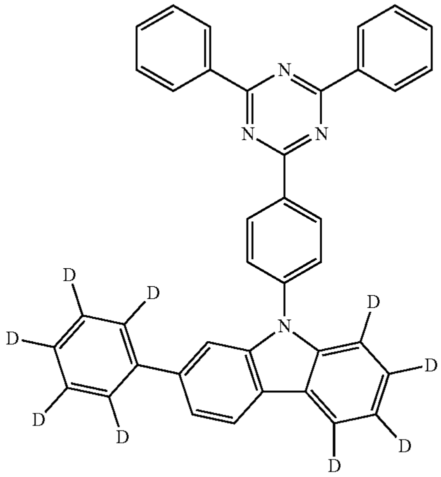

-continued
C14
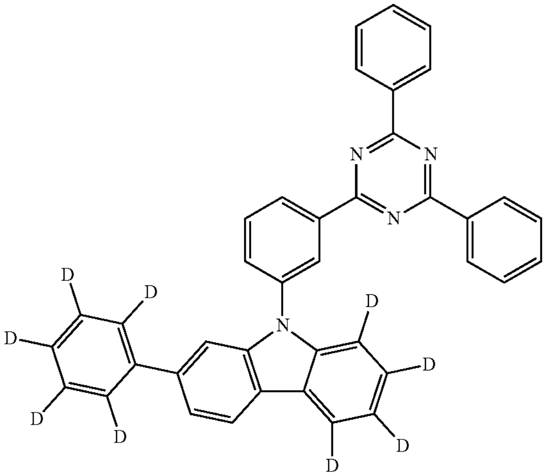
C15
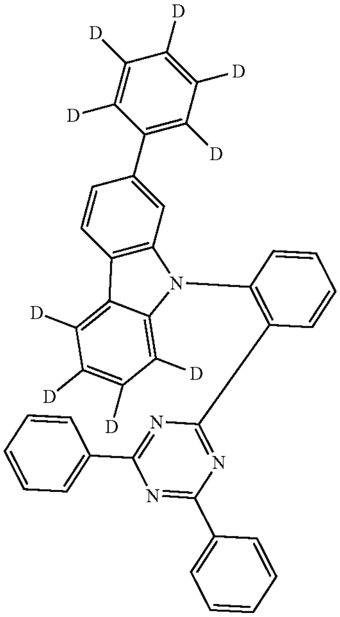
C16
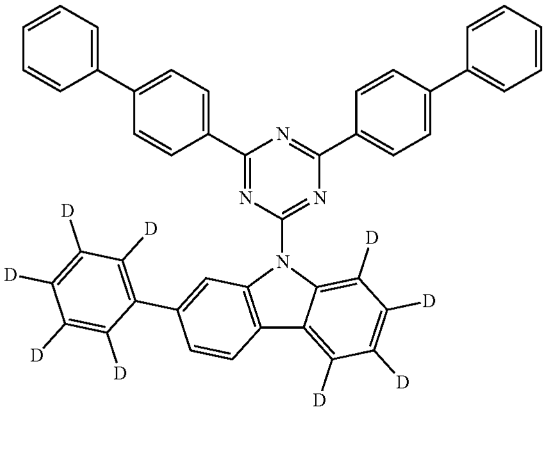
-continued
C17
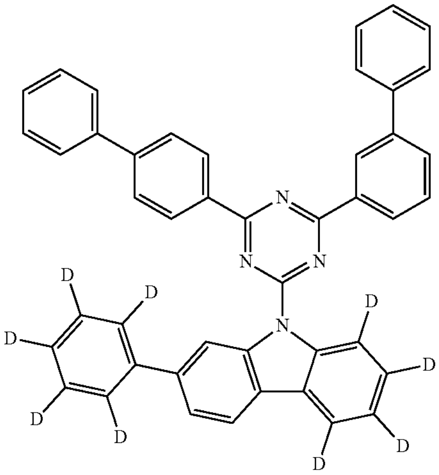
C18
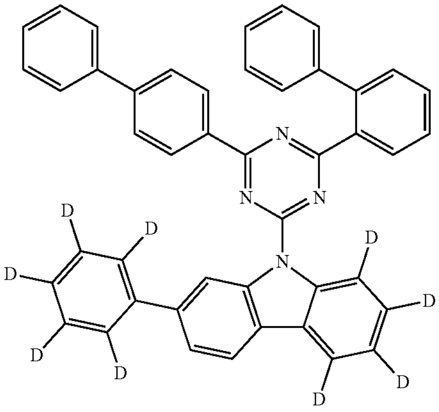
C19
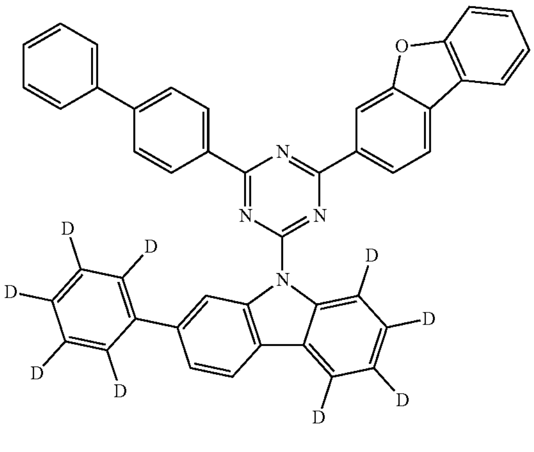

-continued
C20
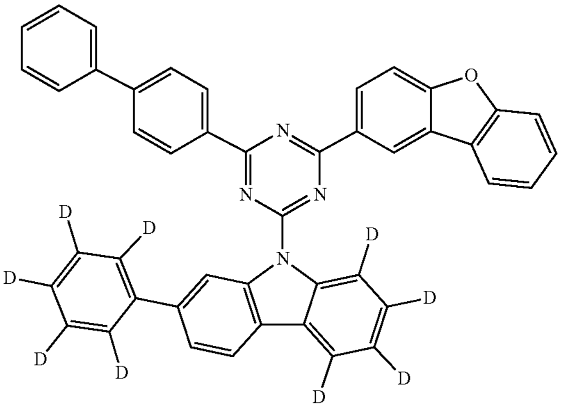
C21
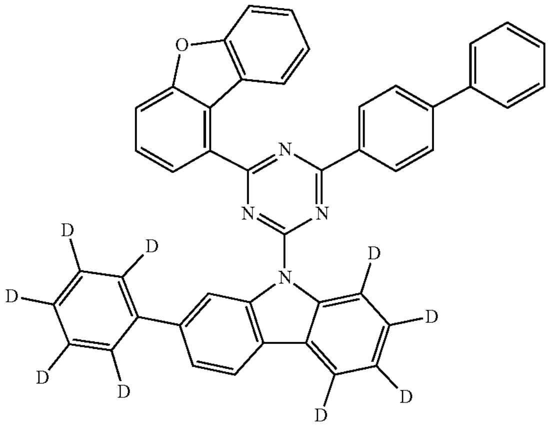
C22
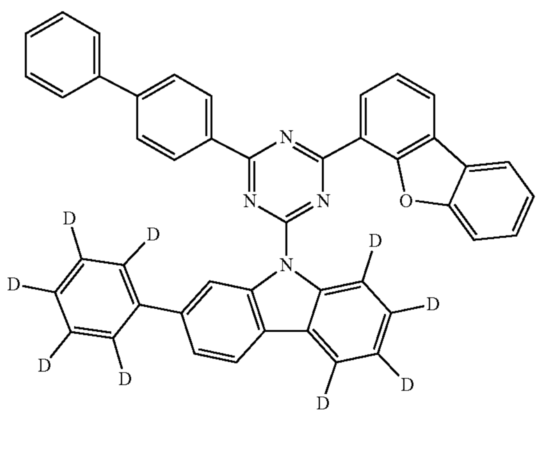
-continued
C23
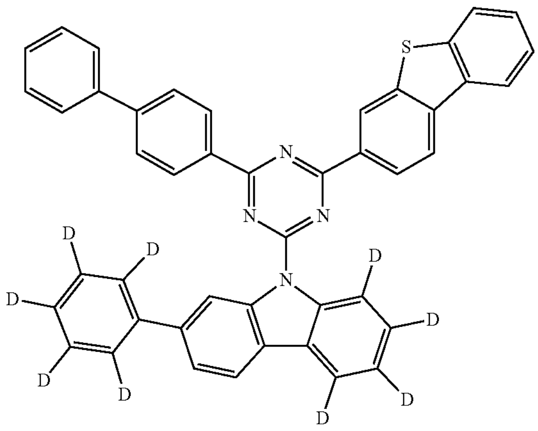
C24
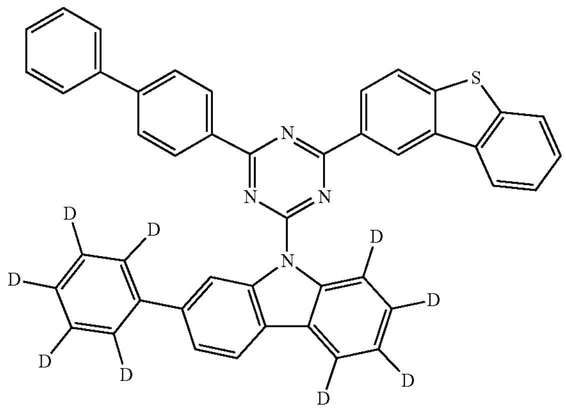
C25
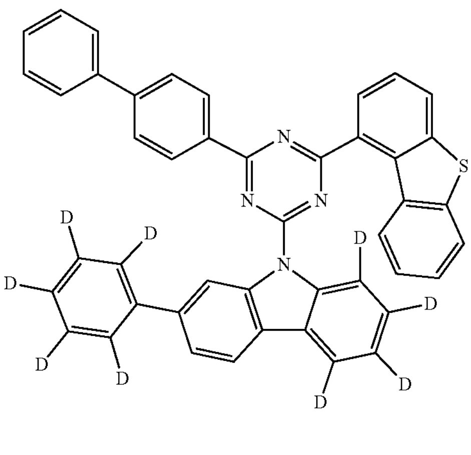

-continued
C26
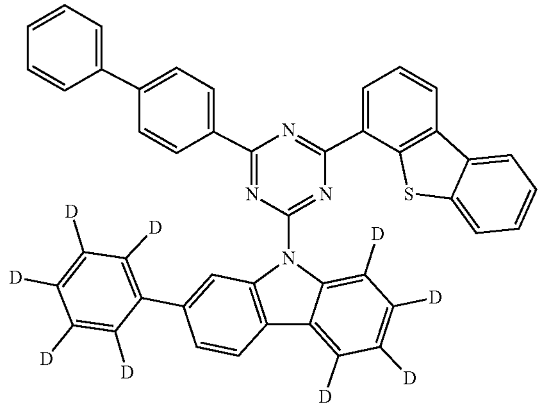
C27
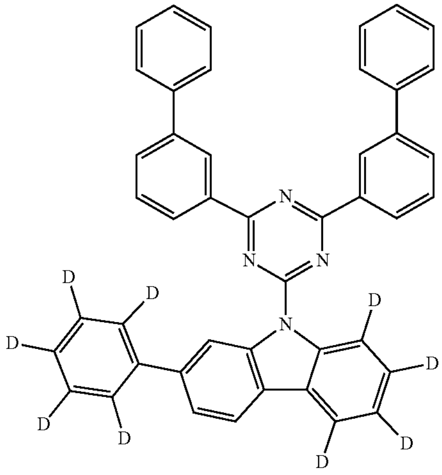
C28
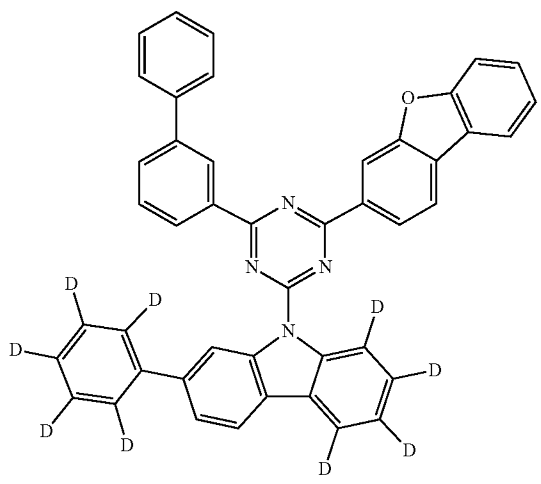
-continued
C29
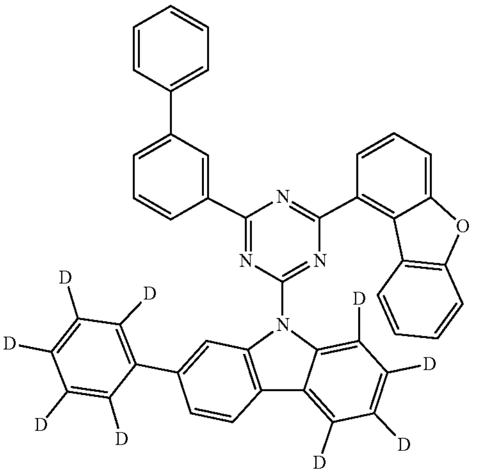
C30
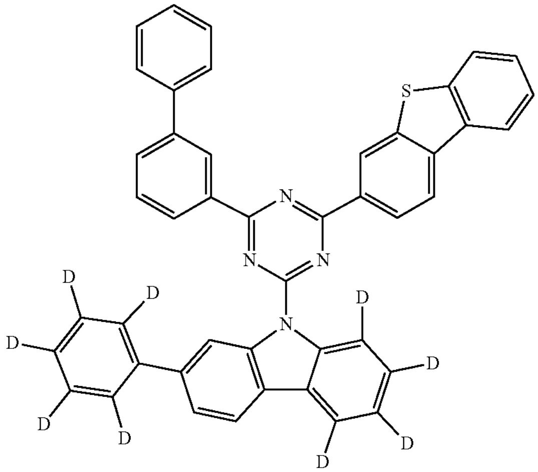
C31
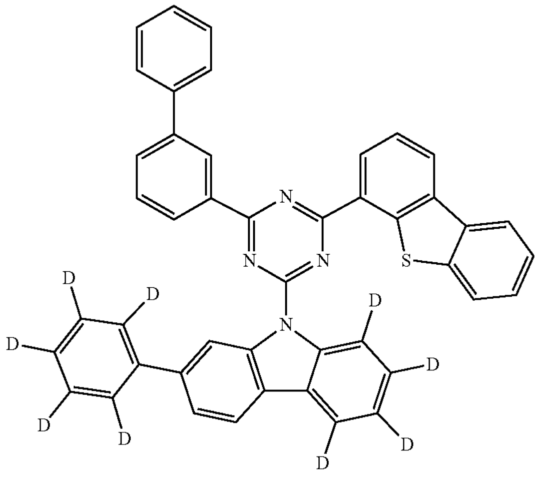

-continued
C35
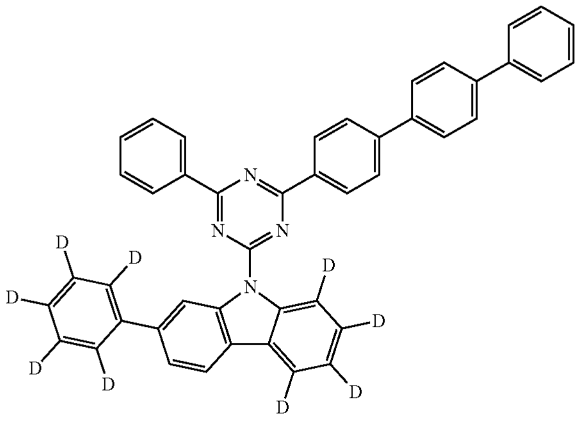
C36
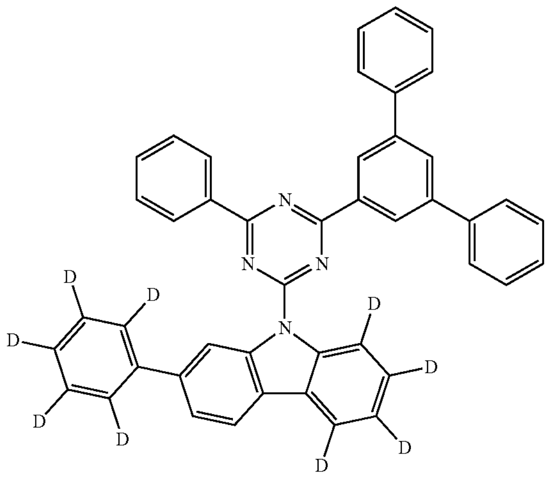
C37
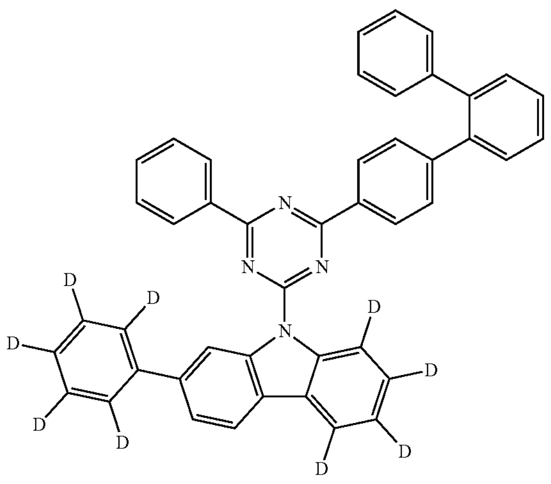
C38
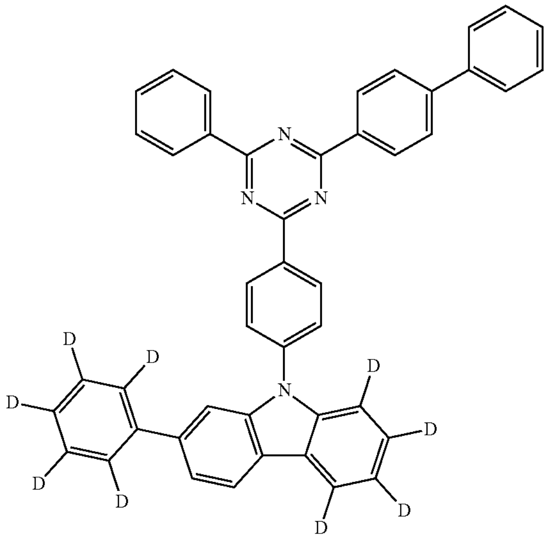
C39
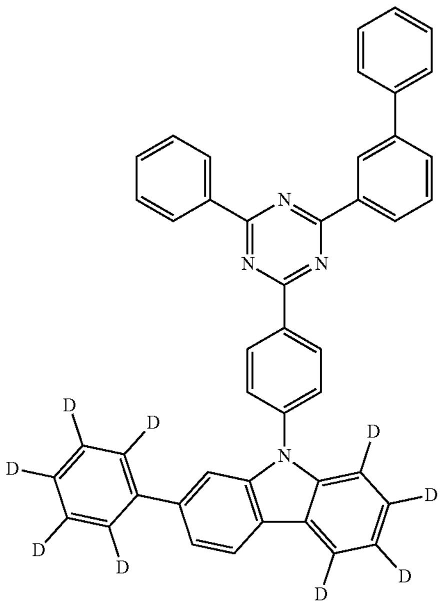

-continued
C40
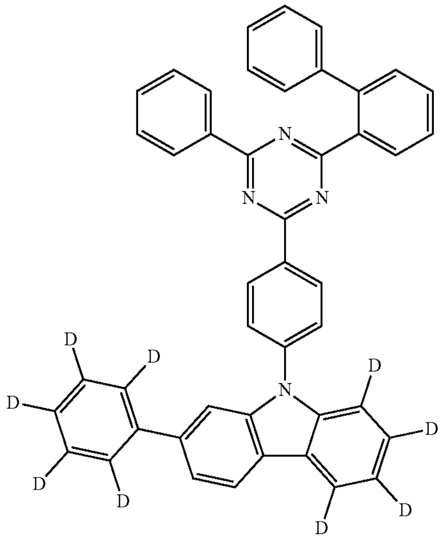
C41
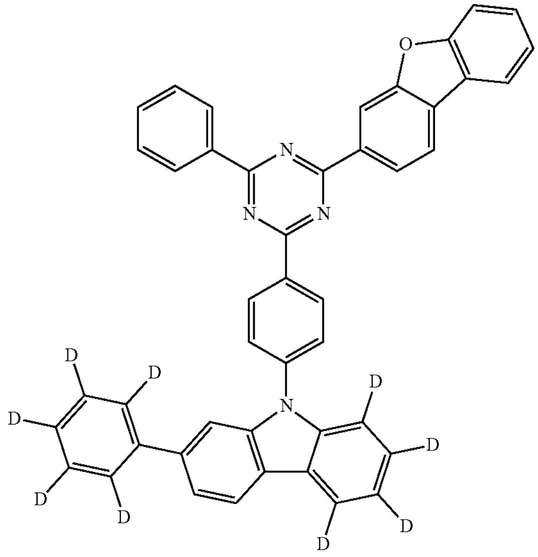
C42
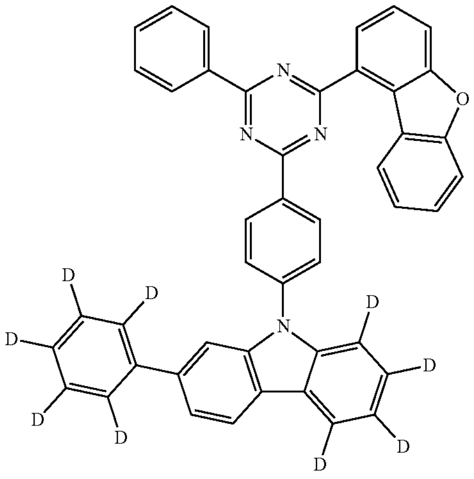
-continued
C43
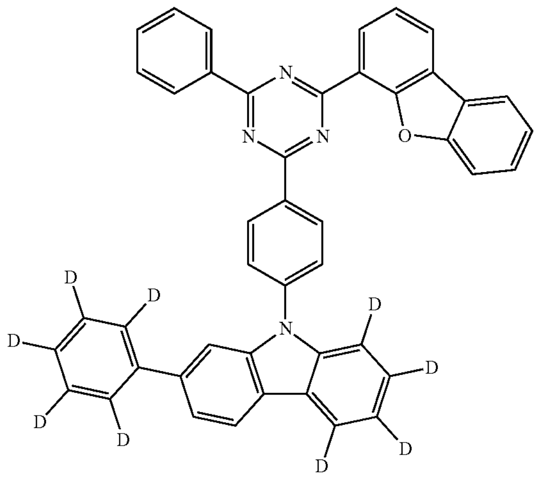
C44
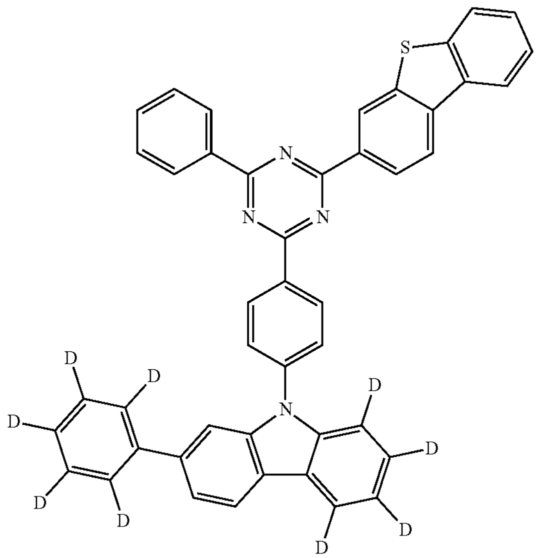
C45
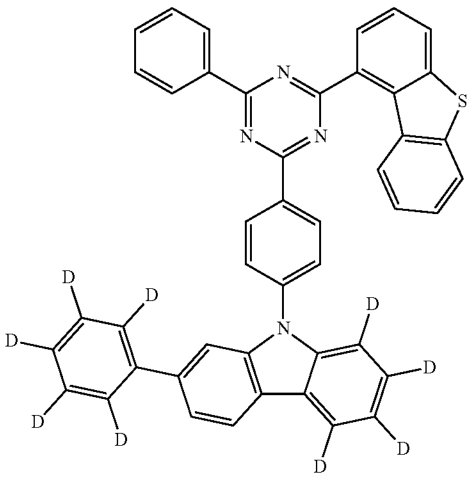

C46
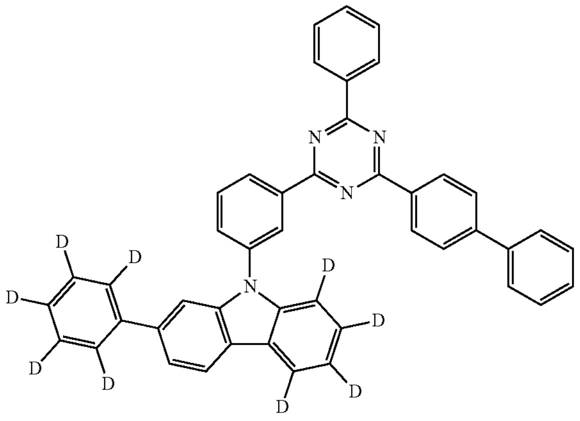
C47
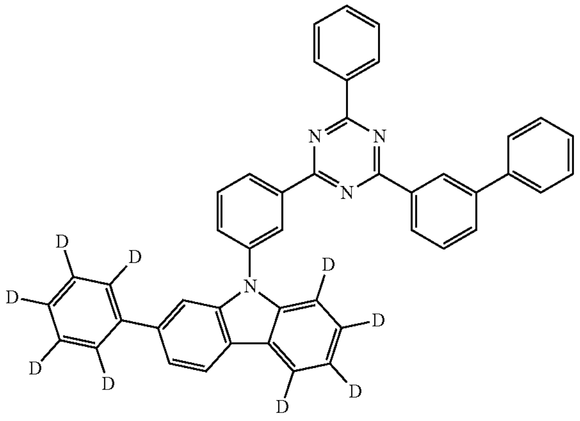
C48
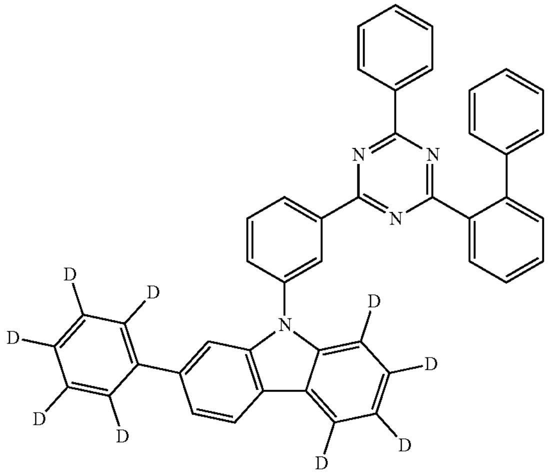
C49
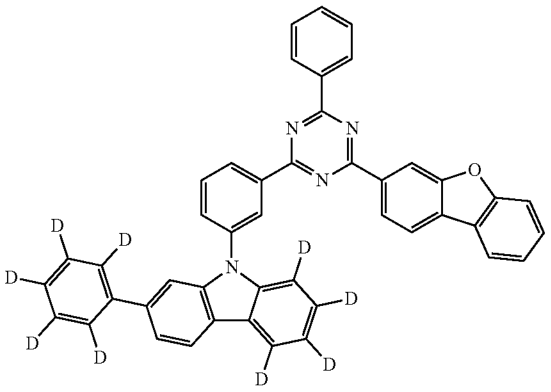
C50
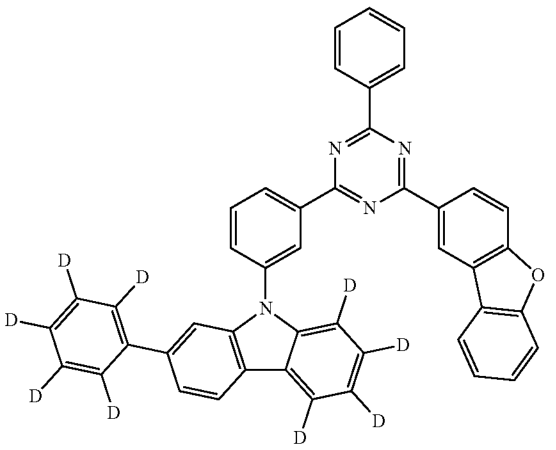
C51
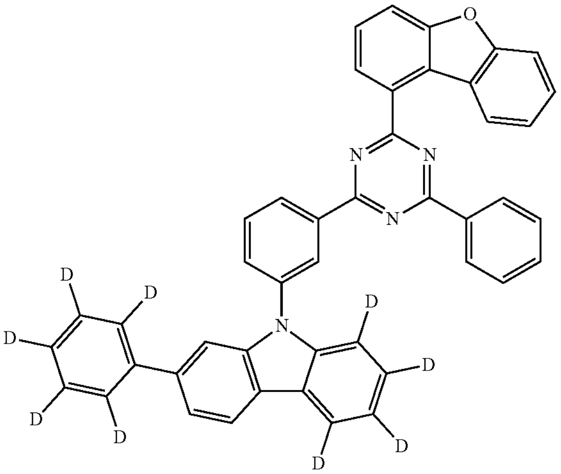

-continued
C52
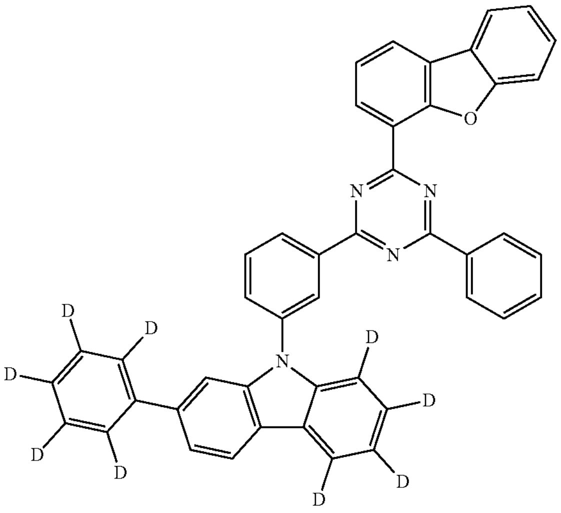
C35
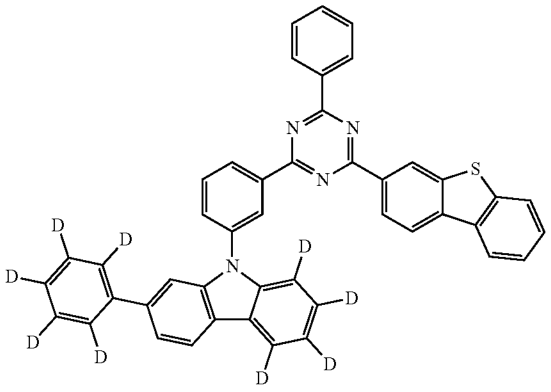
C54
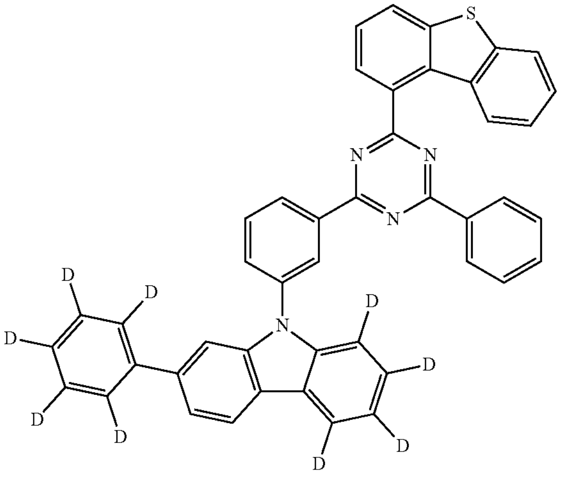
-continued
C55
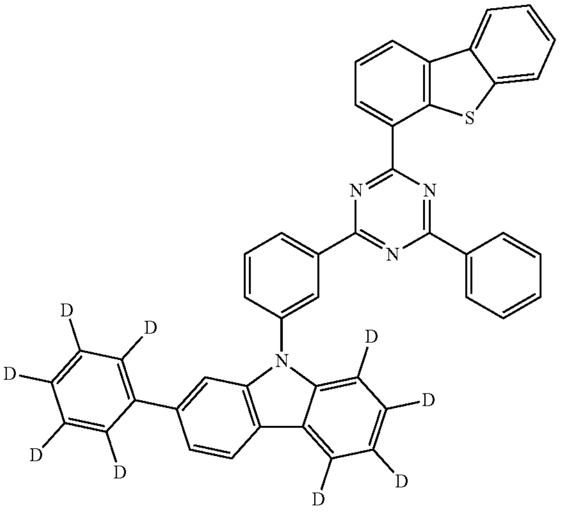
C56
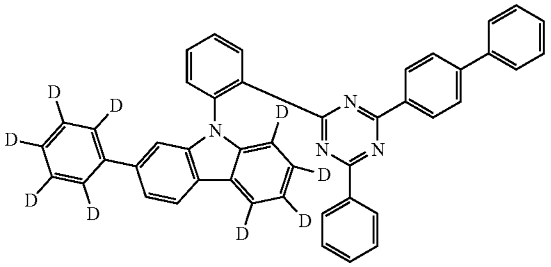
C57
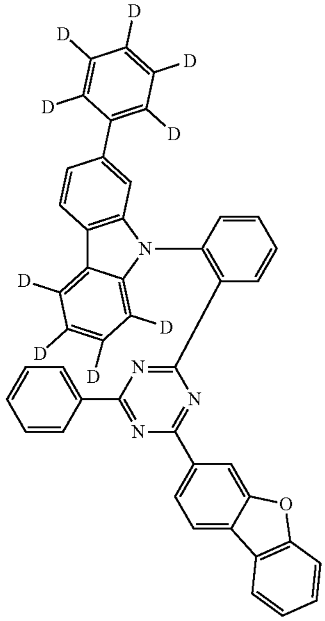

-continued
C58
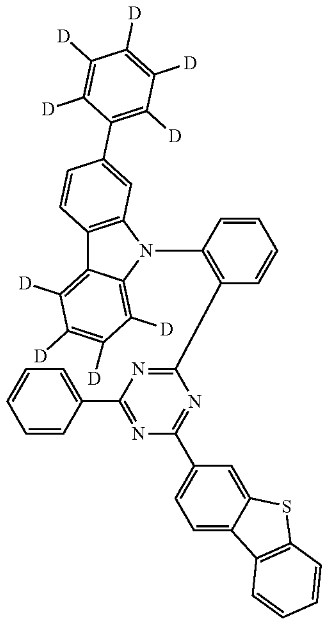
C59
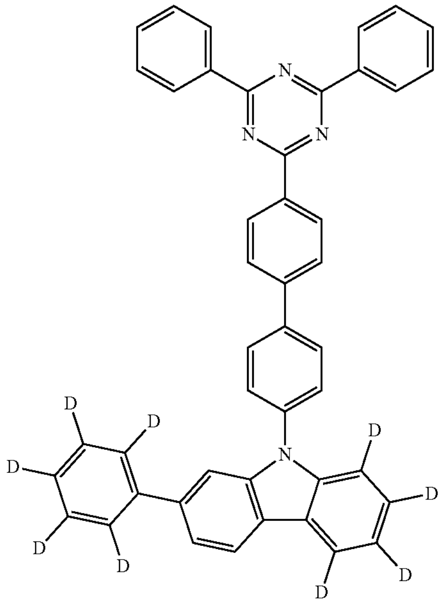
-continued
C60
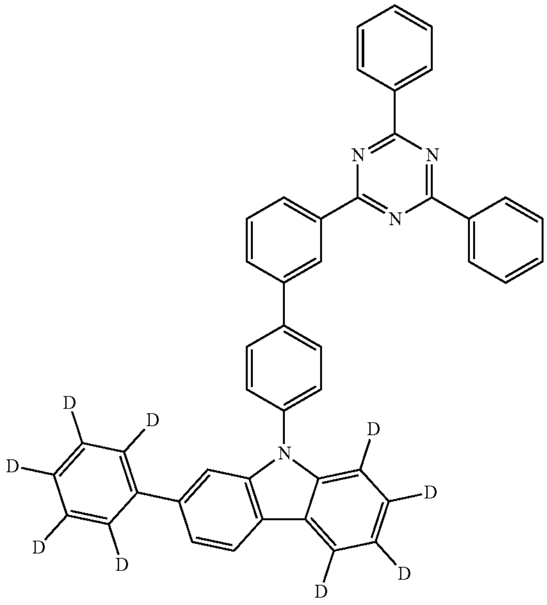
C61
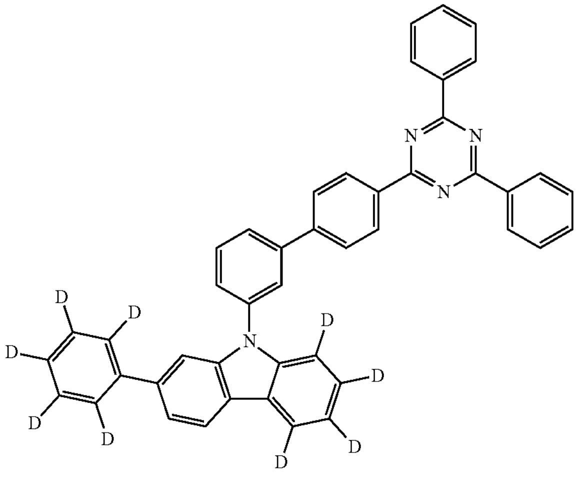

-continued
C62
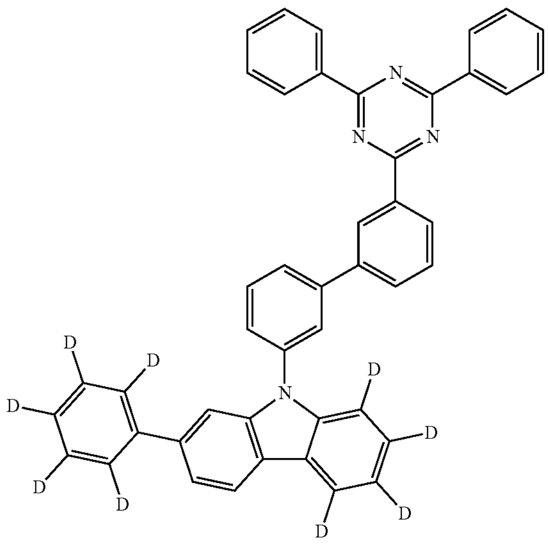
C63
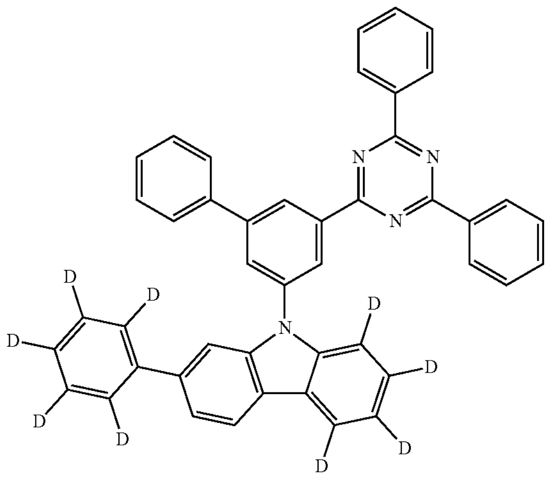
C64
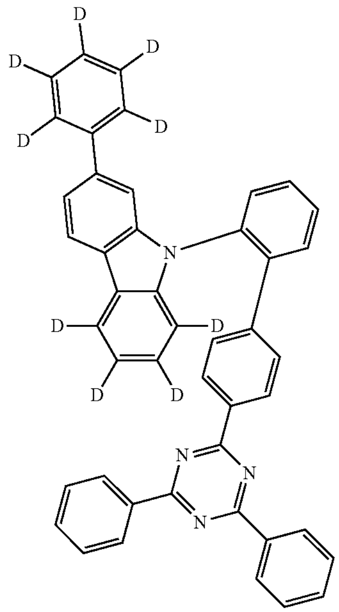
-continued
C65
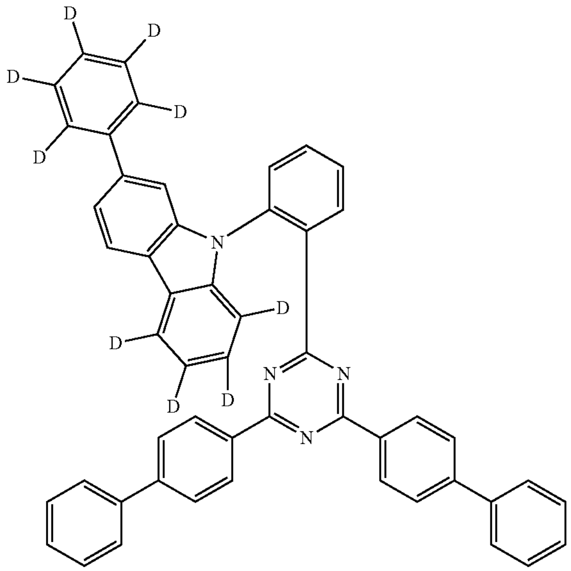
C66
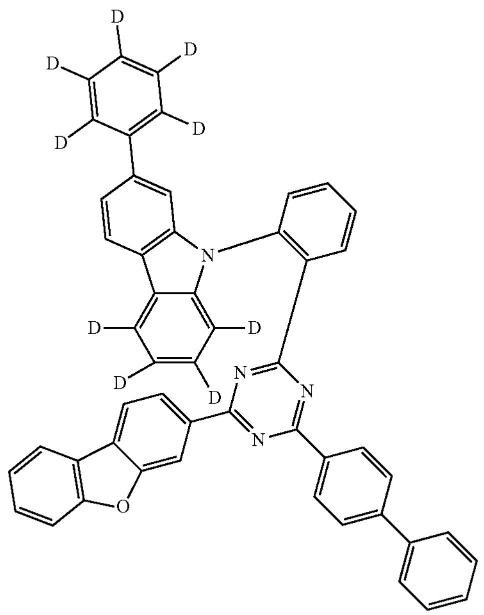
C67
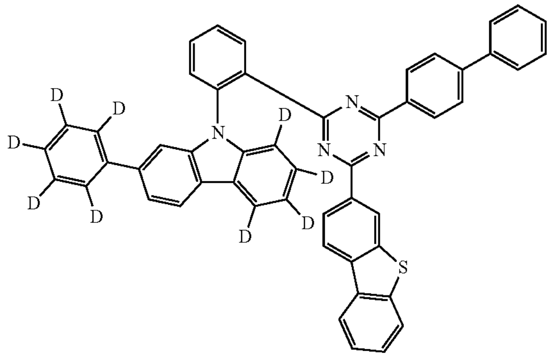

C68
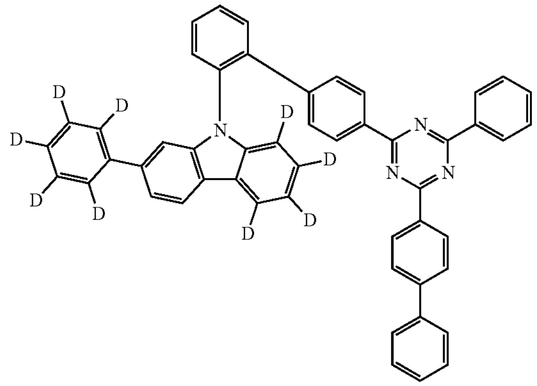
C69
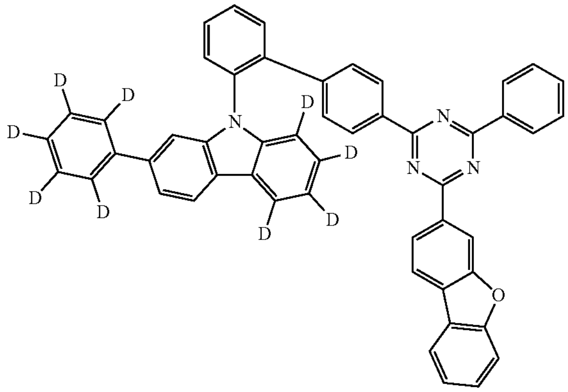
C70
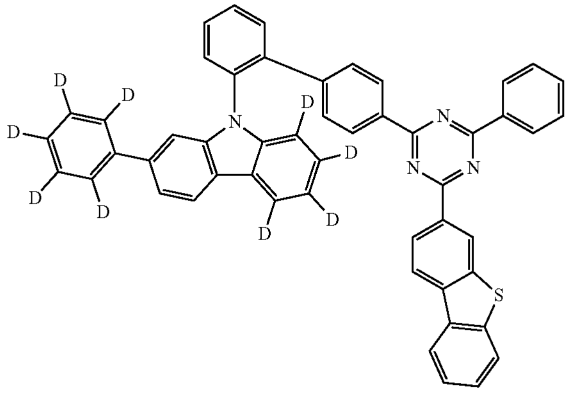
C71
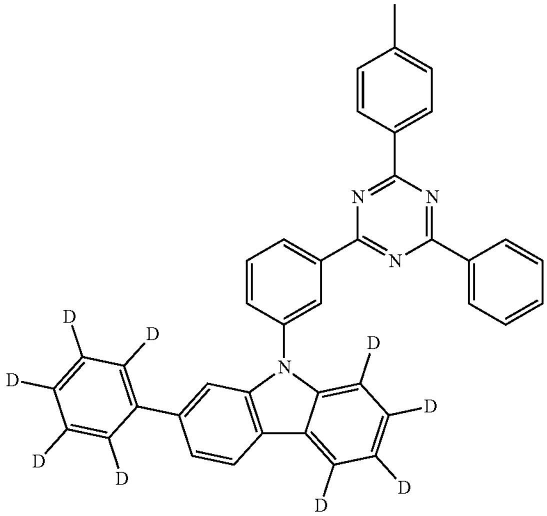
C72
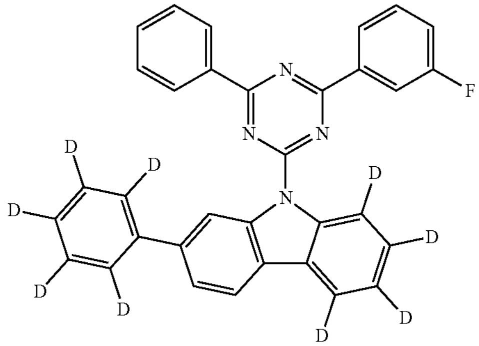
D1
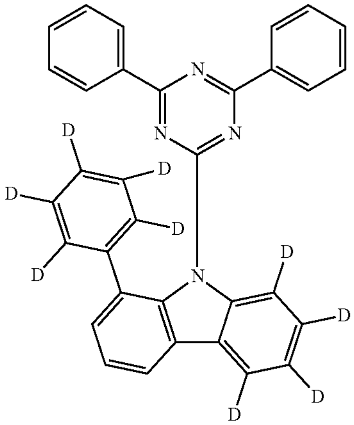

-continued
D2
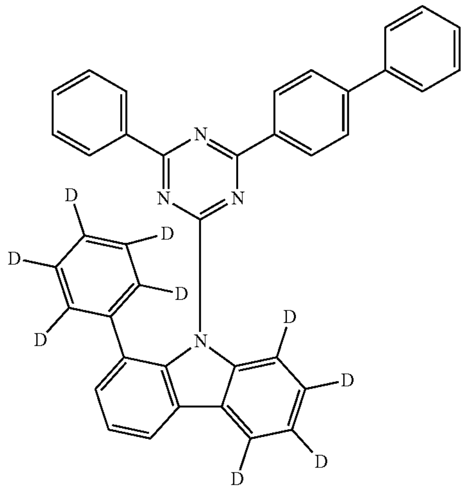
D3
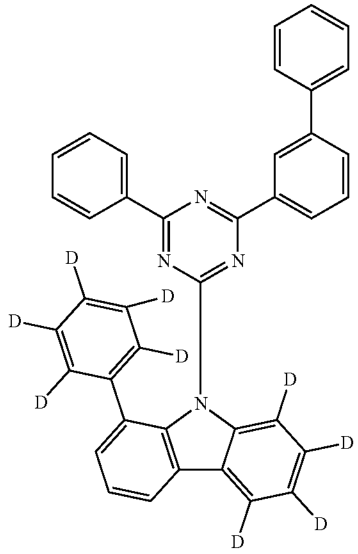
D4
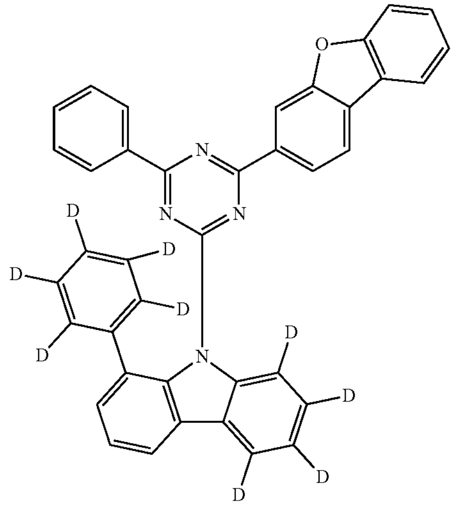
-continued
D5
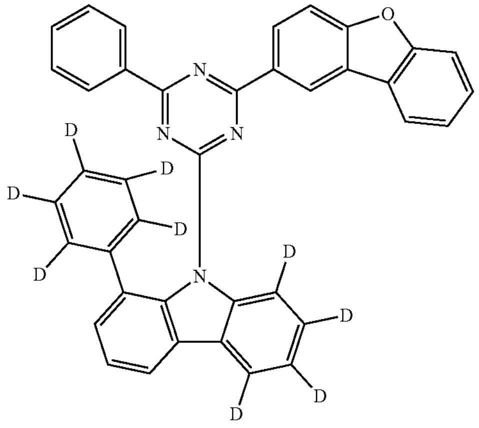
D6
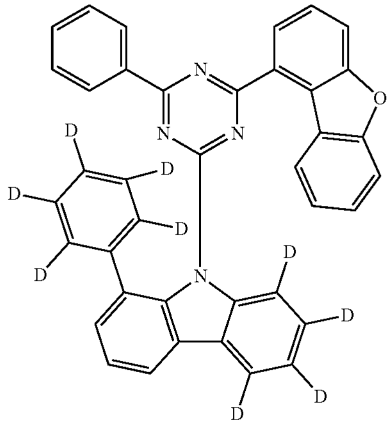
D7
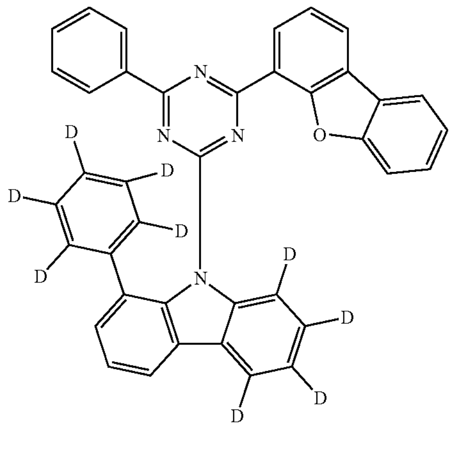

-continued
D8
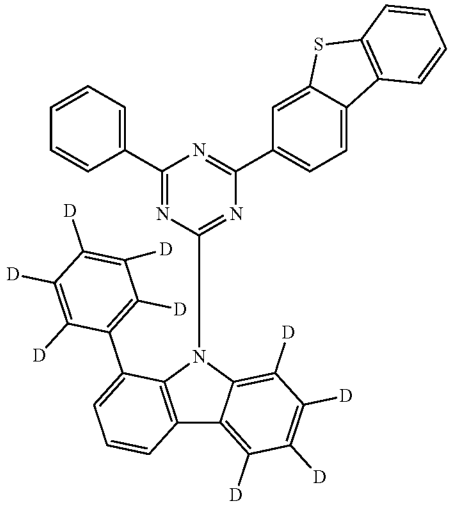
D9
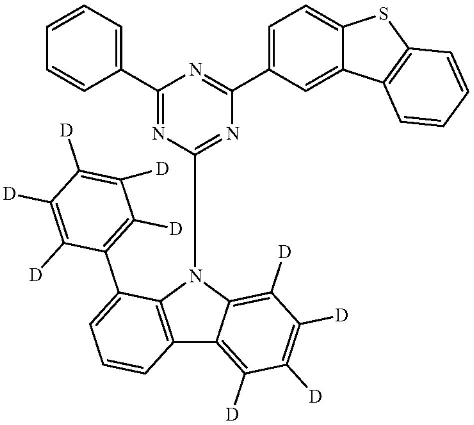
D10
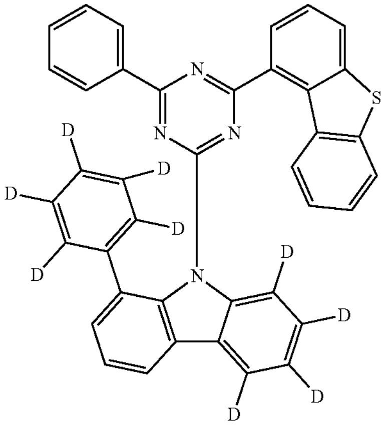
-continued
D11
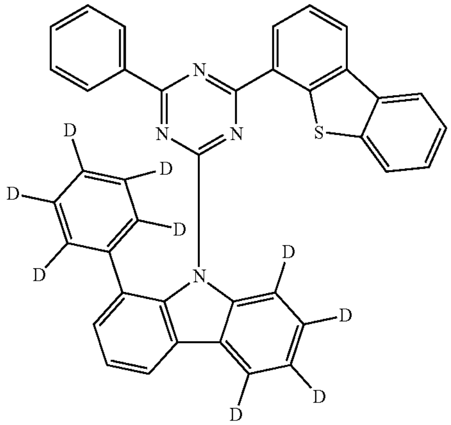
D12
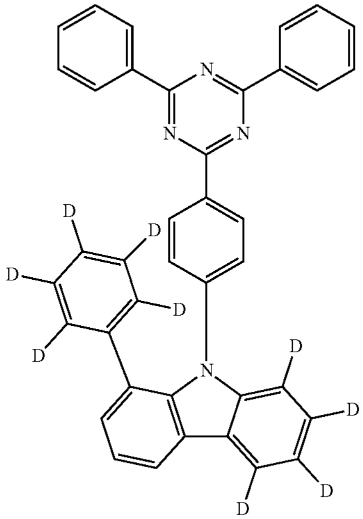
D13
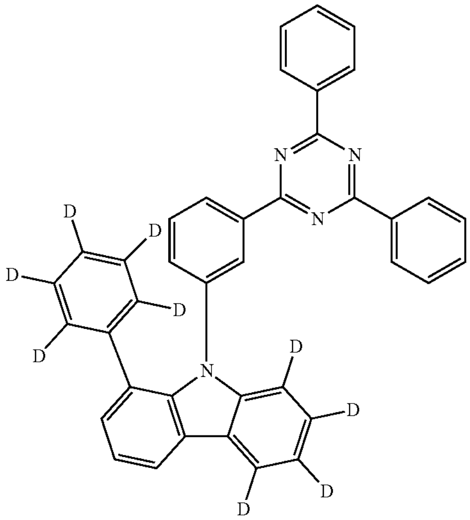

-continued
D14
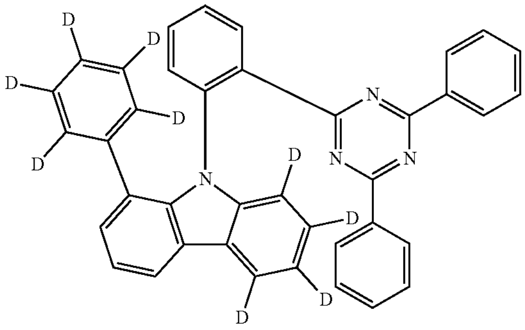
D15
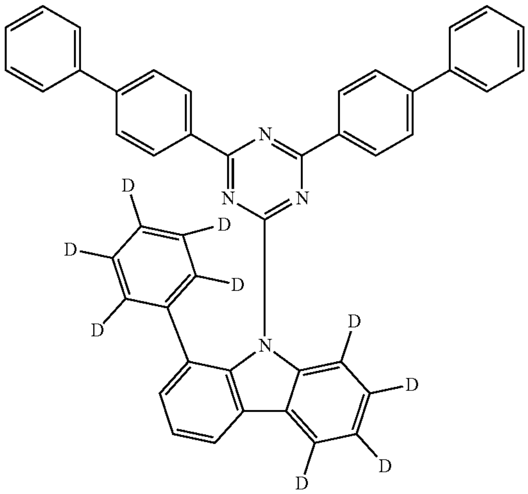
D16
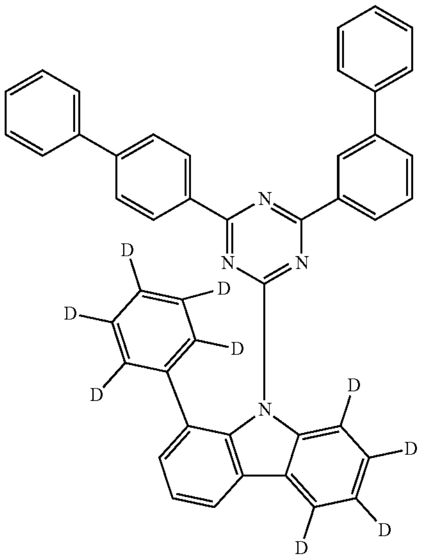
-continued
D17
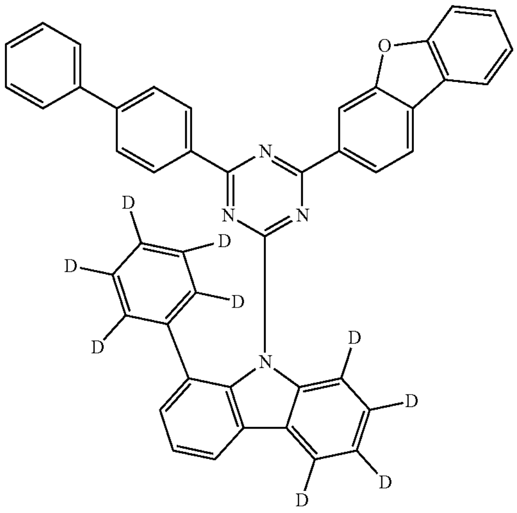
D18
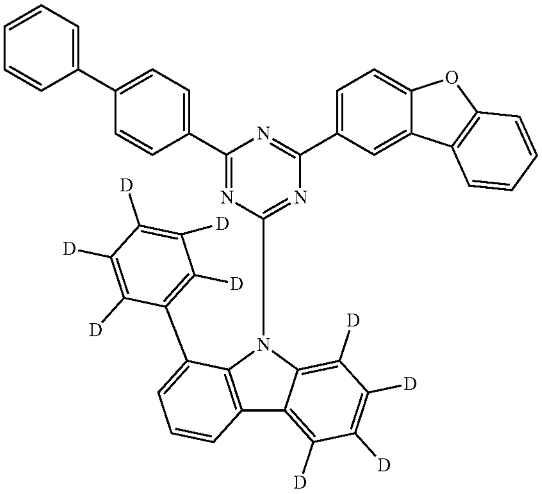
D19
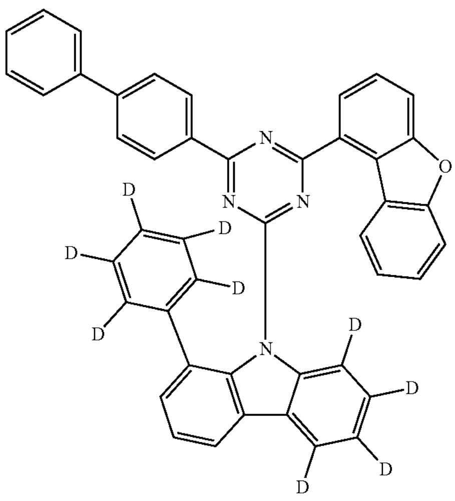

-continued
D20
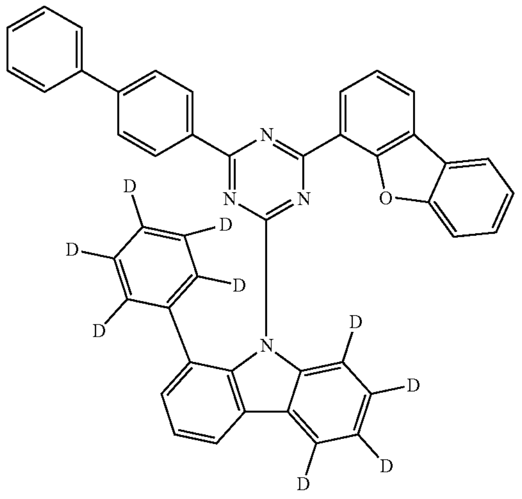
D21
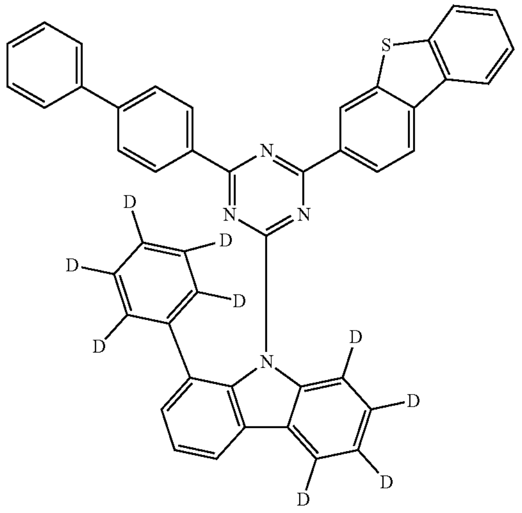
D22
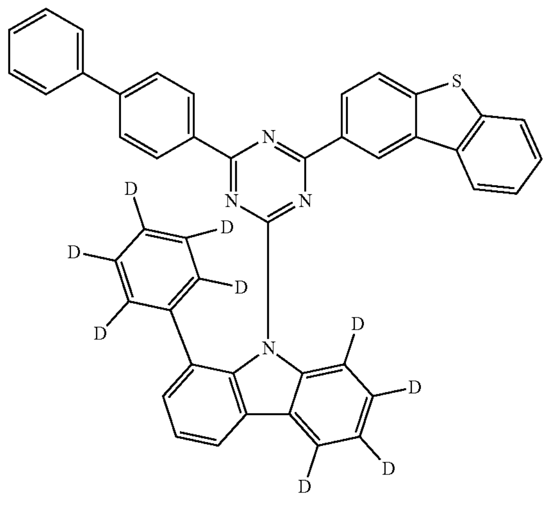
-continued
D23
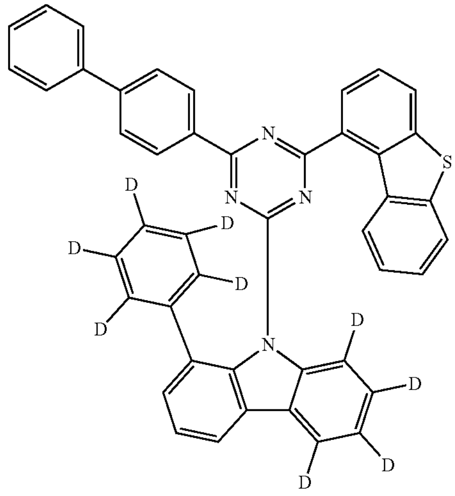
D24
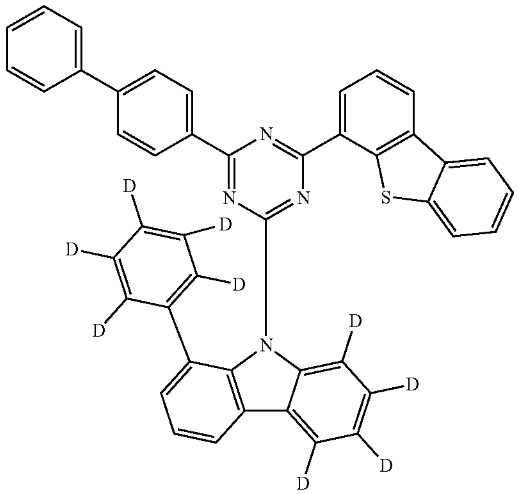
D25
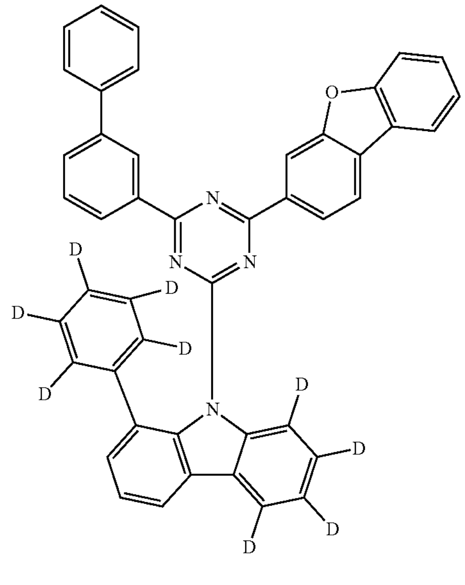

-continued
D26
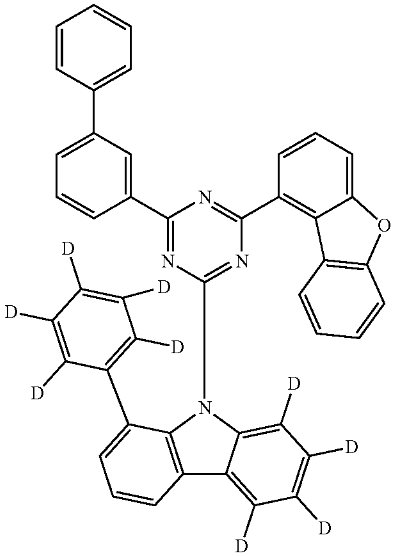
D27
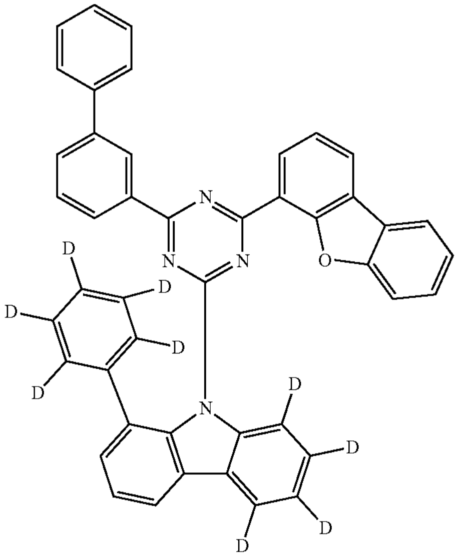
-continued
D28
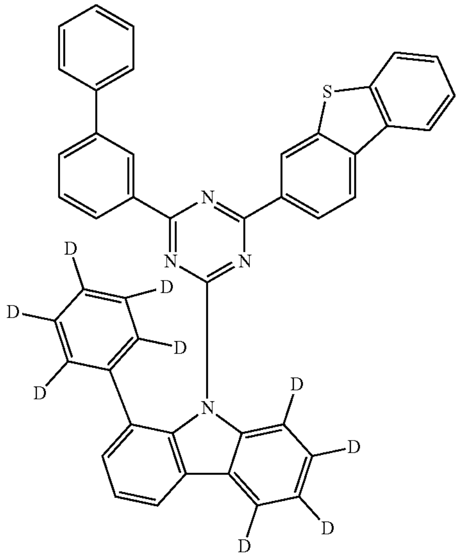
D29
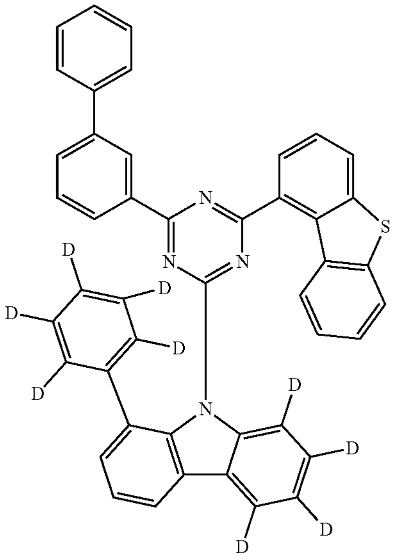

-continued
D30
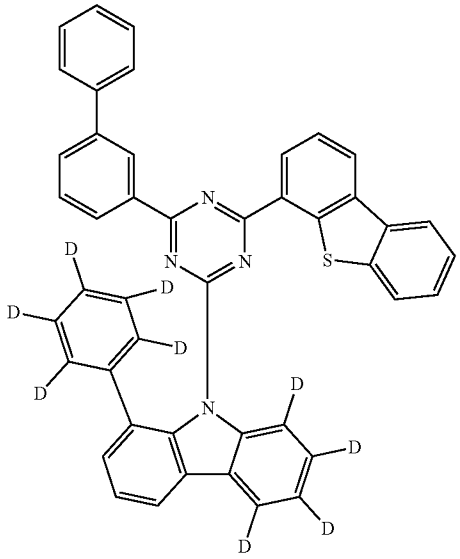
D34
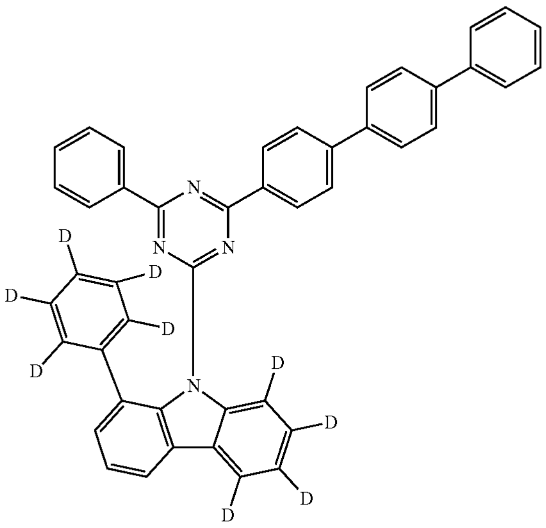
-continued
D35
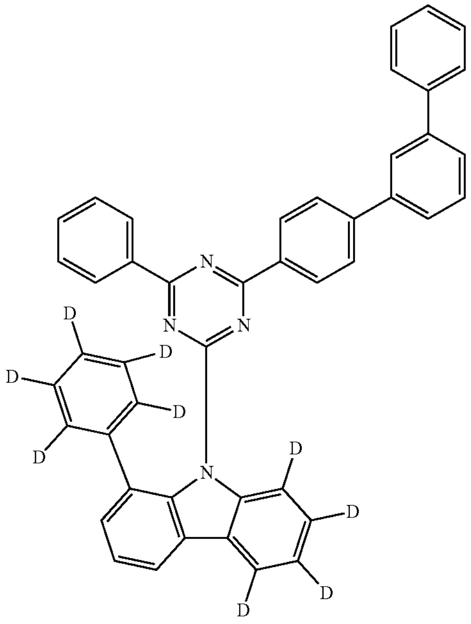
D36
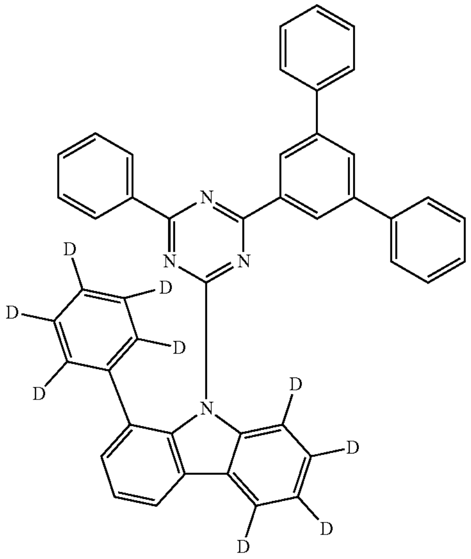

-continued
D37
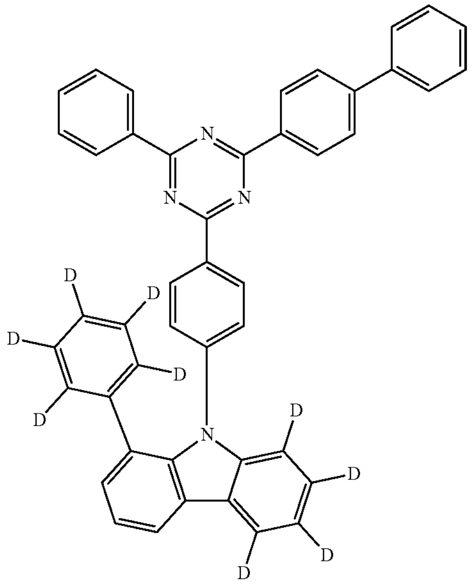
D38
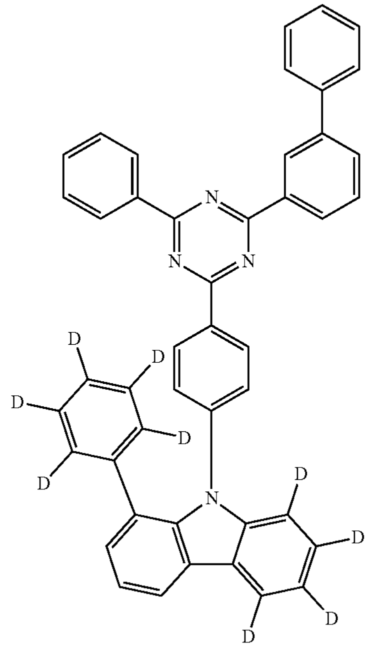
-continued
D39
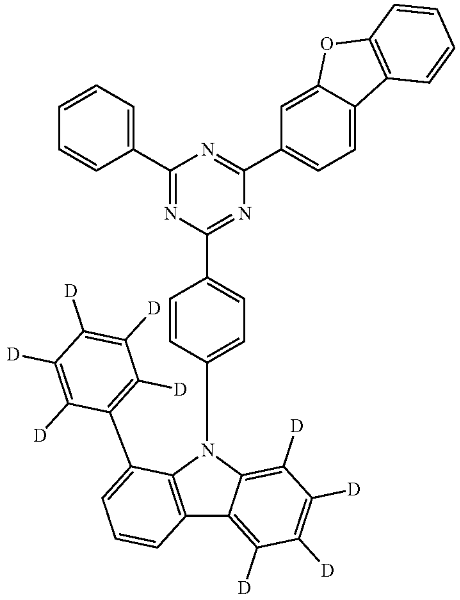
D40
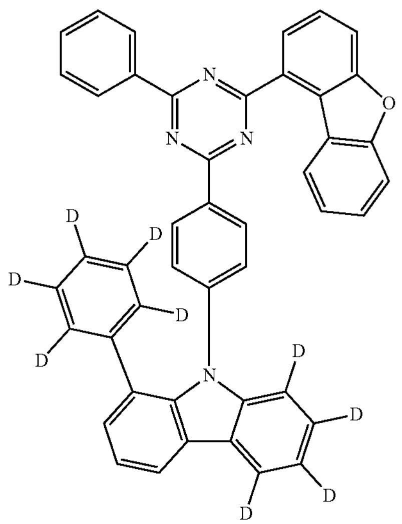

-continued
D41
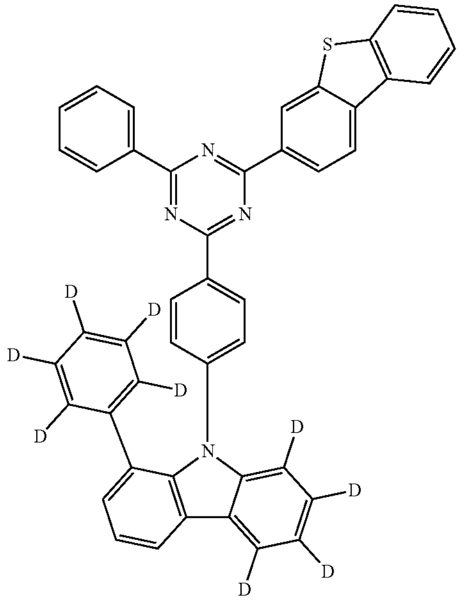
D42
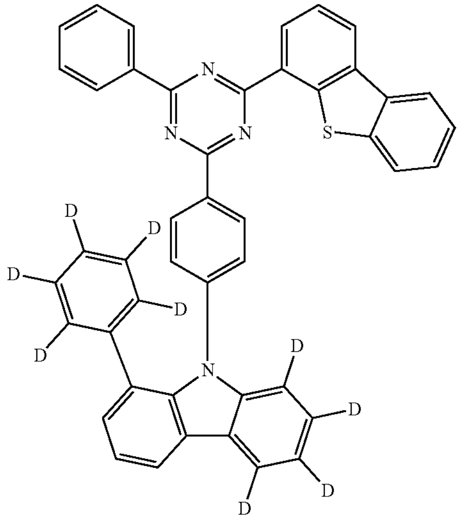
D43
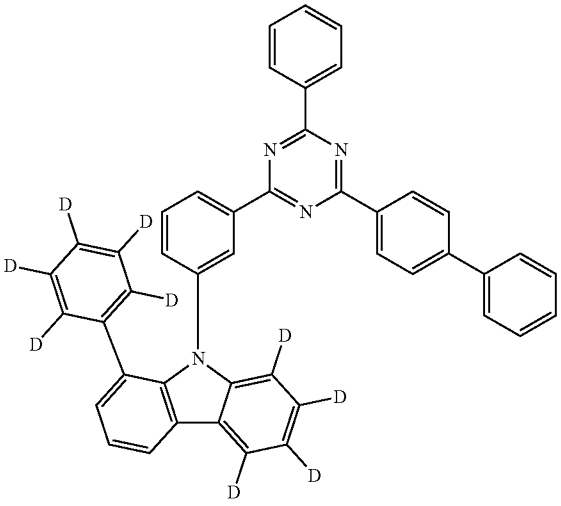
-continued
D44
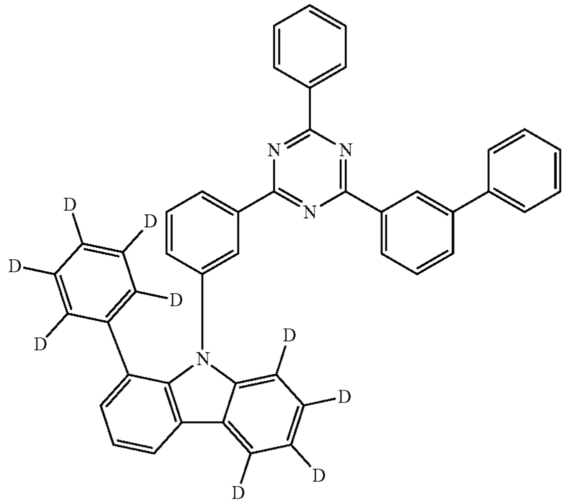
D45
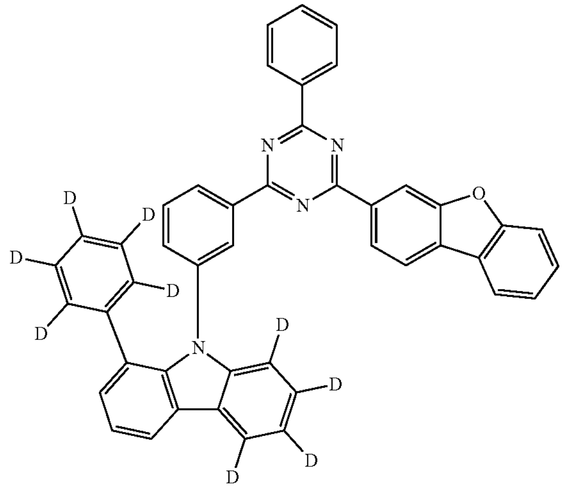
D46
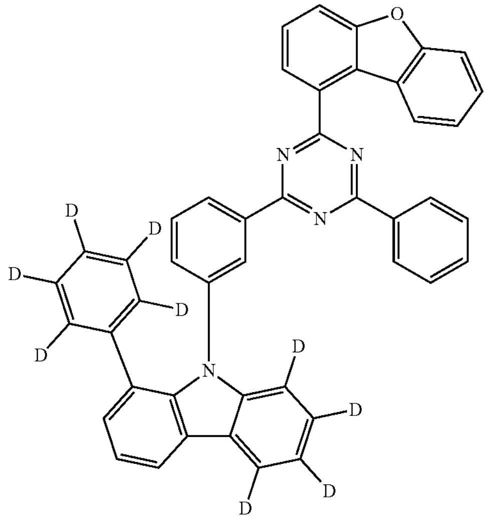

D47
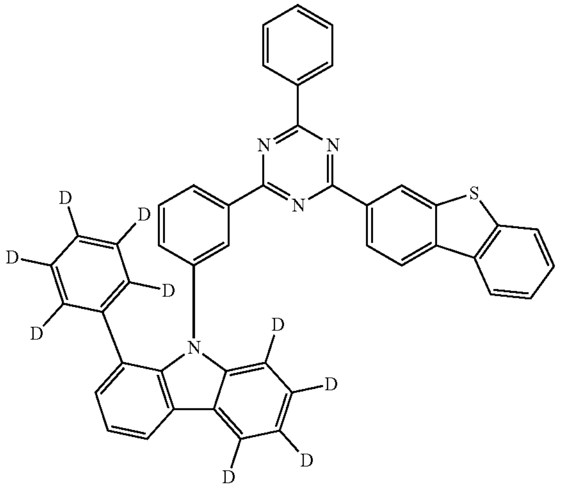
D48
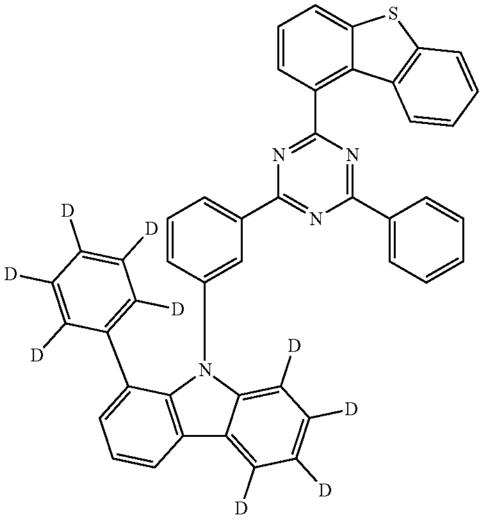
D49
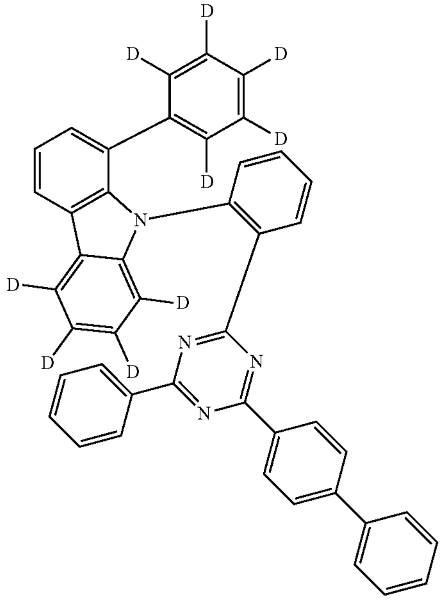
D50
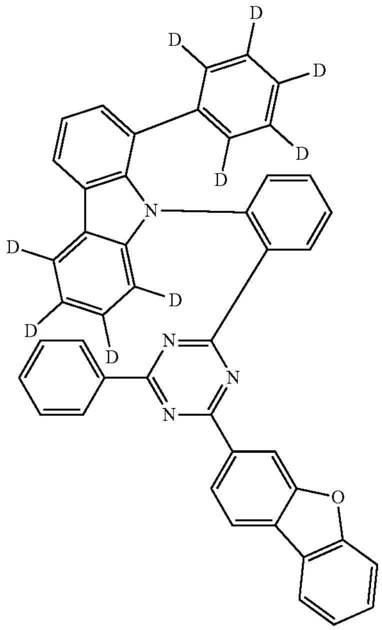
D51
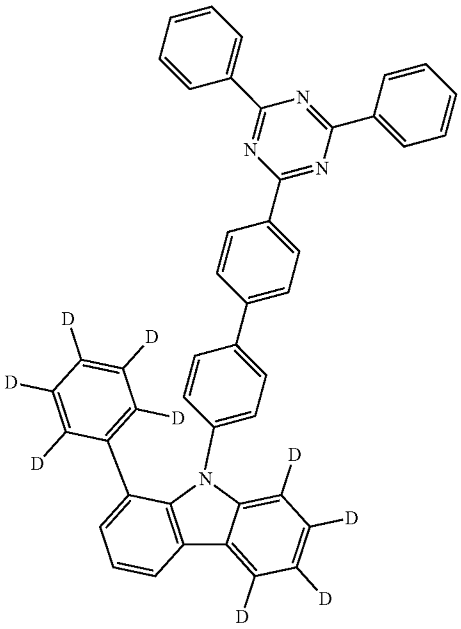

-continued
D52
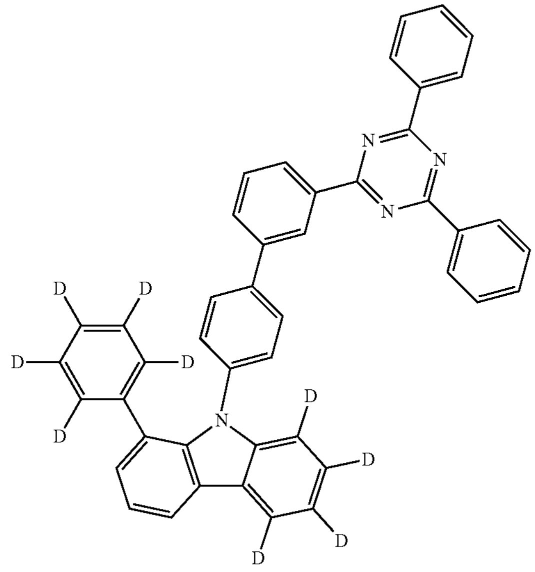
D53
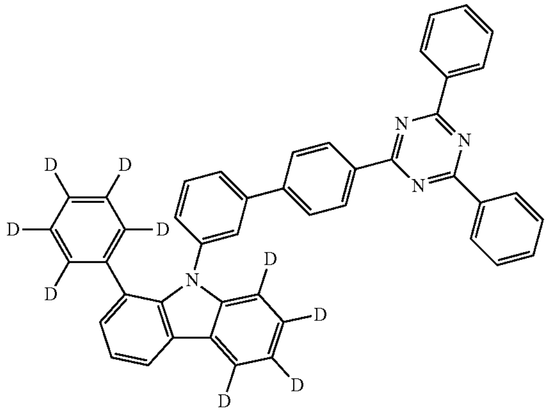
D54
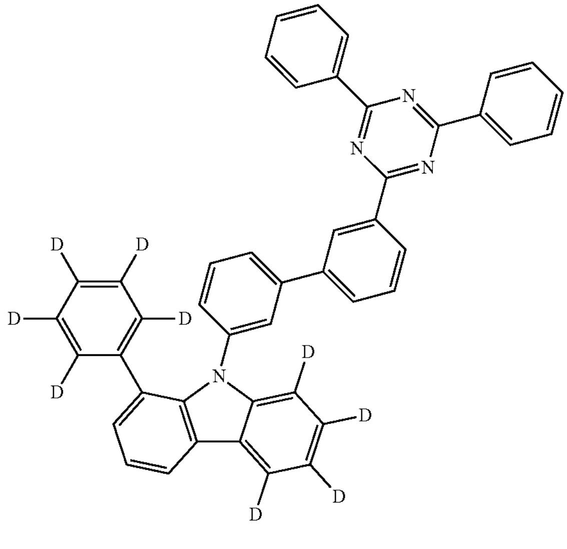
-continued
D55
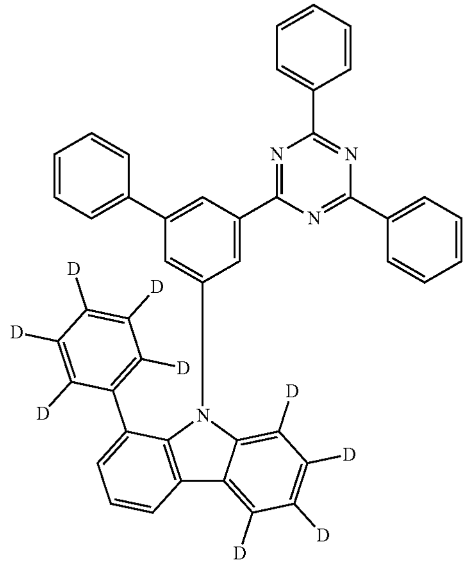
D56
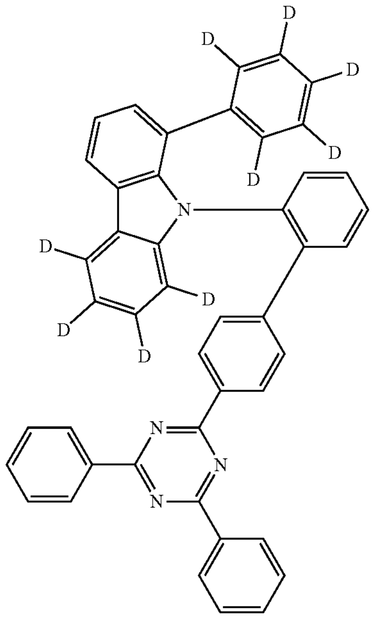

-continued
D57
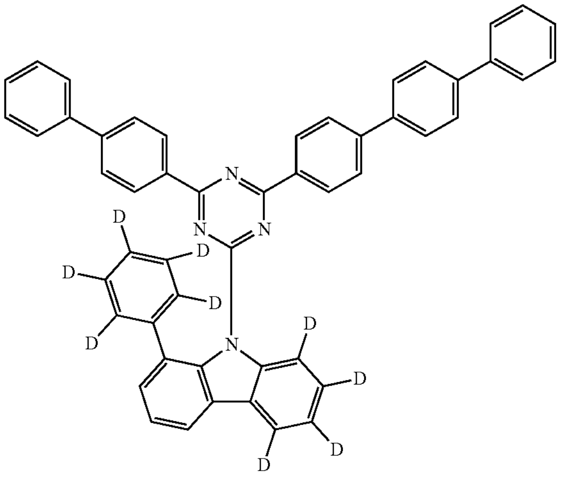
D58
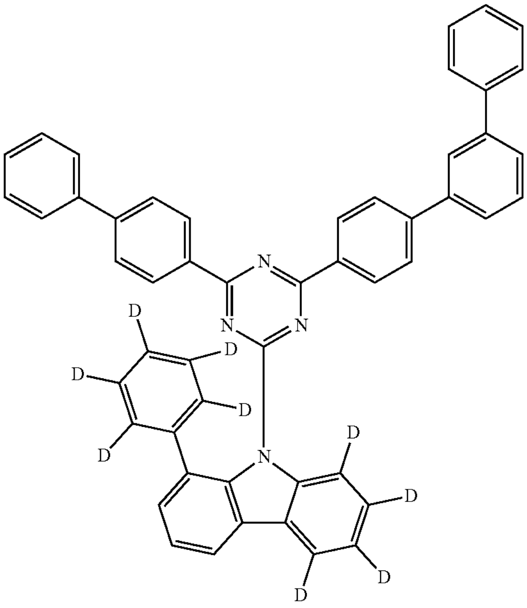
-continued
D59
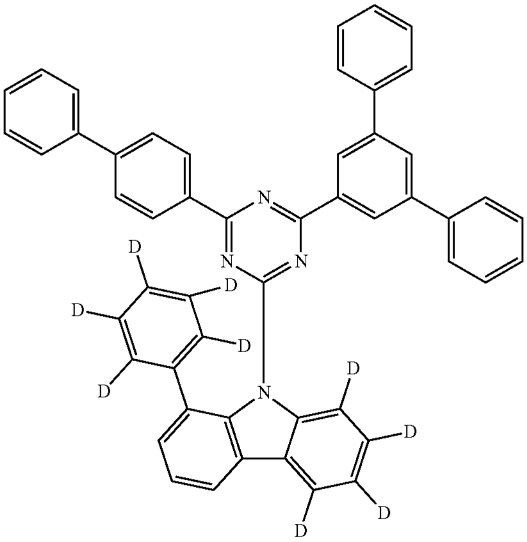
D60
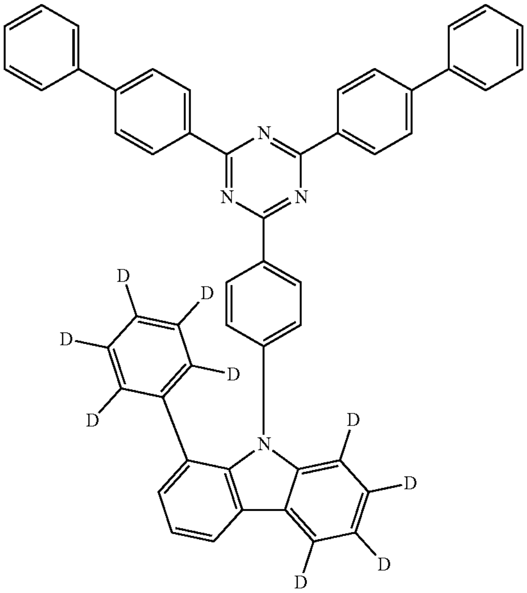

-continued
D61
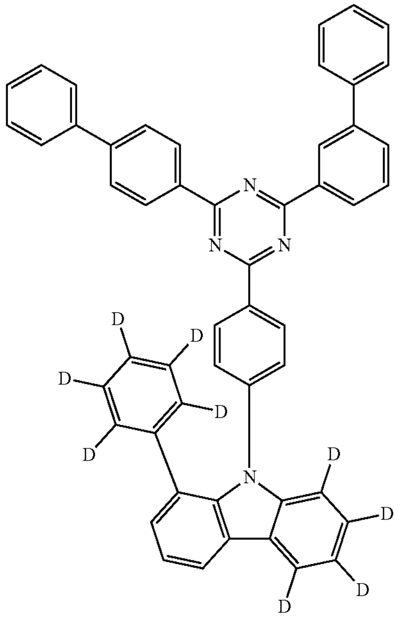
D62
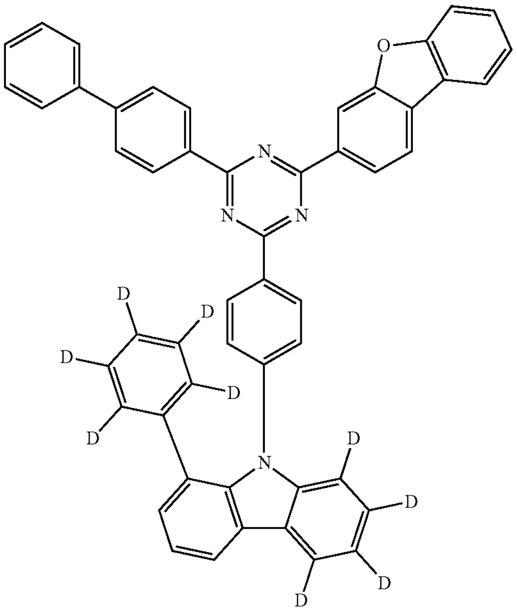
-continued
D63
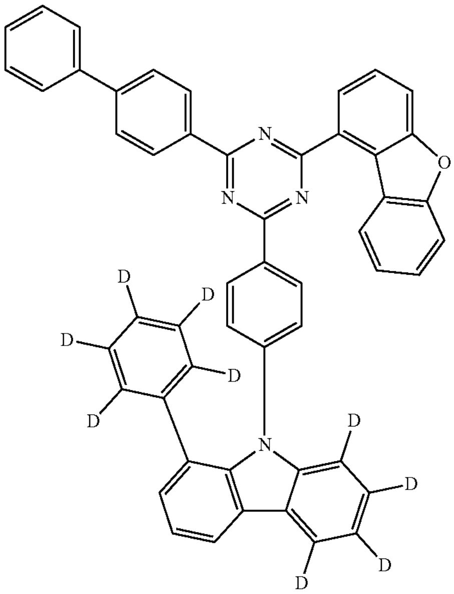
D64
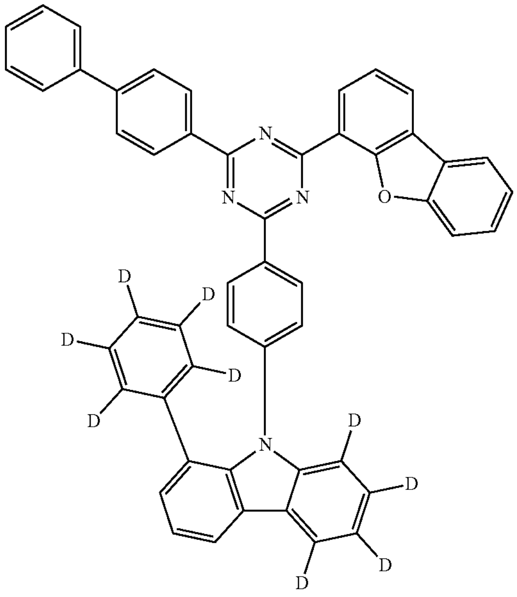

-continued
D65
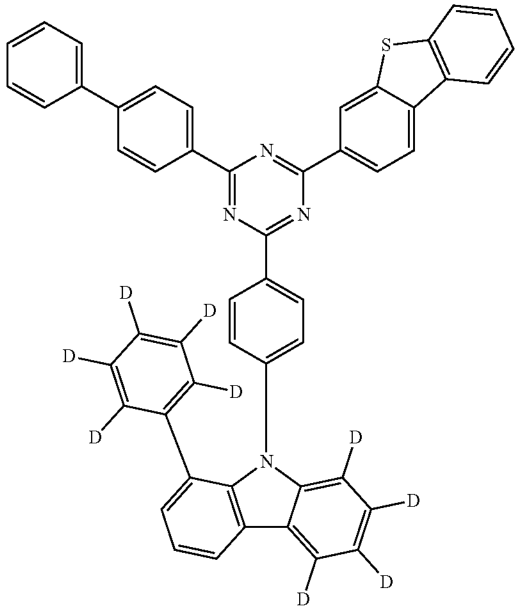
D66
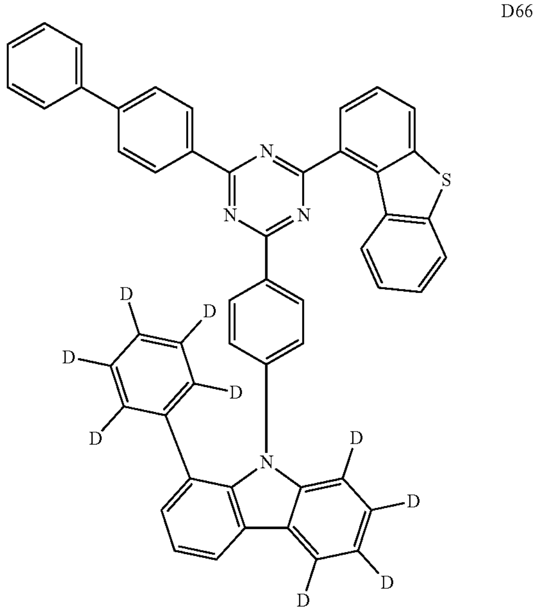
-continued
D67
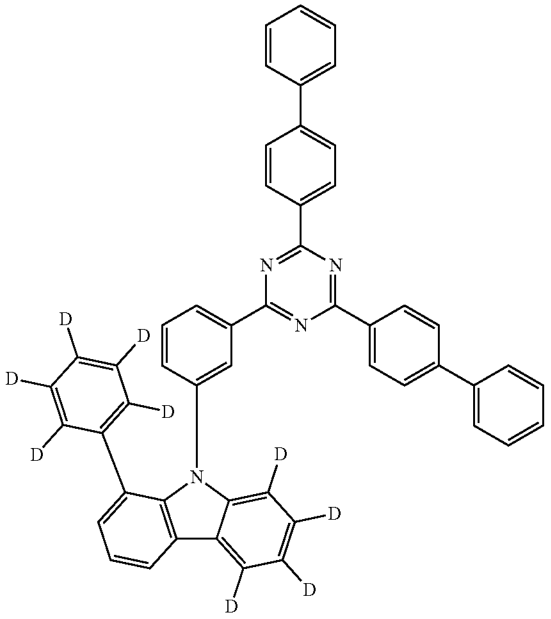
D68
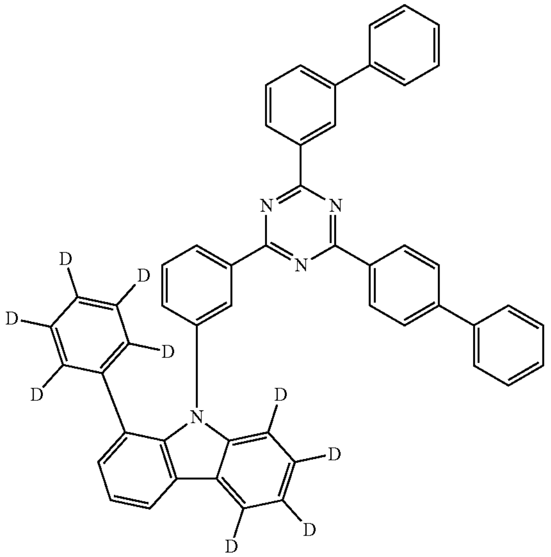

-continued
D69
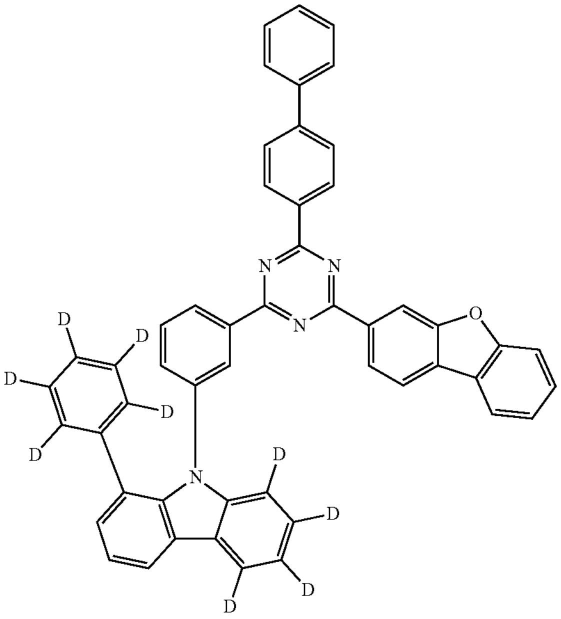
D70
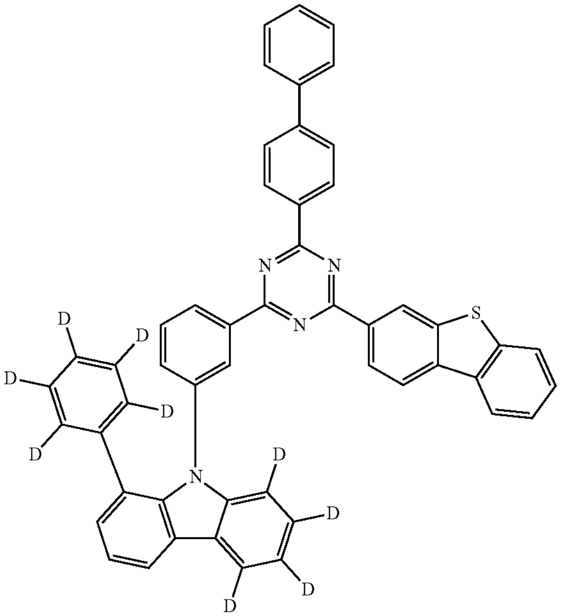
-continued
D71
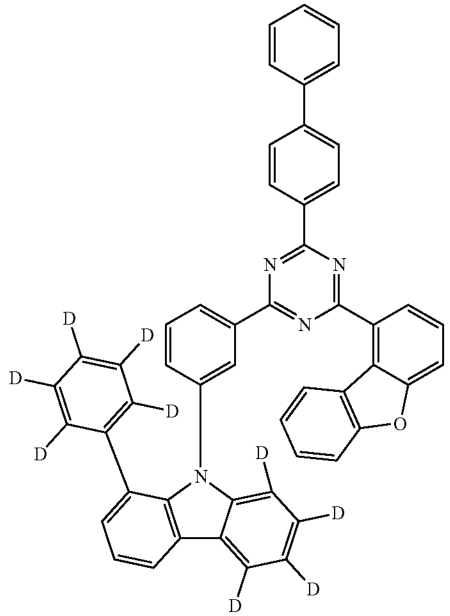
D72
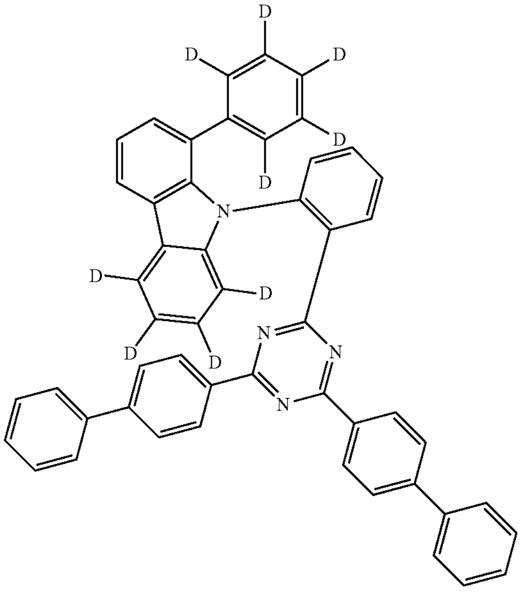

-continued
D73
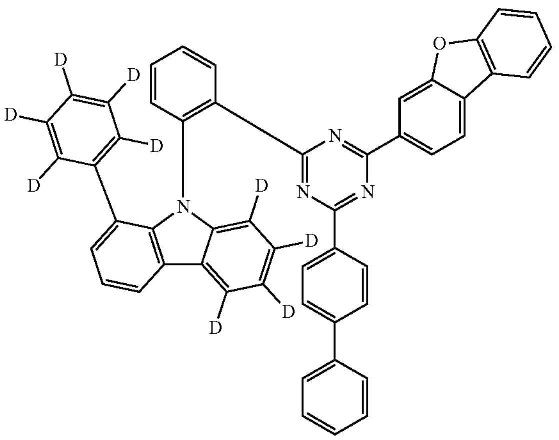
D74
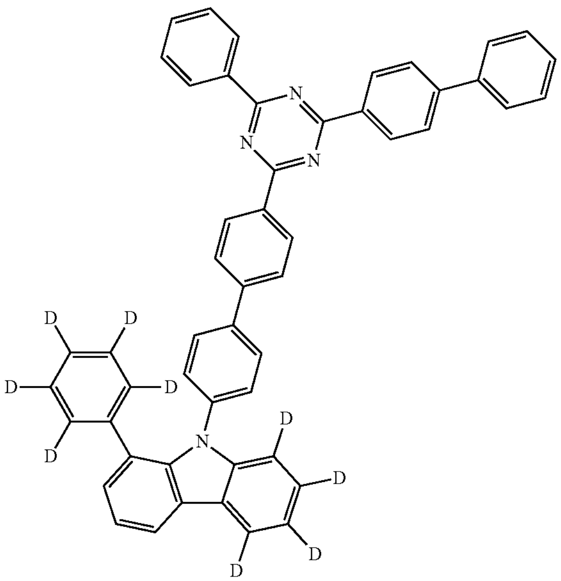
D75
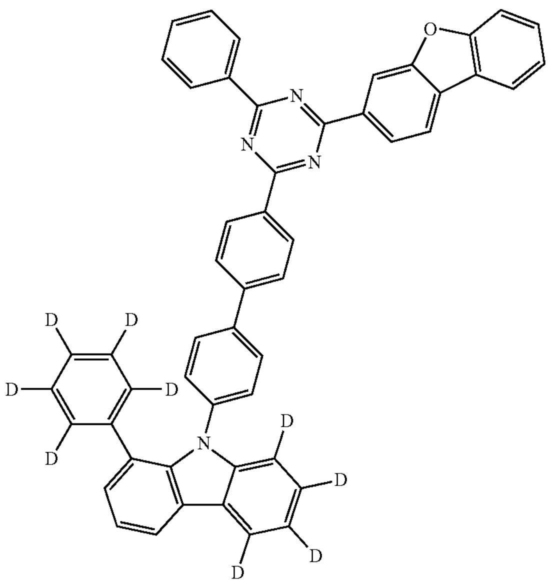
-continued
D76
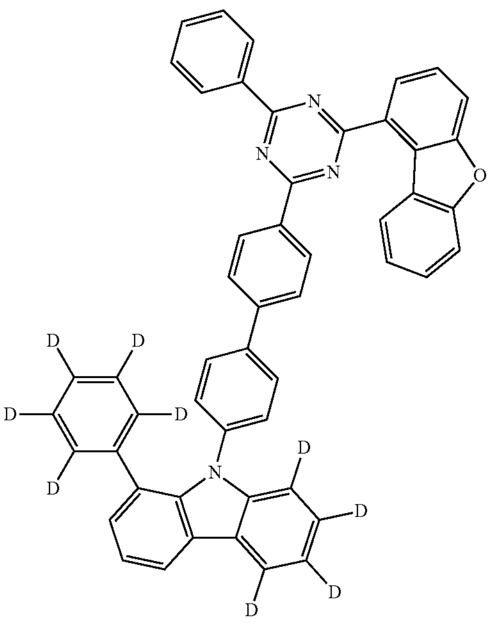
D77
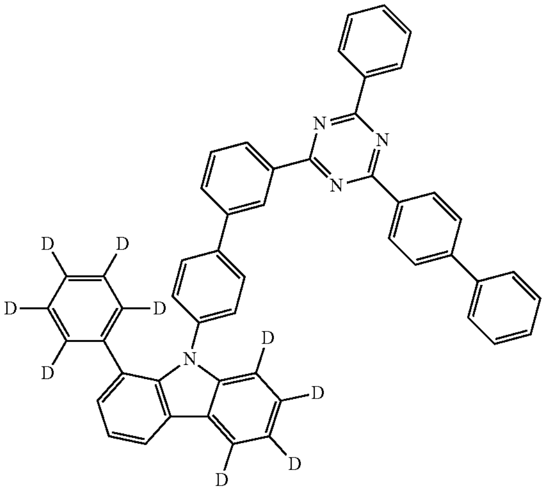
D78
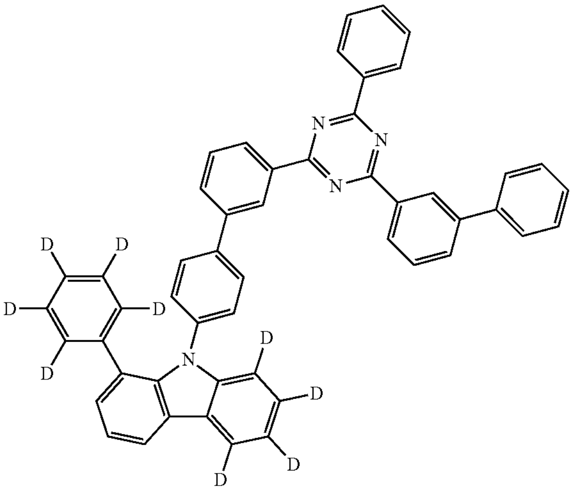

-continued
D79
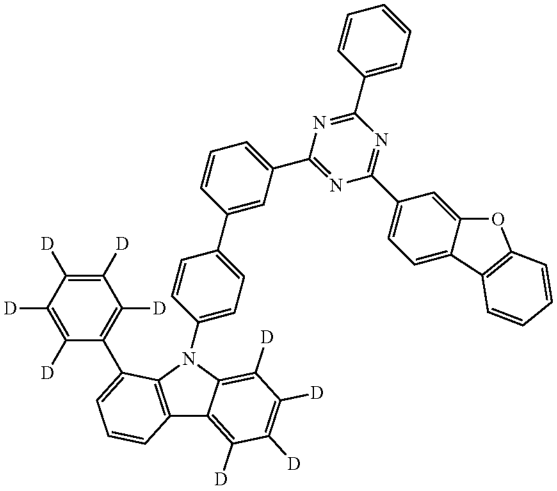
D80
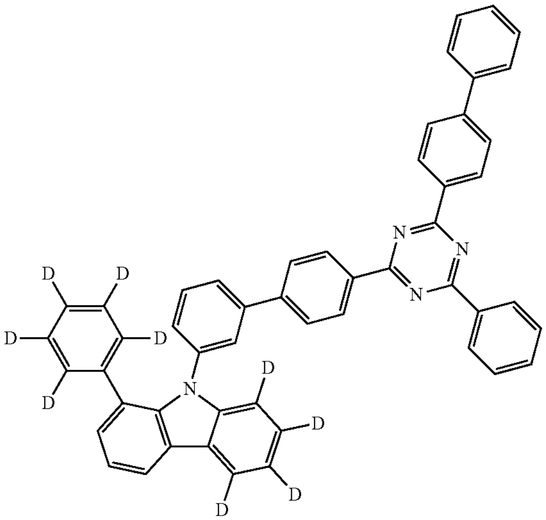
D81
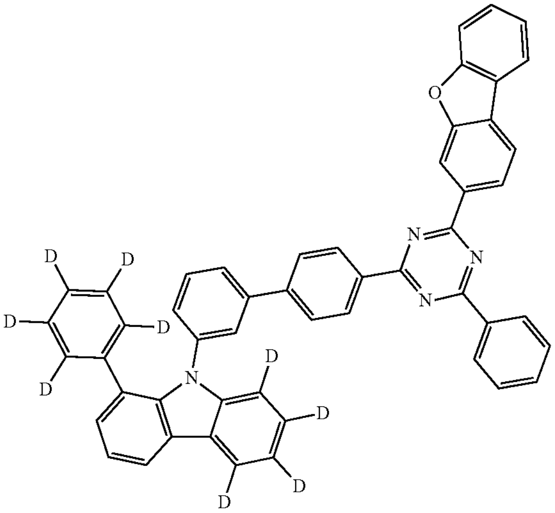
D82
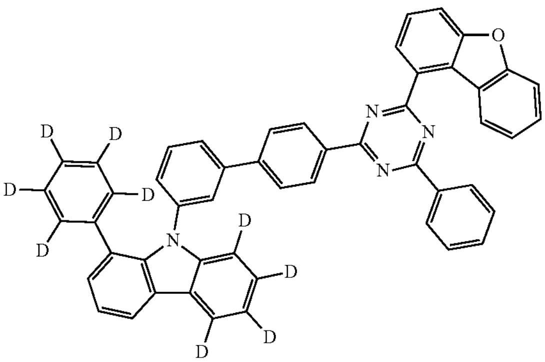
83
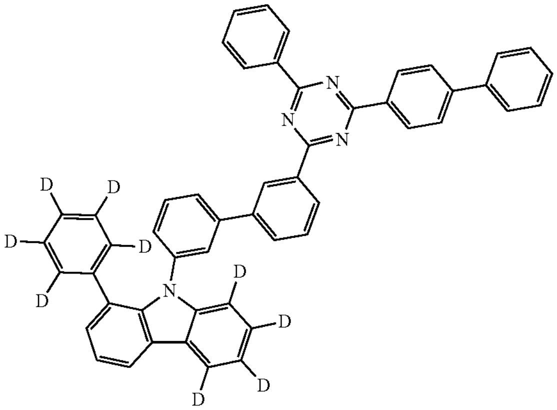

-continued
D84
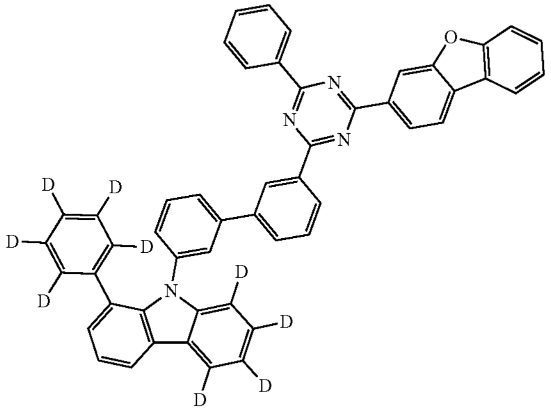
D85
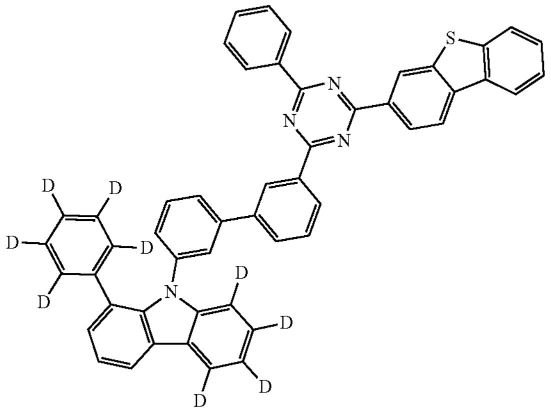
D86
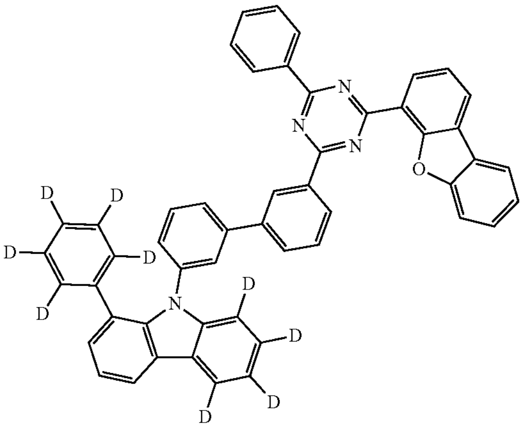
-continued
D87
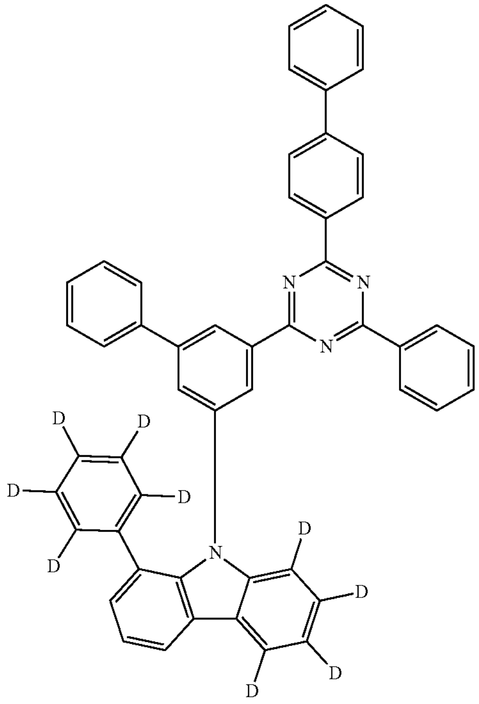
D88
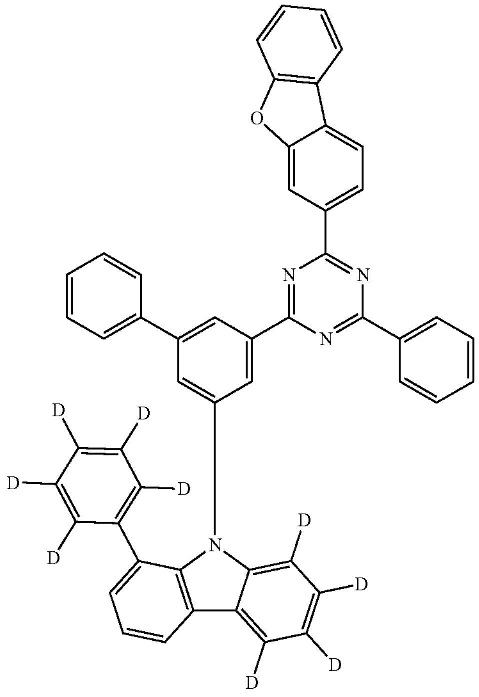

-continued
D89
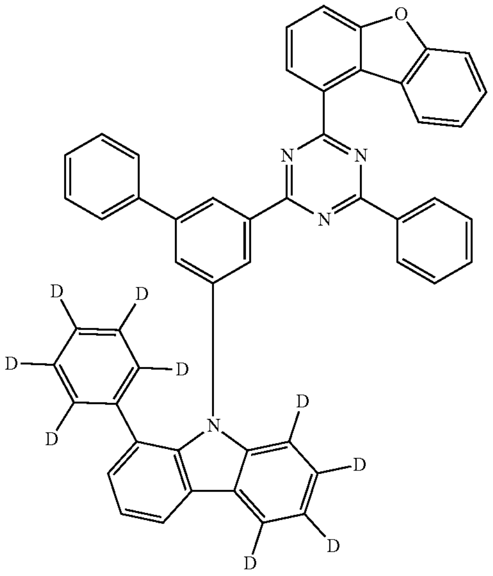
D90
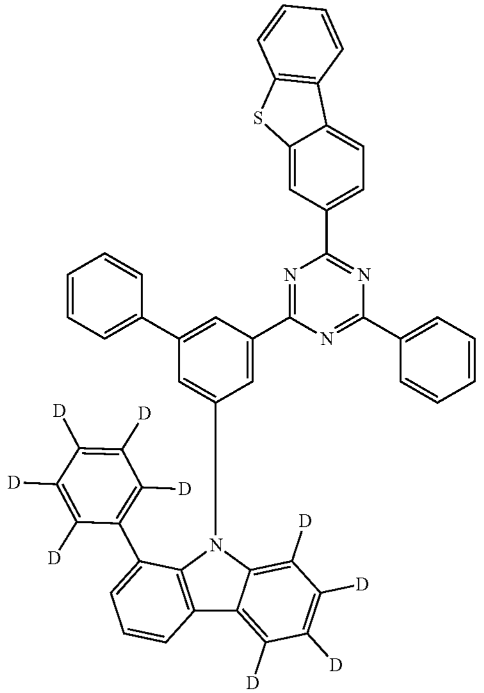
-continued
D91
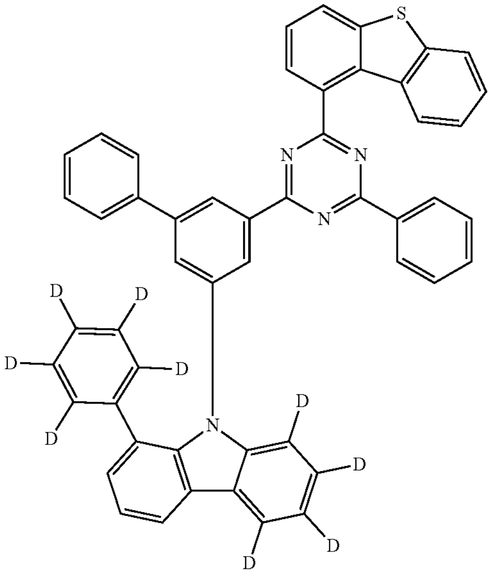
D92
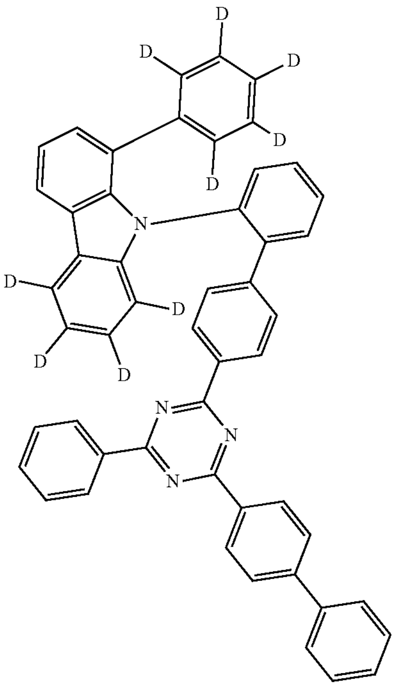

-continued
D93
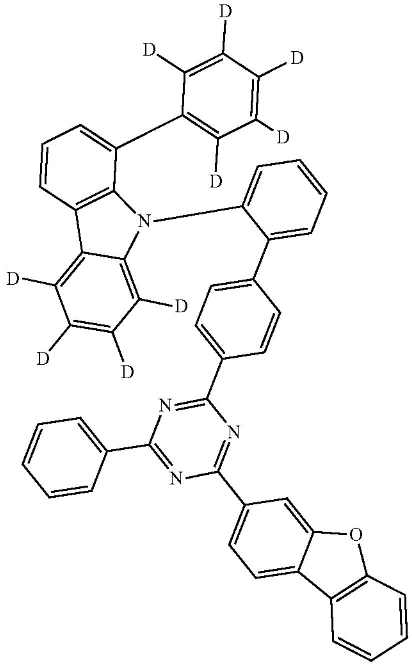
D94
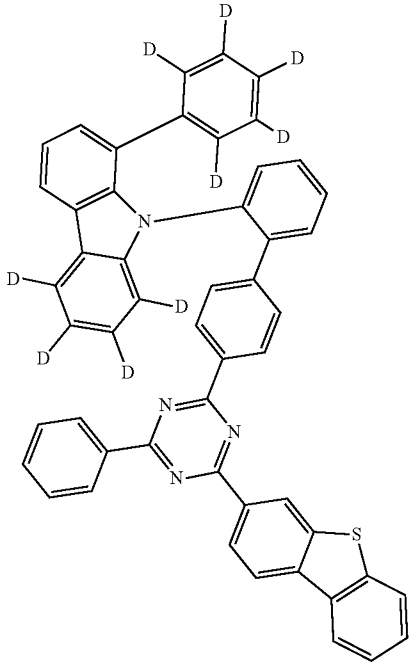
-continued
A224
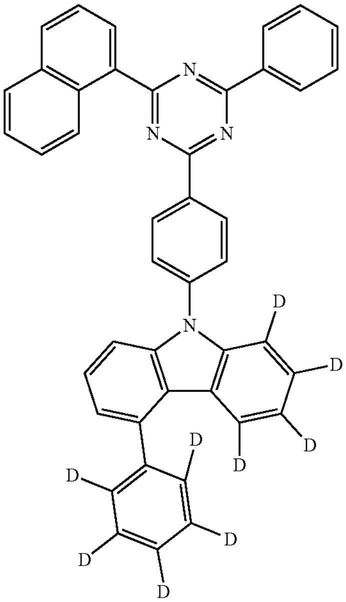
A225
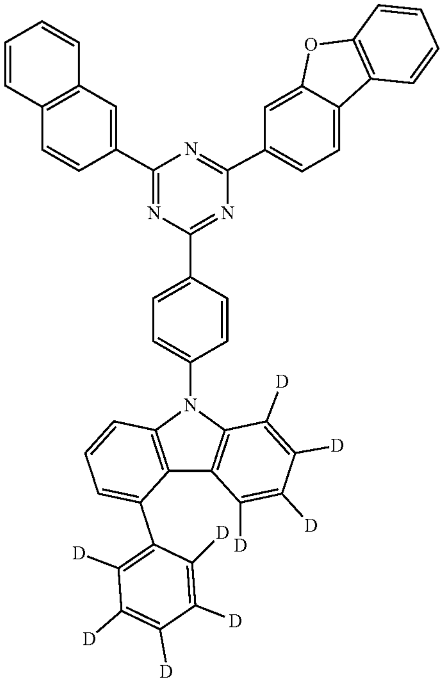

-continued
A226
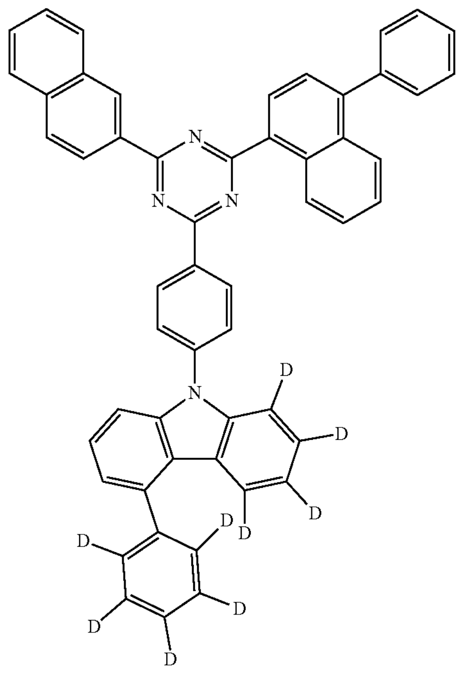
A227
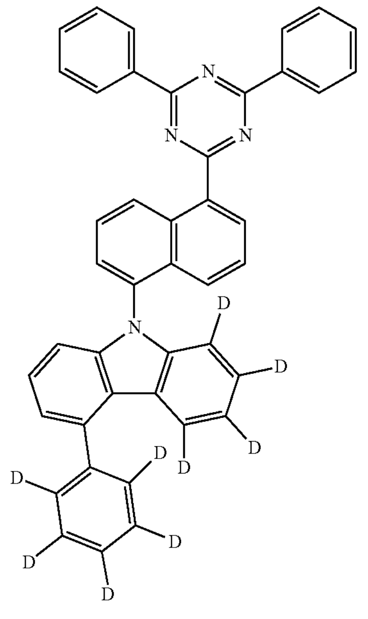
-continued
A228
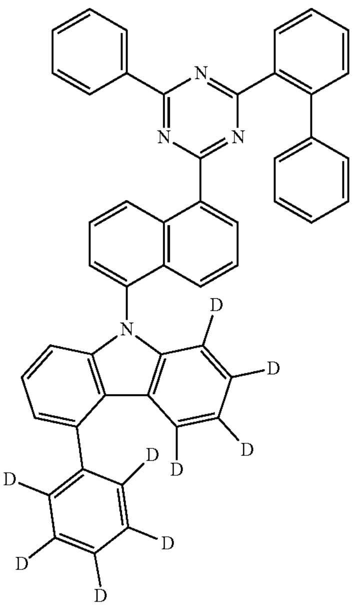
A229
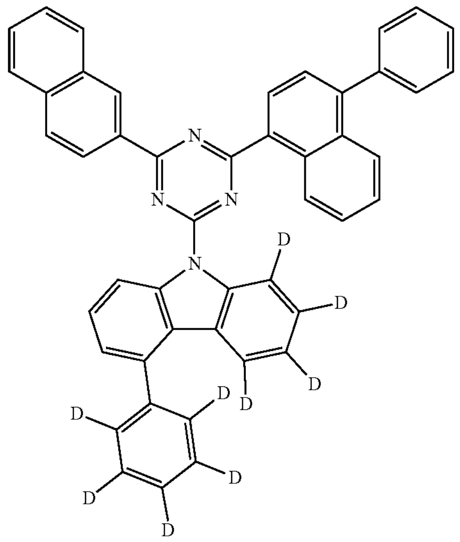

-continued
A230
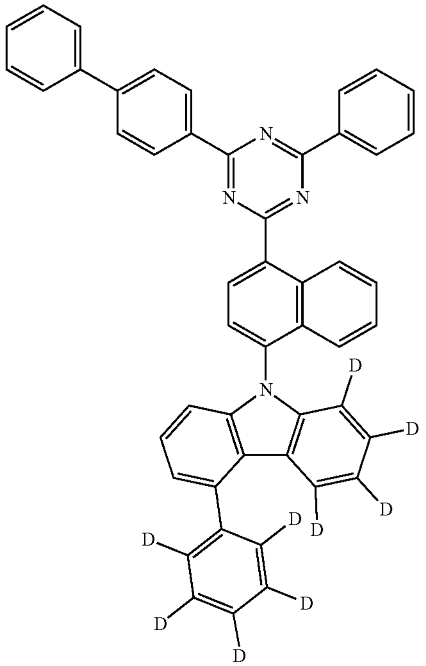
A231
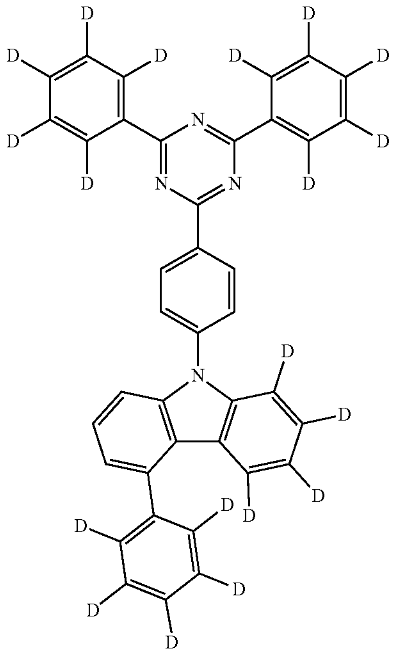
-continued
B73
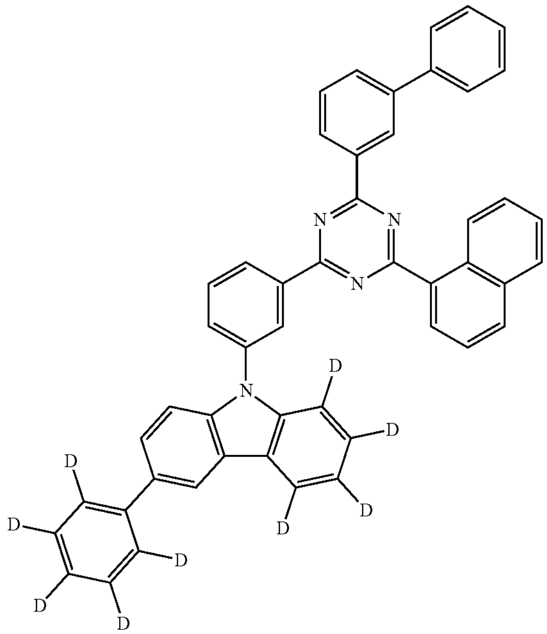
B74
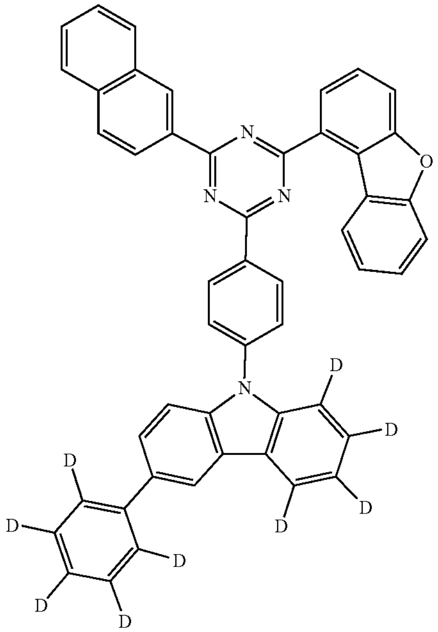

-continued
B75
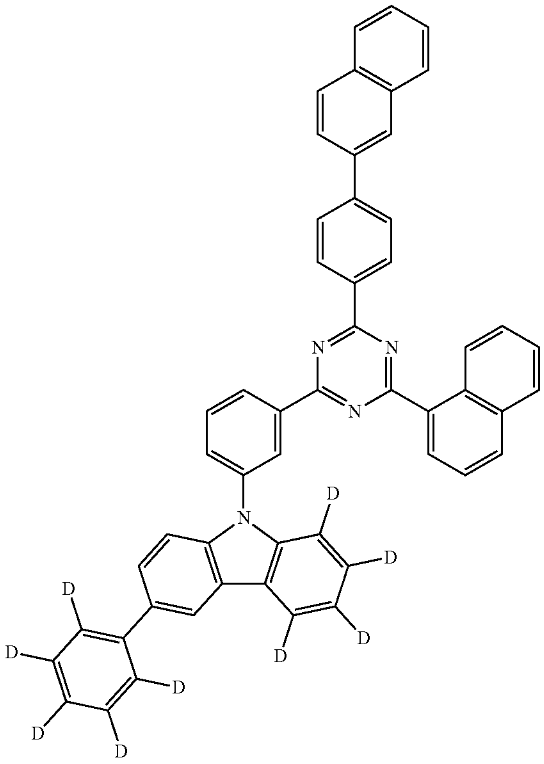
B76
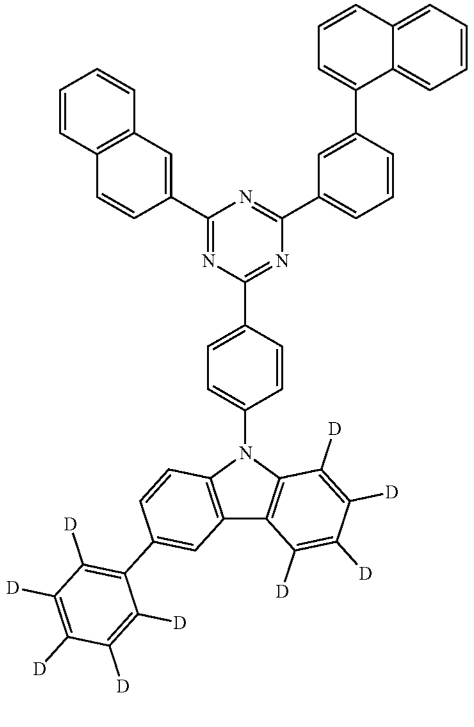
-continued
B77
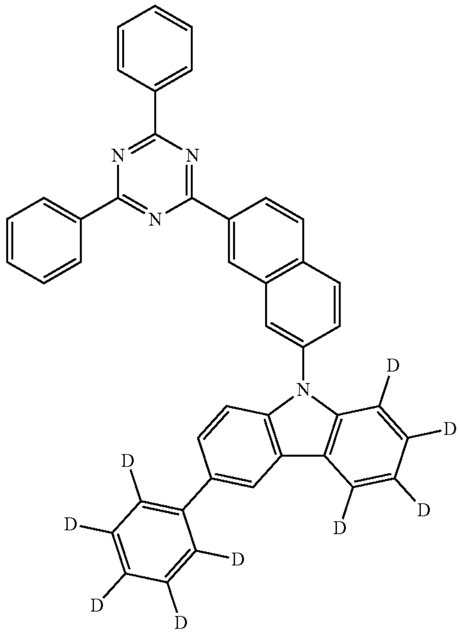
B78
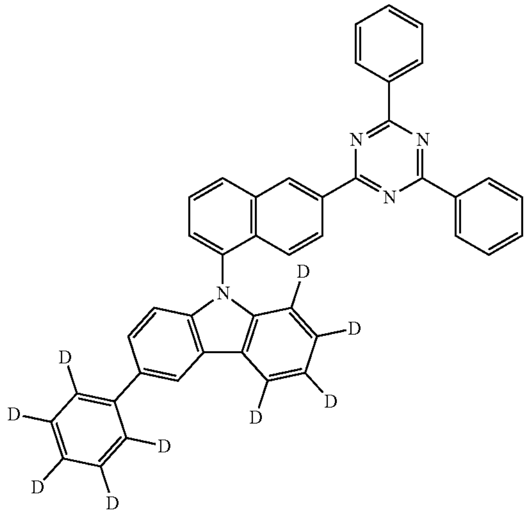

-continued
B79
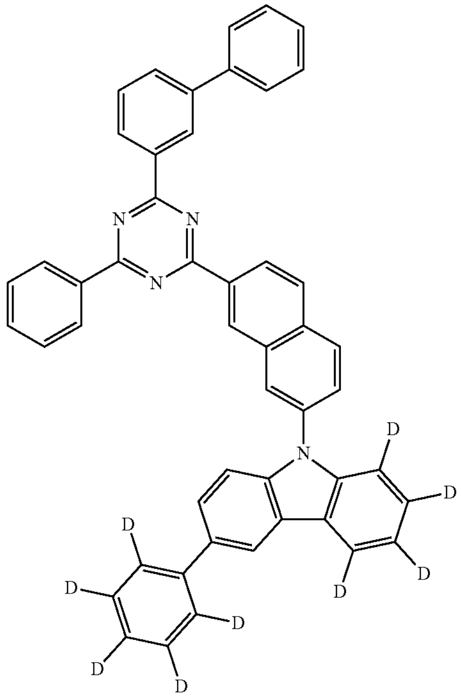
B80
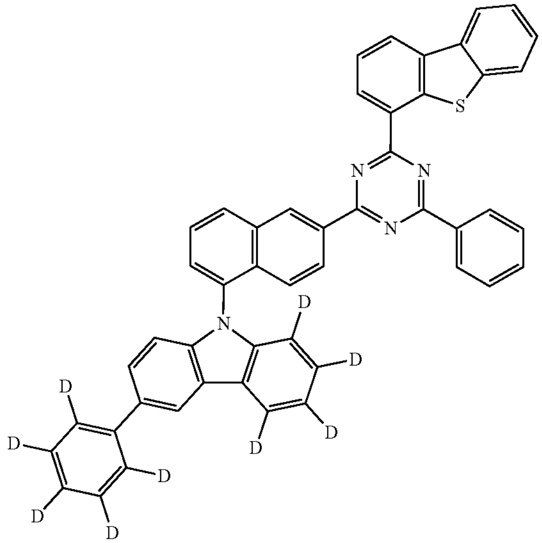
-continued
C73
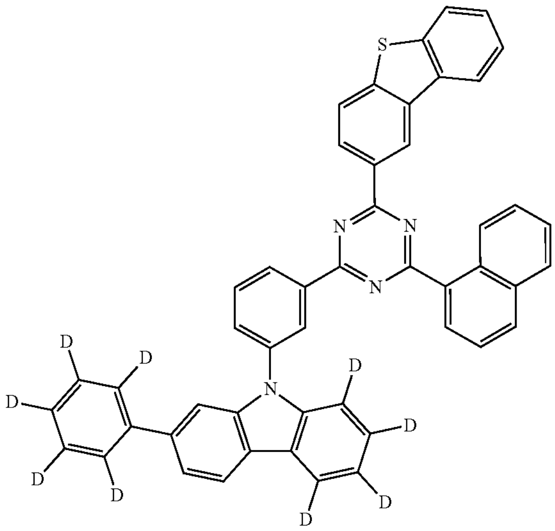
C74
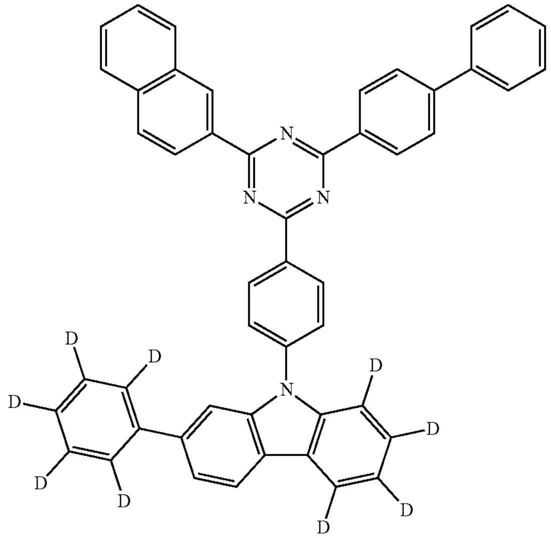
C75
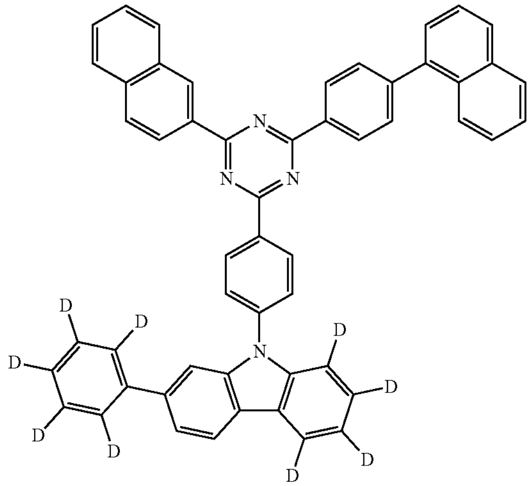

-continued
C76
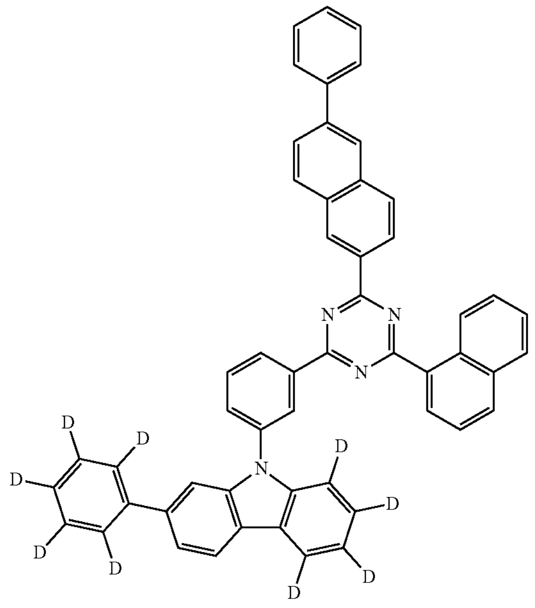
C77
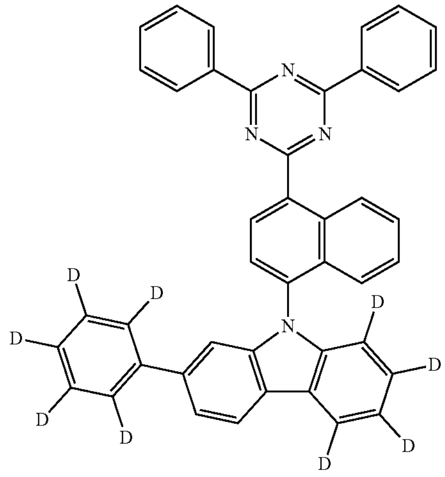
C78
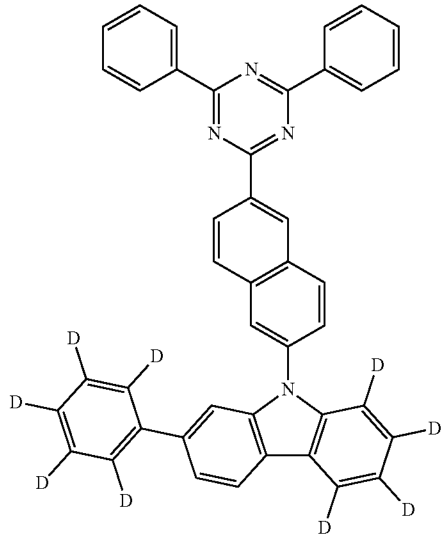
-continued
C79
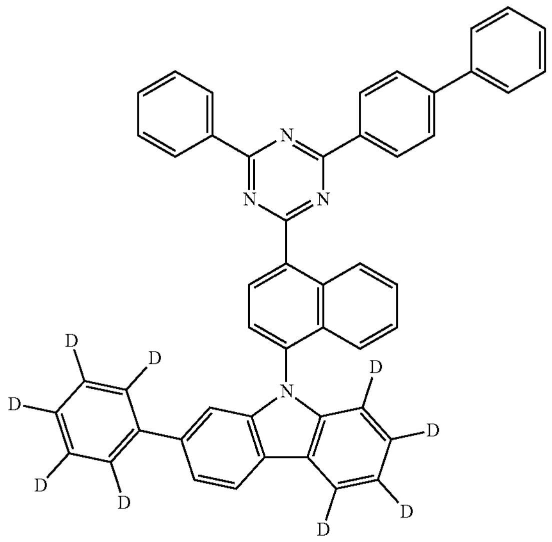
C80
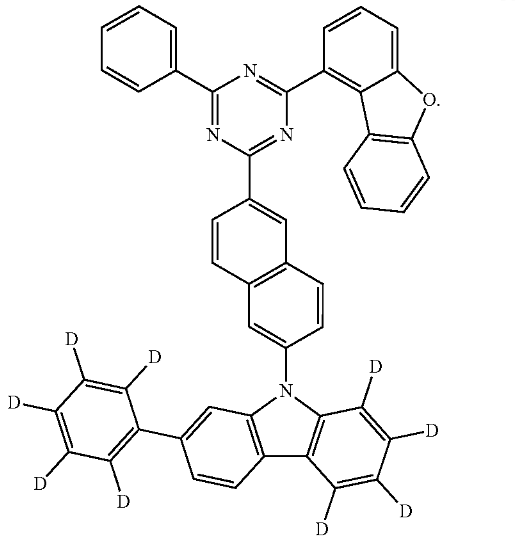
5. A composition, comprising a first compound and a second compound, wherein
the first compound is selected from the organic compound according to claim 1, and the second compound is selected from compounds shown in a formula 2-3-3:

Formula 2-3-3

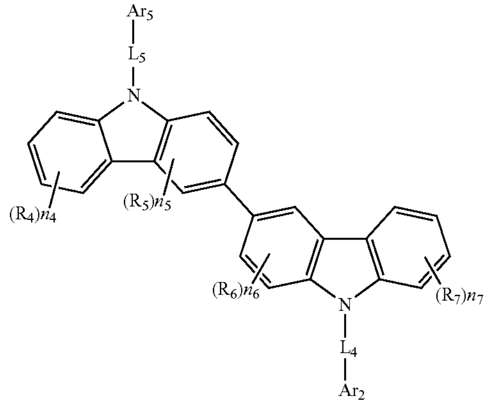

wherein each $R_4$, each $R_5$, each $R_6$, and each $R_7$ are respectively and independently selected from hydrogen, deuterium, a fluorine, a methyl, an ethyl, a n-propyl, an isopropyl, a tert-butyl, a phenyl, a naphthyl, a biphenyl, or a pentadeuterophenyl;

$n_4$ represents the number of substituents $R_4$, $n_4$ is selected from 1, 2, 3 or 4, and in the case where $n_4$ is greater than 1, any two $R_4$ are the same or different;

$n_5$ represents the number of substituents $R_5$, $n_5$ is selected from 1, 2 or 3, and in the case where $n_5$ is greater than 1, any two $R_5$ are the same or different;

$n_6$ represents the number of substituents $R_6$, $n_6$ is selected from 1, 2 or 3, and in the case where $n_6$ is greater than 1, any two $R_6$ are the same or different;

$n_7$ represents the number of substituents $R_7$, $n_7$ is selected from 1, 2, 3 or 4, and in the case where $n_7$ is greater than 1, any two $R_7$ are the same or different;

$L_4$ and $L_5$ are the same or different, and are respectively and independently selected from a single bond, a substituted or unsubstituted phenylene, a substituted or substituted naphthylene, a substituted or unsubstituted biphenylene, a substituted or unsubstituted dibenzofurylene, a substituted or unsubstituted dibenzothenylene, or a substituted or unsubstituted carbazolylene;

substituent(s) in $L_4$ and $L_5$ are respectively and independently selected from deuterium, a fluorine, a cyano, a methyl, an ethyl, a n-propyl, an isopropyl, a tert-butyl, a phenyl, or a pentadeuterophenyl;

$Ar_4$ and $Ar_5$ are the same or different, and are respectively and independently selected from a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted dibenzofuranyl, a substituted or unsubstituted dibenzothienyl, a substituted or unsubstituted carbazolyl, or a substituted or unsubstituted triphenylene; and substituent(s) in $Ar_4$ and $Ar_5$ are respectively and independently selected from deuterium, a fluorine, a cyano, a halogen group, a methyl, an ethyl, a n-propyl, an isopropyl, a tert-butyl, a phenyl, or a pentadeuterophenyl.

6. The composition according to claim 5, wherein the second compound is selected from the group consisting of the following compounds:

1

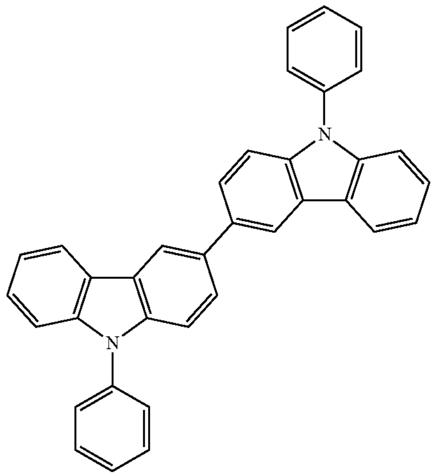

2

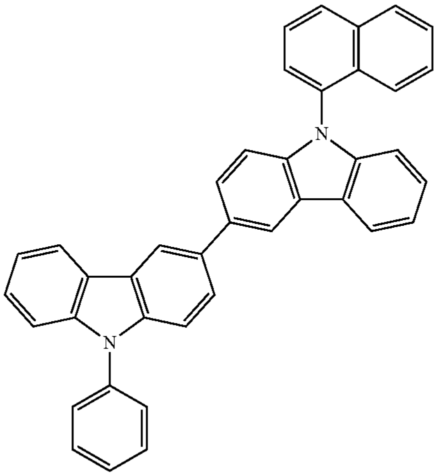

3

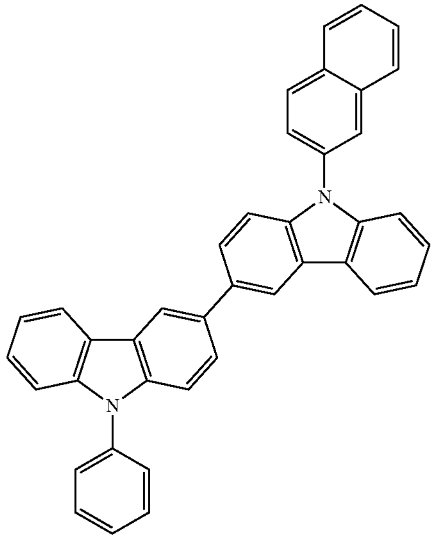

-continued
4
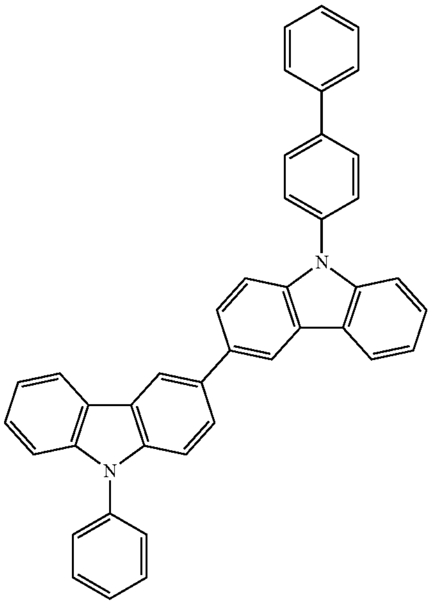
5
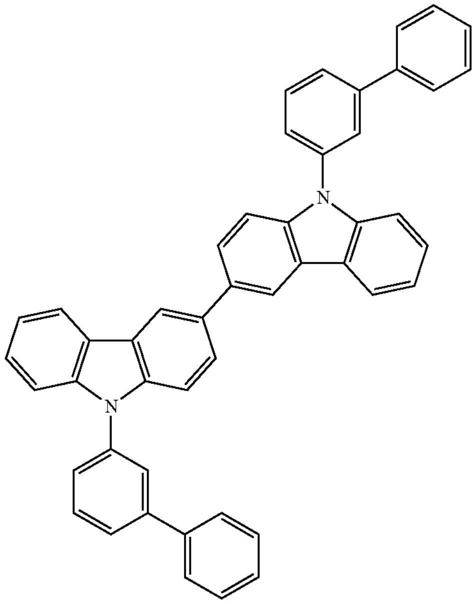
-continued
6
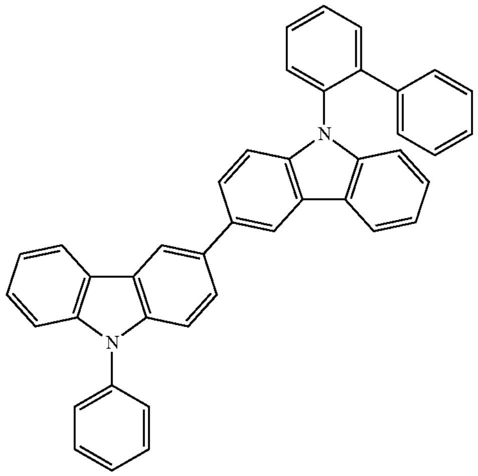
7
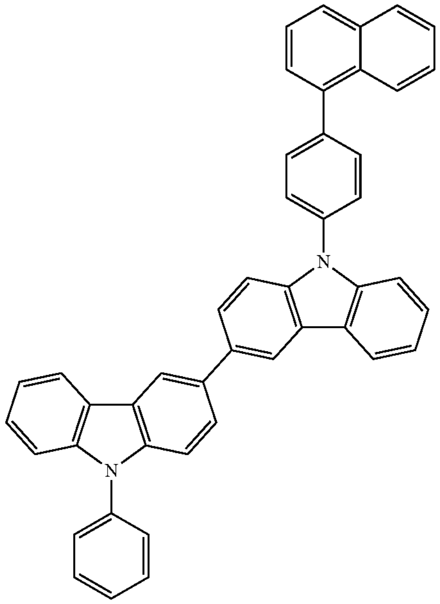

-continued
8
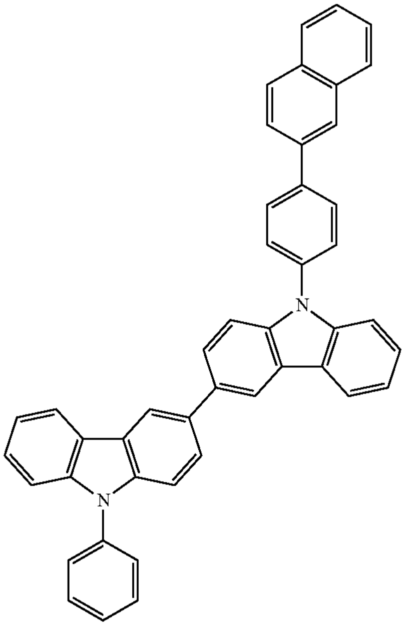
9
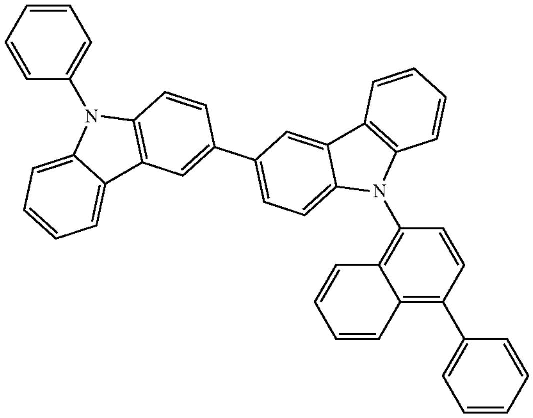
10
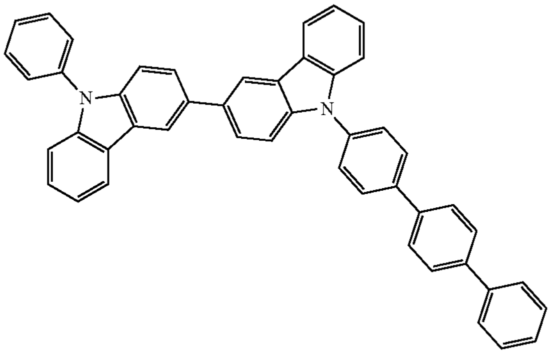
-continued
11
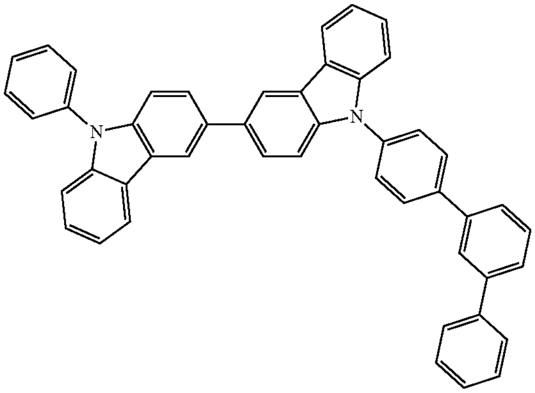
12
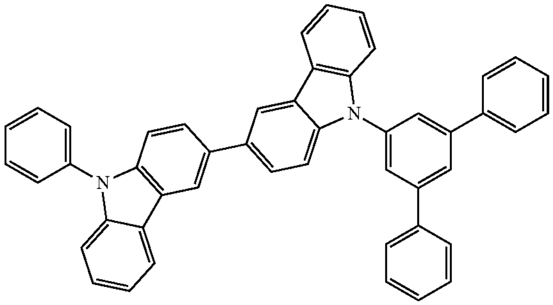
13
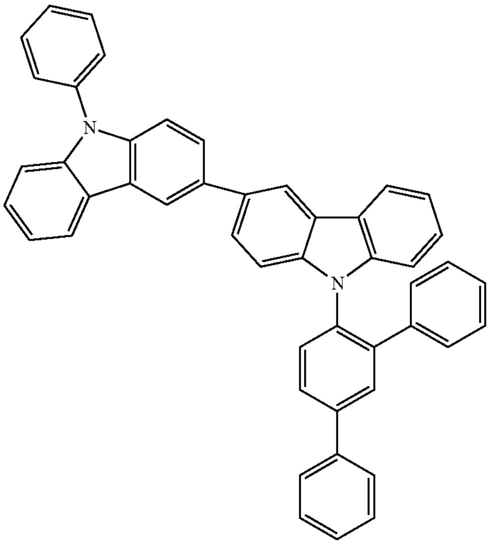

-continued
14
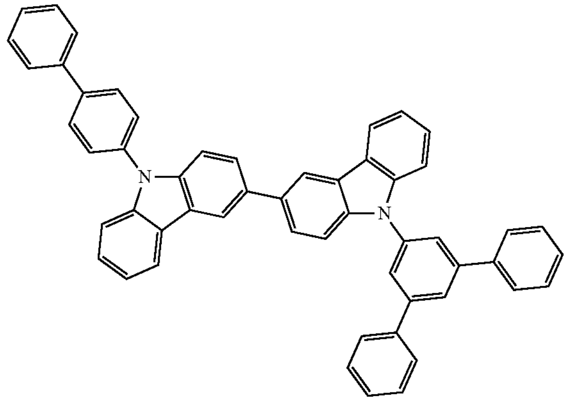
15
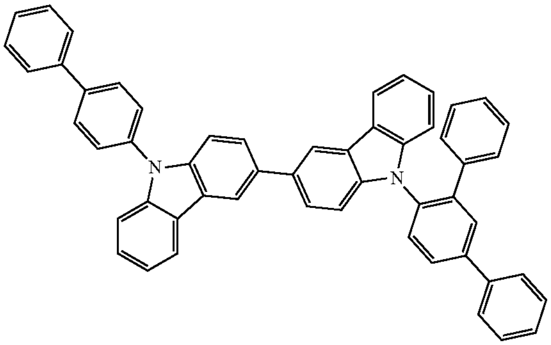
16
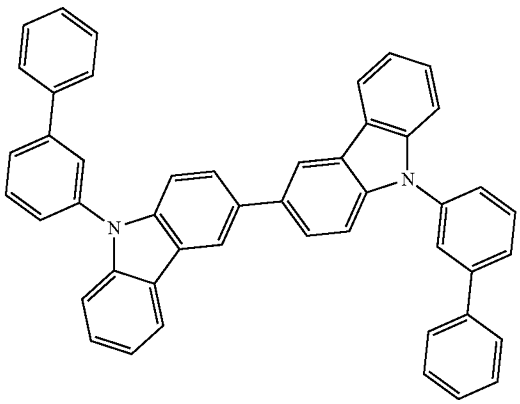
-continued
17
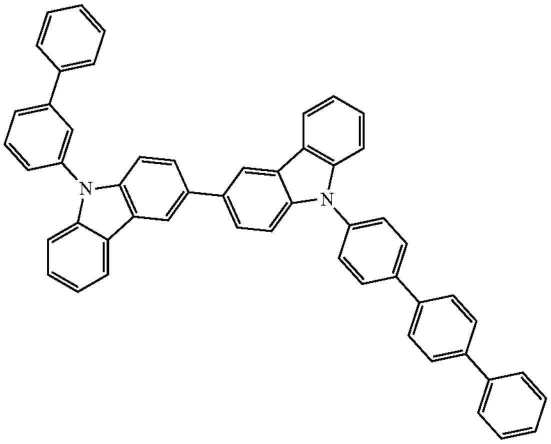
18
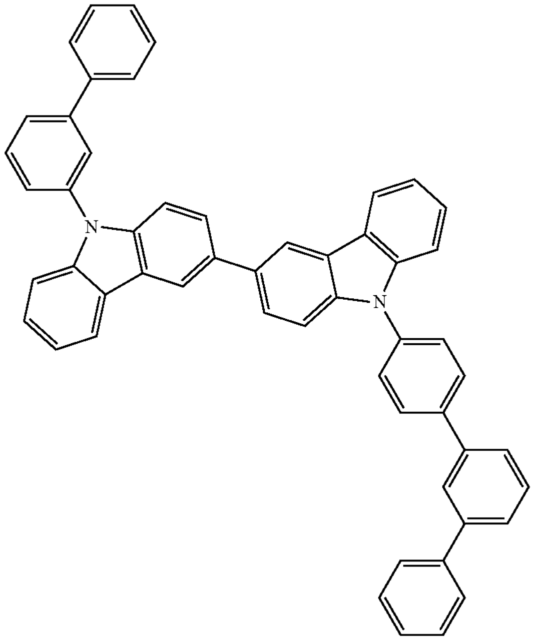
19
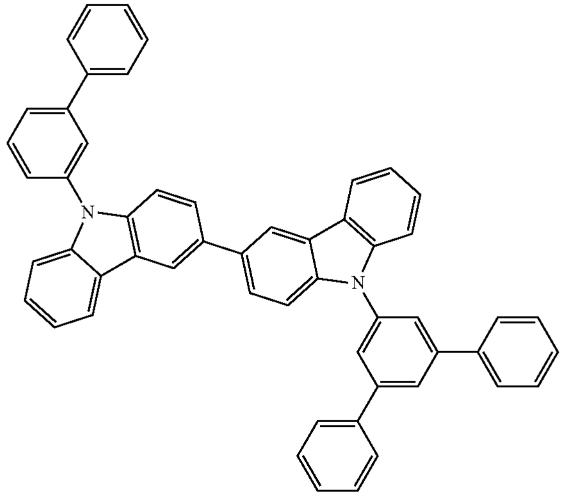

-continued
20
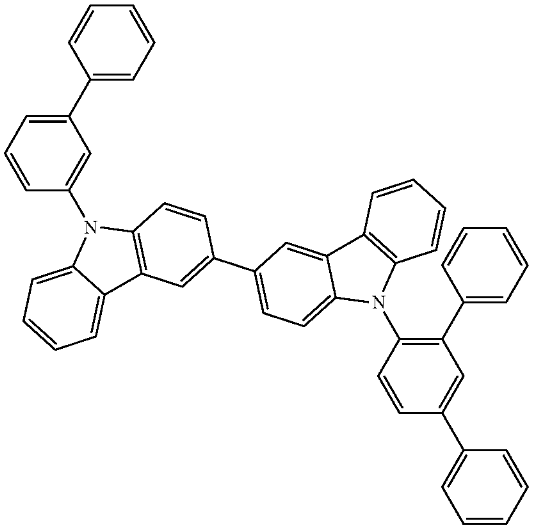
21
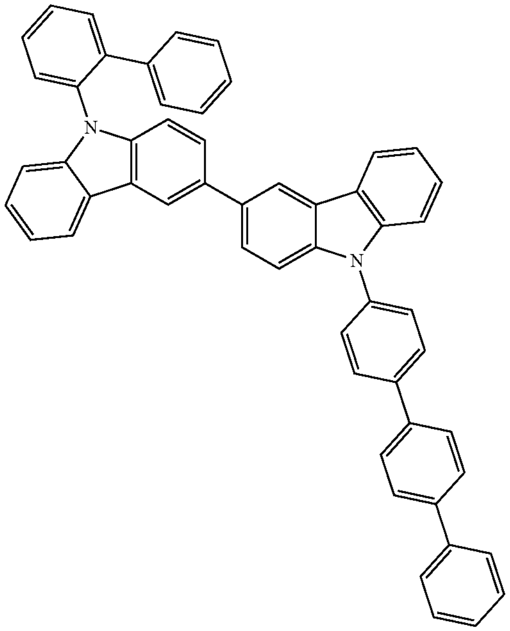
-continued
22
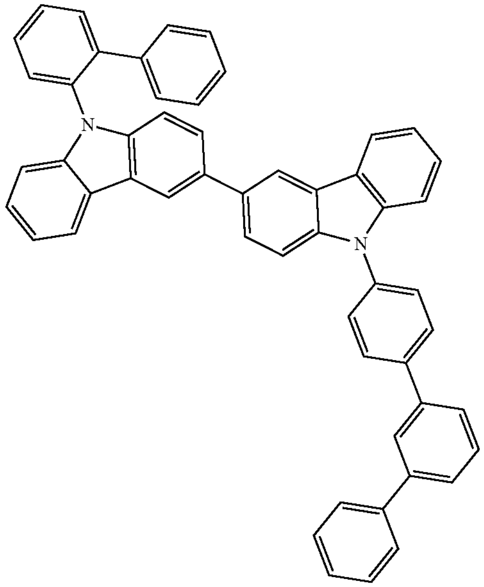
23
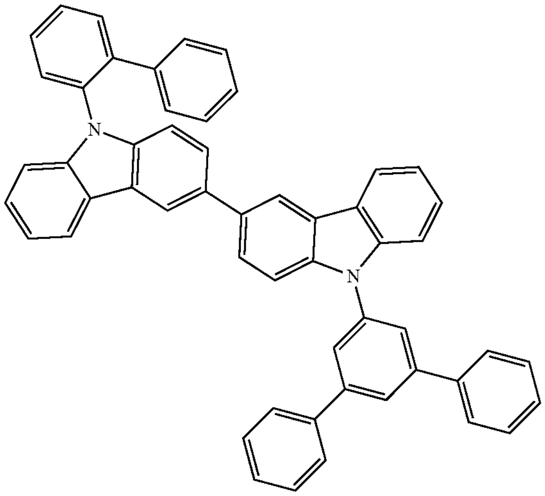
24
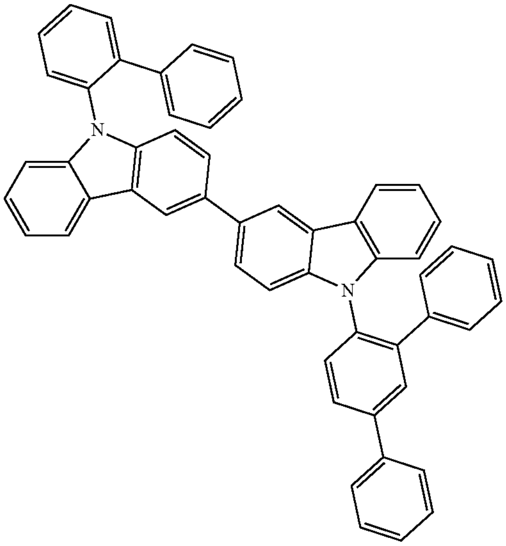

-continued
25
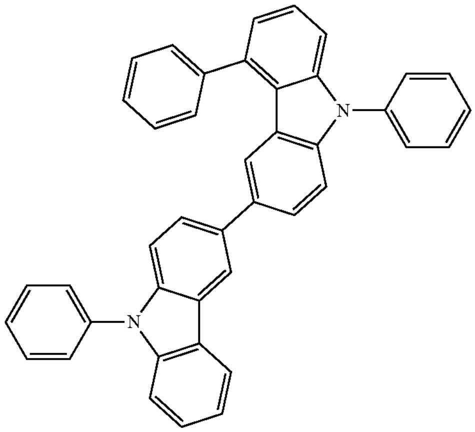
26
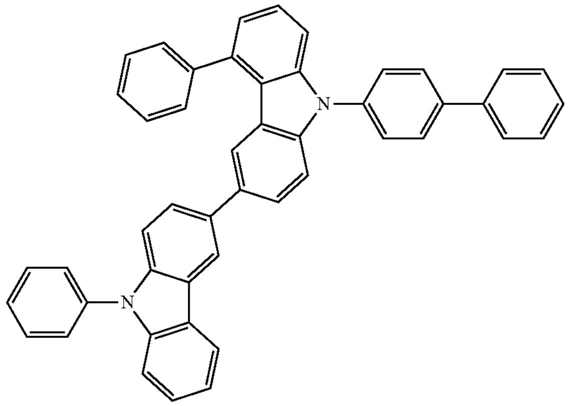
27
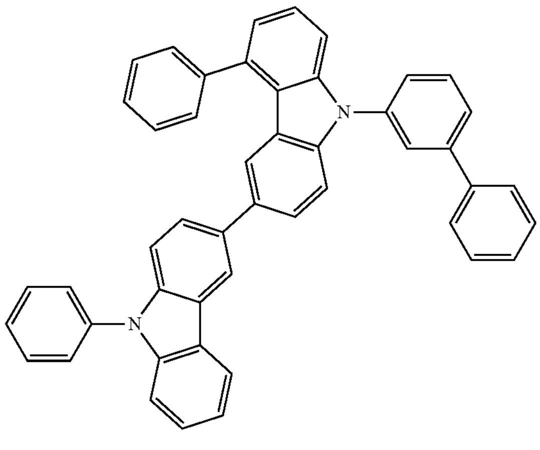
-continued
28
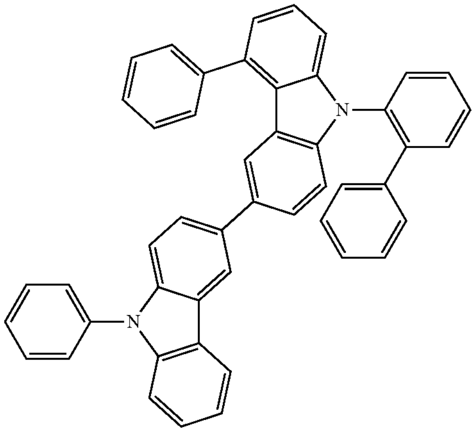
29
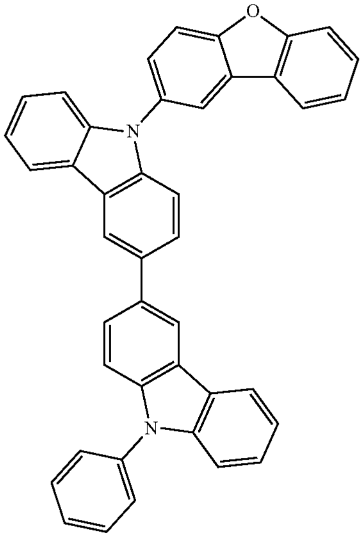
30
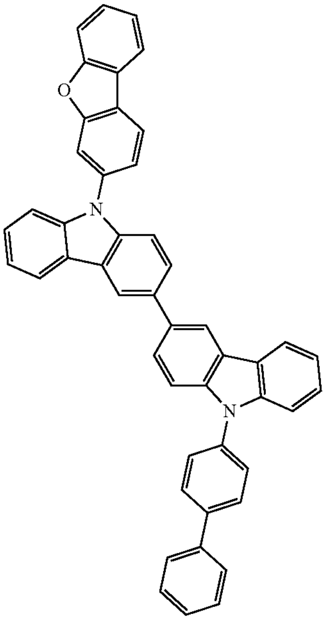

31
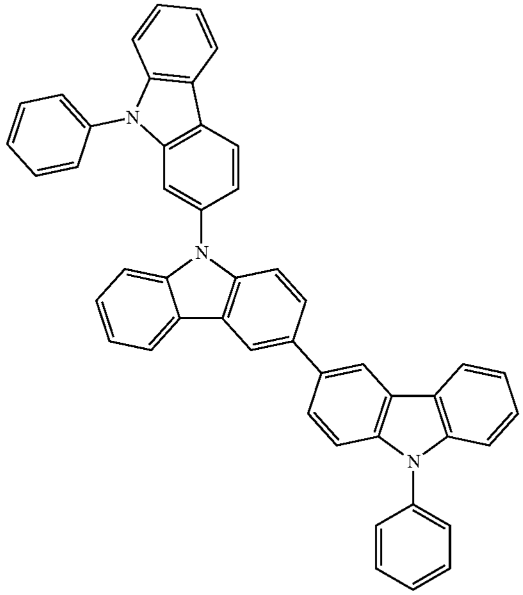
32
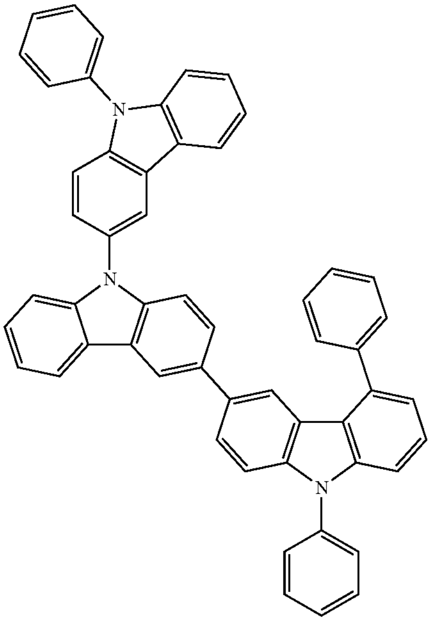
33
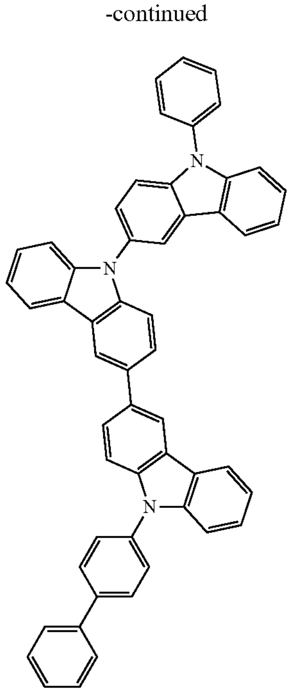
34
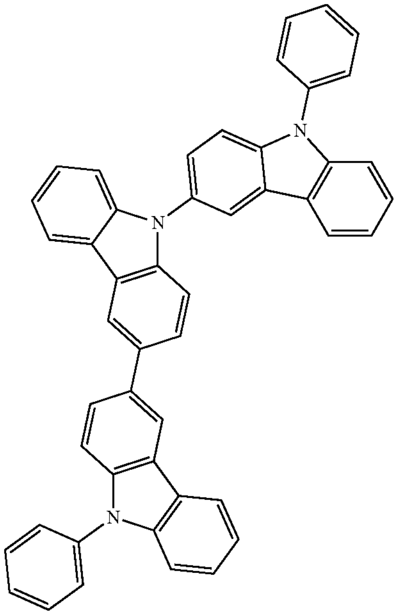

-continued
35
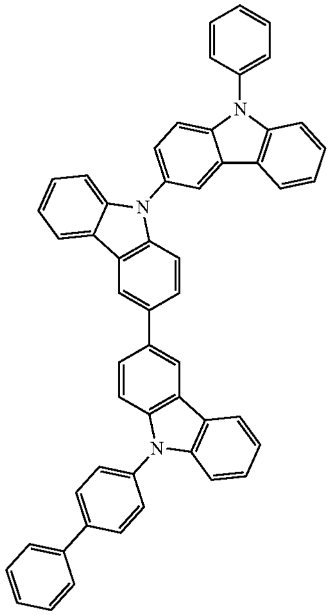
36
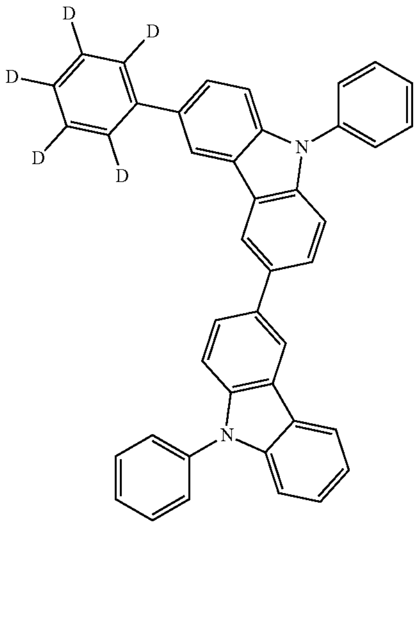
-continued
37
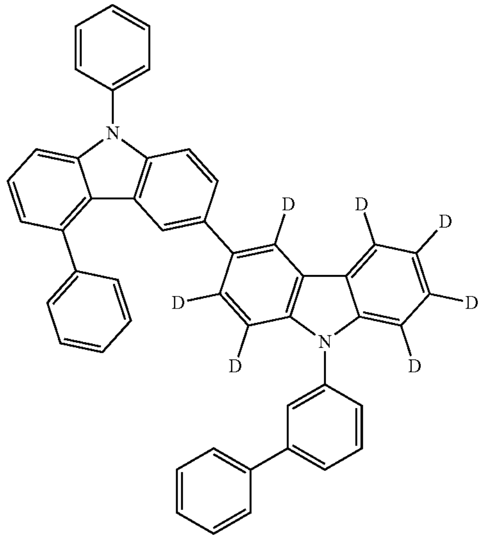
38
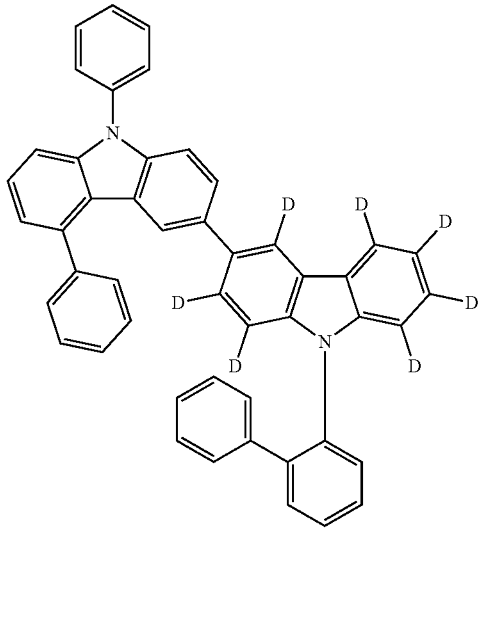

-continued
39
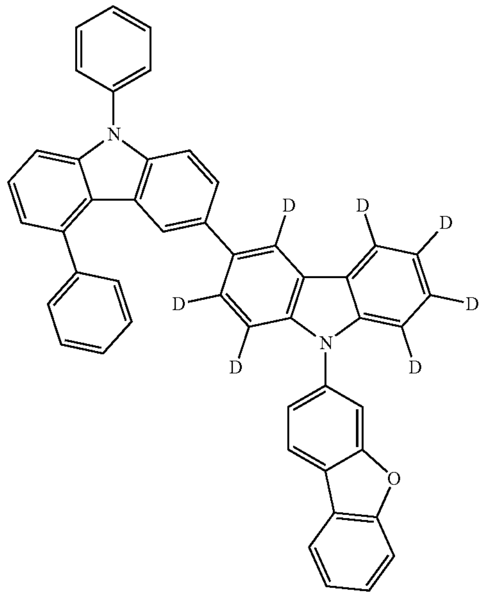
40
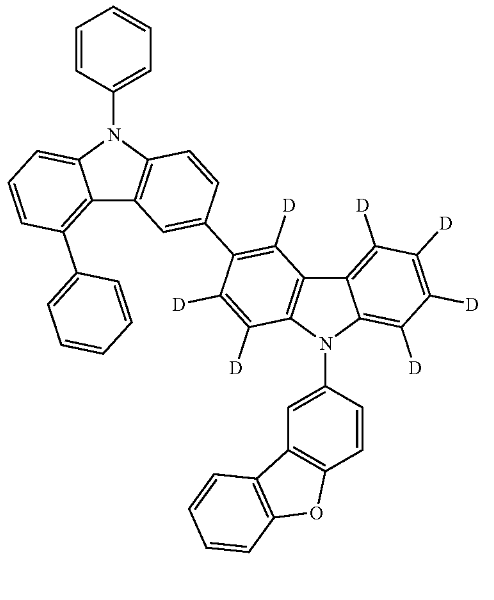
-continued
41
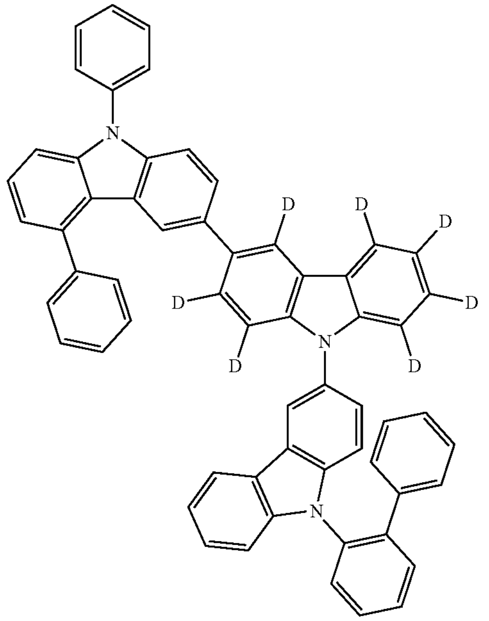
42
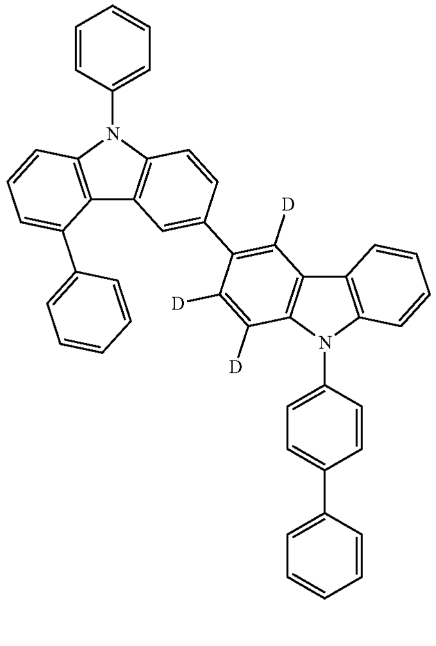

43
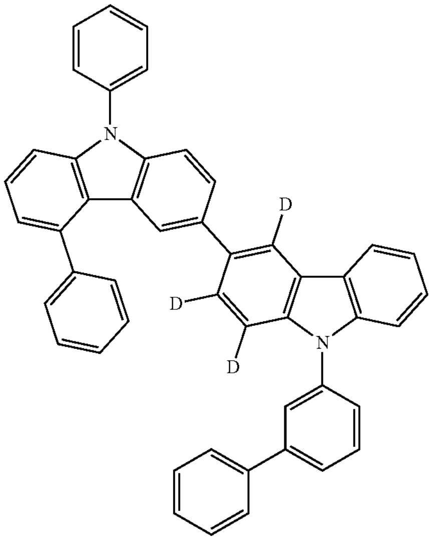
44
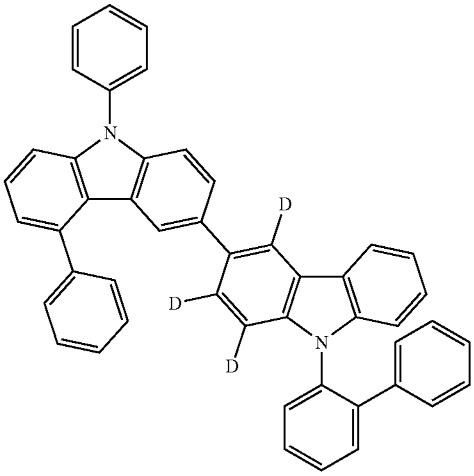
45
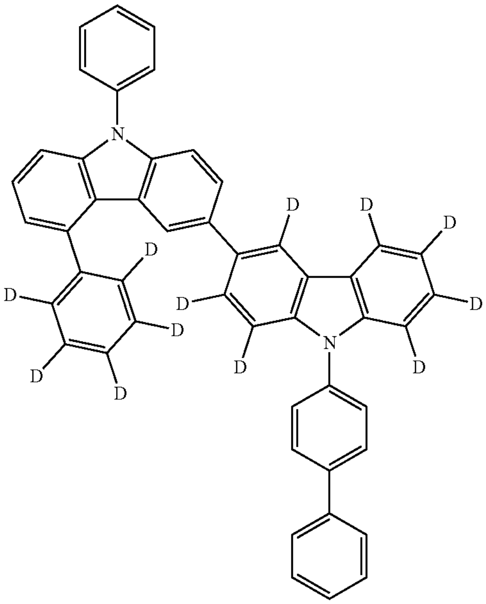
46
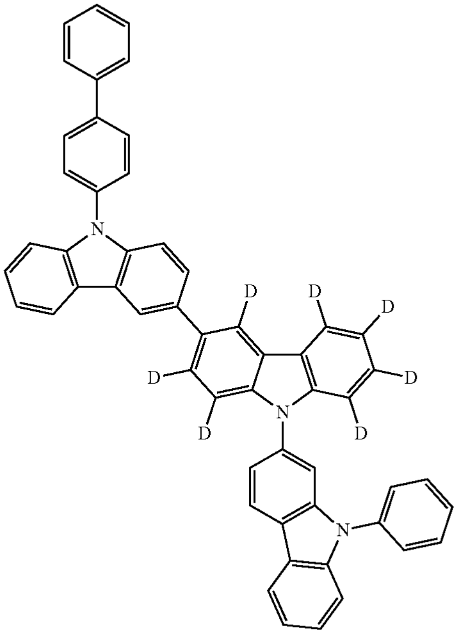
47
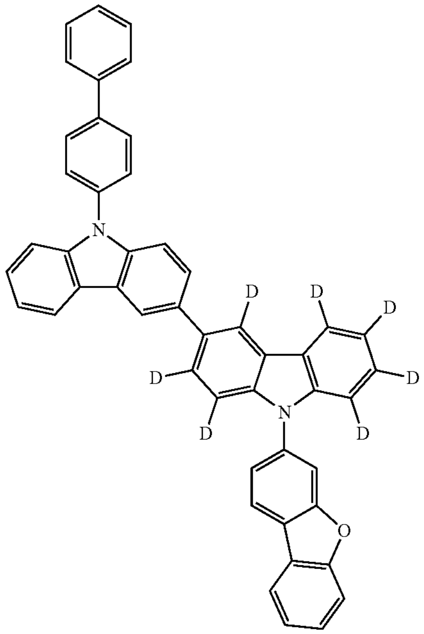

-continued
48
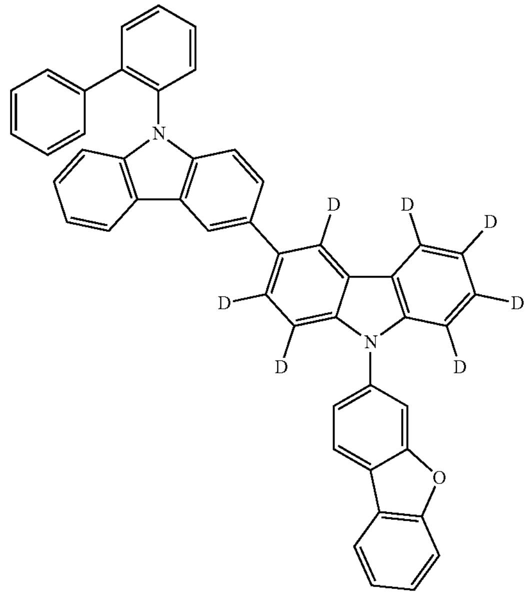
49
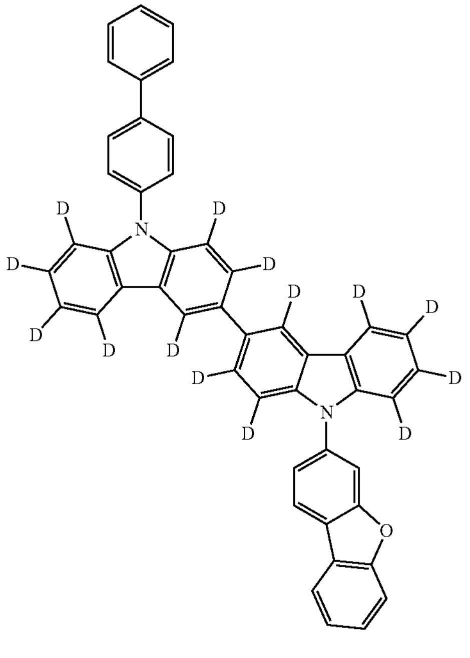
-continued
50
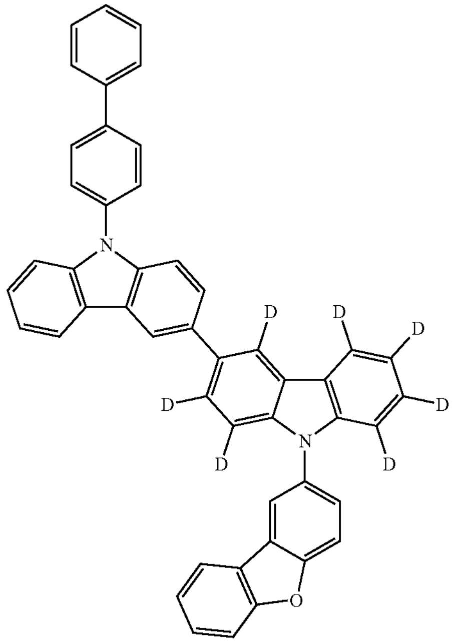
51
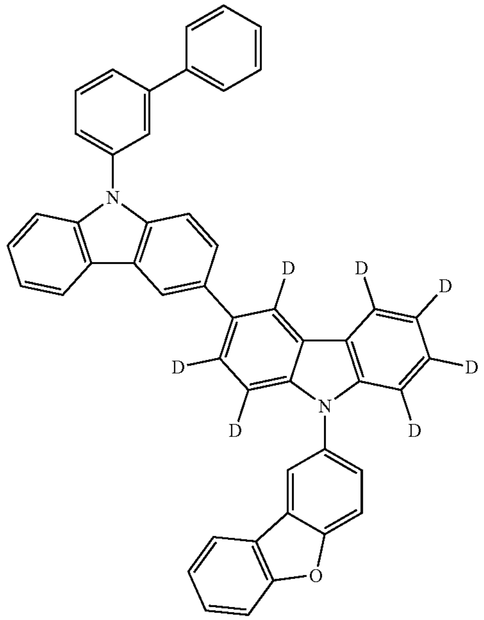

-continued
52
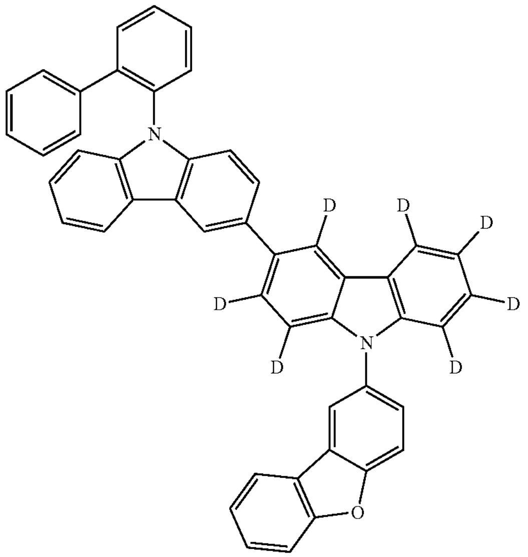
53
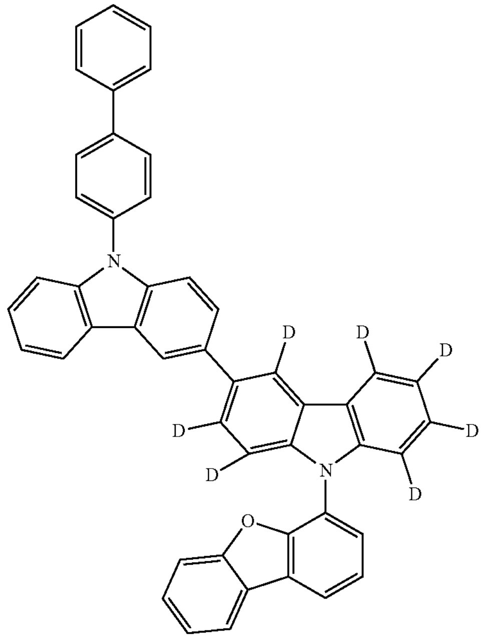
-continued
54
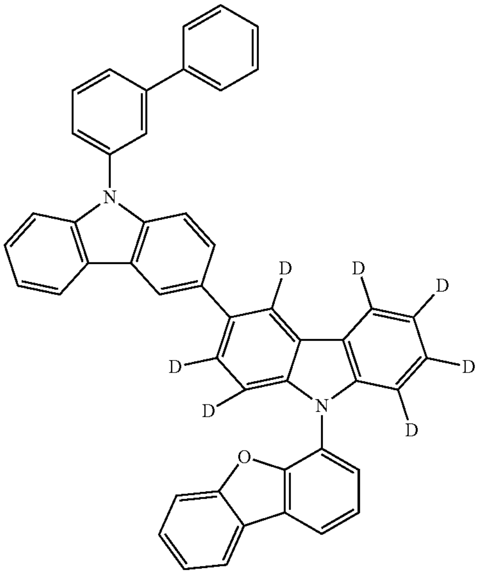
55
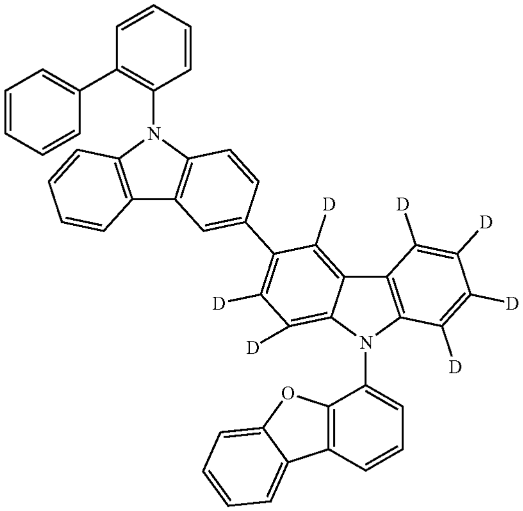

56
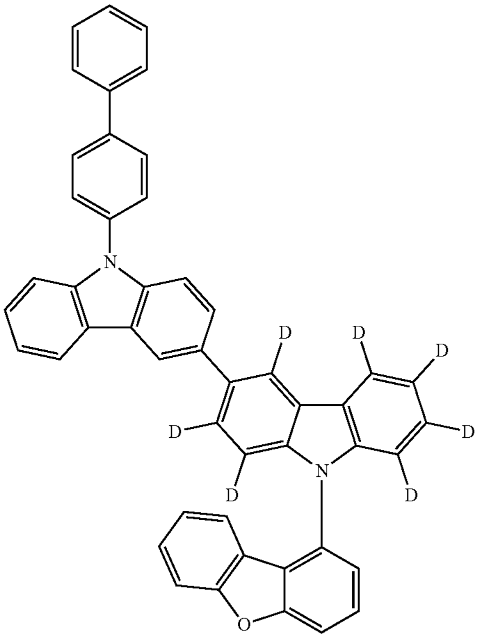
57
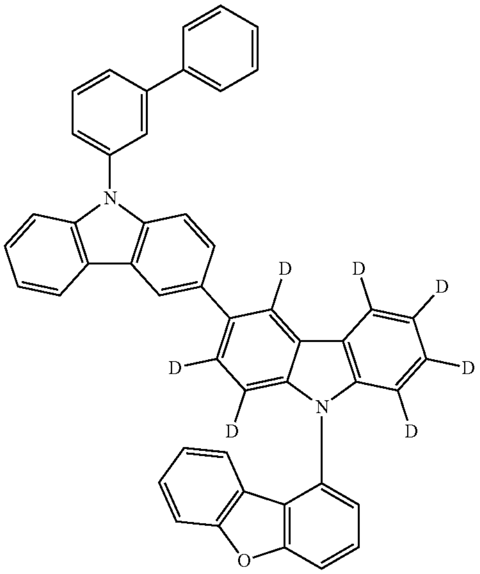
58
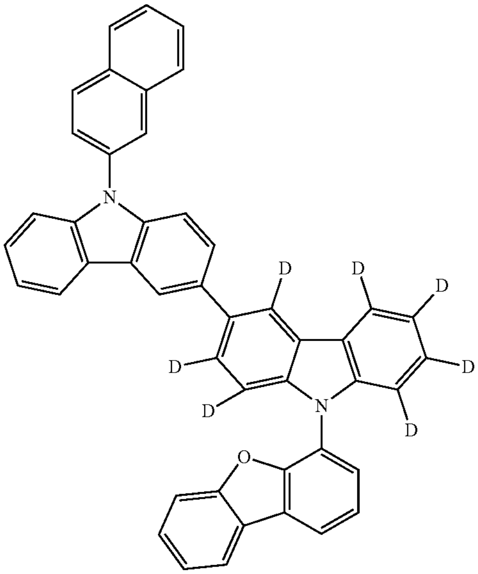
59
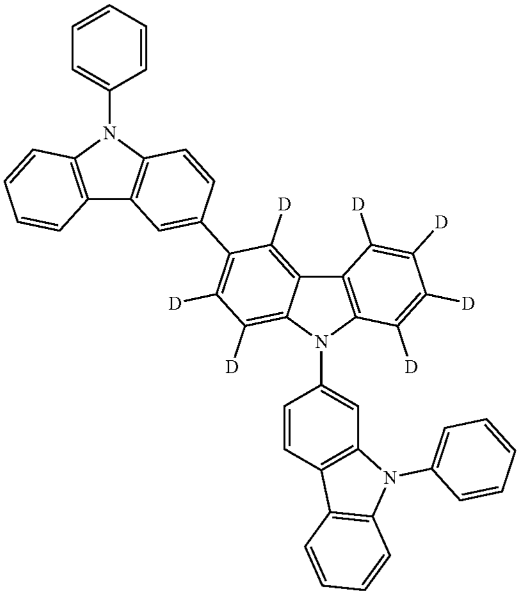

60
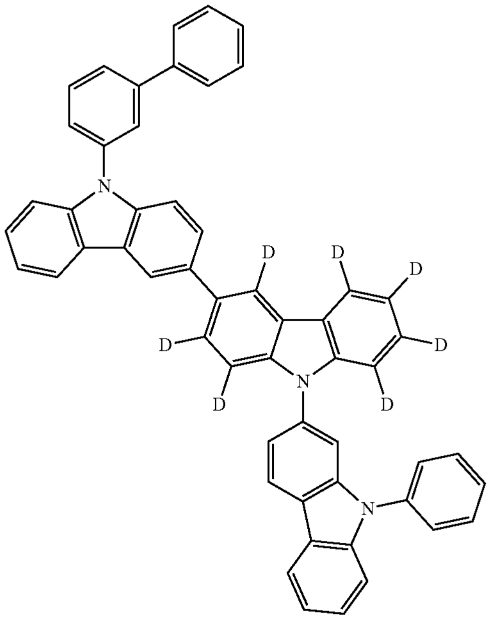
61
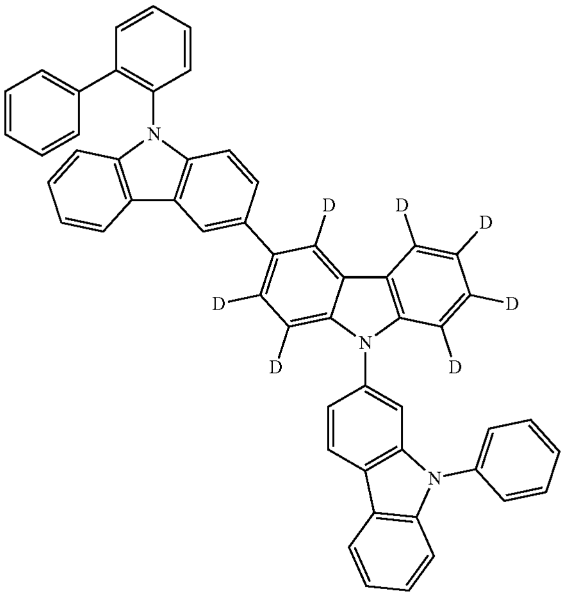
62
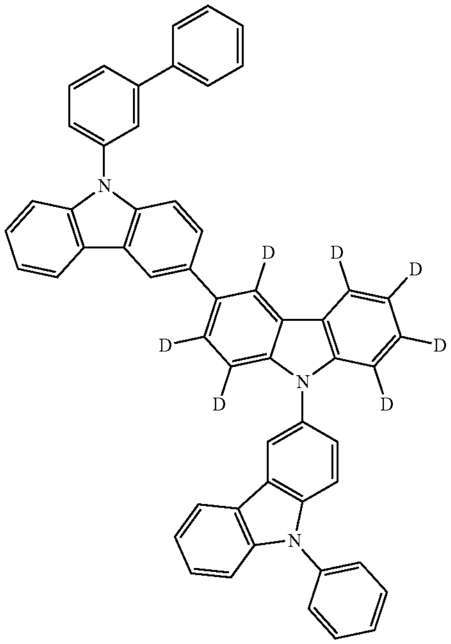
63
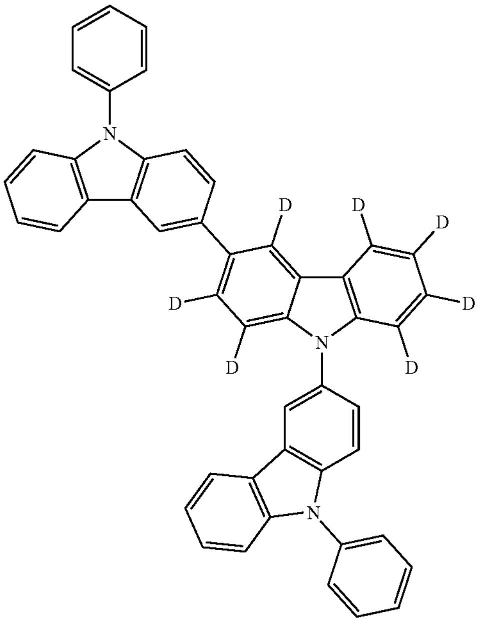

-continued
64
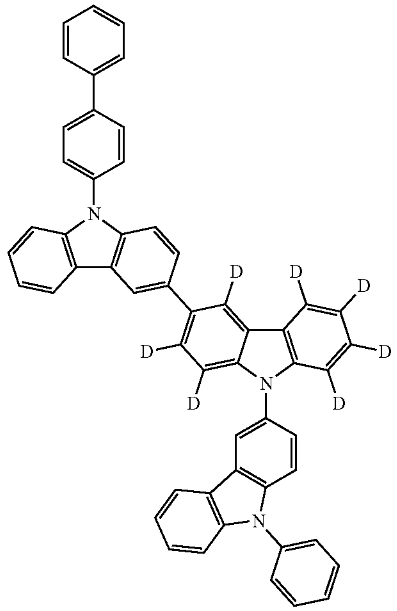
65
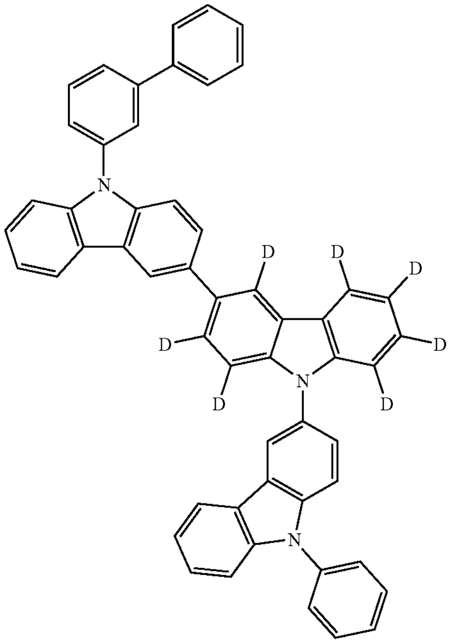
-continued
66
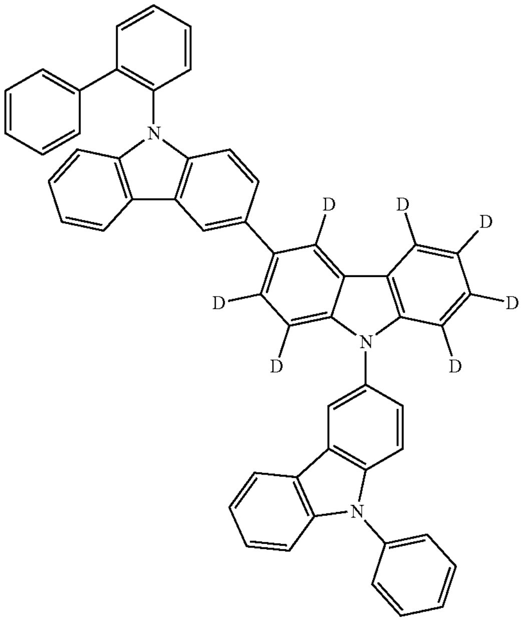
67
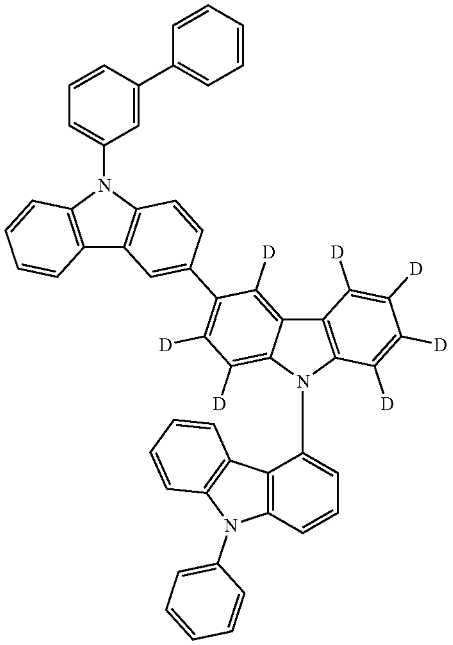

-continued
68
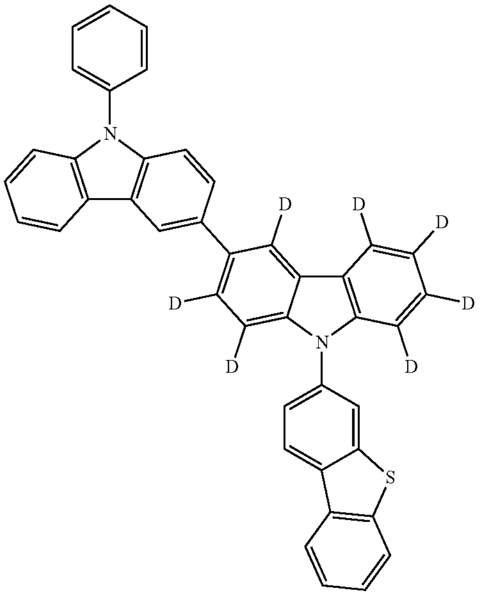
69
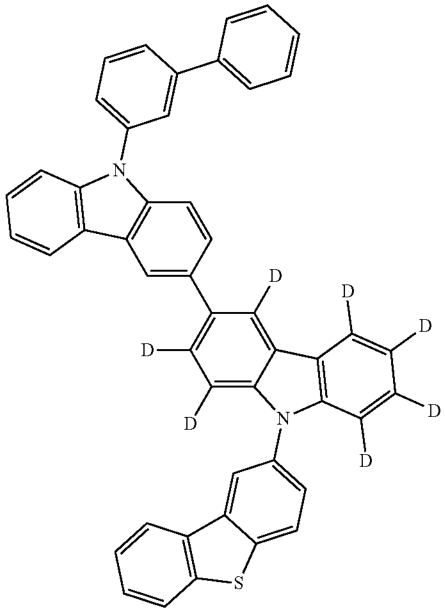
-continued
70
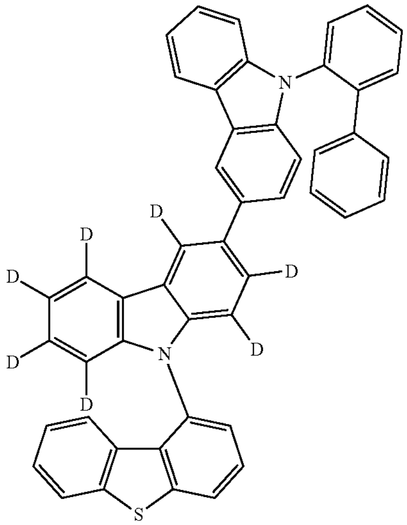
71
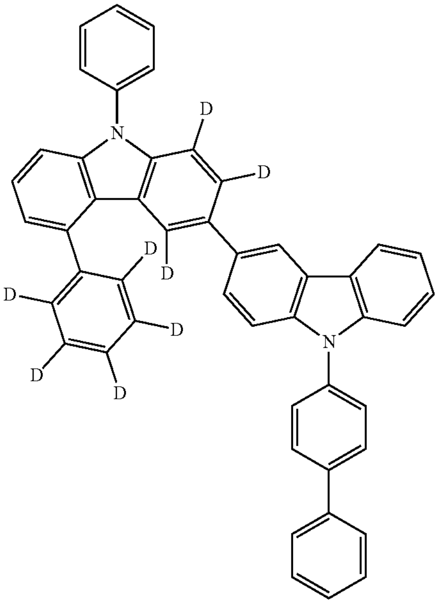

-continued
72
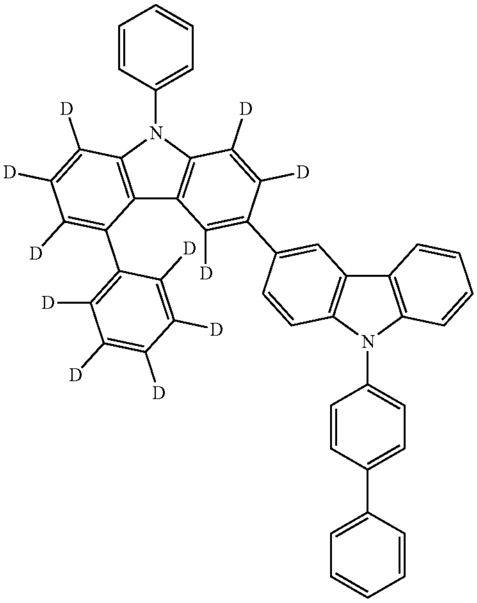
73
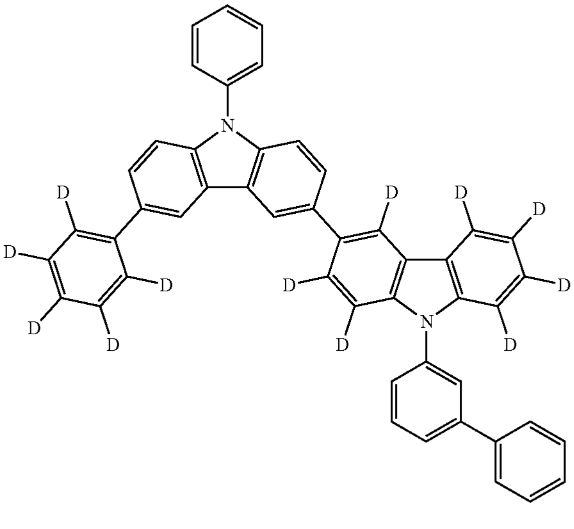
-continued
74
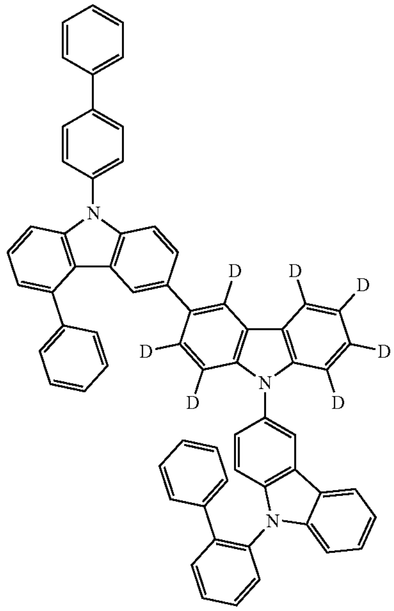
75
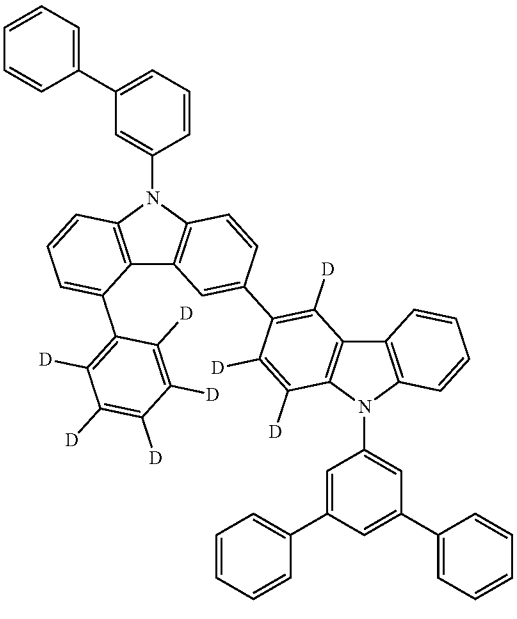

-continued
76
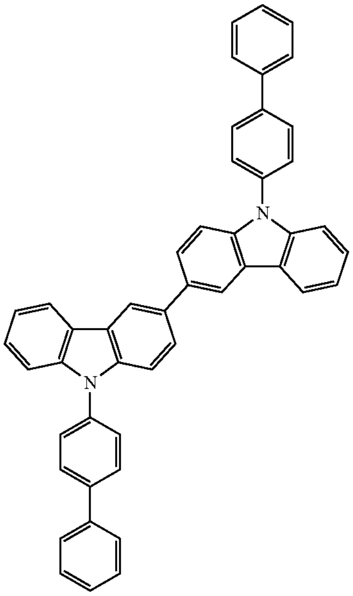
77
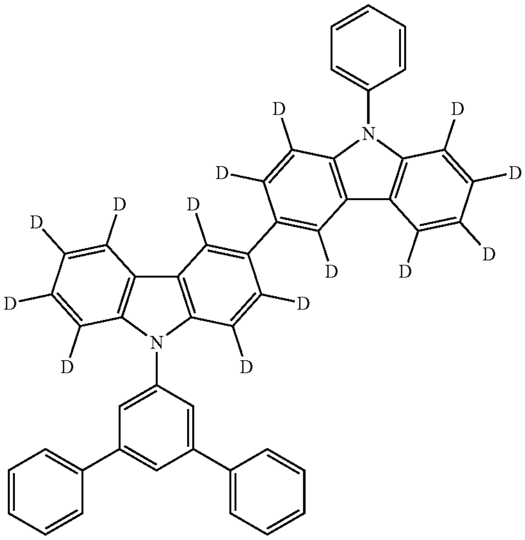
-continued
78
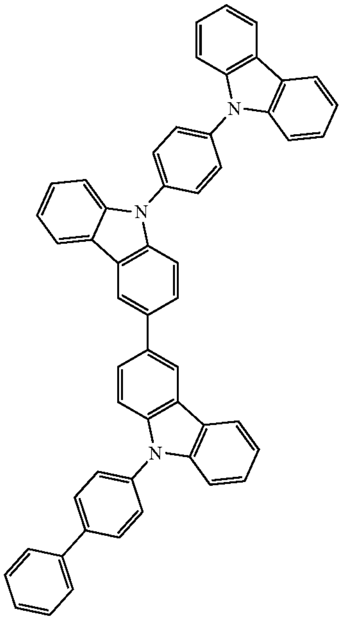
79
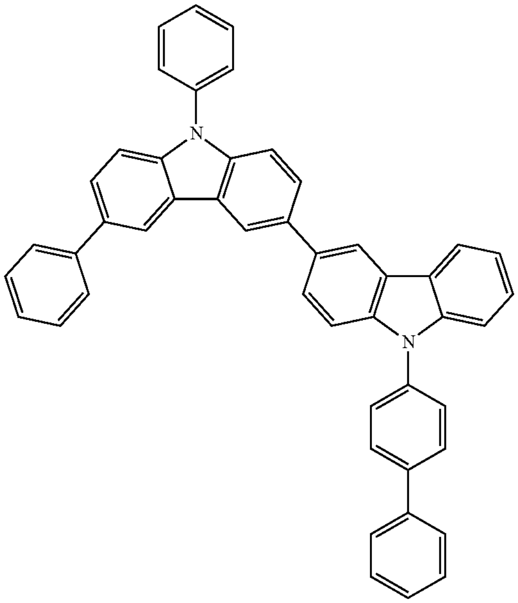

-continued

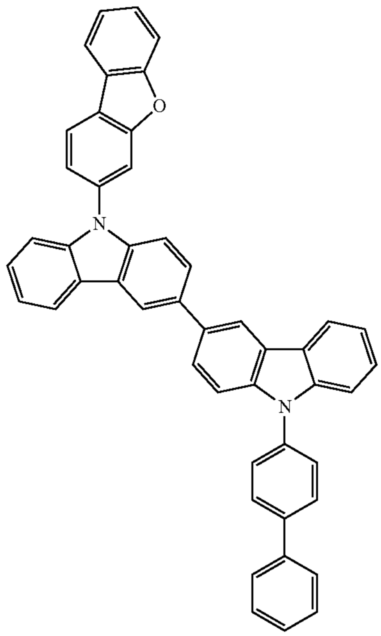

.

7. An organic electroluminescent device, comprising an anode and a cathode which are oppositely disposed, and a functional layer disposed between the anode and the cathode, wherein the functional layer comprises the organic compound according to claim 1.

8. An electronic apparatus, comprising the organic electroluminescent device according to claim 7.

9. The organic electroluminescent device according to claim 7, wherein the functional layer comprises an organic light-emitting layer comprising the organic compound.

10. The organic electroluminescent device according to claim 7, wherein the organic electroluminescent device is a green organic electroluminescent device.

11. An organic electroluminescent device, comprising an anode and a cathode which are oppositely disposed, and a functional layer disposed between the anode and the cathode, wherein the functional layer comprises the composition according to claim 5.

12. The organic electroluminescent device according to claim 11, wherein the functional layer comprises an organic light-emitting layer comprising the composition.

13. The organic electroluminescent device according to claim 11, wherein the organic electroluminescent device is a green organic electroluminescent device.

14. An electronic apparatus, comprising the composition according to claim 11.

* * * * *